US010030024B2

(12) United States Patent
Farmer et al.

(10) Patent No.: US 10,030,024 B2
(45) Date of Patent: Jul. 24, 2018

(54) IMIDAZOPYRIDAZINES USEFUL AS INHIBITORS OF THE PAR-2 SIGNALING PATHWAY

(71) Applicant: Vertex Pharmaceuticals Incorporated, Boston, MA (US)

(72) Inventors: Luc J. Farmer, Montreal (CA); Pierre-Andre Fournier, Vaudreuil-Dorion (CA); Stephanie Lessard, St-Jean-sur-Richelieu (CA); Bingcan Liu, Montreal (CA); Miguel St-Onge, Vaudreuil-Dorion (CA); Claudio Sturino, Ile Bizard (CA); Janek Szychowski, Montreal (CA); Constantin Yannopoulos, Notre-Dame de I'Ile Perrot (CA); Frederic Vallee, Montreal (CA); Jean-Eric Lacoste, Laval (CA); Julien Martel, Montreal (CA); Monica Bubenik, Mascouche (CA); Yeeman Ramtohul, Pierrefonds (CA); Camil Elie Sayegh, Dorval (CA)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 15/081,076

(22) Filed: Mar. 25, 2016

(65) Prior Publication Data

US 2016/0311825 A1 Oct. 27, 2016

Related U.S. Application Data

(63) Continuation of application No. PCT/US2014/057390, filed on Sep. 25, 2014.

(60) Provisional application No. 61/882,173, filed on Sep. 25, 2013, provisional application No. 61/901,617, filed on Nov. 8, 2013.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 519/00
USPC .............................. 514/217.05, 207.05, 207
See application file for complete search history.

(56) References Cited

U.S. PATENT DOCUMENTS 6,414,149 B1 * 7/2002 Chu-Moyer .......... C04B 35/632 544/194
6,660,740 B1 * 12/2003 Chu-Moyer .......... C04B 35/632 514/183
6,869,943 B2 * 3/2005 Chu-Moyer .......... C04B 35/632 514/183
8,389,480 B2 3/2013 Kuliopulos et al.
8,563,519 B2 10/2013 Kuliopulos et al.
8,802,623 B2 8/2014 Riteau et al.
8,852,569 B2 10/2014 Lerner et al.
8,927,503 B2 1/2015 Fairlie et al.
9,028,819 B2 5/2015 MacDonald et al.
9,044,510 B2 6/2015 Chen et al.
9,084,811 B2 7/2015 Lebaron et al.
9,125,861 B2 9/2015 Vergnolle et al.
9,333,152 B2 5/2016 Ferrer Montiel et al.
9,376,499 B2 6/2016 Kuliopulos et al.
2007/0123508 A1 5/2007 Olsson et al.
2013/0165652 A1 6/2013 Gwak et al.
2013/0184226 A1 7/2013 Fairlie et al.

(Continued)

FOREIGN PATENT DOCUMENTS

EP 2617721 A2 7/2013
EP 2668157 A1 12/2013

(Continued)

OTHER PUBLICATIONS

Chu-Moyer et al. (AN 2000:725471 CAPLUS; DN 133:281794 abstract of WO 2000059510).*

(Continued)

*Primary Examiner* — Sabiha N Qazi
(74) *Attorney, Agent, or Firm* — Proskauer Rose LLP; Fangli Chen

(57) ABSTRACT

The present invention relates to compounds useful as inhibitors of the PAR-2 signaling pathway. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of GPCRs in biological and pathological phenomena; the study of intracellular signal transduction pathways mediated by such GPCRs; and the comparative evaluation of new inhibitors of the PAR-2 signaling pathway. The compounds of this invention have formula I:

I

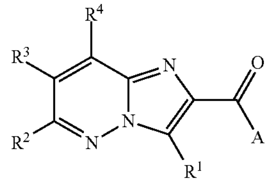

wherein the variables are as defined herein.

23 Claims, No Drawings

(56) References Cited

U.S. PATENT DOCUMENTS

| | | | |
|---|---|---|---|
| 2013/0316033 | A1 | 11/2013 | Lebaron et al. |
| 2013/0324556 | A1 | 12/2013 | Boyd et al. |
| 2013/0331333 | A1 | 12/2013 | Bar-Shavit |
| 2014/0087993 | A1 | 3/2014 | Kuliopulos et al. |
| 2014/0170166 | A1 | 6/2014 | Virca et al. |
| 2014/0227718 | A1 | 8/2014 | Kuliopulos et al. |
| 2014/0308296 | A1 | 10/2014 | Riteau et al. |
| 2014/0315796 | A1 | 10/2014 | Fairlie et al. |
| 2014/0363818 | A1 | 12/2014 | Fasano et al. |
| 2015/0038402 | A1 | 2/2015 | Fairlie et al. |
| 2015/0184163 | A1 | 7/2015 | Wilson et al. |
| 2015/0231187 | A1 | 8/2015 | Lebaron et al. |
| 2016/0000791 | A1 | 1/2016 | Scarisbrick et al. |
| 2016/0095897 | A1 | 4/2016 | Riteau et al. |

FOREIGN PATENT DOCUMENTS

| | | | |
|---|---|---|---|
| EP | 1981913 | B1 | 6/2014 |
| EP | 2791360 | A2 | 10/2014 |
| EP | 2416799 | B1 | 7/2015 |
| EP | 2990051 | A1 | 3/2016 |
| EP | 2791360 | A4 | 4/2016 |
| EP | 3061460 | A1 | 8/2016 |
| JP | 2004170323 | | 6/2004 |
| JP | 2013538192 | A | 10/2013 |
| JP | 5356636 | B2 | 12/2013 |
| JP | 2014101378 | A | 6/2014 |
| JP | 2014514246 | A | 6/2014 |
| JP | 2014524923 | A | 9/2014 |
| JP | 5719050 | B2 | 5/2015 |
| JP | 2015518367 | A | 7/2015 |
| JP | 5883863 | B2 | 3/2016 |
| KR | 1020130034701 | A | 4/2013 |
| WO | WO03104268 | A1 | 12/2003 |
| WO | WO2005030773 | A1 | 4/2005 |
| WO | WO2006035936 | A1 | 4/2006 |
| WO | WO2006035937 | A1 | 4/2006 |
| WO | WO2006070780 | A1 | 7/2006 |
| WO | WO2006104190 | A1 | 10/2006 |
| WO | WO2006127379 | A2 | 11/2006 |
| WO | WO2006127396 | A1 | 11/2006 |
| WO | WO2007076055 | A2 | 7/2007 |
| WO | WO2009117481 | A1 | 9/2009 |
| WO | WO2010017086 | A1 | 2/2010 |
| WO | WO2010128016 | A2 | 11/2010 |
| WO | WO2012012843 | A1 | 2/2012 |
| WO | WO2012026765 | A2 | 3/2012 |
| WO | WO2012026766 | A2 | 3/2012 |
| WO | WO2012101453 | A1 | 8/2012 |
| WO | WO2012139137 | A2 | 10/2012 |
| WO | WO2013013273-AI | | 1/2013 |
| WO | WO2013173676 | A1 | 11/2013 |
| WO | WO2014020350 | A1 | 2/2014 |
| WO | WO2014020351 | A1 | 2/2014 |
| WO | WO2014138727 | A1 | 9/2014 |
| WO | WO2014173859 | A2 | 10/2014 |
| WO | WO2015048245 | A1 | 4/2015 |
| WO | WO2015117956 | A1 | 8/2015 |
| WO | WO2016005369 | A1 | 1/2016 |
| WO | WO2016138132 | A1 | 9/2016 |

OTHER PUBLICATIONS

US 8,901,085, 12/2/2014, The University of Queensland (withdrawn).

Yau, Mei-Kwan, Toward Drugs for Protease-Activated Receptor 2 (PAR2), Journal of Medicinal Chemistry, vol. 56, No. 19, Jul. 30, 2013, pp. 7477-7497.

Cottrell, et al., Protease-activated receptor 2: activation, signalling and function, Biochemical Society Transactions, Dec. 1, 2003, pp. 1191-1197.

Nhu, et al. Protease-activated receptor 2 activation promotes an anti-inflammatory and alternatively activated phenotype in LPS-stimulated murine macrophages, Innate immunity, Jan. 14, 2011, pp. 1-11.

Nathalie Vergnolle, Proteinase-activated receptors and nociceptive pathways, Drug Development Research, Aug. 1, 2003, vol. 59, pp. 382-385.

Fiorucci, et al., PAR1 antagonism protects against experimental liver fibrosis. Role of proteinase receptors in stellate cell activation, Hepatology (Baltimore, Md.), Feb. 9, 2004, pp. 365-375.

Myatt, et al., Trypsin stimulates the phosphorylation of p42,44 mitogen-activated protein kinases via the proteinase-activated receptor-2 and protein kinase C epsilon in human cultured prostate stromal cells, The Prostate, May 30, 2005, vol. 64, pp. 175-185.

Devlin, et al., Hepta and octapeptide agonists of protease-activated receptor 2, Journal of Peptide Science, Dec. 6, 2007, vol. 13, pp. 856-861.

Maryanoff, et al., Protease-activated receptor-2 (PAR-2): structure-function study of receptor activation by diverse peptides related to tethered-ligand epitopes, Archives of Biochemistry and Biophysics, May 22, 2001, vol. 386, No. 2, pp. 195-204.

Cocks, et al., Protease-activated receptor-2 (PAR2) in the airways, Pulmonary Pharmacology & Therapeutics, Jul. 12, 2001, vol. 14, pp. 183-191.

Barry, et al., A refined agonist pharmacophore for protease activated receptor 2, Bioorganic & Medicinal Chemistry Letters, Aug. 16, 2007, pp. 5552-5557.

Fyfe, et al., PAR-2 activation in intestinal epithelial cells potentiates interleukin-1beta-induced chemokine secretion via MAP kinase signaling pathways, Cytokine, Aug. 22, 2005, vol. 31, pp. 358-367.

Reed, et al., The role of protease activation of inflammation in allergic respiratory diseases, The Journal of Allergy and Clinical Immunology, Nov. 2004, pp. 997-1008.

Demaude, et al., Acute stress increases colonic paracellular permeability in mice through a mast cell-independent mechanism: involvement of pancreatic trypsin, Life Sciences, vol. 84, Apr. 5, 2009, pp. 847-852.

Adams, et al., Structure, function and pathophysiology of protease activated receptors, Pharmacology & Therapeutics, vol. 130, Jan. 26, 2011, pp. 248-282.

Van De Walle, et al., Influence of deoxynivalenol on NF-kappaB activation and IL-8 secretion in human intestinal Caco-2 cells, Toxicology letters, vol. 177, Feb. 8, 2008, pp. 205-204.

Blakeney, et al., Nonpeptidic ligands for peptide-activated G protein-coupled receptors, Chemical Reviews, vol. 107, Jul. 11, 2007, pp. 2960-3041.

Barry, et al., Novel agonists and antagonists for human protease activated receptor 2, Journal of Medicinal Chemistry, vol. 53, Oct. 28, 2010, pp. 7428-7440.

Seitzbe, et al., Discovery of potent and selective small-molecule PAR-2 agonists, Journal of Medicinal Chemistry, vol. 51, Aug. 23, 2008, pp. 5490-5493.

Vergnolle, et al., Proteinase-activated receptor-2 and hyperalgesia: A novel pain pathway, Nature Medicine, vol. 7, Jul. 2, 2001, 821-826.

Al-Ani, et al., Proteinase activated receptor 2: Role of extracellular loop 2 for ligand-mediated activation, British journal of pharmacology, vol. 128, Jan. 24, 199, pp. 1105-1113.

Kawabata, et al., Dual modulation by thrombin of the motility of rat oesophageal muscularis mucosae via two distinct protease-activated receptors (PARs): a novel role for PAR-4 as opposed to PAR-1, British Journal of Pharmacology, vol. 131, Nov. 6, 2000, pp. 578-584.

Cicala, C., Protease activated receptor 2 and the cardiovascular system, vol. 135, Jan. 11, 2002, pp. 14-20.

De Campo, et al., Stimulation of protease-activated receptor-2 inhibits airway eosinophilia, hyperresponsiveness and bronchoconstriction in a murine model of allergic inflammation, British journal of pharmacology, vol. 144, Apr. 8, 2005, pp. 1100-1108.

Kanke, et al., Binding of a highly potent protease-activated receptor-2 (PAR2) activating peptide, [3H]2-furoyl-LIGRL-NH2, to human PAR2, vol. 145, May 17, 2005, pp. 255-263.

(56) References Cited

OTHER PUBLICATIONS

Kawabata, et al., Suppression of pancreatitis-related allodynia/hyperalgesia by proteinase-activated receptor-2 in mice, British Journal of Pharmacology, vol. 148, May 1, 2006, pp. 54-60.
Ramachandran, et al., Proteinases and signalling: pathophysiological and therapeutic implications via PARs and more, British Journal of Pharmacology, vol. 153, 2008, pp. S263-S282.
Turner, et al., Dietary wheat reduction decreases the level of urinary deoxynivalenol in UK adults, Journal of Exposure Science & Environmental Epidemiology, vol. 18, 2008, pp. 392-399.
Wilson, et al., The membrane-anchored serine protease, TMPRSS2, activates PAR-2 in prostate cancer cells, The Biochemical Journal, vol. 388, Jun. 6, 2005, pp. 967-972.
Scott, et al., The proteinase-activated receptor-2 mediates phagocytosis in a Rho-dependent manner in human keratinocytes, The Journal of investigative dermatology, vol. 121, 2003, pp. 529-541.
Namkung, et al., Protease-activated receptor 2 exerts local protection and mediates some systemic complications in acute pancreatitis, vol. 126, Jun. 1, 2004, pp. 1844-1859.
Darmoul, et al., Initiation of human colon cancer cell proliferation by trypsin acting at protease-activated receptor-2, British journal of cancer , vol. 85, Sep. 4, 2001, pp. 772-779.
Hansen, et al., A major role for proteolytic activity and proteinase-activated receptor-2 in the pathogenesis of infectious colitis, Proceedings of the National Academy of Sciences of the United States of America, vol. 102, 2005, pp. 8363-8368.
Sevigny, et al., Interdicting protease-activated receptor-2-driven inflammation with cell-penetrating pepducins, Proceedings of the National Academy of Sciences of the United States of America, vol. 108, May 17, 2011, pp. 8491-8496.
Fiorucci, et al., Proteinase-activated receptor 2 is an anti-inflammatory signal for colonic lamina propria lymphocytes in a mouse model of colitis, Proceedings of the National Academy of Sciences of the United States of America, vol. 98, Nov. 20, 2001, pp. 13963-13941.
Emilsson, K., Ligand Cross-reactivity within the Protease-activated Receptor Family, Journal of Biological Chemistry, vol. 271, Jul. 12, 1996, pp. 16466-16471.
Miyata, S., Trypsin Stimulates Integrin alpha 5beta 1-dependent Adhesion to Fibronectin and Proliferation of Human Gastric Carcinoma Cells through Activation of Proteinase-activated Receptor-2, Journal of Biological Chemistry, vol. 275, No. 7, Feb. 18, 2000, pp. 4592-4598.
Darmoul; et al., Protease-activated receptor 2 in colon cancer: trypsin-induced MAPK phosphorylation and cell proliferation are mediated by epidermal growth factor receptor transactivation, British journal of cancer, vol. 279, No. 20, Mar. 9, 2004, pp. 20927-20934.
Harmar, et al., IUPHAR-DB: The IUPHAR database of G protein-coupled receptors and ion channels, Nucleic acids research, vol. 37, 2009, pp. D680-D685.
Maeda, et al., Proinflammatory Role of Trypsin and Protease-activated Receptor-2 in a Rat Model of Acute Pancreatitis, Pancreas, vol. 31, No. 1, 2005, pp. 54-62.
Buddenkotte, et al., Agonists of proteinase-activated receptor-2 stimulate upregulation of intercellular cell adhesion molecule-1 in primary human keratinocytes via activation of NF-kappa B, The Journal of investigative dermatology, vol. 124, No. 1, Jan. 18, 2005, pp. 38-45.
Ramelli, et al., Protease-activated receptor 2 signalling promotes dendritic cell antigen transport and T-cell activation in vivo, Immunology, vol. 129, No. 1, Jun. 22, 2009, pp. 1-8.
Bueno, et al., Protease-activated receptor 2 and gut permeability: a review, Neurogastroenterology and motility : the official journal of the European Gastrointestinal Motility Society, Vo. 20, No. 6, May 16, 2008, pp. 580-587.
Uehara, et al., Gingipains from Porphyromonas gingivalis synergistically induce the production of proinflammatory cytokines through protease-activated receptors with Toll-like receptor and NOD1/2 ligands in human monocytic cells, Cellular microbiology, vol. 10, No. 5, Jan. 7, 2008, 1181-1189.
Kanke, et al., Novel antagonists for proteinase-activated receptor 2: inhibition of cellular and vascular responses in vitro and in vivo, British journal of pharmacology, vol. 158, No. 1, Sep. 1, 2009, pp. 361-371.
Soh, et al., Signal transduction by protease-activated receptors, British journal of pharmacology, Vo. 160, No. 2, Apr. 28, 2010, pp. 191-203.
Cenac, et al., PAR2 activation alters colonic paracellular permeability in mice via IFN-gamma-dependent and -independent pathways, The Journal of physiology, vol. 558, Pt. 3, Jun. 11, 2004, pp. 913-925.
Kawabata, et al., Potent and metabolically stable agonists for protease-activated receptor-2: evaluation of activity in multiple assay systems in vitro and in vivo,The Journal of pharmacology and experimental therapeutics, vol. 309, No. 3, Feb. 19, 2004, pp. 1098-1107.
McGuire, et al., 2-furoyl-LIGRLO-amide: a potent and selective proteinase-activated receptor 2 agonist, The Journal of pharmacology and experimental therapeutics, vol. 309, No. 3, Feb. 19, 2004, pp. 1124-1131.
Masamune, et al., Protease-activated receptor-2-mediated proliferation and collagen production of rat pancreatic stellate cells, The Journal of pharmacology and experimental therapeutics, vol. 312, No. 2, 2005, pp. 651-658.
Kelso, et al., Therapeutic promise of proteinase-activated receptor-2 antagonism in joint inflammation, The Journal of pharmacology and experimental therapeutic, vol. 316, No. 3, 2006, pp. 1017-1024.
Abey, et al., Protease-activated receptor-2 peptides activate neurokinin-1 receptors in the mouse isolated trachea, The Journal of pharmacology and experimental therapeutics, vol. 317, No. 2, 2006, pp. 598-605.
Gardell, et al., Identification and characterization of novel small-molecule protease-activated receptor 2 agonists, The Journal of pharmacology and experimental therapeutics, vol. 327, No. 3, Sep. 3, 2008, pp. 799-808.
Ishikawa, et al., Tetracyclines modulate protease-activated receptor 2-mediated proinflammatory reactions in epidermal keratinocytes, Antimicrobial agents and chemotherapy, vol. 53, No. 5, May 2009, pp. 1760-1765.
Hyun et al., Protease-activated receptor-2 activation: a major actor in intestinal inflammation, Gut, vol. 57, No. 9, 2008, pp. 1222-1229.
Lee, et al., Activation of proteinase-activated receptor-2 in mesothelial cells induces pleural inflammation, American journal of physiology. Lung cellular and molecular physiology, vol. 288, No. 4, Dec. 10, 2004, pp. L734-L740.
Vesey, et al., Proinflammatory and proliferative responses of human proximal tubule cells to PAR-2 activation. American journal of physiology, Renal physiology, vol. 293, No. 5, Aug. 15, 2007, pp. F1441-F1449.
Ossovskaya, et al., Protease-activated receptors: contribution to physiology and disease, Physiological reviews, vol. 84, No. 2, Mar. 26, 2004, pp. 579-621.
Versteeg, et al., Protease-activated receptor (PAR) 2, but not PAR1, signaling promotes the development of mammary adenocarcinoma in polyoma middle T mice, Cancer research, vol. 68, No. 17, Sep. 1, 2008, pp. 7219-7227.
Uusitalo-Jar; Tor, et al., Role of protease activated receptor 1 and 2 signaling in hypoxia-induced angiogenesis, Arteriosclerosis, thrombosis, and vascular biology, vol. 27, No. 6, Mar. 15, 2007, pp. 1456-1462.
Kawabata, et al., The protease-activated receptor-2 agonist induces gastric mucus secretion and mucosal cytoprotection, The Journal of clinical investigation, vol. 107, No. 11, Jun. 6, 2001, pp. 1443-1450.
Rohani, et al., Modulation of expression of innate immunity markers CXCL5/ENA-78 and CCL20/MIP3alpha by protease-activated receptors (PARs) in human gingival epithelial cells, Innate immunity, vol. 16, No. 2, Jun. 30, 2009, pp. 104-114.
Versteeg, et al., Inhibition of tissue factor signaling suppresses tumor growth, Blood, vol. 111, No. 1, 2008, pp. 190-199.

(56) References Cited

OTHER PUBLICATIONS

Wang, et al, Beta-arrestin inhibits CAMKKbeta-dependent AMPK activation downstream of protease-activated-receptor-2, BMC biochemistry, vol. 11, Sep. 21, 2010, pp. 1-15.
Steinhoff, et al., Proteinase-activated receptors: transducers of proteinase-mediated signaling in inflammation and immune response, Endocrine reviews, vol. 26, No. 1, Feb. 3, 2005, pp. 1-43.
Takizawa, et al., Abrogation of Bronchial Eosinophilic Inflammation and Attenuated Eotaxin Content in Protease-Activated Receptor 2-Deficient Mice, Journal of Pharmacological Sciences, vol. 98, No. 1, Jan. 1, 2005, pp. 99-102.
Holzhausen, et al., Role of protease-activated receptor-2 in inflammation, and its possible implications as a putative mediator of periodontitis, Memórias do Instituto Oswaldo Cruz, vol. 100, Jan. 1, 2005, pp. 177-180.
Barry et al., Agonists and Antagonists of Protease Activated Receptors (PARs) Current Medicinal Chemistry, vol. 13, No. 3, Feb. 1, 2006, pp. 243-265.
Shichijo, et al., PAR-2 deficient CD4+ T cells exhibit downregulation of IL-4 and upregulation of IFN-gamma after antigen challenge in mice, Allergology international : official journal of the Japanese Society of Allergology, vol. 55 No. 3, Oct. 31, 2006, pp. 271-278.
Dabek, et al., Luminal cathepsin g and protease-activated receptor 4: a duet involved in alterations of the colonic epithelial barrier in ulcerative colitis, The American journal of pathology, vol. 175, No. 1, Jun. 15, 2009, pp. 207-214.
Matsuwaki; et al., Recognition of fungal protease activities induces cellular activation and eosinophil-derived neurotoxin release in human eosinophils, Journal of immunology (Baltimore, Md. : 1950), vol. 183, No. 10, Oct. 28, 2009, pp. 6708-6716.
Jacob et al., Mast cell tryptase controls paracellular permeability of the intestine. Role of protease-activated receptor 2 and beta-arrestins, The Journal of biological chemistry, vol. 280, No. 36, Jul. 18, 2005, pp. 31936-31948.
Sawamukai, et al., Mast cell-derived tryptase inhibits apoptosis of human rheumatoid synovial fibroblasts via rho-mediated signaling, Arthritis and rheumatism , vol. 62, No. 4, Apr. 14, 2010, pp. 952-959.
Frungieri, et al., Proliferative action of mast-cell tryptase is mediated by PAR2, COX2, prostaglandins, and PPARgamma : Possible relevance to human fibrotic disorders, Proceedings of the National Academy of Sciences of the United States of America, vol. 99, No. 23, Oct. 23, 2002, pp. 15072-15077.
Chichlowski, et al., Role of mast cells in inflammatory bowel disease and inflammation-associated colorectal neoplasia in IL-10-deficient mice, PloS one, vol. 5, No. 8, Aug. 17, 2010, p. e12220.
Uehara, et al., Antibodies to proteinase 3 prime human monocytic cells via protease-activated receptor-2 and NF-kappaB for Toll-like receptor- and NOD-dependent activation, Molecular immunology, vol. 44, No. 14, Apr. 23, 2007, pp. 3552-3562.
Johansson, et al., Human peripheral blood monocytes express protease receptor-2 and respond to receptor activation by production of IL-6, IL-8, and IL-1{beta}, Journal of leukocyte biology, vol. 78, No. 4, Jul. 6, 2005, pp. 967-975.
Shpacovitch, et al., Agonists of proteinase-activated receptor-2 modulate human neutrophil cytokine secretion, expression of cell adhesion molecules, and migration within 3-D collagen lattices, Journal of leukocyte biology, vol. 76, No. 2, May 20, 2004, pp. 388-398.
Wang, et al., Induction of lactoferrin and IL-8 release from human neutrophils by tryptic enzymes via proteinase activated receptor-2, Cell biology international, vol. 30, No. 9, May 10, 2006, pp. 688-697.
St-Onge, et al., Proteinase-activated receptor-2 up-regulation by Fcgamma-receptor activation in human neutrophils, The FASEB journal : official publication of the Federation of American Societies for Experimental Biolog, vol. 24, No. 6, Feb. 12, 2010, pp. 2116-2125.
Kaufmann, et al., Proteinase-activated receptor 2-mediated calcium signaling in hepatocellular carcinoma cells, Journal of cancer research and clinical oncology, vol. 137 No. 6, 2011, pp. 965-973.
Perez, et al. Discovery of novel protease activated receptors 1 antagonists with potent antithrombotic activity in vivo, Journal of medicinal chemistry, vol. 52 No. 19, Oct. 1, 2009, pp. 5826-5836.
Chackalamanni, et al, Discovery of a novel, orally active himbacine-based thrombin receptor antagonist (SCH 530348) with potent antiplatelet activity, Journal of medicinal chemistry, vol. 51, No. 11, May 1, 2008, pp. 3061-3064.
Peters, et al., Protease-activated receptors and prostaglandins in inflammatory lung disease, British journal of pharmacology, vol. 158, No. 4, Oct. 22, 2009, pp. 1017-1033.
Serebruany, et al., The in-vitro effects of E5555, a protease-activated receptor (PAR)-1 antagonist, on platelet biomarkers in healthy volunteers and patients with coronary artery disease. Thrombosis and haemostasis, vol. 102, No. 1, 2009, 111-119.
Cenac et al., Induction of Intestinal Inflammation in Mouse by Activation of Proteinase-Activated Receptor-2, The American Journal of Pathology, vol. 161, No. 5, Nov. 1, 2002, pp. 1903-1915.
Androuts et al., Design, synthesis and biological evaluation of non-peptide PAR1 thrombin receptor antagonists based on small bifunctional templates: arginine and phenylalanine side chain groups are keys for receptor activity, Amino acids, vol. 38, No. 4, May, 31, 2009, pp. 985-990.
Nishimura, et al., The proteinase/proteinase-activated receptor-2/transient receptor potential vanilloid-1 cascade impacts pancreatic pain in mice, Life sciences, vol. 87, No. 19-22, Oct. 13, 2010, pp. 643-650.
Wang, et al., Activation of protease activated receptor 2 by exogenous agonist exacerbates early radiation injury in rat intestine. International journal of radiation oncology, biology, physics, vol. 77, No. 4, Jul. 8, 2010, pp. 1206-1212.
Lam, et al., Serine proteases and protease-activated receptor 2-dependent allodynia: a novel cancer pain pathway, Pain, vol. 149, No. 2, Mar. 1, 2010, pp. 263-272.
Pagano, et al., Involvement of proteinase-activated receptors 1 and 2 in spreading and phagocytosis by murine adherent peritoneal cells: modulation by the C-terminal of S100A9 protein, European journal of pharmacology, vol. 628, No. 1-3, Nov. 24, 2009, pp. 240-246.
McIntosh, et al. Proteinase-activated receptor-2 mediated inhibition of TNFalpha-stimulated JNK activation—A novel paradigm for G(q/11) linked GPCRs, Cellular signaling, vol. 22, No. 2, Sep. 23, 2010, pp. 265-273.
Zhu, et al., Induction of leukotriene B(4) and prostaglandin E(2) release from keratinocytes by protease-activated receptor-2-activating peptide in ICR mice, International immunopharmacology, vol. 9, No. 11, Aug. 25, 2009, pp. 1332-1336.
Lohman, et al., A regulatory role for protease-activated receptor-2 in motivational learning in rats, Neurobiology of learning and memory, vol. 92, No. 3, May 4, 2009, pp. 301-309.
Matsumoto, et al. Mechanisms underlying enhanced vasorelaxant response to protease-activated receptor 2-activating peptide in type 2 diabetic Goto-Kakizaki rat mesenteric artery, Peptides, vol. 30, No. 9, Jun. 21, 2009, pp. 1729-1734.
Jian, et al., Protease-activated receptors in neuropathic pain: an important mediator between neuron and glia, Journal of Medical Colleges of PLA, vol. 24, No. 4, Aug. 1, 2009, pp. 244-249.
Tanaka, et al, PAR2 triggers IL-8 release via MEK/ERK and PI3-kinase/Akt pathways in GI epithelial cells. Biochemical and biophysical research communications, vol. 377, No. 2, Oct. 12, 2008, pp. 622-626.
Lohman, Protease-Activated Receptor-2 Regulates Trypsin Expression in The Brain and Protects Against Seizures and Epileptogenesis, Neurobiology of Disease, vol. 30, No. 1, Jan. 5, 2008, pp. 84-93.
Miike, et al. Trypsin induces activation and inflammatory mediator release from human eosinophils through protease-activated receptor-2, Journal of immunology (Baltimore, Md. : 1950), vol. 167, No. 11, Nov. 20, 2001, pp. 6615-6622.

(56) References Cited

OTHER PUBLICATIONS

Kim, et al. Expression of protease-activated receptor 2 in ulcerative colitis, Inflammatory bowel diseases, vol. 9, No. 4, Aug. 6, 2003, pp. 224-229.
Akers, et al, Mast cell tryptase stimulates human lung fibroblast proliferation via protease-activated receptor-2, American journal of physiology. Lung cellular and molecular physiology, vol. 78, No. 1, Mar. 3, 2000, pp. L193-L201.
Feld, et al., Agonists of proteinase-activated receptor-2 enhance IFN-gamma-inducible effects on human monocytes: role in influenza A infection, Journal of immunology (Baltimore, Md. : 1950), vol. 180, No. 10, May, 5, 2008, pp. 6903-6910.
Howells, et al., Proteinase-activated receptor-2: expression by human neutrophils., Journal of cell science, vol. 110 ( Pt 7), Aug. 21, 1997, pp. 881-887.
Moffatt, et al., Protease-activated receptor-2 activating peptide SLIGRL inhibits bacterial lipopolysaccharide-induced recruitment of polymorphonuclear leukocytes into the airways of mice, American journal of respiratory cell and molecular biology, vol. 26, No. 6, May 29, 2002, pp. 680-684.
Vergnolle, et al., Proteinase-activated receptor 2 (PAR2)-activating peptides: identification of a receptor distinct from PAR2 that regulates intestinal transport, Proceedings of the National Academy of Sciences of the United States of America, vol. 95, No. 13, Aug. 6, 1998, pp. 7766-7771.
Hollenberg, Getting the message across: pathophysiology and signaling via receptors for polypeptide hormones and proteinases, Clinical and investigative medicine. Médecine clinique et experimentale, vol. 33, No. 2, Apr. 1, 2010, p. E133-E144.
Seiler, et al., Peptide-derived protease-activated receptor-1 (PAR-1) antagonists, Current medicinal chemistry. Cardiovascular and hematological agents , vol. 1, No. 1, 2003, pp. 1-11.
Shpacovitch, et al., Role of proteinase-activated receptor-2 in anti-bacterial and immunomodulatory effects of interferon-γ on human neutrophils and monocytes, Immunology, vol. 133, No. 3, Apr. 19, 2011, pp. 329-339.
Ramachandran, et al., Neutrophil Elastase Acts as a Biased Agonist for Proteinase-activated Receptor-2 (PAR2), The Journal of biological chemistry, vols. 286, No. 28, May 16, 2011, pp. 1-24.
Chen, et al. ,Anti-Inflammatory mechanisms of the proteinase-activated receptor 2-inhibiting peptide in human synovial cells, Journal of biomedical science, vol. 18, 2011, pp. 1-9.
Botham, et al., Palmitoylation of human proteinase-activated receptor-2 differentially regulates receptor-triggered ERK1/2 activation, calcium signalling and endocytosis, The Biochemical journal, vol. 438, No. 2, Jun. 2, 2011, pp. 359-367.
Notice of Retraction, Kumar, et al., Potential link between alpha 1 anti-trypsin and PAR-2 in the prevention of beta cell dysfunction, Molecular and cellular endocrinology, dated Sep. 8, 2011.
Mueller, et al., Activity of Protease-Activated Receptors in the Human Submucous Plexus, Gastroenterology, vol. 141, Aug. 27, 2011, pp. 2088-2097.
Kim, et al, Membrane-bound proteinase 3 and PAR2 mediate phagocytosis of non-opsonized bacteria in human neutrophils, Molecular immunology, vol. 48, No. 15-16, Jun. 22, 2011, pp. 1966-1974.
Velin, et al., PAR2 Promotes Vaccine-Induced Protection Against Helicobacter Infection in Mice, Gastroenterology, vol. 141, No. 4, Jun. 23, 2011, pp. 1273-1282.e1.
Chen, et al., Proteinase-activated receptor 2 sensitizes transient receptor potential vanilloid 1, transient receptor potential vanilloid 4, and transient receptor potential ankyrin 1 in paclitaxel-induced neuropathic pain, Neuroscience, vol. 193, Jul. 14, 2011, pp. 440-451.
Hoffman, et al., Lanthanide labeling of a potent protease activated receptor-2 agonist for time-resolved fluorescence analysis, Bioconjugate Chemistry, vol. 23, Sep. 20, 2012, pp. 1-32.
Hovnanian, Netherton syndrome: skin inflammation and allergy by loss of protease inhibition., Cell and tissue research, vol. 351, No. 2, Jan. 24, 2013, pp. 289-300.
Liu, et al, PAR2-mediated epigenetic upregulation of α-synuclein contributes to the pathogenesis of Parkinson's disease, Brain research, vol. 1565, Apr. 1, 2014, pp. 82-89.
McAleer, et al., The multifunctional role of filaggrin in allergic skin disease, The Journal of allergy and clinical immunology, vol. 131, No. 2, Dec. 12, 2012, pp. 280-291.
Grace, et al., The Tyrosine Kinase Inhibitor Bafetinib Inhibits PAR2-induced Activation of TRPV4 In Vitro and Pain In Vivo, British journal of pharmacology, Apr. 30, 2014, pp. 3881-3894.
Xu, et al., Formation of Unsaturated Vicinal Zr+/P Frustrated Lewis Pairs by the Unique 1,1-Carbozirconation Reactions, Journal of the American Chemical Society, vol. 136, Aug. 4, 2014, pp. 12431-12443.
Geremia, et al., Innate and adaptive immunity in inflammatory bowel disease, Autoimmunity reviews, vol. 13, No. 1, 2014, pp. 3-10.
Lennernäs, et al., Oral biopharmaceutics tools—time for a new initiative—an introduction to the IMI project OrBiTo, European journal of pharmaceutical sciences : official journal of the European Federation for Pharmaceutical Sciences, vol. 57, 2014, pp. 292-299.
Esaki, et al., Use of capsule endoscopy in patients with Crohn's disease in Japan: a multicenter survey, Journal of gastroenterology and hepatology, vol. 29, No. 1, Aug. 29, 2014, pp. 96-101.
Kerlin, et al., Differential transit of liquids and solid residue through the human ileum, The American journal of physiology, vol. 245, No. 1, Jul. 1, 1983, pp. G38-G43.
Cummings, et al., Measurement of the mean transit time of dietary residue through the human gut, Gut, vol. 17, No. 3, Mar. 1, 1976, pp. 210-218.
Jackson, et al., Depletion of protease activated receptor (PAR)-2 but not PAR-1 is protective in osteoarthritis through extra-cartilaginous mechanisms, Arthritis & rheumatology (Hoboken, N.J.), vol. 66, Sep. 8, 2014, 3337-3348.
Abdel-Magid, Inhibitors of the PAR-2 Signaling Pathway May Treat Pain and Inflammation, ACS Medicinal Chemistry Letters, vol. 6, Apr. 5, 2015, pp. 487-488.
Tillu, et al, Protease-activated receptor 2 activation is sufficient to induce the transition to a chronic pain state, Pain, vol. 156, No. 5, Mar. 4, 2015, pp. 859-867.
Yau, Potent Small Agonists of Protease Activated Receptor 2, ACS Medicinal Chemistry Letters, vol. 7, Dec. 3, 2015, pp. 105-110.
Maher, et al., Rat Epidermal Keratinocytes as an Organotypic Model for Examining the Role of Cx43 and Cx26 in Skin Differentiation, Cell Communication & Adhesion, vol. 12, Nos. 5-6, Jan. 9, 2005, pp. 219-230.
Yau, et al., Protease activated receptor 2 (PAR2) modulators: a patent review (2010-2015), Expert Opinion on Therapeutic Patents, Mar. 3, 2016, pp. 1-13.
Sakai, et al., Combined Benefits of a PAR2 Inhibitor and Stratum Corneum Acidification for Murine Atopic Dermatitis, The Journal of investigative dermatology, vol. 136, No. 2, Nov. 20, 2015, pp. 538-541.
Kenakin, Theoretical Aspects of GPCR-Ligand Complex Pharmacology, Chemical Reviews, Sep. 2, 2016, pp. A-Q.
Venkatakrishnan, et al., Diverse activation pathways in class A GPCRs converge near the G-protein-coupling region., Nature, Aug. 15, 2016, pp. 1-8.
CAS Registry No. 1340897-31-5, STN Entry Date Nov. 4, 2011; Methanone, (6-chloroimidazo[1,2-b] pyridazin-2-yl)[4-(1-methylethyl)-1-piperazinyl], Chemical Library, ChemDiv, Inc., 2 pages.
CAS Registry No. 1340835-64-4, STN Entry Date Nov. 4, 2011; Methanone, (6-chloroimidazo[1,2-b]pyridazin-2-yl)[4-(2-methylpropyl)-1-piperazinyl], Chemical Library, ChemDiv, Inc., 2 pages.
CAS Registry No. 1340817-92-6, STN Entry Date Nov. 4, 2011; Methanone, (6-chloroimidazo[1,2-b]pyridazin-2-yl)[4-(1-methyl-4-piperidinyl)-1-piperazinyl], Chemical Library, ChemDiv, Inc., 2 pages.
CAS Registry No. 1340782-96-8, STN Entry Date Nov. 4, 2011; Methanone, (4-butyl-1-piperazinyl)(6-chloroimidazo[1,2-b]pyridazin-2-yl), Chemical Library, ChemDiv, Inc., 2 pages.

(56) References Cited

OTHER PUBLICATIONS

CAS Registry No. 1340700-31-3, STN Entry Date Nov. 4, 2011; Methanone, (6-chloroimidazo[1,2-b]pyridazin-2-yl)[4-(4-methylphenyl)-1-piperazinyl], Chemical Library, ChemDiv, Inc., 2 pages.
CAS Registry No. 300550-61-2, STN Entry Date Oct. 31, 2000; Methanone, (6-chloroimidazo[1,2-b]pyridazin-2-yl)[(3R,5S)-4-[2-[(1R)-1-hydroxyethyl]-4-pyrimidinyl]-3,5-dimethyl-1-piperazinyl], 9 pages.

* cited by examiner

IMIDAZOPYRIDAZINES USEFUL AS INHIBITORS OF THE PAR-2 SIGNALING PATHWAY

RELATED APPLICATIONS

The present application is a continuation of PCT Application No. PCT/US2014/057390 which claims priority to U.S. Provisional Application No. 61/882,173 filed on Sep. 25, 2013 and 61/901,617 filed Nov. 8, 2013. The entire contents of these applications are incorporated herein by reference.

BACKGROUND OF THE INVENTION

Protease-Activated Receptors (PARs) are a family of G-protein coupled receptors (GPCRs) comprising PAR-1, 2, 3, and 4. PARs are typically activated when enzymes (such as thrombin or trypsin) proteolytically cleave a portion of their N-terminal region. This cleavage exposes a region of the N-terminal extracellular domain (called the "tethered ligand") which is believed to bind to residues contained within the second extracellular loop of the PAR receptors, resulting in the stabilization of an active conformation. Short synthetic peptides mimicking the tethered ligand sequence have been successfully used to activate all of the PAR receptors, except PAR-3.

PAR-2 is activated by several host and pathogen-derived serine proteases, including trypsin, mast cell tryptase, tissue kallikreins, and members of the coagulation cascade TF-FVIIa and FVa-FXa. Synthetic ligands such as SLIGKV-$NH_2$ can selectively activate human PAR-2, although modified PAR-2 synthetic agonists such as 2-fluoryl-LIGRLO-NH2 have been reported to be more potent activators of this receptor.

PAR-2 has been shown to be an important receptor in mediating inflammation, pain and itch. For example, PAR-2 activation results in inflammatory cytokine and chemokine release from keratinocytes, endothelial cells and from human epithelial cell lines such as A549. Moreover, the administration of PAR-2 activating proteases and synthetic agonists in vivo induce inflammatory responses. In particular, several studies have shown that intraplantar administration of PAR-2 agonists in rodents results in an edema response that is dependent in part on neuronal PAR-2 activation.

Similar studies have implicated PAR-2 as a mediator of neurogenic inflammation, nociception and in transmission of pain. This is mediated in part by the activation of PAR-2 dependent signaling pathways in dorsal root ganglia, the release of neuropeptides from C-fibers in peripheral tissues and spinal cord and the potentiation of transient receptor potential vaniloid 1 and 4 receptors in sensory neurons.

Several studies have demonstrated a role for PAR-2 activation in pruritus. Both direct activation of PAR-2 on nerve endings and indirect effects of PAR-2 on resident cells including keratinocytes are thought to contribute to itch.

Further, both in vitro and in vivo studies have demonstrated a role for PAR-2 activation in tissue remodeling. First, activation of PAR-2 can promote fibroblast and myofibroblast proliferation, and the secretion of growth factors such as CTGF and extracellular matrix components including collagen. In addition, PAR-2 activation was shown to be implicated in cellular migration and activation of this pathway has recently been shown to promote tumor growth and metastasis.

Numerous studies relying on the use of PAR-2 deficient mice, blocking PAR-2 antibodies or PAR-2 antagonists such as GB88 revealed an important role for PAR-2 activation in the pathophysiology of a variety of diseases including asthma, chronic pain, rheumatoid arthritis, periodontitis, inflammatory bowel diseases, irritable bowel syndrome, skin diseases, cancer, fibrotic diseases and neurological disease (reviewed in Yau et al, Journal of Medicinal Chemistry, July 2013). Other studies have shown that diet-induced obesity, adipose inflammation, and metabolic dysfunction correlating with PAR-2 expression are attenuated by PAR-2 antagonism.

For all of these reasons, there is a need for the development of potent and selective inhibitors of the PAR-2 signaling pathway for the treatment of inflammation and nociception (pain) caused by inflammation, cancer, or injury.

SUMMARY OF THE INVENTION

The present invention relates to compounds useful as inhibitors of the PAR-2 signaling pathway. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications.

In one aspect, the invention is directed to compounds of formula (I):

I

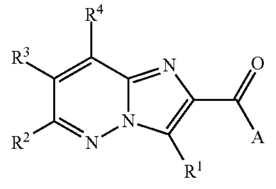

or pharmaceutically acceptable salts thereof, wherein

A is

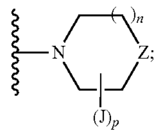

wherein n is 1 or 2;

Z is —O—, —$CH_2$—, or —NX—;

X is $R^5$, —C(O)$R^5$, or —$S(O)_2R^5$;

J is CN, oxo, a $C_{1-6}$aliphatic wherein up to three carbon units of said $C_{1-6}$aliphatic can each be optionally and independently replaced with —O—, —NR—, —S— or —C(O)—; or a 3-7 membered saturated, partially unsaturated, or aromatic monocyclic ring having 0-4 heteroatoms selected from oxygen, nitrogen, or sulfur; wherein said J is optionally and independently substituted with 1-3 occurrences of halo or $C_{1-4}$alkyl, wherein up to one methylene unit of said $C_{1-4}$alkyl is optionally and independently replaced with —O—, —NR—, or —S—;

or two J groups on the same or different atom(s), together with the atom(s) to which they are bound, form a 3-6 membered saturated monocyclic ring having 0-2 heteroatoms selected from oxygen, nitrogen, or sulfur; wherein said 3-6 membered ring is optionally substituted with one occurrence of oxo;

p is 0-4;

$R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(O)—; wherein V is optionally and independently substituted with 1-3 occurrences of halo or $C_{1-6}$alkyl, wherein up to three methylene units of said $C_{1-6}$alkyl are optionally and independently replaced with —O—, —NR—, —S—, or C(O);

Y is H, CN, a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein Y is optionally substituted with 1-4 occurrences of $J^Y$;

$J^Y$ is oxo, halo, CN, —OP(═O)(OR)$_2$, phenyl, or $C_{1-6}$aliphatic, wherein up to three carbon units of said $C_{1-6}$aliphatic can each be optionally and independently replaced with O, NR, S, or C(O), wherein said $C_{1-6}$aliphatic optionally and independently substituted with 1-3 occurrences of halo or —OR; and $R^1$ is H or F;

$R^2$ is —$(V^2)_a$—$Y^2$; wherein $V^2$ is a $C_{1-4}$aliphatic;

$Y^2$ is halo, $C_{1-6}$aliphatic; or a 3-7 membered saturated, partially unsaturated, or aromatic monocyclic ring having 0-4 heteroatoms selected from oxygen, nitrogen, or sulfur; wherein $Y^2$ is optionally substituted with 1-4 occurrences of $J^Y$; and a and b are each independently 0 or 1;

$R^3$ is H or F; and $R^4$ is H, halo, CN, $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein said $R^4$ is optionally and independently substituted with 1-3 occurrences of oxo, halo, or $C_{1-6}$aliphatic wherein up to three carbon units of said $C_{1-6}$aliphatic can each be optionally and independently replaced with O, NR, S or C(O); and each R independently is H or $C_{1-4}$alkyl.

In another aspect, the invention is directed to a compound of formula (I), wherein:

A is

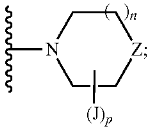

wherein n is 1 or 2;

Z is —O—, —$CH_2$—, or —NX—;

X is $R^5$, —C(O)$R^5$, or —S(O)$_2R^5$;

J is CN, oxo, a $C_{1-6}$aliphatic wherein up to three carbon units of said $C_{1-6}$aliphatic can each be optionally and independently replaced with —O—, —NR—, —S— or —C(O)—; or a 3-7 membered saturated, partially unsaturated, or aromatic monocyclic ring having 0-4 heteroatoms selected from oxygen, nitrogen, or sulfur; wherein said J is optionally and independently substituted with 1-2 occurrences of halo or $C_{1-4}$alkyl, wherein up to one methylene unit of said $C_{1-4}$alkyl is optionally replaced with —O—, —NR—, or —S—;

or two J groups on the same or different atom(s), together with the atom(s) to which they are bound, form a 3-6 membered saturated monocyclic ring having 0-2 heteroatoms selected from oxygen, nitrogen, or sulfur; wherein said 3-6 membered ring is optionally substituted with one occurrence of oxo;

p is 0-4;

$R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(O)—; wherein V is optionally substituted with 1-3 occurrences of halo or $C_{1-4}$alkyl, wherein up to two methylene units of said $C_{1-4}$alkyl are optionally replaced with —O—, —NR—, —S—, or C(O);

Y is H, a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein Y is optionally substituted with 1-4 occurrences of $J^Y$;

$J^Y$ is oxo, halo, phenyl, or $C_{1-6}$aliphatic, wherein up to three carbon units of said $C_{1-6}$aliphatic can each be optionally and independently replaced with O, NR, S, or C(O); and R is H or $C_{1-4}$alkyl;

$R^1$ is H or F;

$R^2$ is —$(V^2)_a$—$Y^2$; wherein $V^2$ is a $C_{1-4}$aliphatic;

$Y^2$ is halo, $C_{1-6}$aliphatic; or a 3-7 membered saturated, partially unsaturated, or aromatic monocyclic ring having 0-4 heteroatoms selected from oxygen, nitrogen, or sulfur; wherein $Y^2$ is optionally substituted with 1-4 occurrences of $J^Y$; and a and b are each independently 0 or 1;

$R^3$ is H or F; and $R^4$ is halo, CN, $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein said $R^4$ is optionally and independently substituted with 1-3 occurrences of oxo, halo, or $C_{1-6}$aliphatic wherein up to three carbon units of said $C_{1-6}$aliphatic can each be optionally and independently replaced with O, NR, S or C(O).

The compounds of the invention can be very potent inhibitors of the PAR-2 signaling pathway.

DETAILED DESCRIPTION OF THE INVENTION

One aspect of the invention provides a compound of formula (I):

I

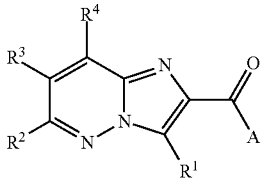

or a pharmaceutically acceptable salt thereof, wherein the variables of formula (I) are each and independently as described below.

A is

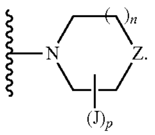

In a specific embodiment, A is

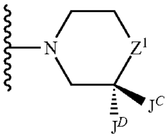 , 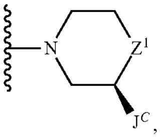 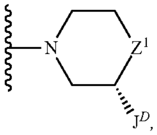

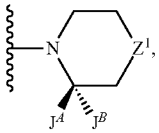 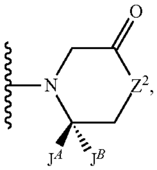 or 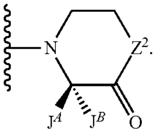

In another specific embodiment, A is

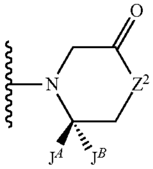 or 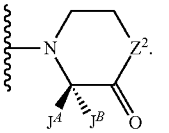

In another specific embodiment, A is

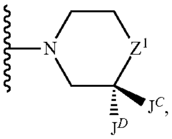 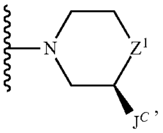 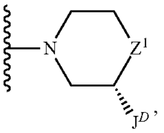 or

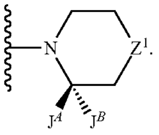

In another specific embodiment, A is

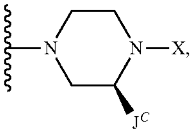 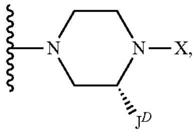

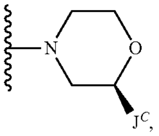 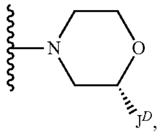

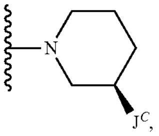 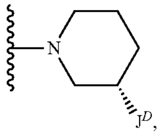

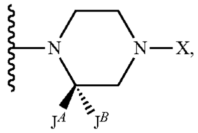 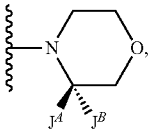

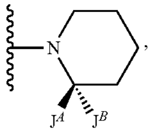 , 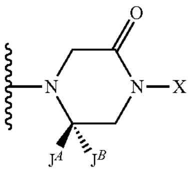 or

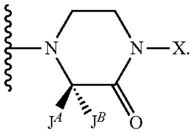

In another specific embodiment, A is

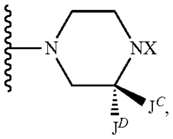 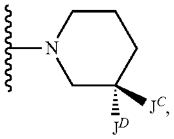 or 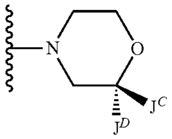

In another specific embodiment, A is

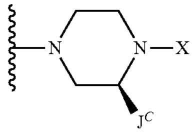 or 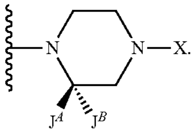

In another specific embodiment, A is

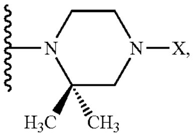 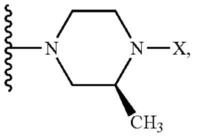

-continued

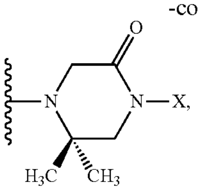 or 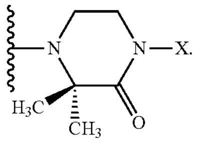

In another specific embodiment, A is

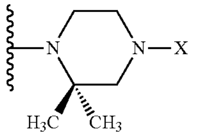 or 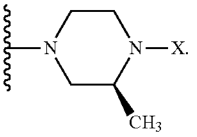

In another specific embodiment, A is

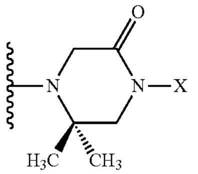 or 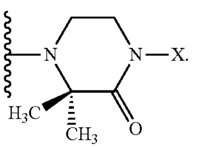

In another specific embodiment, A is

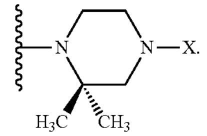

J is an optional substituent for Ring A, and it is understood that $CH_2$ of Z of Ring A can also be optionally substituted with J. J is CN, oxo, a $C_{1-6}$aliphatic wherein up to three carbon units of said $C_{1-6}$aliphatic can each be optionally and independently replaced with —O—, —NR—, —S— or —C(O)—; or a 3-7 membered saturated, partially unsaturated, or aromatic monocyclic ring having 0-4 heteroatoms selected from oxygen, nitrogen, or sulfur; or two J groups on the same or different atom(s), together with the atom(s) to which they are bound, form a 3-6 membered saturated monocyclic ring having 0-2 heteroatoms selected from oxygen, nitrogen, or sulfur. J is optionally and independently substituted with 1-3 occurrences of halo or $C_{1-4}$alkyl, wherein up to one methylene unit of said $C_{1-4}$alkyl is optionally and independently replaced with —O—, —NR—, or —S—. The 3-6 membered ring formed by two J is optionally substituted with one occurrence of oxo. In a specific embodiment, J is optionally and independently substituted with 1-2 occurrences of halo or $C_{1-4}$alkyl, wherein up to one methylene unit of said $C_{1-4}$alkyl is optionally and independently replaced with —O—, —NR—, or —S—. In another specific embodiment, J is oxo, CN, halo, —OH, —O($C_{1-6}$ alkyl), —NHC(=O)O($C_{1-6}$ alkyl), —C(=O)NR, —C(=O)O($C_{1-6}$alkyl), or $C_{1-4}$alkyl optionally substituted with 1-3 occurrences of halo. In another specific embodiment, J is $C_{1-4}$alkyl optionally substituted with 1-3 occurrences of halo. In another specific embodiment, J is methyl. In another specific embodiment, J is $J^A$, $J^B$ JC, or $J^D$, wherein each of $J^A$ and $J^B$ independently $C_{1-4}$alkyl, or $J^A$ and $J^B$, together with the carbon atom to which they are bound, form a 3-6 membered saturated monocyclic ring having 0-1 heteroatom selected from oxygen, nitrogen, or sulfur, and wherein each of $J^A$ and $J^B$ independently is methyl.

n is 1 or 2. In a specific embodiment, n is 1.

p is 0, 1, 2, 3, or 4. In a specific embodiment, p is 1, 2, or 3. In another specific embodiment, p is 1 or 2.

Z is —O—, —$CH_2$—, or —NX—. In a specific embodiment, Z is —NX—. In another specific embodiment, Z is $Z^1$ or $Z^2$. $Z^1$ is —O—, —$CH_2$—, or —NX—, wherein X is $X^1$. $Z^2$ is —$CH_2$— or —NX—, wherein X is $X^2$.

X is $R^5$, —C(O)$R^5$, or —S$(O)_2R^5$. In one specific embodiment, X is $R^5$ or —C(O)$R^5$. In another specific embodiment, X is —C(O)$R^5$. In another specific embodiment, X is $X^1$ or $X^2$. $X^1$ is $R^5$, —C(O)$R^5$, or —S$(O)_2R^5$. $X^2$ is $R^5$.

$R^5$ is —$(V)_b$—Y; wherein b is 0 or 1. In a specific embodiment, b is 0. In another specific embodiment, b is 1.

V is $C_{1-6}$aliphatic wherein up to three carbon units of said $C_{1-6}$aliphatic can each be optionally and independently replaced with —O—, —NR—, —S— or —C(O)—, and wherein V is optionally and independently substituted with 1-3 occurrences of halo or $C_{1-6}$alkyl, and up to three methylene units of the $C_{1-6}$alkyl are optionally and independently replaced with —O—, —NR—, —S—, or C(O). In a specific embodiment, V is $C_{1-6}$aliphatic wherein up to three carbon units of said $C_{1-6}$aliphatic can each be optionally and independently replaced with —O—, —NR—, —S— or —C(O)—, and wherein V is optionally and independently substituted with 1-3 occurrences of halo or $C_{1-4}$alkyl, and up to two methylene units of the $C_{1-4}$alkyl are optionally and independently replaced with —O—, —NR—, —S—, or C(O). In a specific embodiment, V is $C_{1-6}$aliphatic wherein up to three carbon units of said $C_{1-6}$aliphatic can each be optionally and independently replaced with —O—, —NR—, —S— or —C(=O)—; wherein V is optionally substituted with halo, $C_{1-4}$alkyl, OH, NHR, N$(C_{1-4}alkyl)_2$, or —NRC(O)$C_{1-4}$alkyl. In a specific embodiment, V is $C_{1-6}$aliphatic wherein up to three carbon units of the $C_{1-6}$aliphatic can each be optionally and independently replaced with —O—, —NR—, —S— or —C(=O)—, wherein V is optionally substituted with halo, $C_{1-4}$alkyl, OH, $NH_2$, —NRC(O)$C_{1-4}$alkyl. In a specific embodiment, V is $C_{1-6}$alkyl, wherein up to three carbon units of the $C_{1-6}$alkyl can each be optionally and independently replaced with —O—, —NR—, —S— or —C(=O)—, and V is optionally substituted with halo, $C_{1-4}$alkyl, OH, $NH_2$, —NRC(O)$C_{1-4}$alkyl. In another specific embodiment, V is —CH(OH)—, —CH(OH)$CH_2$—, —$CH_2$—, —$CH_2CH_2$—, or —O—

Y is H; CN; a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur. Y is optionally substituted with 1-4 occurrences of $J^Y$. In a specific embodiment, Y is H; a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein Y is optionally substituted with 1-4 occurrences of $J^Y$. In another specific embodiment, Y is H or a 3-7 membered saturated, partially unsaturated, or aromatic monocyclic ring having 0-4 heteroatoms selected from oxygen, nitrogen, or sulfur; wherein Y is optionally substituted with 1-4 occurrences of $J^Y$. In another specific embodiment, Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl, triazolyl, thienyl, oxadiazolyl, tetrazolyl, pyrimidinyl, pyridazinyl, isothiazolyl, or bicycle[1.1.1.]pentanyl; wherein Y is optionally substituted with 1-4 occurrences of $J^Y$. In another specific embodiment, Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl; wherein Y is optionally substituted with 1-4 occurrences of $J^Y$. In another specific embodiment, Y is H, $C_{1-4}$aliphatic, a 3-6 membered cycloalkyl, isoxazolyl, oxetanyl, thienyl, phenyl, azetidinyl, tetrahydrofuranyl, tetrahydropyranyl, piperidinyl, imidazolyl, pyrazolyl, pyridinyl, triazolyl, oxadiazolyl, tetrazolyl, pyrimidinyl, pyridazinyl, isothiazolyl, or bicycle[1.1.1.]pentanyl, wherein Y is optionally substituted with 1-4 occurrences of $J^Y$. In another specific embodiment, Y is H, $C_{1-4}$aliphatic, a 3-6 membered cycloalkyl, isoxazolyl, thienyl, or phenyl, wherein Y is optionally substituted with 1-4 occurrences of $J^Y$.

$J^Y$ is oxo, halo, CN, —OP(═O)(OR)$_2$, phenyl, or $C_{1-6}$aliphatic, wherein up to three carbon units of said $C_{1-6}$aliphatic can each be optionally and independently replaced with O, NR, S, or C(O), wherein said $C_{1-6}$aliphatic optionally and independently substituted with 1-3 occurrences of halo or —OR. In another specific embodiment, $J^Y$ is oxo, halo, phenyl, or $C_{1-6}$aliphatic, wherein up to three carbon units of said $C_{1-6}$aliphatic can each be optionally and independently replaced with O, NR, S, or C(O). In another specific embodiment, $J^Y$ is oxo, halo, phenyl, or $C_{1-6}$aliphatic, wherein up to three carbon units of the $C_{1-6}$aliphatic can each be optionally and independently replaced with O, NR, S or C(O), and wherein the $C_{1-6}$aliphatic optionally and independently substituted with 1-3 occurrences of halo. In another specific embodiment, $J^Y$ is oxo, halo, CN, OH, O($C_{1-4}$ alkyl), —C(═O)OH, —C(═O)O($C_{1-4}$ alkyl), —C(═O)NHR, —C(═O)N($C_{1-4}$alkyl)$_2$, —NRC(═O)O($C_{1-4}$ alkyl), phenyl, or $C_{1-4}$ alkyl optionally substituted with 1-3 occurrences of halo. In another specific embodiment, $J^Y$ is oxo, $OCH_3$ or phenyl. In another specific embodiment, $J^Y$ is halo or $C_{1-4}$ alkyl optionally substituted with 1-3 occurrences of halo. In another specific embodiment, $J^Y$ is halo or $C_{1-4}$ alkyl.

$R^1$ is H or F. In one specific embodiment, $R^1$ is H.

$R^2$ is —$(V^2)_a$—$Y^2$. In one specific embodiment, a is 0. In another specific embodiment, a is 1.

$V^2$ is a $C_{1-4}$aliphatic. In one specific embodiment, $V^2$ is $C_{1-4}$alkyl. In another specific embodiment, $V^2$ is —C≡C—.

$Y^2$ is halo; $C_{1-6}$aliphatic; or a 3-7 membered saturated, partially unsaturated, or aromatic monocyclic ring having 0-4 heteroatoms selected from oxygen, nitrogen, or sulfur; wherein $Y^2$ is optionally substituted with 1-4 occurrences of $J^Y$. In yet another specific embodiment, $Y^2$ is halo, methyl, phenyl, a 3-6 membered cycloaliphatic, or a 3-7 membered heterocyclyl wherein said heterocyclyl has 1-2 heteroatoms selected from oxygen, nitrogen, or sulfur, wherein $Y^2$ is optionally substituted. In yet another specific embodiment, $Y^2$ is an optionally substituted, 3-6 membered, cycloaliphatic, such as cyclopropyl or cyclohexyl. In another specific embodiment, $Y^2$ is chloro, methyl, 4-fluorophenyl, cyclopropyl, cyclohexyl, or tetrahydrofurenyl. In another specific embodiment, $Y^2$ is phenyl optionally substituted with 1-4 occurrences of $J^Y$ selected from halo or $C_{1-4}$ alkyl optionally substituted with 1-3 occurrences of halo. In another specific embodiment, $Y^2$ is phenyl optionally substituted with halo. In another specific embodiment, $Y^2$ is 4-fluorophenyl.

$R^3$ is H or F. In a specific embodiment, $R^3$ is H.

$R^4$ is H; halo; CN; $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur. $R^4$ is optionally and independently substituted with 1-3 occurrences of oxo, halo, or $C_{1-6}$aliphatic wherein up to three carbon units of the $C_{1-6}$aliphatic can each be optionally and independently replaced with O, NR, S or C(O). In one specific embodiment, $R^4$ is optionally substituted and selected from halo; CN; $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur. In another specific embodiment, $R^4$ is H, $C_{1-4}$ aliphatic, or a 3-7 membered saturated, partially saturated, or aromatic monocyclic ring having 0-4 heteroatoms selected from oxygen, nitrogen, or sulfur, wherein the $C_{1-4}$ aliphatic is optionally substituted with 1-3 occurrences of halo, —OH, or —O($C_{1-4}$ alkyl), and wherein the monocyclic ring is optionally substituted with 1-3 occurrences of halo, $C_{1-4}$ alkyl, —$CF_3$, —OH, or —O($C_{1-4}$ alkyl). In another specific embodiment, $R^4$ is optionally substituted $C_{1-4}$ alkyl or optionally substituted monocyclic ring. In another specific embodiment, $R^4$ is optionally substituted $C_{1-4}$ alkyl or optionally substituted monocyclic ring selected from tetrahydropyranyl, cyclopropyl, morpholinyl, or thienyl. In another specific embodiment, $R^4$ is optionally substituted $C_{1-4}$ alkyl. In another specific embodiment, $R^4$ is optionally substituted $C_{1-4}$ alkyl. In another specific embodiment, $R^4$ is methyl, $CF_3$, isopropyl, or tert-butyl. In another specific embodiment, $R^4$ is methyl, $CF_3$, or isopropyl. In another specific embodiment, $R^4$ is $CF_3$.

Each R independently is H or $C_{1-4}$alkyl. In a specific embodiment, each R independently is H, methyl or ethyl.

In some embodiments, Z is —NX—. In other embodiments, J is methyl. In yet other embodiments, p is 1 or 2. In some embodiments, n is 1.

In some embodiments, J is oxo, CN, halo, —OH, —O($C_{1-6}$ alkyl), —NHC(═O)O($C_{1-6}$ alkyl), —C(═O)NR, —C(═O)O($C_{1-6}$alkyl), or $C_{1-4}$alkyl optionally substituted with 1-3 occurrences of halo.

In some embodiments, A is

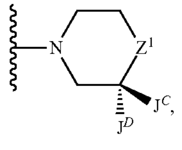, 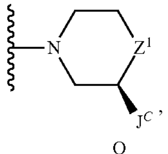, 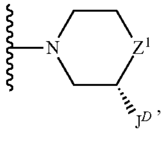,

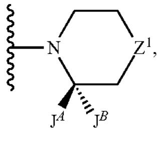, 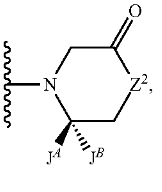, or 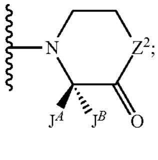;

wherein $Z^1$ is —O—, —$CH_2$—, or —NX—; wherein X is $X^1$;

$Z^2$ is —$CH_2$— or —NX—; wherein X is $X^2$;

$X^1$ is $R^5$, —C(O)$R^5$, or —S(O)$_2R^5$;

$X^2$ is $R^5$;

$J^A$ is $C_{1-4}$alkyl;

$J^B$ is $C_{1-4}$alkyl;

or $J^A$ and $J^B$, together with the carbon atom to which they are bound, form a 3-6 membered saturated monocyclic ring having 0-1 heteroatom selected from oxygen, nitrogen, or sulfur; and $J^C$ is methyl; and $J^D$ is methyl.

In some embodiments, A is

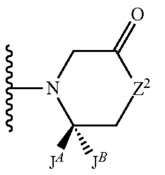 or 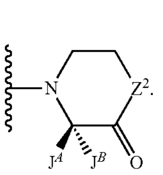

In some embodiments, A is

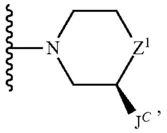 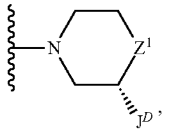 or 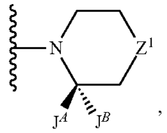

wherein each of $Z^1$, 2, $Z^2$, $J^A$, $J^B$, $J^C$, and $J^D$ independently are as described above.

In some embodiments, A is

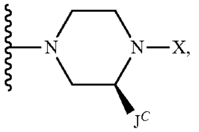 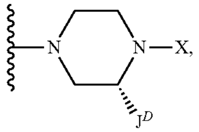

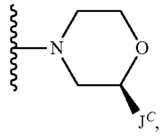 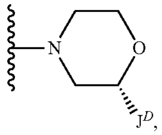

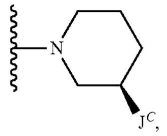 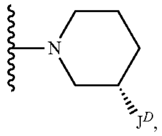

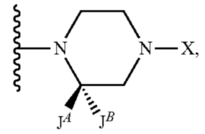 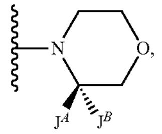

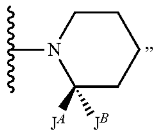 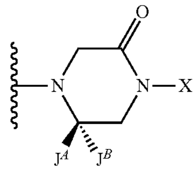 or

-continued

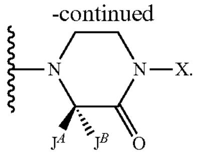

In some embodiments, A is

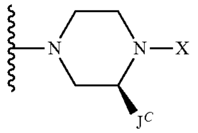 or 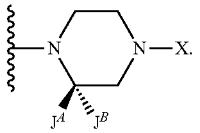

Each of X, $J^A$, $J^B$, $J^C$, and $J^D$ independently are as described above.

In some embodiments, A is as described in the preceding paragraph and:

$R^5$ is —$(V)_b$—Y;

V is $C_{1-6}$aliphatic wherein up to three carbon units of said $C_{1-6}$aliphatic can each be optionally and independently replaced with —O—, —NR—, —S— or —C(O)—; wherein V is optionally and independently substituted with halo, $C_{1-4}$alkyl, OH, $NH_2$, or —NRC(O)$C_{1-4}$alkyl;

Y is H or a 3-7 membered saturated, partially unsaturated, or aromatic monocyclic ring having 0-4 heteroatoms selected from oxygen, nitrogen, or sulfur; wherein Y is optionally substituted with 1-4 occurrences of $J^Y$; and $J^Y$ is oxo, halo, phenyl, or $C_{1-6}$aliphatic, wherein up to three carbon units of said $C_{1-6}$aliphatic can each be optionally and independently replaced with O, NR, S or C(O).

In some embodiments, A is as described above in any one of the preceding paragraphs, and X is —$R^5$ or C(O)$R^5$.

In some embodiments, A and X of formula (I) are each and independently as described above in any one of the preceding paragraphs, and $R^5$ is —$(V)_b$—Y; wherein V is $C_{1-6}$aliphatic wherein up to three carbon units of said $C_{1-6}$aliphatic can each be optionally and independently replaced with —O—, —NR—, —S— or —C(═O)—; wherein V is optionally substituted with halo, $C_{1-4}$alkyl, OH, NHR, N($C_{1-4}$alkyl)$_2$, —NRC(O)$C_{1-4}$alkyl; and Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl, triazolyl, thienyl, oxadiazolyl, tetrazolyl, pyrimidinyl, pyridazinyl, isothiazolyl, or bicycle[1.1.1.]pentanyl; wherein Y is optionally substituted with 1-4 occurrences of $J^Y$;

$J^Y$ is oxo, halo, CN, OH, O($C_{1-4}$ alkyl), —C(═O)OH, —C(═O)O($C_{1-4}$ alkyl), —C(═O)NHR, —C(═O)N($C_{1-4}$ alkyl)$_2$, —NRC(═O)O($C_{1-4}$ alkyl), phenyl, or $C_{1-4}$ alkyl optionally substituted with 1-3 occurrences of halo; and b is 0 or 1.

In some embodiments, A and X of formula (I) are each and independently as described above in any one of the preceding paragraphs, and $R^5$ is —$(V)_b$—Y; wherein V is $C_{1-6}$aliphatic wherein up to three carbon units of said $C_{1-6}$aliphatic can each be optionally and independently replaced with —O—, —NR—, —S— or —C(═O)—; wherein V is optionally substituted with halo, $C_{1-4}$alkyl, OH, $NH_2$, —NRC(O)$C_{1-4}$alkyl; and Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl; wherein Y is optionally substituted with 1-4 occurrences of $J^Y$;

$J^Y$ is oxo, $OCH_3$ or phenyl; and b is 0 or 1.

In some embodiments, A is

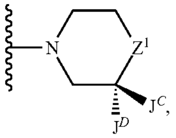
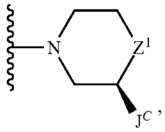
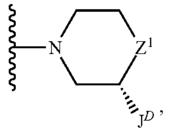
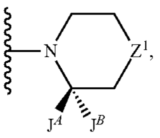
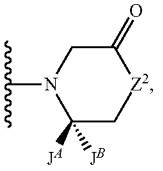
or
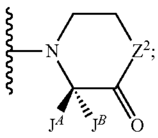

wherein $Z^1$ is —O—, —$CH_2$—, or —NX—;

$Z^2$ is —$CH_2$— or —NX—;

X is —C(O)$R^5$;

$R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(O)—; wherein V is optionally and independently substituted with halo, $C_{1-4}$alkyl, OH, NHR, $NH_2$, —NRC(O)$C_{1-4}$alkyl;

Y is H or a 3-7 membered saturated, partially unsaturated, or aromatic monocyclic ring having 0-4 heteroatoms selected from oxygen, nitrogen, or sulfur; wherein Y is optionally substituted with 1-4 occurrences of $J^Y$;

$J^Y$ is oxo, halo, phenyl, or $C_{1-6}$aliphatic, wherein up to three carbon units of said $C_{1-6}$aliphatic can each be optionally and independently replaced with O, NR, S or C(O); and R is H or $C_{1-4}$alkyl;

b is 0 or 1;

$J^A$ is methyl;

$J^B$ is methyl;

or $J^A$ and $J^B$, together with the carbon atom to which they are bound, form a 3-6 membered saturated monocyclic ring having 0-1 heteroatom selected from oxygen, nitrogen, or sulfur; and $J^C$ is methyl; and $J^D$ is methyl.

In some embodiments, A is

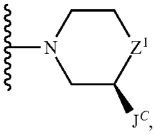
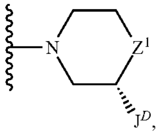
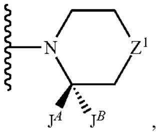
,

-continued

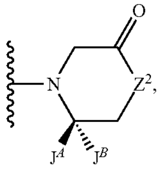
or
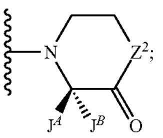

wherein $Z^1$ is —O—, —$CH_2$—, or —NX—;

$Z^2$ is —$CH_2$— or —NX—;

X is —C(O)$R^5$;

$R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(O)—; wherein V is optionally substituted with halo, $C_{1-4}$alkyl, OH, $NH_2$, —NRC(O)$C_{1-4}$alkyl;

Y is H or a 3-7 membered saturated, partially unsaturated, or aromatic monocyclic ring having 0-4 heteroatoms selected from oxygen, nitrogen, or sulfur; wherein Y is optionally substituted with 1-4 occurrences of $J^Y$;

$J^Y$ is oxo, halo, phenyl, or $C_{1-6}$aliphatic, wherein up to three carbon units of said $C_{1-6}$aliphatic can each be optionally and independently replaced with O, NR, S or C(O); and R is H or $C_{1-4}$alkyl;

b is 0 or 1;

$J^A$ is methyl;

$J^B$ is methyl;

or $J^A$ and $J^B$, together with the carbon atom to which they are bound, form a 3-6 membered saturated monocyclic ring having 0-1 heteroatom selected from oxygen, nitrogen, or sulfur; and $J^C$ is methyl; and $J^D$ is methyl.

In some embodiments, $J^A$ is methyl. In other embodiments, $J^B$ is methyl. In yet other embodiments, both $J^A$ and $J^B$ are methyl.

In some embodiments, X is —C(O)$R^5$.

In some embodiments X is $R^5$.

In some embodiments, X is as describe above in the preceding paragraphs, and $R^5$ is —$(V)_b$—Y; wherein V is $C_{1-6}$aliphatic wherein up to three carbon units of said $C_{1-6}$aliphatic can each be optionally and independently replaced with —O—, —NR—, —S— or —C(=O)—; wherein V is optionally substituted with halo, $C_{1-4}$alkyl, OH, NHR, $N(C_{1-4}alkyl)_2$, —NRC(O)$C_{1-4}$alkyl; and Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl, triazolyl, thienyl, oxadiazolyl, tetrazolyl, pyrimidinyl, pyridazinyl, isothiazolyl, or bicycle[1.1.1.]pentanyl; wherein Y is optionally substituted with 1-4 occurrences of $J^Y$;

$J^Y$ is oxo, halo, CN, OH, O($C_{1-4}$ alkyl), —C(=O)OH, —C(=O)O($C_{1-4}$ alkyl), —C(=O)NHR, —C(=O)N($C_{1-4}$ alkyl)$_2$, —NRC(=O)O($C_{1-4}$ alkyl), phenyl, or $C_{1-4}$ alkyl optionally substituted with 1-3 occurrences of halo; and b is 0 or 1.

In some embodiments, $R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(═O)—; wherein V is optionally substituted with halo, $C_{1-4}$alkyl, OH, $NH_2$, —NRC(O)$C_{1-4}$alkyl; and Y is H, cyclopropyl, cyclobutyl, cyclopentyl, cxyclohexyl, oxetanyl, azetidinyl, tetrahydrofuranyl, tetrahydropyranyl, piperidinyl, imidazolyl, isoxazolyl, pyrazolyl, pyridinyl, phenyl; wherein Y is optionally substituted with 1-4 occurrences of $J^Y$;

$J^Y$ is oxo, $OCH_3$ or phenyl; and b is 0 or 1.

According to another embodiment, $R^5$ is as described above in the preceding two paragraphs, and $R^2$ is —$(V^2)_a$—$Y^2$. In some embodiments, a is 1 and $V^2$ is —C≡C—. In other embodiments, a is 0. In some embodiments, $Y^2$ is halo, methyl, phenyl, a 3-6 membered cycloaliphatic, or a 3-7 membered heterocyclyl wherein said heterocyclyl has 1-2 heteroatoms selected from oxygen, nitrogen, or sulfur, wherein $Y^2$ is optionally substituted. In other embodiments, $Y^2$ is chloro, methyl, 4-fluorophenyl, cyclopropyl, cyclohexyl, or tetrahydrofurenyl. In yet other embodiments, $Y^2$ is phenyl optionally substituted with 1-4 occurrences of $J^Y$ selected from halo or $C_{1-4}$ alkyl optionally substituted with 1-3 occurrences of halo. In yet other embodiments, $Y^2$ is phenyl optionally substituted with halo. In some embodiments, a is 0 and $Y^2$ is 4-fluorophenyl.

In some embodiments, $R^4$ is H, $C_{1-4}$ aliphatic, or a 3-7 membered saturated, partially saturated, or aromatic monocyclic ring having 0-4 heteroatoms selected from oxygen, nitrogen, or sulfur, wherein said $C_{1-4}$ aliphatic is optionally substituted with 1-3 occurrences of halo, —OH, or —O($C_{1-4}$ alkyl), and wherein said monocyclic ring is optionally substituted with 1-3 occurrences of halo, $C_{1-4}$ alkyl, —$CF_3$, —OH, or —O($C_{1-4}$ alkyl). In some embodiments, $R^4$ is optionally substituted $C_{1-4}$ alkyl or optionally substituted monocyclic ring. In some embodiments, $R^4$ is optionally substituted $C_{1-4}$ alkyl or optionally substituted monocyclic ring selected from tetrahydropyranyl, cyclopropyl, morpholinyl, or thienyl. In some embodiments, $R^4$ is optionally substituted $C_{1-4}$ alkyl. In some embodiments, $R^4$ is methyl, $CF_3$, isopropyl, or tert-butyl. In some embodiments, $R^4$ is methyl, $CF_3$, or isopropyl. In some embodiments, $R^4$ is methyl, $CF_3$, or isopropyl. In other embodiments, $R^4$ is $CF_3$.

In some embodiments, $R^1$ is H, and $R^3$ is H.

Another embodiment provides compounds represented by formula (II):

II

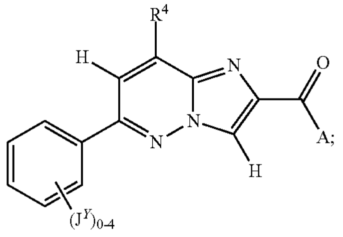

wherein $R^4$, A, and $J^Y$ are as defined herein.

In some embodiments,

A is

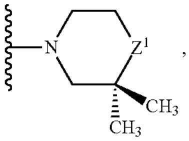,
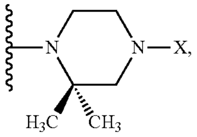

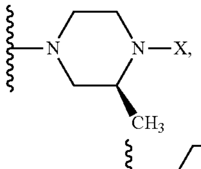,
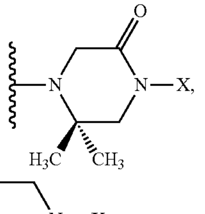, or

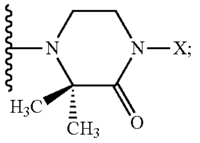;

$R^4$ is iso-propyl, tert-butyl, cyclopropyl, methylcyclopropyl, or $CF_3$;

X is $R^5$ or —C(O)$R^5$;

$R^5$ is $(V)_b$—Y; wherein

V is —CH(OH)—, —CH(OH)$CH_2$—, —$CH_2$—, —$CH_2CH_2$—, or —O—; and

Y is H, $C_{1-4}$aliphatic, a 3-6 membered cycloalkyl, isoxazolyl, oxetanyl, thienyl, phenyl, azetidinyl, tetrahydrofuranyl, tetrahydropyranyl, piperidinyl, imidazolyl, pyrazolyl, pyridinyl, triazolyl, oxadiazolyl, tetrazolyl, pyrimidinyl, pyridazinyl, isothiazolyl, or bicycle[1.1.1.]pentanyl, wherein Y is optionally substituted with 1-4 occurrences of $J^Y$;

$J^Y$ is halo or $C_{1-4}$alkyl optionally substituted with 1-3 occurrences of halo; and b is 0 or 1.

In some embodiments, A, $R^4$, X, $R^5$, and $J^Y$ are each independently as described above in the preceding paragraph, and b is 0.

In some embodiments, A, $R^4$, X, $R^5$, $J^Y$, and b are each independently as described above in the preceding paragraph, and X is —C(O)$R^5$.

In some embodiments,

A is

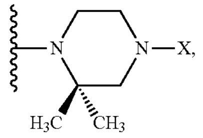,
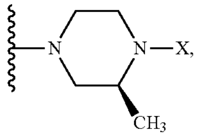,

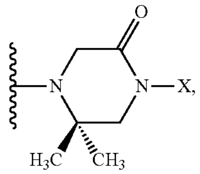 or
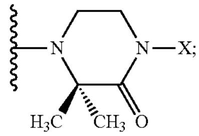;

$R^4$ is iso-propyl, tert-butyl, cyclopropyl, methylcyclopropyl, or $CF_3$;

X is $R^5$ or —C(O)$R^5$;

$R^5$ is V—Y; wherein

V is —CH(OH)—, —CH(OH)$CH_2$—, —$CH_2$—, —$CH_2CH_2$—, or —O—; and

Y is H, $C_{1-4}$aliphatic, a 3-6 membered cycloalkyl, isoxazolyl, thienyl, or phenyl, wherein Y is optionally substituted with 1-4 occurrences of $J^Y$; and
$J^Y$ is halo or $C_{1-4}$alkyl.
Another embodiment provides a compound represented by any one of the following structural formulae or a pharmaceutically acceptable salt thereof:
I-1
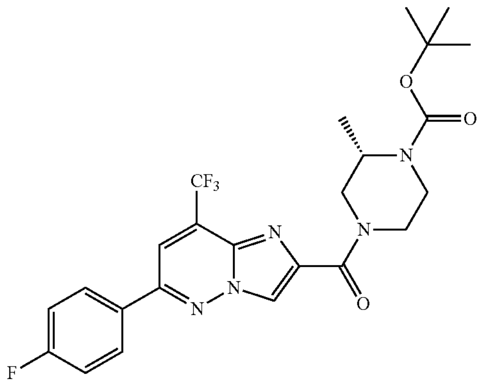
I-2
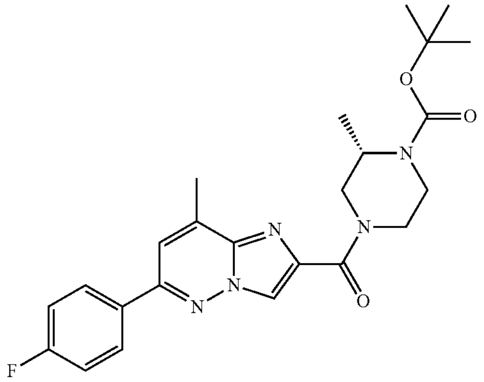
I-3
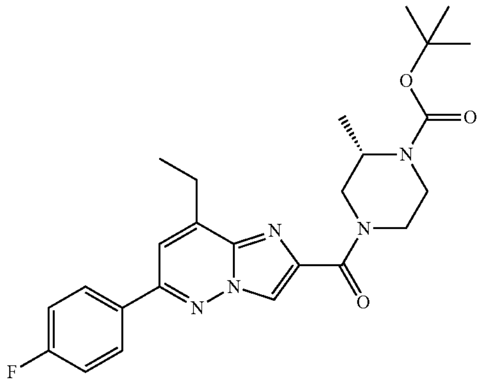
-continued
I-4
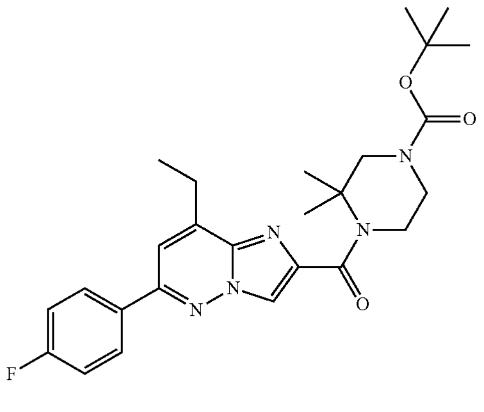
I-5
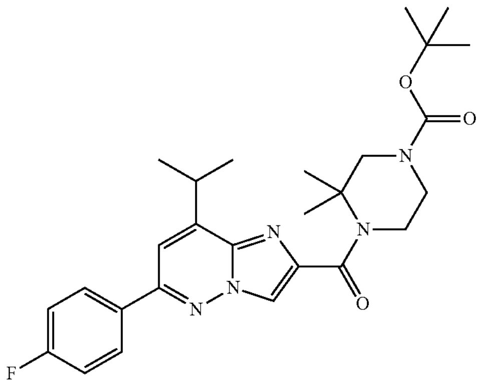
I-6
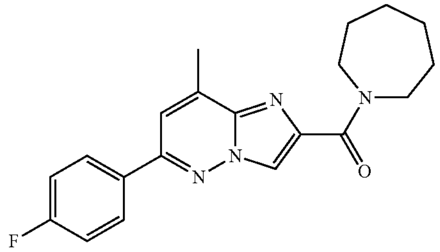
I-7
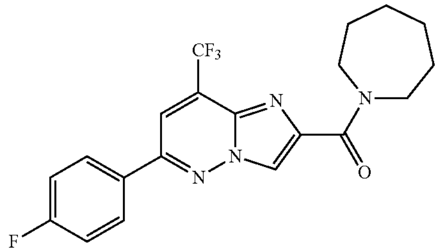

-continued
I-8
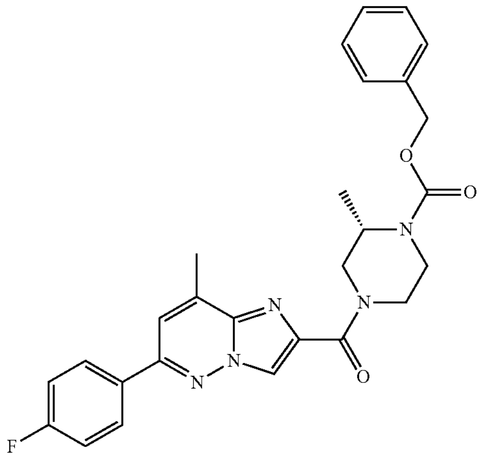
I-9
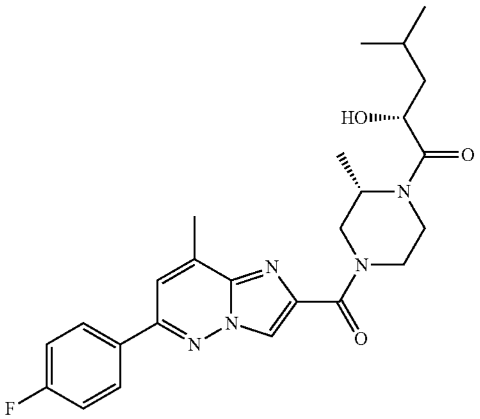
I-10
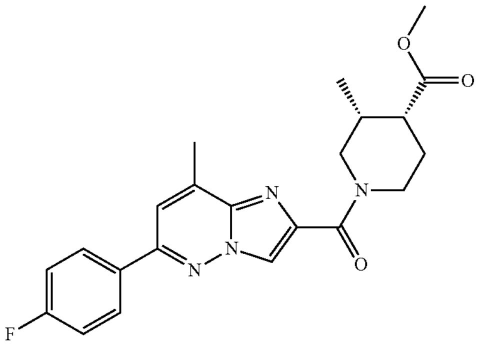
-continued
I-11
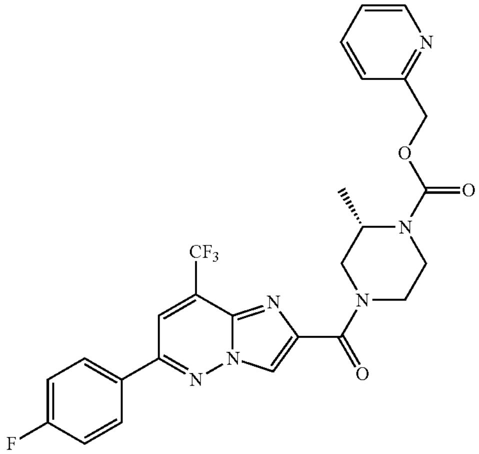
I-12
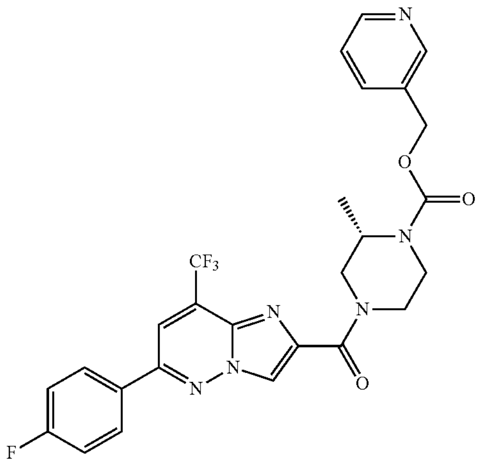
I-13
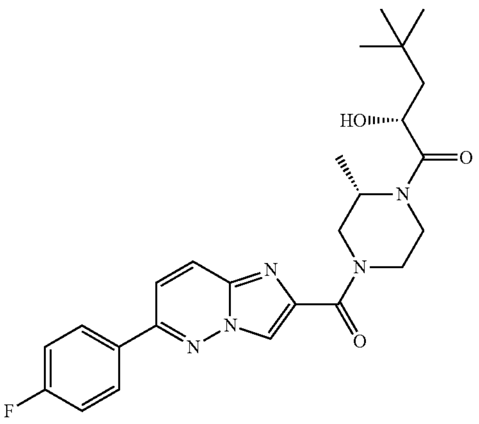

-continued
I-14
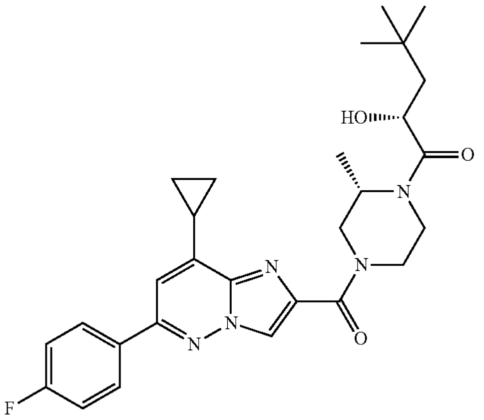
I-15
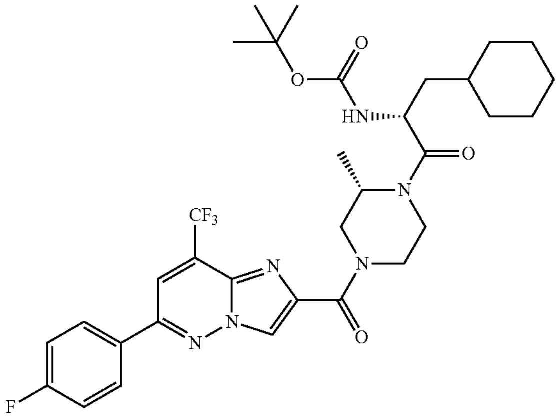
I-16
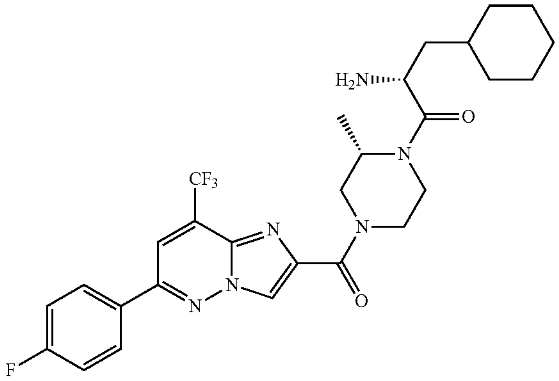
I-17
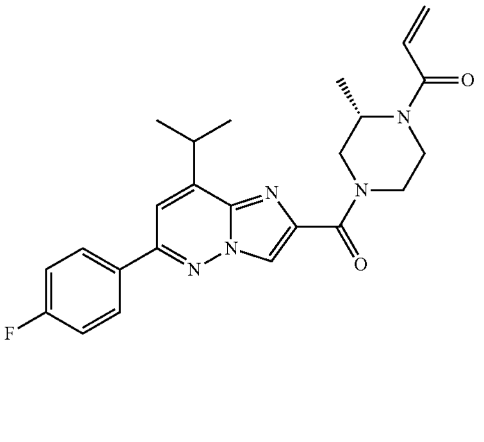
-continued
I-18
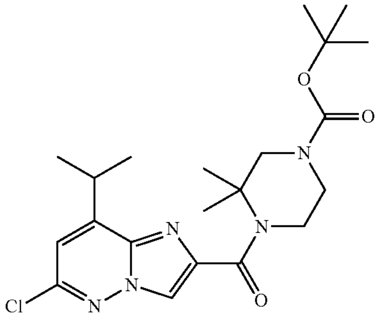
I-19
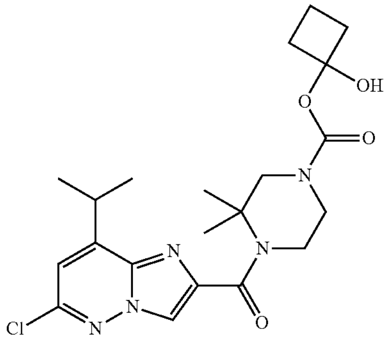
I-20
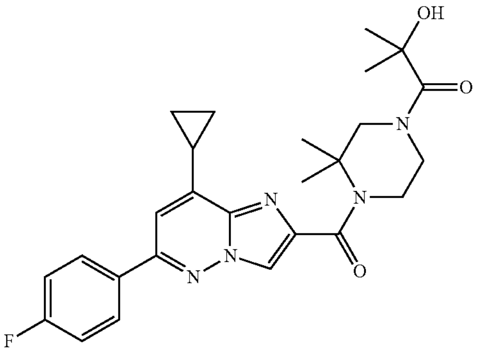
I-21
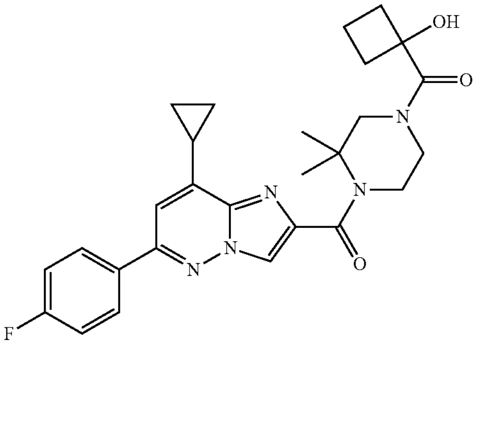

-continued
I-22
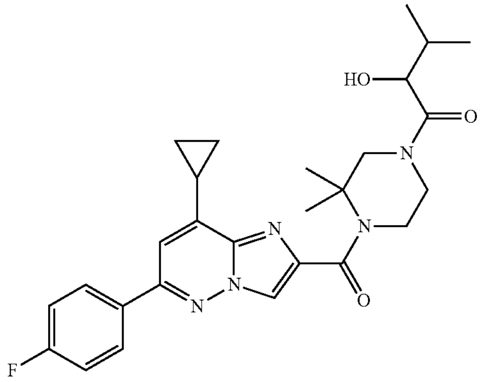
I-23
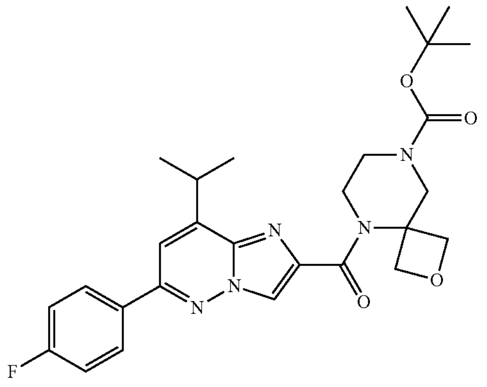
I-24
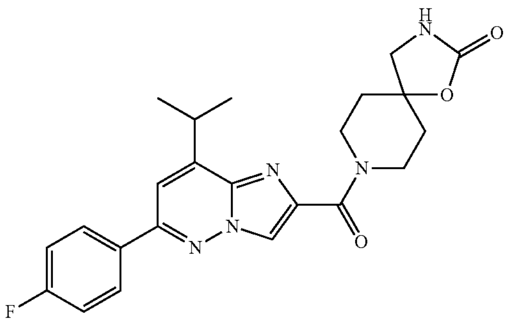
I-25
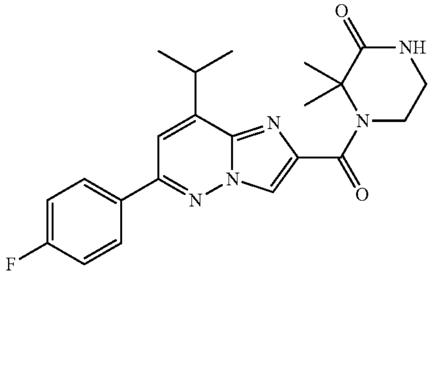
-continued
I-26
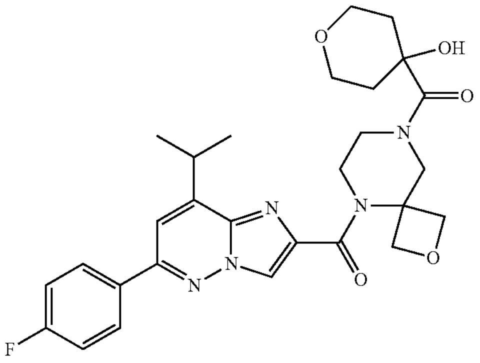
I-27
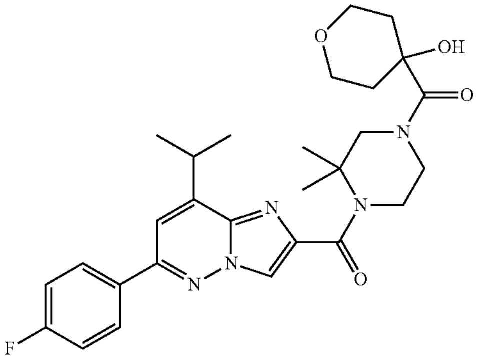
I-28
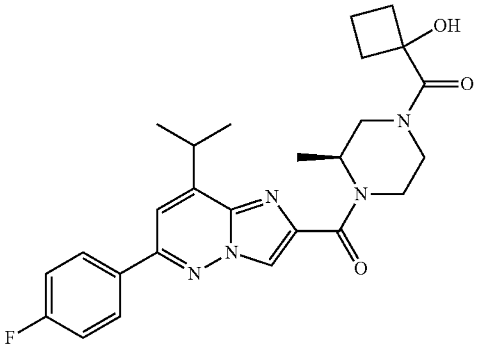
I-29
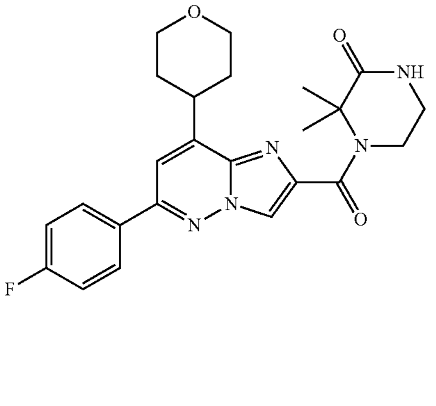

-continued
I-30
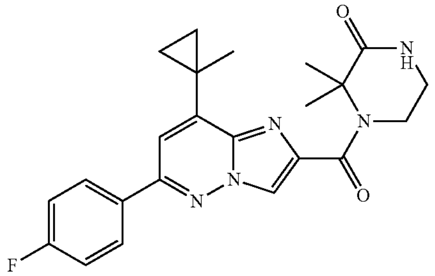
I-31
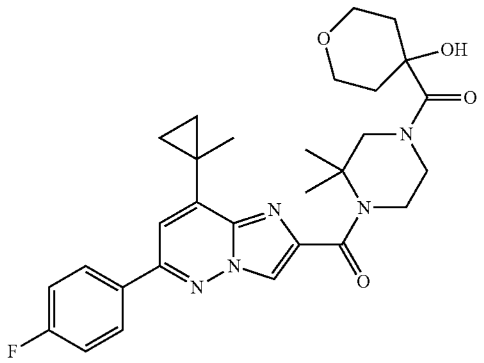
I-32
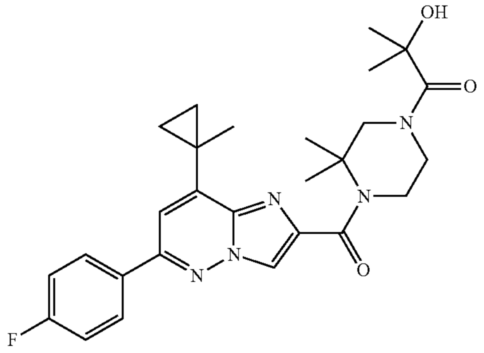
I-33
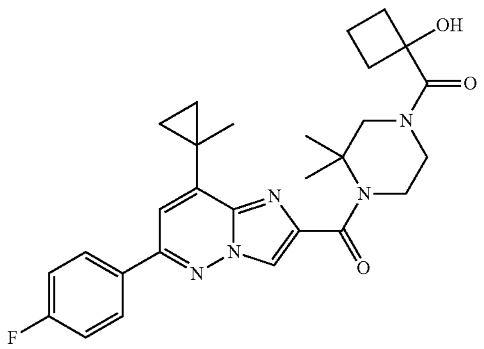
-continued
I-34
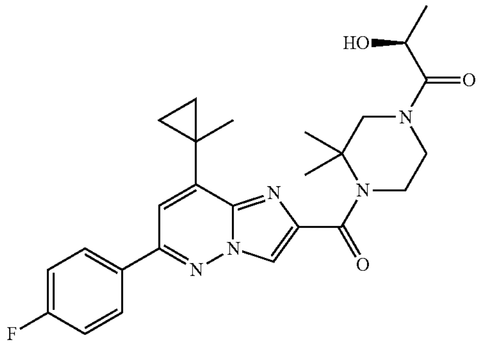
I-35
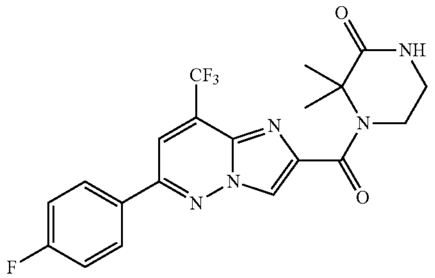
I-36
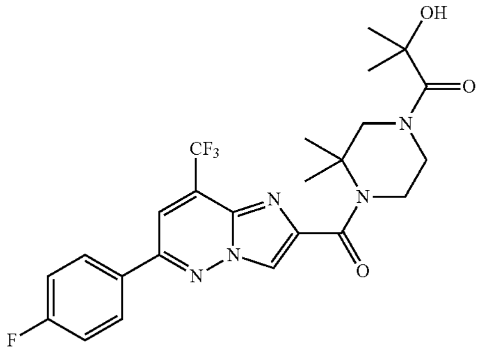
I-37
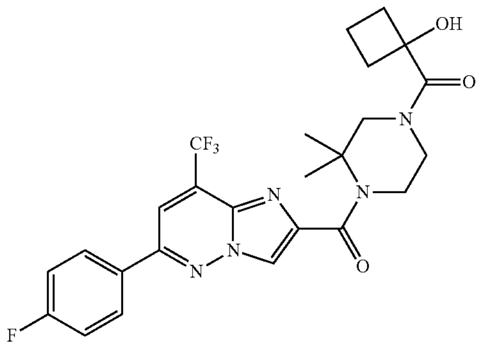

-continued
I-38
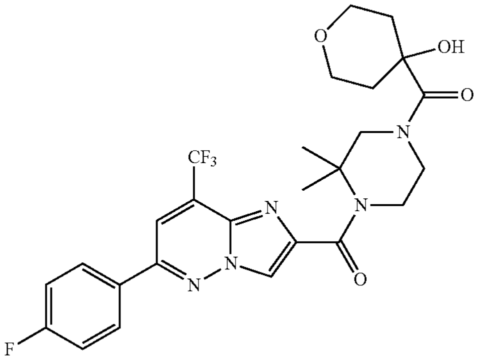
I-39
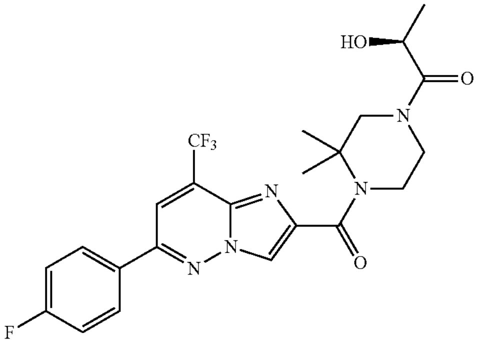
I-40
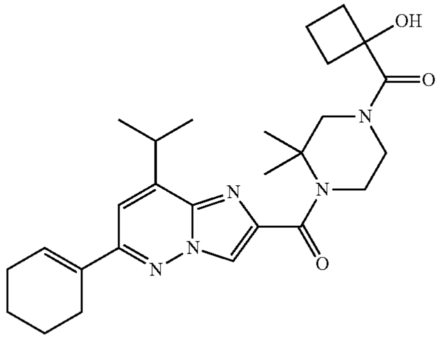
I-41
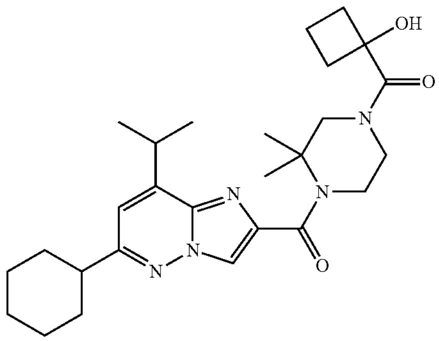
-continued
I-42
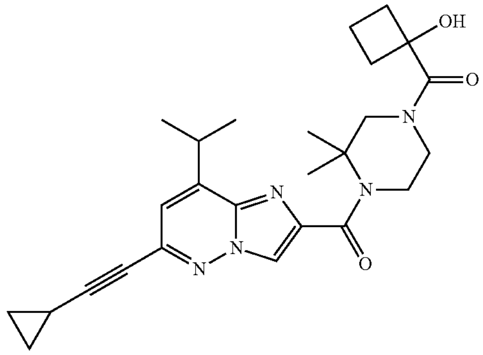
I-43
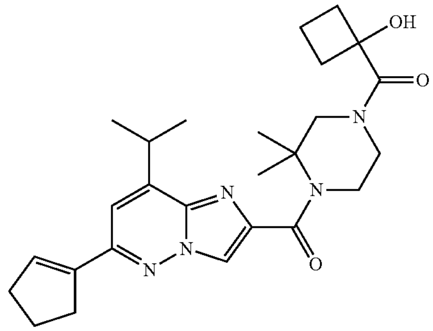
I-44
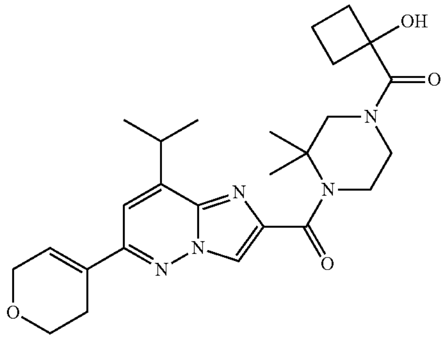
I-45
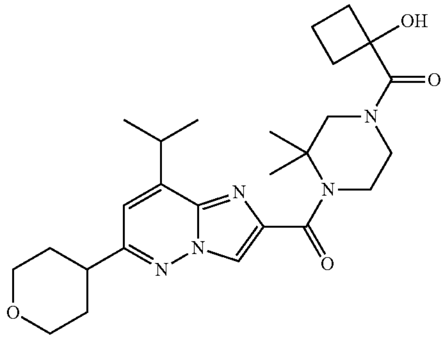

-continued
I-46
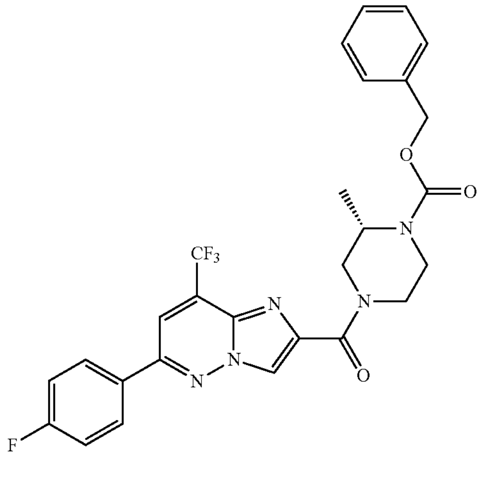
I-47
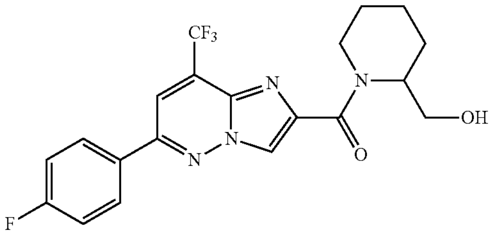
I-48
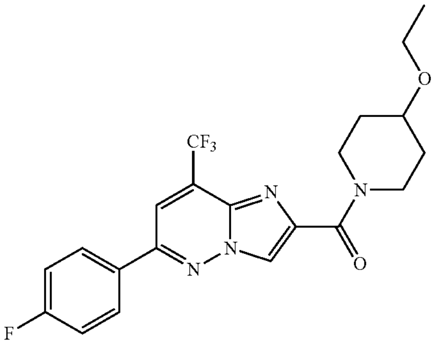
I-49
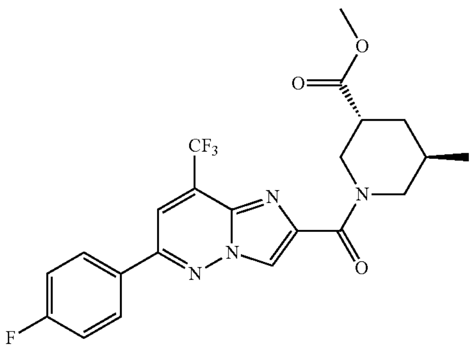
-continued
I-50
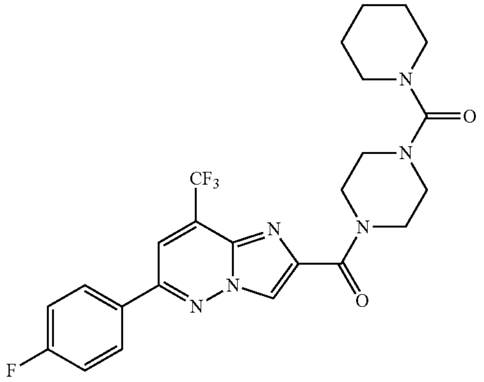
I-51
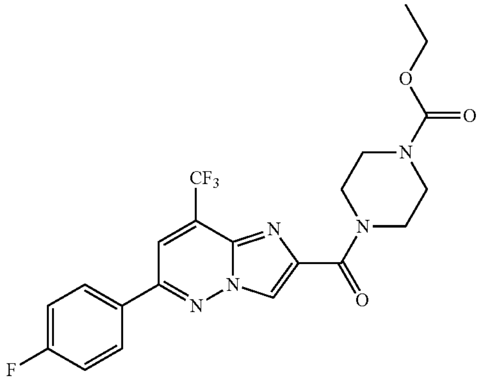
I-52
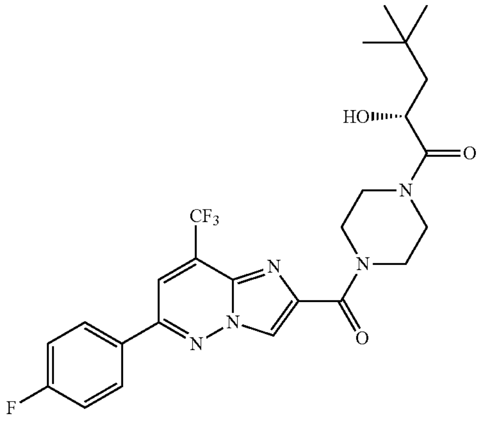

-continued
I-53
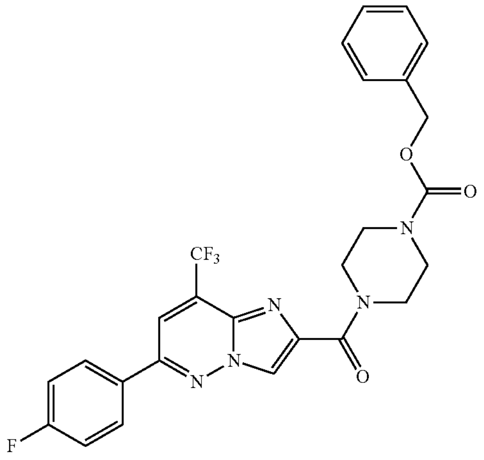
I-54
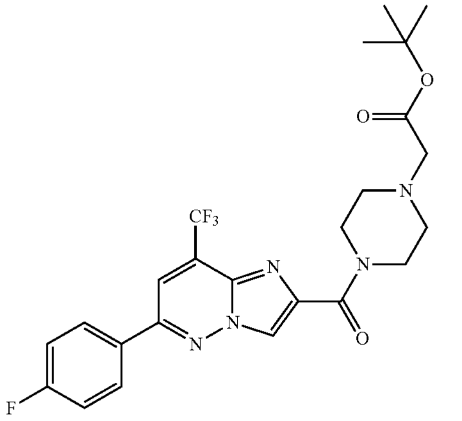
I-55
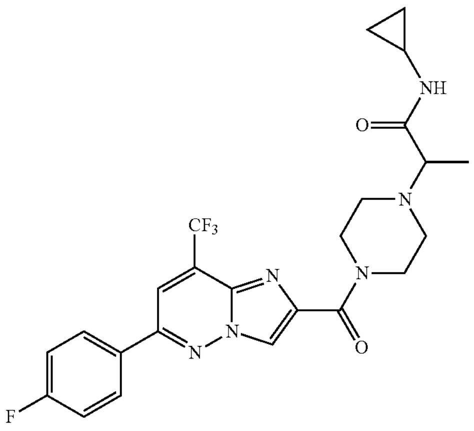
-continued
I-56
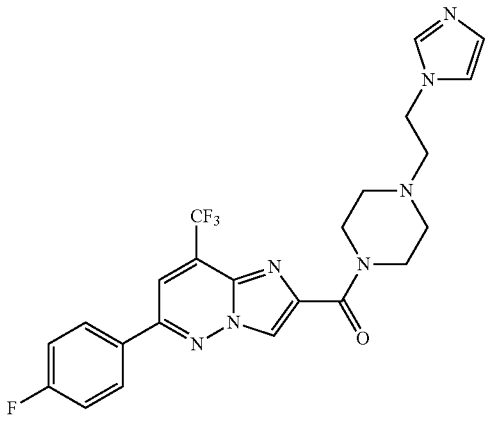
I-57
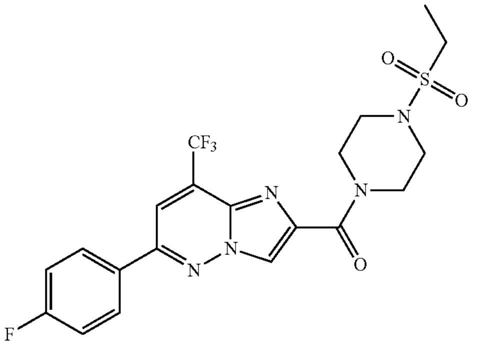
I-58
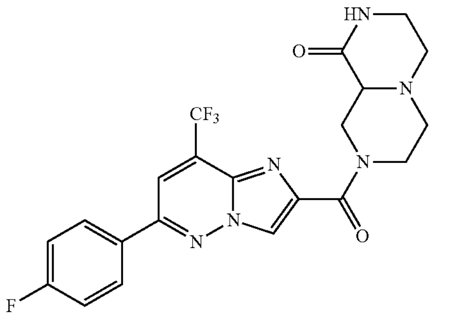
I-59
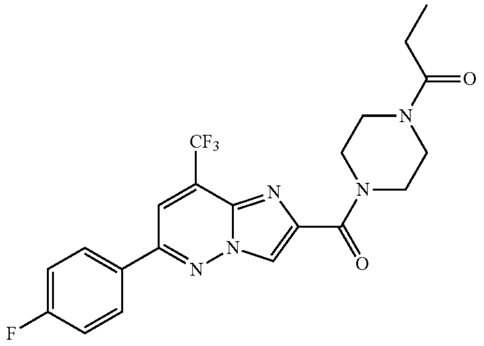

-continued
I-60
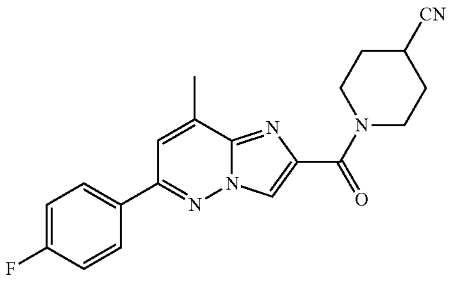
I-61
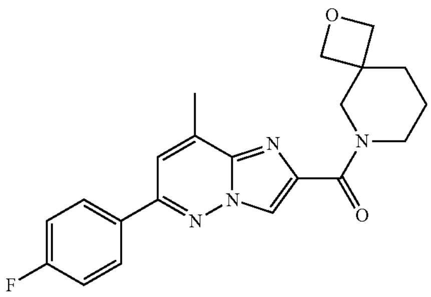
I-62
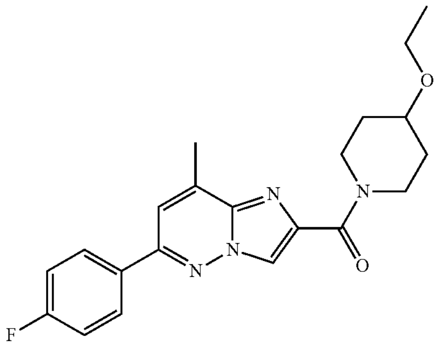
I-63
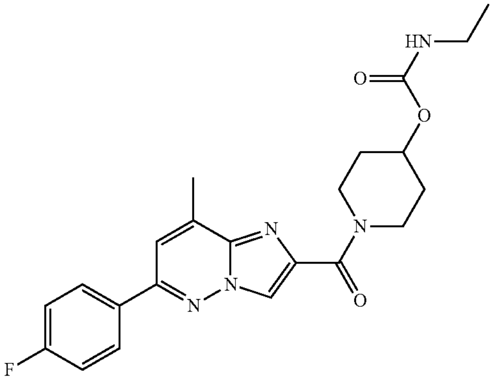
-continued
I-64
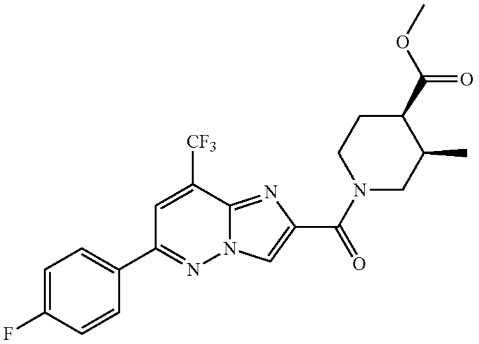
I-65
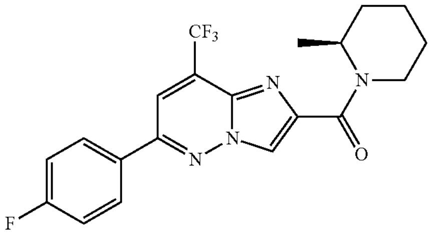
I-66
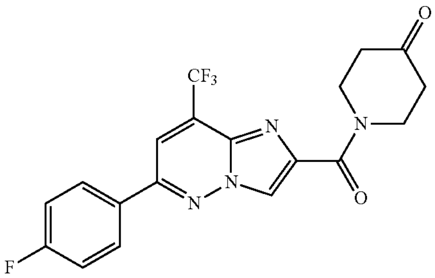
I-67
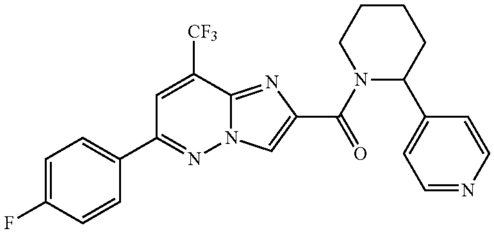
I-68
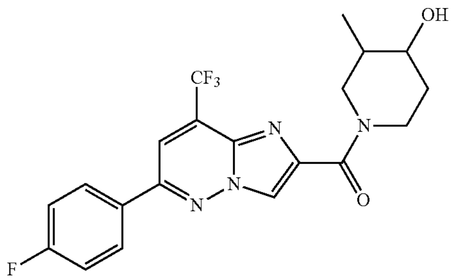

-continued
I-69
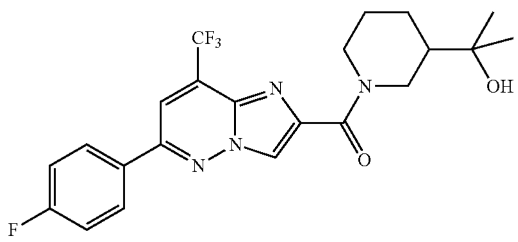
I-70
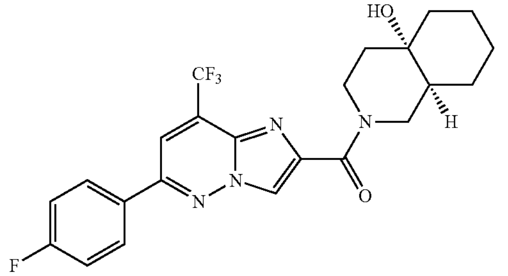
I-71
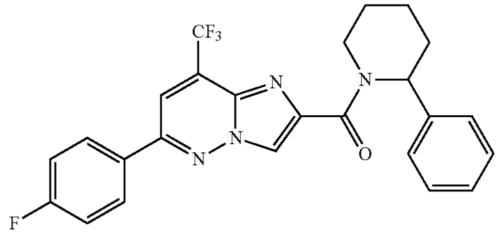
I-72
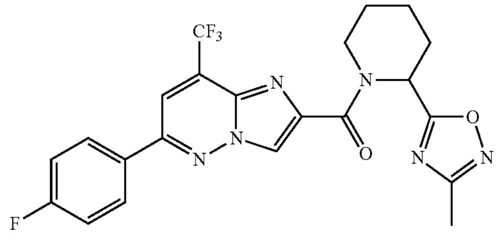
I-73
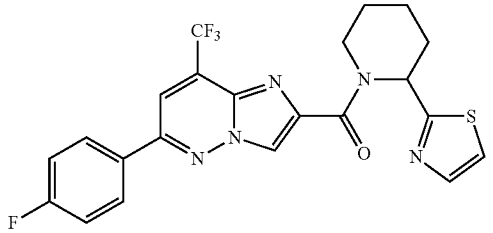
-continued
I-74
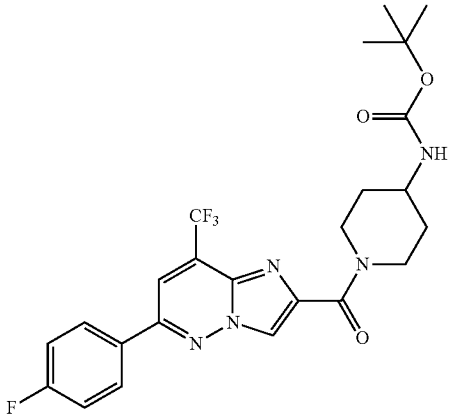
I-75
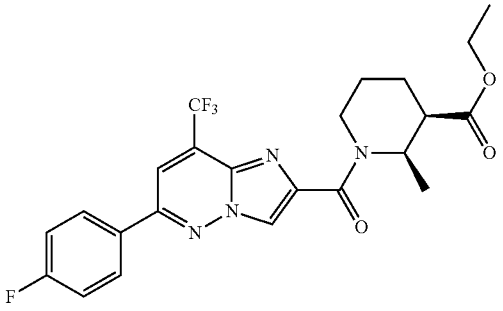
I-76
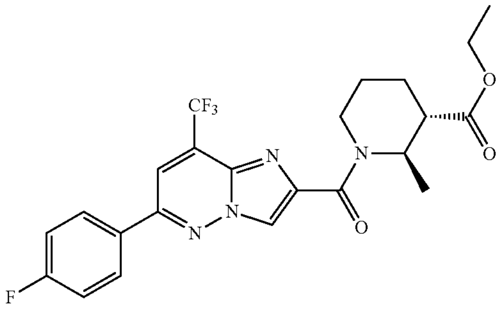
I-77
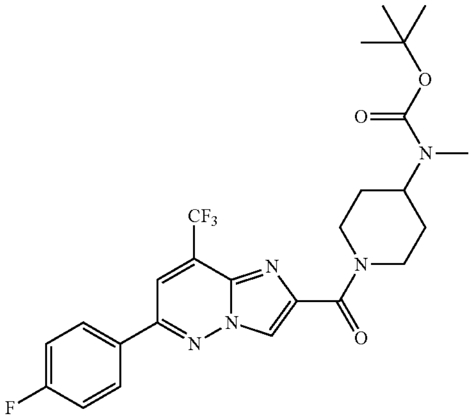

-continued
I-78
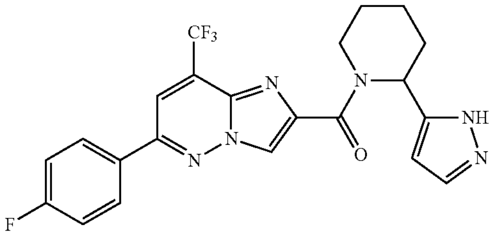
I-79
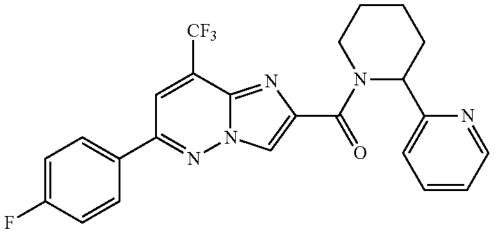
I-80
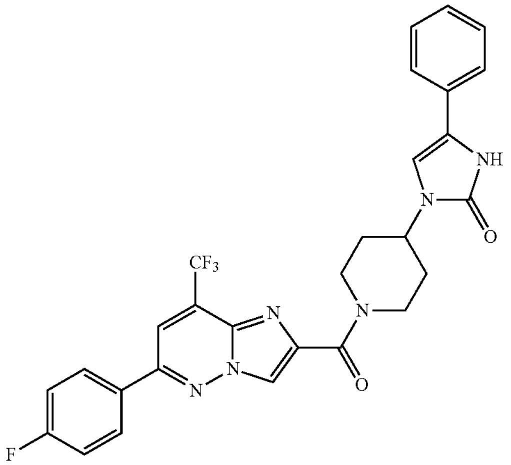
I-81
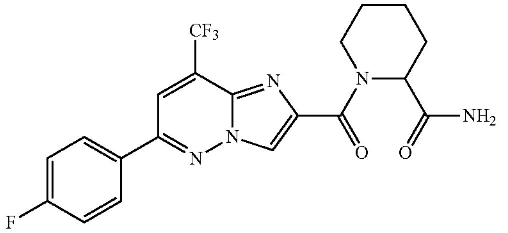
I-82
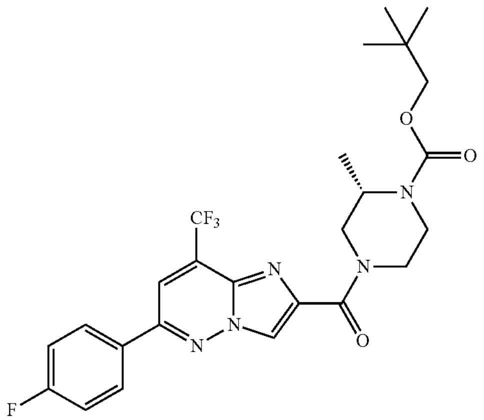
-continued
I-83
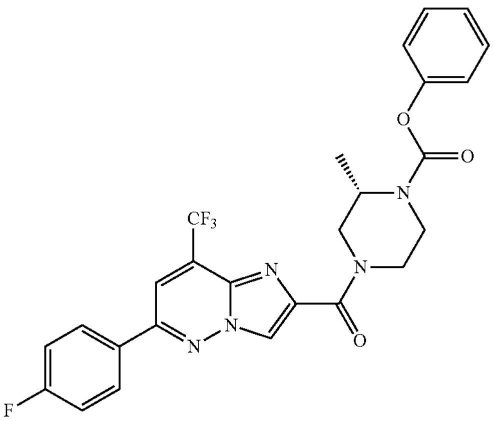
I-84
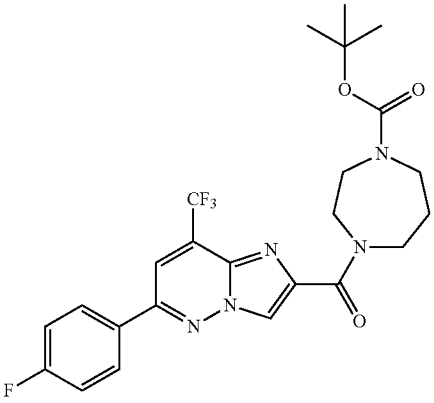
I-85
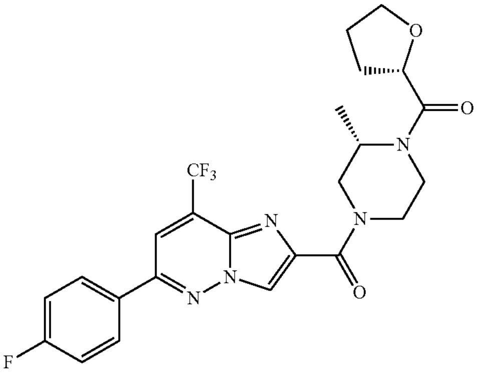
I-86
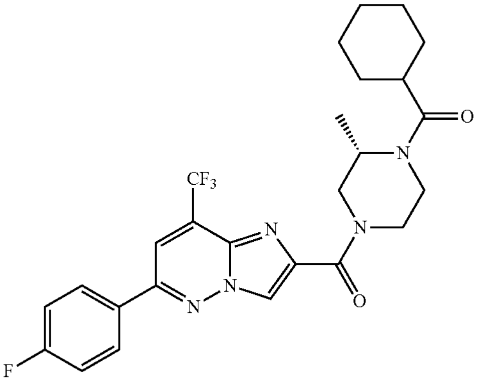

-continued
I-87
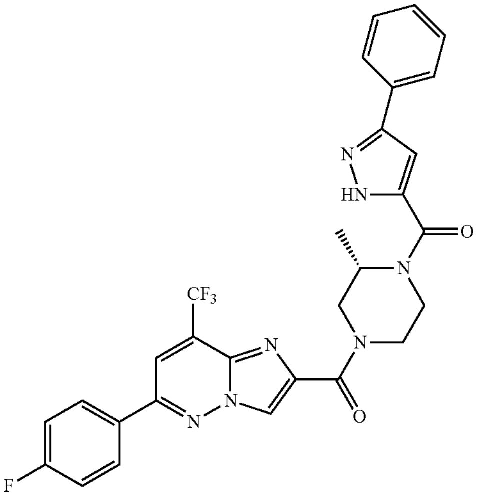
I-88
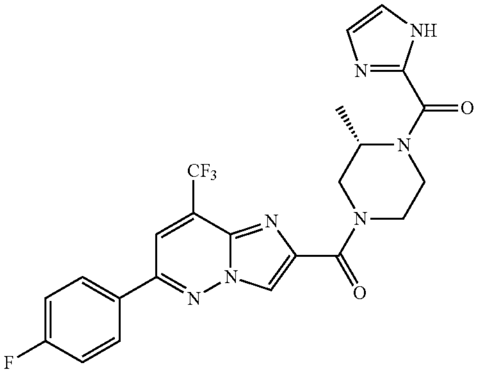
I-89
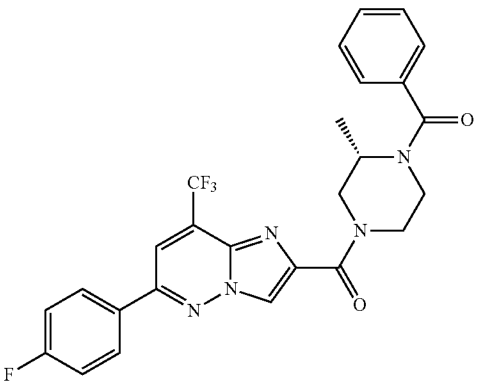
-continued
I-90
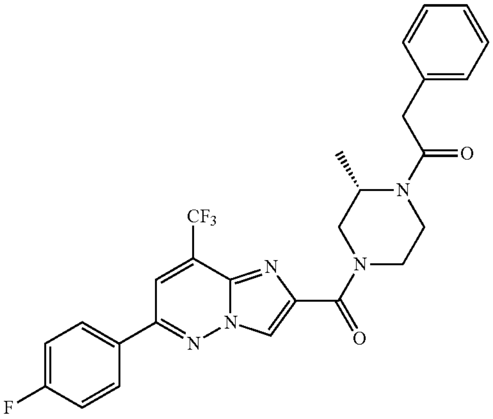
I-91
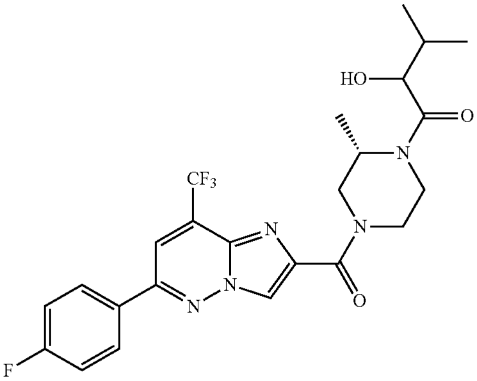
I-92
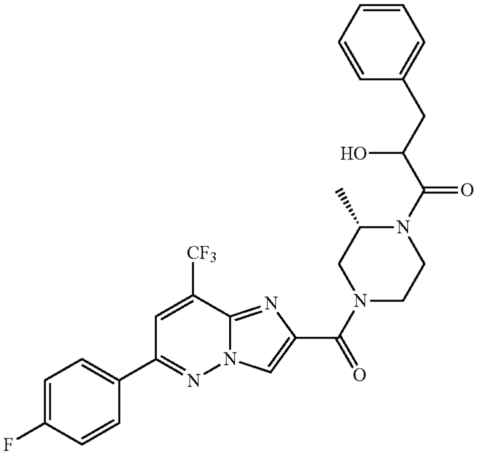

-continued
I-93
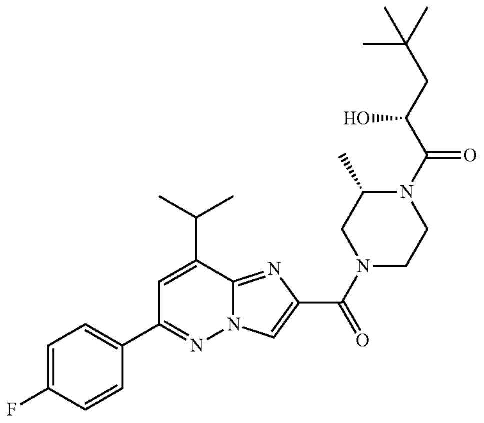
I-94
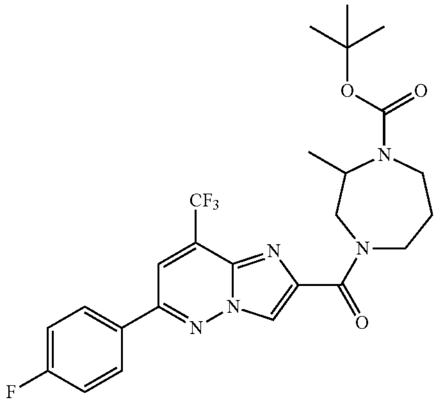
I-95
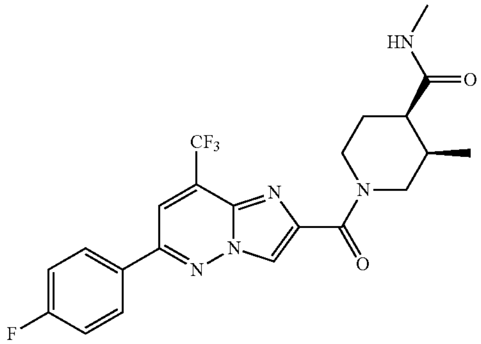
I-96
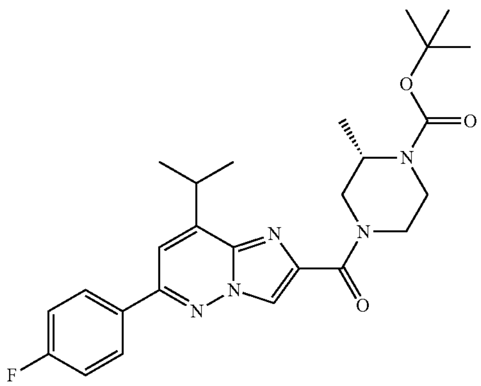
-continued
I-97
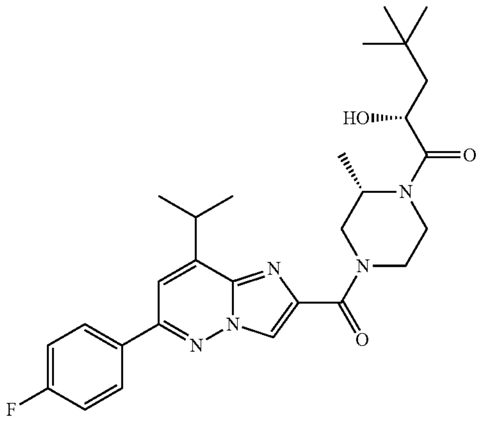
I-98
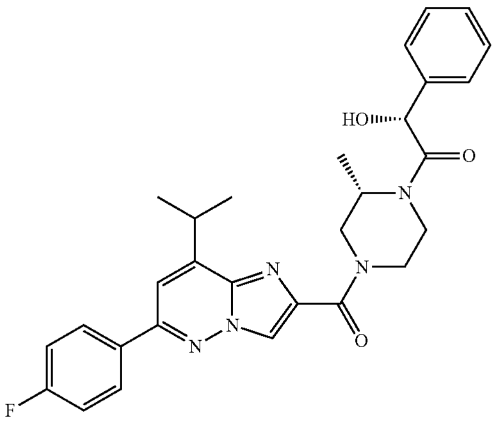
I-99
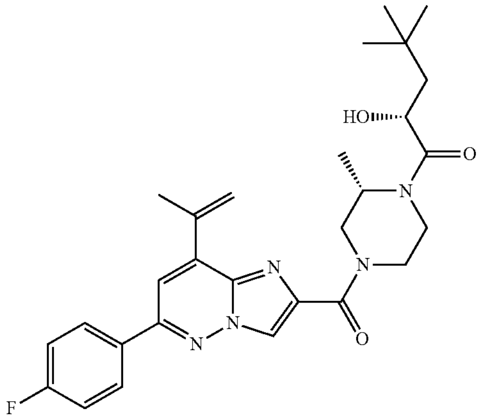

-continued
I-100
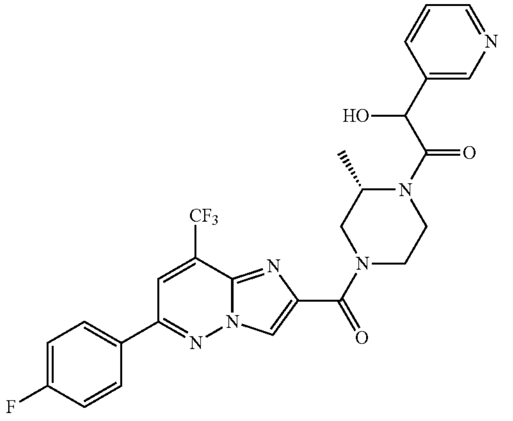
I-101
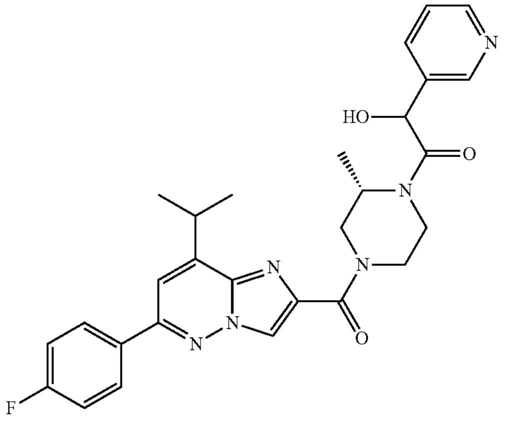
I-102
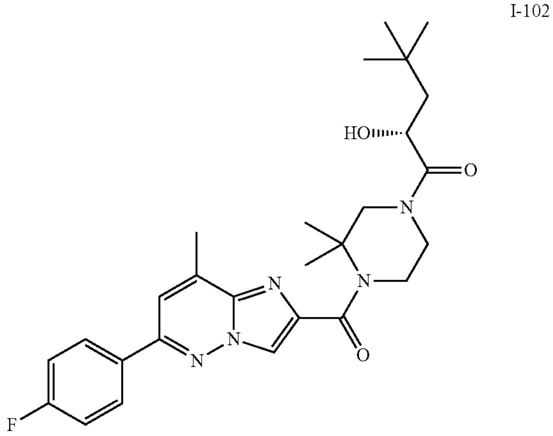
-continued
I-103
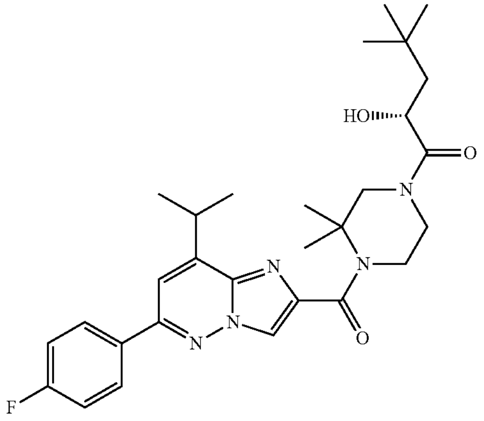
I-104
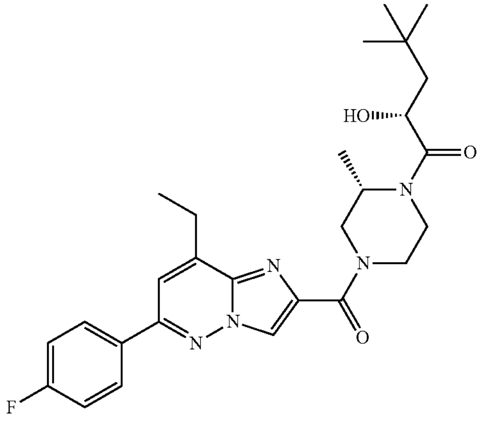
I-105
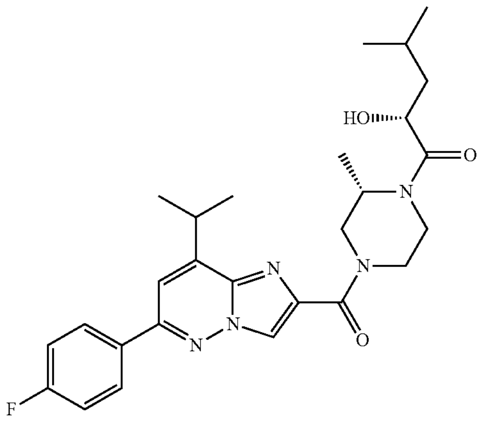

-continued
I-106
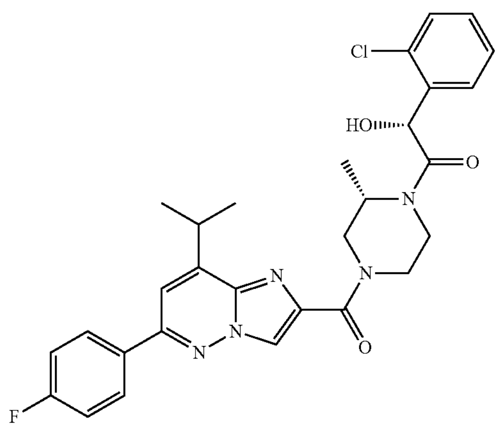
I-107
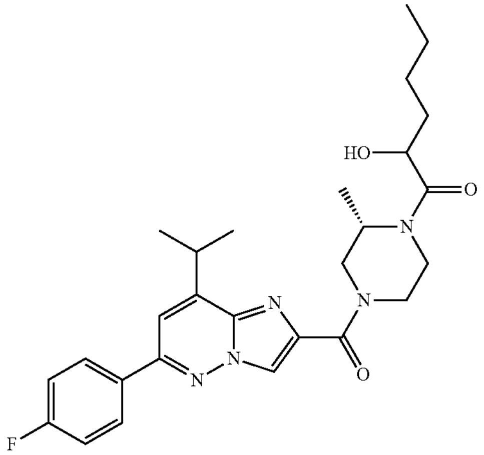
I-108
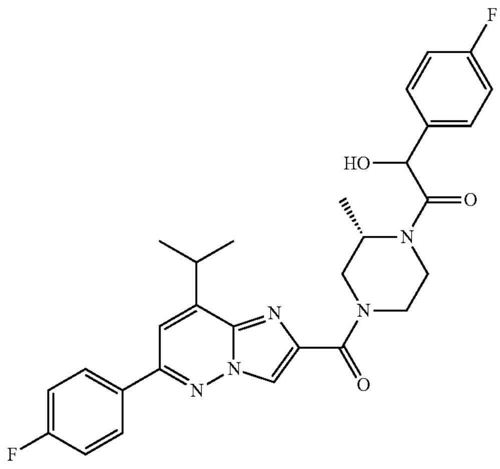
-continued
I-109
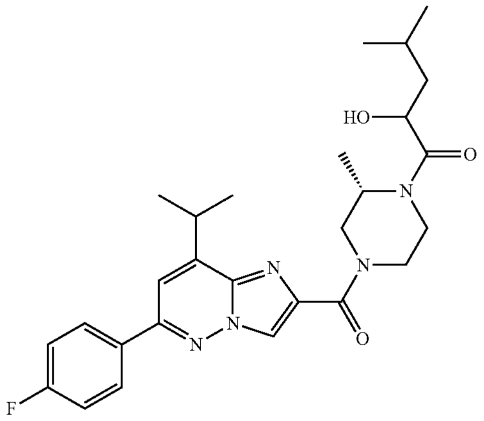
I-110
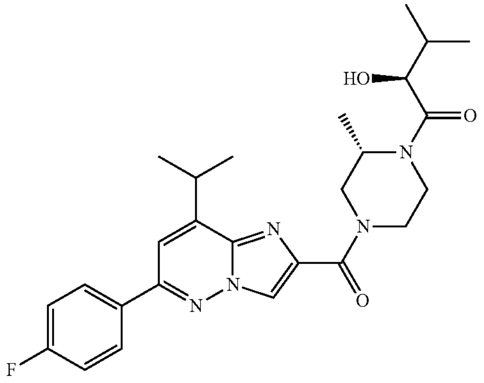
I-111
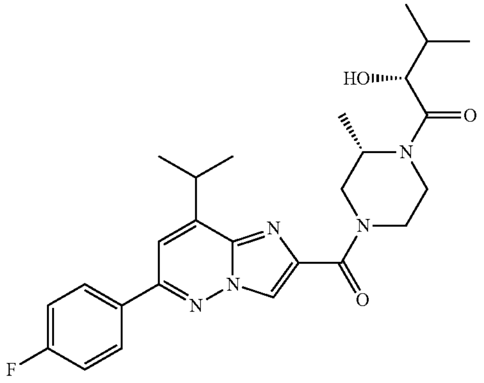
I-112
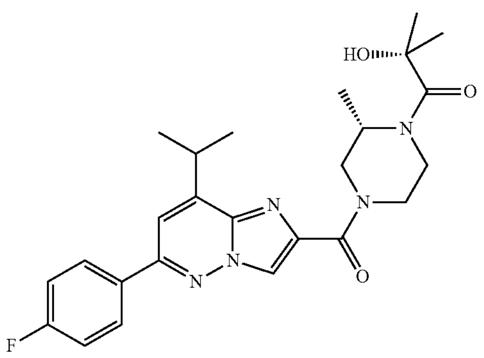

-continued
I-113
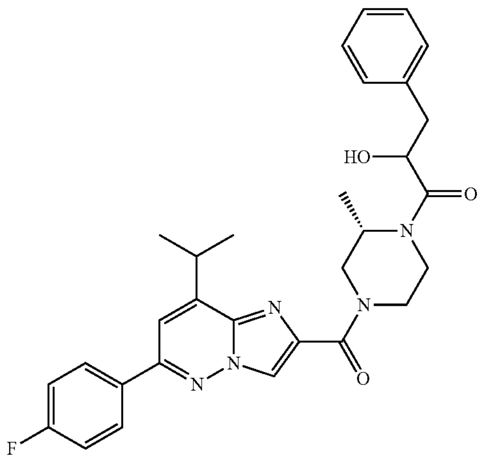
I-114
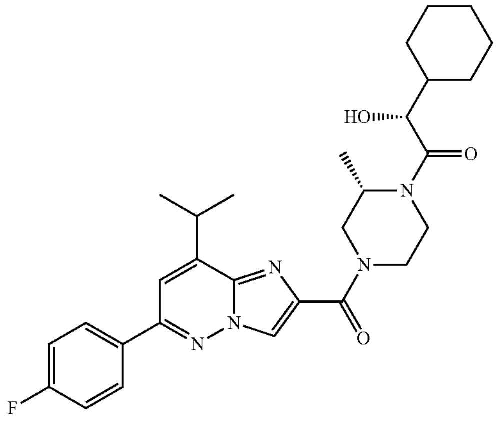
I-115
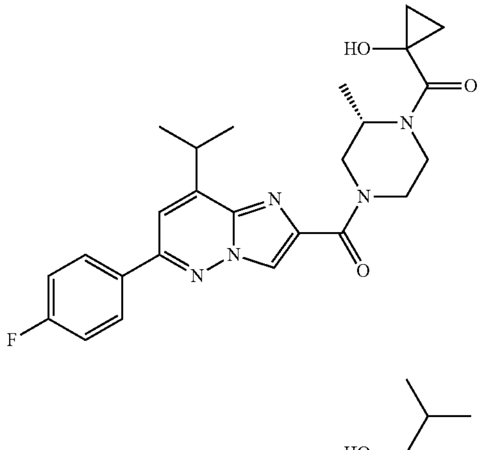
I-116
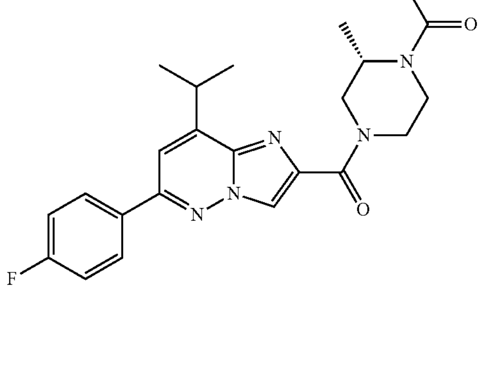
-continued
I-117
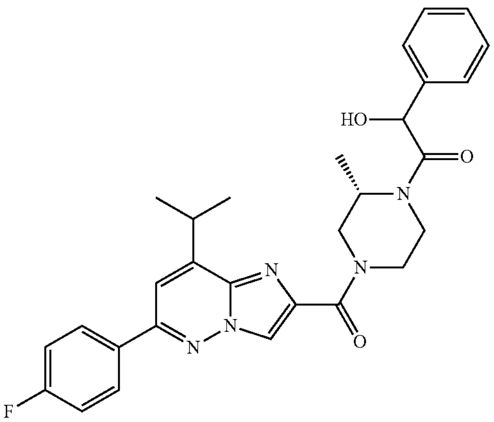
I-118
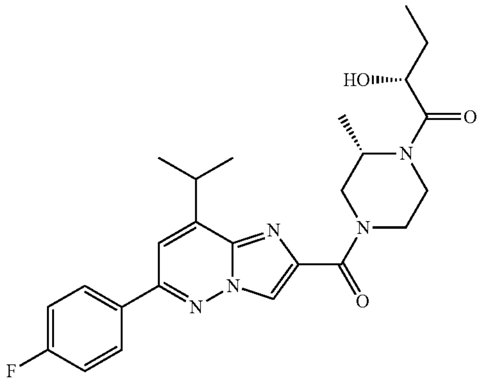
I-119
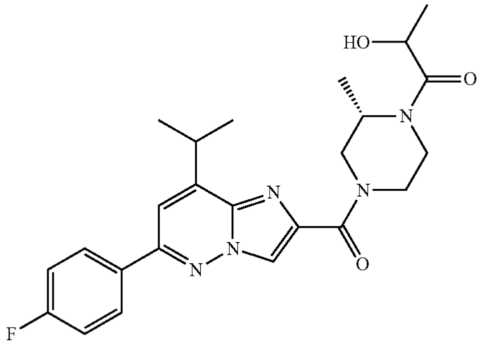
I-120
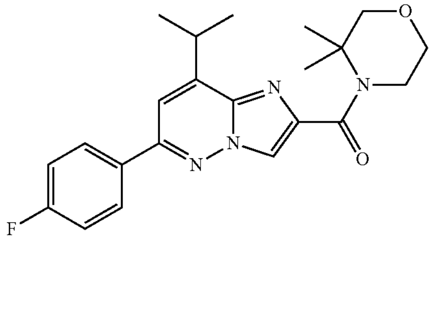

-continued
I-121
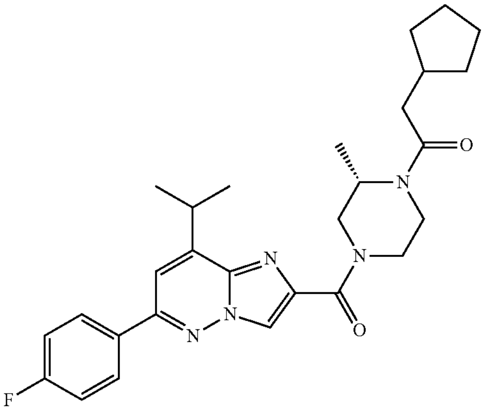
I-122
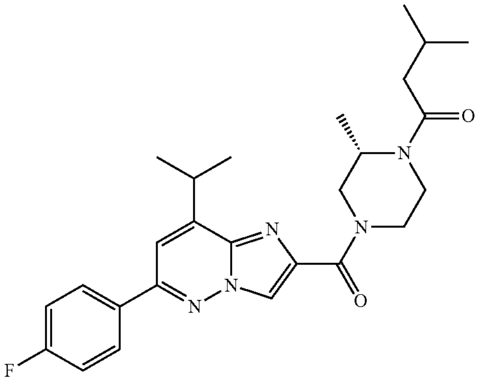
I-123
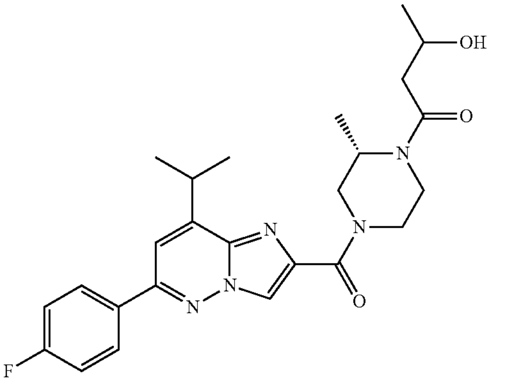
I-124
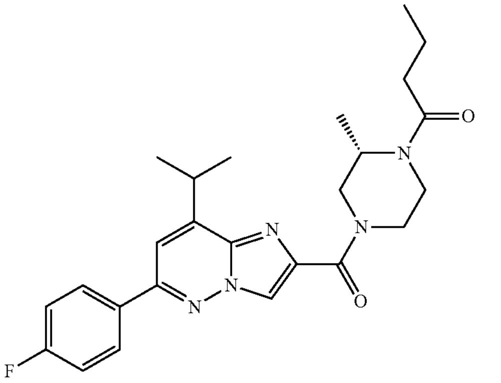
-continued
I-125
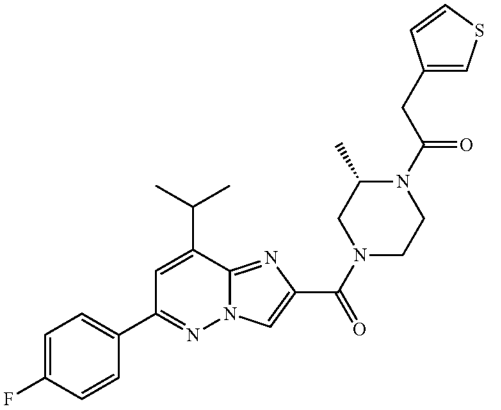
I-126
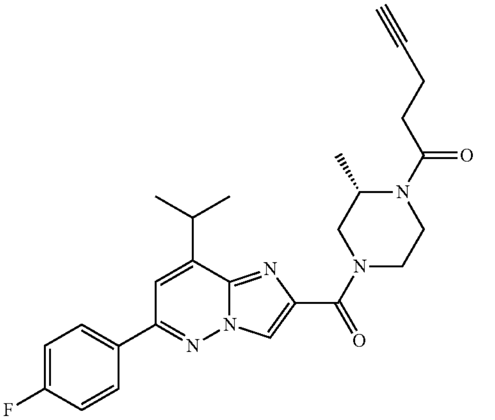
I-127
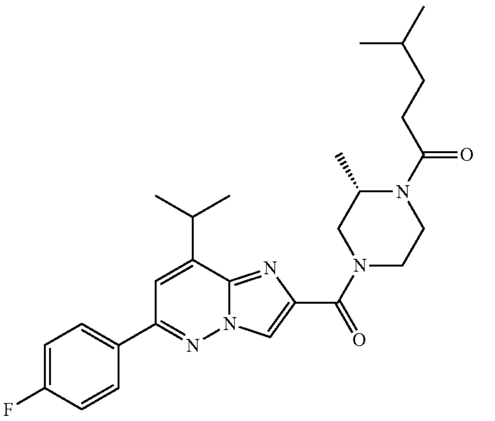

-continued
I-128
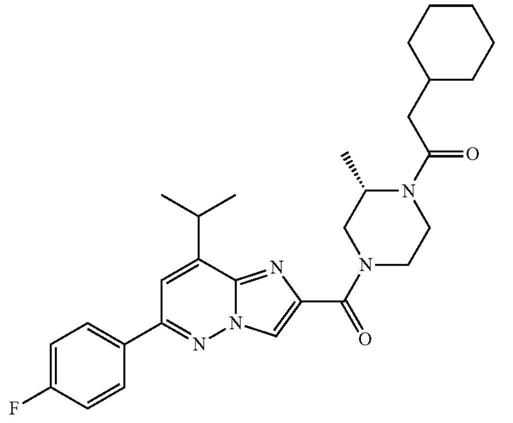
I-129
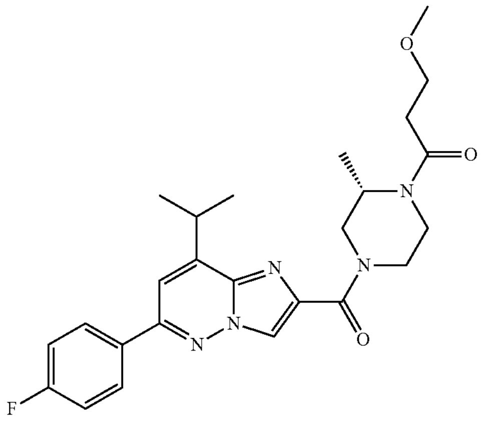
I-130
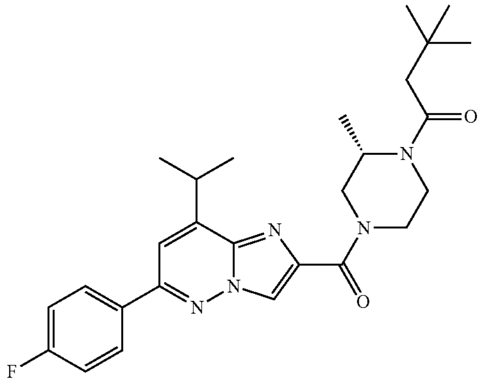
I-131
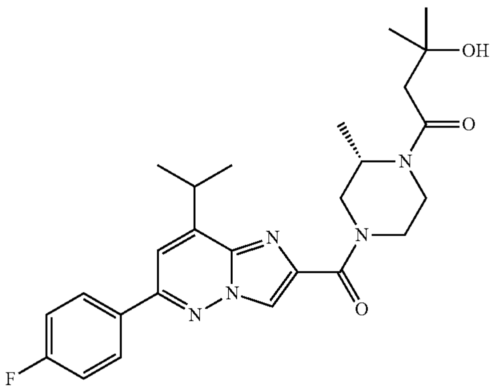
-continued
I-132
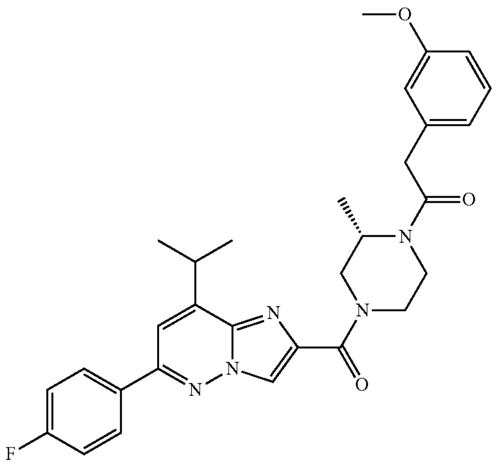
I-133
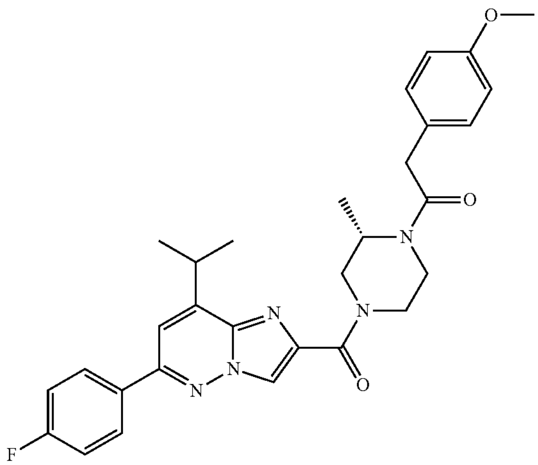
I-134
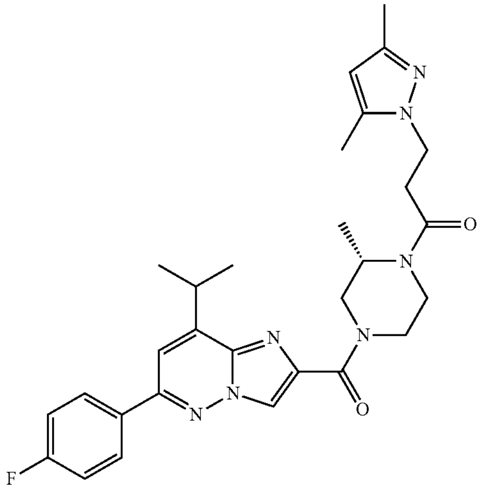

-continued
I-135
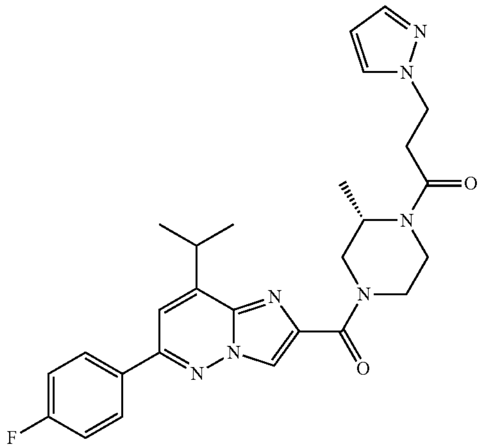
I-136
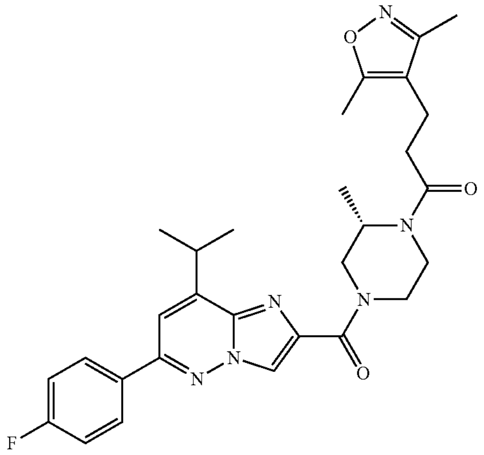
I-137
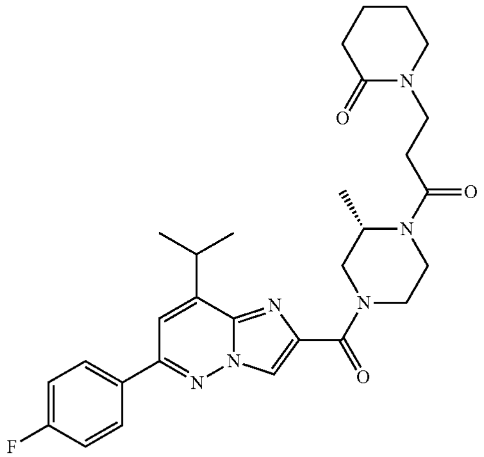
-continued
I-138
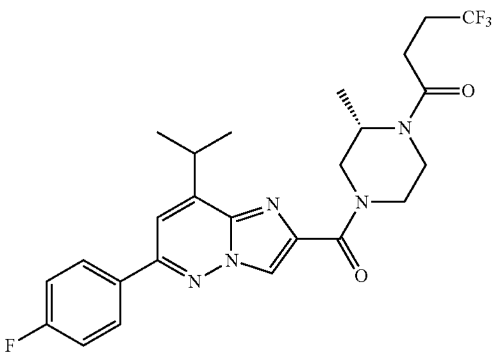
I-139
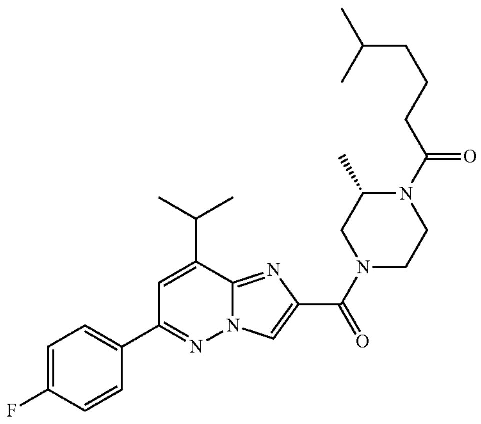
I-140
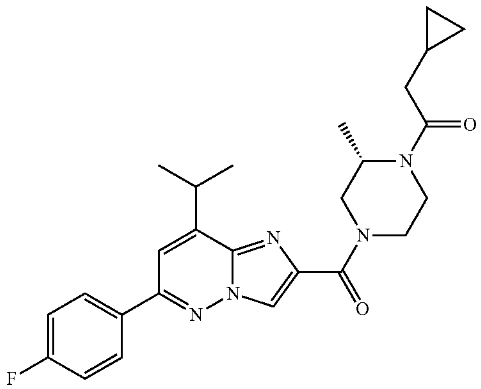

-continued
I-141
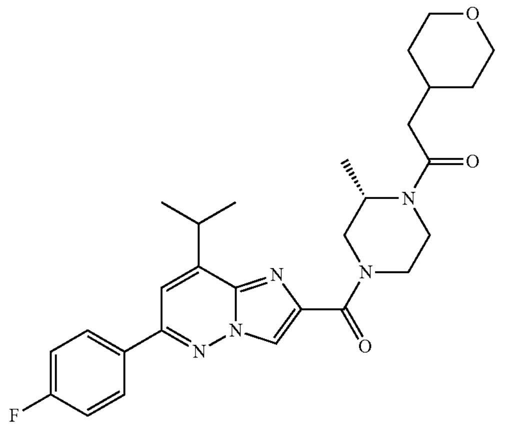
I-142
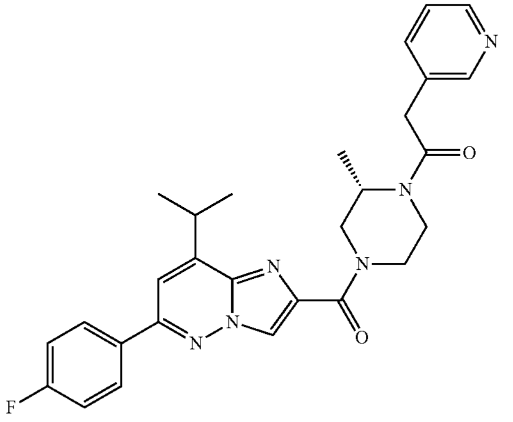
I-143
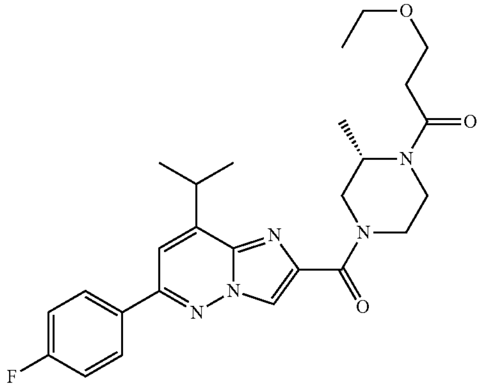
-continued
I-144
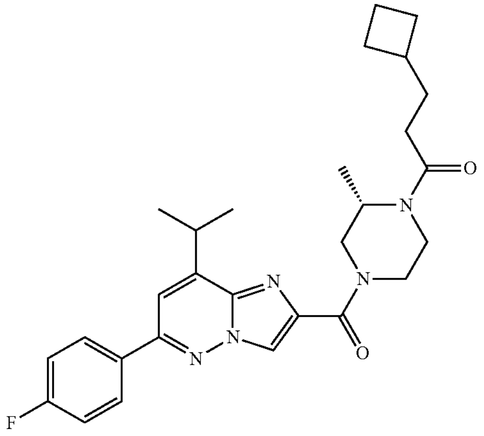
I-145
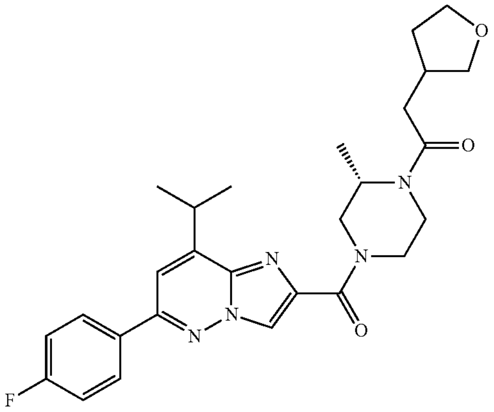
I-146
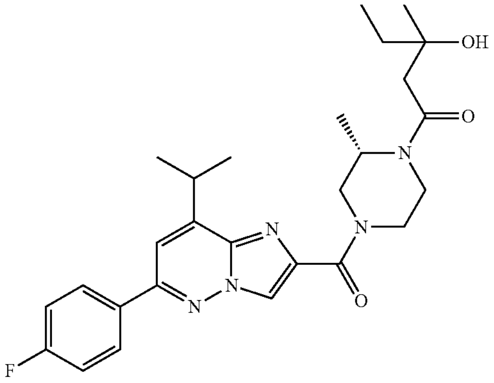
I-147
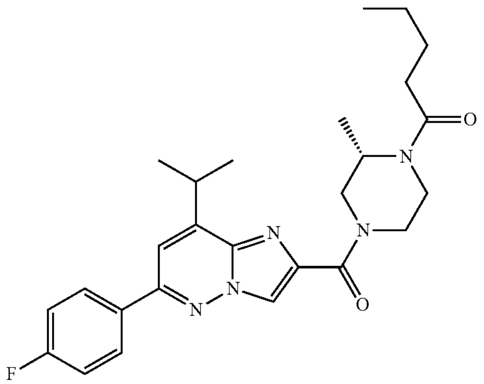

-continued
I-148
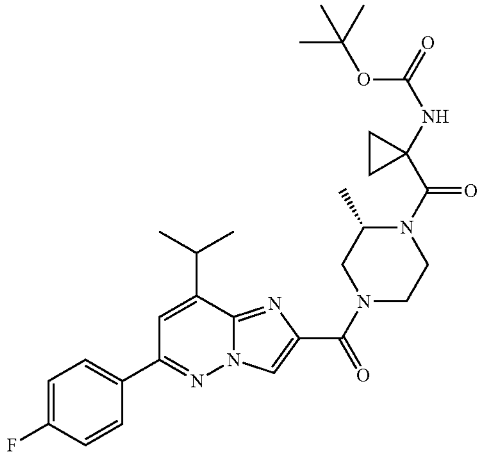
I-149
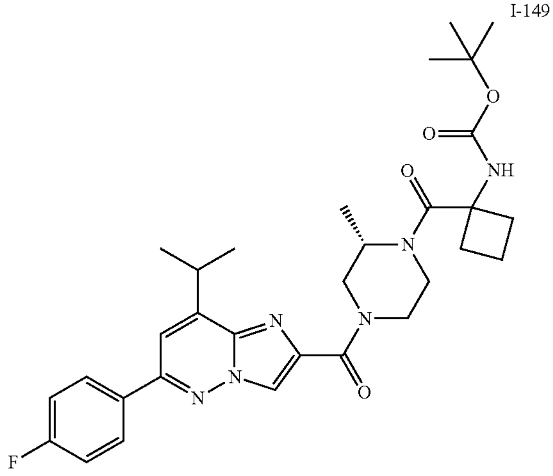
I-150
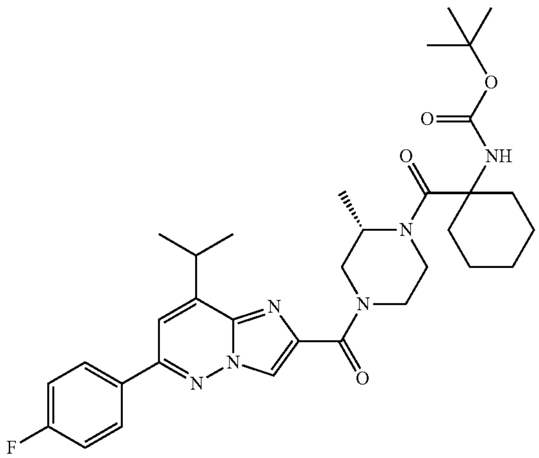
-continued
I-151
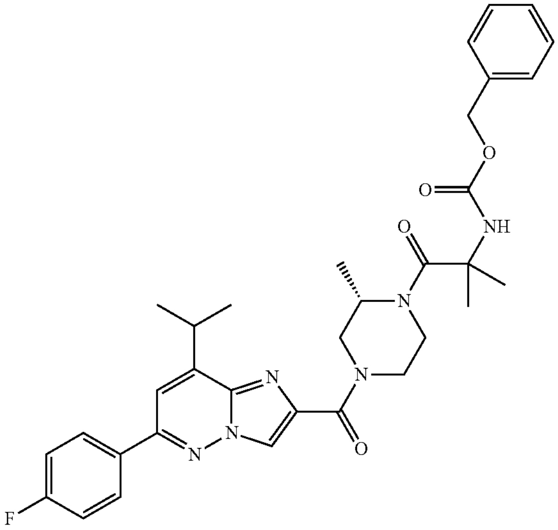
I-152
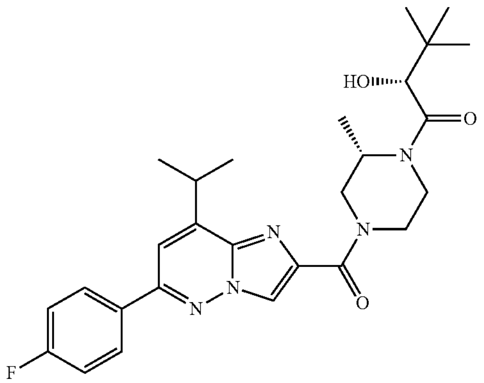
I-153
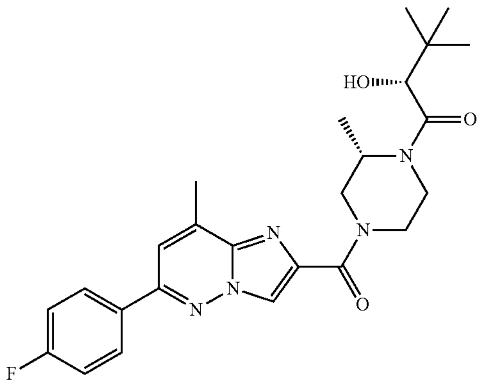

-continued
I-154
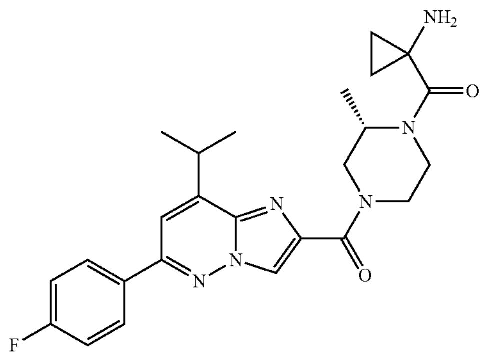
I-155
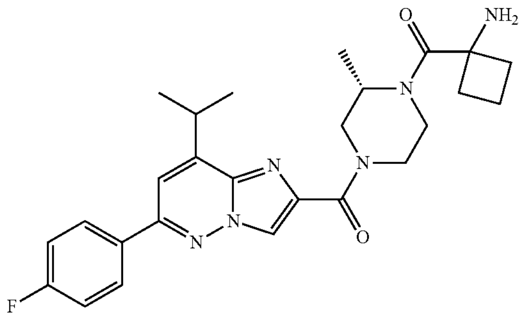
I-156
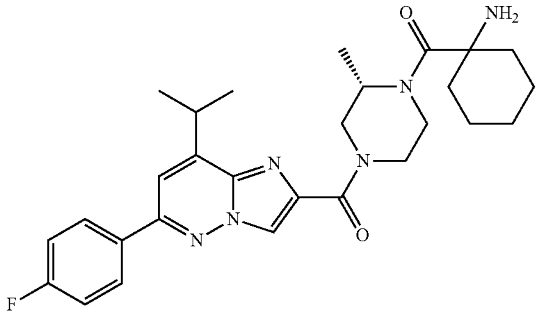
I-157
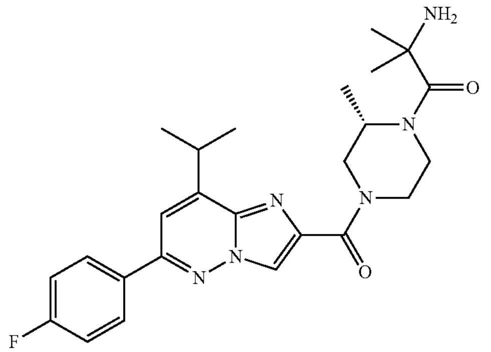
-continued
I-158
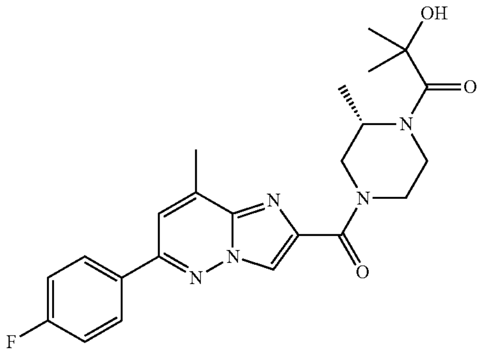
I-159
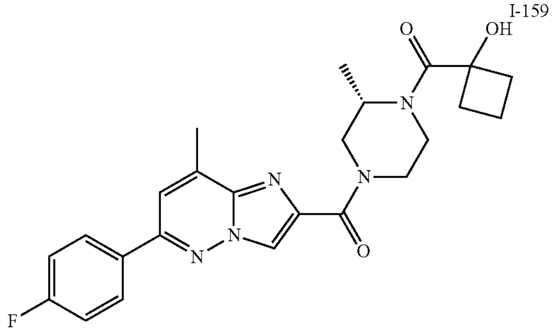
I-160
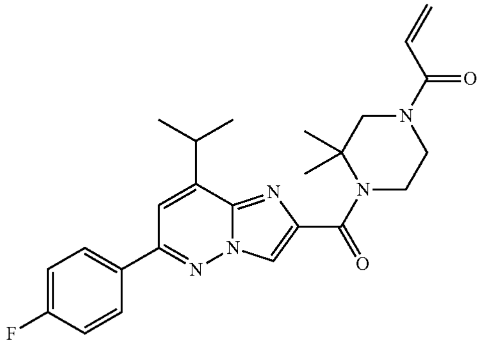
I-161
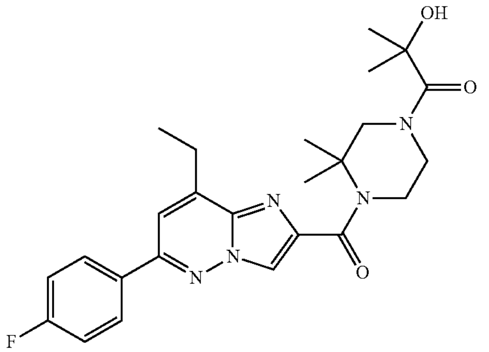

I-162
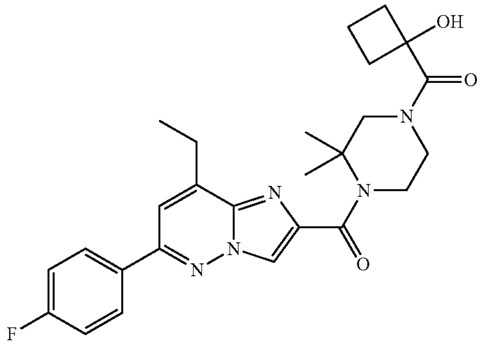
I-163
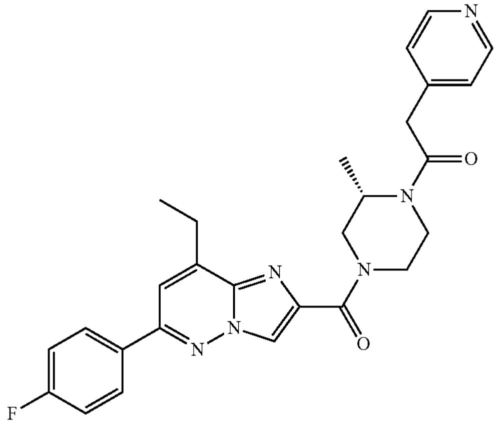
I-164
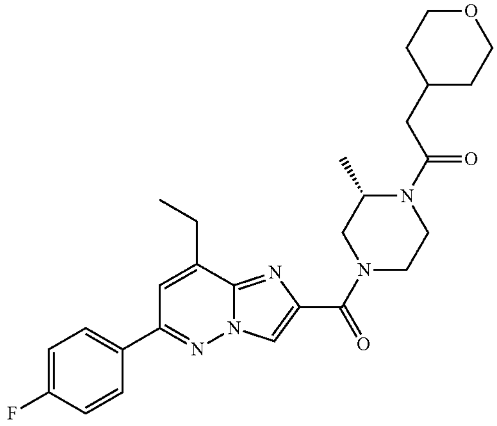
I-165
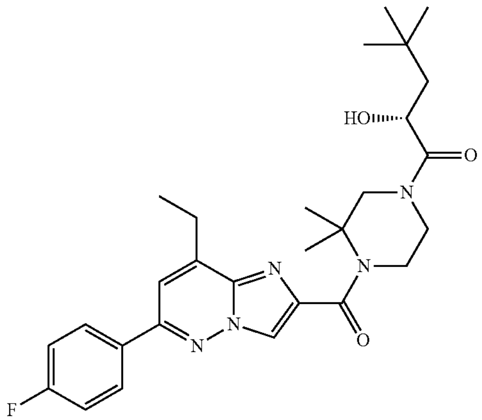
I-166
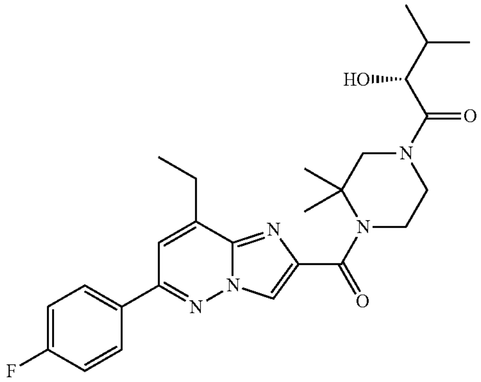
I-167
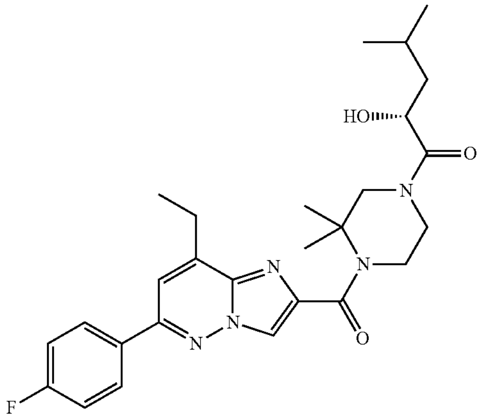
I-168
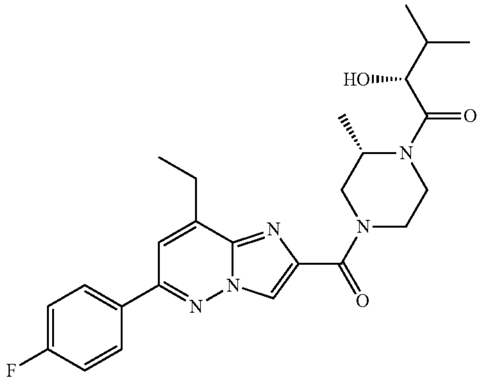
I-169
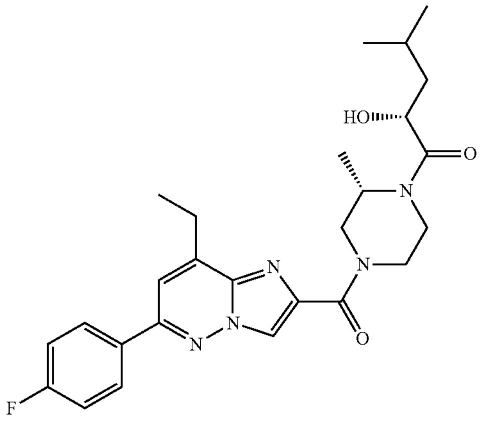

-continued
I-170
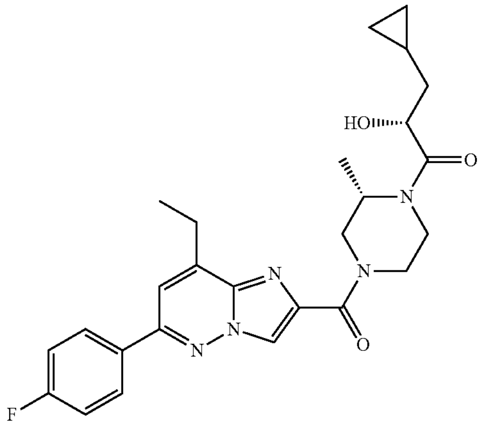
I-171
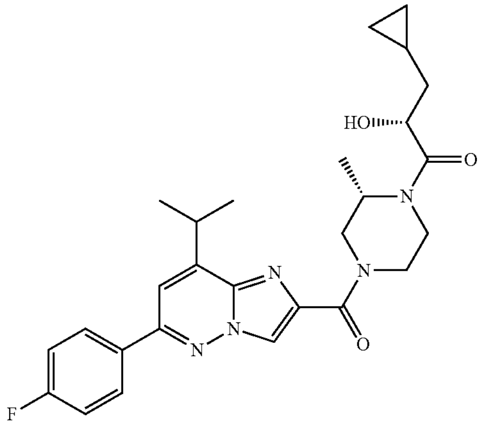
I-172
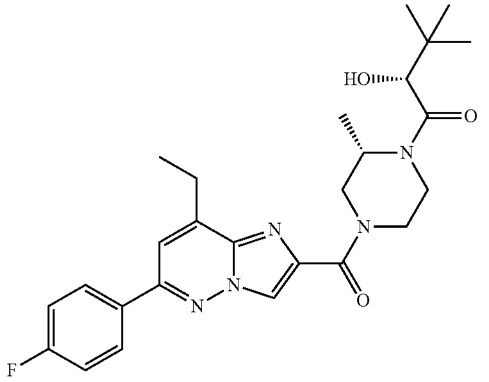
-continued
I-173
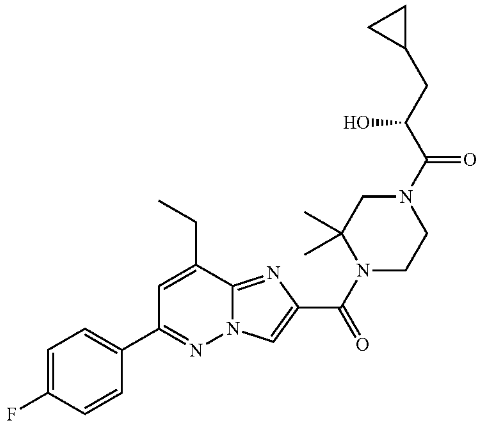
I-174
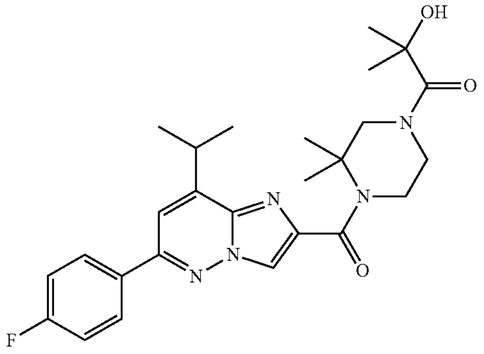
I-175
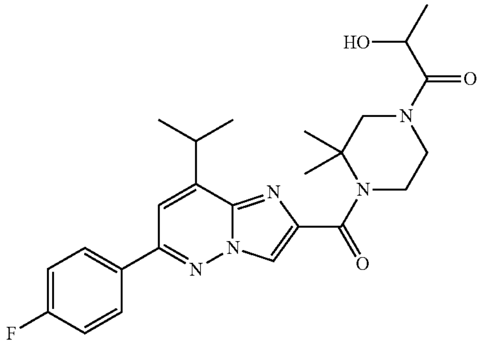
I-176
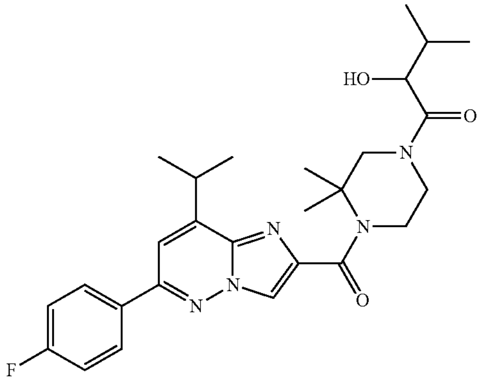

-continued
I-177
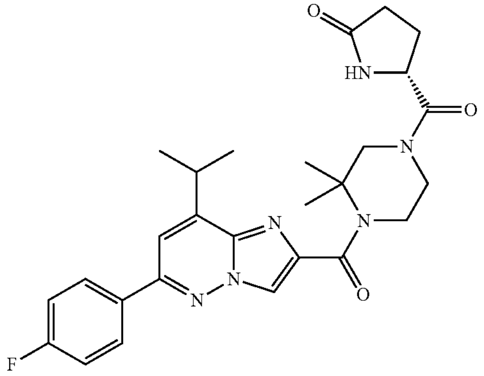
I-178
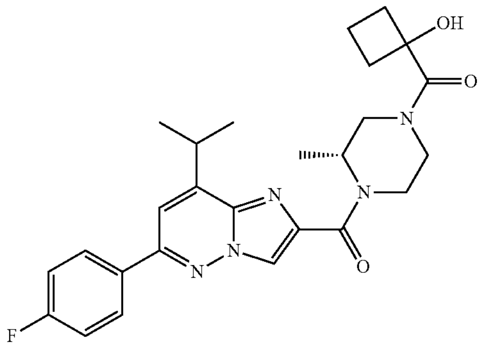
I-179
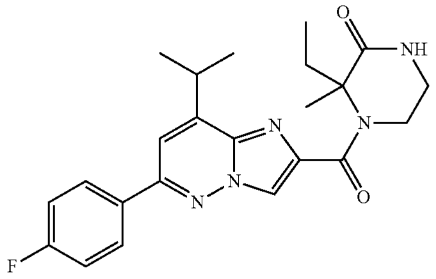
I-180
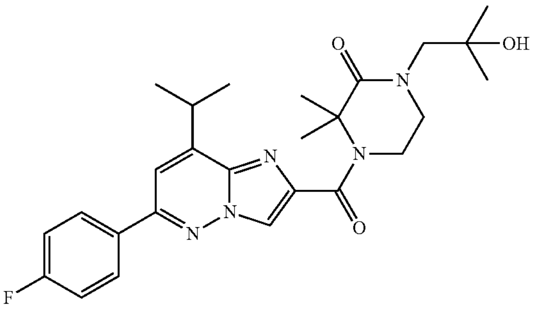
-continued
I-181
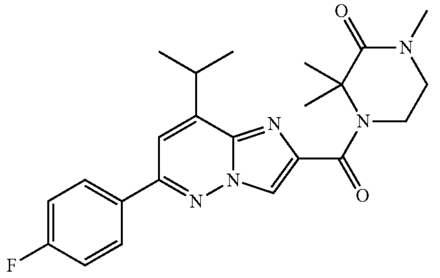
Another embodiment provides a compound represented by any one of the following structural formulae or a pharmaceutically acceptable salt thereof:
I-182
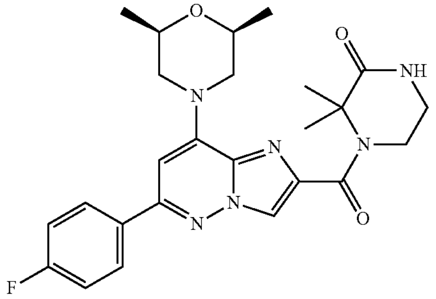
I-183
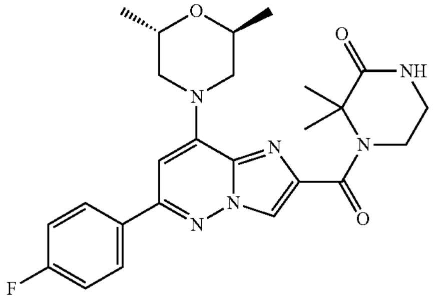
I-184
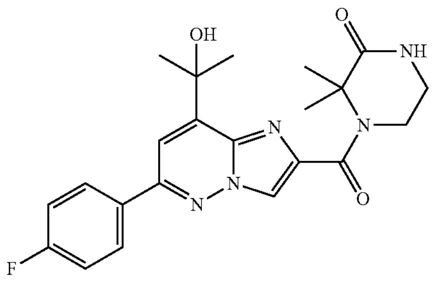

I-185
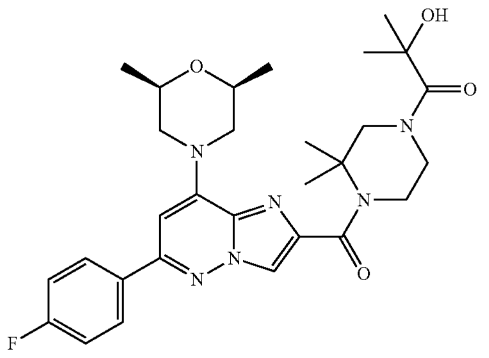
I-186
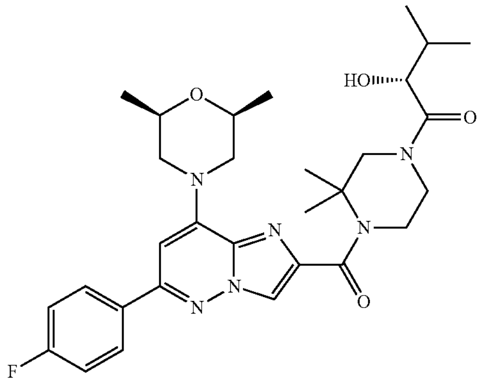
I-187
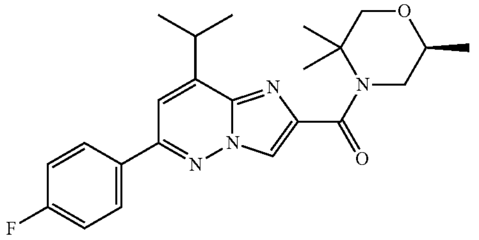
I-188
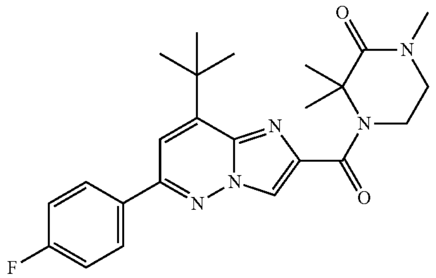
I-189
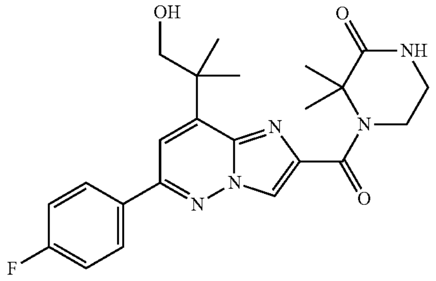
I-190
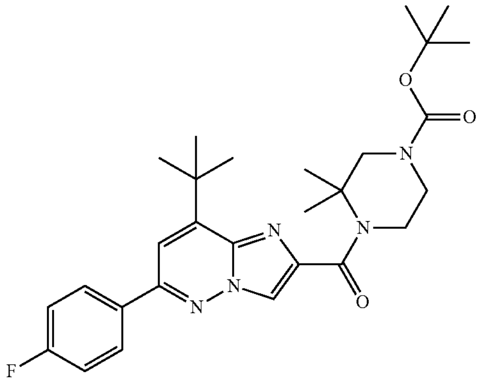
I-191
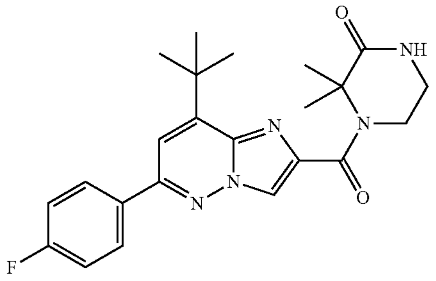
I-192
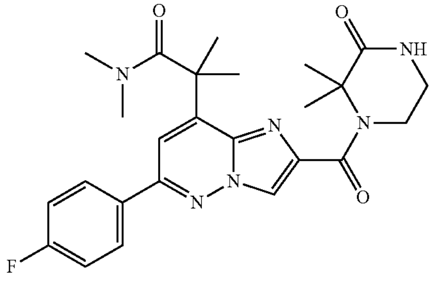
I-193
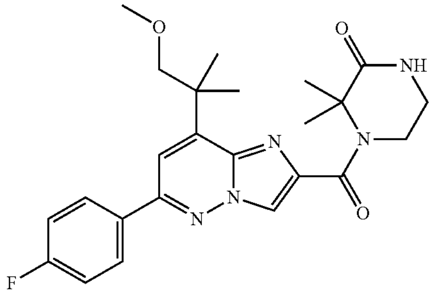
I-194
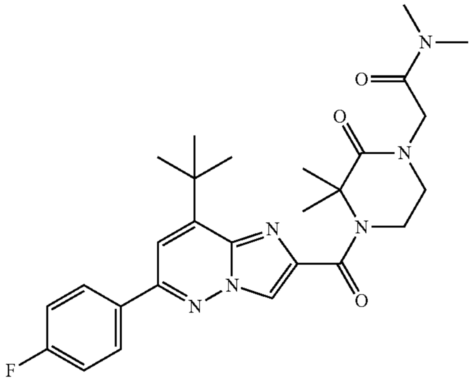

-continued
I-195
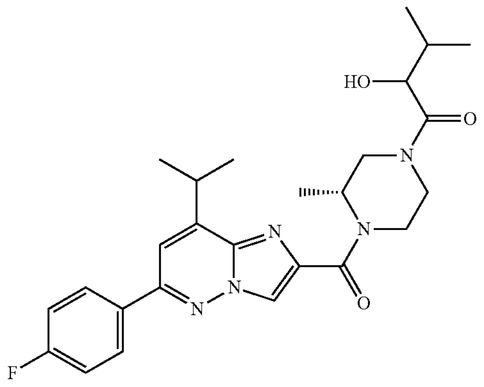
I-196
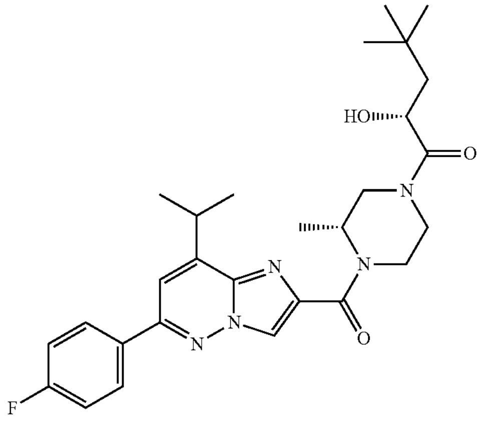
I-197
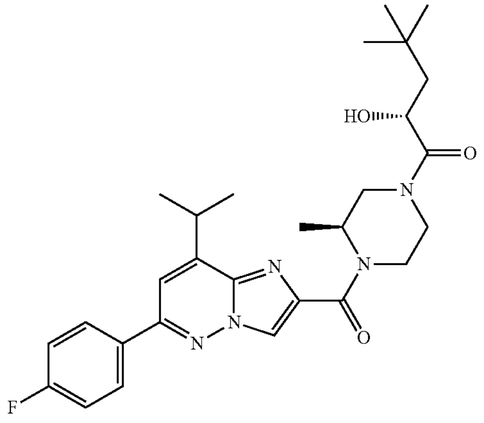
I-198
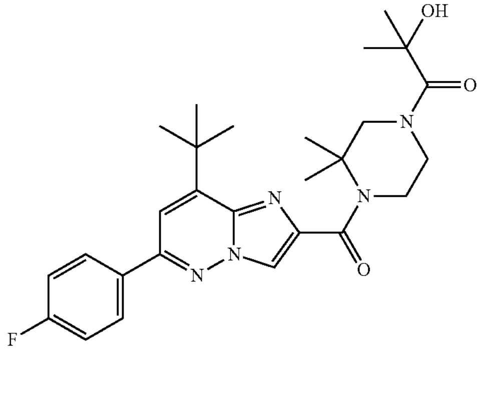
-continued
I-199
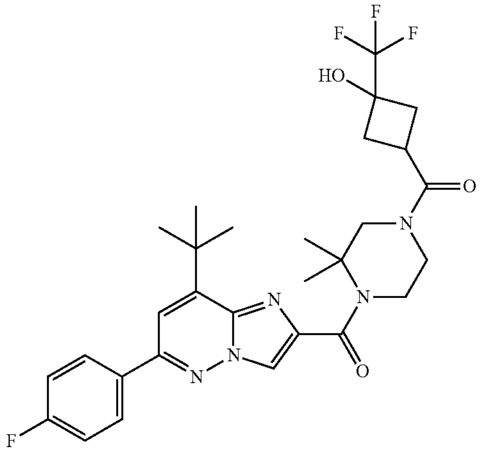
I-200
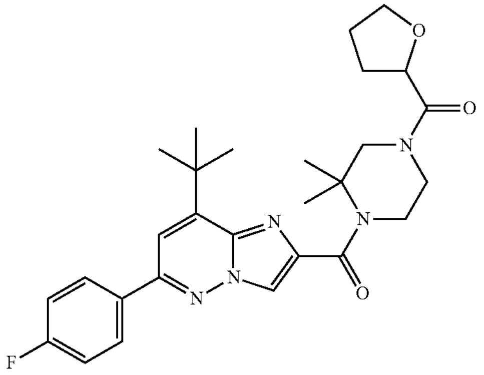
I-201
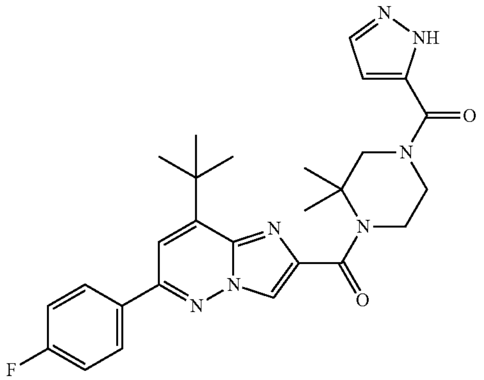
I-202
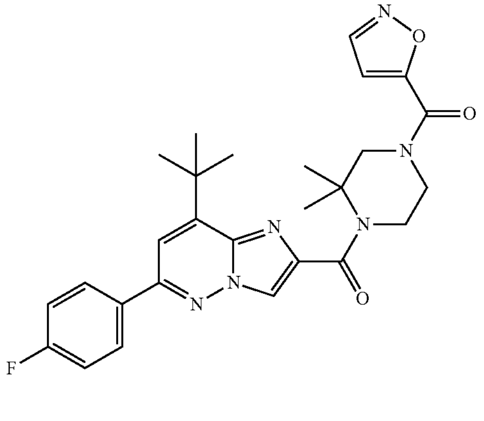

-continued
I-203
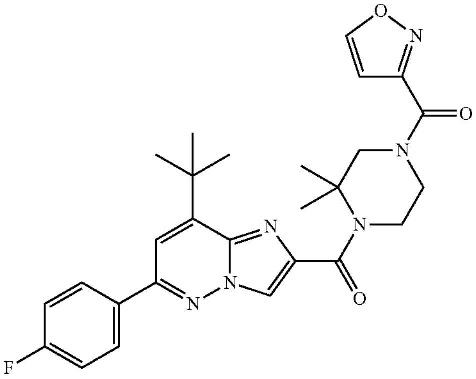
I-204
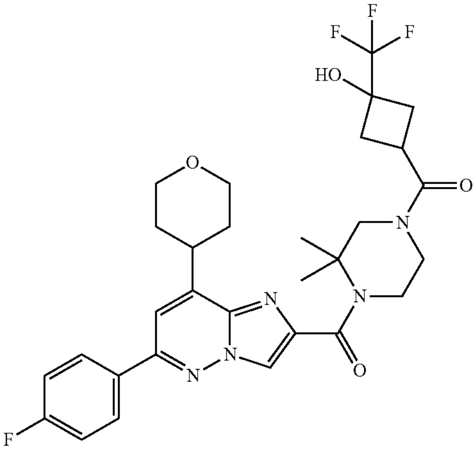
I-205
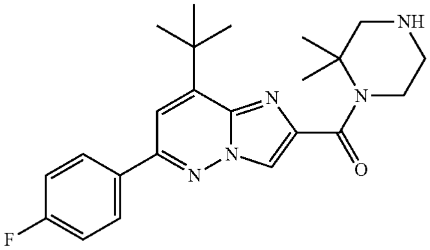
I-206
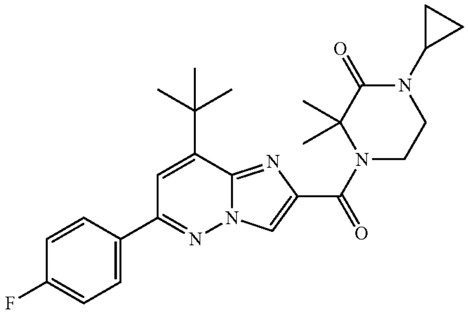
-continued
I-207
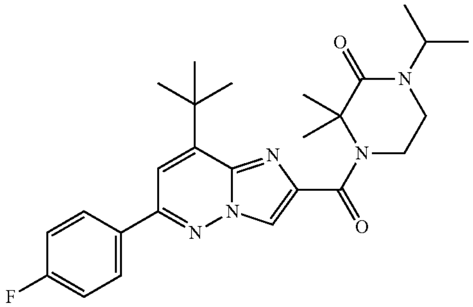
I-208
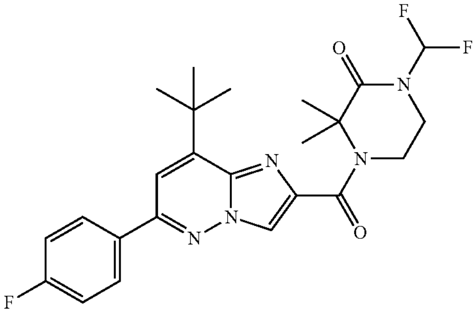
I-209
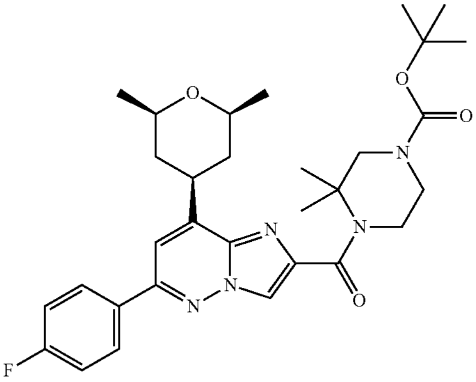
I-210
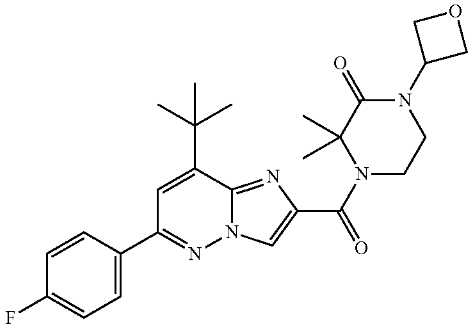
I-211
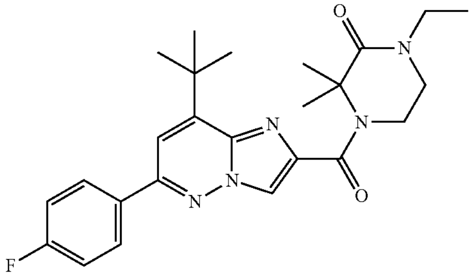

-continued
I-212
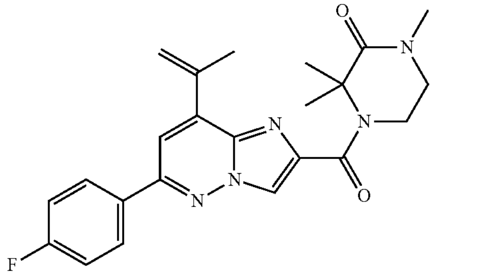
I-213
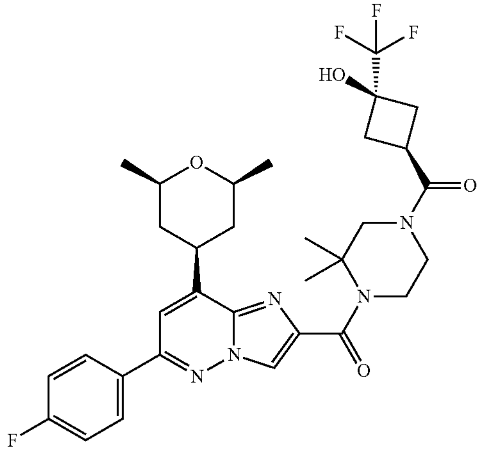
I-214
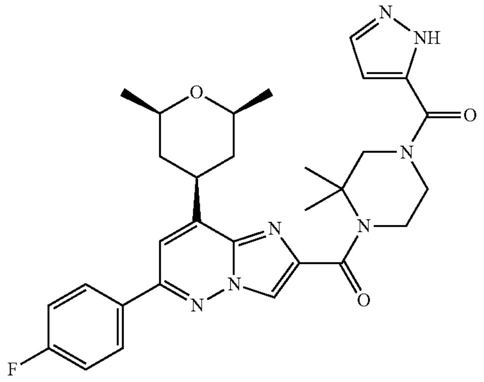
I-215
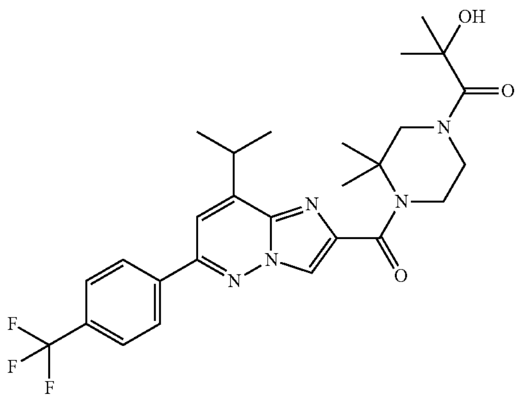
-continued
I-216
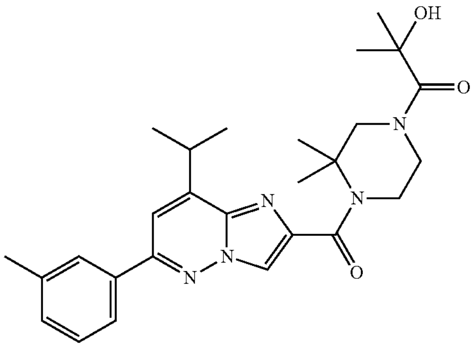
I-217
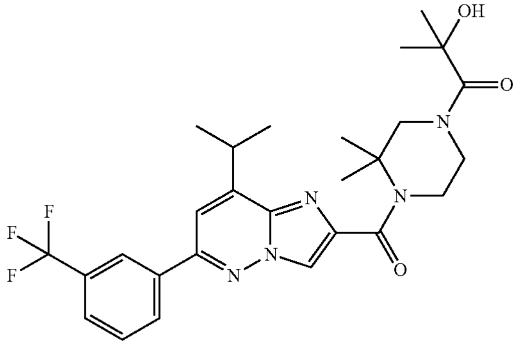
I-218
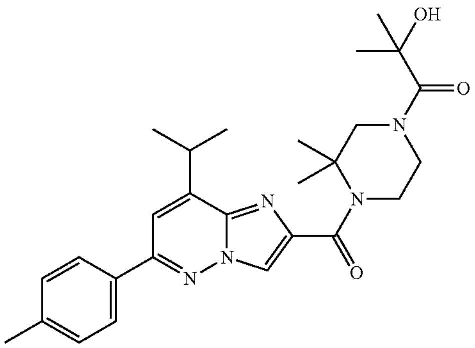
I-219
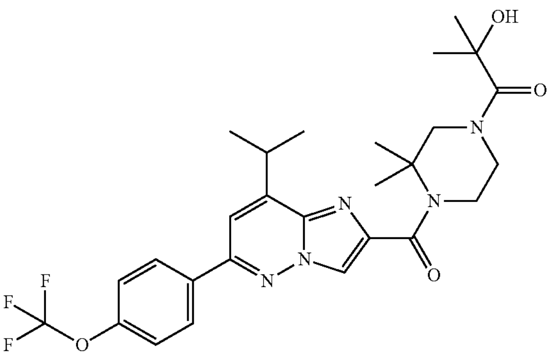

-continued
I-220
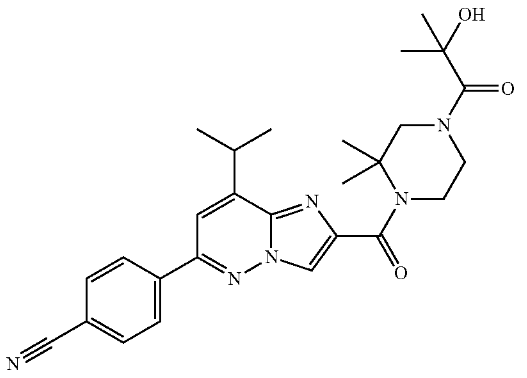
I-221
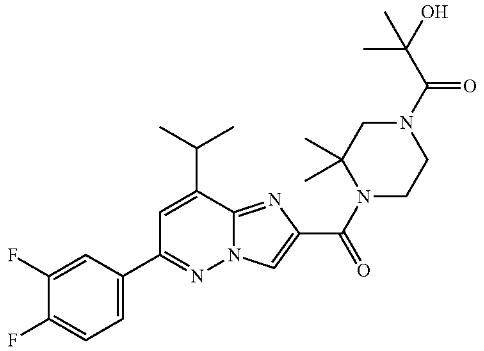
I-222
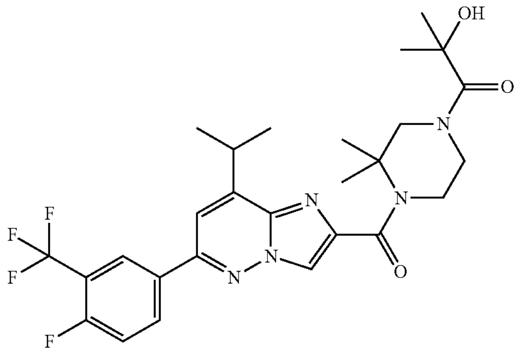
I-223
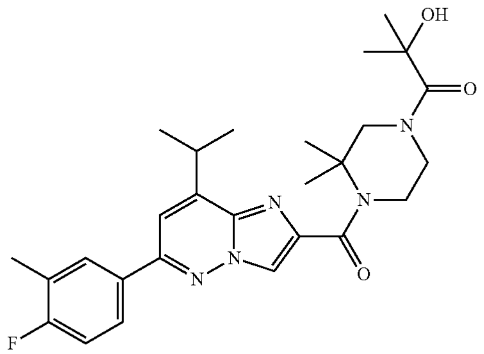
-continued
I-224
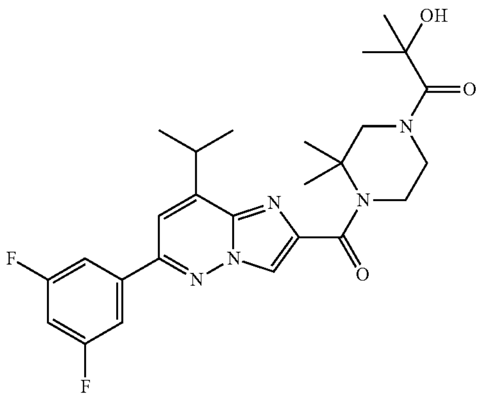
I-225
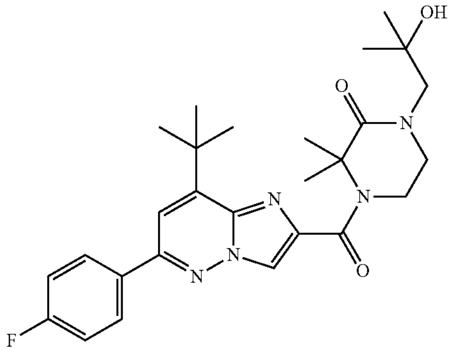
I-226
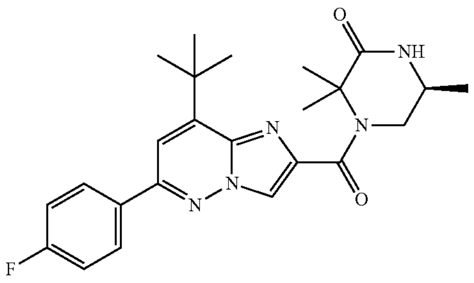
I-227
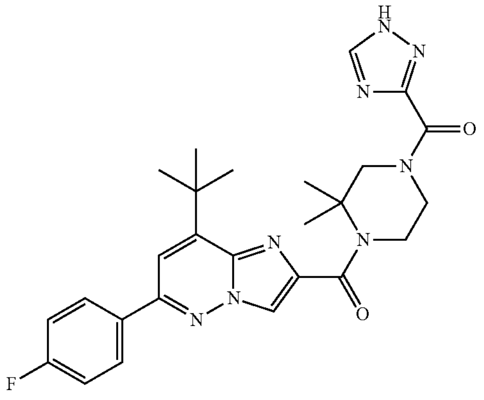

I-228
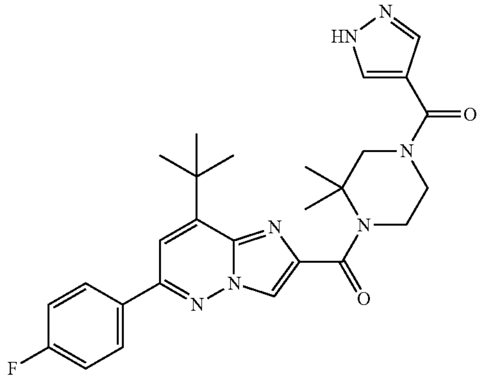
I-229
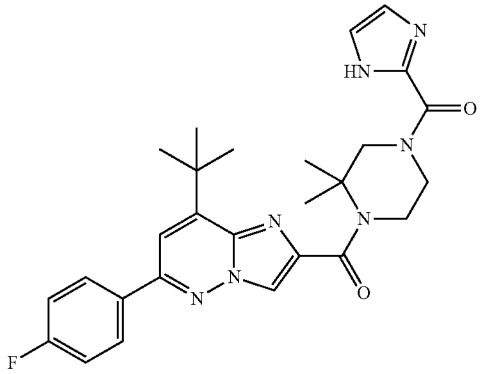
I-230
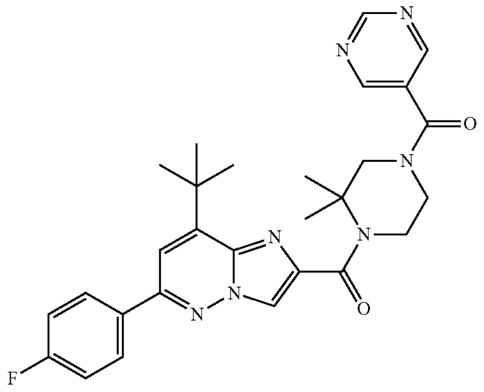
I-231
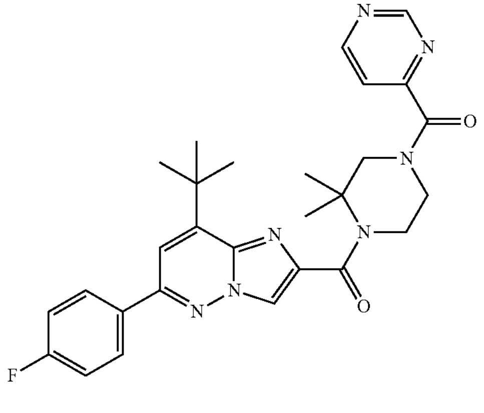
I-232
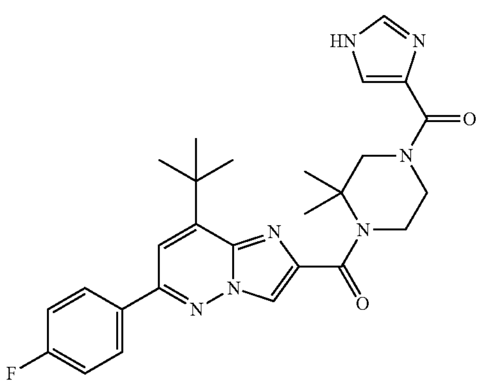
I-233
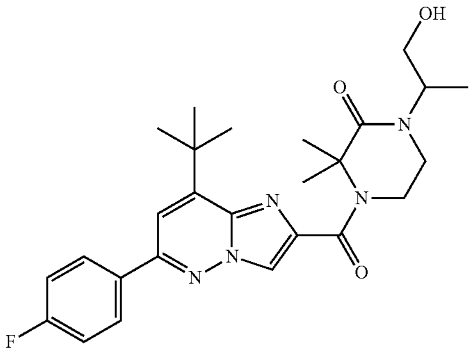
I-234
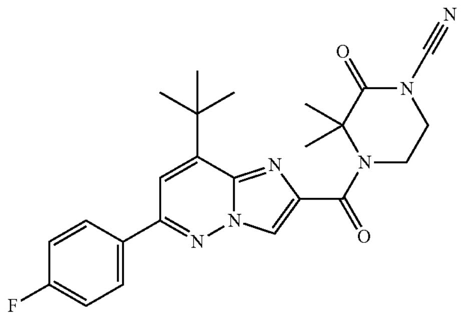
I-235
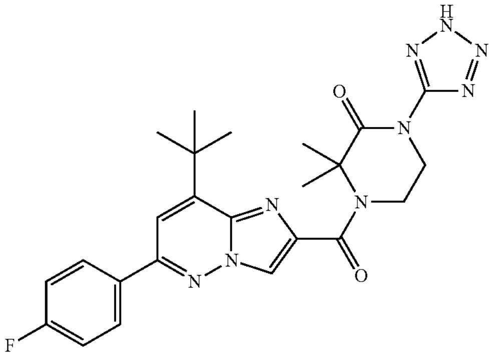

-continued
I-236
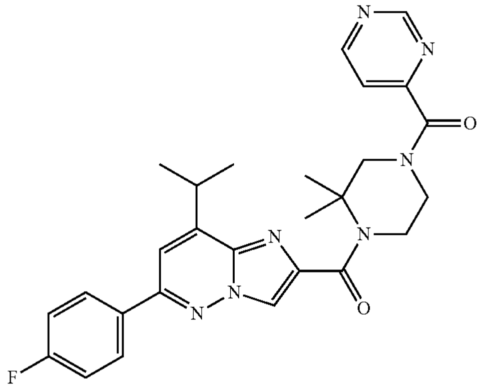
I-237
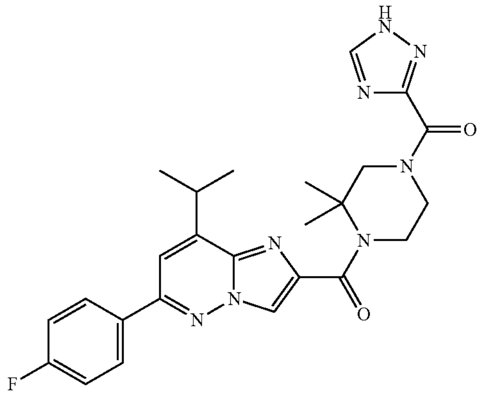
I-238
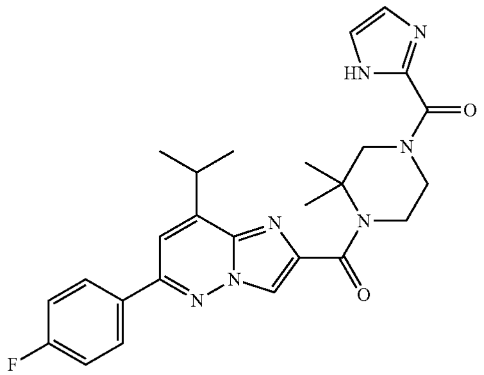
I-239
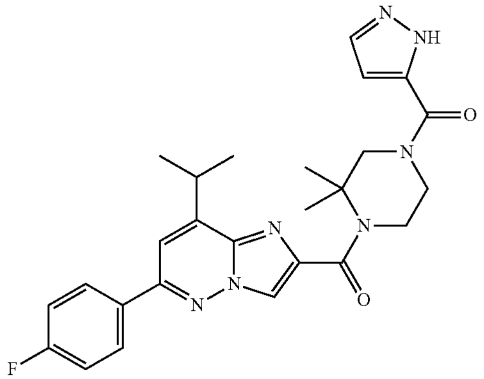
-continued
I-240
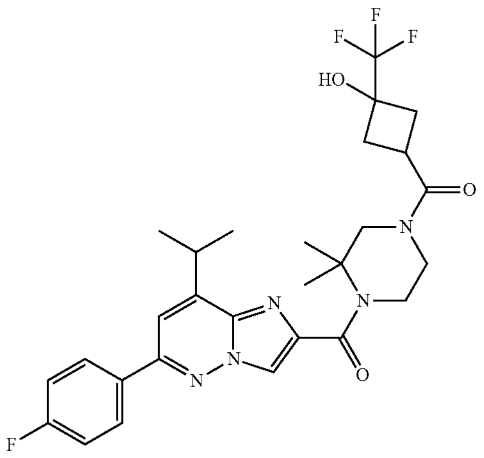
I-241
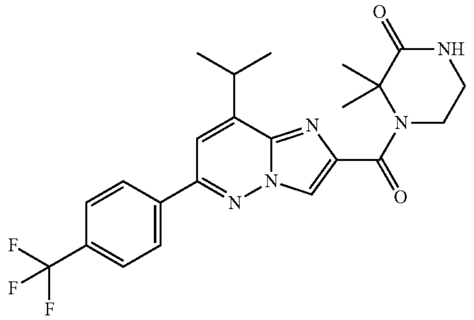
I-242
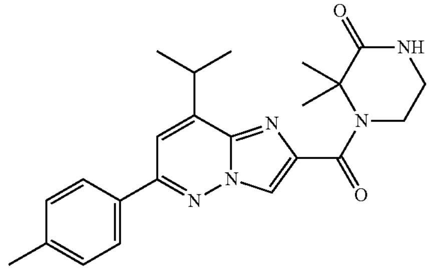
I-243
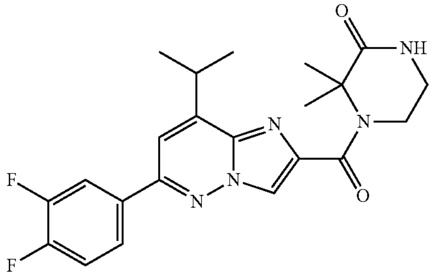
I-244
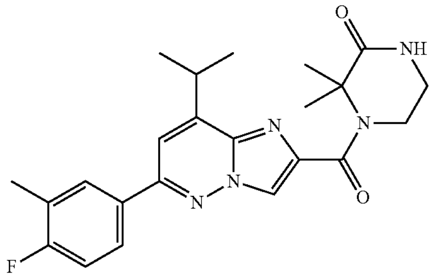

-continued
I-245
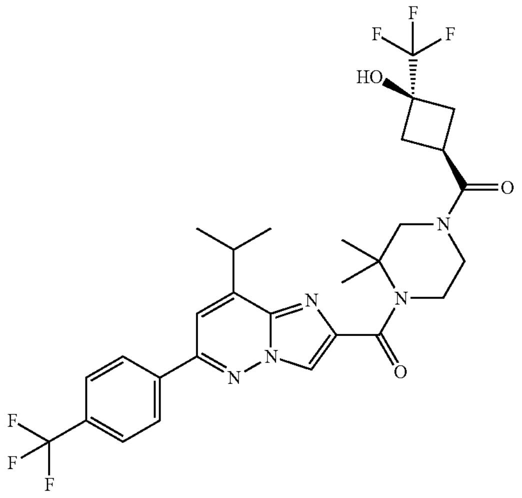
I-246
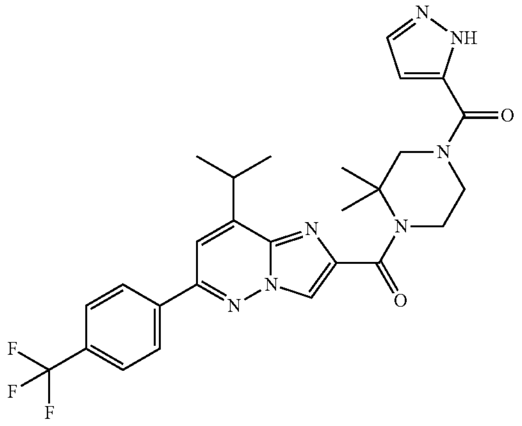
I-247
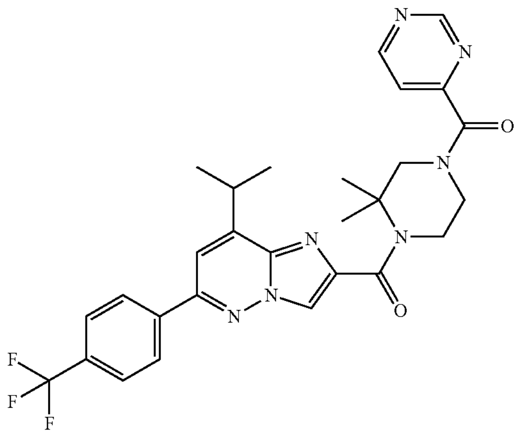
-continued
I-248
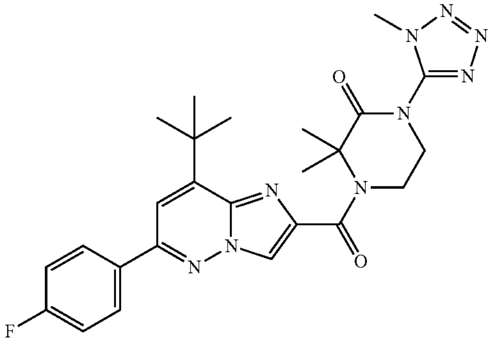
I-249
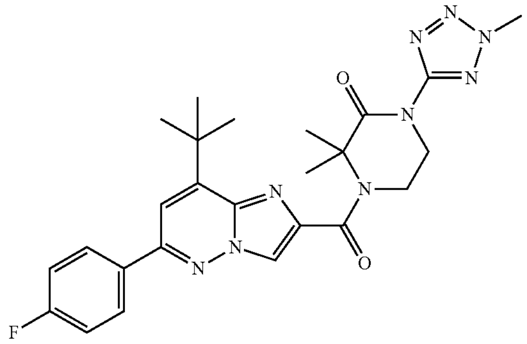
I-250
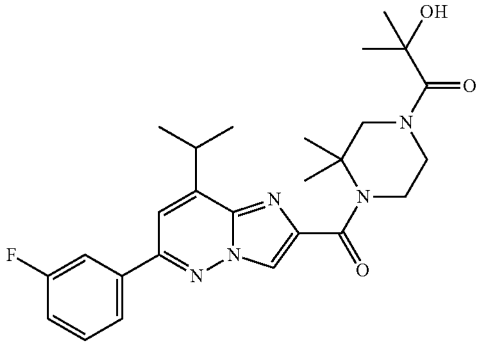
I-251
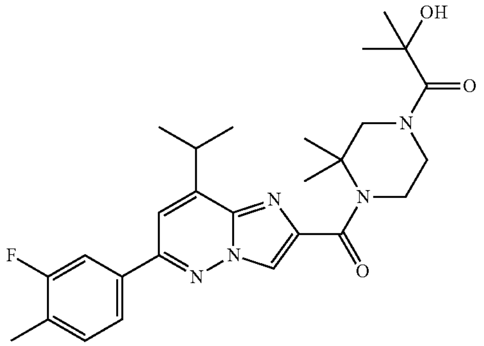

-continued
I-252
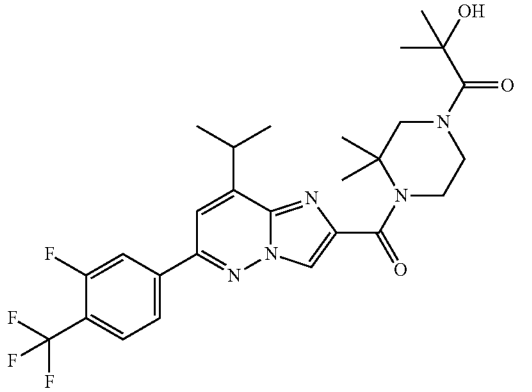
I-253
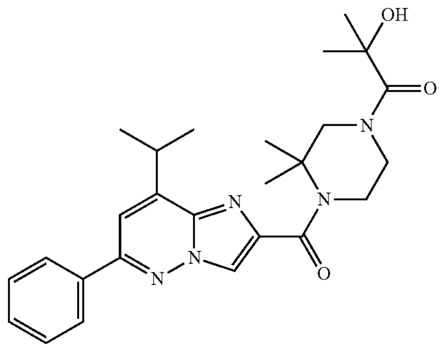
I-254
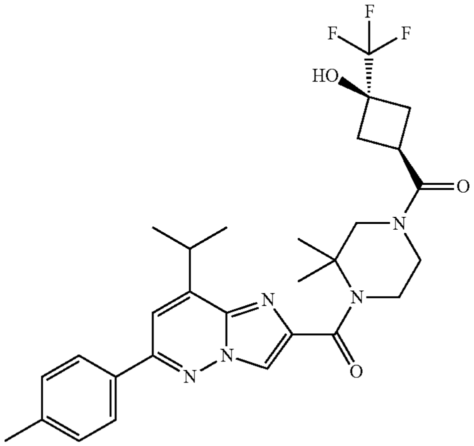
I-255
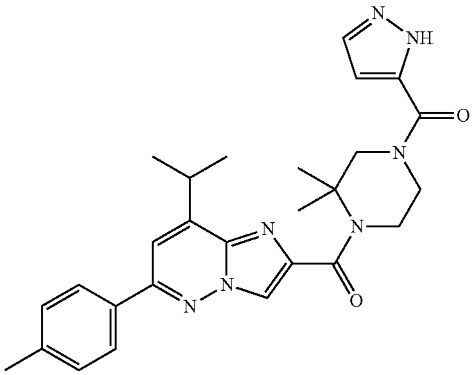
-continued
I-256
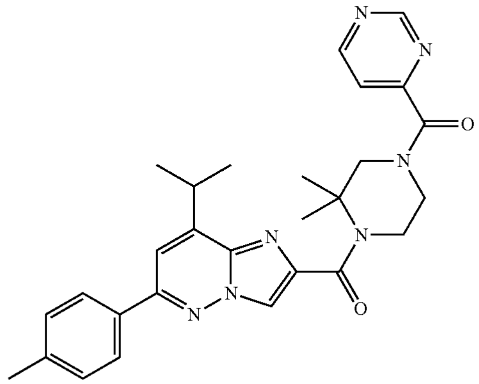
I-257
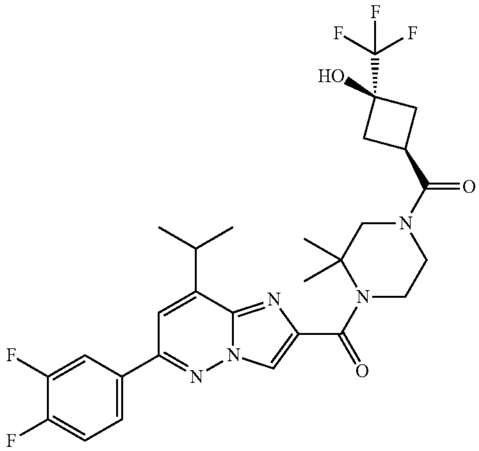
I-258
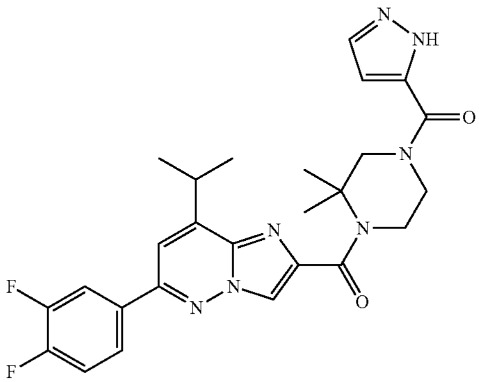
I-259
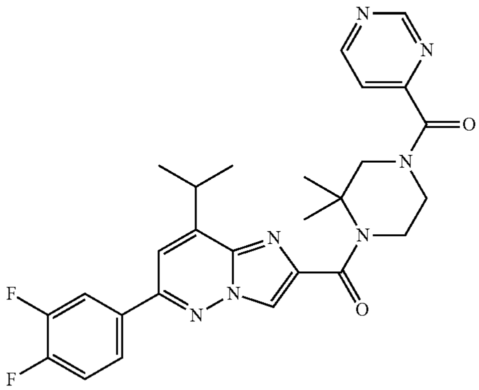

-continued
I-260
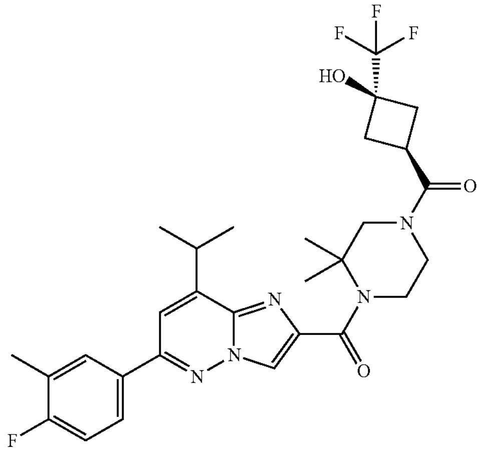
I-261
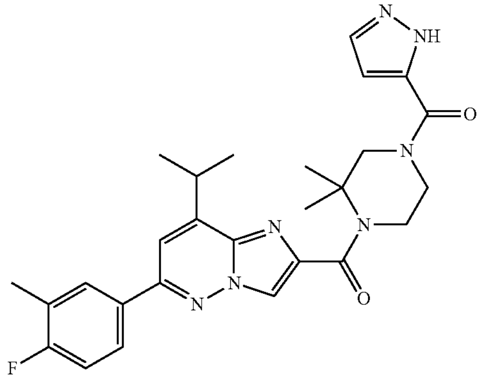
I-262
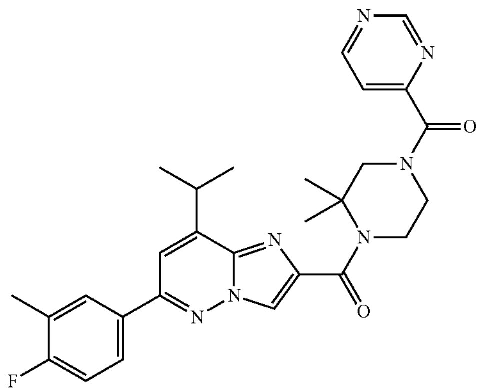
-continued
I-263
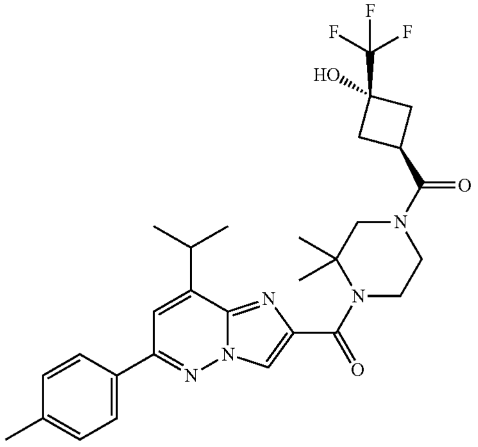
I-264
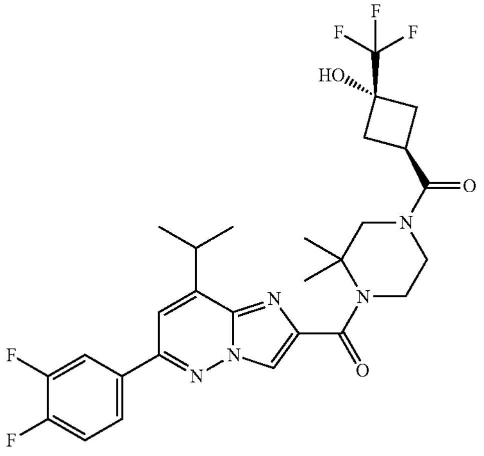
I-265
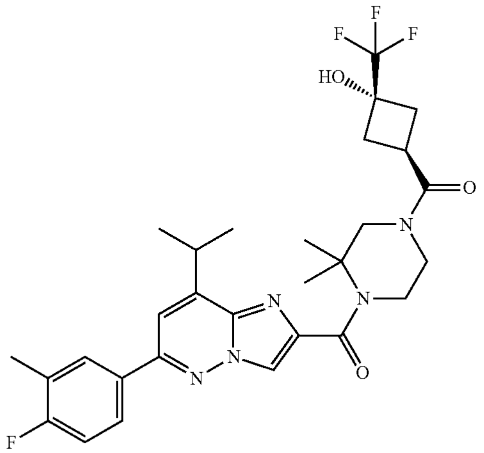

-continued
I-266
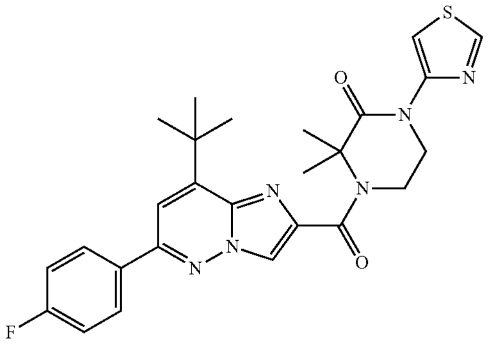
I-267
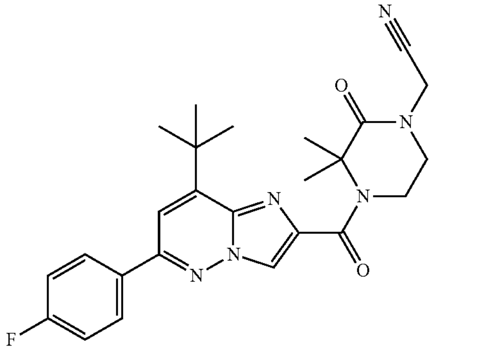
I-268
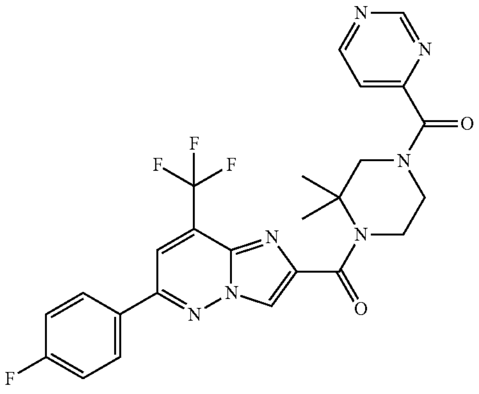
I-269
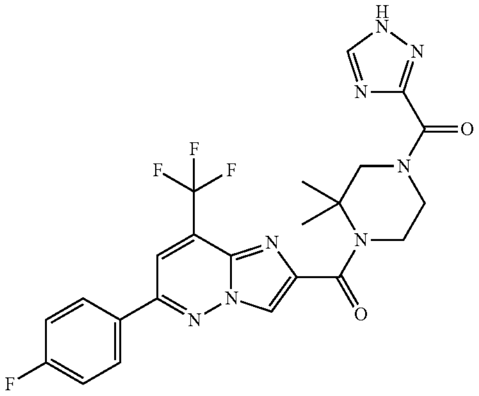
-continued
I-270
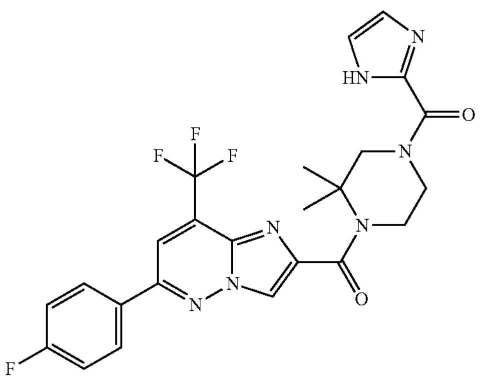
I-271
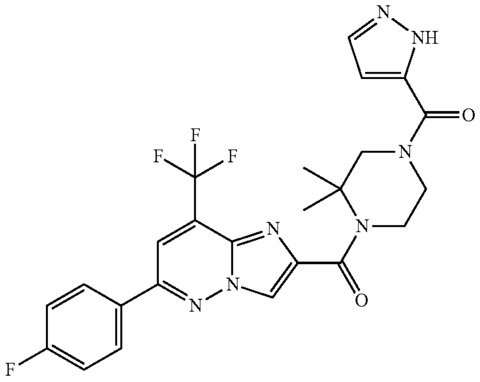
I-272
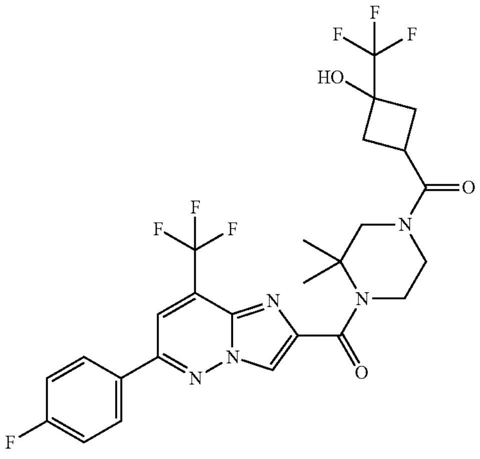
I-273
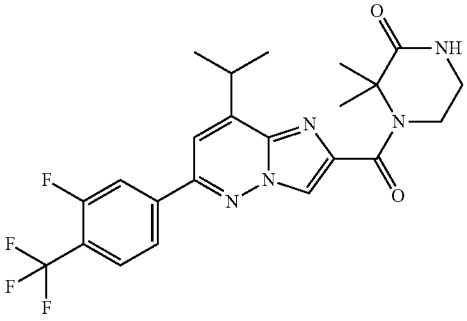

-continued
I-274
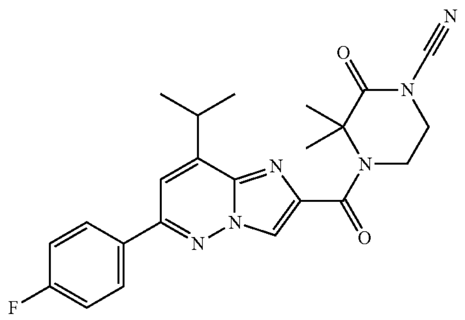
I-275
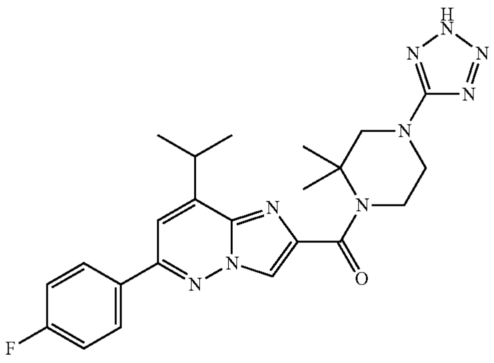
I-276
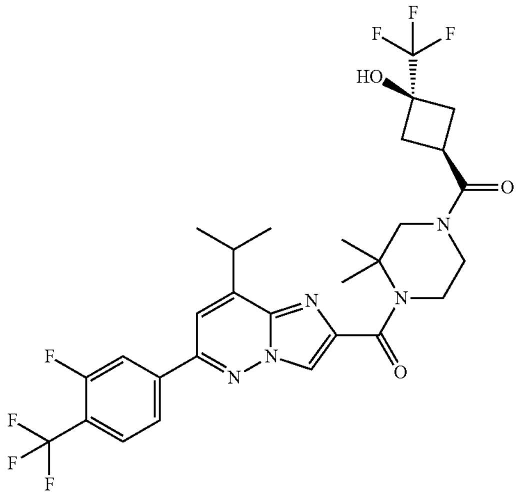
-continued
I-277
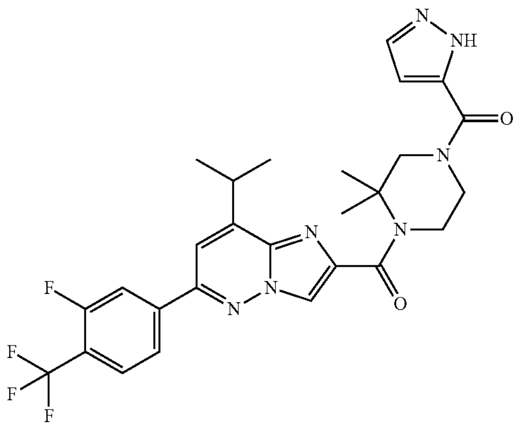
I-278
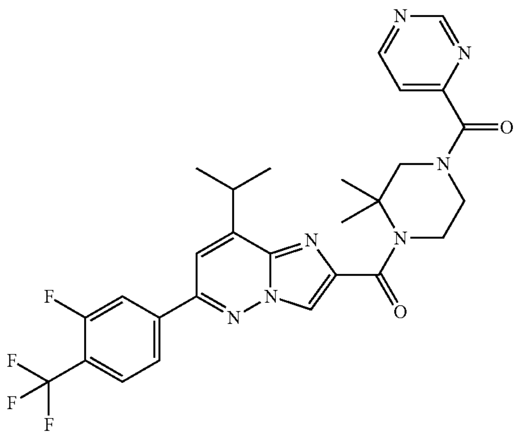
I-279
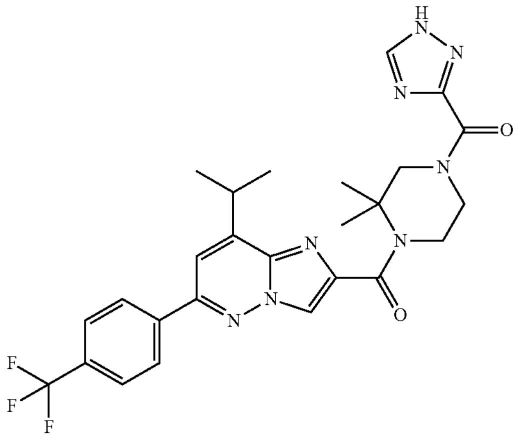

-continued
I-280
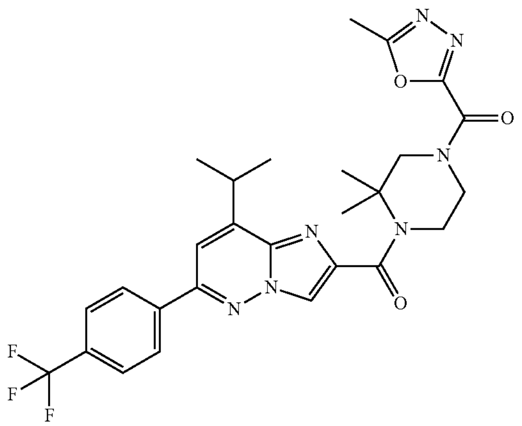
I-281
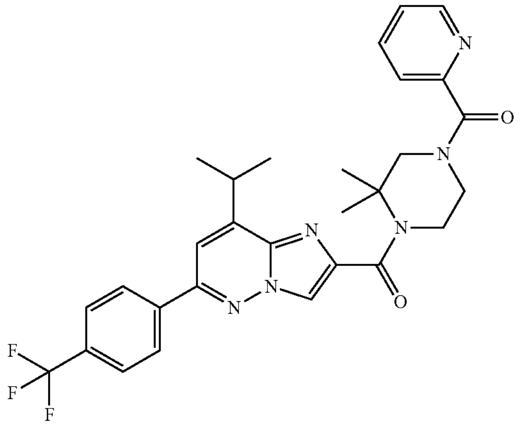
I-282
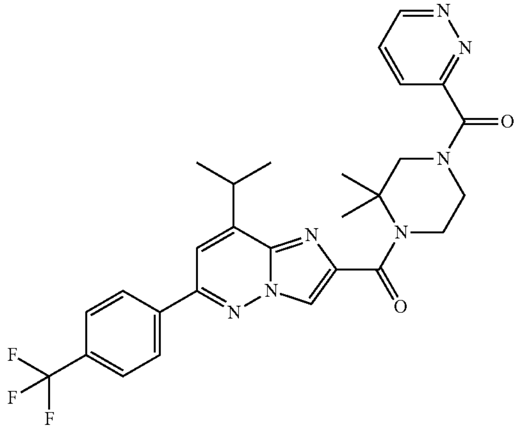
-continued
I-283
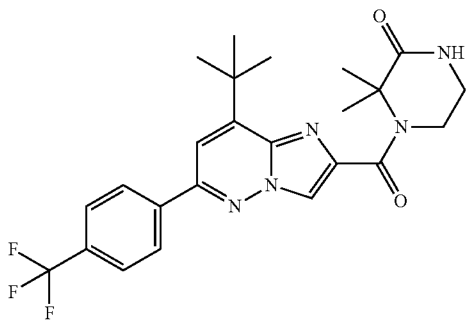
I-284
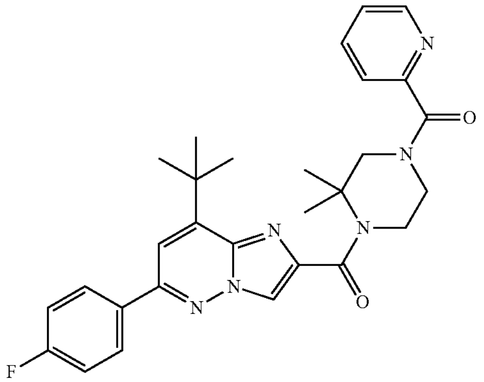
I-285
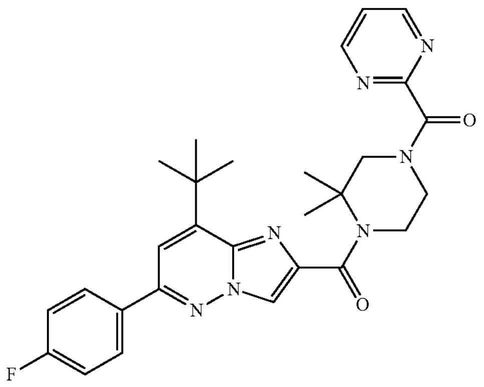
I-286
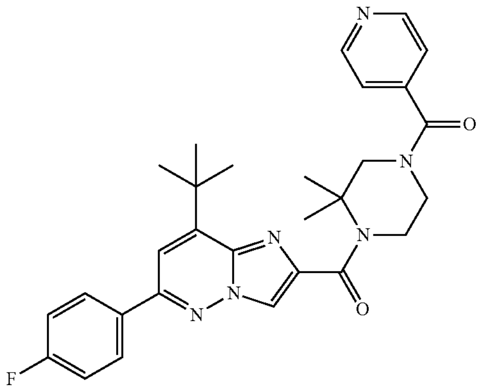

-continued
I-287
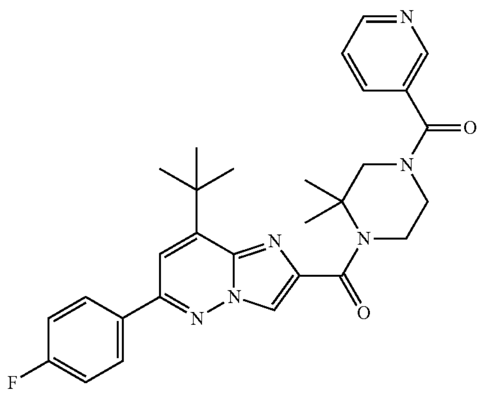
I-288
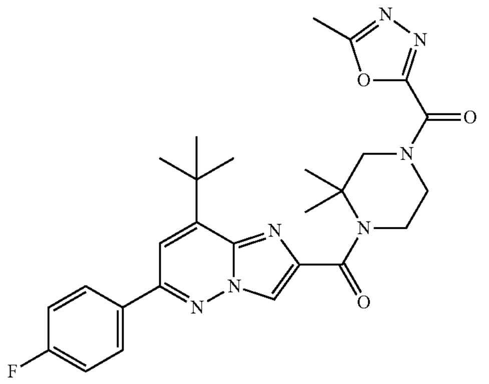
I-289
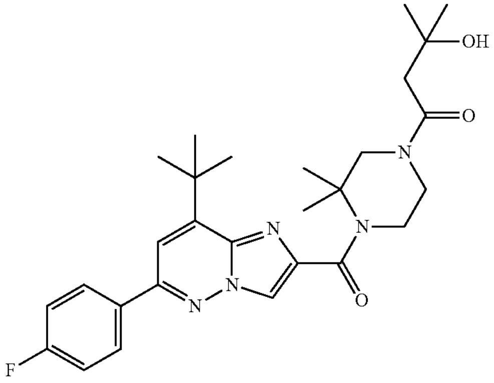
I-290
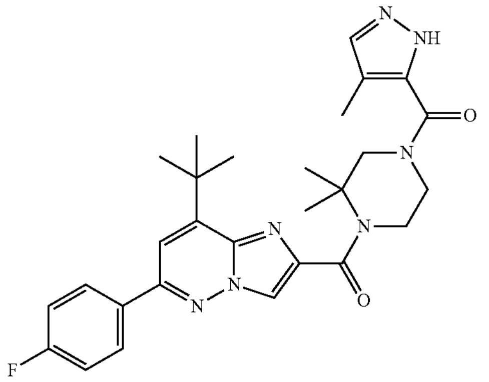
-continued
I-291
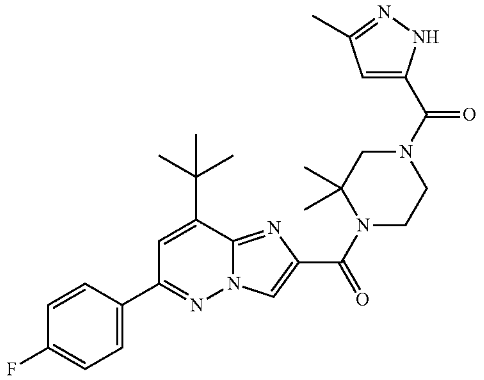
I-292
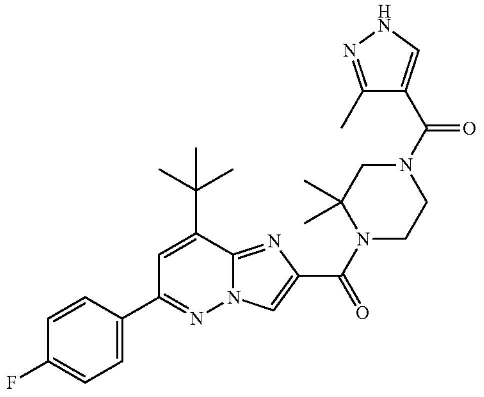
I-293
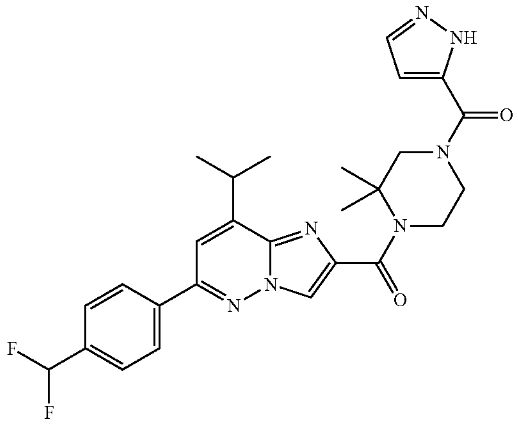

-continued
I-294
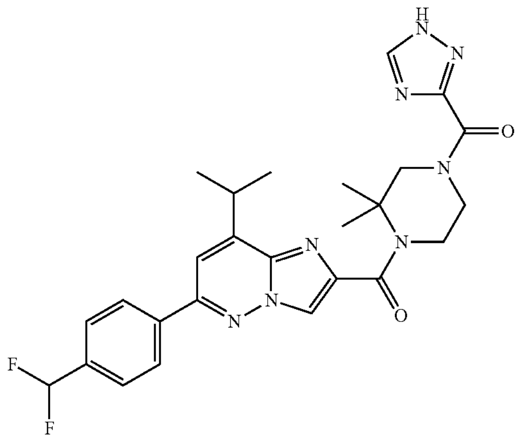
I-295
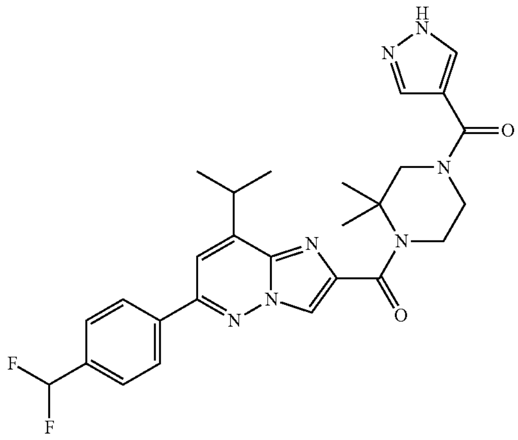
I-296
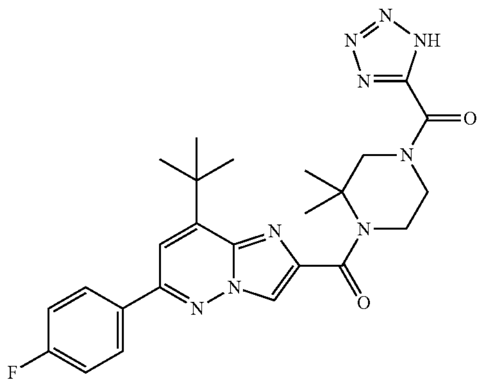
I-297
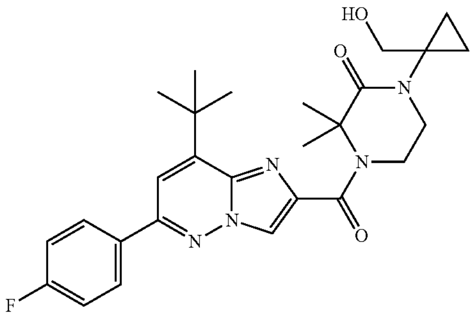
-continued
I-298
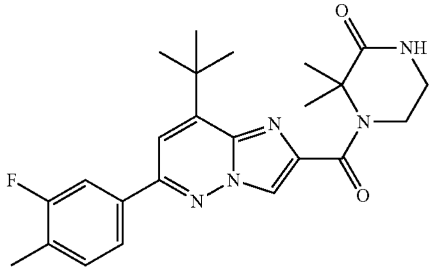
I-299
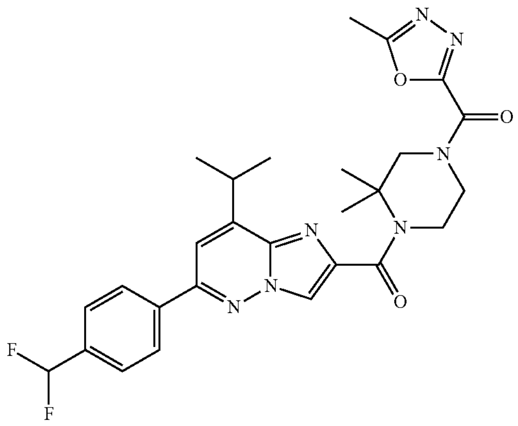
I-300
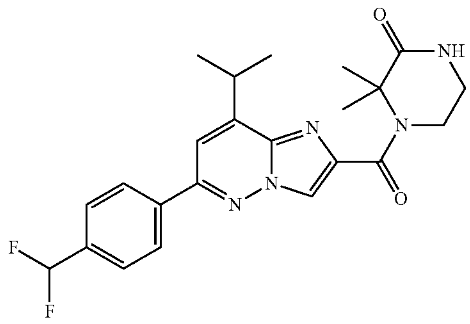
I-301
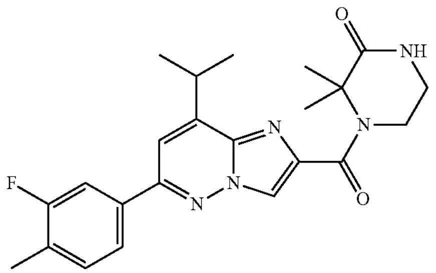

-continued
I-302
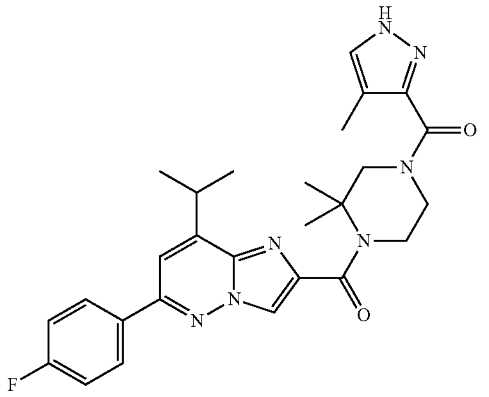
I-303
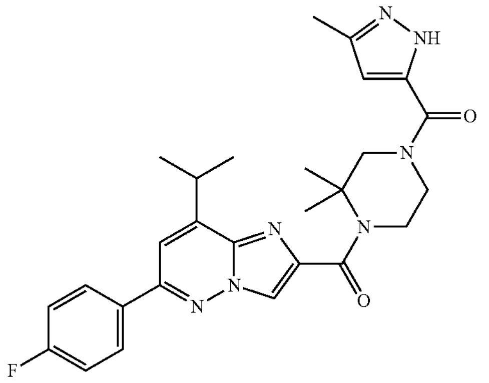
I-304
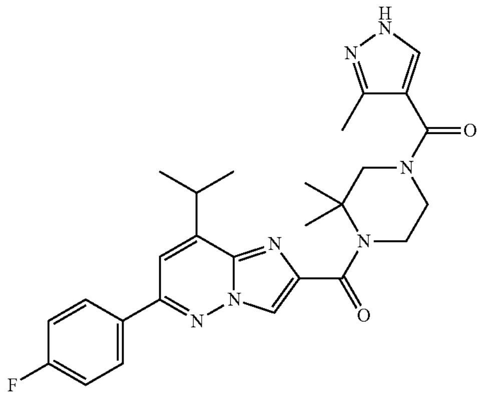
I-305
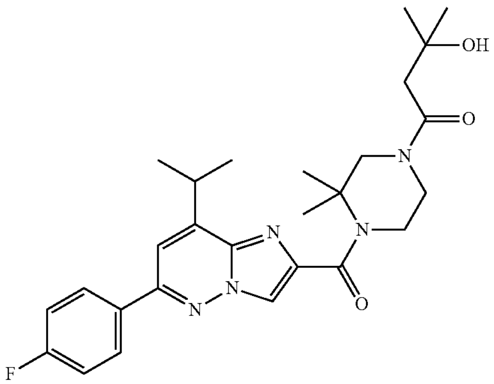
-continued
I-306
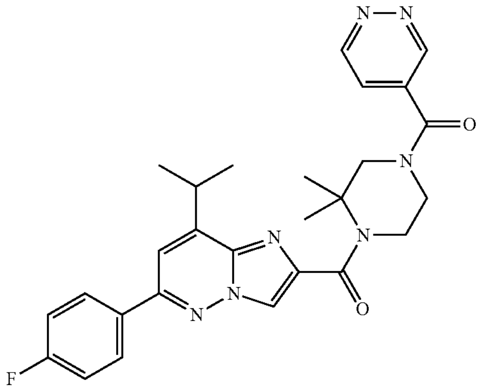
I-307
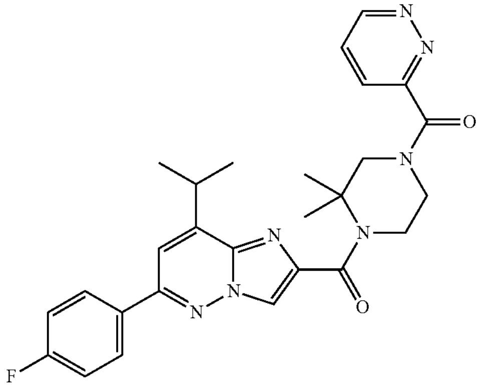
I-308
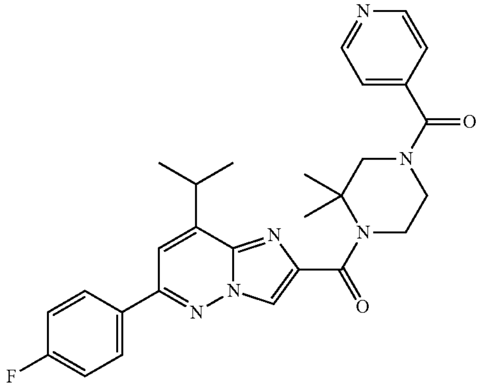
I-309
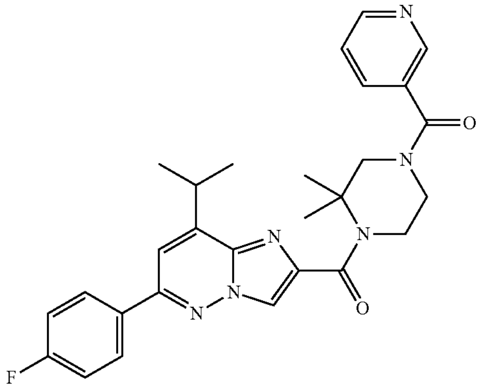

-continued
I-310
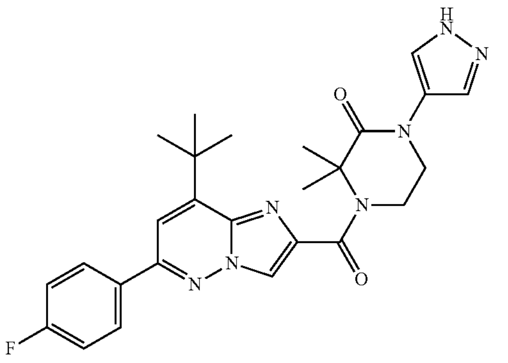
I-311
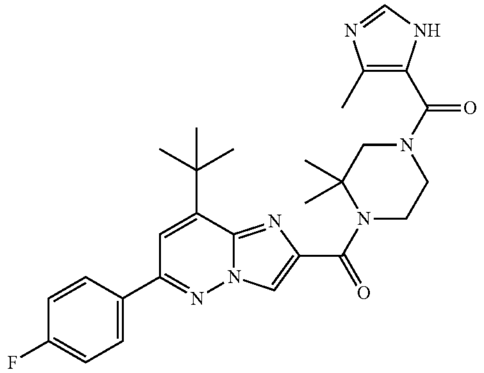
I-312
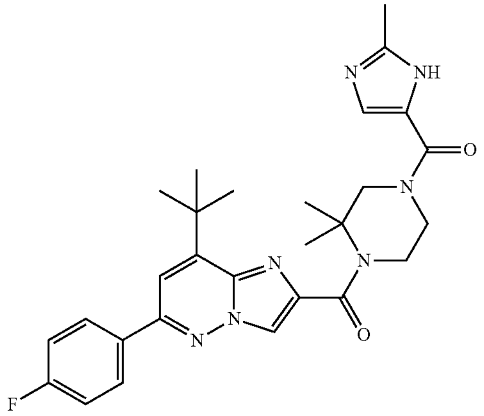
I-313
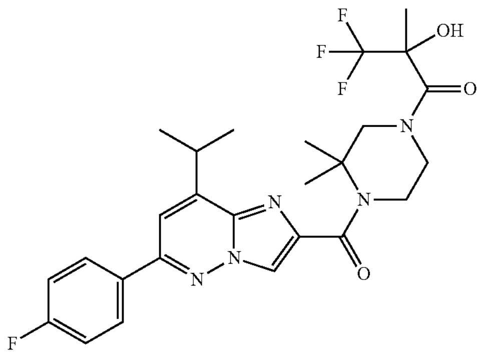
-continued
I-314
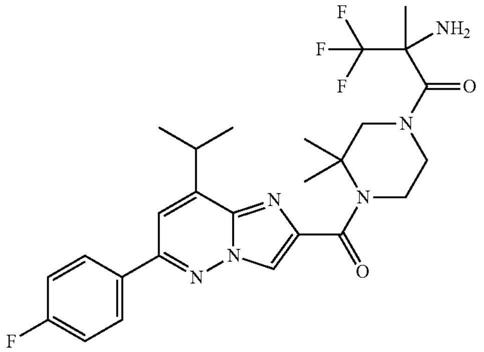
I-315
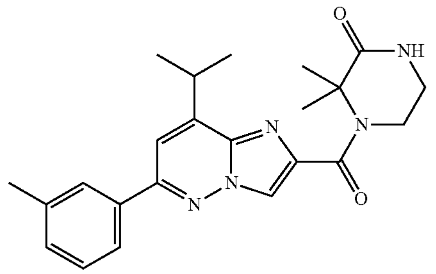
I-316
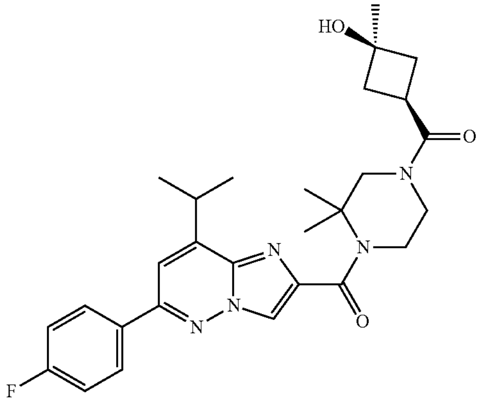
I-317
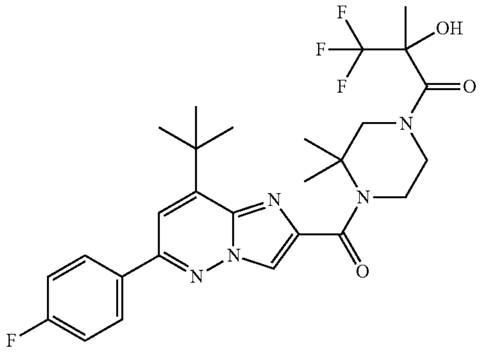

-continued
I-318
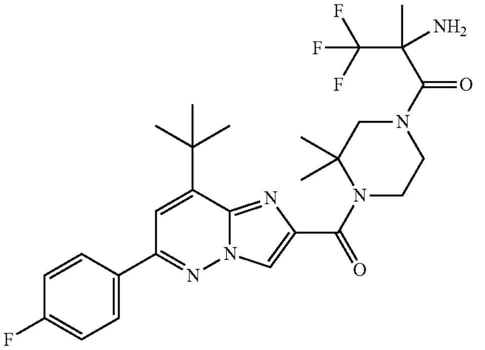
I-319
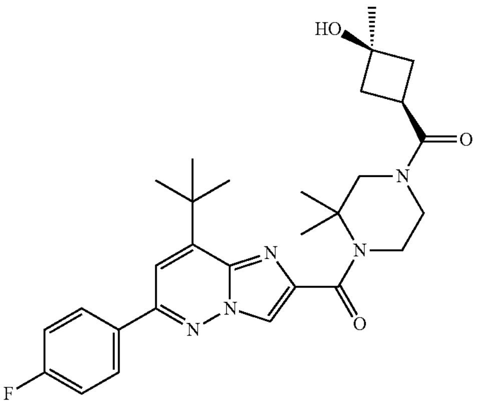
I-320
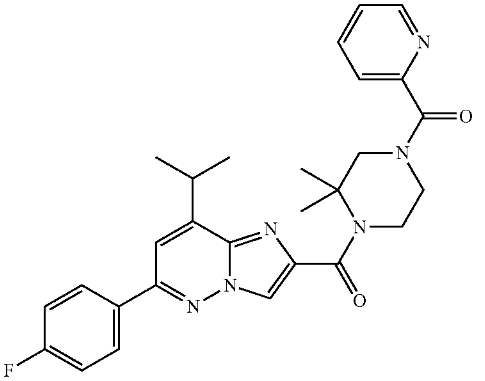
I-321
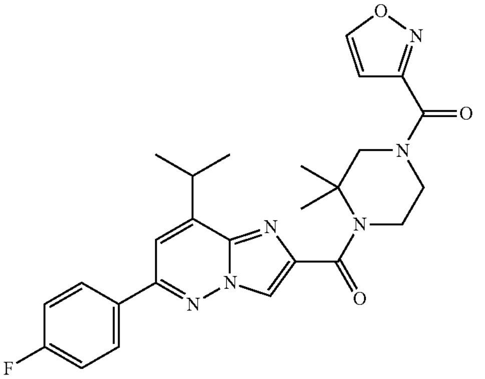
-continued
I-322
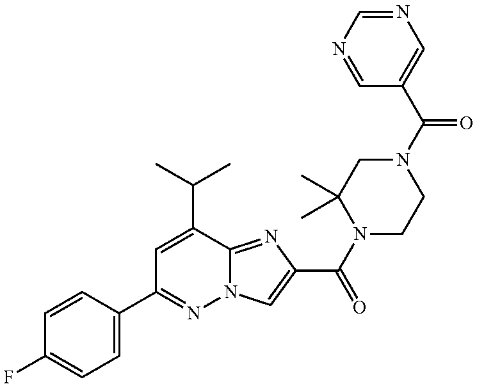
I-323
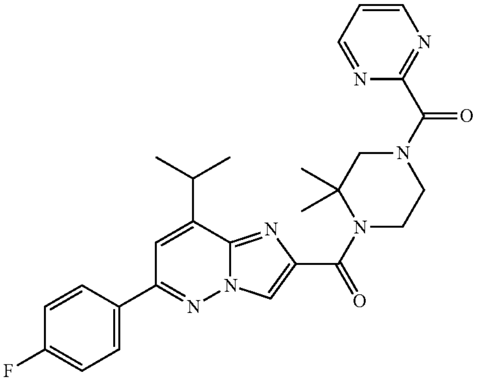
I-324
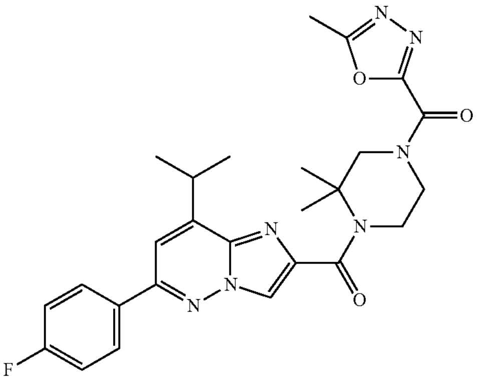
I-325
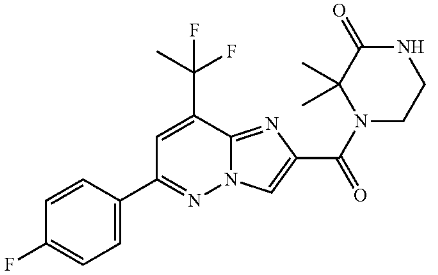

-continued
I-326
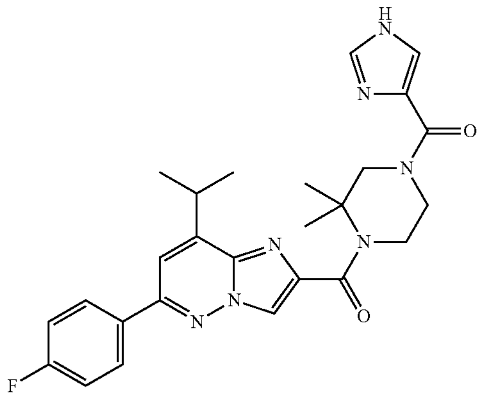
I-327
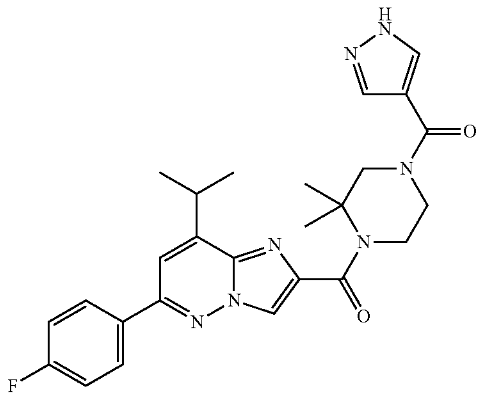
I-328
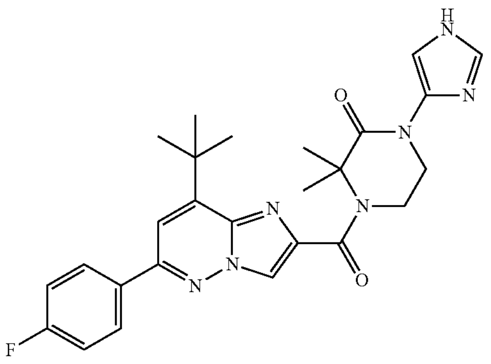
I-329
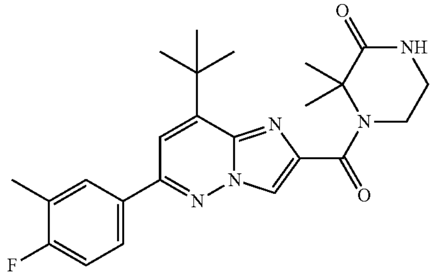
-continued
I-330
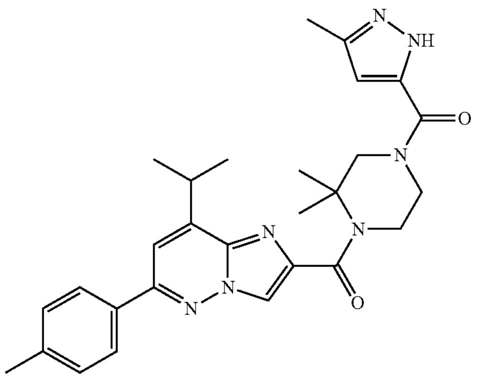
I-331
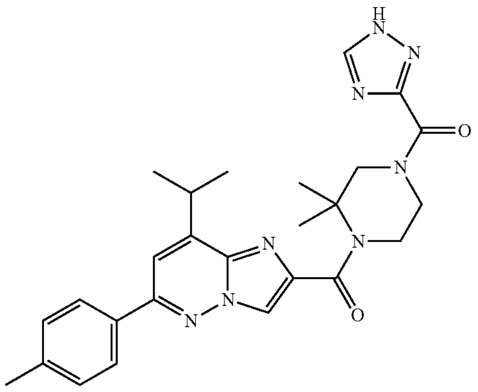
I-332
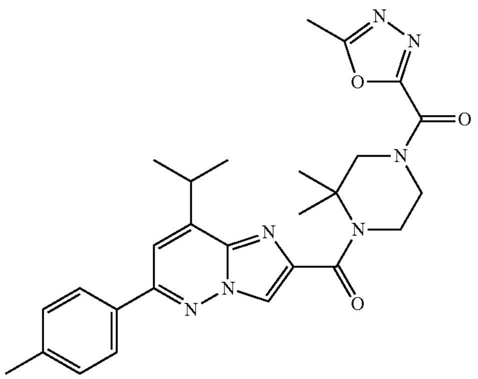
I-333
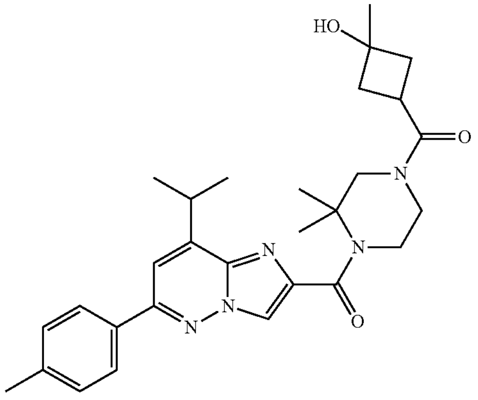

-continued
I-334
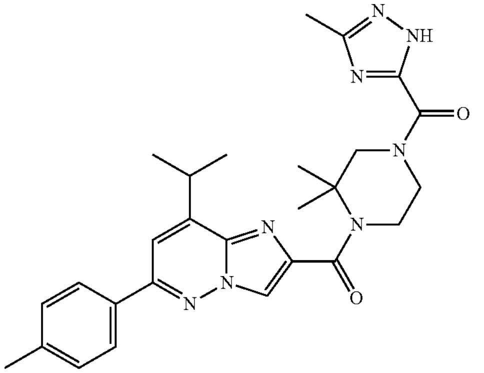
I-335
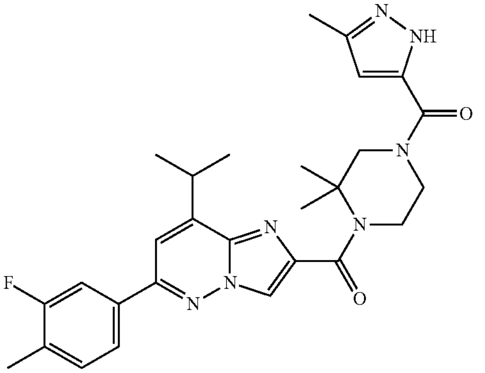
I-336
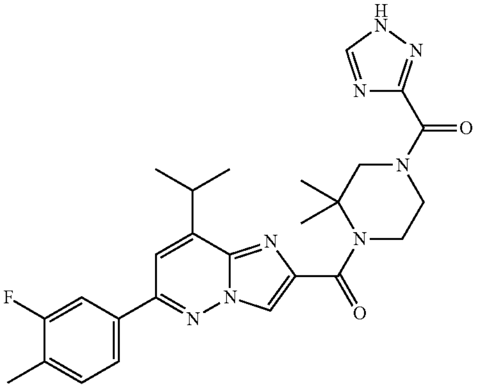
I-337
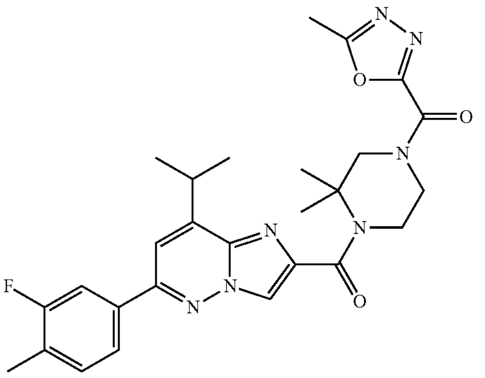
-continued
I-338
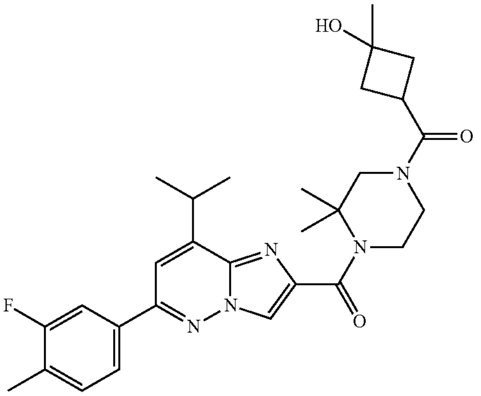
I-339
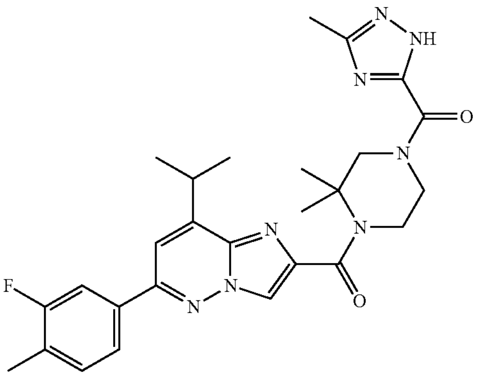
I-340
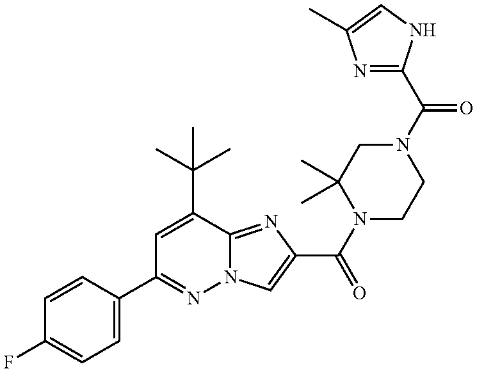
I-341
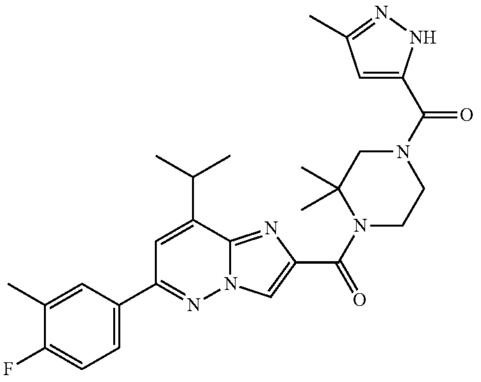

-continued
I-342
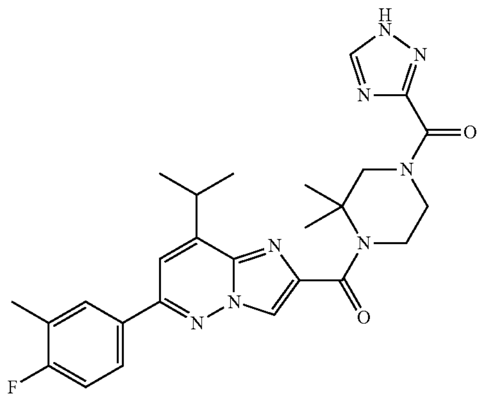
I-343
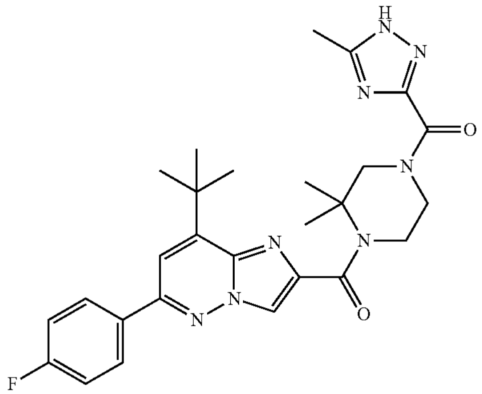
I-344
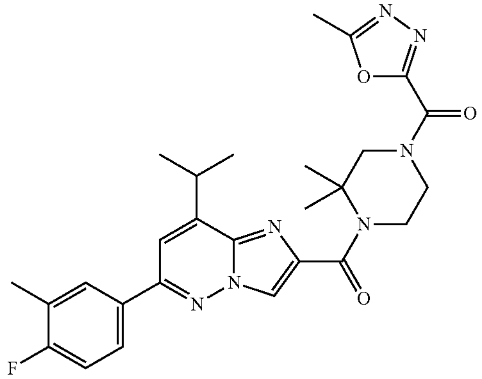
I-345
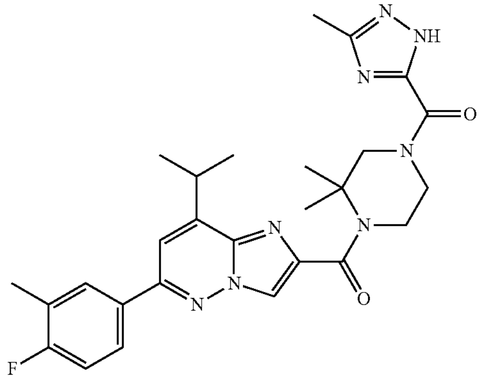
-continued
I-346
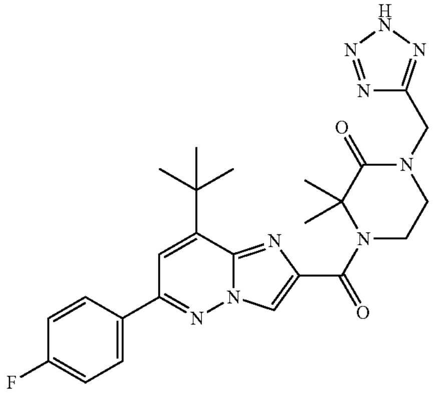
I-347
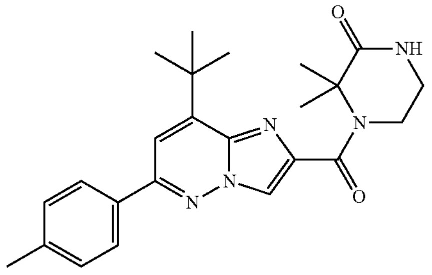
I-348
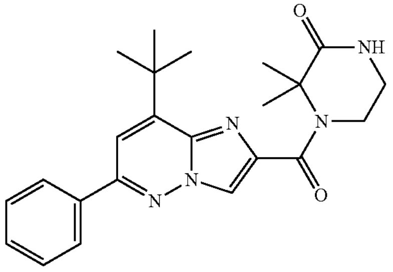
I-349
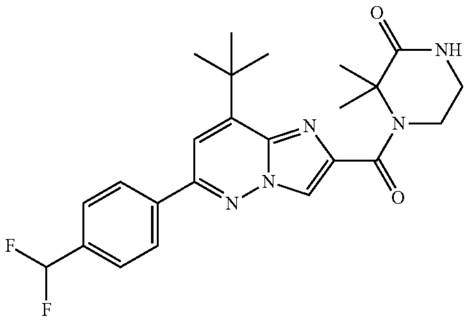
I-350
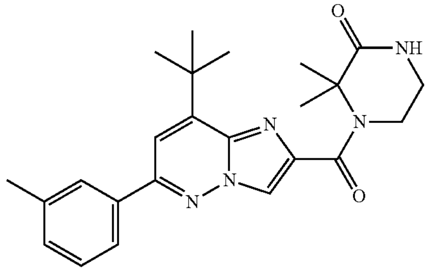

-continued
I-351
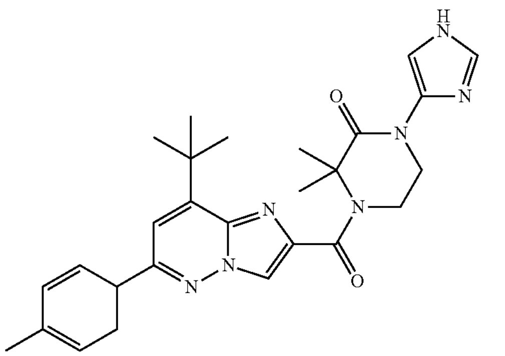
I-352
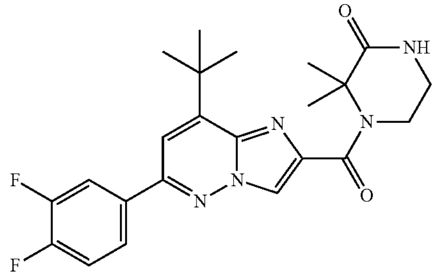
I-353
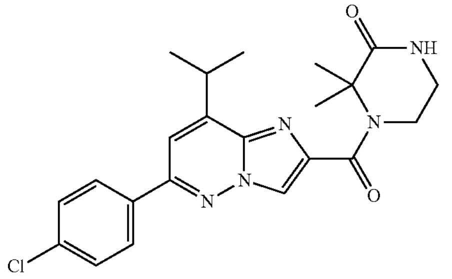
I-354
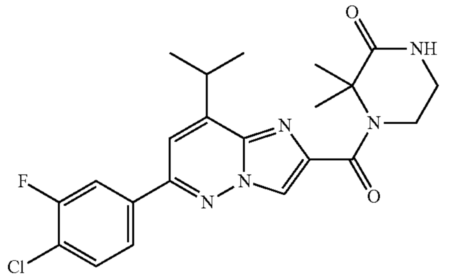
I-355
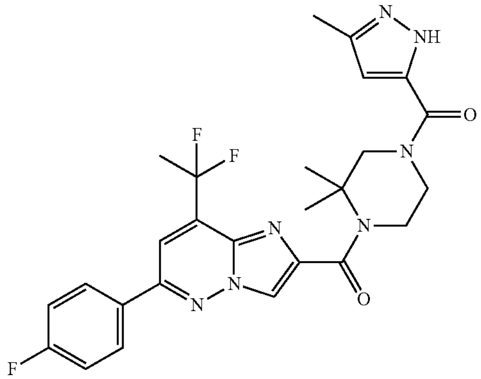
-continued
I-356
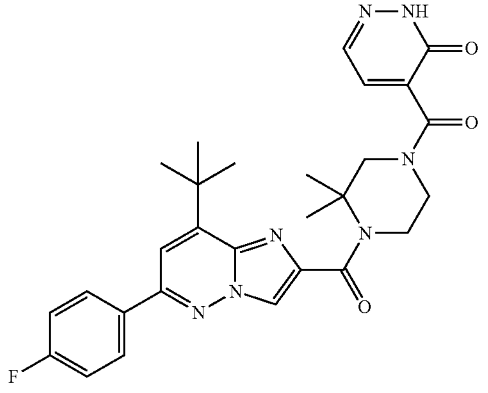
I-357
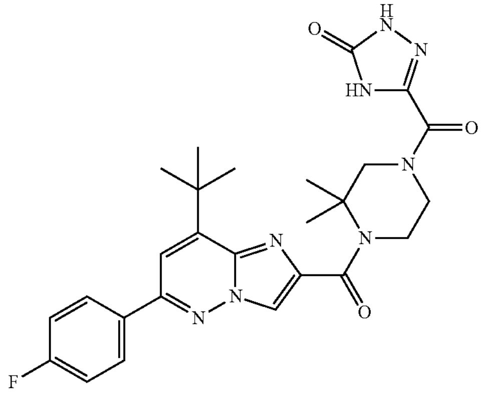
I-358
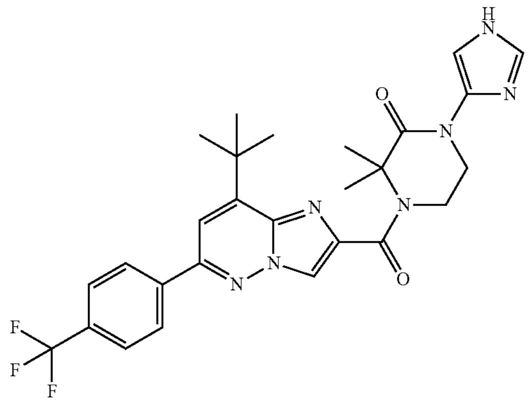
I-359
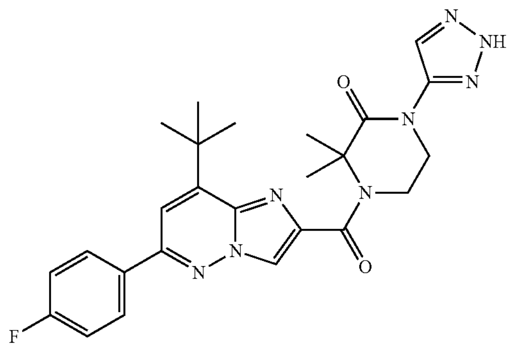

I-360
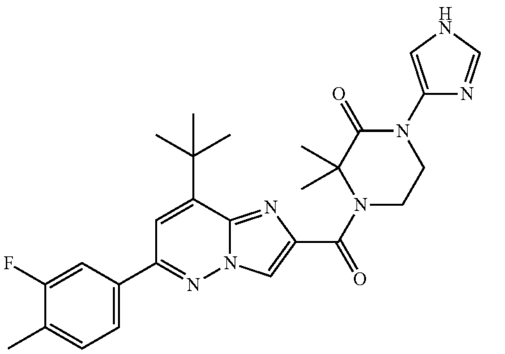
I-361
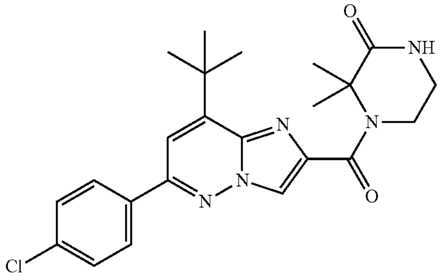
I-362
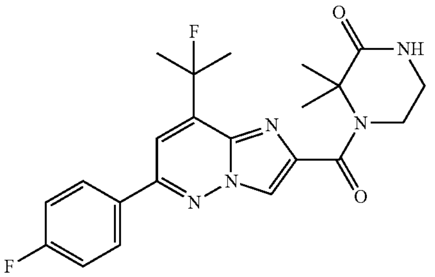
I-363
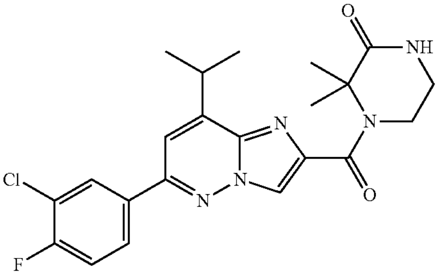
I-364
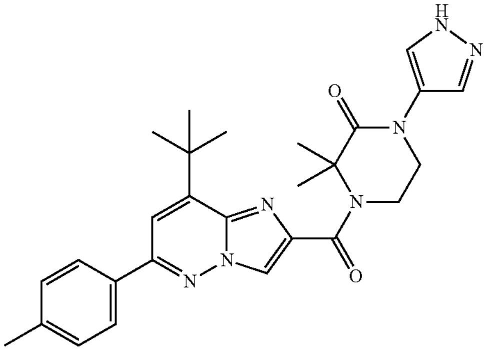
I-365
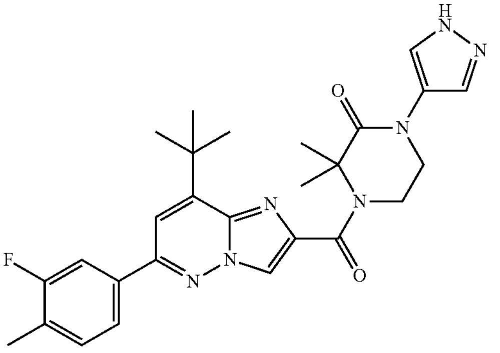
I-366
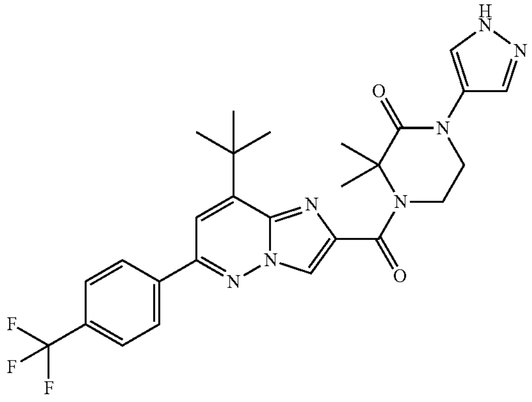
I-367
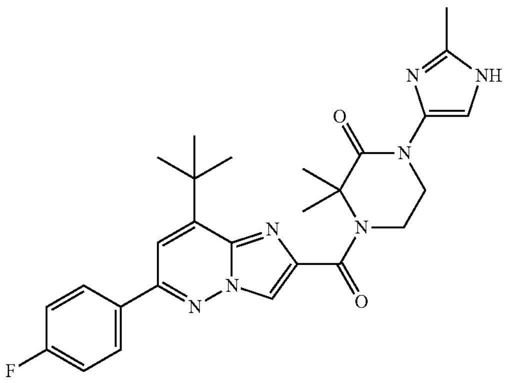
I-368
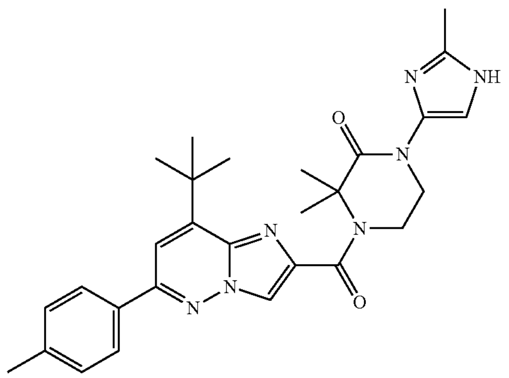

-continued
I-369
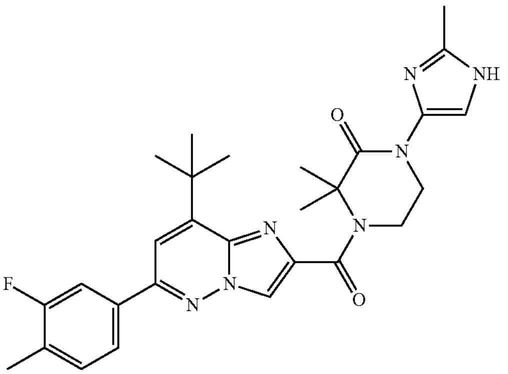
I-370
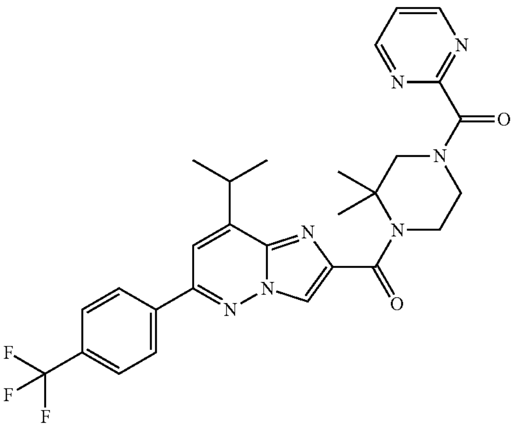
I-371
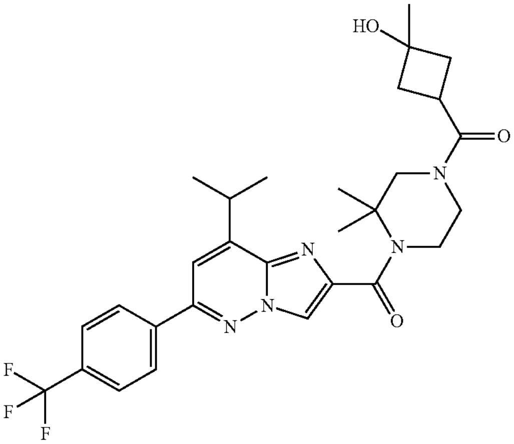
I-372
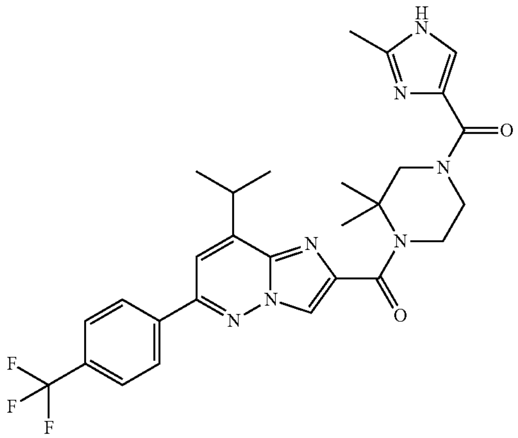
I-373
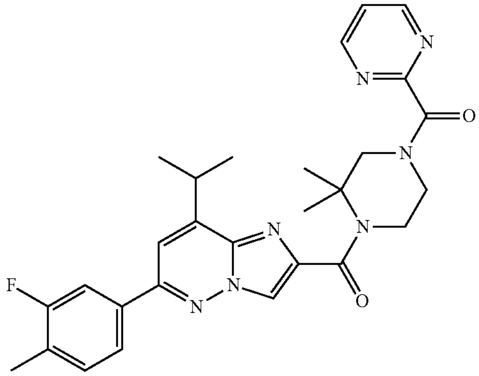
I-374
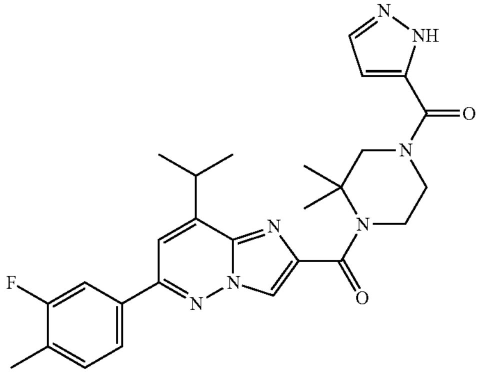
I-375
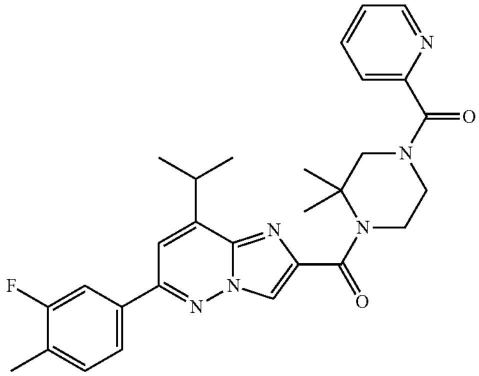

-continued
I-376
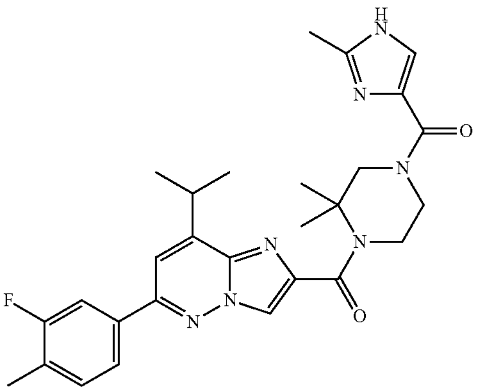
I-377
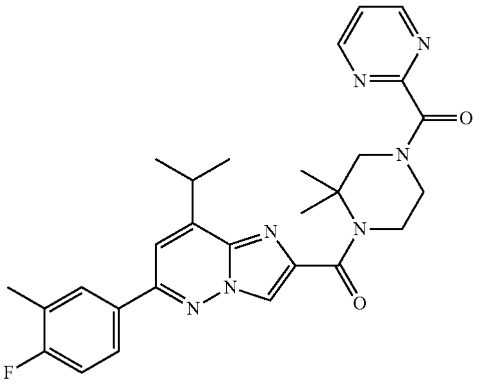
I-378
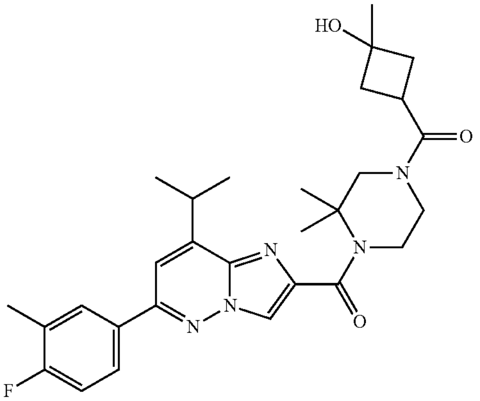
I-379
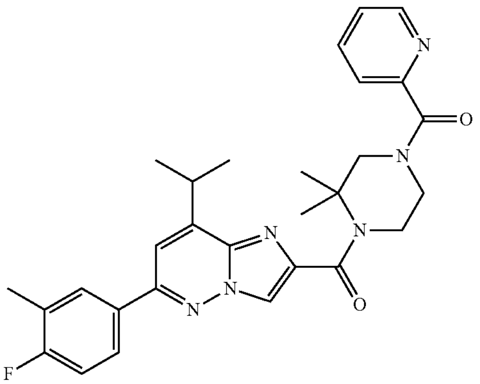
-continued
I-380
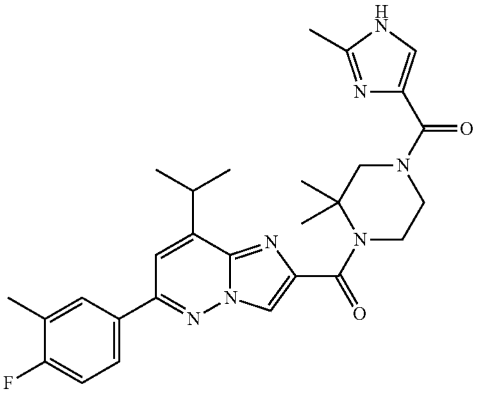
I-381
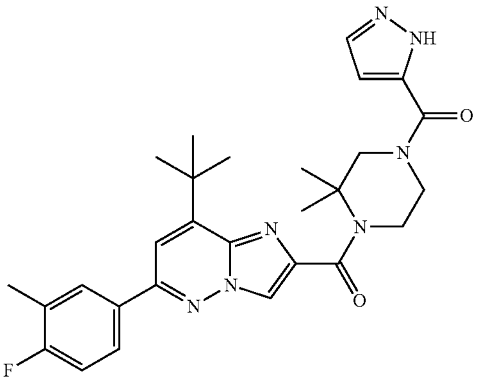
I-382
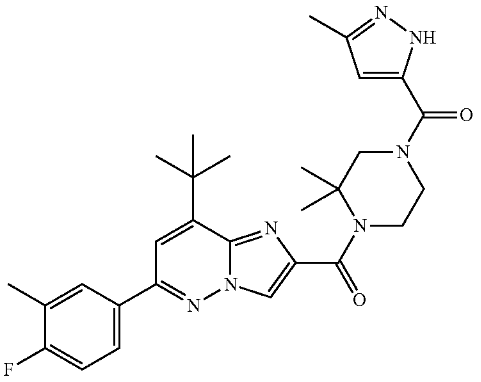
I-383
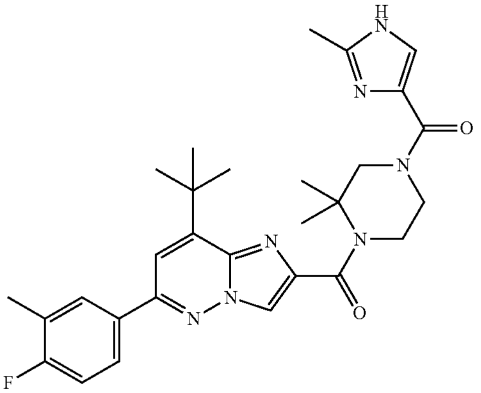

-continued
I-384
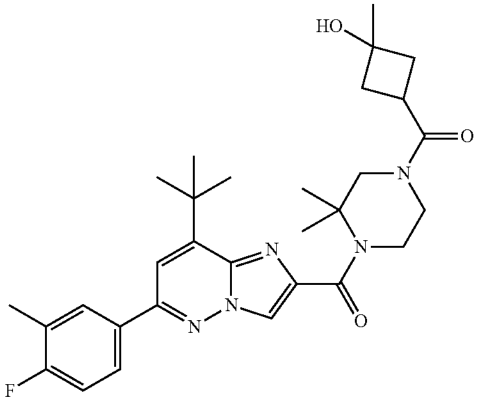
I-385
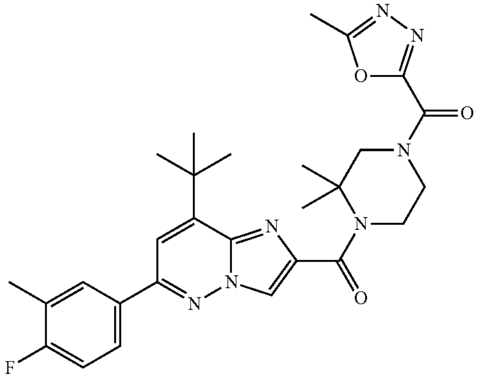
I-386
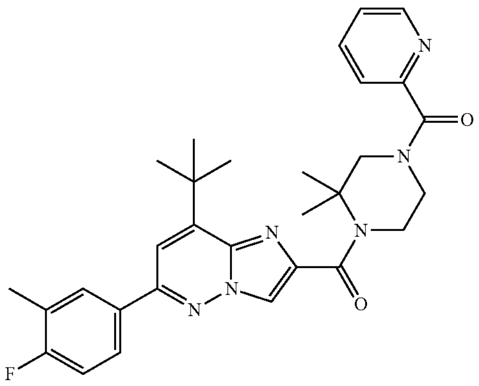
I-387
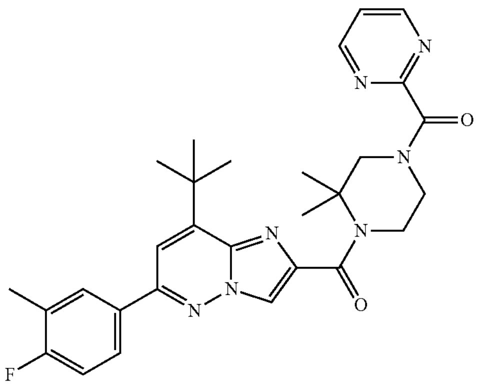
-continued
I-388
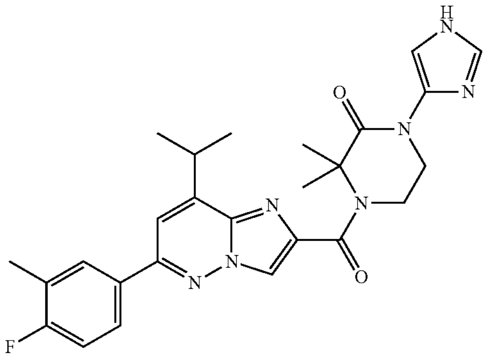
I-389
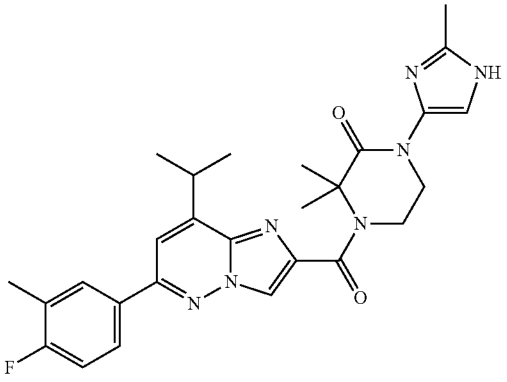
I-390
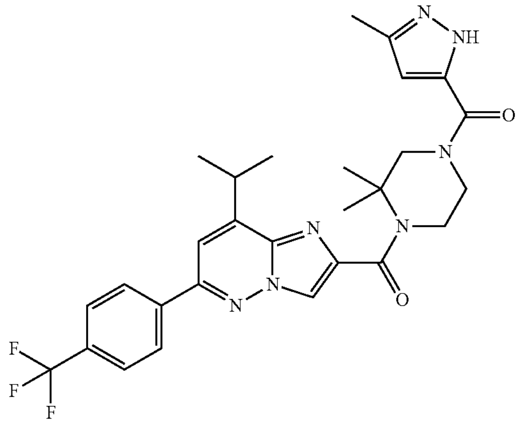
I-391
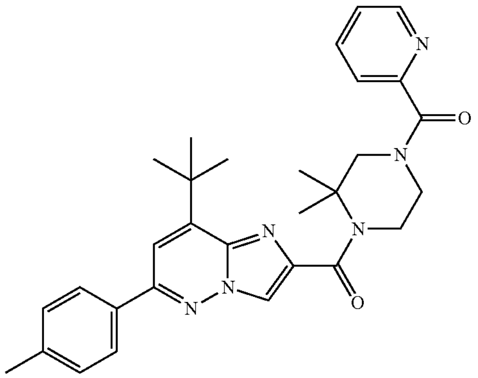

-continued
I-392
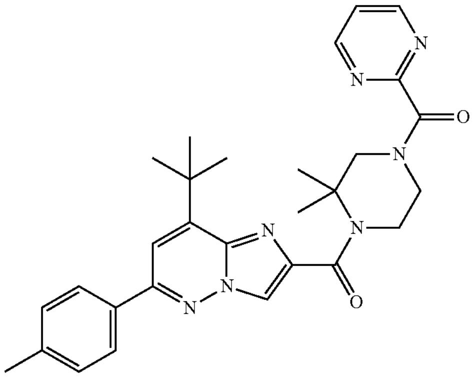
I-393
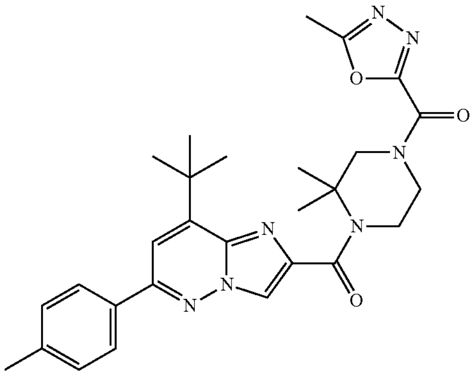
I-394
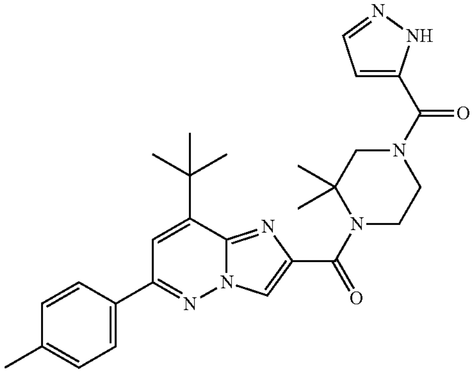
I-395
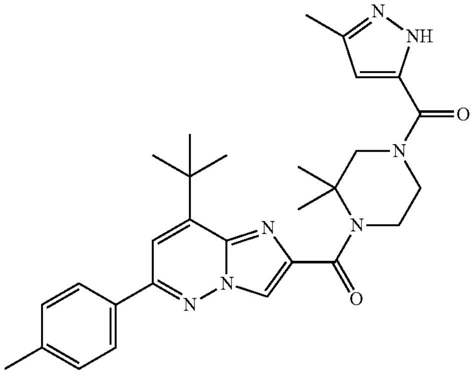
-continued
I-396
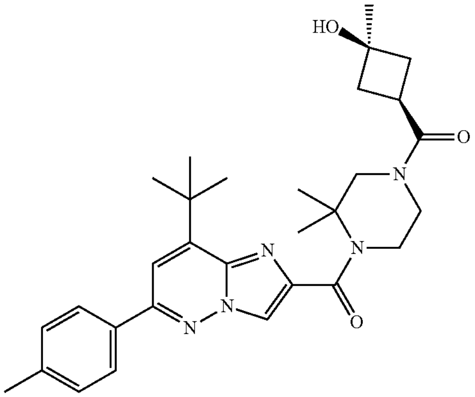
I-397
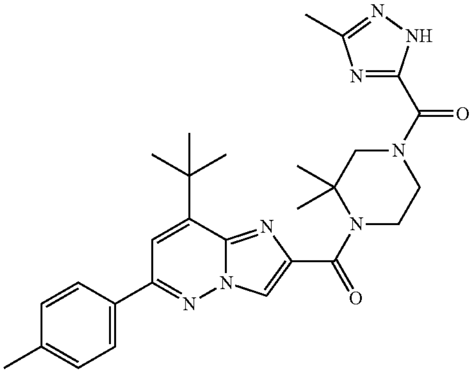
I-398
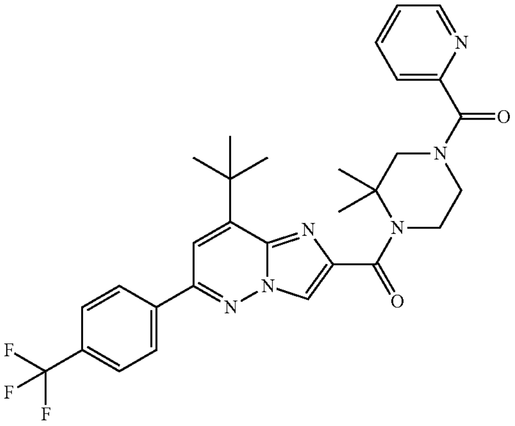

-continued
I-399
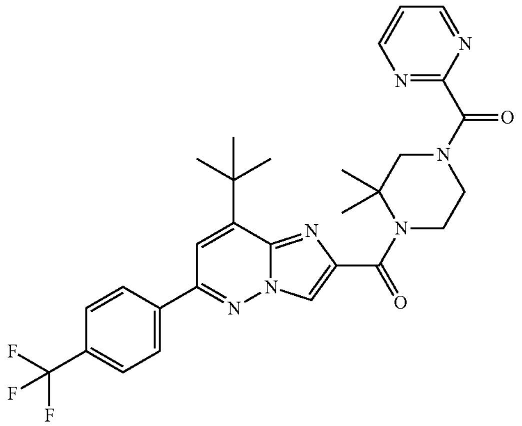
I-400
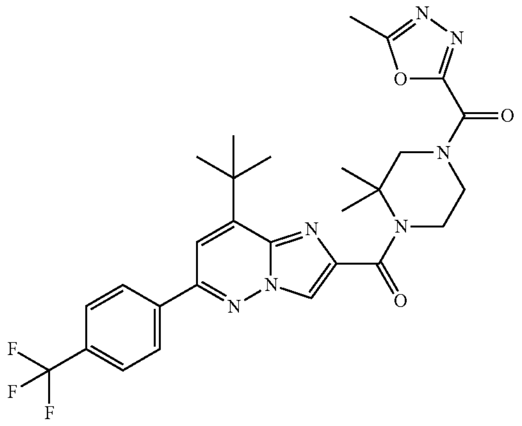
I-401
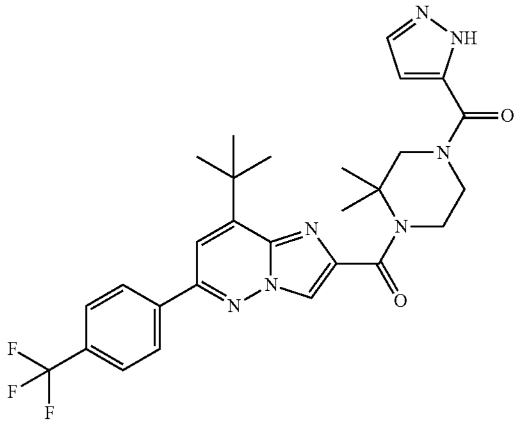
-continued
I-402
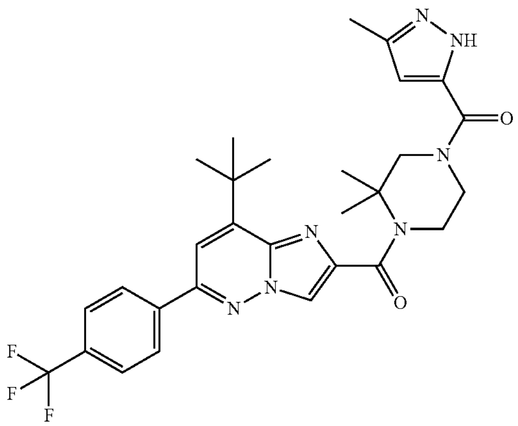
I-403
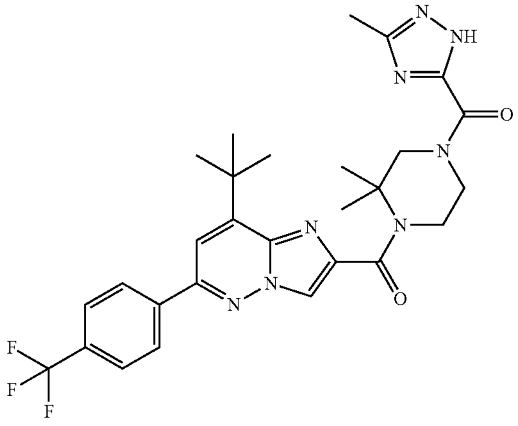
I-404
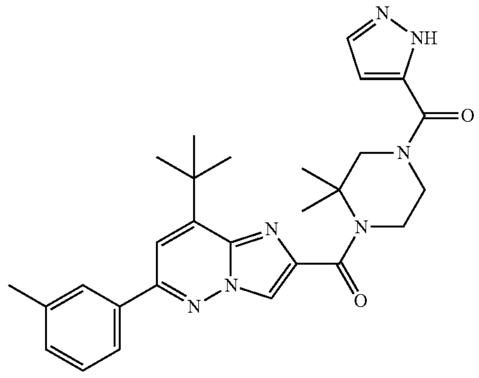

-continued
I-405
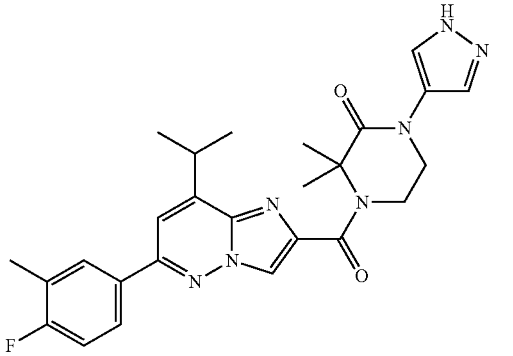
I-406
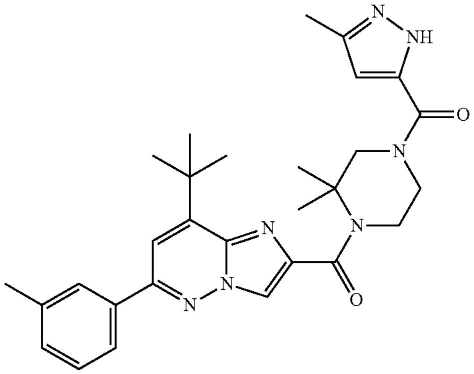
I-407
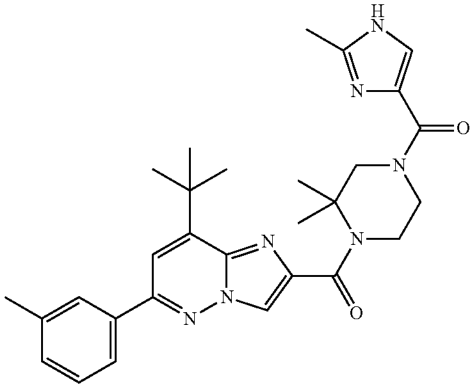
I-408
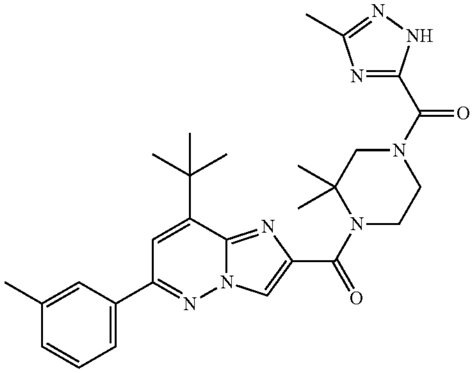
-continued
I-409
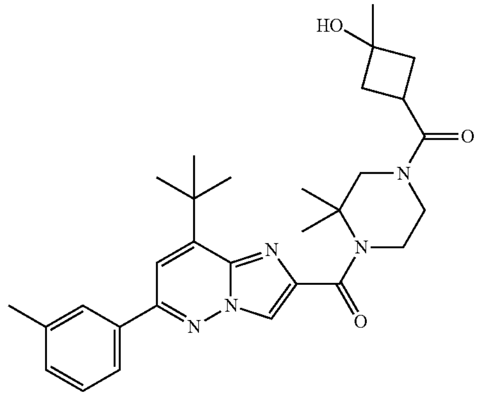
I-410
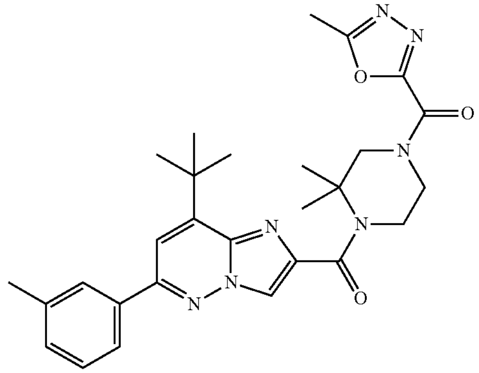
I-411
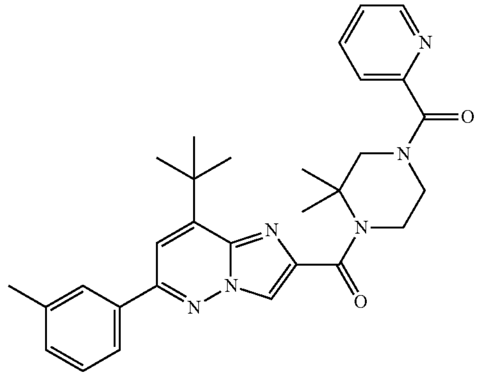
I-412
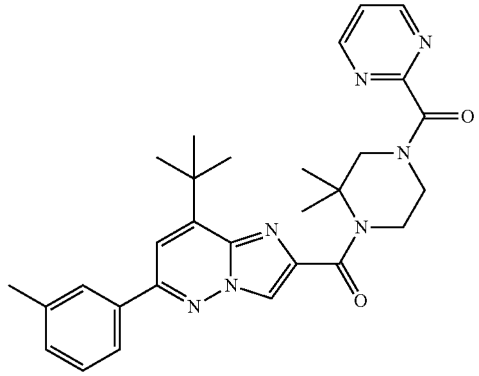

-continued
I-413
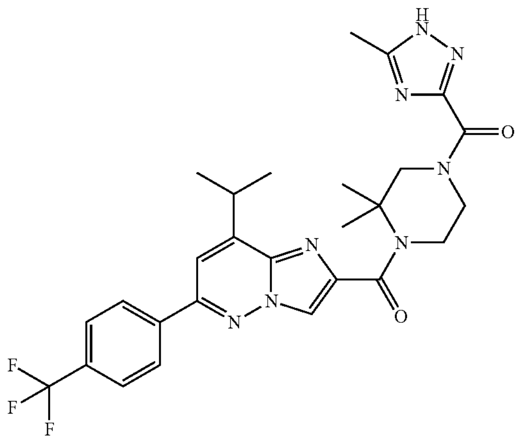
I-414
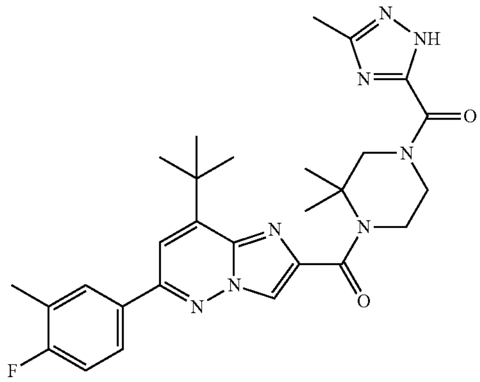
I-415
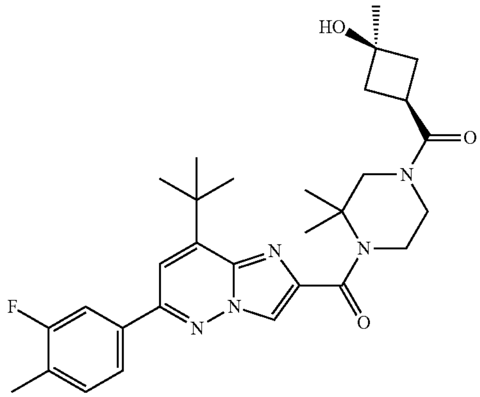
-continued
I-416
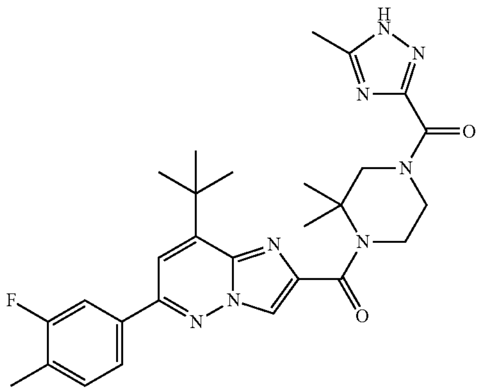
I-417
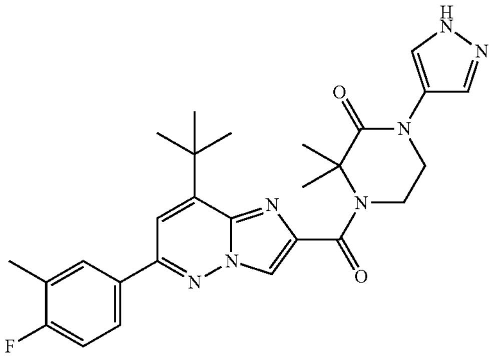
I-418
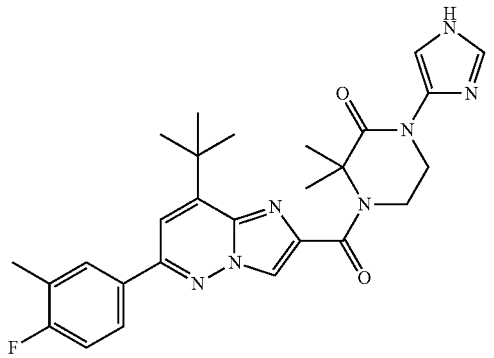
I-419
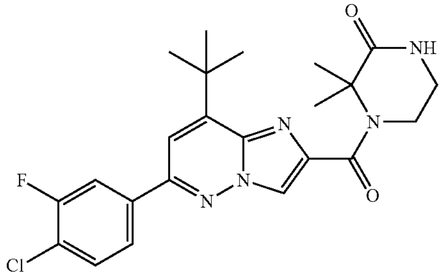

-continued
I-420
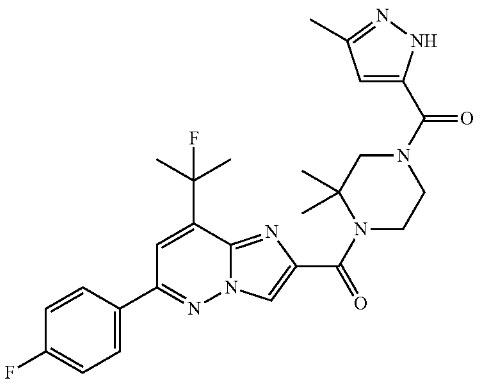
I-421
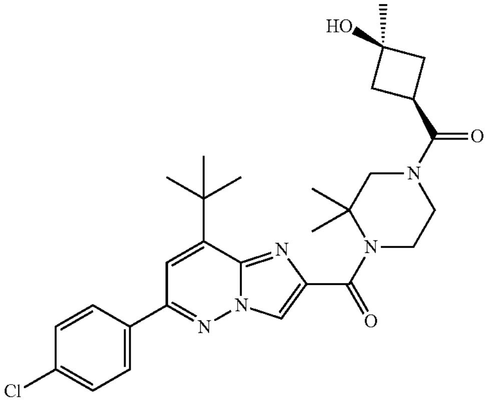
I-422
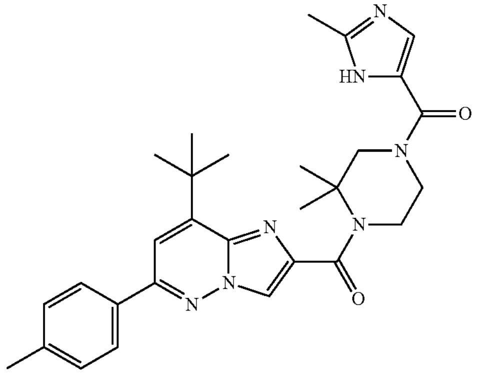
I-423
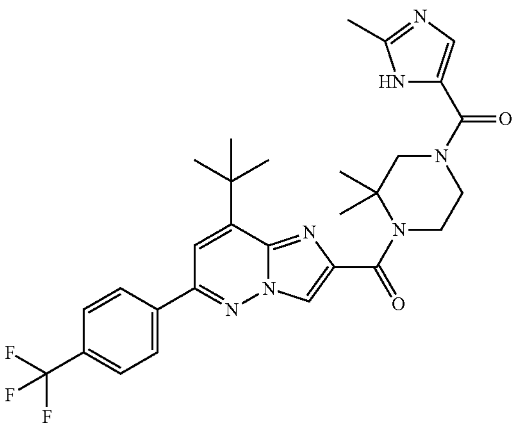
-continued
I-424
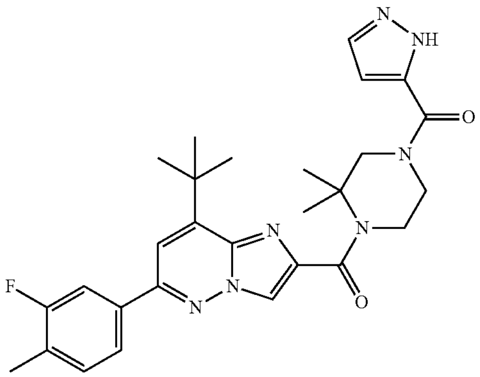
I-425
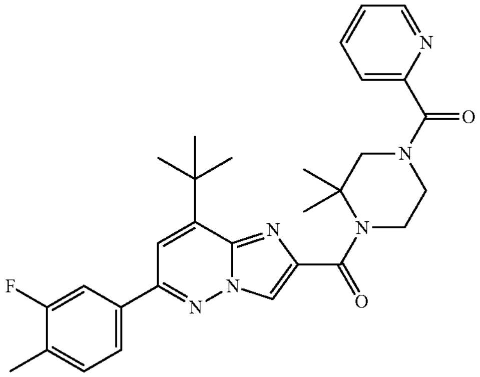
I-426
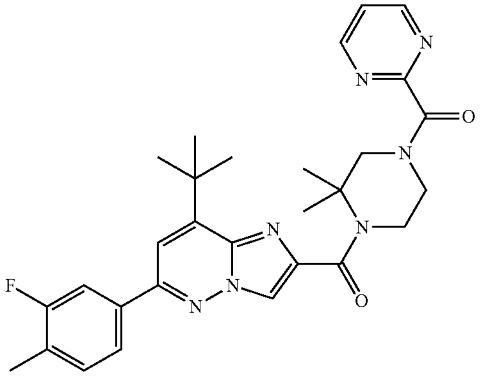
I-427
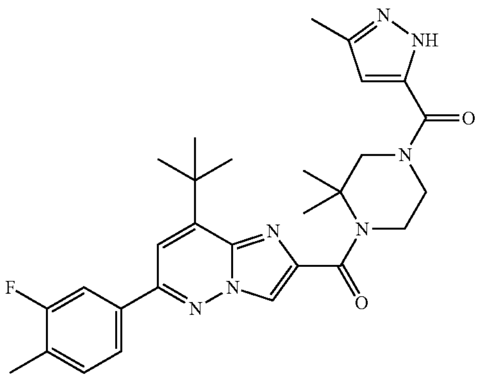

-continued
I-428
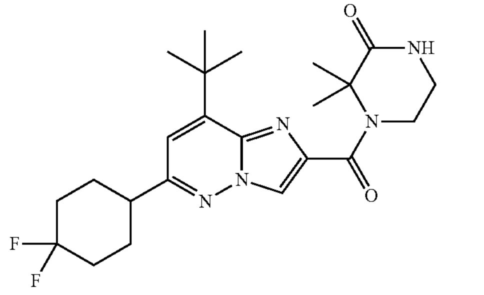
I-429
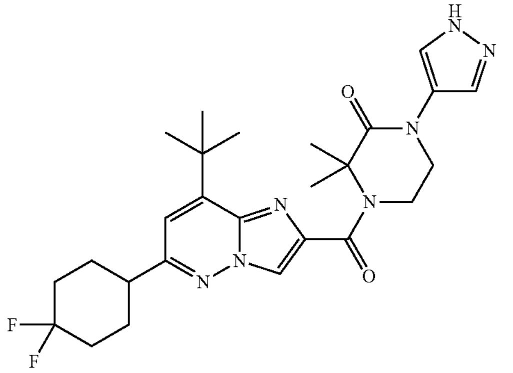
I-430
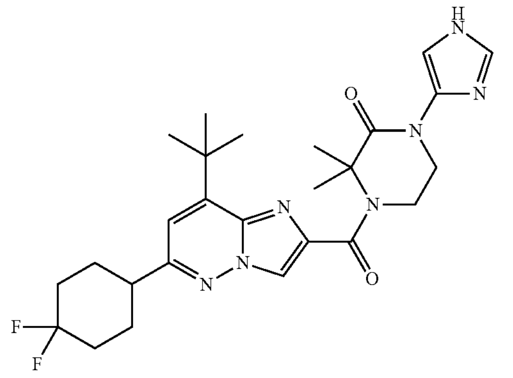
I-431
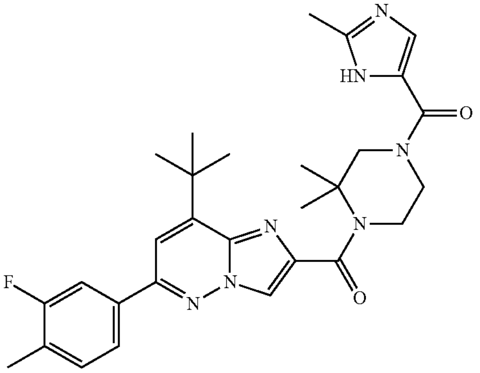
-continued
I-432
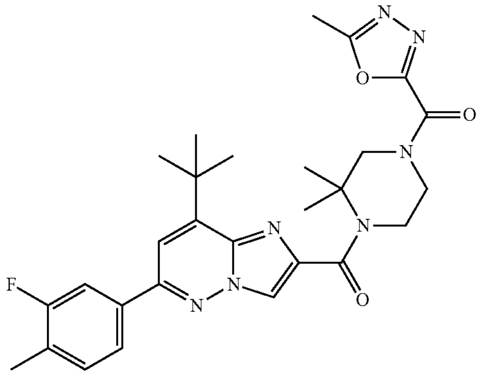
I-433
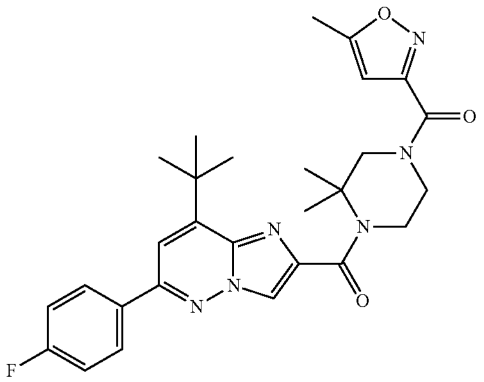
I-434
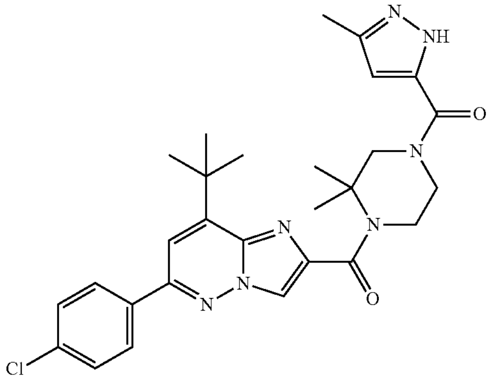
I-435
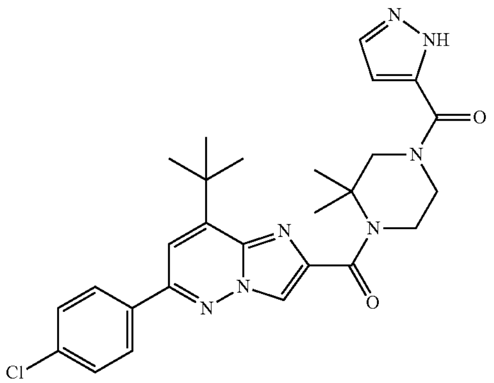

-continued
I-436
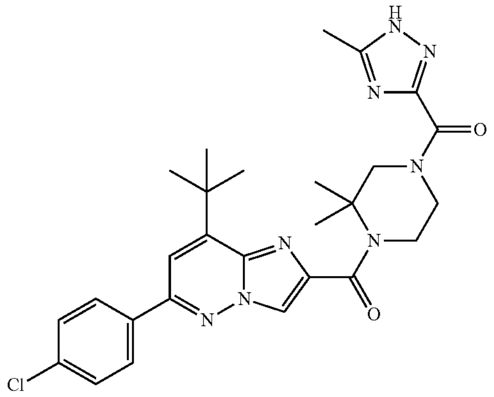
I-437
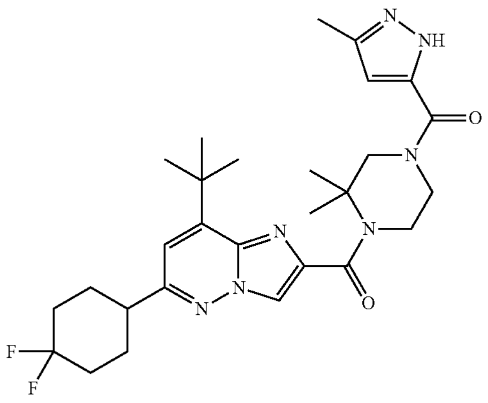
I-438
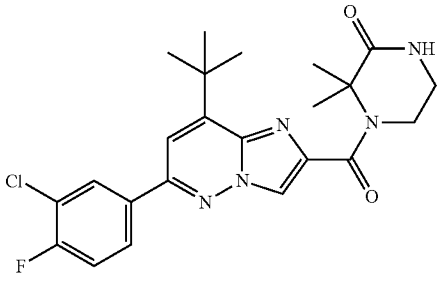
I-439
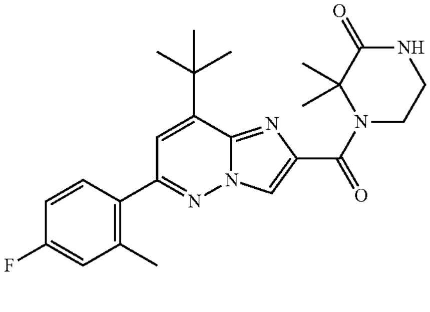
-continued
I-440
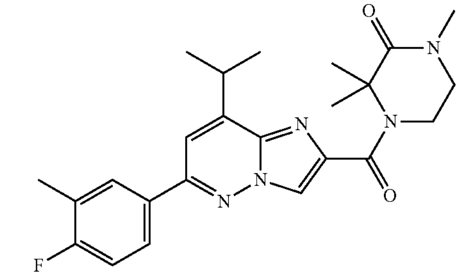
I-441
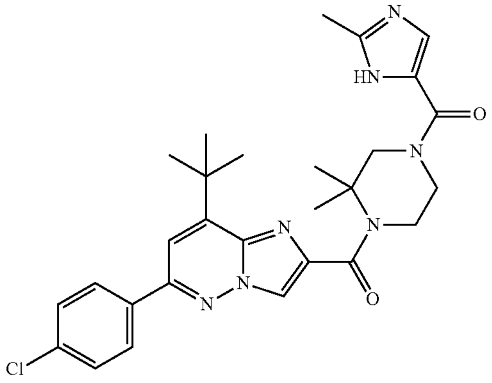
I-442
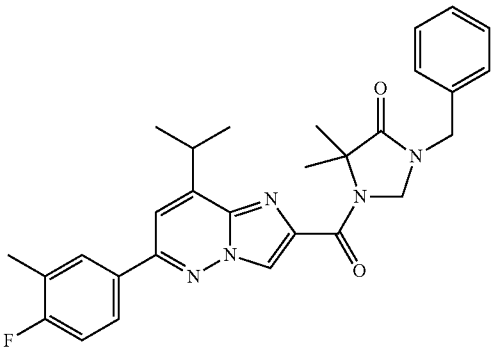
I-443
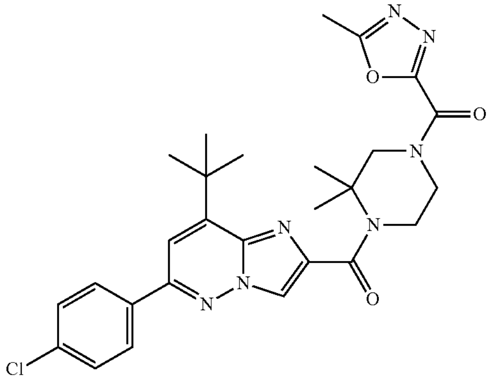

-continued
I-444
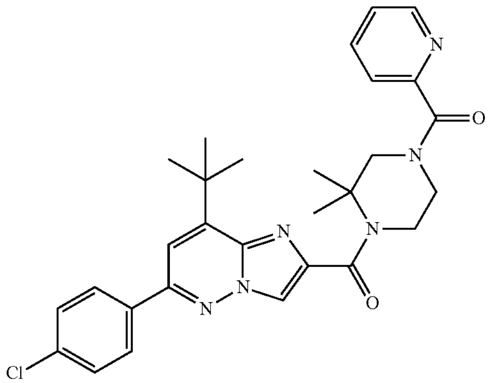
I-445
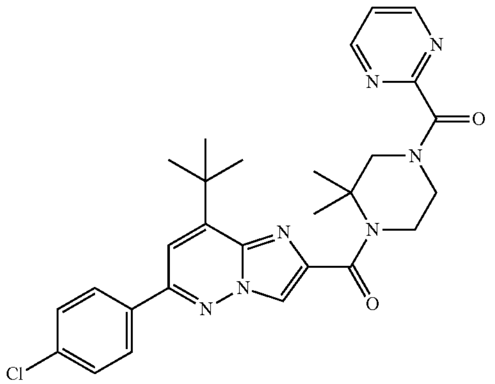
I-446
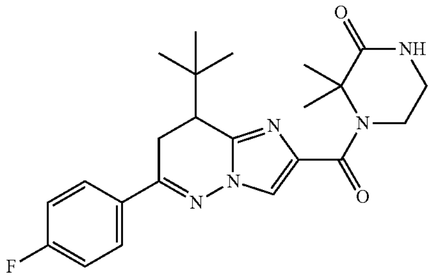
I-447
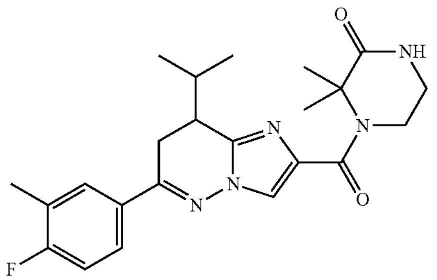
-continued
I-448
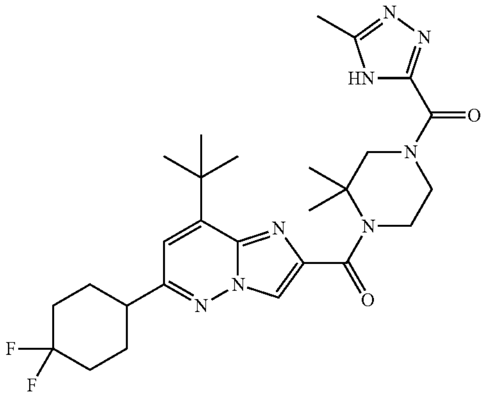
I-449
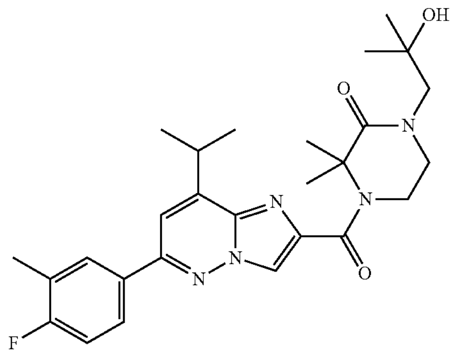
I-450
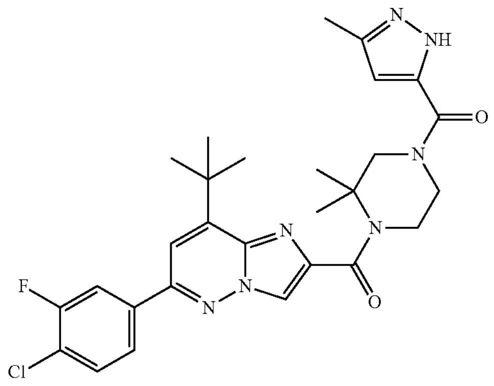
I-451
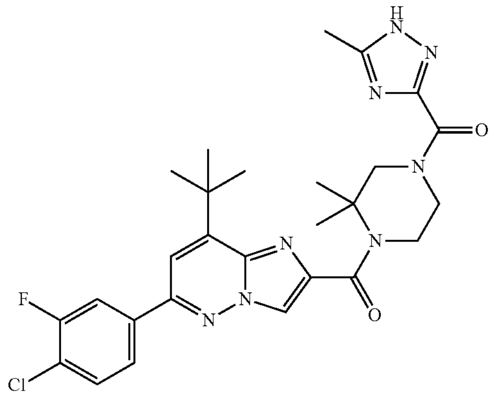

-continued
I-452
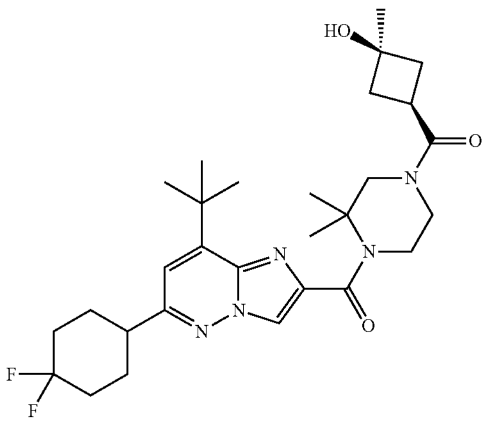
I-453
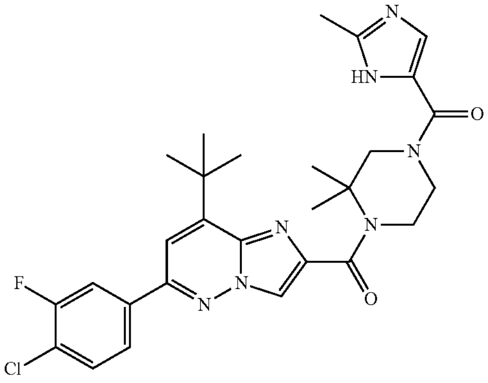
I-454
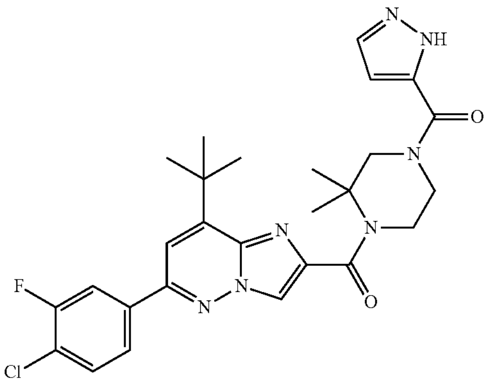
I-455
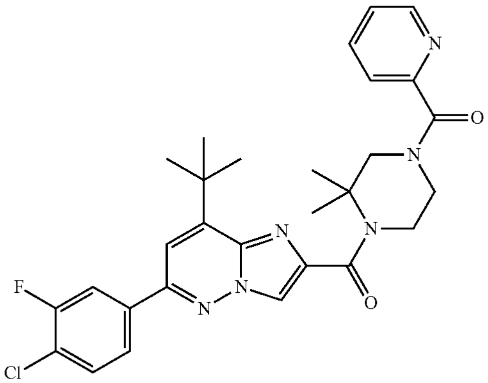
-continued
I-456
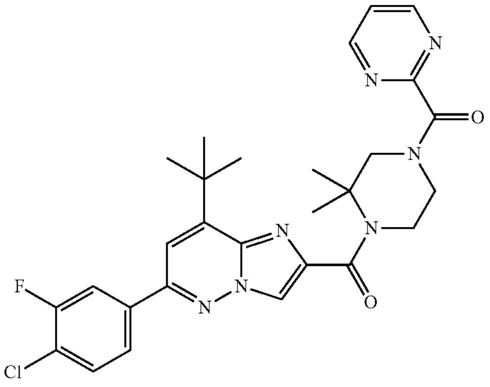
I-457
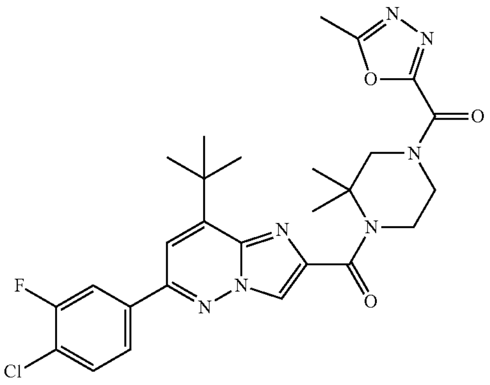
I-458
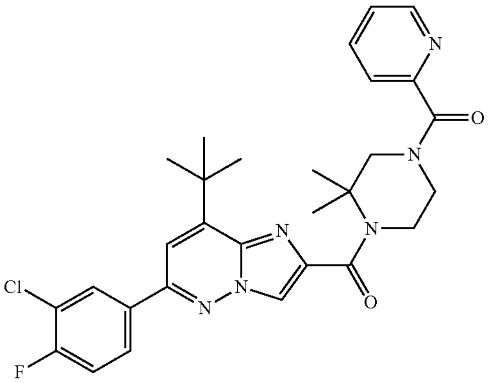
I-459
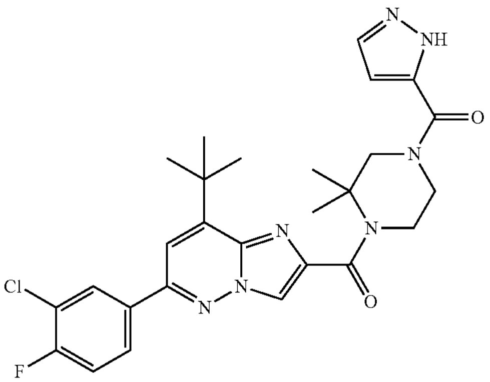

-continued
I-460
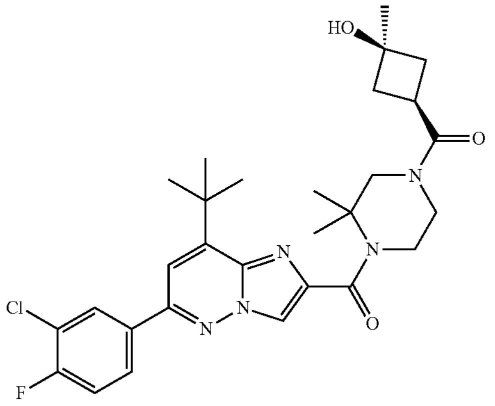
I-461
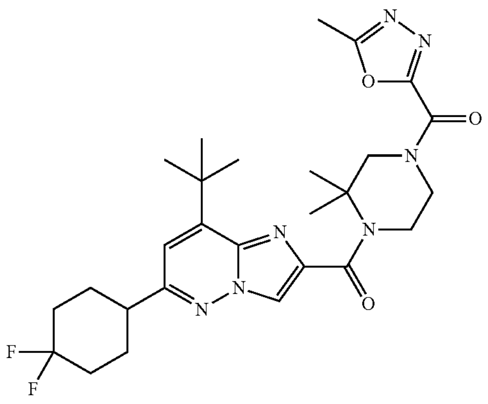
I-462
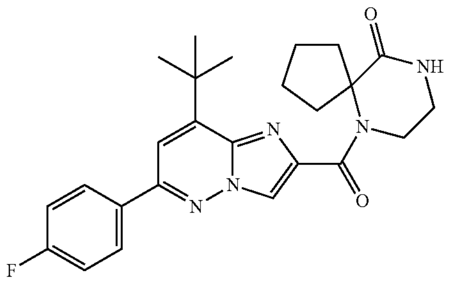
I-463
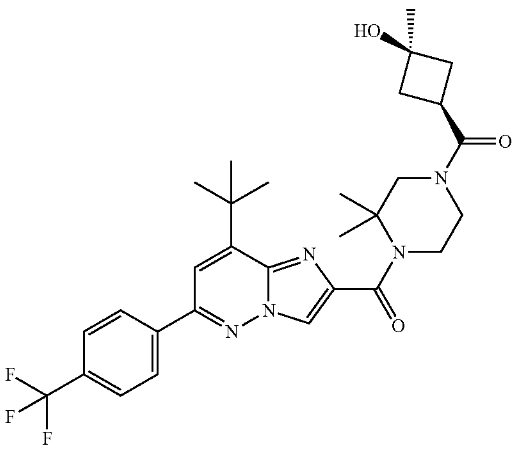
-continued
I-464
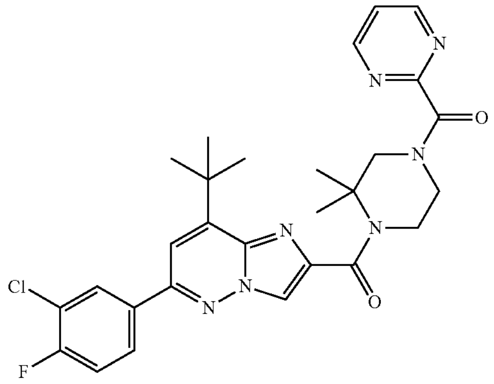
I-465
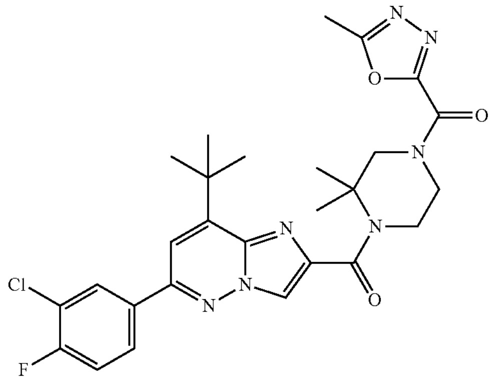
I-466
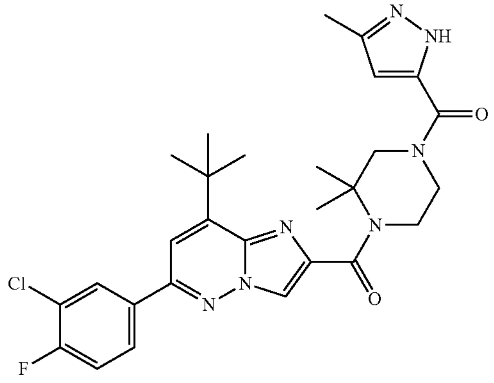
I-467
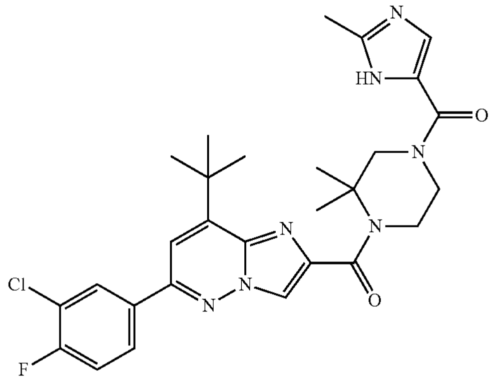

-continued
I-468
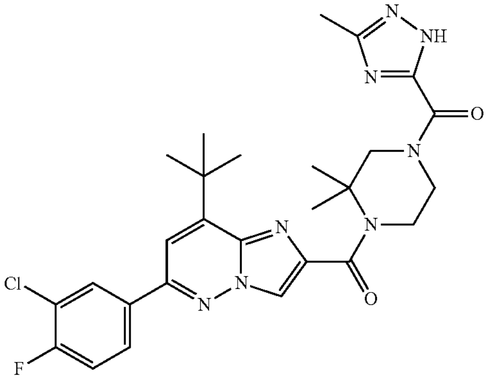
I-469
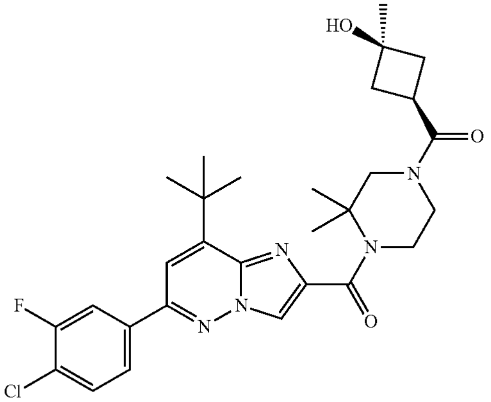
I-470
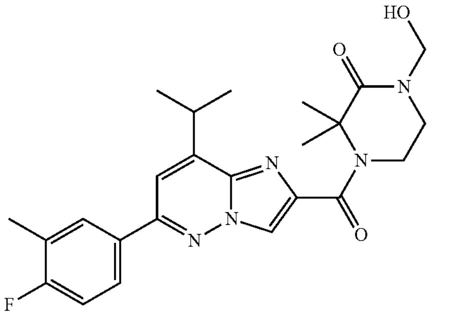
I-471
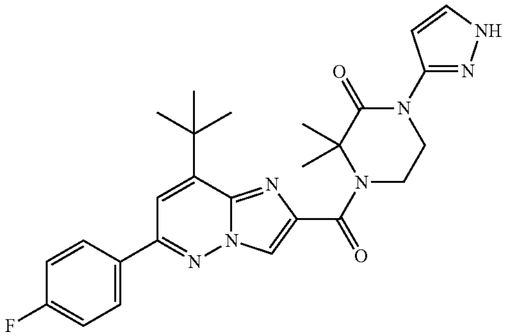
-continued
I-472
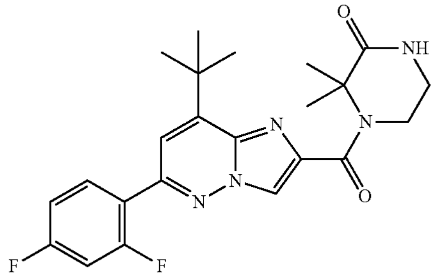
I-473
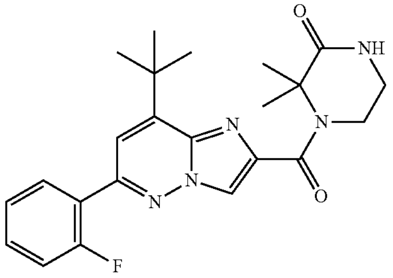
I-474
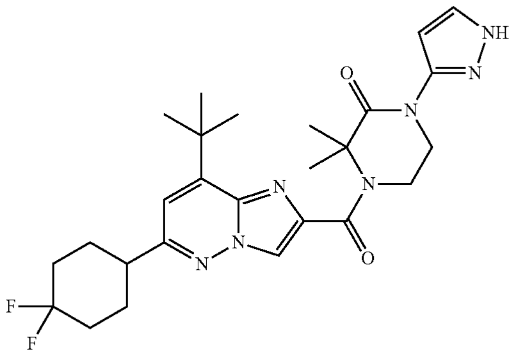
I-475
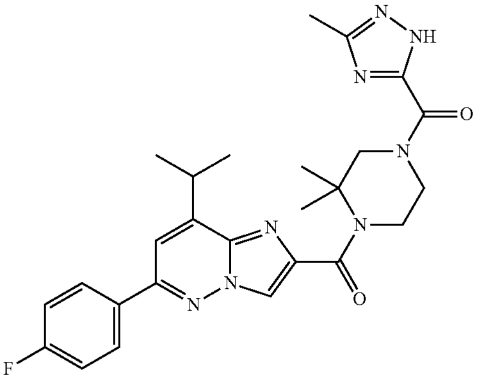
I-476
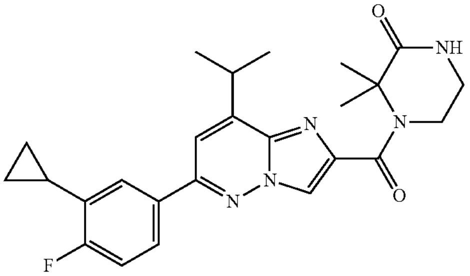

-continued
I-477
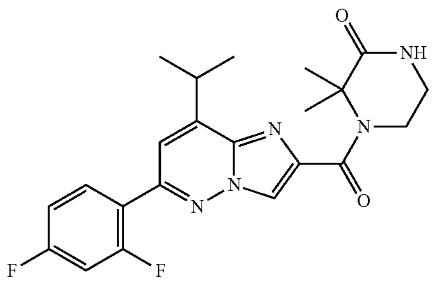
I-478
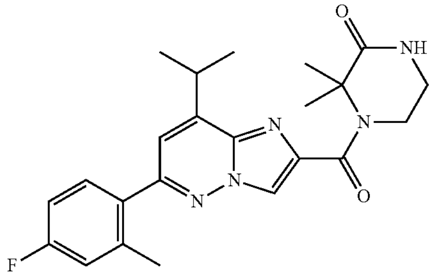
I-479
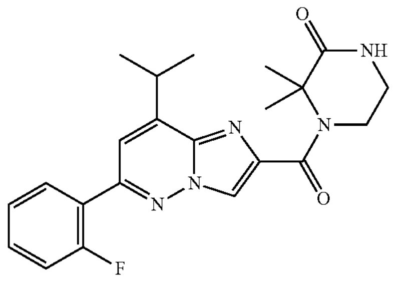
I-480
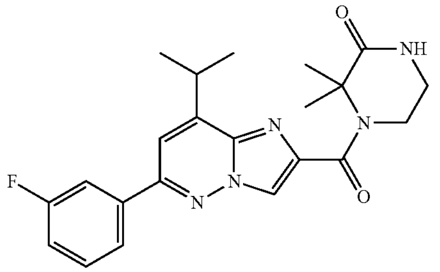
I-481
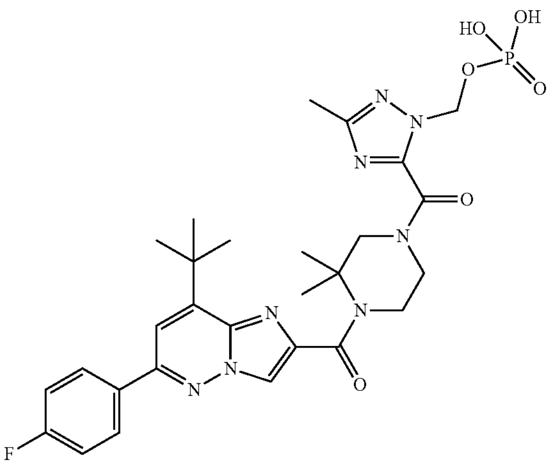
-continued
I-482
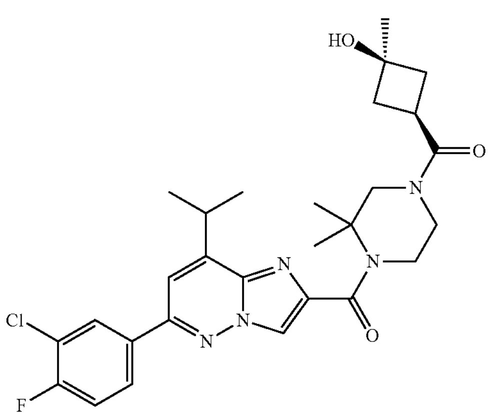
I-483
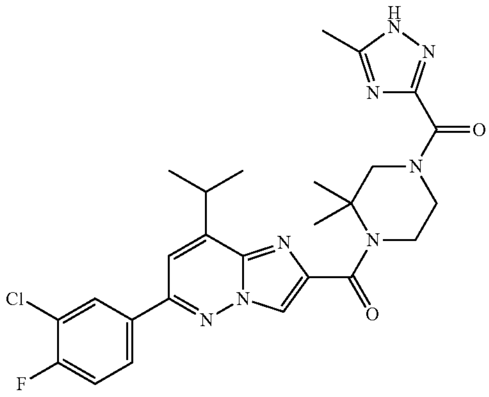
I-484
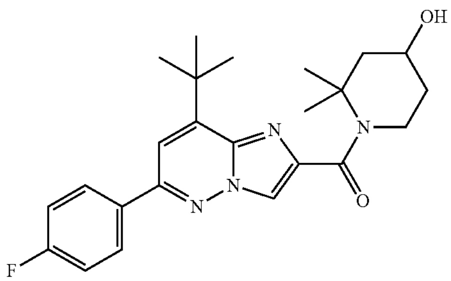
I-485
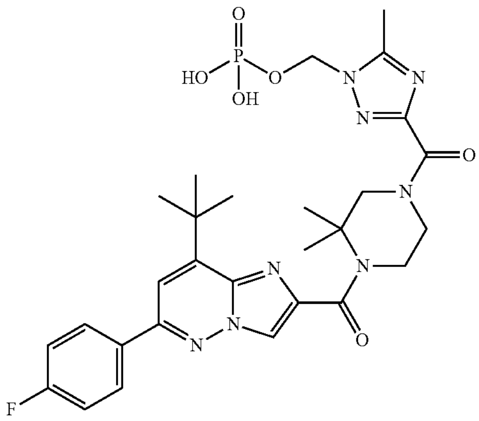

-continued
I-486
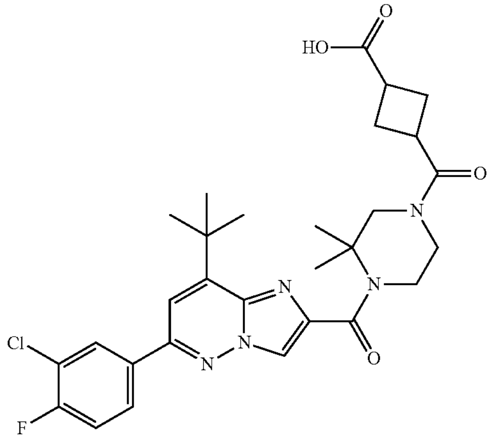
I-487
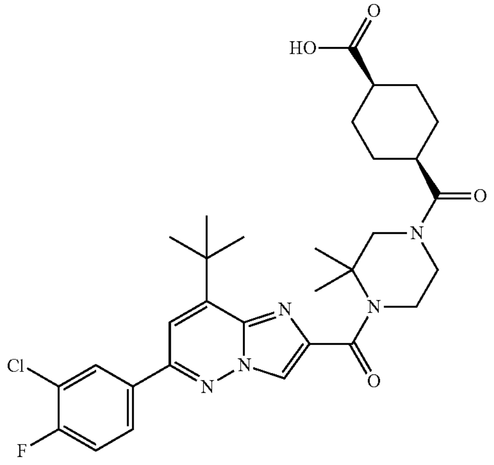
I-488
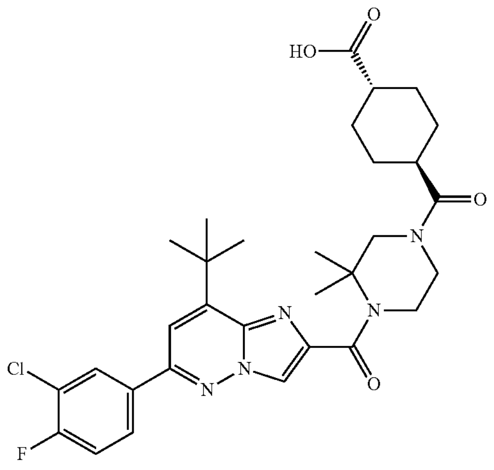
-continued
I-489
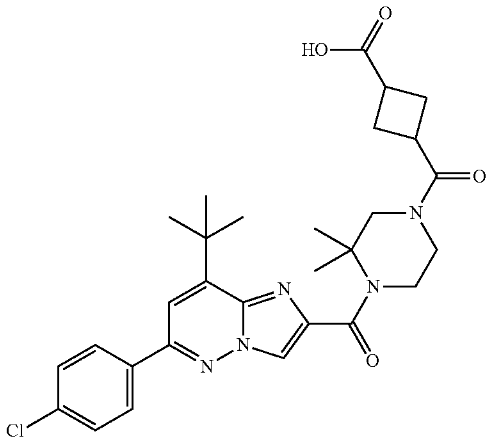
I-490
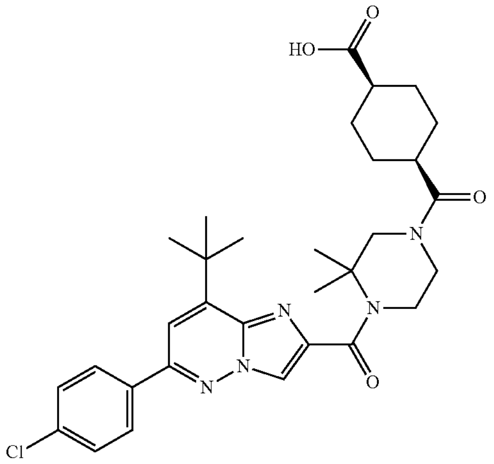
I-491
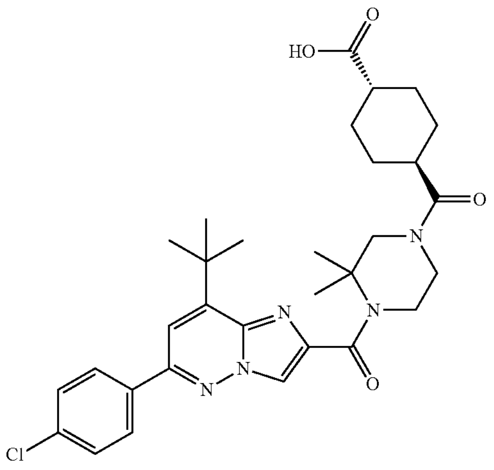

-continued
I-492
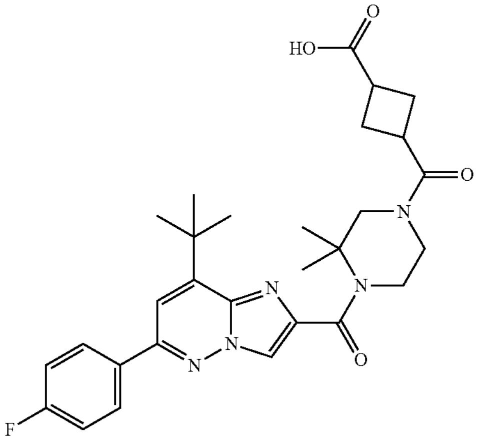
I-493
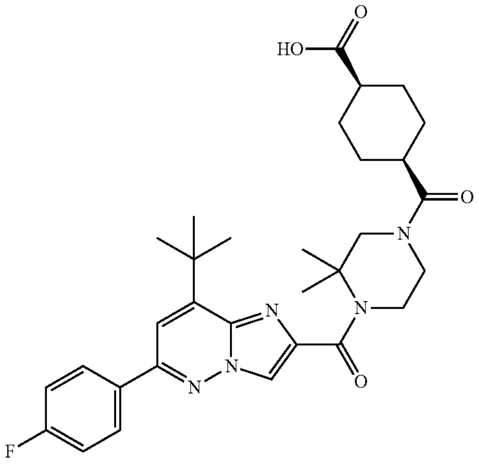
I-494
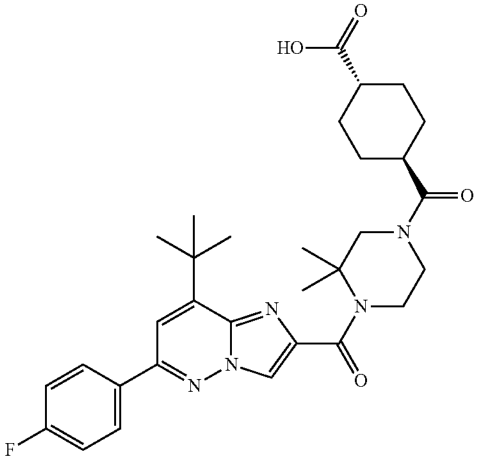
-continued
I-495
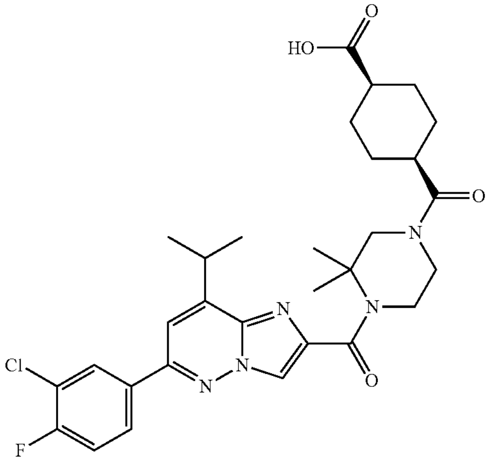
I-496
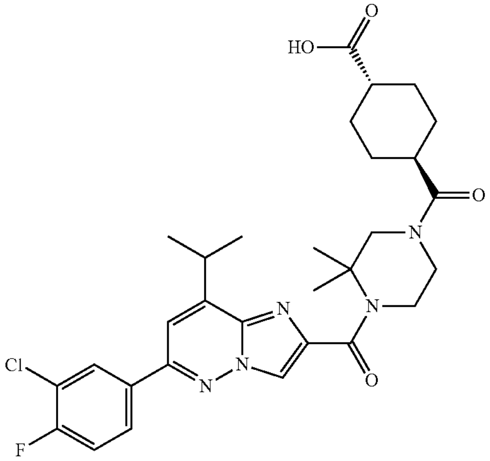
I-497
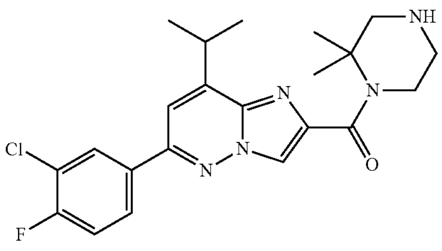
I-498
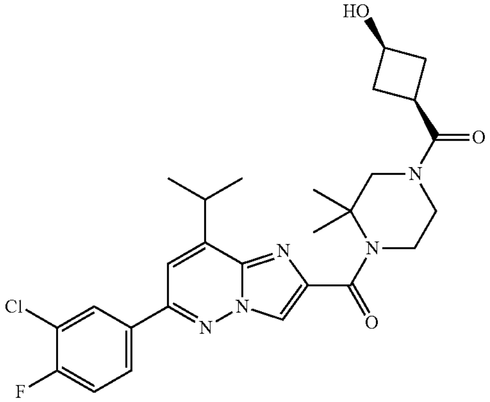

-continued
I-499
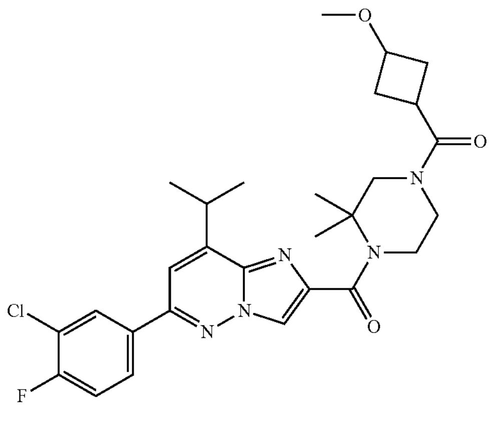
I-500
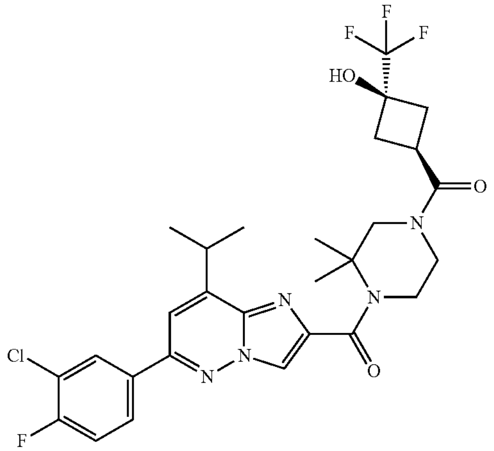
I-501
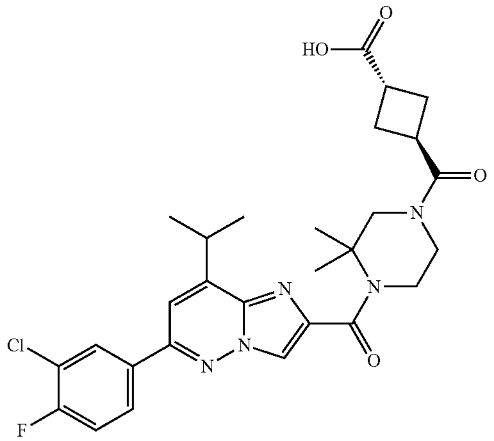
-continued
I-502
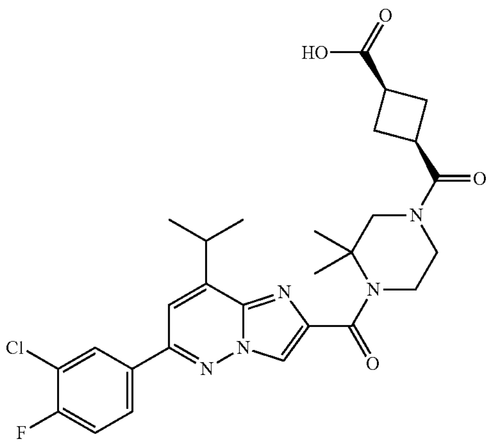
I-503
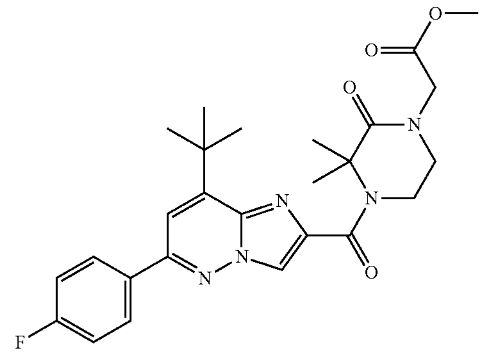
I-504
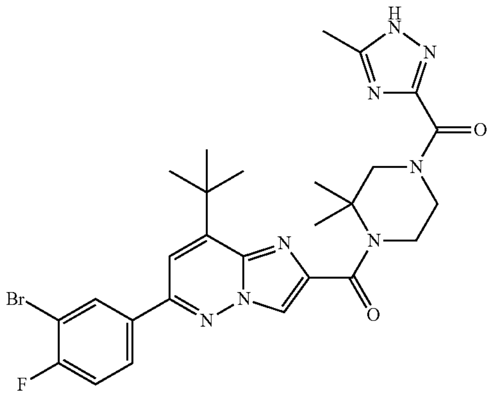
I-505
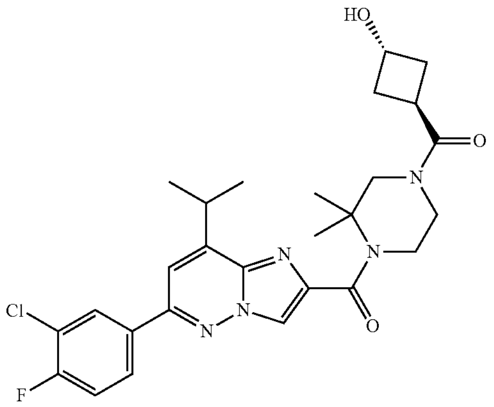

-continued
I-506
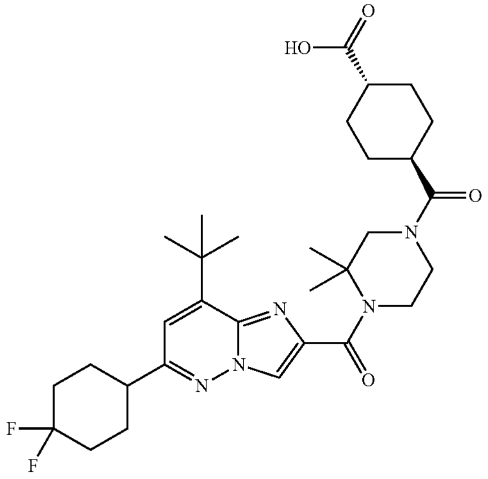
I-507
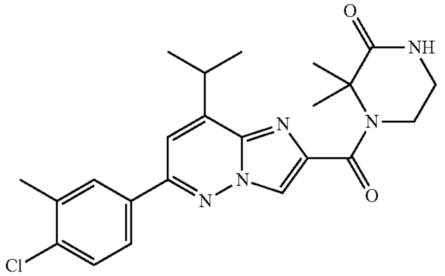
I-508
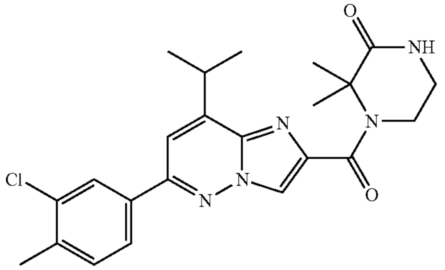
I-509
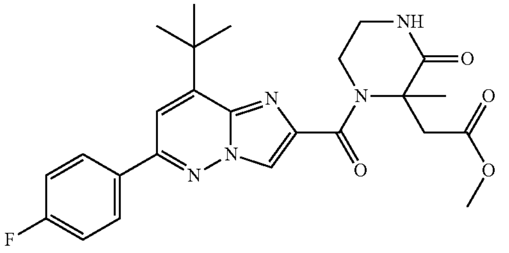
I-510
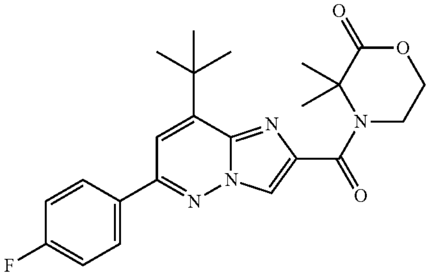
-continued
I-511
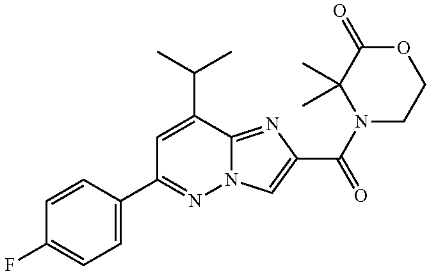
I-512
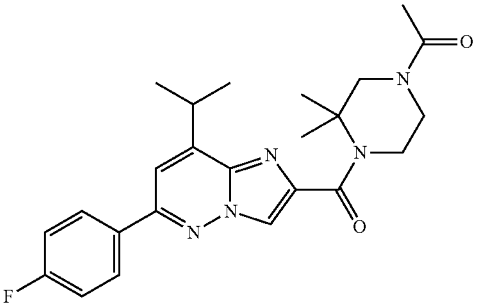
I-513
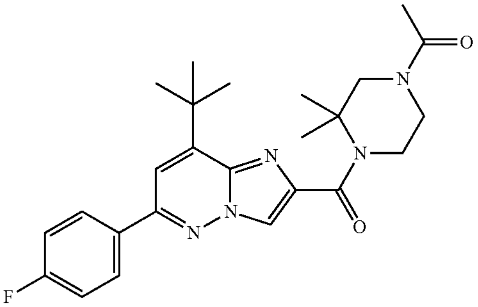
I-514
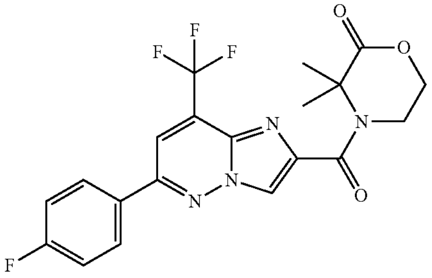

-continued
I-515
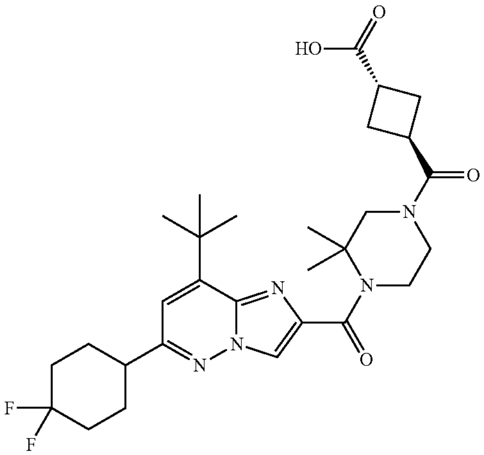
I-516
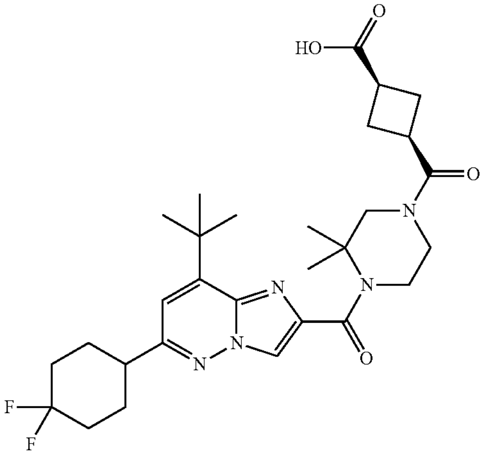
I-517
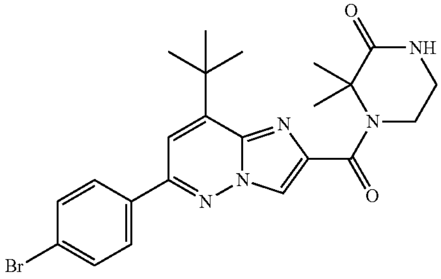
I-518
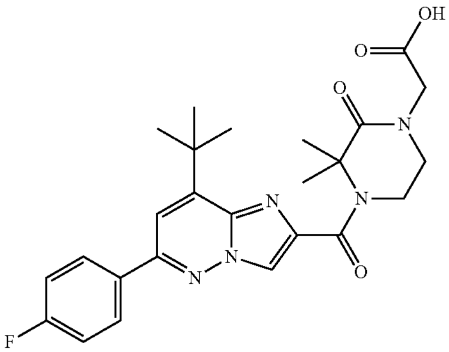
-continued
I-519
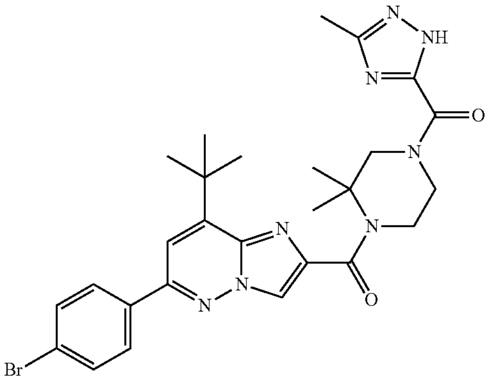
I-520
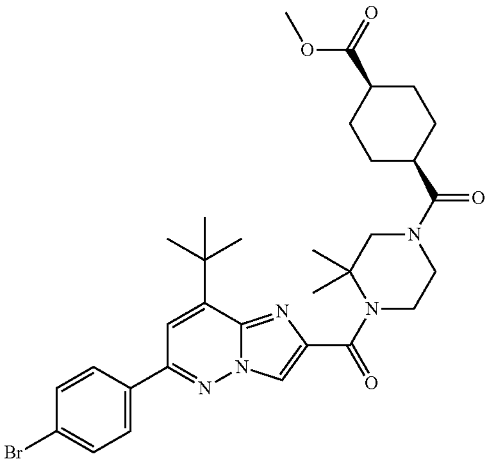
I-521
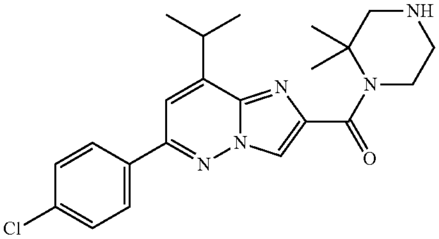
I-522
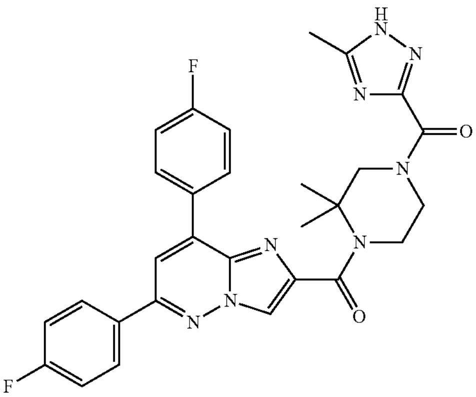

-continued
I-523
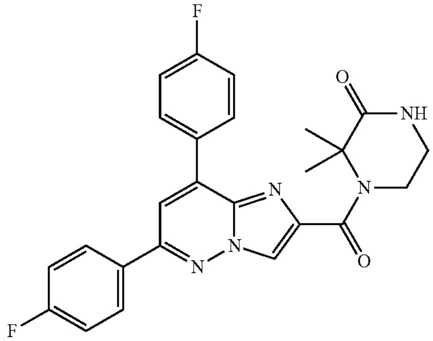
I-524
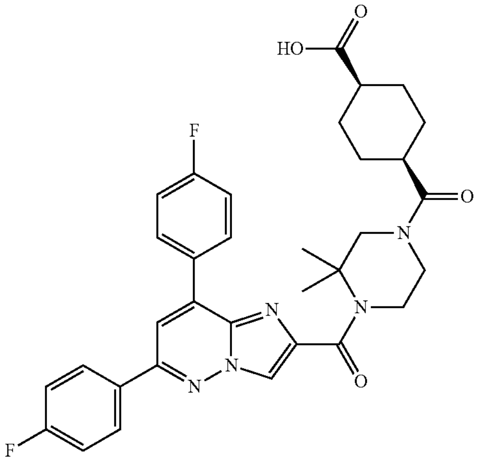
I-525
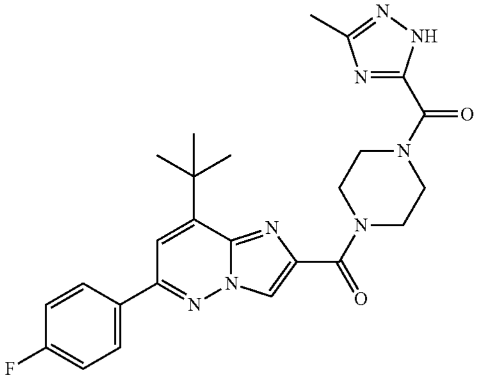
-continued
I-526
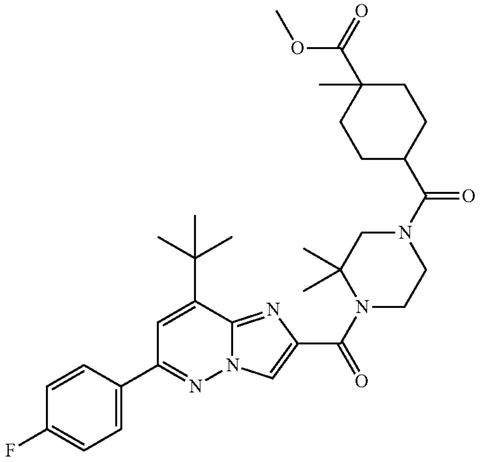
I-527
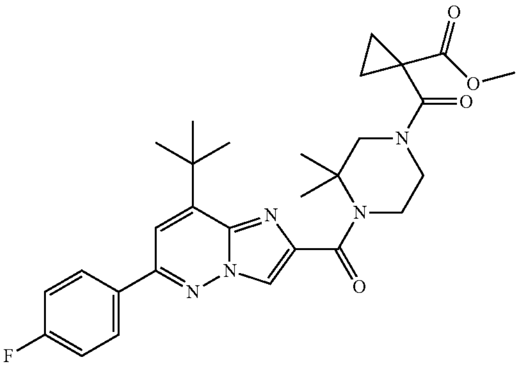
I-528
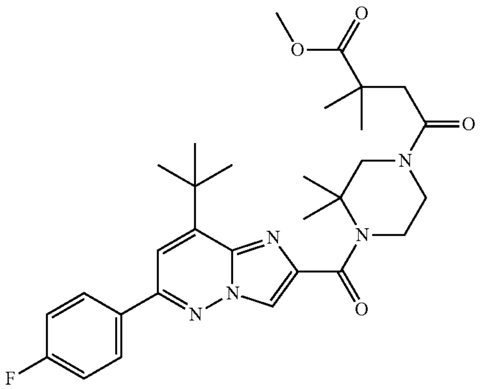
I-529
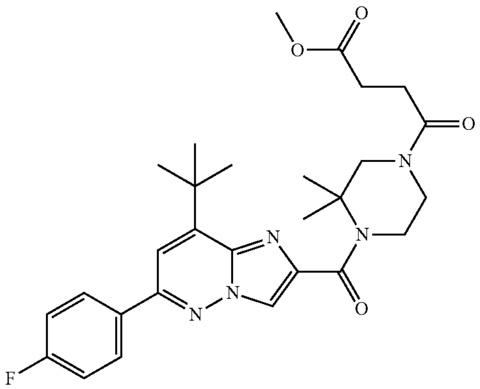

-continued
I-530
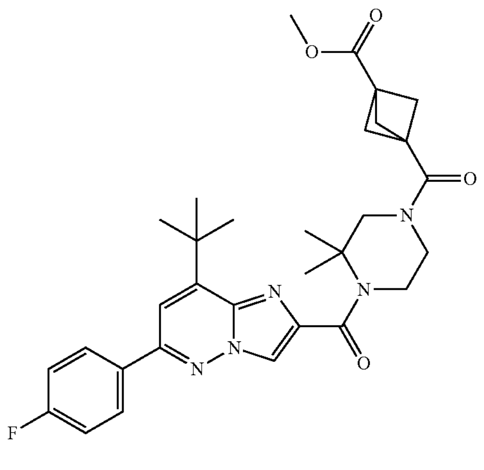
I-531
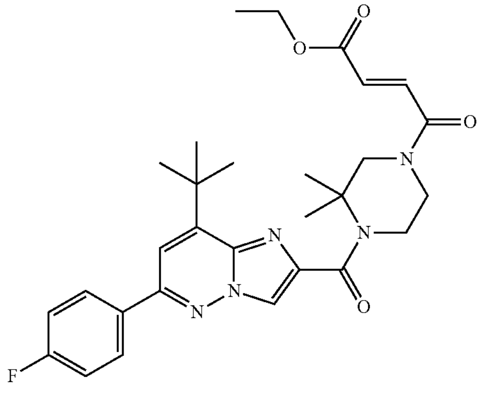
I-532
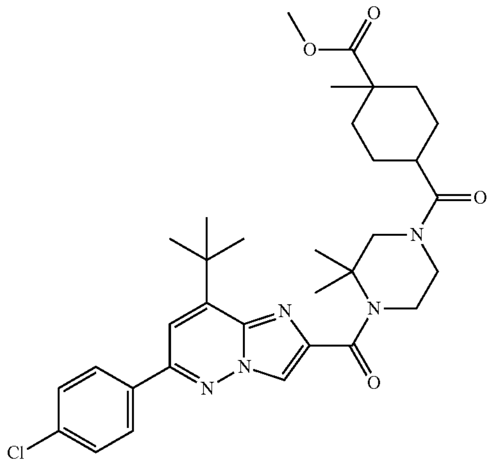
-continued
I-533
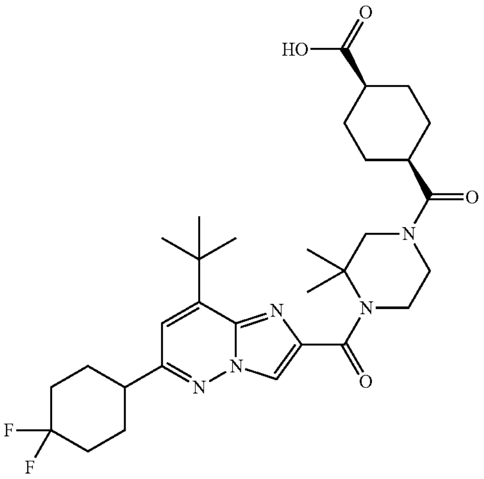
I-534
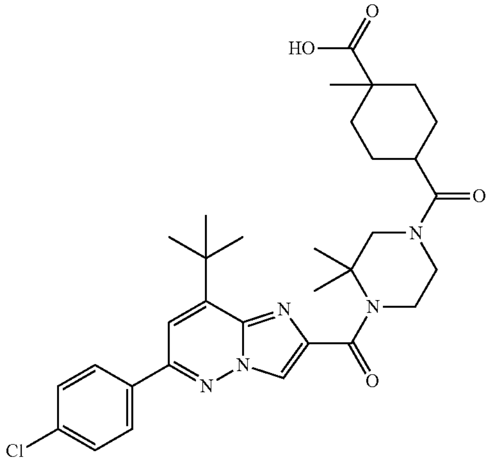
I-535
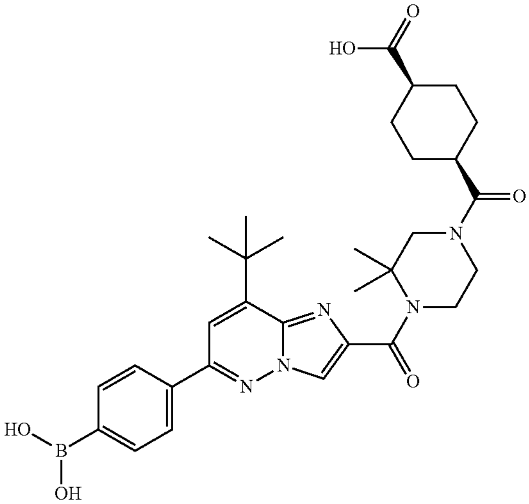

-continued
I-536
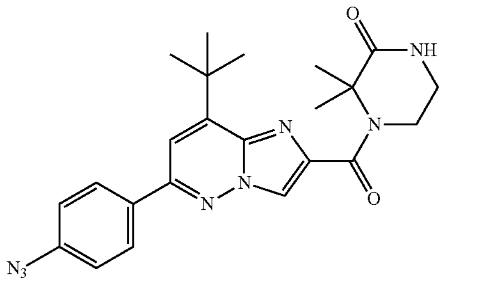
I-537
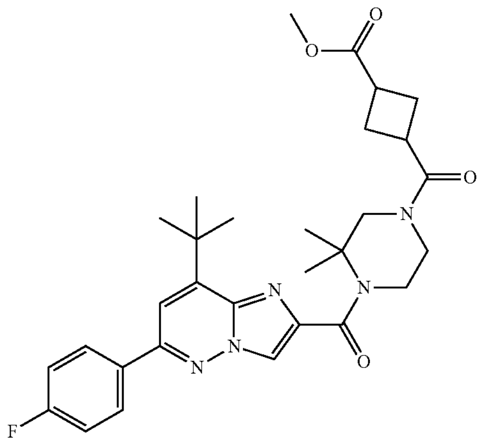
I-538
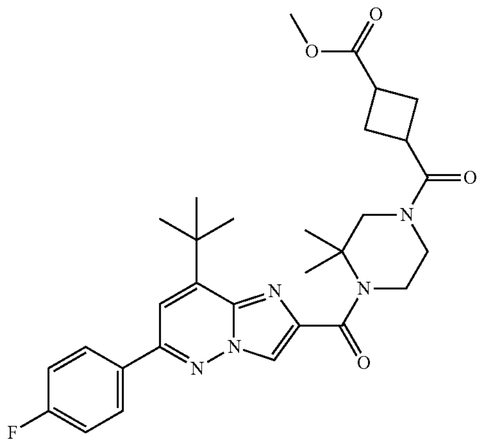
I-539
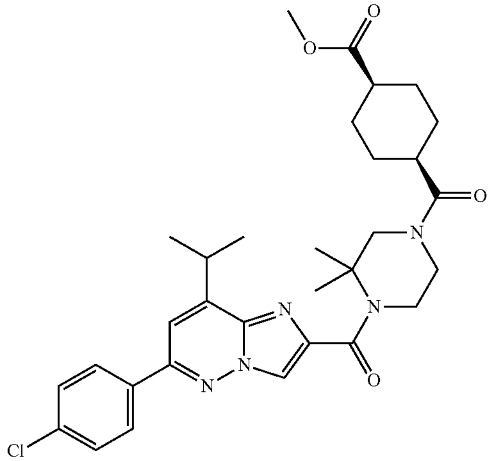
-continued
I-540
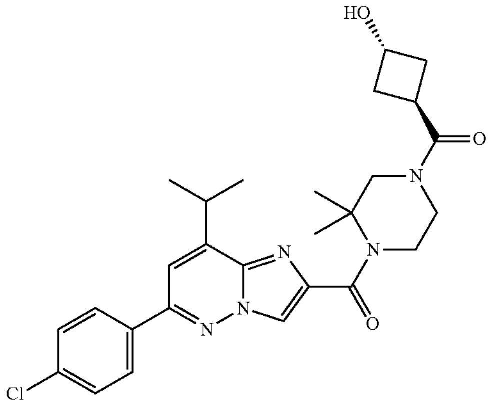
I-541
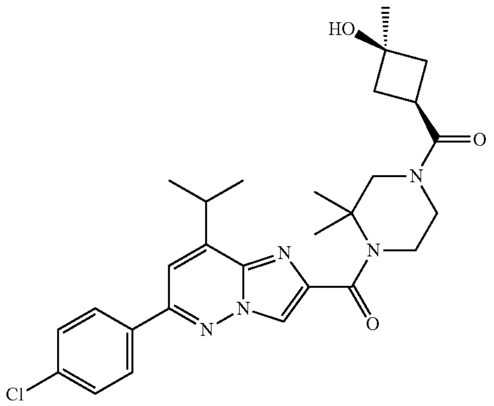
I-542
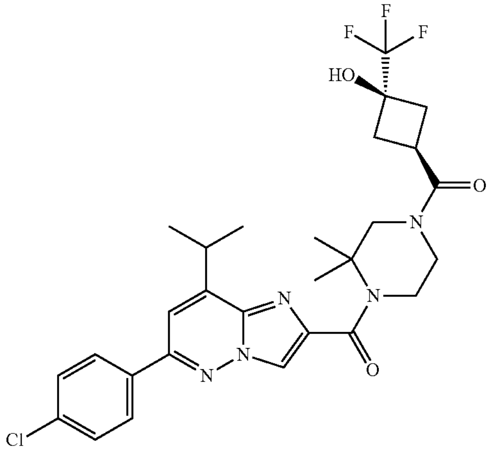

-continued
I-543
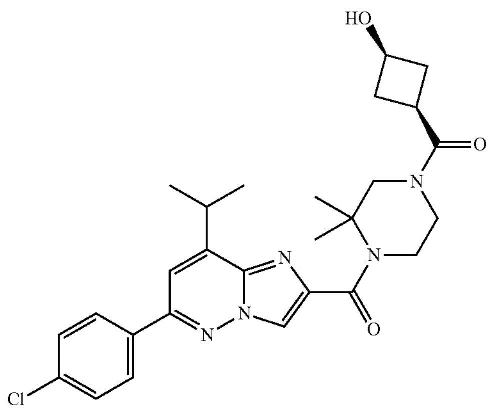
I-544
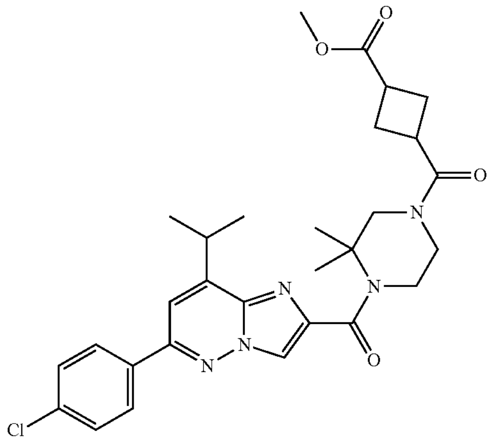
I-545
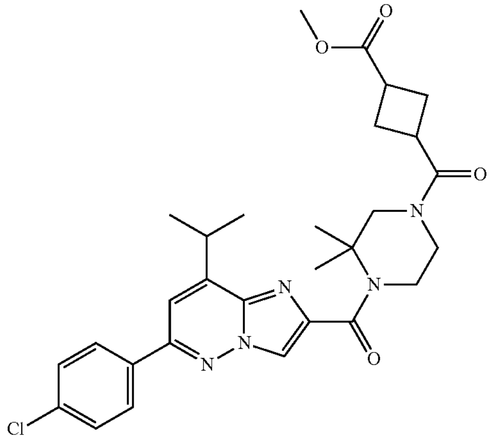
-continued
I-546
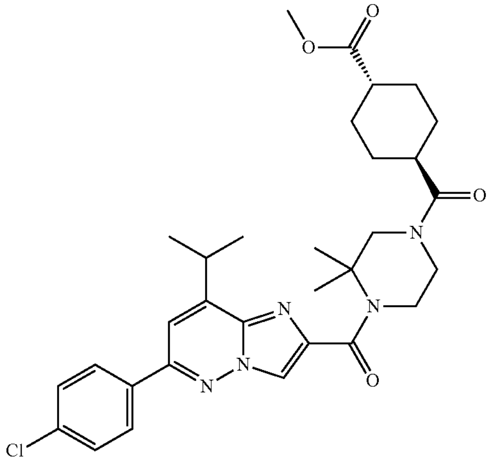
I-547
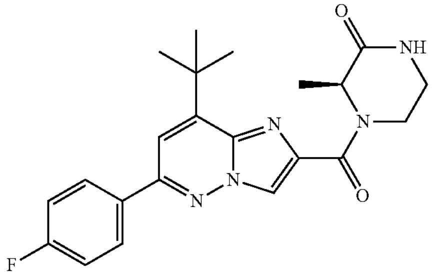
I-548
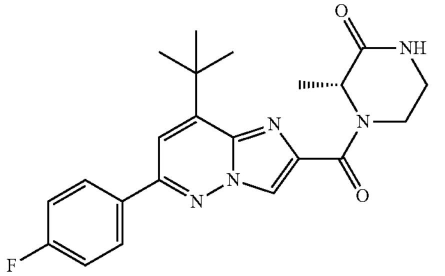
I-549
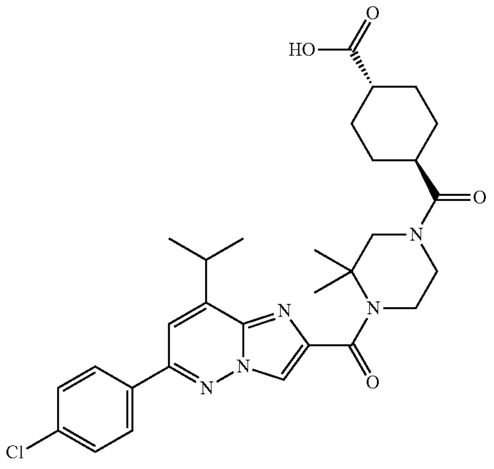

-continued
I-550
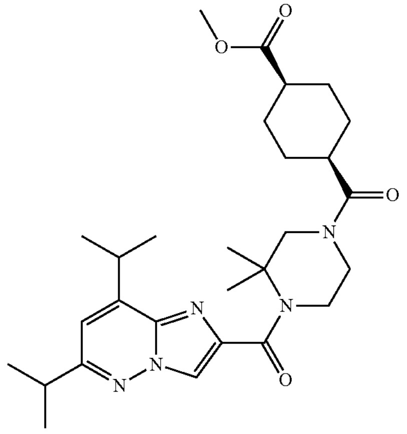
I-551
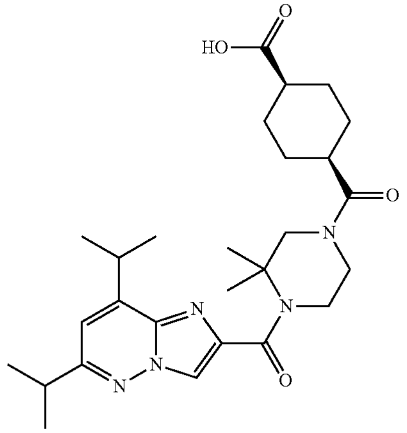
I-552
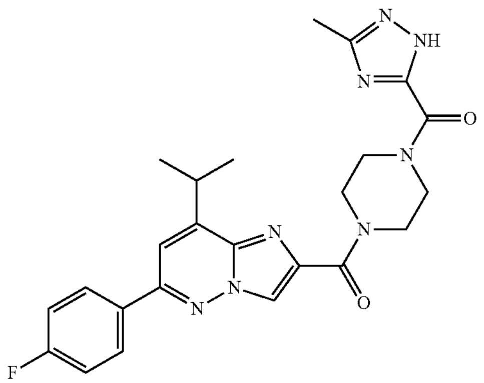
-continued
I-553
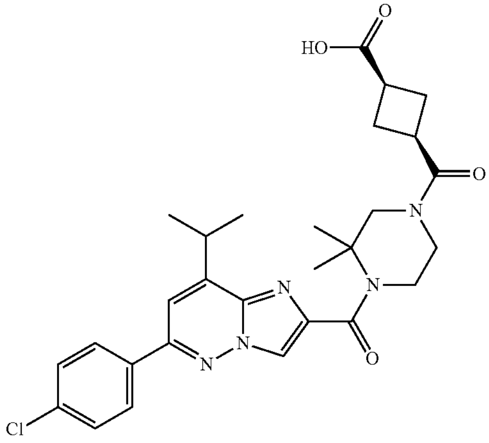
I-554
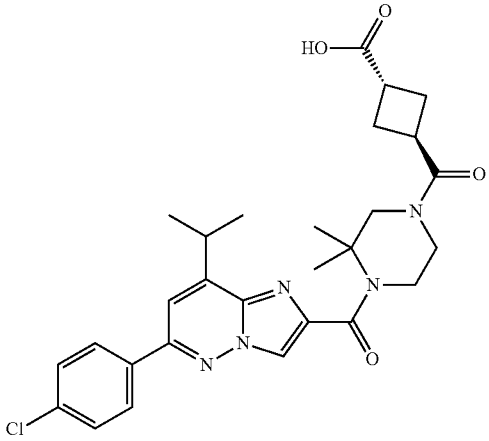
I-555
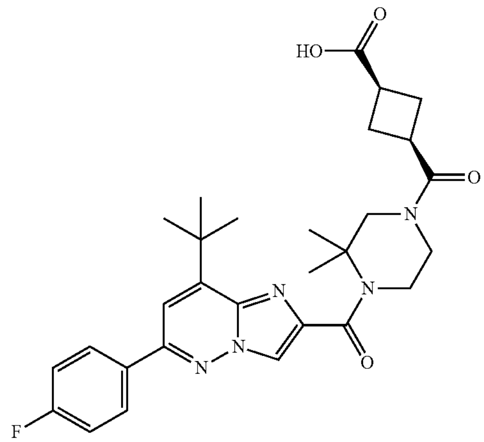

-continued
I-556
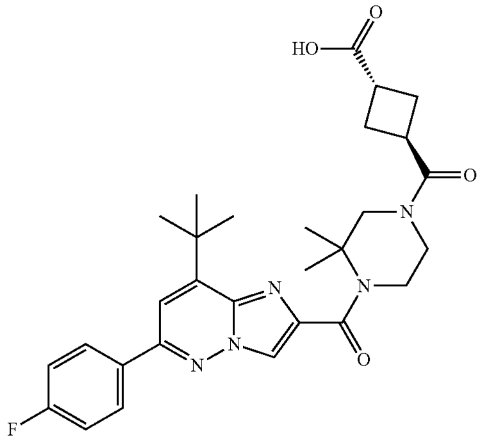
I-557
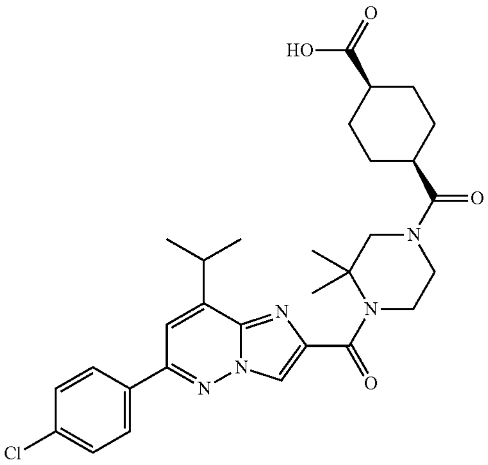
I-558
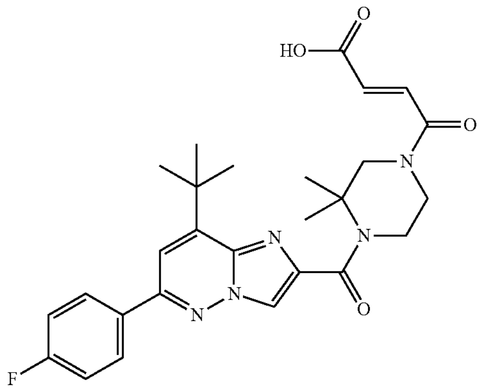
-continued
I-559
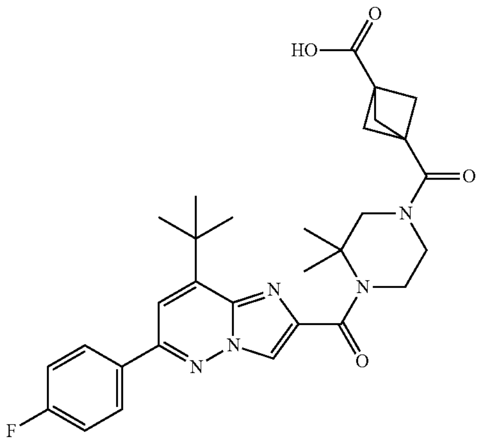
I-560
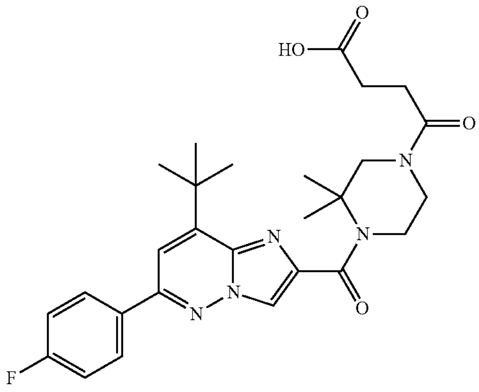
I-561
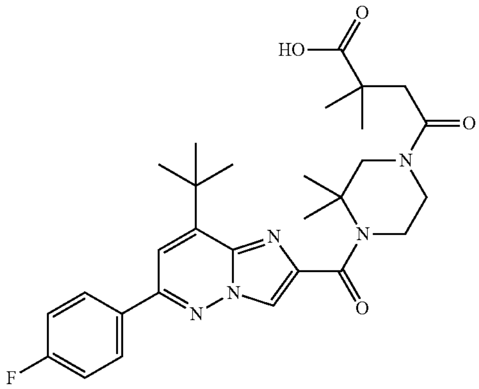
I-562
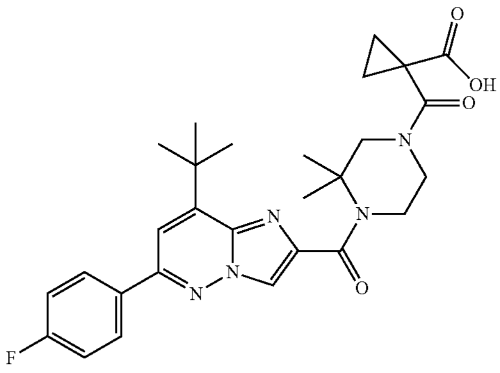

-continued
I-563
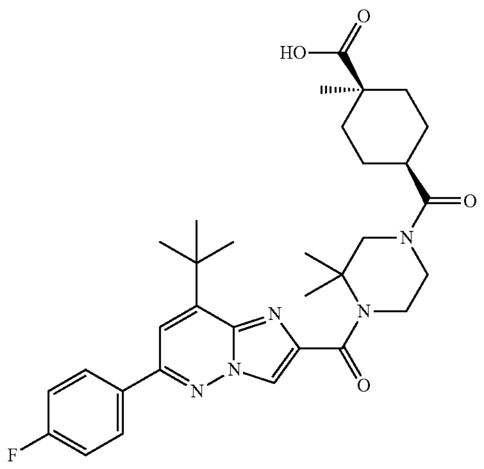
I-564
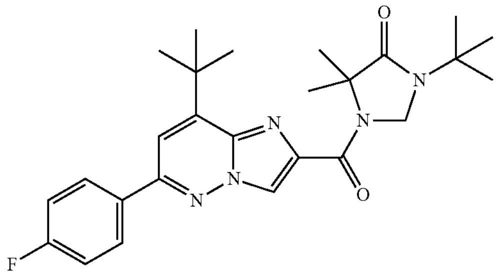
I-565
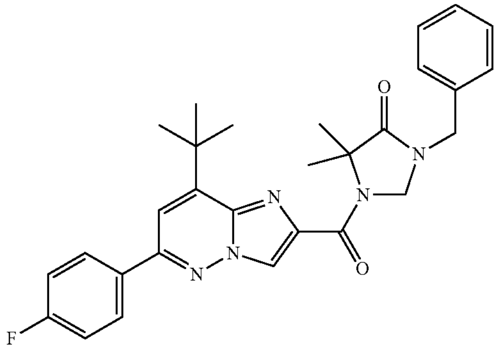
I-566
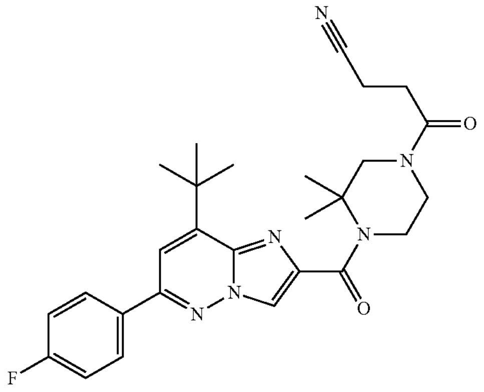
-continued
I-567
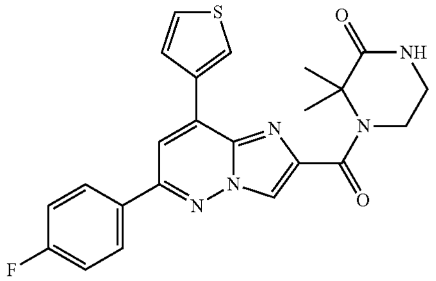
I-568
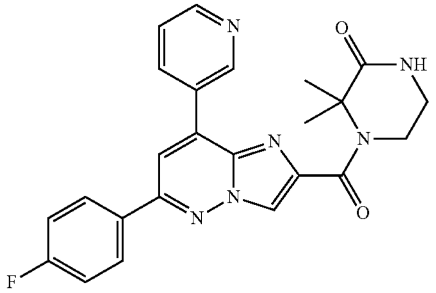
I-569
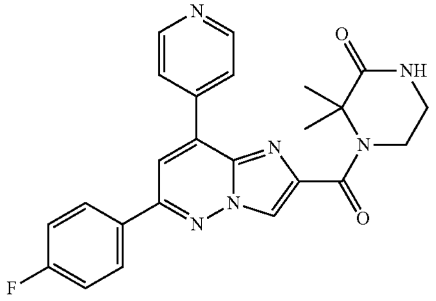
I-570
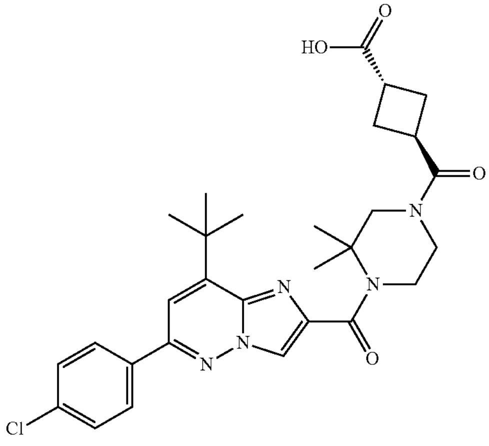

-continued

I-571

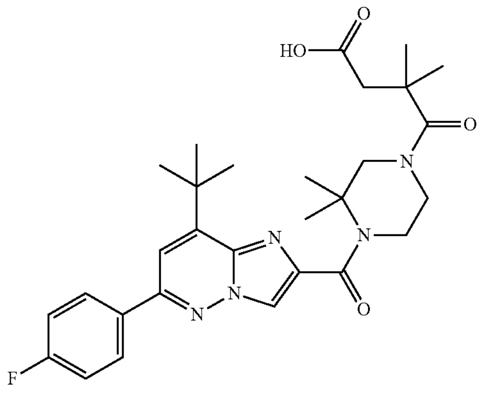

I-572

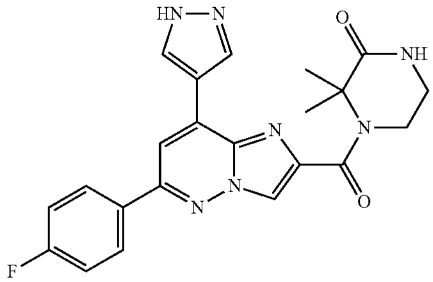

I-573

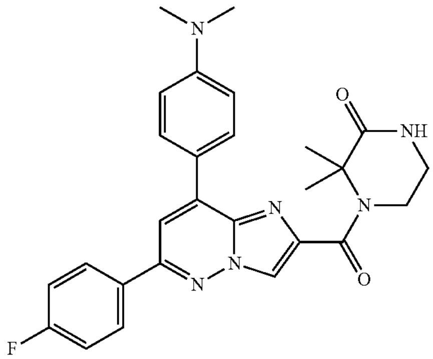

I-574

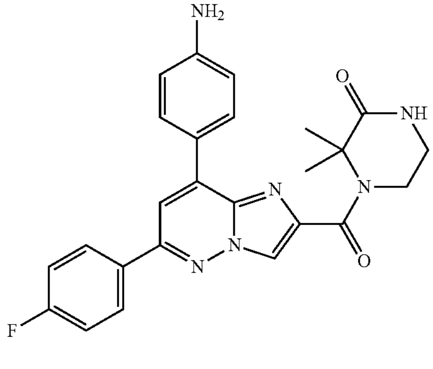

-continued

I-575

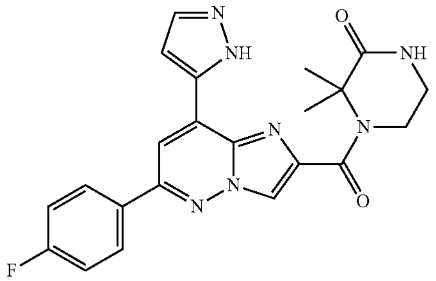

I-576

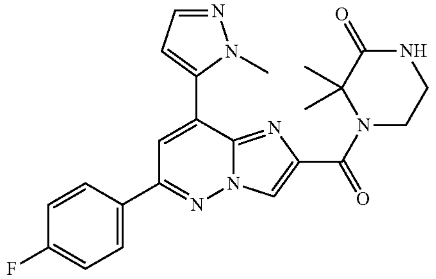

I-577

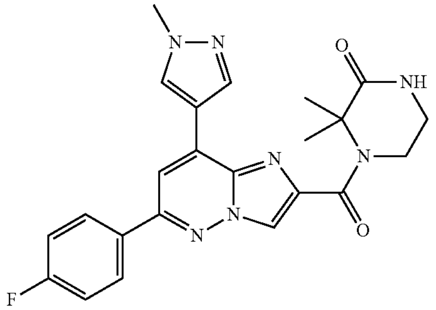

In some embodiments, the variables of each of formulae (I) and (II) are as depicted in the compounds of the disclosure including compounds in the tables above.

In general, the compounds of the invention may be prepared by methods described herein or by other methods known to those skilled in the art. Specific exemplary preparations of the compounds of the invention are described in the Exemplification section below.

In one embodiment, the methods of preparing compounds represented by Formula (I) or pharmaceutically acceptable salts thereof employ the step of reacting Compound (X-1) with Compound (Y-1) under suitable conditions to form a compound represented by formula (I) or a pharmaceutically acceptable salt thereof:

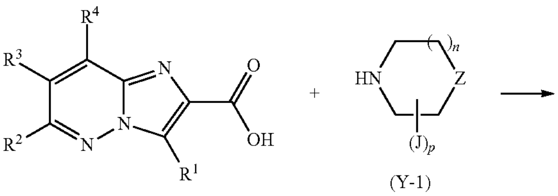

(X-1) (Y-1)

-continued

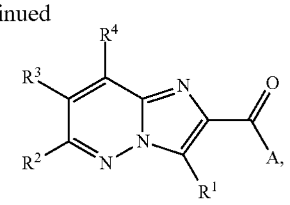

(I)

wherein the variables of Compound (X-1) with Compound (Y-1) are each and independently as described above for formula (I). Any suitable conditions known in the art to effectuate the reaction, such as those for amidations, can be used. Specific suitable conditions are as described in the Exemplification section below.

In another embodiment, the methods of preparing compounds represented by Formula (I) or pharmaceutically acceptable salts thereof, wherein A is

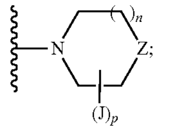

Z is —NX—; and the remaining variables of formula (I) are each and independently as described above, employ the step of reacting Compound (X-2) with X-$L^1$ under suitable conditions to form a compound of formula (I) or a pharmaceutically acceptable salt thereof:

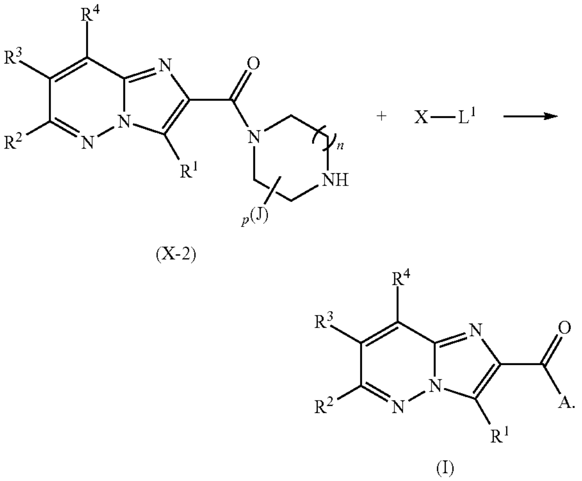

(X-2)

(I)

X of X-$L^1$ is as described above for formula (I) and $L^1$ of X-$L^1$ is halo (e.g., —Cl) or —OH, and the variables of Compound (X-2) are each and independently as described for above Formula (I). Any suitable conditions known in the art to effectuate the reaction, such as those for carbon-nitrogen coupling reactions (e.g., nucleophilic substitution, amidation, etc.), can be used. Specific suitable conditions are as described in the Exemplification section below.

In another embodiment, the methods of preparing compounds represented by Formula (I) or pharmaceutically acceptable salts thereof employ the step of reacting Compound (X-3) with $R^2$-$L^3$ under suitable conditions to form a compound of formula (I) or a pharmaceutically acceptable salt thereof:

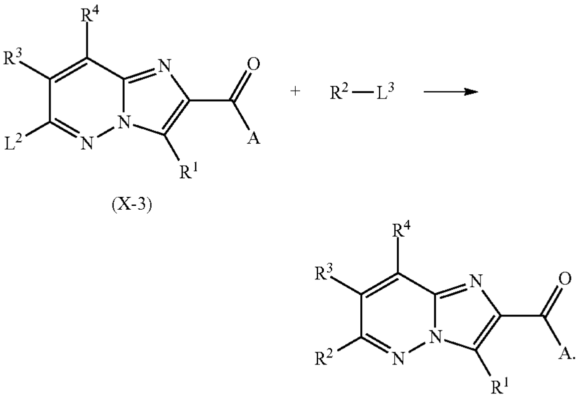

(X-3)

(I)

$L^2$ of Compound (X-3) is halo (e.g., —Cl), and the remaining variables of Compound (X-3) are each and independently as described above for formula (I), and wherein $L^3$ of $R^2$-$L^3$ is —$B(OR^a)_2$, wherein $R^a$ is —H or two $R^a$ together with the atom to which they are attached form a dioxaborolane optionally substituted with $C_{1-2}$alkyl, and $R^2$ of $R^2$-$L^3$ is as described above for formula (I). In one specific embodiment, two $R^a$ together with the atom to which they are attached form 4,4,5,5-tetramethyl-1,3,2-dioxaborolane. Any suitable conditions known in the art to effectuate the reaction, such as those for Suzuki coupling reactions, can be used. Specific suitable conditions are as described in the Exemplification section below.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example ii below, for instance, $J^1$ can be bonded to the 5-membered ring (on the nitrogen atom, for instance), and to the 6-membered ring.

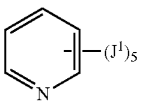

i

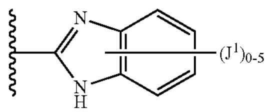

ii

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, $-CH_2$-cyclopropyl, $CH_2CH_2CH(CH_3)$-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as $-CF_3$ and $-CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of"heteroaryl."

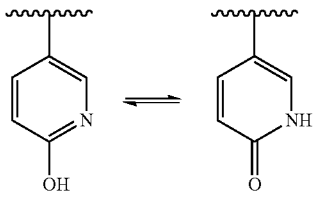 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound.

Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene or carbon unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —$SO_2$—. These atoms or groups can be combined to form larger groups. Examples of such larger groups include, but are not limited to, —OC(O)—, —C(O)CO—, —$CO_2$—, —C(O)NR—, —C(=N—CN), —NRCO—, —NRC(O)O—, —$SO_2$NR—, —NR$SO_2$—, —NRC(O)NR—, —OC(O)NR—, and —NR$SO_2$NR—, wherein R is, for example, H or $C_{1-6}$aliphatic. It should be understood that these groups can be bonded to the methylene or carbon units of the aliphatic chain via single, double, or triple bonds. An example of an optional replacement (nitrogen atom in this case) that is bonded to the aliphatic chain via a double bond would be —$CH_2CH$=N—$CH_3$. In some cases, especially on the terminal end, an optional replacement can be bonded to the aliphatic group via a triple bond. One example of this would be $CH_2CH_2CH_2C \equiv N$. It should be understood that in this situation, the terminal nitrogen is not bonded to another atom.

It should also be understood that, the term "methylene unit" or "carbon unit" can also refer to branched or substituted methylene or carbon units. For example, in an isopropyl moiety [—$CH(CH_3)_2$], a nitrogen atom (e.g. NR) replacing the first recited "methylene unit" would result in dimethylamine [—$N(CH_3)_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a $C_3$ aliphatic can be optionally replaced by 2 nitrogen atoms to form —C—N≡N. The optional replacements can also completely replace all of the carbon atoms in a chain. For example, a $C_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —$CH_2CH_2CH_3$ were optionally replaced with —O—, the resulting compound could be —$OCH_2CH_3$, —$CH_2OCH_3$, or —$CH_2CH_2OH$. It should be understood that if the terminal atom does not contain any free valence electrons, then a hydrogen atom is not required at the terminal end (e.g., —$CH_2CH_2CH$=O or —$CH_2CH_2C \equiv N$).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

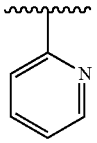 [SMILES: *c1ccccn1]

also represents

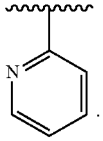 [SMILES: *c1ccccn1]

.

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Pharmaceutically Acceptable Salts

The compounds of this invention can exist in free form for treatment, or where appropriate, as a pharmaceutically acceptable salt.

A "pharmaceutically acceptable salt" means any non-toxic salt of a compound of this invention that, upon administration to a recipient, is capable of providing, either directly or indirectly, a compound of this invention or an inhibitory active metabolite or residue thereof.

As used herein, the term "inhibitory active metabolite or residue thereof" means that a metabolite or residue thereof is also an inhibitors of the PAR-2 signaling pathway.

Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Compound Uses and Methods of Treatment

One aspect of this invention provides compounds that are inhibitors of the PAR-2 signaling pathway, and thus are useful for treating or lessening the severity of a disease, condition, or disorder where PAR-2 is implicated in the disease, condition, or disorder.

Another embodiment provides a method of treating a PAR-2 mediated disease, condition, or disorder in a subject in need thereof, by administrating to the subject a compound described herein. Without intending to be bound to a particular theory, PAR-2 drives major mechanisms, such as leaky epithelial barrier, tissue remodeling, neuroimmunomodulation, endothelial activation and cell recruitment, and inflammation, contributing to chronic inflammatory diseases. In some embodiments, said compounds are selected from the group consisting of a compound of formula (I) or (II).

In some embodiments, said disease, condition, or disorder is selected from an inflammatory disease, nociception (pain), pruritus (itch). In some embodiments, the nociception is caused by inflammation, cancer or injury. Examples of such diseases in which inhibitors of the PAR-2 signaling pathway may show therapeutic benefit include, but are not limited to, inflammatory bowel disease (e.g., Crohn's disease or ulcerative colitis), irritable bowel syndrome, asthma, rheumatoid arthritis, osteoarthritis, fibrosis, gingivitis, periodontitis, vasculitis (e.g., Wegener's granulomatosis), atopic dermatitis, psoriasis, Netherton syndrome, systemic lupus erythematosus (SLE), scleroderma, interstitial lung disease, polymyositis, dermatomyositis, uveitis, Alzheimer's disease, Parkinson's disease, multiple sclerosis, inflammatory pain, post-operative incision pain, neuropathic pain, fracture pain, osteoporotic fracture pain, and gout joint pain. Additional diseases that show an increased proteolytic activity may benefit from inhibitors of the PAR-2 signaling pathway.

In another embodiment, said disease, condition, or disorder is selected from diet-induced obesity, adipose inflammation, or metabolic dysfunction. In some embodiments, the metabolic dysfunction correlates with PAR-2 expression.

In another embodiment, said disease, condition, or disorder is selected from cancers including but not limited to colorectal cancer, pancreatic cancer, breast cancer, gastric cancer, ovarian cancer, squamous cell carcinoma, uterine endometrial cancer, nasopharyngeal carcinoma, esophageal adenocarcinoma, renal cell carcinoma and glioblastoma. Additional cancers that show an increased proteolytic activity or involvement of tissue factor and the coagulation cascade may benefit from inhibitors of the PAR-2 signaling pathway.

In another embodiment, said disease, condition, or disorder is selected from defects of excessive angiogenesis as manifested in solid tumor growth, tumor metastasis, multiple myeloma, lymphoma, ocular angiogenesis-mediated disorders (diabetic retinopathy, macular degeneration, and other ocular angiogenesis disorders), and angiogenesis-mediated inflammatory disorders.

In another embodiment, said disease, condition, or disorder is fibrosis. In some embodiments, the fibrosis includes, but is not limited to, liver fibrosis, pulmonary fibrosis, cystic fibrosis, renal fibrosis, peritoneal fibrosis, pancreatic fibrosis, scleroderma, and cardiac fibrosis. In some embodiments, the fibrosis includes, but is not limited to, skin fibrosis and intestinal fibrosis.

The term "cancer" means a disease characterized by unregulated cell growth.

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitory active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of the PAR-2 signaling pathway.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions for Administration into a Subject

The inhibitors of the PAR-2 signaling pathway or pharmaceutical salts thereof may be formulated into pharmaceutical compositions for administration to animals or humans. These pharmaceutical compositions, which comprise an amount of the PAR-2 signaling pathway inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray or via inhalation, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavouring or colouring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular conditions to be treated or prevented, additional drugs, which are normally administered to treat or prevent that condition, may be administered together with the compounds of this invention.

Those additional agents may be administered separately, as part of a multiple dosage regimen. Alternatively, those agents may be part of a single dosage form, mixed together with the inhibitor of the PAR-2 signaling pathway in a single composition.

Another aspect of this invention is directed towards a method of treating cancer in a subject in need thereof, comprising the sequential or co-administration of a compound of this invention or a pharmaceutically acceptable salt thereof, and another agent.

Biological Samples

As inhibitors of the PAR-2 signaling pathway, the compounds and compositions of this invention are also useful in biological samples. One aspect of the invention relates to inhibiting PAR-2 activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I.

Inhibition of PAR-2 activity in a biological sample is useful for a variety of purposes that are known to one of skill in the art. Examples of such purposes include, but are not limited to, blood transfusion, organ-transplantation, and biological specimen storage.

Study of GPCRs

Another aspect of this invention relates to the study of GPCRs in biological and pathological phenomena; the study of pathways mediated by such GPCRs; and the comparative evaluation of new GPCRs. Examples of such uses include, but are not limited to, biological assays such as enzyme assays and cell-based assays.

The activity of the compounds as inhibitors of the PAR-2 signaling pathway may be assayed in vitro, in vivo or in a cell line. In vitro assays include assays that determine inhibition of either synthetic activators of PAR-2 such as SLIGKV-$NH_2$ or protease-dependent activators such as trypsin activation of PAR-2.

Another aspect of the invention provides a method for modulating PAR-2 activation by contacting a compound described herein with PAR-2.

Methods of Treatment

In one aspect, the present invention provides a method for treating or lessening the severity of a disease, condition, or disorder where PAR-2 is implicated in the disease state. In another aspect, the present invention provides a method for treating or lessening the severity of a disease, condition, or disorder where inhibition of PAR-2 is implicated in the treatment of the disease. In another aspect, this invention provides a method for treating or lessening the severity of a disease, condition, or disorder with compounds that modulate the PAR-2 signaling pathway.

One aspect of the invention relates to a method of inhibiting the PAR-2 signaling pathway in a patient, which method comprises administering to the patient a compound described herein, or a composition comprising said compound. In some embodiments, said method is used to treat or prevent inflammation or pain.

Another aspect of this invention provides a method for treating, preventing, or lessening the severity of an inflammatory diseases comprising administering an effective amount of a compound, or a pharmaceutically acceptable composition comprising a compound, to a subject in need thereof. In some embodiments, said subject is a patient. The term "patient", as used herein, means an animal, preferably a human.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting PAR-2 in a patient comprising administering a compound described herein as described herein. Another embodiment provides a method of reducing inflammation comprising administering to a patient a compound described herein, wherein the variables are as defined herein.

Some embodiments comprising administering to said patient an additional therapeutic agent, wherein said additional therapeutic agent is appropriate for the disease being treated; and said additional therapeutic agent is administered together with said compound as a single dosage form or separately from said compound as part of a multiple dosage form.

Compounds and Compositions for Use

This invention also provides a compound of formula I or a composition comprising the compound for use in treating a PAR-2 mediated disease in a patient. Another embodiment provides a compound of formula I or a composition comprising the compound for use in treating, preventing, or reducing inflammation, nociception (pain) or pruritus in a patient. Yet another embodiment provides a compound of formula I or a composition comprising the compound for treating inflammatory bowel disease (e.g., Crohn's disease or ulcerative colitis), irritable bowel syndrome, asthma, rheumatoid arthritis, osteoarthritis, fibrosis (liver fibrosis, pulmonary fibrosis, cystic fibrosis, renal fibrosis, peritoneal fibrosis, pancreatic fibrosis, scleroderma, cardiac fibrosis, skin fibrosis, or intestinal fibrosis), gingivitis, periodontitis, vasculitis (e.g., Wegener's granulomatosis), atopic dermatitis, psoriasis, Netherton syndrome, systemic lupus erythematosus (SLE), scleroderma, interstitial lung disease, polymyositis, dermatomyositis, uveitis, Alzheimer's disease, Parkinson's disease, multiple sclerosis, inflammatory pain, post-operative incision pain, neuropathic pain, fracture pain, osteoporotic fracture pain, and gout joint pain in a patient.

Another aspect provides a compound of formula I or a composition comprising the compound for use in inhibiting proteolytic activation of PAR-2 in a cell. Another aspect provides a compound of formula I or a composition comprising the compound for inhibiting PAR-2 activity in a cell.

Another aspect provides a compound of formula I or a composition comprising the compound for use for treating a disease, condition, or disorder elected from diet-induced obesity, adipose inflammation, or metabolic dysfunction. In some embodiments, the metabolic dysfunction correlates with PAR-2 expression. In another aspect, the disease, condition, or disorder is cancer. Specific examples of cancer are as described above.

Manufacture of Medicaments

This invention also provides the use of a compound of formula I or a composition comprising the compound in the manufacture of a medicament for use in treating a PAR-2 mediated disease in a patient. Another embodiment provides the use of a compound of formula I or a composition comprising the compound in the manufacture of a medicament for treating, preventing, or reducing inflammation or nociception (pain) in a patient. Yet another embodiment provides the use compound of a compound of formula I or a composition comprising the compound in the manufacture of a medicament for treating inflammatory bowel disease, Crohn's disease, ulcerative colitis, asthma, rheumatoid arthritis, osteoarthritis, gingivitis, atopic dermatitis, psoriasis, systemic lupus erythematosus (SLE), scleroderma, interstitial lung disease, ploymyositis, dermatomyositis, uveitis, Alzheimer's disease, Parkinson's disease, multiple sclerosis, inflammatory pain, post-operative incision pain, neuropathic pain, fracture pain, osteroporotic fracture pain, and gout joint pain in a patient.

Another aspect provides the use of a compound of formula I or a composition comprising the compound in the manufacture of a medicament for use in inhibiting proteolytic activation of PAR-2 in a cell. Another aspect provides a compound of formula I or a composition comprising the compound in the manufacture of a medicament for inhibiting PAR-2 activity in a cell.

One embodiment provides the use of a compound or composition described herein for the manufacture of a medicament for use in treating inflammation or pain.

In some embodiments, the compound or composition is combined with an additional therapeutic agent appropriate for the disease to be treated.

EXEMPLIFICATION

The compounds of the disclosure may be prepared in light of the specification according to the schemes below as well as according to steps generally known to those of ordinary skill in the art. Tho compounds may be analyzed by known methods, including but not limited to LCMS (liquid chromatography mass spectrometry) and NMR (nuclear magnetic resonance).

Mass spec. samples are analyzed on a Waters UPLC Acquity mass spectrometer operated in single MS mode with electrospray ionization. Samples are introduced into the mass spectrometer using chromatography. Mobile phase for the mass spec. analyses consisted of 0.1% formic acid and acetonitrile-water mixture. As used herein, the term "Rt time" refers to the LC-MS retention time, in minutes, associated with the compound. Unless otherwise indicated, the LC-MS methods utilized to obtain the reported retention time are as detailed below:

Method A: 5%-85% acetonitrile-water over 6 minutes run time, Waters AcquityHSS T3 1.8 μm, 2.1 mm ID×50 mm. Flow rate is 1.0 mL/min.

Method B: 50%-100% acetonitrile-water over 6 minutes run time, Waters AcquityHSS T3 1.8 μm, 2.1 mm ID×50 mm. Flow rate is 1.0 mL/min.

Method C: 5%-85% acetonitrile-water over 3 minutes run time, Waters AcquityHSS T3 1.8 μm, 2.1 mm ID×50 mm. Flow rate is 1.0 mL/min.

Method D: 10%-100% acetonitrile-water over 6 minutes run time, Waters XSelect CHS™ C18 2.5 μm, 4.6 mm ID×30 mm Column XP. Flow rate is 1.0 mL/min.

Method E: 5%-85% acetonitrile-water over 6 minutes run time, Waters Acquity UPLC® HSS C18 SB 1.8 μm, 2.1 mm ID×50 mm. Flow rate is 1.0 mL/min.

Method F: 5-85% acetonitrile-water over 2 minutes run time, Waters AcquityHSS T3 1.8 μm, 2.1 mm ID×50 mm. Flow rate is 1.0 mL/min Method G: 50%-90% acetonitrile-water over 6 minutes run time, Waters AcquityHSS T3 1.8 μm, 2.1 mm ID×50 mm. Flow rate is 1.0 mL/min.

Method H: 50%-100% acetonitrile-water over 3 minutes run time, Waters AcquityHSS T3 1.8 μm, 2.1 mm ID×50 mm. Flow rate is 1.0 mL/min.

Purification by reverse phase HPLC is carried out under standard conditions using a Phenomenex Gemini 21.2 mm ID×250 mm column, 5μ and Gemini 21.2 mm ID×75 mm column, 5μ, 110 Λ. Elution is performed using a linear gradient $CH_3CN$—$H_2O$ (with or without 0.01% TFA buffer) as mobile phase. Solvent system is tailored according to the polarity of the compound, Flow rate, 20 mL/min. Compounds are collected either by UV or Waters 3100 Mass Detector, ESI Positive Mode. Fractions containing the desired compound are combined, concentrated (rotary evaporator) to remove excess $CH_3CN$ and the resulting aqueous solution is lyophilized to afford the desired material.

Nuclear magnetic resonance (NMR) spectra are recorded on INOVA 400 MHz Varian instrument. The residual solvent protons ($^1H$) are used as internal standards. The following solvents are used: chloroform-d, methanol-$d_4$, DMSO-$d_6$. $^1H$ NMR data are presented as follows: chemical shift in ppm downfield from tetramethylsilane (multiplicity, coupling constant, integration). The following abbreviations are used in reporting NMR data: s, singlet; d, doublet; t, triplet; q, quartet; p, pentuplet; h, hextuplet; dd, doublet of doublets; ddd, doublet of doublets of doublets; dddd, doublet of doublets of doublets of doublets; dt, doublet of triplets; dtd, doublet of triplets of doublets; ddt, doublet of doublets of triplets; dq, doublet of quartets; dp, doublet of pentuplets; td, triplet of doublets; qd, quintet of doublets; m, multiplet.

Purification by flash chromatography on silica gel is carried out under standard conditions using, but not restricted to, either of the following instruments and supplies: Biotage™ SP1 or SP2 purification system with Biotage® SNAP Cartridge KP-Sil column 10 g, 25 g, 50 g, 100 g or 340 g and, CombiFlash®Rf Teledyne Isco purification system with Silica RediSep®Rf normal phase column 12 g, 24 g, 40 g, 80 g, 120 g, 220 g or 330 g. Solvent system is tailored according to the polarity of the compound. Fractions containing the desired compound are combined and concentrated (rotary evaporator) to remove the solvent and to afford the desired material.

LIST OF ABBREVIATIONS

The following abbreviations are used in the examples below:

Ac acetyl

AcOH acetic acid $Ac_2O$ acetic anhydride
aq aqueous
ATP adenosine triphosphate
$BF_3.OEt_2$ boron trifluoride diethyl ether
Bn benzyl
$Br_2$ Bromine
ACN, $CH_3CN$ acetonitrile
$CD_3OD$ methanol-d4
$CDCl_3$ chloroform-d
conc concentrate
$Cs_2CO_3$ cesium carbonate
CuI copper(I) iodide
$CuSO_4$ copper(II) sulfate
CV column volume
° C. degree Celcius
DBU 1,8-diazabicyclo[5.4.0]undec-7-ene
DCM methylene chloride or dichloromethane
DIPEA N,N-diisopropylethylamine
DMAP 4-dimethylaminopyridine
DMF dimethylformamide
DMSO dimethylsulfoxide
DMSO-d6 deutered dimethylsulfoxide
Equiv equivalent
EtOAc ethyl acetate
g gram(s)
HATU O-(7-azabenzotriazol-1-yl),N,N,N",N"-tetramethyluroniumhexafluorophosphate
h hour(s)
HCl hydrochloric acid
Hex hexanes
HPLC high pressure liquid chromatography
IPA iso-propyl alcohol
iPAc iso-propyl acetate
$K_3EDTA$ Ethylenediaminetetraacetic acid tripotassium salt
LCMS liquid chromatography mass spectrometry
LiOH lithium hydroxide
M molar
MHz megahertz
MC methyl cellulose or methocel
mg milligram(s)
mL milliliter(s)
mM millimolar
MeOH methanol
MeONa sodium methoxide
$MgSO_4$ magnesium sulfate
min minute(s)
MS mass spectrometer
MTBE methyl tert-butyl ether
μM micromolar
N normal (molar) concentration
$NaHCO_3$ sodium bicarbonate
$Na_2CO_3$ sodium carbonate
$NaIO_4$ sodium periodate
$Na_2SO_4$ sodium sulfate
$Na_2S_2O_3$ sodium thiosulfate
$NH_4Cl$ ammonium chloride
$^1$HNMR proton nuclear magnetic resonance
NMO N-methylmorpholine-N-oxide
$OsO_4$ osmium tetroxide
ON overnight
PBS phosphate buffered saline
$Pd_2(dba)_3$ Tris(dibenzylideneacetone)dipalladium(O)
Pd/C palladium on carbon
$PdCl_2$ palladium (II)chloride
$Pd(OAc)_2$ palladium(II) acetate
$PdCl_2(dppf)$.DCM (1,1'-Bis-(diphenylphosphino)-ferrocene)palladium (II) dichloride
$Pd(OH)_2$ dihydroxy palladium
$Pd(PPh_3)_4$ tetrakis(triphenylphospine)palladium (O)
psi pound per square inch
Py pyridine
r.b.f (rbf) round bottom flask
RT (rt or r. t.) room temperature
SDS sodium dodecyl sulfate or sodium lauryl sulfate
S-Phos 2-Dicyclohexylphosphino-2',6'-dimethoxybiphenyl
TBAF tetrabutylammonium fluoride
TBDMSOTf tert-butyldimethylsilyl trifluoromethanesulfonate
TBS tert-butyldimethylsilyl
TEA triethylamine
Tf trifluoromethanesulfonyl
TFA trifluoroacetic acid
THF tetrahydrofuran
TLC thin layer chromatography
TMS trimethylsilyl
TMSI trimethylsilyl iodide
$TMSN_3$ trimethylsilyl azide
TMSOTf trimethylsilyl trifluoromethanesulfonate
TNBS 2,4,6-Trinitrobenzenesulfonic acid
UPLC ultra performance liquid chromatography
Vitamin E-TPGS D-α-Tocopherol polyethylene glycol 1000 succinate The following generic schemes and examples illustrate how to prepare the compounds of the present disclosure. In the following General Synthetic Routes (e.g., General Synthetic Routes 1-4):

$R_6$: H or O;
$R_7$: alkyl, aryl, heteroalkyl, or heteroaryl;
$R_8$: A' O-alkyl, or O-aryl;
$R_9$: halogene, OMs, OTf, or ONf;
$R_{10}$: aryl, heteroaryl, alkyl, or heteroalkyl;
$R_{11}$: —$Si(R_7)_3$; and
AA:

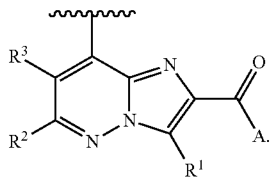

The following generic schemes and examples illustrate how to prepare the compounds of the present disclosure General Synthetic Route 1

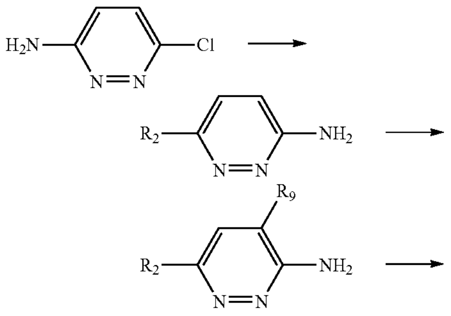

-continued

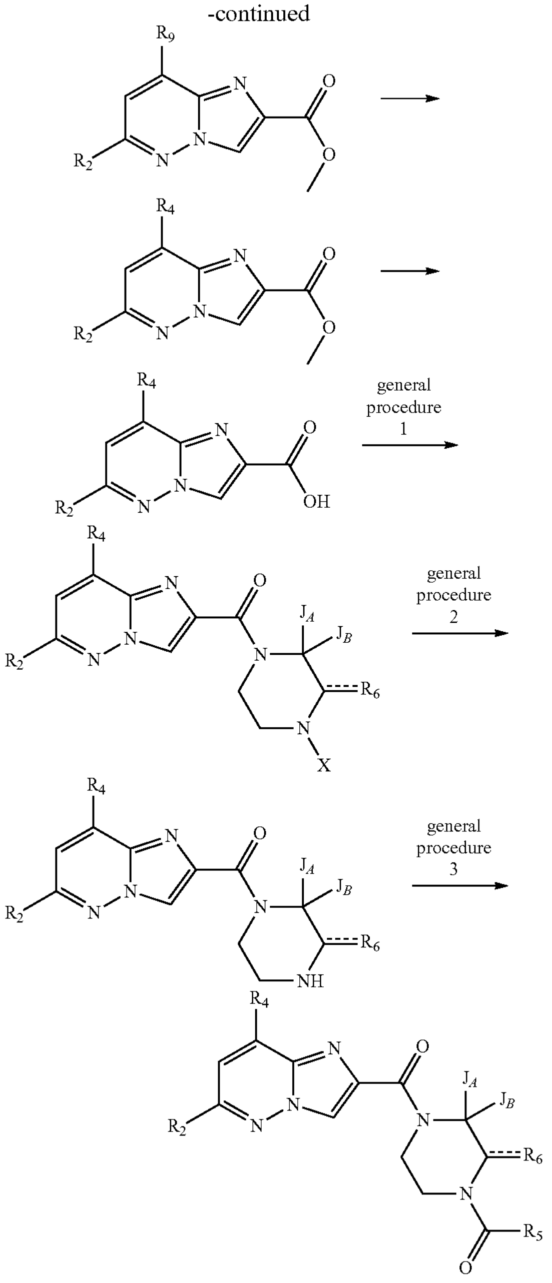

General Procedure 1: Amide Formation

The appropriate carboxylic acid (1.0 equiv) is dissolved in DMF or NMP (0.15 to 0.3M) before HATU (1.1 to 1.5 equiv), the corresponding amine (1.1-1.2 equiv) and Hünig's base (2.5 to 3.5 equiv) are added. The mixture is stirred at room temperature between 45 min. and 16 h. Either one of these 4 work-up procedures can be employed 1. Water is added and the solids are filtered affording the desired product;
2. Water is added and the solids are filtered affording the desired product, recrystallized from EtOH;
3. Water and 15% NaOH are added and the solids are filtered affording the desired product, recrystallized from EtOH;
4. Water is added along with EtOAc and the phases are separated. The organic phase is washed 2 other times with water and brine (1:1 mixture), dried over MgSO4, filtered and evaporated under reduced pressure.

General Procedure 2: BOC Deprotection

The appropriate BOC-protected amine (1.0 equiv) and 4N HCl solution in 1,4-dioxane (5.0 equiv) in 1,4-dioxane (0.2M) and MeOH (0.02M) are stirred at room temperature for 1 h to 16 h. The solvents are removed under vacuum affording the desired product as a hydrochloride salt.

General Procedure 3: Amide Formation

The appropriate carboxylic acid (1.2 equiv) is dissolved in DMF or NMP (0.02 to 0.4M) before HATU (1.1 to 1.5 equiv), the corresponding amine (1.0 equiv) and Hünig's base (3.0 to 5.0 equiv) are added. The mixture is stirred at room temperature for 45 min. to 16 h. Either one of these 4 work-up procedures can be employed 1. Water is added and the solids are filtered to obtain the crude ester
2. The ester is purified by Prep HPLC
3. Water is added and the solids are filtered to obtain the crude ester then purified by Prep HPLC
4. Water is added along with EtOAc and the phases are separated. The organic phase is washed 2 other times with water and brine (1:1 mixture), dried over MgSO4, filtered and evaporated under reduced pressure.

General Synthetic Route 2

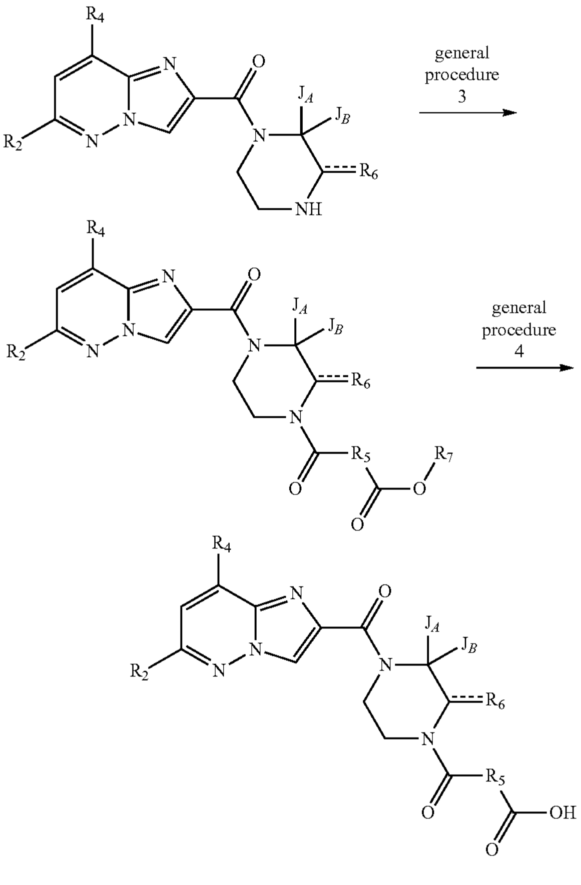

General Procedure 4: Ester Hydrolysis

The appropriate ester (1.0 equiv) is dissolved in Dioxane (0.05 to 0.3M) before 2M LiOH (1.5 to 2.5 equiv) is added. The mixture is stirred at room temperature for 45 min. to 16 h. Either one of these 2 work-up procedures can be employed 1. Water is added along with EtOAc or DCM and the phases are separated. The organic phase is washed 2 other times with water and brine (1:1 mixture), dried over $MgSO_4$, filtered and evaporated under reduced pressure;

2. Water is added and the solids are filtered to obtain the crude acid then purified by Prep HPLC if needed.

General Synthetic Route 3

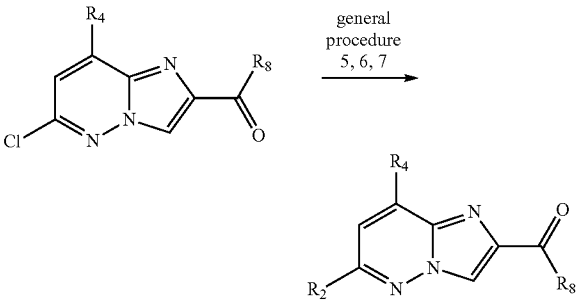

General Procedure 5: Suzuki Coupling (1)

To a solution of the appropriate aryl halide (1 equiv) in DMF (0.03 to 0.4M) are added associated boronic acid or boronate ester (1 to 1.5 equiv), $PdCl_2(dppf)_2$-DCM (0.01 to 0.25 equiv) and $Na_2CO_3$ (2-5 equiv.). After degassing by bubbling $N_2$ for 5 min, the mixture is heated between (60 and 105° C.) for 2 to 18 h. The following work-up can be used:

1. Water was added along with EtOAc and the phases are separated. The organic phase is washed 2 other times with water and brine (1:1 mixture), dried over MgSO4, filtered and evaporated under reduced pressure to afford crude product.
2. The mixture is cooled to rt and 4 mL of water is added to reaction solution. The precipitate is filtered over Büchner and rinsed with cold water to afford product General Procedure 6: Suzuki Coupling (2)

To a rbf containing a solution of the appropriate aryl halide (1 equiv) in dioxane (0.03 to 0.4M) is added $Pd_2(DBA)_3.CHCl_3$ (0.02 to 0.25 equiv) and S-Phos (0.05 to 0.5, 2 equiv of Pd atom). The resulting solution is degassed with nitrogen for 5 minutes prior to addition of respectively $K_3PO_4$ (2 to 5 equiv.) and associated boronic acid or boronate ester (1 to 2.5 equiv). It is then stirred between 60 and 105° C. for 2 to 18 h. DCM and $NaHCO_3$ are added to the mixture. The layers are separated and the aqueous phase is extracted with DCM twice more. The combined organic layers are dried with $MgSO_4$, filtered and concentrated under reduced pressure to afford a crude product.

General Procedure 7: Suzuki Coupling (3)

To a rbf containing a solution of the appropriate aryl halide (1 equiv) is dissolved in THF (0.03 to 0.4M) and $Na_2CO_3$ 2M (2-5 equiv.). The reaction mixture is degassed with $N_2$ for 5 minutes, then the appropriate boronic ester or boronic acid (1 to 1.5 equiv) is added followed by $Pd(PPh_3)_4$ (0.01 to 0.25 equiv). The reaction mixture is stirred while heated between (60 and 85° C.) for 2 to 18 h. Water and EtOAc are added and the phases are separated. This step is done two other times before organic phase is dried over MgSO4, filtered and evaporated under reduced pressure to afford crude product.

General Synthetic Route 4

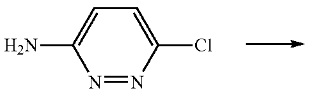

-continued

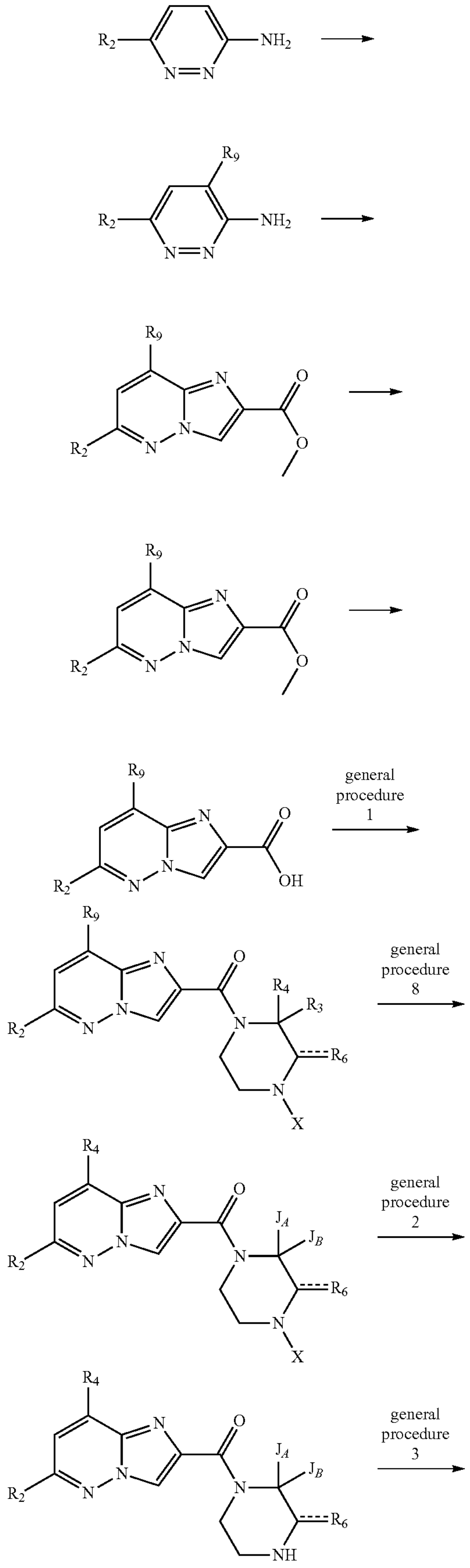

-continued

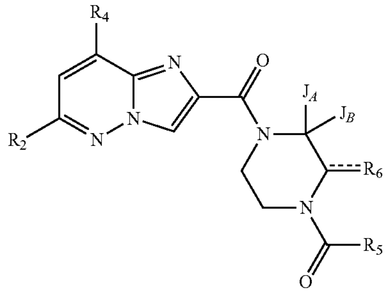

General Procedure 8: Suzuki Coupling (4)

To a rbf containing a solution of the appropriate aryl halide (1 equiv) in DMF (0.03 to 0.4M) is added $Na_2CO_3$ 2M (2-5 equiv.). The reaction mixture is degassed with $N_2$ for 5 minutes, then the appropriate boronic ester or boronic acid (1 to 1.5 equiv) is added followed by $Pd(PPh_3)_4$(0.01 to 0.25 equiv). The reaction mixture is stirred heated between (60 and 85° C.) for 2 to 18 h.

1. Water is added along with EtOAc and the phases are separated. The organic phase is washed 2 other times with water and brine (1:1 mixture), dried over MgSO4, filtered and evaporated under reduced pressure to afford crude product.
2. The mixture is cooled to rt and 4 mL of water is added to reaction solution. The precipitate is filtered over Büchner and rinsed with cold water to afford product.

General Synthetic Route 5

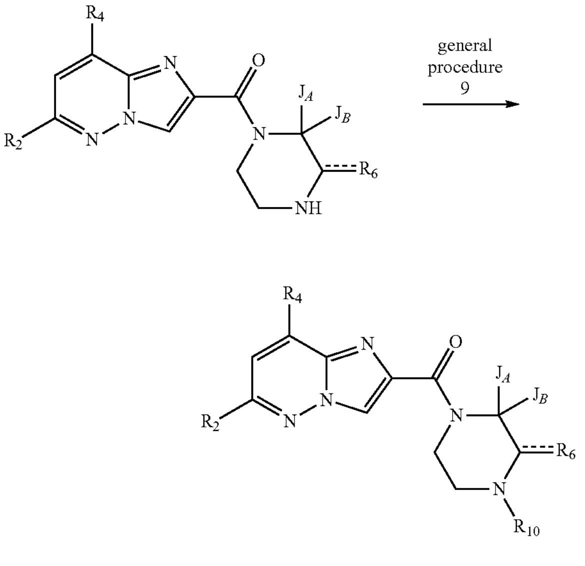

General Procedure 9: C—N Coupling

To the appropriate piperazinone (1.0 equiv) in dioxane (0.1M) or toluene (0.05M) is added N,N'-dimethylethane-1,2-diamine (0.3 to 0.4 equiv), the iodo-aryl or bromo-aryl (1.5 equiv), CuI (0.15 to 0.2 equiv) and $K_2CO_3$ (3.0 equiv) or potassium tert-butoxide (2 equiv). The mixture is stirred at 170° C. for 2 h in the microwave reactor or at 120° C. for 16 h. The residue is purified on silica gel cartridge to afford the desired product.

General Synthetic Route 6

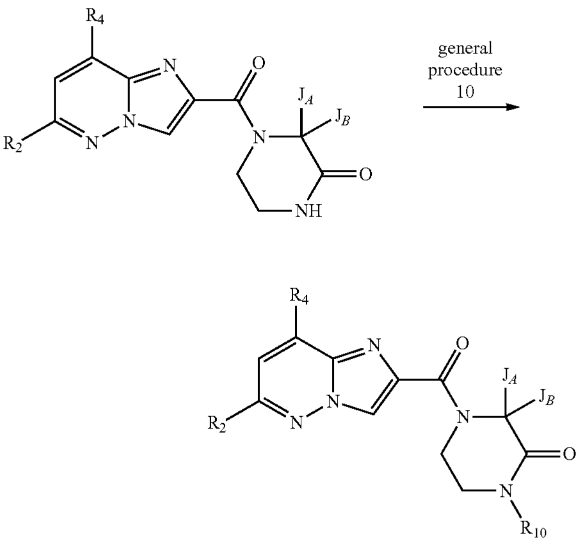

General Procedure 10: N-Alkylation

To the appropriate piperazin-2-one (1 equiv) dissolved in DMF (1 mL) is added appropriate base such as NaH (1 to 2 equiv) and stirred at that temperature for 10 minutes. The electrophile (2 to 5 equiv) is added and the reaction is stirred for 1 to 18 h ranging from room temperature to 100° C. affording the desired product.

General Synthetic Route 7

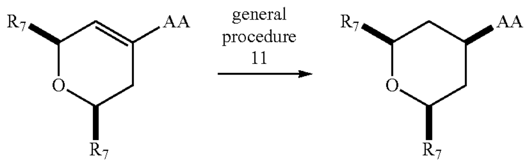

General Procedure 11: Hydrogenation

To the appropriate alkene (1.0 equiv) in MeOH (0.01M) is added a source of palladium on charcoal (0.1 equiv). The mixture is stirred at room temperature for 1 h to 16 h under an atmosphere of hydrogen. The residue is filtered over Celite to afford the desired product.

General Synthetic Route 8

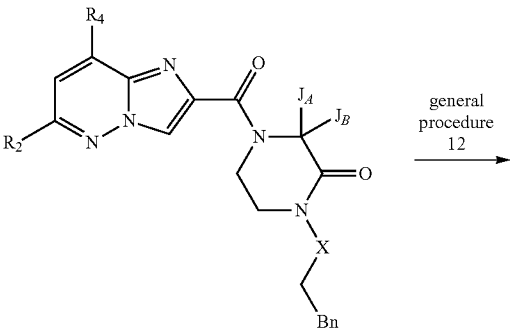

-continued

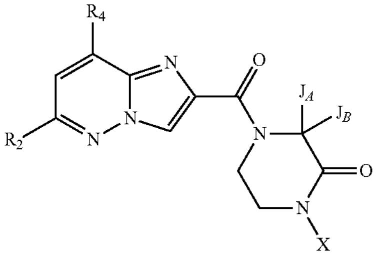

General Procedure 12: Hydrogenation

To the appropriate benzylated aryl (1.0 equiv) in EtOH (0.05 to 0.5M) is added 20% $Pd(OH)_2/C$ (0.05 to 0.25 equiv). The mixture is stirred at 75° C. for 1 h to 18 h under $H_2$ (g). The residue is filtered over Celite to afford the desired product.

General Synthetic Route 9

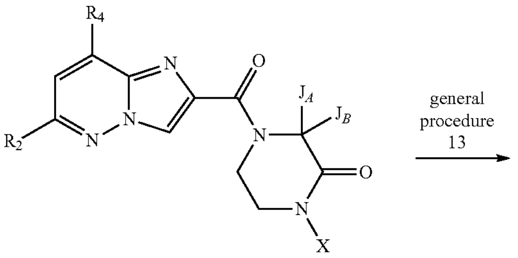

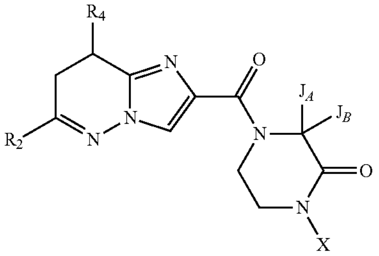

General Procedure 13: Reduction by Zinc Dust

To the appropriate alkene (1.0 equiv) in AcOH (0.1M) is added Zinc dust (10 equiv). The mixture is stirred at room temperature or 40° C. for 2 h to afford the desired product.

General Synthetic Route 10

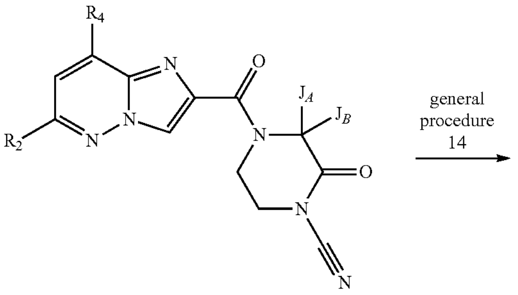

-continued

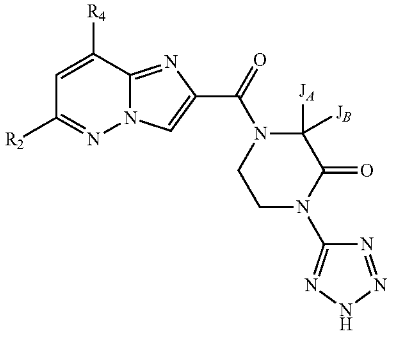

General Procedure 14: Tetrazole Formation

To the appropriate cyano (1.0 equiv) in DMF (0.08 to 0.1M), IPA (0.1 to 0.15M) and water (0.2 to 0.3M) is added $NaN_3$ (3 equiv) and $ZnBr_2$ (1 eq). The mixture is stirred at 60° C. for 2 h to afford the desired product.

General Synthetic Route 11

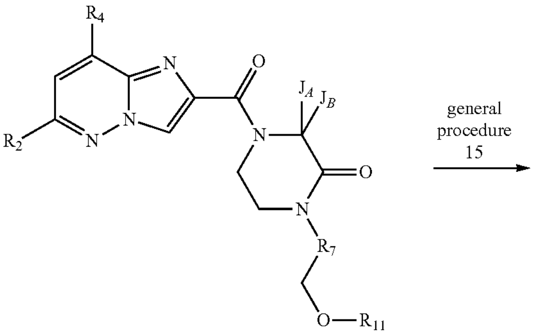

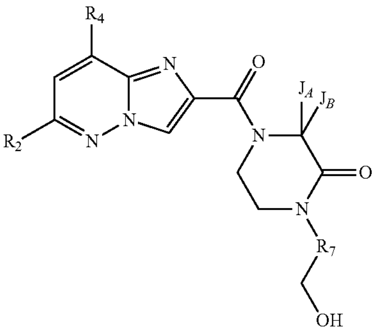

General Procedure 15: TBS Deprotection

This intermediate is dissolve in THF (0.1M) then TBAF (1 equiv) is added. The mixture is stirred at room temperature for 2 h to afford the desired product.

General Synthetic Route 12

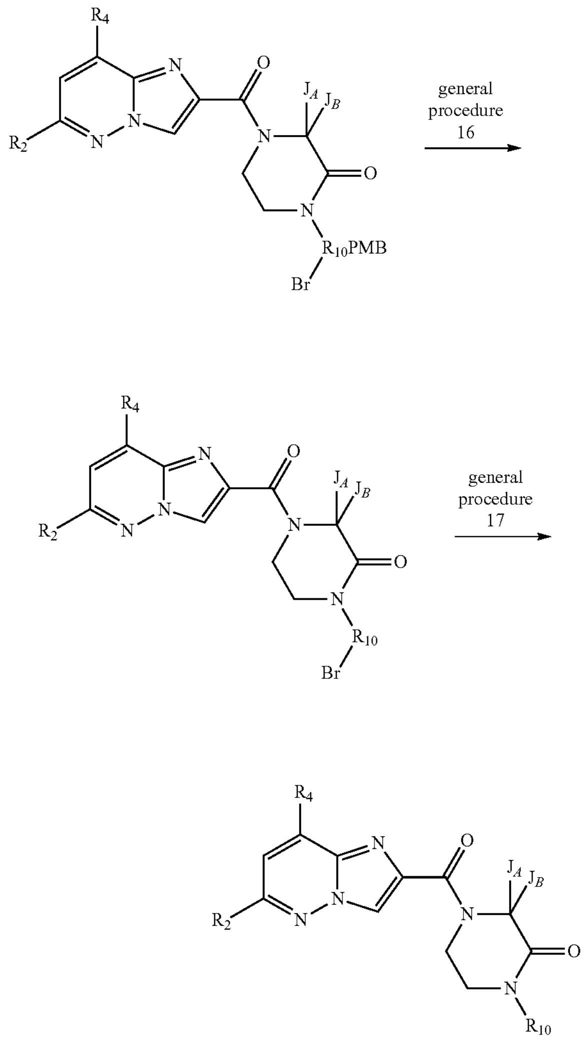

General Procedure 16: PMB Deprotection

A mixture of the appropriate PMB protected aryl in TFA (0.03M) is heated at 60° C. for 3 h to afford the desired product.

General Procedure 17: Debromination

A mixture of the appropriate bromo-aryl (1 equiv), MeOH (0.01M), 20% $Pd(OH)_2/C$ (0.1 equiv) is heated at 60° C. for 1 h to afford the desired product.

General Synthetic Route 13

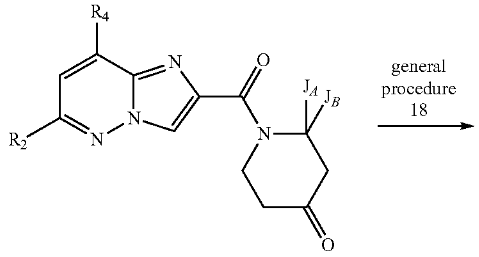

-continued

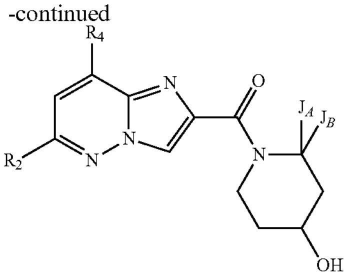

General Procedure 18: Ketone Reduction

To the appropriate ketone (1.0 equiv) in MeOH (0.03M) is added $NaBH_4$ (2 equiv). The mixture is stirred at room temperature for 1 to 72 h affording the desired product.

General Synthetic Route 14

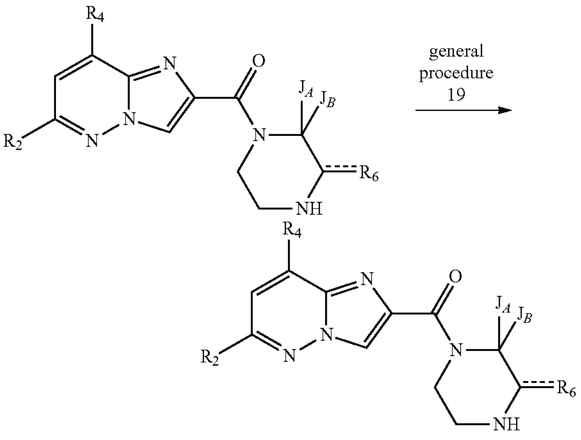

General Procedure 19: $S_NAr$

To the appropriate aryl halide (1.0 equiv) dissolved in THF (0.2M), a base such as DIPEA (2-5 eq) and the corresponding amine (2 equiv) are added. The mixture is heated at 120° C. in a microwave reactor for 30 min to afford the desired product.

General Synthetic Route 15

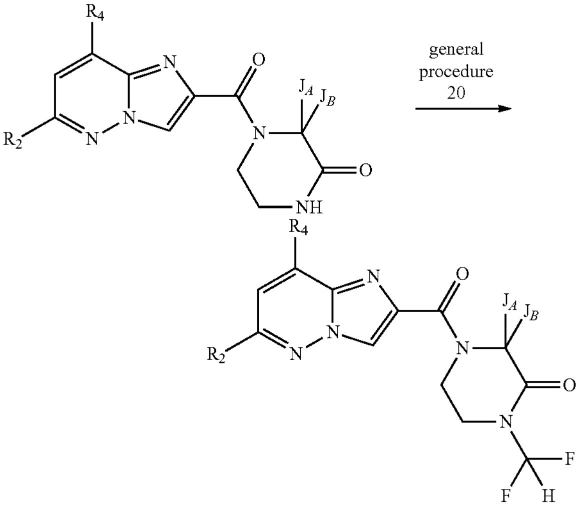

General Procedure 20: Difluoroalylation-Decarboxylation

A mixture of Piperazin-2-one (1 equiv), $K_2CO_3$ (3 equiv) and ethyl 2-bromo-2,2-difluoro-acetate (2 equiv) in DMSO (0.05M to 0.2M) is stirred at room temperature for 16 h then at 100° C. for 1 to 12 h to afford the desired product.

General Synthetic Route 16

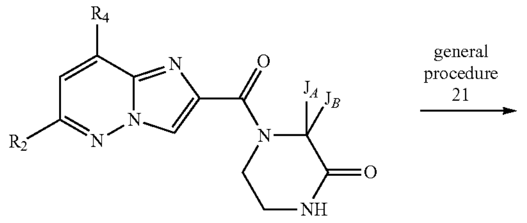

-continued

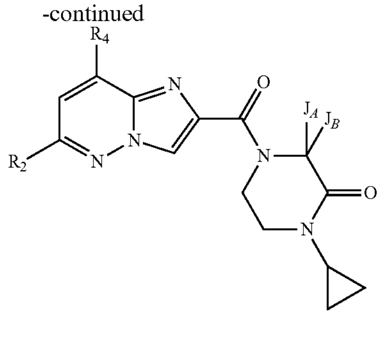

General Procedure 21: Suzuki Coupling

A mixture of Piperazin-2-one (1 equiv), DMAP (3 equiv), a copper source such as diacetoxycopper (0.1 to 0.25 equiv), an appropriate base such as NaHMDS (1 equiv), cyclopropylboronic acid (2 equiv) and Toluene (0.1 to 0.25M) is stirred at 95° C. for 18 h to afford the desired product.

General Synthetic Route 17

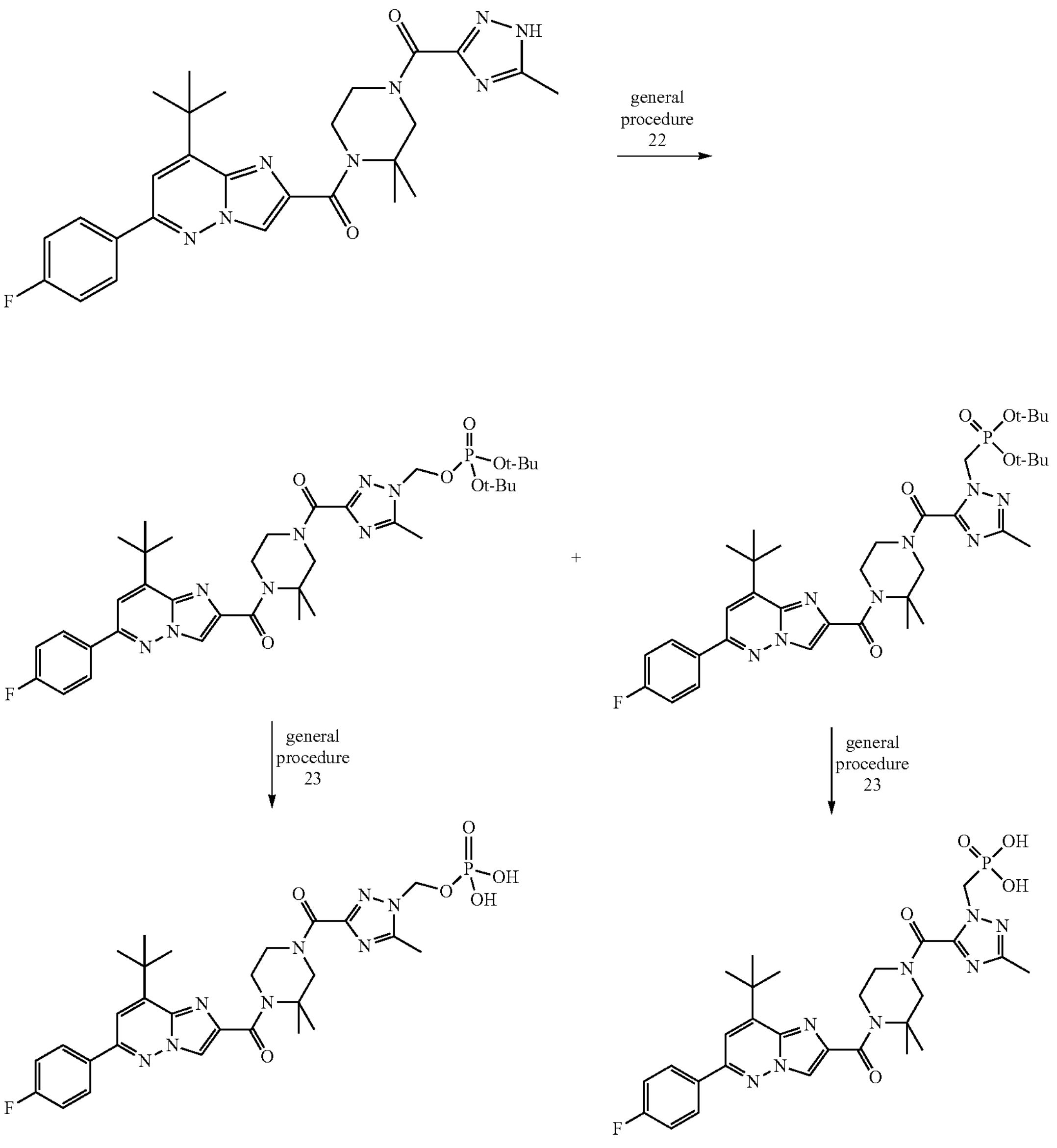

General Procedure 22: Triazole Alkylation

I-343 (1 equiv) in DCM (0.2M) before ditertbutyl chloromethyl phosphate (1.3 equiv), TBAI (0.2 equiv) and $Cs_2CO_3$ (1.5 equiv) is added and the solution is stirred at 60° C. for 6 h. The regioisomers are separated by silica gel chromatography affording the title compounds.

General Procedure 23: Phosphate Hydrolysis

To a solution of the appropriate ditertbutyl phosphate analogue (1 equiv) in DCM (0.15M) at 0° C. is added TFA (30 equiv) and the solution stirred for 30 minutes affording the title compound.

General Synthetic Route 18

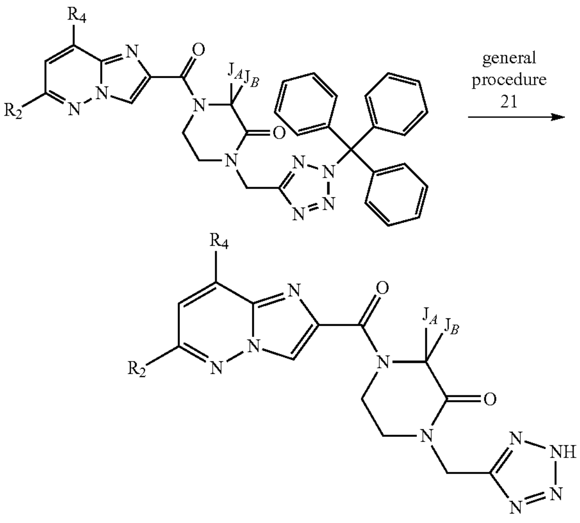

General Procedure 24: Deprotection

To a solution of protected tetrazole (1 equiv) in DCM (0.02M to 0.1 M) is added HCl (20 equiv). Stir at room temperature for 1 to 5 h to obtain the desired product.

General Synthetic Route 19

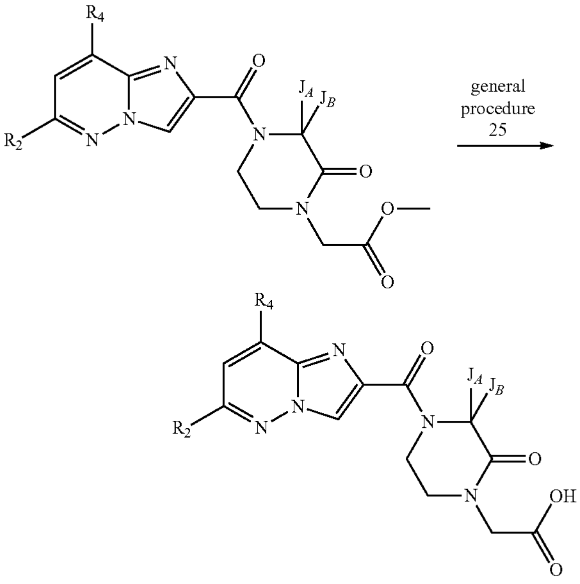

General Procedure 25: Ester Hydrolysis

A solution of ester (1 equiv) in water and HCl 1M (3 to 10 equiv) is heated at 85° C. for 72 h. Prep HPLC purification affords the desired product.

List of Intermediates

A

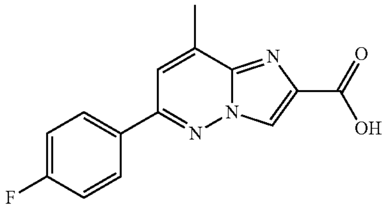

B

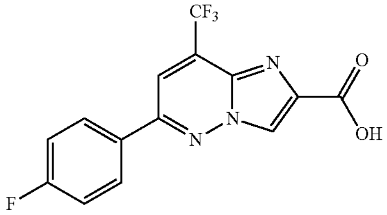

C

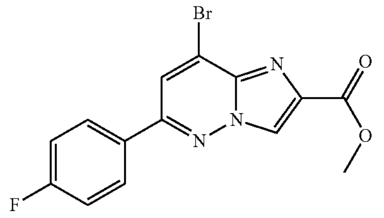

D

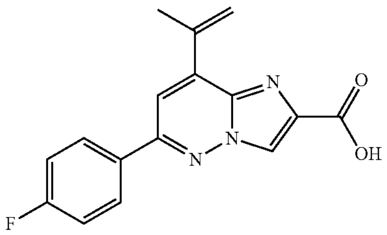

E

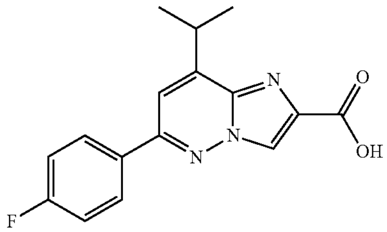

F

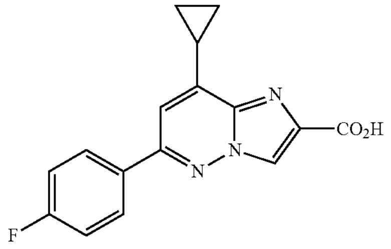

G

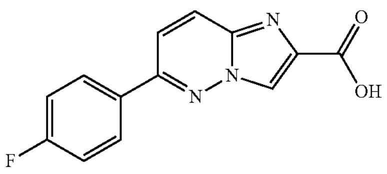

-continued
H
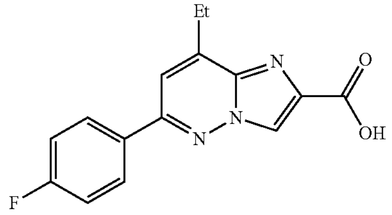
I
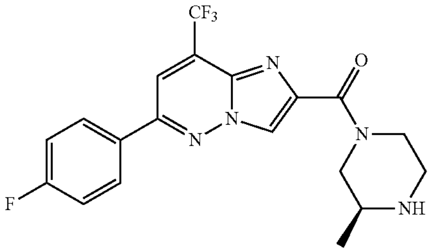
J
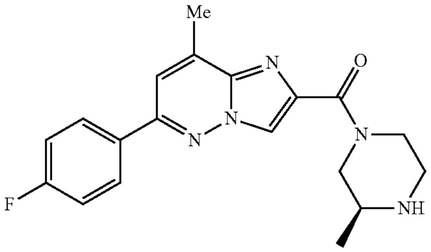
K
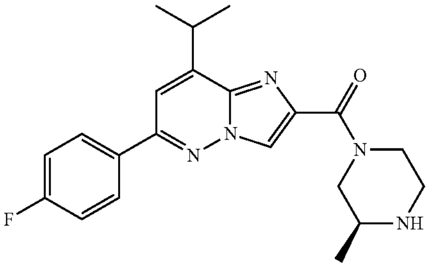
L
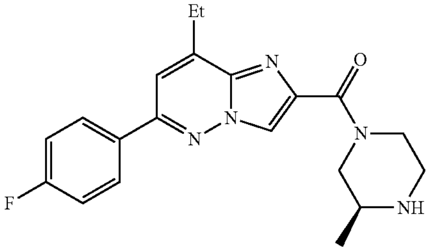
M
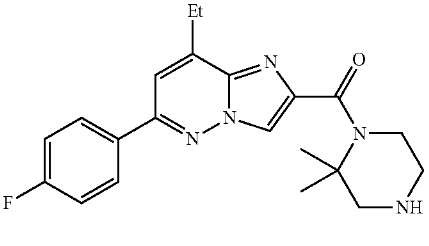
-continued
N
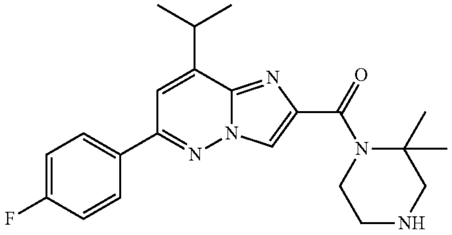
O
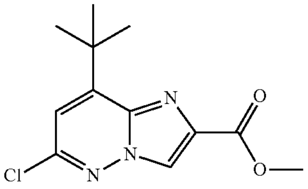
P
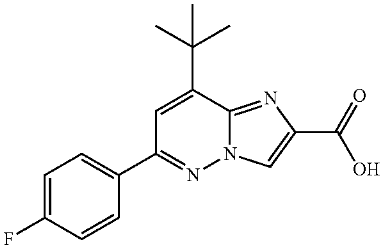
Q
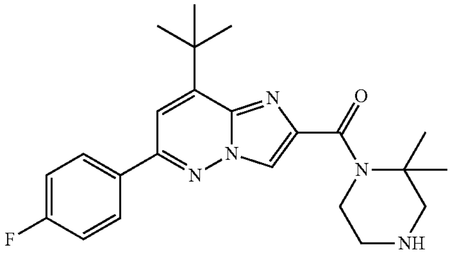
R
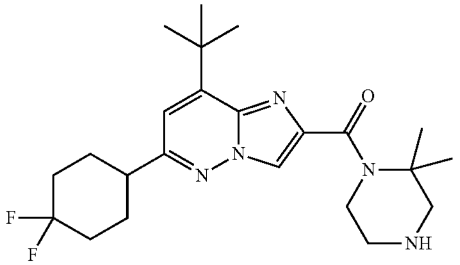
Preparation of Intermediate A: 6-(4-Fluorophenyl)-8-methyl-imidazo[1,2-b]pyridazine-2-carboxylic acid
Scheme 1
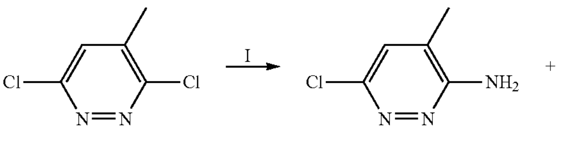

-continued

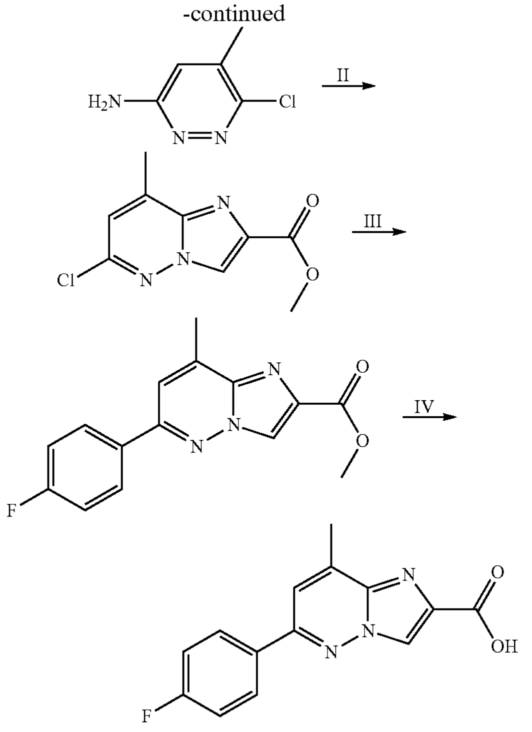

A

Step I: 6-Chloro-4-methyl-pyridazin-3-amine and 6-chloro-5-methyl-pyridazin-3-amine A suspension of 3,6-dichloro-4-methyl-pyridazine (3 g, 18.40 mmol) in concentrated ammonia (20 mL, 1.057 mol) in a sealed vessel was heated to 130° C. for 15 h. After cooling to rt, it was diluted with water and filtered. The solid was dried under reduced pressure and used directly in the next step (2.2 g). NMR showed it contained two isomers; 6-chloro-4-methyl-pyridazin-3-amine and 6-chloro-5-methyl-pyridazin-3-amine in about 1:1.8 ratio.

Step II: Methyl 6-chloro-8-methyl-imidazo[1,2-b]pyridazine-2-carboxylate

To a solution of the mixture from Step I (305 mg) in DMF (3 mL) was added methyl 3-bromo-2-oxo-propanoate (769 mg, 4.25 mmol). The mixture was heated at 70° C. ON. The solvent was removed under reduced pressure and the residue was purified by flash chromatography eluting with EtOAc/hexanes 0-50% in 20 CV to obtain methyl 6-chloro-8-methyl-imidazo[1,2-b]pyridazine-2-carboxylate (156 mg) as a solid. $^1$H NMR (400 MHz, $CDCl_3$) δ 8.43 (s, 1H), 6.99 (m, 1H), 4.01 (s, 3H), 2.72 (d, 3H).

Step III: Methyl 6-(4-fluorophenyl)-8-methyl-imidazo[1,2-b]pyridazine-2-carboxylate To a solution of methyl 6-chloro-8-methyl-imidazo[1,2-b]pyridazine-2-carboxylate (53 mg, 0.2 mmol) in dioxane (2 mL) were added (4-fluorophenyl)boronic acid (49.3 mg, 0.35 mmol), $PdCl_2$(dppf)-DCM (9.6 mg, 0.012 mmol) and $Na_2CO_3$ (235 μL of a 2 M aqueous solution, 0.47 mmol). After degassing, the mixture was heated to 100° C. and stirred for 5 h under nitrogen. The volatiles were removed under reduced pressure and the residue was purified by flash chromatography eluting with EtOAc/hexanes 0-50% in 20 CV to obtain methyl 6-(4-fluorophenyl)-8-methyl-imidazo[1,2-b]pyridazine-2-carboxylate (54 mg, 75% yield) as a white solid. $^1$H NMR (400 MHz, $CDCl_3$) δ 8.52 (s, 1H), 8.09-7.84 (m, 2H), 7.34 (m, 1H), 7.25-7.11 (m, 2H), 4.01 (s, 3H), 2.77 (d, 3H).

Step IV: 6-(4-Fluorophenyl)-8-methyl-imidazo[1,2-b]pyridazine-2-carboxylic acid (Intermediate A)

To a solution of methyl 6-(4-fluorophenyl)-8-methyl-imidazo[1,2-b]pyridazine-2-carboxylate (50 mg) in MeOH (1.6 mL)/water (0.4 mL) was added an aqueous LiOH solution (16 mg, 0.38 mmol) and the mixture was stirred at 50° C. for 2 h. It was then neutralized with resin Amberlite IR 120(H), filtrated and concentrated to dryness to obtain 6-(4-fluorophenyl)-8-methyl-imidazo[1,2-b]pyridazine-2-carboxylic acid (40 mg), which was used directly in the next step. $^1$H NMR (400 MHz, $CDCl_3$) δ 8.58 (s, 1H), 8.16-7.82 (m, 2H), 7.38 (t, 1H), 7.23 (t, 2H), 2.76 (d, 3H).

Preparation of Intermediate B: 6-(4-fluorophenyl)-8-(trifluoromethyl)imidazo[1,2-b]pyridazine-2-carboxylic acid Scheme 2

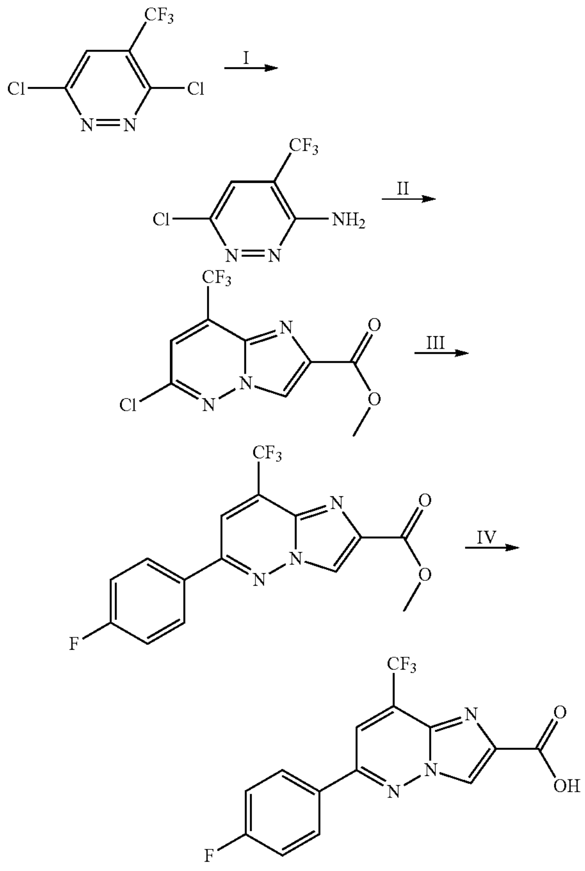

B

Step I: 6-Chloro-4-(trifluoromethyl)pyridazin-3-amine

A solution of 3,6-dichloro-4-(trifluoromethyl)pyridazine (2 g, 9.22 mmol) in dioxane (20 mL)/ammonia (5.6 g, 6.2 mL, 92.1 mmol) in a sealed vessel was heated at 50° C. for 2 days. The resulting reaction mixture was diluted with EtOAc (60 mL), washed with water and brine consecutively, dried and concentrated to dryness. The residue was purified by flash chromatography eluting with EtOAc/hexanes 0-50% in 20 CV to obtain 6-chloro-4-(trifluoromethyl) pyridazin-3-amine (1.27 g). $^1H$ NMR (400 MHz, $CDCl_3$) δ 7.47 (s, 1H), 5.50 (s, 2H).

Step II: Methyl 6-chloro-8-(trifluoromethyl)imidazo [1,2-b]pyridazine-2-carboxylate To a solution of 6-chloro-4-(trifluoromethyl)pyridazin-3-amine (1.22 g, 6.18 mmol) in DMF (20 mL) was added methyl 3-bromo-2-oxo-propanoate (3.10 g, 1.8 mL, 15.44 mmol). The mixture was heated at 70° C. for 5 h. The solvent was removed under reduced pressure and the residue was purified by flash chromatography eluting with EtOAc/hexanes 0-30% in 20 CV to obtain methyl 6-chloro-8-(trifluoromethyl)imidazo[1,2-b]pyridazine-2-carboxylate (1.21 g, 70% yield). $^1H$ NMR (400 MHz, $CDCl_3$) δ 8.58 (s, 1H), 7.44 (m, 1H), 4.02 (s, 3H).

Step III: Methyl 6-(4-fluorophenyl)-8-(trifluoromethyl)imidazo[1,2-b]pyridazine-2-carboxylate To a solution of methyl 6-chloro-8-(trifluoromethyl)imidazo[1,2-b]pyridazine-2-carboxylate (40 mg, 0.14 mmol) in dioxane (2 mL) were added (4-fluorophenyl)boronic acid (30.0 mg, 0.21 mmol), $PdCl_2$(dppf)-DCM (5.8 mg, 0.0071 mmol) and $Na_2CO_3$ (143 μL of a 2 M aqueous solution, 0.29 mmol). After degassing, the mixture was heated to 100° C. and stirred for 5 h under nitrogen. The volatiles were removed under reduced pressure and the residue was purified by flash chromatography eluting with EtOAc/hexanes 0-80% in 20 CV to obtain methyl 6-(4-fluorophenyl)-8-(trifluoromethyl)imidazo[1,2-b]pyridazine-2-carboxylate (48 mg) as a white solid. $^1H$ NMR (400 MHz, $CDCl_3$) δ 8.65 (s, 1H), 8.08-7.97 (m, 2H), 7.82 (t, 1H), 7.31-7.22 (m, 2H), 4.02 (s, 3H).

Step IV: 6-(4-Fluorophenyl)-8-(trifluoromethyl) imidazo[1,2-b]pyridazine-2-carboxylic acid (Intermediate B)

To a solution of methyl 6-(4-fluorophenyl)-8-(trifluoromethyl)imidazo[1,2-b]pyridazine-2-carboxylate (45 mg) in MeOH (1.6 mL)/water (0.4 mL) was added an aqueous LiOH solution (16 mg, 0.38 mmol) and the mixture was stirred at 50° C. for 2 h. It was then neutralized with resin Amberlite IR 120(H), filtrated and concentrated to dryness to obtain 6-(4-fluorophenyl)-8-(trifluoromethyl)imidazo[1,2-b]pyridazine-2-carboxylic acid (40 mg), which is used directly in the next step. LC-MS: 326.26 (M+H$^+$).

Preparation of Intermediate C: Methyl 8-bromo-6-(4-fluorophenyl)imidazo[1,2-b]pyridazine-2-carboxylate Scheme 3

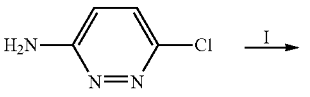

-continued

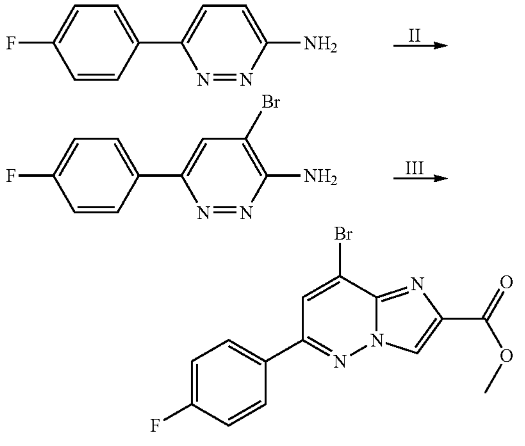

C

Step I: 6-(4-Fluorophenyl)pyridazin-3-amine

To a solution of 6-chloropyridazin-3-amine (7.5 g, 57.89 mmol) in dioxane (120 mL) were added (4-fluorophenyl) boronic acid (9.09 g, 63.68 mmol), $PdCl_2$(dppf)-DCM (945.7 mg, 1.16 mmol) and $Na_2CO_3$ (57.9 mL of a 2 M aqueous solution, 115.8 mmol). After degassing, the mixture was heated at 110° C. under nitrogen ON. It was then diluted with EtOAc (150 mL) and water (50 mL). The mixture was filtered over a pad of celite and washed with EtOAc. The organic layer was separated from the aqueous layer, washed with water and brine consecutively, dried over anhydrous sodium sulfate, filtered and concentrated to dryness. The residue was triturated with EtOAc several times to obtain 6-(4-fluorophenyl)pyridazien-3-amine (8.5 g) as a brown solid. LC-MS: 190.08 (M+H$^+$).

Step II: 4-Bromo-6-(4-fluorophenyl)pyridazin-3-amine

To a solution of 6-(4-fluorophenyl)pyridazin-3-amine (5 g, 26.43 mmol) and $NaHCO_3$ (4.44 g, 52.86 mmol) in MeOH (100 mL) was added $Br_2$ (4.65 g, 1.5 mL, 29.1 mmol) as a MeOH solution (10 mL) dropwise over a period of 20 min. The mixture was stirred at rt ON and then filtered. The solid was washed with MeOH. The filtrate was diluted with EtOAc, washed with an aqueous $Na_2S_2O_3$ solution, water and brine consecutively, dried over anhydrous sodium sulfate, filtered, and concentrated to dryness. The residue was purified by flash chromatography eluting with MeOH/DCM 0-6% in 20 CV to obtain 4-bromo-6-(4-fluorophenyl) pyridazin-3-amine (3.5 g) as a grey solid. $^1H$ NMR (400 MHz, $CDCl_3$) δ 7.97-7.87 (m, 2H), 7.85 (s, 1H), 7.20-7.07 (m, 2H), 5.26 (s, 2H).

Step III: Methyl 8-bromo-6-(4-fluorophenyl)imidazo[1,2-b]pyridazine-2-carboxylate (Intermediate C)

To a solution of 4-bromo-6-(4-fluorophenyl)pyridazin-3-amine (3.4 g, 12.68 mmol) in DMF (30 mL) was added methyl 3-bromo-2-oxo-propanoate (4.59 g, 25.4 mmol). The mixture was heated at 70° C. for 6 h. After cooling to rt, it was then diluted with water and filtered. The solid was washed with water and dried under reduced pressure to provide methyl 8-bromo-6-(4-fluorophenyl)imidazo[1,2-b]pyridazine-2-carboxylate (3.4 g) as brown solid.

$^1$H NMR (400 MHz, $CD_3OD$) δ 8.76 (d, 1H), 8.22 (d, 1H), 8.11 (m, 2H), 7.27 (m, 2H), 3.96 (s, 3H).

Alternative Method to for the Synthesis of Intermediate C

To a solution of 4-bromo-6-(4-fluorophenyl)pyridazin-3-amine (20 g, 74.6 mmol) in DMF (176.5 mL) was added methyl 3-bromo-2-oxo-propanoate (17.6, 97.0 mmol). The mixture is heated at 75° C. for 4 h. The mixture was cooled by adding ice into the reaction mixture and water was added to adjust the total volume to 2 L. The mixture was then stirred for 1 h and the precipitate formed was collected by filtration with a Büchner funnel. The resulting precipitate was washed with water and air dried ON to afford methyl 8-bromo-6-(4-fluorophenyl)imidazo[1,2-b]pyridazine-2-carboxylate (19.9 g) as a greenish solid. LC-MS: m/z=351.25 (M+H$^+$).

Preparation of Intermediate D: 6-(4-Fluorophenyl)-8-isopropenyl-imidazo[1,2-b]pyridazin-2-carboxylic acid Scheme 4

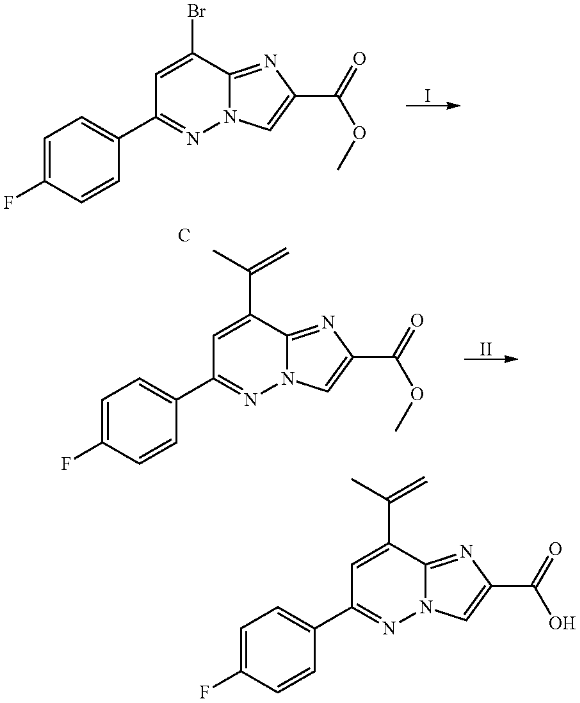

C

D

Step I: Methyl 6-(4-fluorophenyl)-8-isopropenyl-imidazo[1,2-b]pyridazin-2-carboxylate To a solution of Intermediate C (170 mg, 0.49 mmol) in dioxane (2 mL) were added 2-isopropenyl-4,4,5,5-tetramethyl-1,3,2-dioxaborolane (163.2 mg, 0.9710 mmol), $PdCl_2$(dppf)-DCM (19.8 mg, 0.024 mmol) and $Na_2CO_3$ (728.0 μL of a 2 M aqueous solution, 1.46 mmol). The mixture was degassed and heated at 110° C. for 5 h. It was then diluted with EtOAc, washed with water and brine consecutively, dried over sodium sulfate, filtered and concentrated to dryness. The residue was purified by flash chromatography eluting with EtOAc/hexanes 0-40% in 20 CV to obtain methyl 6-(4-fluorophenyl)-8-isopropenyl-imidazo[1,2-b]pyridazin-2-carboxylate (108 mg). $^1$H NMR (400 MHz, $CDCl_3$) δ 8.51 (s, 1H), 8.11-7.74 (m, 2H), 7.38 (s, 1H), 7.21 (m, 2H), 6.84 (m, 1H), 5.78 (t, 1H), 3.98 (s, 3H), 2.33 (m, 3H).

Step II: 6-(4-Fluorophenyl)-8-isopropenyl-imidazo[1,2-b]pyridazine-2-carboxylic acid (Intermediate D)

To a solution of methyl 6-(4-fluorophenyl)-8-isopropenyl-imidazo[1,2-b]pyridazine-2-carboxylate (31 mg) in MeOH (1 mL)/THF (1 mL)/water (0.5 mL) was added an aqueous LiOH solution (9 mg, 0.21 mmol). The mixture was heated to 60° C. and stirred for 2 h. It was then neutralized with resin Amberlite IR (120) H, filtered and concentrated to dryness. The residue 6-(4-fluorophenyl)-8-isopropenyl-imidazo[1,2-b]pyridazine-2-carboxylic acid (22 mg) was used directly in the next step. LC-MS: 298.3 (M+H$^+$).

Alternative procedure for the preparation of methyl 6-(4-fluorophenyl)-8-isopropenyl-imidazo[1,2-b]pyridazine-2-carboxylate Scheme 5

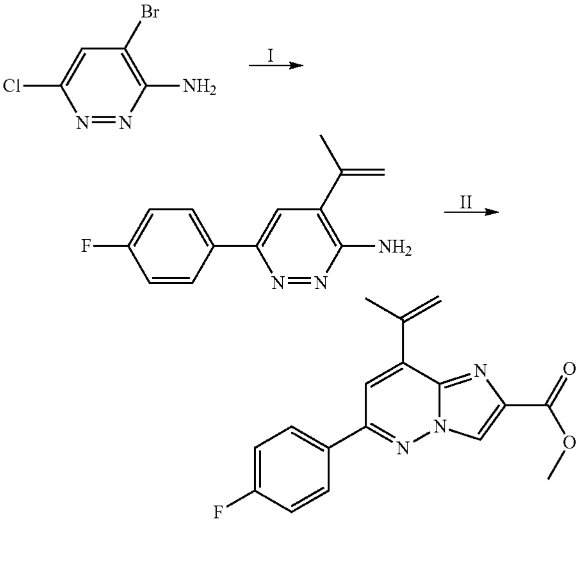

Step I: 6-(4-Fluorophenyl)-4-isopropenyl-pyridazin-3-amine

To a solution of 4-bromo-6-chloro-pyridazin-3-amine (2.15 g, 10.31 mmol) in dioxane (50 mL) were added 2-isopropenyl-4,4,5,5-tetramethyl-1,3,2-dioxaborolane (1.73 g, 10.31 mmol), $PdCl_2$(dppf)-DCM (421 mg, 0.52 mmol) and $Na_2CO_3$ (10.3 mL of a 2 M solution, 20.6 mmol). The mixture was degassed and heated at 100° C. for 5 h under nitrogen. Then, to the mixture, were added (4-fluorophenyl)boronic acid (1.73 g, 12.37 mmol), additional quantity of $PdCl_2$(dppf)-DCM (210 mg, 0.26 mmol) and $Na_2CO_3$ (10.3 mL of a 2 M aqueous solution, 20.6 mmol). The mixture was further stirred at 110° C. ON. It was then diluted with EtOAc and water, and then filtered over a pad of celite. The organic fraction was washed with water and brine, dried over anhydrous sodium sulfate, filtered and concentrated to dryness. The residue was purified by flash chromatography eluting with EtOAc/hexanes 0-50% in 20 CV to obtain 6-(4-fluorophenyl)-4-isopropenyl-pyridazin-3-amine (3.4 g) as a grey solid. $^1$H NMR (400 MHz, $CDCl_3$) δ 8.01-7.84 (m, 2H), 7.37 (s, 1H), 7.19-6.97 (m, 2H), 5.50-5.42 (m, 1H), 5.30 (m, 1H), 5.03-4.90 (m, 2H), 2.12 (m, 3H).

Step II: Methyl 6-(4-Fluorophenyl)-8-isopropenyl-imidazo[1,2-b]pyridazine-2-carboxylate To a solution of 6-(4-fluorophenyl)-4-isopropenyl-pyridazin-3-amine (2.72 g, 11.86 mmol) in DMF (30 mL) was added methyl 3-bromo-2-oxo-propanoate (4.77 g, 2.8 mL, 23.72 mmol). The mixture was heated at 70° C. ON and then diluted with EtOAc, washed with water and brine consecutively, dried over anhydrous sodium sulfate, filtered and concentrated to dryness. The mixture was triturated several times with EtOAc to obtain methyl 6-(4-fluorophenyl)-8-isopropenyl-imidazo[1,2-b]pyridazine-2-carboxylate (1.97 g) as a solid. $^1$H NMR (400 MHz, $CDCl_3$) δ 8.51 (s, 1H), 7.95 (m, 2H), 7.38 (s, 1H), 7.23-7.08 (m, 2H), 6.85 (t, 1H), 5.78 (t, 1H), 3.98 (s, 3H), 2.34 (m, 3H).

Preparation of Intermediate E: 6-(4-Fluorophenyl)-8-isopropyl-imidazo[1,2-b]pyridazin-2-carboxylic acid Scheme 6

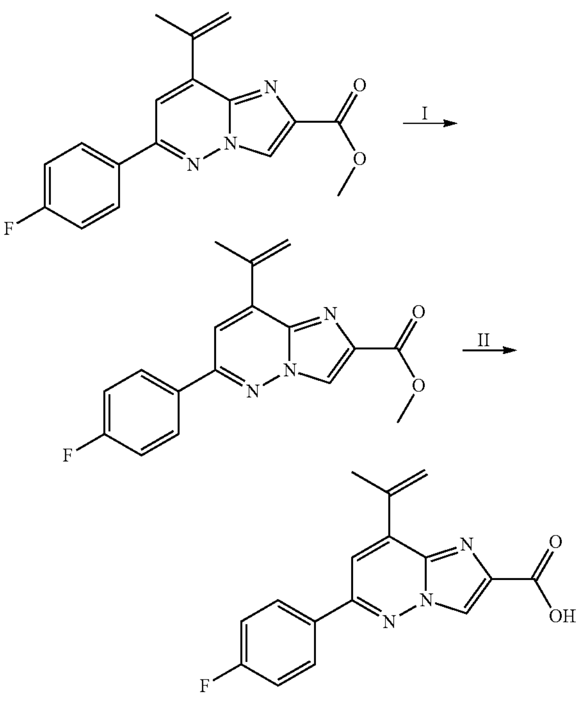

E

Step I: Methyl 6-(4-fluorophenyl)-8-isopropyl-imidazo[1,2-b]pyridazine-2-carboxylate To a solution of methyl 6-(4-fluorophenyl)-8-isopropenyl-imidazo[1,2-b]pyridazine-2-carboxylate (1.59 g, 5.11 mmol) in DCM (20 mL)/MeOH (10 mL) was added 10% Pd/C (200 mg). The mixture was hydrogenated under an atmosphere of $H_2$ (balloon) and stirred at rt for 3 h. Following filtration of the mixture over Celite, the solvent was removed under reduced pressure to provide methyl 6-(4-fluorophenyl)-8-isopropyl-imidazo[1,2-b]pyridazine-2-carboxylate (1.59 g) as a solid. $^1$H NMR (400 MHz, $CDCl_3$) δ 8.51 (s, 1H), 8.13-7.79 (m, 2H), 7.30 (d, 1H), 7.23-7.08 (m, 2H), 3.99 (s, 3H), 3.87 (m, 1H), 1.43 (d, 6H).

Step II: 6-(4-Fluorophenyl)-8-isopropyl-imidazo[1,2-b]pyridazine-2-carboxylic acid (Intermediate E)

To a solution of methyl 6-(4-fluorophenyl)-8-isopropyl-imidazo[1,2-b]pyridazine-2-carboxylate (1.59 g) in MeOH (10 mL)/THF (5 mL)/water (2 mL) was added an aqueous LiOH solution (321.5 mg, 7.66 mmol). The mixture was heated at 60° C. for 2 h. It was then neutralized with resin Amberlite IR 120 (H), filtered and concentrated to dryness. The residue 6-(4-fluorophenyl)-8-isopropyl-imidazo[1,2-b]pyridazine-2-carboxylic acid (1.48 g) was used directly in the next step. LC-MS: 300.3 (M+H$^+$).

Preparation of Intermediate F: 8-Cyclopropyl-6-(4-fluorophenyl)imidazo[1,2-b]pyridazine-2-carboxylic acid Scheme 7

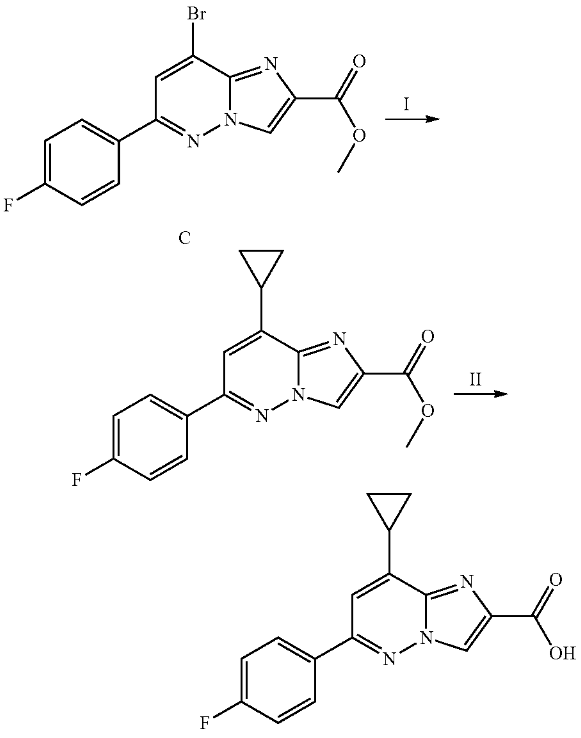

C

F

Step I: Methyl 8-cyclopropyl-6-(4-fluorophenyl)imidazo[1,2-b]pyridazine-2-carboxylate To a solution of Intermediate C (30 mg, 0.086 mmol) in dioxane (2 mL) were added cyclopropylboronic acid (14.7 mg, 0.1714 mmol), $PdCl_2$(dppf)-DCM (3.5 mg, 0.0043 mmol) and $K_3PO_4$ (54.5 mg, 0.257 mmol). The mixture was degassed and heated at 100° C. for 5 h under nitrogen. It was diluted with EtOAc, washed with water and brine consecutively, dried over anhydrous sodium sulfate, filtered and concentrated to dryness. The residue was purified by flash chromatography eluting with EtOAc/hexanes 0-50% in 20 CV to obtain methyl 8-cyclopropyl-6-(4-fluorophenyl)imidazo[1,2-b]pyridazine-2-carboxylate (21 mg). $^1H$ NMR (400 MHz, $CDCl_3$) δ 8.49 (s, 1H), 7.94-7.82 (m, 2H), 7.22-7.07 (m, 2H), 6.85 (d, 1H), 3.99 (s, 3H), 2.81 (m, 1H), 1.37-1.28 (m, 2H), 1.18-1.05 (m, 2H).

Step II: 8-Cyclopropyl-6-(4-fluorophenyl)imidazo[1,2-b]pyridazine-2-carboxylic acid (Intermediate F)

To a solution of methyl 8-cyclopropyl-6-(4-fluorophenyl)imidazo[1,2-b]pyridazine-2-carboxylate (21 mg) in MeOH (1 mL)/THF (1 mL)/water (0.5 mL) was added an aqueous LiOH solution (6 mg, 0.1430 mmol). The mixture was heated to 60° C. and stirred for 1 h. It was then neutralized with resin Amberlite IR (120) H, filtered and concentrated to dryness. The residue 8-cyclopropyl-6-(4-fluorophenyl)imidazo[1,2-b]pyridazine-2-carboxylic acid (17 mg) was used directly in the next step. LC-MS: 298.09 ($M+H^+$).

Preparation of Intermediate G: 6-(4-Fluorophenyl)imidazo[1,2-b]pyridazine-2-carboxylic acid Scheme 8

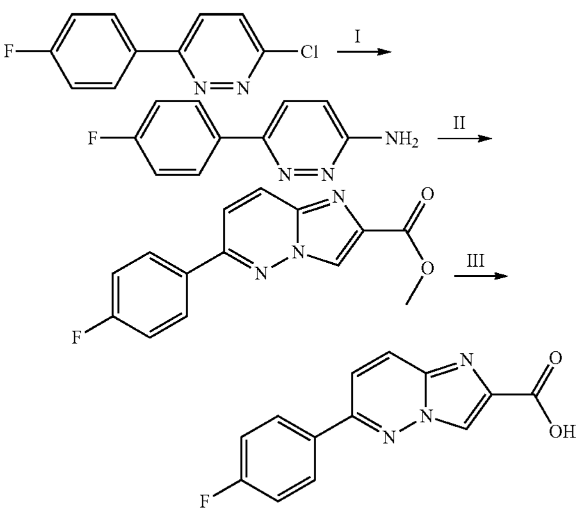

G

Step I: 6-(4-Fluorophenyl)pyridazin-3-amine

A suspension of 3-chloro-6-(4-fluorophenyl)pyridazine (1.6 g, 7.67 mmol) in concentrated ammonia (20 mL, 1.06 mol) in a sealed vessel was heated to 130° C. for 2 days. After cooling to rt, the mixture was diluted with water and then filtered. The solid was washed with water, dried in vacuo, and purified by flash chromatography eluting with MeOH/DCM 3-8% in 20 CV to obtain 6-(4-fluorophenyl)pyridazin-3-amine (880 mg) as a white solid. $^1H$ NMR (400 MHz, $CD_3OD$) δ 8.14-7.89 (m, 2H), 7.80-7.62 (m, 1H), 7.28-7.10 (m, 2H), 6.99 (d, 1H).

Step II: Methyl 6-(4-fluorophenyl)imidazo[1,2-b]pyridazine-2-carboxylate

To a solution of 6-(4-fluorophenyl)pyridazin-3-amine (760 mg, 4 mmol) in dioxane (10 mL)/DMF (10 mL) was added methyl 3-bromo-2-oxo-propanoate (640 μL, 6.01 mmol). The mixture was heated at 60° C. for 1 h. Then an additional 0.5 eq. of methyl 3-bromo-2-oxo-propanoate was added and the resulting mixture was stirred for one hour. After cooling to rt, the mixture was filtered and the filtrate treated with methanesulfonic acid (260 μL, 4.0 mmol) before being heated to 75° C. for 3 h. The reaction mixture was then diluted with EtOAc, washed with water and brine consecutively, dried over sodium sulfate, filtered and concentrated to dryness. The resulting residue was purified by flash chromatography eluting with EtOAc/hexanes 50-100% in 20 CV to obtain methyl 6-(4-fluorophenyl)imidazo[1,2-b]pyridazine-2-carboxylate (550 mg). $^1H$ NMR (400 MHz, $CDCl_3$) δ 8.55 (d, 1H), 8.17-8.04 (m, 1H), 8.00-7.81 (m, 2H), 7.55 (d, 1H), 7.24 (t, 2H), 4.02 (s, 3H).

Step III: 6-(4-Fluorophenyl)imidazo[1,2-b]pyridazine-2-carboxylic acid (Intermediate G)

To the solution of methyl 6-(4-fluorophenyl)imidazo[1,2-b]pyridazine-2-carboxylate (62 mg, 0.23 mmol) in MeOH (3 mL)/water (1 mL) was added an aqueous LiOH solution (19.2 mg, 0.46 mmol) and the mixture was subsequently heated at 60° C. for 1 h. The reaction mixture was then neutralized with resin Amberlite IR 120 (H), filtered and concentrated to dryness. The residue 6-(4-fluorophenyl)imidazo[1,2-b]pyridazine-2-carboxylic acid (50 mg) was used directly in the next step. LC-MS: 258.28 ($M+H^+$).

Preparation of Intermediate H: 8-Ethyl-6-(4-fluorophenyl)imidazo[1,2-b]pyridazine-2-carboxylic acid Scheme 9

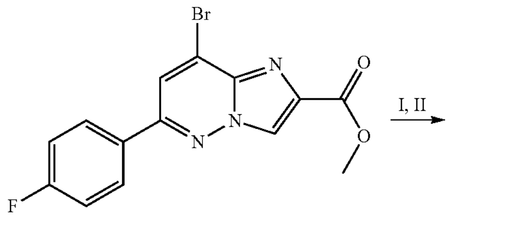

C

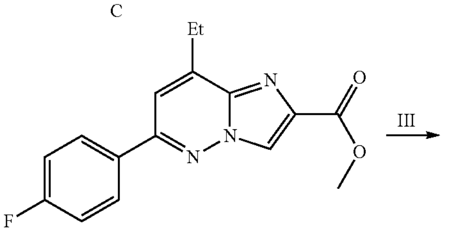

-continued

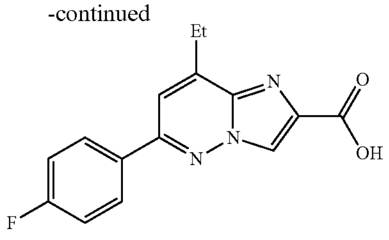

H

Step I: Methyl 6-(4-fluorophenyl)-8-vinyl-imidazo[1,2-b]pyridazine-2-carboxylate To a solution of Intermediate C (1.3 g, 3.71 mmol) in dioxane (30 mL) were added 4,4,5,5-tetramethyl-2-vinyl-1,3,2-dioxaborolane (857.9 mg, 5.57 mmol), $PdCl_2$(dppf)-DCM (151.6 mg, 0.1856 mmol) and $Na_2CO_3$ (3.7 mL of a 2 M aqueous solution, 7.4 mmol). The mixture was degassed and heated at 100° C. for 5 h under nitrogen. It was then diluted with EtOAc, washed with water and brine consecutively, dried over sodium sulfate, filtered and concentrated to dryness. The residue was purified by flash chromatography eluting with EtOAc/hexanes 0-50% in 20 CV to obtain a mixture mainly containing the desired methyl 6-(4-fluorophenyl)-8-vinyl-imidazo[1,2-b]pyridazine-2-carboxylate (1 g), which was used directly in the next step without further purification.

Step II: Methyl 8-ethyl-6-(4-fluorophenyl)imidazo[1,2-b]pyridazine-2-carboxylate To the solution of methyl 6-(4-fluorophenyl)-8-vinyl-imidazo[1,2-b]pyridazine-2-carboxylate (750 mg) in MeOH (3 mL)/DCM (15 mL) was added a catalytic quantity of 10% Pd/C. The mixture was hydrogenated under an atmosphere of $H_2$ (balloon) at rt for 1 h. After filtration over celite, the solvent was removed under reduced pressure and the residue methyl 8-ethyl-6-(4-fluorophenyl)imidazo[1,2-b]pyridazine-2-carboxylate (664 mg) was used directly in the next step. $^1$H NMR (400 MHz, $CDCl_3$) δ 8.50 (s, 1H), 8.17-7.77 (m, 2H), 7.31 (t, 1H), 7.24-7.02 (m, 2H), 3.99 (s, 3H), 3.19 (m, 2H), 1.44 (t, 3H).

Step III: 8-Ethyl-6-(4-fluorophenyl)imidazo[1,2-b]pyridazine-2-carboxylic acid (Intermediate H)

To a solution of methyl 8-ethyl-6-(4-fluorophenyl)imidazo[1,2-b]pyridazine-2-carboxylate (664 mg) in water (2 mL)/MeOH (10 mL) was added an aqueous LiOH solution (140 mg, 3.34 mmol) and the resulting mixture was heated to 60° C. for 1 h. It was then neutralized with resin Amnerlite IR 120 (H), filtered and concentrated to dryness. The residue 8-ethyl-6-(4-fluorophenyl)imidazo[1,2-b]pyridazine-2-carboxylic acid (536 mg) was used directly in the next step. LC-MS: 286.3 (M+H$^+$).

Preparation of I-1 and Intermediate I: [6-(4-Fluorophenyl)-8-(trifluoromethyl)imidazo[1,2-b]pyridazine-2-yl]-[(3S)-3-methylpiperazin-1-yl]methanone Scheme 10

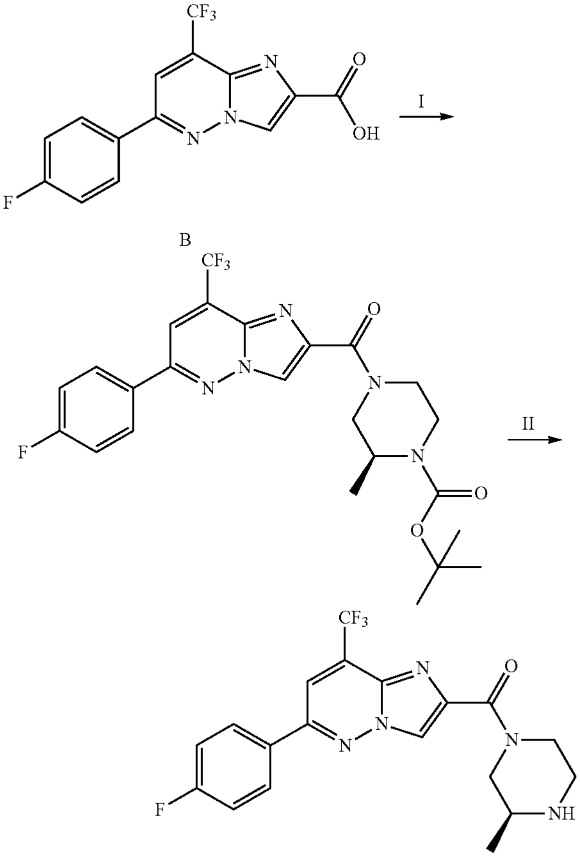

I

Step I (I-1): tert-Butyl (2S)-4-[6-(4-fluorophenyl)-8-(trifluoromethyl)imidazo[1,2-b]pyridazine-2-carbonyl]-2-methyl-piperazine-1-carboxylate To a solution of Intermediate B (190 mg, 0.58 mmol) in DMF (5 mL) were added HATU (333.2 mg, 0.88 mmol), DIPEA (226.6 mg, 305 μL, 1.75 mmol) and tert-butyl (2S)-2-methylpiperazine-1-carboxylate (175.5 mg, 0.88 mmol). The mixture was stirred at rt ON. The volatiles were removed under reduced pressure and the residue was purified by flash chromatography eluting with EtOAc/hexanes 0-50% in 20 CV to obtain tert-butyl (2S)-4-[6-(4-fluorophenyl)-8-(trifluoromethyl)imidazo[1,2-b]pyridazine-2-carbonyl]-2-methyl-piperazine-1-carboxylate (259 mg) as a white solid. $^1$H NMR (400 MHz, $CDCl_3$) δ 8.62 (d, 1H), 8.11-7.97 (m, 2H), 7.76 (s, 1H), 7.27-7.13 (m, 3H), 5.34 (d, 1H), 4.78-4.27 (m, 2H), 3.97 (t, 1H), 3.57-2.83 (m, 3H), 1.49 (s, 9H), 1.22 (d, 3H).

Step II: [6-(4-Fluorophenyl)-8-(trifluoromethyl) imidazo[1,2-b]pyridazin-2-yl]-[(3S)-3-methylpiperazin-1-yl]methanone (Intermediate I)

To a solution of tert-butyl (2S)-4-[6-(4-fluorophenyl)-8-(trifluoromethyl)imidazo[1,2-b]pyridazine-2-carbonyl]-2-methyl-piperazine-1-carboxylate (259 mg) in DCM (1.5 mL) was added 4M HCl (1 mL of a 4 M solution, 4 mmol). The mixture was stirred at rt for 2 h. Removal of the volatiles under reduced pressure provided [6-(4-fluorophenyl)-8-(trifluoromethyl)imidazo[1,2-b]pyridazin-2-yl]-[(3S)-3-methylpiperazin-1-yl]methanone (hydrochloric acid salt, 220 mg) as a solid, which was used in the next step without purification. The tert-Butyl (2S)-4-[6-(4-fluorophenyl)-8-(trifluoromethyl)imidazo[1,2-b]pyridazine-2-carbonyl]-2-methyl-piperazine-1-carboxylate were deprotected using DCM/TFA (1:1 ratio) to obtain Intermediate I as TFA salt and used as it is. $^1$H NMR (400 MHz, $CD_3OD$) δ 8.73 (s, 1H), 8.27-7.94 (m, 3H), 7.51-7.12 (m, 2H), 5.35 (s, 1H), 4.69 (s, 1H), 3.84-3.42 (m, 3H), 3.33 (s, 1H), 3.17-3.01 (m, 1H), 1.38 (s, 3H). LC-MS: 508.4 (M+H$^+$).

Preparation of I-2 and Intermediate J: [6-(4-Fluorophenyl)-8-methyl-imidazo[1,2-b]pyridazin-2-yl]-[(3S)-3-methylpiperazin-1-yl]methanone Scheme 11

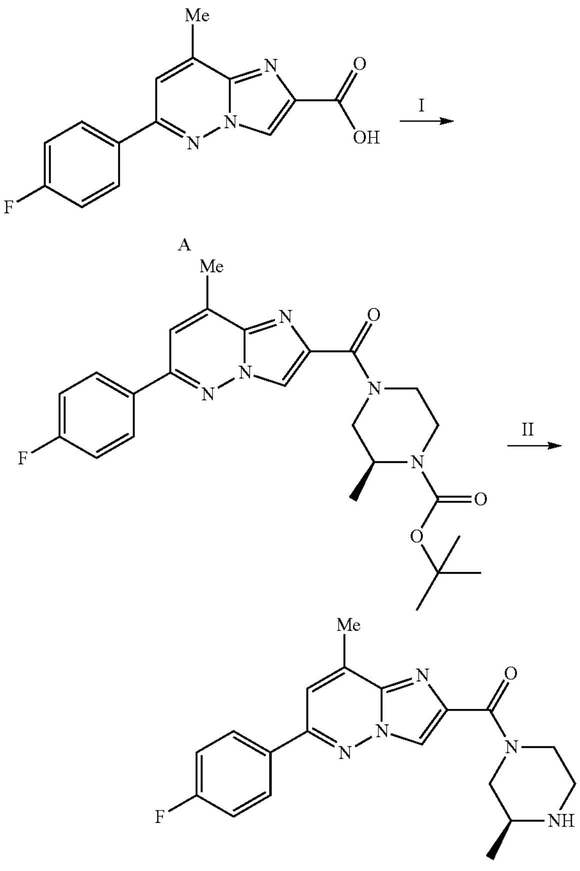

A

J

Step I (I-2): tert-Butyl (2S)-4-[6-(4-fluorophenyl)-8-methyl-imidazo[1,2-b]pyridazine-2-carbonyl]-2-methyl-piperazine-1-carboxylate To a solution of Intermediate A (108 mg, 0.40 mmol) in DMF (2 mL) were added tert-butyl (2S)-2-methylpiperazine-1-carboxylate (119.6 mg, 0.60 mmol), HATU (227.1 mg, 0.60 mmol) and DIPEA (102.9 mg, 140 μL, 0.80 mmol). The mixture was stirred at rt ON. It was then diluted with EtOAc, washed with water and brine consecutively, dried over anhydrous sodium sulfate, filtered and concentrated to dryness. The residue was purified by flash chromatography eluting with EtOAc/hexanes 0-60% in 20 CV to obtain tert-butyl (2S)-4-[6-(4-fluorophenyl)-8-methyl-imidazo[1,2-b]pyridazine-2-carbonyl]-2-methyl-piperazine-1-carboxylate (142 mg) as a white solid. $^1$H NMR (400 MHz, $CDCl_3$) δ 8.43 (s, 1H), 8.06-7.86 (m, 2H), 7.29 (m, 1H), 7.22-7.00 (m, 2H), 5.26 (d, H), 4.78-4.19 (m, 2H), 4.03-3.82 (m, 1H), 3.59-2.83 (m, 3H), 2.69 (d, 3H), 1.47 (s, 9H), 1.19 (s, 3H).

LC-MS: 455.7 (M+H$^+$).

Step II: [6-(4-Fluorophenyl)-8-methyl-imidazo[1,2-b]pyridazin-2-yl]-[(3S)-3-methylpiperazin-1-yl] methanone (Intermediate J)

To a solution of tert-butyl (2S)-4-[6-(4-fluorophenyl)-8-methyl-imidazo[1,2-b]pyridazine-2-carbonyl]-2-methyl-piperazine-1-carboxylate (140 mg) in DCM (1 mL) was added HCl (500 μL of a 4 M solution in dioxane, 2.0 mmol) and the resulting mixture was stirred at rt for 1 h. The volatiles were removed under reduced pressure to provide [6-(4-fluorophenyl)-8-methyl-imidazo[1,2-b]pyridazin-2-yl]-[(3S)-3-methylpiperazin-1-yl]methanone (hydrochloride salt, 122 mg) as a solid which was used directly in the next step. LC-MS: 355.41 (M+H$^+$).

Preparation of Intermediate K: [6-(4-Fluorophenyl)-8-isopropyl-imidazo[1,2-b]pyridazin-2-yl]-[(3S)-3-methylpiperazin-1-yl]methanone (hydrochloric acid salt)

Scheme 12

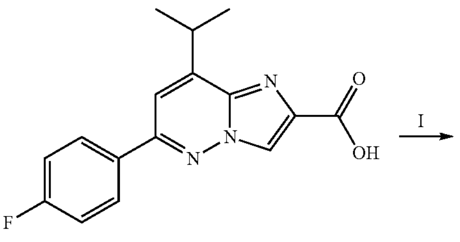

E

-continued

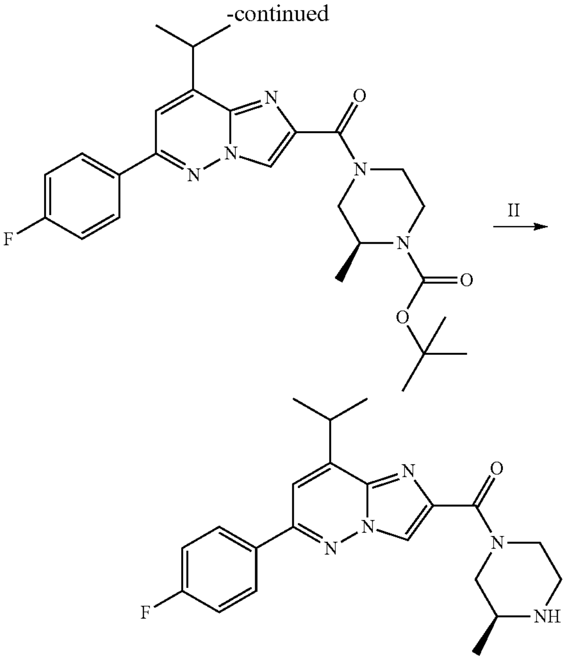

K

Step I: tert-Butyl (2S)-4-[6-(4-fluorophenyl)-8-isopropyl-imidazo[1,2-b]pyridazine-2-carbonyl]-2-methyl-piperazine-1-carboxylate To a solution of Intermediate E (1.37 g, 4.58 mmol) in DMF (15 mL) were added tert-butyl (2S)-2-methylpiperazine-1-carboxylate (1.1 g, 5.5 mmol), HATU (2.26 g, 5.95 mmol) and DIPEA (1.775 g, 2.4 mL, 13.73 mmol). The mixture was stirred at rt ON. It was then diluted with EtOAc, washed with water and brine consecutively, dried over anhydrous sodium sulfate, filtered and concentrated to dryness. The residue was purified by flash chromatography eluting with EtOAc/hexanes 0-50% in 20 CV to obtain tert-butyl (2S)-4-[6-(4-fluorophenyl)-8-isopropyl-imidazo[1,2-b]pyridazine-2-carbonyl]-2-methyl-piperazine-1-carboxylate (1.9 g). $^1$H NMR (400 MHz, $CDCl_3$) δ 8.45 (s, 1H), 8.00-7.75 (m, 2H), 7.30 (d, 1H), 7.23-7.17 (m, 2H), 5.34 (s, 1H), 4.56 (m, 1H), 4.33 (s, 1H), 3.93 (s, 1H), 3.60 (d, 1H), 3.54-2.76 (m, 3H), 1.47 (d, 15H), 1.21 (d, 3H).

Step II: [6-(4-Fluorophenyl)-8-isopropyl-imidazo[1,2-b]pyridazin-2-yl]-[(3S)-3-methylpiperazin-1-yl]methanone (hydrochloric acid salt) (Intermediate K)

To a solution of tert-butyl (2S)-4-[6-(4-fluorophenyl)-8-isopropyl-imidazo[1,2-b]pyridazine-2-carbonyl]-2-methyl-piperazine-1-carboxylate (1.8 g) in DCM (5 mL) was added hydrogen chloride (10 mL of a 4 M solution in dioxane, 40 mmol) and the resulting mixture was stirred at rt for 2 h. The volatiles were removed under reduced pressure and the residue [6-(4-fluorophenyl)-8-isopropyl-imidazo[1,2-b]pyridazin-2-yl]-[(3S)-3-methylpiperazin-1-yl]methanone (hydrochloric acid salt, 1.7 g) was used directly in the next step. LC-MS: 382.6 (M+H$^+$).

Preparation of I-3 and Intermediate L: [8-Ethyl-6-(4-fluorophenyl)imidazo[1,2-b]pyridazin-2-yl]-[(3S)-3-methylpiperazin-1-yl]methanone (hydrochloric acid salt)

Scheme 13

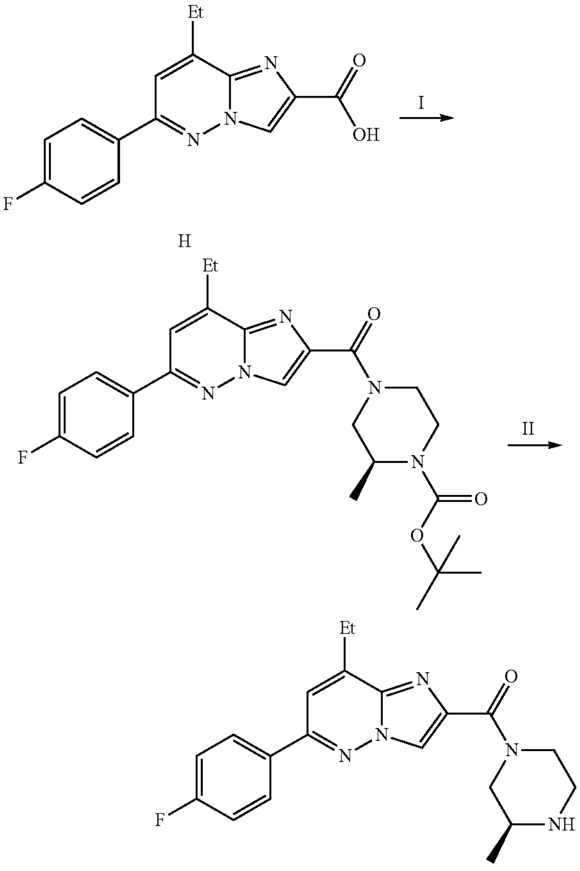

H

L

Step I (I-3): tert-Butyl (2S)-4-[8-ethyl-6-(4-fluorophenyl)imidazo[1,2-b]pyridazine-2-carbonyl]-2-methyl-piperazine-1-carboxylate To a solution of Intermediate H (210 mg, 0.74 mmol) in DMF (5 mL) were added tert-butyl (2S)-2-methylpiperazine-1-carboxylate (176.9 mg, 0.883 mmol), HATU (363.8 mg, 0.96 mmol) and DIPEA (190.2 mg, 256 μL, 1.47 mmol) and the resulting mixture was stirred at rt ON. The reaction mixture was then diluted with EtOAc, washed with water and brine consecutively, dried over anhydrous sodium sulfate, filtered and concentrated to dryness. The residue was purified by flash chromatography eluting with EtOAc/hexanes 0-50% in 20 CV to obtain tert-butyl (2S)-4-[8-ethyl-6-(4-fluorophenyl)imidazo[1,2-b]pyridazine-2-carbonyl]-2-methyl-piperazine-1-carboxylate (293 mg) as a white solid. $^1$H NMR (400 MHz, $CDCl_3$) δ 8.44 (s, 1H), 8.07-7.80 (m, 2H), 7.28 (t, 1H), 7.24-7.12 (m, 2H), 5.29 (d, 1H), 4.80-4.27 (m, 2H), 3.93 (s, 1H), 3.59-2.84 (m, 5H), 1.46 (m, 12H), 1.22 (d, 3H). LC-MS: 468.2 (M+H$^+$).

Step II: [8-Ethyl-6-(4-fluorophenyl)imidazo[1,2-b]pyridazin-2-yl]-[(3S)-3-methylpiperazin-1-yl]methanone (Intermediate L)

To a solution of tert-butyl (2S)-4-[8-ethyl-6-(4-fluorophenyl)imidazo[1,2-b]pyridazine-2-carbonyl]-2-methyl-piperazine-1-carboxylate (290 mg) in DCM (1 mL) was added HCl (1 mL of a 4 M solution in dioxane, 4.0 mmol) and the resulting mixture was stirred at rt for 1 h. The volatiles were removed under reduced pressure to yield [8-ethyl-6-(4-fluorophenyl)imidazo[1,2-b]pyridazin-2-yl]-[(3S)-3-methylpiperazin-1-yl]methanone (hydrochloric acid salt) (258 mg) which was used directly in the next step. LC-MS: 368.19 (M+H$^+$).

Preparation of I-4 and Intermediate M: (2,2-Dimethylpiperazin-1-yl)-[8-ethyl-6-(4-fluorophenyl)imidazo[1,2-b]pyridazin-2-yl]methanone (hydrochloride salt)

Scheme 14

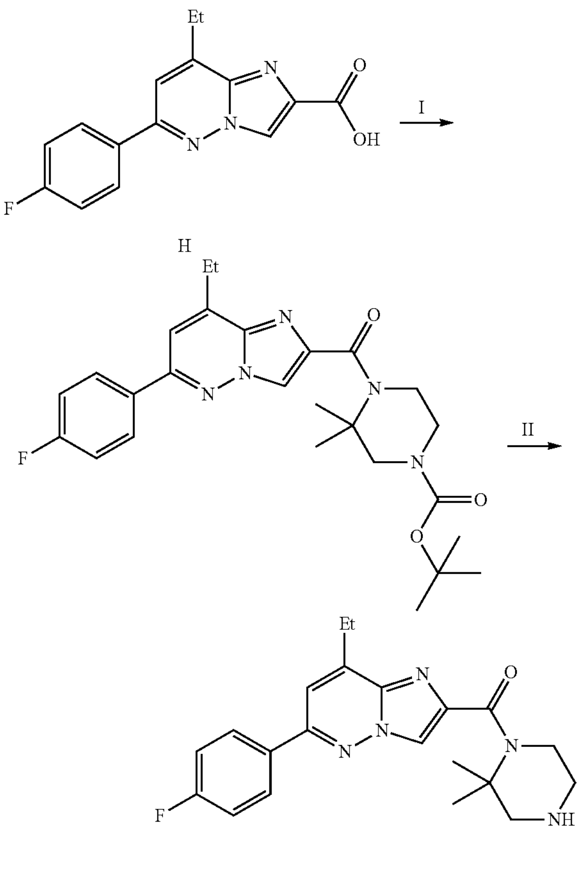

M

Step I (I-4): tert-Butyl 4-[8-ethyl-6-(4-fluorophenyl)imidazo[1,2-b]pyridazine-2-carbonyl]-3,3-dimethyl-piperazine-1-carboxylate To a solution of Intermediate H (190 mg, 0.67 mmol) in DMF (3 mL) were added tert-butyl 3,3-dimethylpiperazine-1-carboxylate (171.3 mg, 0.80 mmol), HATU (329.2 mg, 0.87 mmol) and DIPEA (232 μL, 1.3 mmol) and the mixture was stirred at rt ON. The reaction mixture was then diluted with EtOAc, washed with water and brine consecutively, dried over anhydrous sodium sulfate, filtered and concentrated to dryness. The residue was purified by flash chromatography eluting with EtOAc/hexanes 0-50% in 20 CV to obtain tert-butyl 4-[8-ethyl-6-(4-fluorophenyl)imidazo[1,2-b]pyridazine-2-carbonyl]-3,3-dimethyl-piperazine-1-carboxylate (235 mg) as a white solid. H NMR (400 MHz, $CDCl_3$) δ 8.32 (s, 1H), 8.04-7.86 (m, 2H), 7.26 (s, 1H), 7.22-7.11 (m, 2H), 4.39-3.92 (m, 2H), 3.73-3.40 (m, 4H), 3.09 (m, 2H), 1.65-1.59 (m, 6H), 1.50-1.40 (m, 12H). LC-MS: 482.5 (M+H$^+$).

Step II: (2,2-Dimethylpiperazin-1-yl)-[8-ethyl-6-(4-fluorophenyl)imidazo[1,2-b]pyridazin-2-yl]methanone (hydrochloric acid salt) (Intermediate M)

To a solution of tert-butyl 4-[8-ethyl-6-(4-fluorophenyl)imidazo[1,2-b]pyridazine-2-carbonyl]-3,3-dimethyl-piperazine-1-carboxylate (235 mg) in DCM (1 mL) was added HCl (1 mL of a 4 M solution in dioxane, 4.0 mmol) and the mixture was stirred at rt for 1 h. The volatiles were removed under reduced pressure to yield (2,2-dimethylpiperazin-1-yl)-[8-ethyl-6-(4-fluorophenyl)imidazo[1,2-b]pyridazin-2-yl]methanone (hydrochloride salt, 212 mg) which is used directly in the next step. LC-MS: 382.72 (M+H$^+$).

Preparation of I-5 and Intermediate N: (2,2-Dimethylpiperazin-1-yl)-[6-(4-fluorophenyl)-8-isopropyl-imidazo[1,2-b]pyridazin-2-yl]methanone (hydrochloric acid salt)

Scheme 15

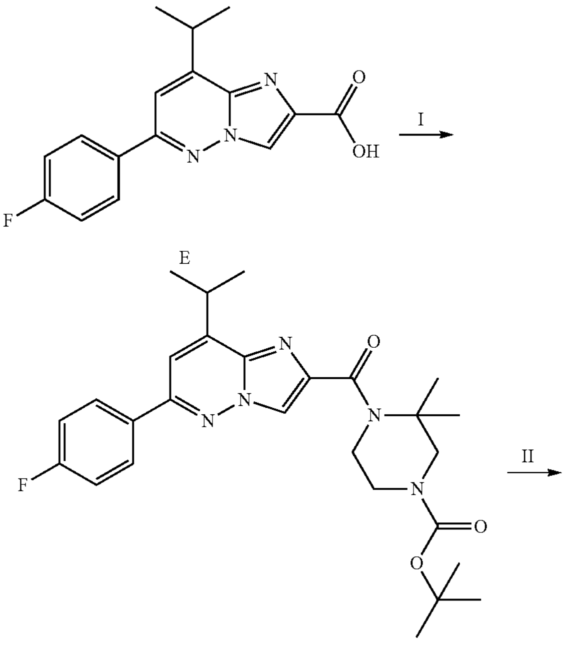

-continued

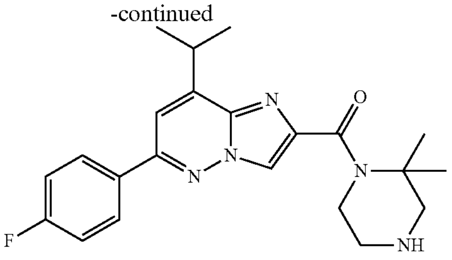

N

Step I (I-5): tert-Butyl 4-[6-(4-fluorophenyl)-8-isopropyl-imidazo[1,2-b]pyridazine-2-carbonyl]-3,3-dimethyl-piperazine-1-carboxylate To a solution of Intermediate E (59 mg, 0.20 mmol) in DMF (3 mL) were added tert-butyl 3,3-dimethylpiperazine-1-carboxylate (50.7 mg, 0.24 mmol), HATU (97.4 mg, 0.26 mmol) and DIPEA (51 mg, 69 μL, 0.39 mmol) and the resulting mixture was stirred at rt ON. The reaction mixture was then diluted with EtOAc, washed with water and brine consecutively, dried over anhydrous sodium sulfate, filtered and concentrated to dryness. The residue was purified by flash chromatography eluting with EtOAc/Hexanes 0-50% in 20 CV to obtain tert-butyl 4-[6-(4-fluorophenyl)-8-isopropyl-imidazo[1,2-b]pyridazine-2-carbonyl]-3,3-dimethyl-piperazine-1-carboxylate (58 mg) as a white solid. $^1$H NMR (400 MHz, $CDCl_3$) δ 8.33 (s, 1H), 8.11-7.87 (m, 2H), 7.24-7.10 (m, 3H), 4.28 (s, 2H), 3.77-3.43 (m, 5H), 1.61 (s, 6H), 1.51-1.40 (m, 15H). LC-MS: 497.5 (M+H$^+$).

Step II: (2,2-Dimethylpiperazin-1-yl)-[6-(4-fluorophenyl)-8-isopropyl-imidazo[1,2-b]pyridazin-2-yl]methanone (Intermediate N)

To a solution of tert-butyl 4-[6-(4-fluorophenyl)-8-isopropyl-imidazo[1,2-b]pyridazine-2-carbonyl]-3,3-dimethyl-piperazine-1-carboxylate (55 mg) in DCM (0.5 mL) was added HCl (0.5 mL of a 4 M solution in dioxane, 2.0 mmol) and the mixture was stirred at rt for 1 h. The volatiles were removed under reduced pressure to furnish (2,2-dimethyl-piperazin-1-yl)-[6-(4-fluorophenyl)-8-isopropyl-imidazo[1,2-b]pyridazin-2-yl]methanone (hydrochloride acid salt, 48 mg) which was used directly in the next step. LC-MS: 397.5 (M+H$^+$).

Preparation of Intermediate O: methyl 8-tert-butyl-6-chloro-imidazo[1,2-b]pyridazine-2-carboxylate Scheme 16

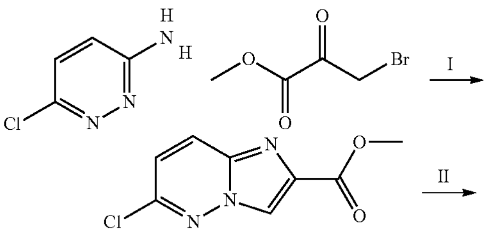

-continued

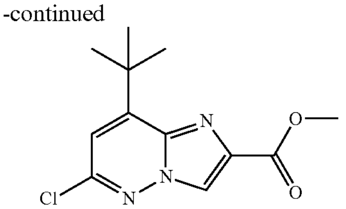

O

Step I: methyl 6-chloroimidazo[1,2-b]pyridazine-2-carboxylate

In a 12 L and 4 necks rbf equipped with a mechanical stirrer, a $N_2$ inlet, a condenser and a temperature probe was charge with 6-chloropyridazin-3-amine (300 g, 2.316 mol) and N,N-dimethylacetamide (3.000 L). Portionwise addition of methyl 3-bromo-2-oxo-propanoate (605.5 g, 3.011 mol) followed. The mixture was maintained at 50° C. for 1 h30. The mixture was cooled to rt with a water/ice bath and water (6 L) was added dropwise over 2 h into the reaction mixture. It was then stirred at rt ON. The precipitate formed was filtered off by filtration on Buchner (≈30 min). The precipitate was washed with 3×500 mL of water and dried under vacuum on the Buchner for 2 hrs then 20 hrs in vacuum oven at 40° C. to afford methyl 6-chloroimidazo[2,1-f]pyridazine-2-carboxylate (330.11 g, 1.521 mol, 65.66%) as a beige solid. $^1$H NMR (400 MHz, DMSO-d$_6$) δ 8.92 (d, J=0.7 Hz, 1H), 8.30 (dd, J=9.7, 0.8 Hz, 1H), 7.50 (d, J=9.6 Hz, 1H), 3.87 (s, 3H). LC-MS: 212.12 (M+H$^+$).

Step II: methyl 8-tert-butyl-6-chloro-imidazo[1,2-b]pyridazine-2-carboxylate (Intermediate O)

A 1 L with 3 necks round bottom flask equipped with a dropping funnel, a $N_2$ inlet, a condenser, a temperature probe and a mechanical stirrer was charged with water (98.10 mL) and TFA (15.86 g, 10.72 mL, 139.1 mmol). Once the exotherm finishes, methyl 6-chloroimidazo[2,1-f]pyridazine-2-carboxylate (20 g, 92.72 mmol), 2,2-dimethylpropanoic acid (37.88 g, 21.30 mL, 370.9 mmol) and MeCN (196.2 mL) were added followed by AgNO3 (7.875 g, 1.810 mL, 46.36 mmol). The reaction mixture was wrapped in aluminium foil and warmed to 80° C. A solution of sulfooxy hydrogen sulfate (Ammonia (1)) (35.24 g, 166.9 mmol) in water (98.10 mL) was added via the dropping funnel over 30 min. When addition is completed, the addition funnel is removed and the mixture was equipped with a condenser and heated at 80° C. for 30 minutes.

The reaction was cooled to rt and diluted with 200 mL of iPAc. The filtrate was cooled to 0° C. in an ice/water bath and $NH_4OH$ was added up to pH=8. After 20 min, the mixture was filtered on celite and washed with iPAc. The layers were separated and the aqueous layer is extracted with 1×200 mL iPAc. The combined organic extracts were washed with 2×200 mL of a solution of 1N NaOH/brine 1:1. The organic phase was filtered on celite again to remove Ag salts, dried over $Na_2SO_4$, filtered and concentrated under reduced pressure to afford 33 g of a dark foamy gum.

The crude product was absorb on silica gel (50 g) then Purification by flash chromatography on silica gel was carried out under standard condition to afford methyl 8-tert-butyl-6-chloro-imidazo[1,2-b]pyridazine-2-carboxylate (7.36 g, 27.28 mmol, 29.43%) as light yellow solid. $^1$H NMR (400 MHz, DMSO-$d_6$) δ 8.85 (s, 1H), 7.17 (s, 1H), 3.88 (s, 3H), 1.53 (s, 9H), 1.11 (s, 1H).

LC-MS: 268.25 ($M+H^+$).

Preparation of Intermediate P: 8-tert-butyl-6-(4-fluorophenyl)imidazo[1,2-b]pyridazine-2-carboxylic acid Scheme 17

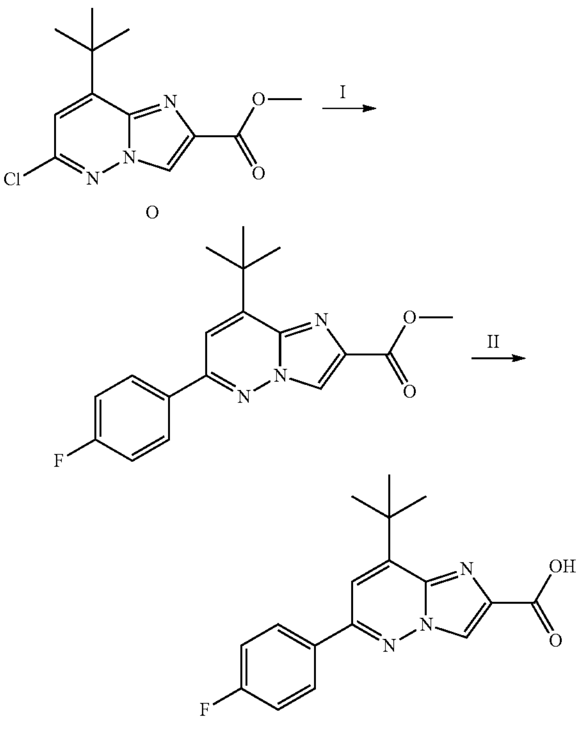

O

P

Step I: Methyl 8-tert-butyl-6-(4-fluorophenyl)imidazo[1,2-b]pyridazine-2-carboxylate To a solution of intermediate O (500 mg, 1.822 mmol) in DMF (7.288 mL) were added (4-fluorophenyl)boronic acid (280.4 mg, 2.004 mmol), $PdCl_2(dppf)_2$-DCM (29.76 mg, 0.03644 mmol) and $Na_2CO_3$ (1.822 mL of 2 M, 3.644 mmol). After degassing by bubbling $N_2$ for 5 min, the mixture was heated at 80° C. for 18 h (ON). Water was added along with EtOAc and the phases were separated. The organic phase was washed 2 other times with water and brine (1:1 mixture), dried over MgSO4, filtered and evaporated under reduced pressure to afford methyl 8-tert-butyl-6-(4-fluorophenyl)imidazo[1,2-b]pyridazine-2-carboxylate (555 mg, 1.695 mmol, 93.06%) as a nice beige solid. $^1$H NMR (400 MHz, DMSO-d6) δ 8.83 (s, 1H), 8.19-8.10 (m, 2H), 7.51 (s, 1H), 7.46-7.36 (m, 2H), 3.89 (s, 3H), 1.60 (s, 9H).

LC-MS: 327.96 ($M+H^+$)

Step II: 8-tert-butyl-6-(4-fluorophenyl)imidazo[1,2-b]pyridazine-2-carboxylic acid (Intermediate P)

Methyl 8-tert-butyl-6-(4-fluorophenyl)imidazo[1,2-b]pyridazine-2-carboxylate (1.1 g, 3.360 mmol) was dissolved in MeOH (53.66 mL) and NaOH (6.720 mL of 2.5 M, 16.80 mmol) was added. The solution was stirred at rt for 2 h. HCl 6N was added until acidic pH was reached. Water was added along with EtOAc and the phases were separated. The organic phase was dried over MgSO4, filtered and evaporated under reduced pressure to afford 8-tert-butyl-6-(4-fluorophenyl)imidazo[1,2-b]pyridazine-2-carboxylic acid (1.05 g, 3.324 mmol, 98.92%) as a beige solid. $^1$H NMR (400 MHz, DMSO-d6) δ 12.98 (s, 1H), 8.74 (s, 1H), 8.19-8.12 (m, 2H), 7.50 (s, 1H), 7.45-7.38 (m, 2H), 1.60 (s, 9H).

LC-MS: 313.97 ($M+H^+$), Retention Time: 3.06

Preparation of Intermediate Q: [8-tert-butyl-6-(4-fluorophenyl)imidazo[1,2-b]pyridazin-2-yl]-(2,2-dimethylpiperazin-1-yl)methanone Scheme 18

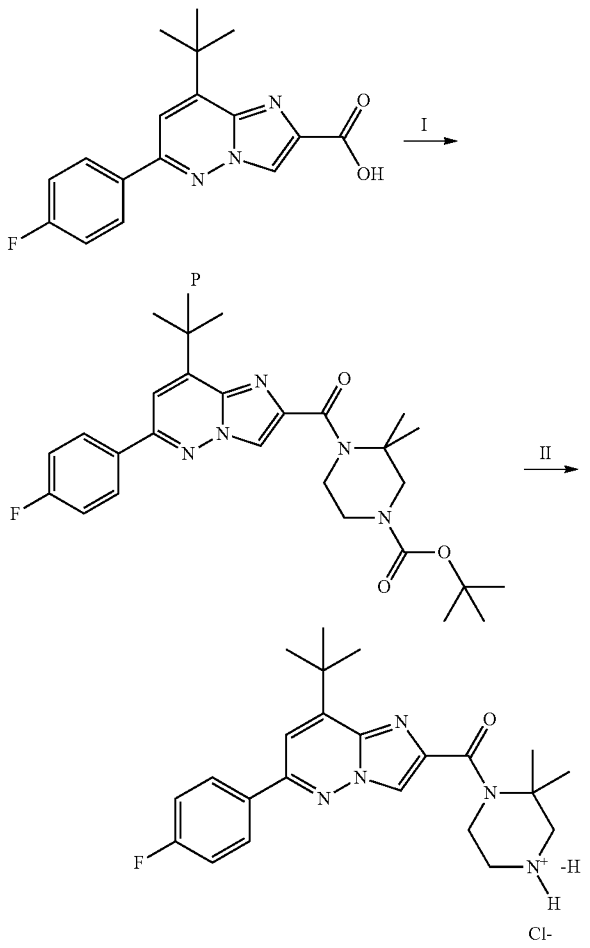

P

Q

Step I: tert-butyl 4-[8-tert-butyl-6-(4-fluorophenyl)imidazo[1,2-b]pyridazine-2-carbonyl]-3,3-dimethylpiperazine-1-carboxylate The intermediate was prepared according to general procedure 1 using Intermediate P (1.0 equiv), DMF (0.3M), HATU (1.1 equiv), tert-butyl 3,3-dimethylpiperazine-1-carboxylate (1.1 equiv) and Hünig's base (2.5 equiv) affording tert-butyl 4-(8-(tert-butyl)-6-(4-fluorophenyl)imidazo[1,2-b]pyridazine-2-carbonyl)-3,3-dimethylpiperazine-1-carboxylate (47.6 g, 93.5 mmol, 97.5%). $^1$H NMR (400 MHz, DMSO-d6) δ 8.52 (s, 1H), 8.18-8.11 (m, 2H), 7.49 (s, 1H), 7.45-7.37 (m, 2H), 4.17-4.05 (m, 2H), 3.59-3.44 (m, 4H), 1.59 (s, 9H), 1.50 (s, 6H), 1.43 (s, 9H). LC-MS: 510.13 (M+H$^+$), retention time: 2.18 minutes using method C.

Step II: [8-tert-butyl-6-(4-fluorophenyl)imidazo[1,2-b]pyridazin-2-yl]-(2,2-dimethylpiperazin-1-yl) methanone (intermediate Q)

The intermediate was prepared according to general procedure 2 using tert-butyl 4-(8-(tert-butyl)-6-(4-fluorophenyl)imidazo[1,2-b]pyridazine-2-carbonyl)-3,3-dimethylpiperazine-1-carboxylate (1.0 equiv) and 4N HCl solution in 1,4-dioxane (5.0 equiv) in 1,4-dioxane (0.2M) and MeOH (0.02M) affording 4-(8-(tert-butyl)-6-(4-fluorophenyl)imidazo[1,2-b]pyridazine-2-carbonyl)-3,3-dimethylpiperazine hydrochloride (52.76 g, 118.3 mmol, 100%) as a solid. 1H NMR (400 MHz, DMSO-d6) δ 9.15 (s, 2H), 8.59 (s, 1H), 8.19-8.10 (m, 2H), 7.51 (s, 1H), 7.47-7.37 (m, 2H), 4.16-4.06 (m, 2H), 3.35 (s, 2H), 3.22 (s, 2H), 1.59 (d, J=3.2 Hz, 15H). LC-MS: 410.71 (M+H$^+$), retention time: 1.15 minutes using method C.

Preparation of Intermediate R: [8-tert-butyl-6-(4,4-difluorocyclohexyl)imidazo[1,2-b]pyridazin-2-yl]-(2,2-dimethylpiperazin-1-yl)methanone Scheme 19

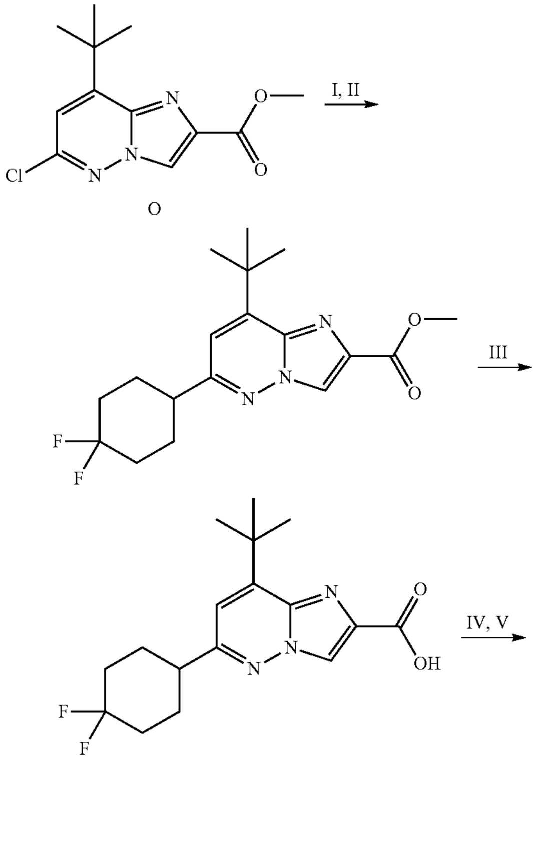

-continued

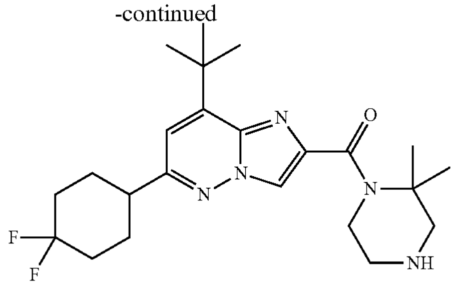

R

Step I: methyl 8-tert-butyl-6-(4,4-difluorocyclohexen-1-yl)imidazo[1,2-b]pyridazine-2-carboxylate The product was prepared according to General Procedure 5 using Intermediate 0 methyl 8-tert-butyl-6-chloro-imidazo[1,2-b]pyridazine-2-carboxylate (18 g, 67.24 mmol), dioxane (150 mL), 2-(4,4-difluorocyclohexen-1-yl)-4,4,5,5-tetramethyl-1,3,2-dioxaborolane (18 g, 73.74 mmol), $PdCl_2$(dppf)$_2$-DCM (2.7 g, 3.306 mmol) and $Na_2CO_3$ (67 mL of 2 M, 134.0 mmol) to afford methyl 8-tert-butyl-6-(4,4-difluorocyclohexen-1-yl)imidazo[1,2-b]pyridazine-2-carboxylate (20.2 g, 57.82 mmol, 85.99%) as an off-white solid.

Step II: methyl 8-tert-butyl-6-(4,4-difluorocyclohexyl)imidazo[1,2-b]pyridazine-2-carboxylate To the solution of methyl 8-tert-butyl-6-(4,4-difluorocyclohexen-1-yl)imidazo[1,2-b]pyridazine-2-carboxylate (20.2 g, 57.82 mmol) in DCM (500 mL) was added a catalytical amount of 20% $Pd(OH)_2/C$ (3 g). The mixture is hydrogenated using a $H_2$ balloon and stirred at rt overnight. The mixture was filtered on celite and the volatiles are removed under reduced pressure to obtain methyl 8-tert-butyl-6-(4,4-difluorocyclohexyl)imidazo[1,2-b]pyridazine-2-carboxylate (20.24 g, 57.60 mmol, 85.65%) as a white solid. $^1$H NMR (400 MHz, Chloroform-d) δ 8.35 (s, 1H), 6.76 (s, 1H), 3.95 (s, 3H), 2.82 (ddt, J=11.2, 7.6, 3.6 Hz, 1H), 2.41-2.17 (m, 2H), 2.12-1.77 (m, 6H), 1.58 (s, 9H).

Step III: 8-tert-butyl-6-(4,4-difluorocyclohexyl)imidazo[1,2-b]pyridazine-2-carboxylic acid The product was prepared according to General Procedure 4 using methyl 8-tert-butyl-6-(4,4-difluorocyclohexyl)imidazo[1,2-b]pyridazine-2-carboxylate (20.24 g, 57.60 mmol) in water (20 mL)/THF (40 mL)/MeOH (40 mL) and LiOH (Water (1)) (4.23 g, 100.8 mmol) at 60° C. for 2 h to obtain 8-(tert-butyl)-6-(4,4-difluorocyclohexyl)imidazo[1,2-b]pyridazine-2-carboxylic (19 g, 56.32 mmol, 83.77%) as an off-white sold. 1H NMR (400 MHz, Chloroform-d) δ 8.41 (s, 1H), 6.83 (s, 1H), 2.85 (tt, J=11.2, 3.6 Hz, 1H), 2.44-2.20 (m, 2H), 2.12-1.78 (m, 6H), 1.56 (s, 9H).

Step IV: tert-butyl 4-[8-tert-butyl-6-(4,4-difluorocyclohexyl)imidazo[1,2-b]pyridazine-2-carbonyl]-3,3-dimethyl-piperazine-1-carboxylate The product was prepared according to General Procedure 1 using 8-tert-butyl-6-(4,4-difluorocyclohexyl)imidazo[1,2-b]pyridazine-2-carboxylic acid (500 mg, 1.482 mmol), DMF (10 mL), HATU (845.3 mg, 2.223 mmol), Hünig's base (775 μL, 4.449 mmol) and tert-butyl 3,3-dimethylpiperazine-1- carboxylate (476.4 mg, 2.223 mmol Purification by flash chromatography on silica gel was carried out under standard condition to afford title compound tert-butyl 4-[8-tert-butyl-6-(4,4-difluorocyclohexyl)imidazo[1,2-b]pyridazine-2-carbonyl]-3,3-dimethyl-piperazine-1-carboxylate (766 mg, 1.435 mmol, 96.85%) as a white solid. $^1$H NMR (400 MHz, Chloroform-d) δ 8.23 (s, 1H), 6.72 (s, 1H), 4.31 (t, J=6.3 Hz, 2H), 3.68-3.34 (m, 4H), 2.81 (t, J=10.9 Hz, 1H), 2.24 (dt, J=12.3, 7.2 Hz, 2H), 2.12-1.72 (m, 6H), 1.59 (s, 6H), 1.52 (t, J=1.9 Hz, 9H), 1.47 (d, J=1.7 Hz, 9H). LC-MS: 534.26 (M+H$^+$).

Step V: [8-tert-butyl-6-(4,4-difluorocyclohexyl)imidazo[1,2-b]pyridazin-2-yl]-(2,2-dimethylpiperazin-1-yl)methanone (Intermediate R)

The product was prepared according to General Procedure 2 using 4-[8-tert-butyl-6-(4,4-difluorocyclohexyl)imidazo[1,2-b]pyridazine-2-carbonyl]-3,3-dimethyl-piperazine-1-carboxylate (766 mg, 1.435 mmol), DCM (3 mL) and 4M HCl/dioxane (1.5 mL of 4 M, 6.000 mmol) to obtain [8-tert-butyl-6-(4,4-difluorocyclohexyl)imidazo[1,2-b]pyridazin-2-yl]-(2,2-dimethylpiperazin-1-yl)methanone (Hydrochloric Acid (1)) (650 mg, 1.383 mmol, 96.38%) as an off-white solid. $^1$H NMR (400 MHz, Methanol-d4) δ 8.49 (s, 1H), 7.26 (s, 1H), 4.37-4.05 (m, 2H), 3.56-3.39 (m, 2H), 3.32 (s, 2H), 3.17-2.86 (m, 1H), 2.35-1.79 (m, 8H), 1.70 (s, 6H), 1.56 (s, 9H).

Example 1 (I-6): Azepan-1-yl-[6-(4-fluorophenyl)-8-methyl-imidazo[1,2-b]pyridazin-2-yl]methanone I-6

Scheme 20

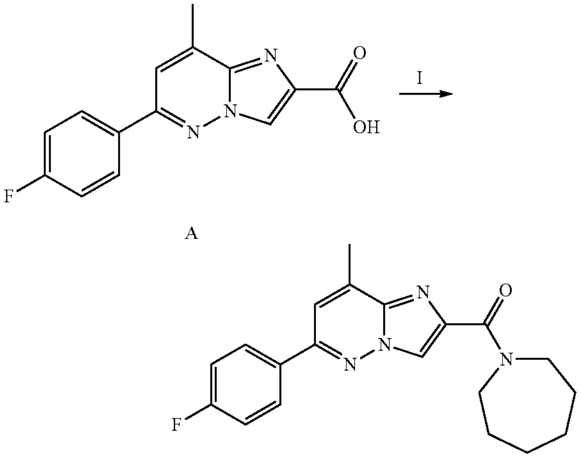

To a solution of Intermediate A (15 mg, 0.055 mmol) in DMF (2 mL) was added HATU (31.5 mg, 0.083 mmol) and azepane (5.48 mg, 6.2 μL, 0.055 mmol). The resulting mixture was stirred at rt for 2 h. The volatiles were removed under reduced pressure and the resulting residue was purified by flash chromatography eluting with EtOAc/hexanes 0-50% in 20 CV to provide azepan-1-yl-[6-(4-fluorophenyl)-8-methyl-imidazo[1,2-b]pyridazin-2-yl]methanone (11 mg, 49% yield). $^1$H NMR (400 MHz, $CDCl_3$) δ 8.36 (s, 1H), 8.06-7.86 (m, 2H), 7.28 (d, 1H), 7.24-7.15 (m, 2H), 4.05 (t, 2H), 3.78-3.48 (m, 2H), 2.70 (d, 3H), 2.00-1.80 (m, 4H), 1.64 (m, 4H); LC-MS: 353.3 (M+H$^+$), retention time: 3.94 minutes using Method B.

Example 2 (I-7): Azepan-1-yl-[6-(4-fluorophenyl)-8-(trifluoromethyl)imidazo[1,2-b]pyridazine-2-yl]methanone I-7

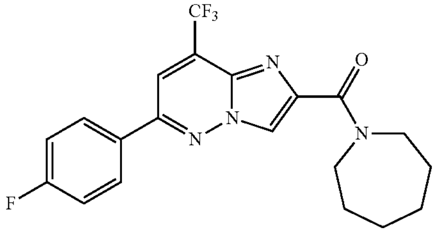 [SMILES: O=C(c1cn2nc(-c3ccc(F)cc3)cc(C(F)(F)F)c2n1)N1CCCCCC1]

The title compound (21 mg) was prepared following a similar procedure as described for example 1 in Scheme 16 using Intermediate B (20 mg) and the corresponding amine (27.7 μL). $^1$H NMR (400 MHz, $CDCl_3$) δ 8.57 (s, 1H), 8.16-7.88 (m, 2H), 7.73 (d, 1H), 7.24 (d, 2H), 4.21-4.01 (m, 2H), 3.85-3.69 (m, 2H), 1.87 (m, 4H), 1.76-1.58 (m, 4H); LC-MS: 407.3 (M+H$^+$), retention time: 4.49 minutes using Method A.

Example 3 (I-8): (S)-Benzyl 4-(6-(4-fluorophenyl)-8-methylimidazo[1,2-b]pyridazine-2-carbonyl)-2-methylpiperazine-1-carboxylate I-8

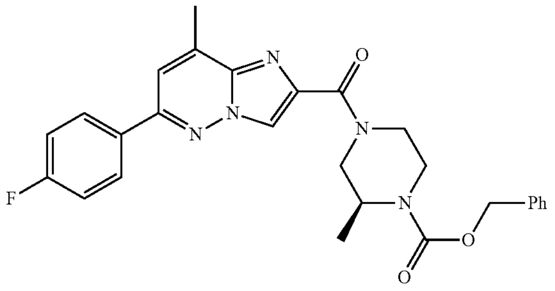 [SMILES: Cc1cc(-c2ccc(F)cc2)nn2cc(C(=O)N3CCN(C(=O)OCc4ccccc4)[C@@H](C)C3)nc12]

The title compound (18 mg) was prepared following a similar procedure as described for Example 1 in Scheme 16 using Intermediate A (16 mg) and the corresponding amine (20.7 mg). $^1$H NMR (400 MHz, $CDCl_3$) δ 8.46 (s, 1H), 8.08-7.88 (m, 2H), 7.51-7.29 (m, 6H), 7.24-7.08 (m, 2H), 5.36 (d, 1H), 5.17 (d, 2H), 4.83-4.31 (m, 2H), 4.04 (s, 1H), 3.41 (d, 2H), 3.03 (d, 1H), 2.69 (s, 3H), 1.26 (d, 3H). LC-MS: 489.4 (M+H$^+$), retention time: 4.36 minutes using Method A.

Example 4 (I-9): (R)-1-((S)-4-(6-(4-Fluorophenyl)-8-methylimidazo[1,2-b]pyridazine-2-carbonyl)-2-methylpiperazin-1-yl)-2-hydroxy-4,4-dimethylpentan-1-one I-9

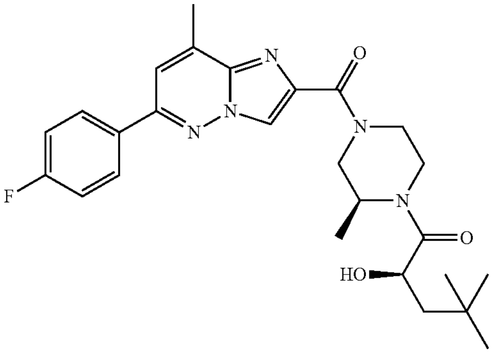 [SMILES: Cc1cc(-c2ccc(F)cc2)nn2cc(C(=O)N3CCN(C(=O)[C@H](O)CC(C)(C)C)[C@@H](C)C3)nc12]

The title compound (16 mg) was prepared using a similar procedure as described for Example 1 in Scheme 16 using Intermediate J (25 mg) and the corresponding amine (31.6 mg).

$^1H$ NMR (400 MHz, $CD_3OD$) δ 8.48 (s, 1H), 8.20-7.97 (m, 2H), 7.65 (d, 1H), 7.38-7.15 (m, 2H), 5.02 (s, 1H), 4.78-4.21 (m, 3H), 4.05-3.42 (m, 2H), 3.25-3.04 (m, 2H), 2.69 (d, 3H), 1.34-1.13 (m, 3H), 1.09-0.94 (m, 10H), 0.90-0.77 (m, 1H). LC-MS: 482.1 ($M+H^+$), retention time: 3.94 minutes using Method A.

Example 5 (I-10): (3R,4R)-Methyl 1-(6-(4-fluorophenyl)-8-methylimidazo[1,2-b]pyridazine-2-carbonyl)-3-methylpiperidine-4-carboxylate I-10

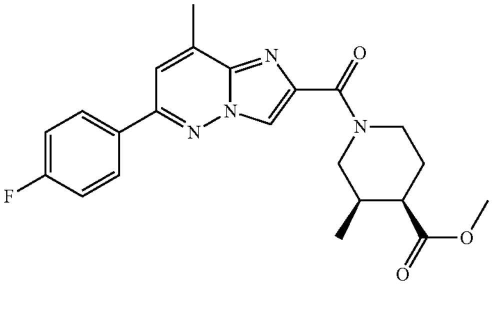 [SMILES: COC(=O)[C@@H]1CCN(C(=O)c2cn3nc(-c4ccc(F)cc4)cc(C)c3n2)C[C@@H]1C]

The title compound (4 mg) was prepared following a similar procedure as described for Example 1 in Scheme 16 using Intermediate A (20 mg) and the corresponding amine (21.4 mg). $^1H$ NMR (400 MHz, $CDCl_3$) δ 8.37 (s, 1H), 8.05-7.90 (m, 2H), 7.34 (d, 1H), 7.25-7.12 (m, 2H), 4.74 (m, 1H), 4.37 (d, 1H), 3.71 (m, 4H), 3.34 (d, 1H), 2.78 (s, 1H), 2.71 (d, 3H), 2.35 (s, 1H), 1.94 (m, 2H), 0.97 (d, 3H). LC-MS: 411.3 ($M+H^+$), retention time: 3.58 minutes using Method A.

Example 6 (I-11): 2-Pyridylmethyl (2S)-4-[6-(4-fluorophenyl)-8-(trifluoromethyl)-imidazo-[1,2-b]pyridazine-2-carbonyl]-2-methyl-piperazine-1-carboxylate I-11

Scheme 21

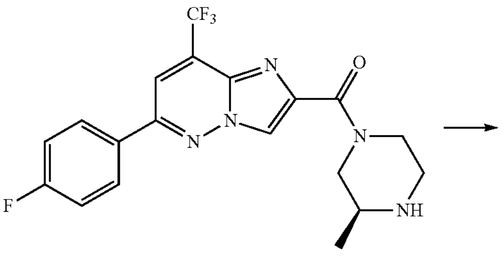

I

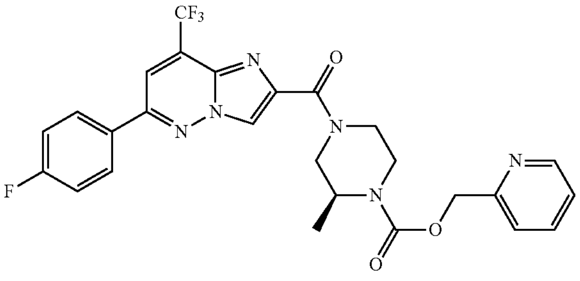

To a solution of 2-pyridylmethanol (10.7 mg, 0.096 mmol) in DCM (2 mL) was added di(imidazol-1-yl)methanone (15.6 mg, 0.096 mmol). The mixture was stirred at rt until the disappearance of 2-pyridylmethanol was observed. Then Intermediate I (TFA salt) (50 mg, 0.096 mmol) and DIPEA (37.2 mg, 50 μL, 0.2882 mmol) were added to the reaction mixture. The resulting mixture is heated to 60° C. under nitrogen for 2 days. After removal of the solvent under reduced pressure, the residue was purified by flash chromatography eluting with MeOH/DCM 0-8% in 20 CV to obtain a mixture, which was further purified using reverse phase HPLC to provide 2-pyridylmethyl (2S)-4-[6-(4-fluorophenyl)-8-(trifluoromethyl)imidazo[1,2-b]pyridazine-2-carbonyl]-2-methyl-piperazine-1-carboxylate (4 mg). $^1H$ NMR (400 MHz, $CD_3OD$) δ 8.60 (s, 1H), 8.43 (m, 1H), 8.17-8.01 (m, 3H), 7.78 (m, 1H), 7.40 (d, 1H), 7.33-7.10 (m, 3H), 5.15 (s, 2H), 5.05 (d, 1H), 4.60-4.21 (m, 2H), 3.97 (d, 1H), 3.53 (d, 1H), 3.43-3.25 (m, 1H), 3.17-2.85 (m, 1H), 1.18 (d, 3H). LC-MS: 543.3 ($M+H^+$), retention time: 3.58 minutes using Method A.

Example 7 (I-12): 3-Pyridylmethyl (2S)-4-[6-(4-fluorophenyl)-8-(trifluoromethyl)-imidazo-[1,2-b]pyridazine-2-carbonyl]-2-methyl-piperazine-1-carboxylate I-12

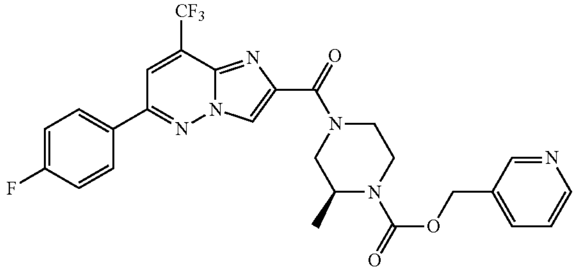 [SMILES: C[C@H]1CN(C(=O)c2cn3nc(-c4ccc(F)cc4)cc(C(F)(F)F)c3n2)CCN1C(=O)OCc1cccnc1]

The title compound (2 mg) was prepared following a similar procedure as described for example 6 in Scheme 17 using Intermediate I (50 mg) and the corresponding 3-pyridylmethanol. $^1$H NMR (400 MHz, $CDCl_3$) δ 8.71-8.62 (m, 2H), 8.60 (m, 1H), 8.04-7.95 (m, 2H), 7.83-7.66 (m, 2H), 7.32 (m, 1H), 7.28 (d, 1H), 7.24 (d, 1H), 5.44 (d, 1H), 5.25-5.14 (m, 2H), 4.74-4.38 (m, 2H), 4.05 (s, 1H), 3.57-2.84 (m, 3H), 1.27 (d, 3H). LC-MS: 543.4 (M+H$^+$), retention time: 3.25 minutes using Method A.

Example 8 (I-13): (2R)-1-[(2S)-4-[6-(4-Fluorophenyl)imidazo[1,2-b]pyridazine-2-carbonyl]-2-methyl-piperazin-1-yl]-2-hydroxy-4,4-dimethyl-pentan-1-one I-13

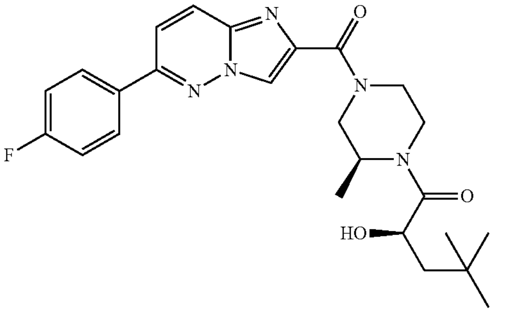 [SMILES: C[C@H]1CN(C(=O)c2cn3nc(-c4ccc(F)cc4)ccc3n2)CCN1C(=O)[C@H](O)CC(C)(C)C]

The title compound (17 mg) was prepared using a similar procedure as described for example 1 in Scheme 16 using Intermediate G (20 mg) and the corresponding amine (25 mg). $^1$H NMR (400 MHz, $CD_3OD$) δ 8.59 (s, 1H), 8.32-8.08 (m, 3H), 7.90 (d, 1H), 7.41-7.23 (m, 2H), 4.92 (s, 1H), 4.47 (d, 3H), 4.09-3.39 (m, 2H), 3.28-2.95 (m, 2H), 1.71-1.15 (m, 5H), 1.03 (s, 9H). LC-MS: 469.45 (M+H$^+$), retention time: 3.61 minutes using Method A.

Example 9 (I-14): (2R)-1-[(2S)-4-[8-Cylopropyl-6-(4-fluorophenyl)imidazo[1,2-b]pyridazine-2-carbonyl]-2-methyl-piperazin-1-yl]-2-hydroxy-4,4-dimethyl-pentan-1-one I-14

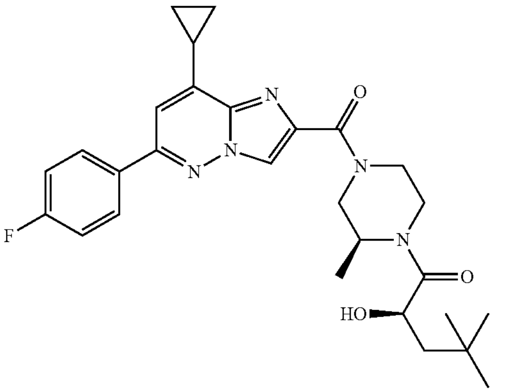 [SMILES: C[C@H]1CN(C(=O)c2cn3nc(-c4ccc(F)cc4)cc(C4CC4)c3n2)CCN1C(=O)[C@H](O)CC(C)(C)C]

The title compound (19 mg) was prepared following a similar procedure as described for example 1 in Scheme 16 using Intermediate F (17 mg) and the corresponding amine (15.7 mg). $^1$H NMR (400 MHz, $CDCl_3$) δ 8.46 (s, 1H), 8.05-7.75 (m, 2H), 7.21-7.10 (m, 2H), 7.02 (d, 1H), 5.52 (s, 1H), 5.01-4.35 (m, 3H), 3.79-2.82 (m, 5H), 2.49 (d, 1H), 1.36-1.21 (m, 7H), 1.07-0.93 (m, 11H). LC-MS: 508.2 (M+H$^+$), retention time: 4.39 minutes using Method A.

Example 10 (I-15) and 11 (I-16): tert-Butyl N-[(1R)-1-(cyclohexylmethyl)-2-[(2S)-4-[6-(4-fluorophenyl)-8-(trifluoromethyl)imidazo[1,2-b]pyridazine-2-carbonyl]-2-methyl-piperazin-1-yl]-2-oxo-ethyl]carbamate (I-15) and (2R)-2-amino-3-cyclohexyl-1-[(2S)-4-[6-(4-fluorophenyl)-8-(trifluoromethyl)imidazo[1,2-b]pyridazine-2-carbonyl]-2-methyl-piperazin-1-yl]propan-1-one (I-16)

Scheme 22

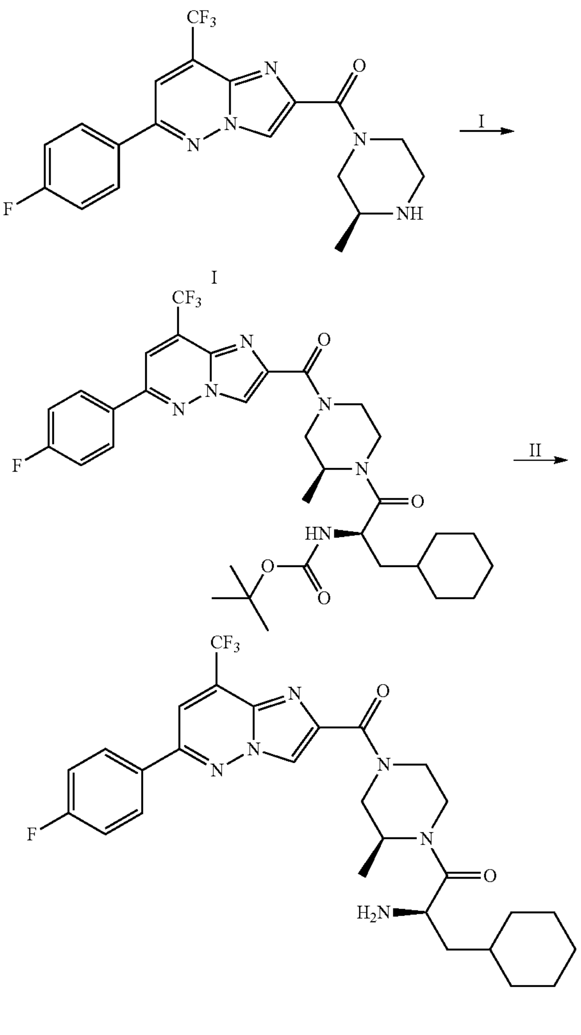

Step I (I-15): tert-Butyl N-[(1R)-1-(cyclohexylmethyl)-2-[(2S)-4-[6-(4-fluorophenyl)-8-(trifluoromethyl)imidazo[1,2-b]pyridazine-2-carbonyl]-2-methyl-piperazin-1-yl]-2-oxo-ethyl]carbamate To a solution of Intermediate I (20 mg, 0.045 mmol) in DMF (2 mL) were added (2R)-2-(tert-butoxycarbonylamino)-3-cyclohexyl-propanoic acid (14.7 mg, 0.054 mmol), HATU (25.7 mg, 0.068 mmol) and DIPEA (23.3 mg, 31 μL, 0.18 mmol). The mixture was then stirred at rt ON.

After removal of the solvent under reduced pressure, the residue was purified by flash chromatography eluting with EtOAc/hexanes 0-50% in 20 CV to yield the title compound tert-butyl N-[(1R)-1-(cyclohexylmethyl)-2-[(2S)-4-[6-(4-fluorophenyl)-8-(trifluoromethyl)-imidazo [1,2-b] pyridazine-2-carbonyl]-2-methyl-piperazin-1-yl]-2-oxo-ethyl]carbamate (26 mg) as a white solid. $^1$H NMR (400 MHz, $CDCl_3$) δ 8.62 (d, 1H), 8.11-7.86 (m, 2H), 7.76 (s, 1H), 7.22 (s, 2H), 5.62-5.36 (m, 1H), 5.20 (m, 1H), 5.02-4.34 (m, 3H), 3.98-2.71 (m, 3H), 1.93 (s, 1H), 1.74-1.60 (m, 4H), 1.51-1.32 (m, 14H), 1.29-1.09 (m, 6H). LC-MS: 661.5 ($M+H^+$), retention time: 5.39 minutes using Method A.

Step II (I-16): (2R)-2-Amino-3-cyclohexyl-1-[(2S)-4-[6-(4-fluorophenyl)-8-(trifluoro-methyl)imidazo[1,2-b]pyridazine-2-carbonyl]-2-methyl-piperazin-1-yl]propan-1-one To a solution of tert-butyl N-[(1R)-1-(cyclohexylmethyl)-2-[(2S)-4-[6-(4-fluoro phenyl)-8-(trifluoromethyl)imidazo [1,2-b]pidazine-2-carbonyl]-2-methyl-piperazin-1-yl]-2-oxo-ethyl]carbamate (20 mg) in DCM (1 mL) was added TFA (0.5 mL, 6.5 mmol) and the mixture was subsequently stirred at rt for 2 h. The volatiles were then removed under reduced pressure to yield the title compound (2R)-2-amino-3-cyclohexyl-1-[(2S)-4-[6-(4-fluorophenyl)-8-(trifluoromethyl)imidazo[1,2-b]pyridazine-2-carbonyl]-2-methyl-piperazin-1-yl]propan-1-one (trifluoroacetic acid salt) (20 mg). $^1$H NMR (400 MHz, $CD_3OD$) δ 8.71 (s, 1H), 8.18 (m, 3H), 7.42-7.17 (m, 2H), 5.16 (d, 1H), 4.54 (d, 2H), 4.22 (d, 1H), 3.90-3.49 (m, 2H), 3.22-2.99 (m, 1H), 2.02-1.54 (m, 8H), 1.36-1.21 (m, 6H), 1.02 (s, 2H); LC-MS: 562.5 ($M+H^+$), retention time: 3.67 minutes using Method A.

Example 12 (I-17): 1-[(2S)-4-[6-(4-Fluorophenyl)-8-isopropyl-imidazo[1,2-b]pyridazine-2-carbonyl]-2-methyl-piperazin-1-yl]prop-2-en-1-one I-17

Scheme 23

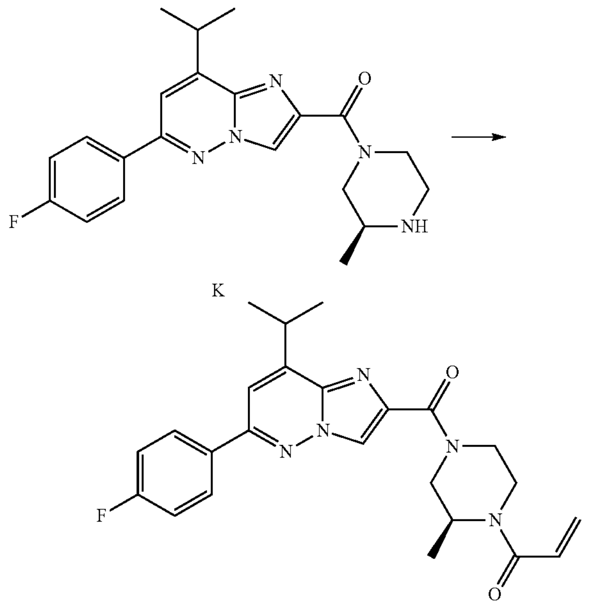

K

To a solution of Intermediate K (32 mg, 0.077 mmol) in dichloromethane (2 mL) was added DIPEA (30 mg, 40 μL, 0.23 mmol) and prop-2-enoyl chloride (10.4 mg, 9.3 μL, 0.11 mmol) at 0° C. The mixture was then slowly warmed to rt and stirred ON. The volatiles were removed under reduced pressure and the residue was purified by flash chromatography eluting with EtOAc/Hexanes 0-100% in 20 CV to provide 1-[(2S)-4-[6-(4-fluorophenyl)-8-isopropyl-imidazo [1,2-b]pyridazine-2-carbonyl]-2-methyl-piperazin-1-yl]prop-2-en-1-one (27 mg). $^1$H NMR (400 MHz, $CDCl_3$) δ 8.48 (s, 1H), 8.02-7.81 (m, 2H), 7.27 (d, 1H), 7.23-7.17 (m, 2H), 6.59 (m, 1H), 6.33 (d, 1H), 5.73 (m, 1H), 5.51 (s, 1H), 5.10-4.04 (m, 3H), 3.61-2.90 (m, 4H), 1.48-1.45 (m, 6H), 1.30 (d, 3H). LC-MS: 436.2 ($M+H^+$), retention time: 3.73 minutes using Method A.

Example 13 (I-19): [6-(4-Fluorophenyl)-8-isopropyl-imidazo[1,2-b]pyridazin-2-yl]-[4-(1-hydroxycyclobutanecarbonyl)-2,2-dimethyl-piperazin-1-yl]methanone Step I: 6-Chloro-4-isopropenyl-pyridazin-3-amine Scheme 24

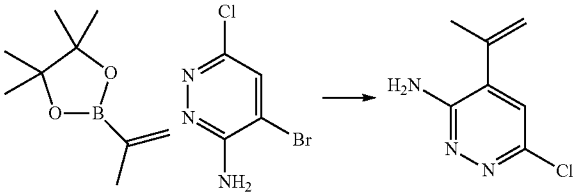

4-Bromo-6-chloro-pyridazin-3-amine (10 g, 48 mmol) was dissolved in tetrahydrofuran (240 mL) and treated with $Na_2CO_3$ (72 mL of a 2 M aqueous solution, 144 mmol). The reaction mixture was degassed with nitrogen for 5 min and then 2-isopropenyl-4,4,5,5-tetramethyl-1,3,2-dioxaborolane (8.5 g, 9.5 mL, 50.4 mmol) was added followed by $Pd(PPh_3)_4$ (5.5 g, 4.8 mmol). The reaction mixture was stirred at 80° C. ON. At this time HCl (2N) was added until the pH of the solution reaches 1. The aqueous layer was washed 3 times with ethyl acetate. Sodium hydroxide pellets was added to the aqueous layer at 0° C. until pH of the solution was basic and then the solution was extracted with ethyl acetate (4 times). The combined organic layers were dried over anhydrous sodium sulfate, filtered and concentrated under vacuum to afford a dark solid.

In addition, a precipitate formed in the aqueous phase from above and this was filtered, the aqueous layer was washed with ethyl acetate, neutralized with sodium hydroxide pellets and extracted 3 times with ethyl acetate. The combined last 3 extracts were dried over sodium sulfate, filtered, concentrated under vacuum and combined to the first dark solid. The combined materials were dissolved in a minimum volume of methanol and water was added. A dark precipitate form and the mixture was stirred in an ice-bath ON before filtering on Büchner funnel to afford the title compound (5.92 g, 72% yield) as a solid. $^1$H NMR (400 MHz, Chloroform-d) δ 7.04 (s, 1H), 5.50-5.42 (m, 1H), 5.34-5.27 (m, 1H), 4.99 (s, 2H), 2.10-2.06 (m, 3H). LCMS: m/z=170.39 ($M+H^+$)

Step II: Methyl 6-chloro-8-isopropenyl-imidazo[1,2-b]pyridazine-2-carboxylate

Scheme 25

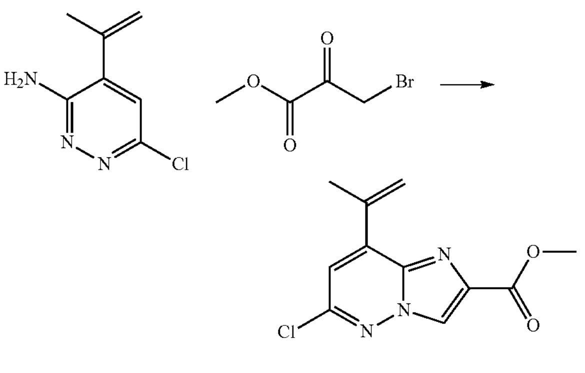

To a solution of 6-chloro-4-isopropenyl-pyridazin-3-amine (2.57 g, 15.2 mmol) in N,N-dimethylformamide (38 mL) was added methyl 3-bromo-2-oxo-propanoate (5.5 g, 3.2 mL, 30.3 mmol). The reaction mixture was heated at 75° C. for 3 h. At this time, ice was added to the mixture which was then stirred until a precipitate was formed. The solid was filtered on a Büchner funnel, rinsed with cold water and dried under vacuum over the weekend to afford the desired product as a dark solid (2.74 g, 72% yield). $^1H$ NMR (400 MHz, Chloroform-d) δ 8.43 (s, 1H), 7.03 (s, 1H), 6.97 (s, 1H), 5.86-5.82 (m, 1H), 3.98 (s, 3H), 2.27 (dd, J=1.4, 0.8 Hz, 3H).

LCMS: m/z=252.05 ($M+H^+$)

Step III: Methyl 6-chloro-8-isopropyl-imidazo[1,2-b]pyridazine-2-carboxylate

Scheme 26

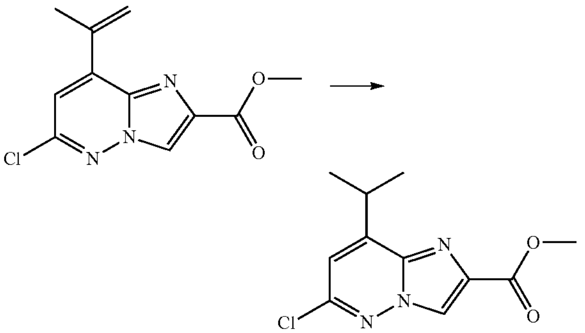

Methyl 6-chloro-8-isopropenyl-imidazo[1,2-b]pyridazine-2-carboxylate (2.74 g, 10.5 mmol) was dissolved in methanol (70 mL) and the resulting solution was degassed with nitrogen for 5 min. Then, $PtO_2$ (118.8 mg, 0.5230 mmol) was added to the reaction mixture and allowed to vigorously stir under a 1 atmosphere of $H_2$ (ballon) for 3 h. Upon completion, the reaction mixture was degassed with nitrogen for several min. The mixture was diluted with dichloromethane and Celite was then added. The resulting mixture was filtered over a pad of Celite and the residue was rinsed with methanol and dichloromethane. The filtrate was concentrated under vacuum and it was taken up in ethyl acetate and water. The layers were separated and the aqueous layer was extracted with ethyl acetate (3 times). The combined organic layers were dried over anhydrous sodium sulfate, filtered and concentrated under vacuum to the yield the title compound (2.4 g, 90% yield). $^1H$ NMR (400 MHz, Chloroform-d) δ 8.42 (s, 1H), 6.95 (d, J=0.8 Hz, 1H), 3.99 (s, 3H), 3.89-3.76 (m, 1H), 1.40 (d, J=6.9 Hz, 6H).

LCMS: m/z=254.24 ($M+H^+$)

Step IV: 6-Chloro-8-isopropyl-imidazo[1,2-b]pyridazine-2-carboxylic acid

Scheme 27

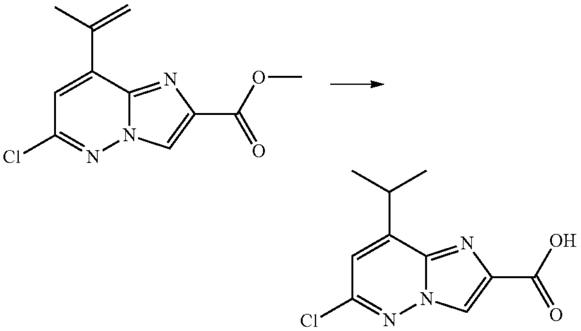

To a solution at 0° C. of methyl 6-chloro-8-isopropyl-imidazo[1,2-b]pyridazine-2-carboxylate (2.4 g, 9.5 mmol) in tetrahydrofuran (35.5 mL) and water (12 mL) was added lithium hydroxide (475.8 mg, 19.87 mmol) in one portion. The reaction mixture was allowed to warm up to r. t. and to stir for 1 hour. Upon completion, ethyl acetate and 1N HCl were added to the solution. The layers were partitioned and the aqueous layer was extracted twice using ethyl acetate. The combined organic extracts were dried over sodium sulfate, filtered and concentrated under vacuum to afford the title compound (2.27 g, quantitative). LCMS: m/z=241.21 ($M+H^+$)

Step V (I-18): tert-Butyl 4-(6-chloro-8-isopropyl-imidazo[1,2-b]pyridazine-2-carbonyl)-3,3-dimethyl-piperazine-1-carboxylate Scheme 28

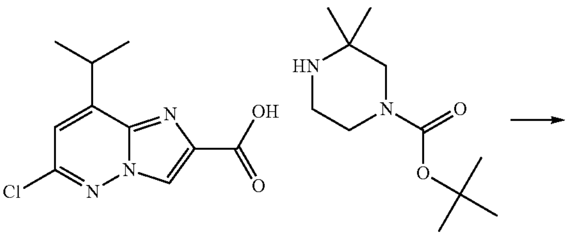

-continued

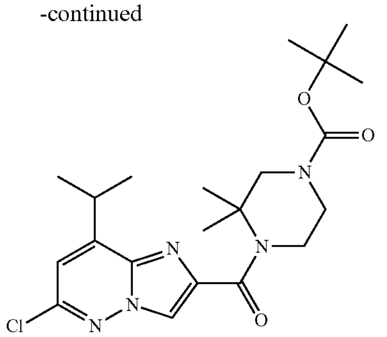

6-Chloro-8-isopropyl-imidazo[1,2-b]pyridazine-2-carboxylic acid (2.3 g, 9.5 mmol) was solubilized in N,N-dimethylformamide (37.8 mL) and DIPEA (3.06 g, 4.12 mL, 23.65 mmol). HATU (3.95 g, 10.4 mmol) was added followed by tert-butyl 3,3-dimethylpiperazine-1-carboxylate (2.23 g, 10.4 mmol). The solution was allowed to stir for 1 hour. Upon completion, a saturated aqueous solution of $NH_4Cl$ was added to the reaction mixture. The layers were partitioned and the aqueous layer was extracted 3 times with ethyl acetate. The combined organic layers were washed with brine, dried over anhydrous sodium sulfate, filtered and concentrated under vacuum. The crude product was purified by flash chromatography using 0-100% ethyl acetate: hexanes to afford the title compound (2.13 g, 51% yield). $^1H$ NMR (400 MHz, Chloroform-d) δ 8.27 (s, 1H), 6.89 (s, 1H), 4.31-4.17 (m, 2H), 3.67-3.45 (m, 5H), 1.63-1.58 (m, 6H), 1.51-1.46 (m, 9H), 1.44-1.37 (m, 6H). LCMS: m/z=436.45 ($M+H^+$)

Step VI: (6-Chloro-8-isopropyl-imidazo[1,2-b]pyridazine-2-yl)-(2,2-dimethylpiperazin-1-yl)methanone Scheme 29

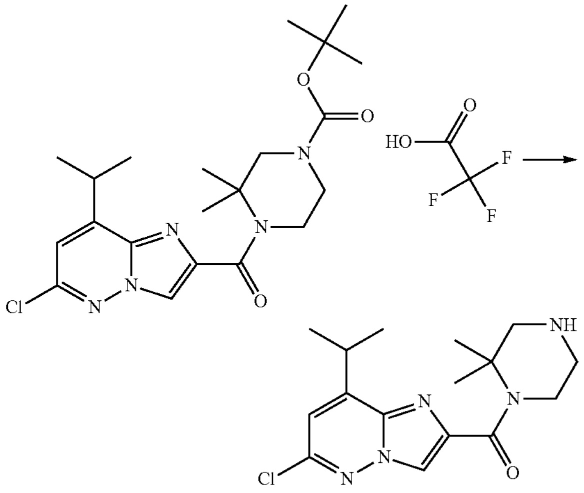

tert-Butyl 4-(6-chloro-8-isopropyl-imidazo[1,2-b]pyridazine-2-carbonyl)-3,3-dimethyl-piperazine-1-carboxylate (1 g, 2.29 mmol) was dissolved in dichloromethane (3 mL) and TFA (3 mL, 38.94 mmol) at r. t. The resulting solution was allowed to stir for 30 min. Upon completion, the reaction mixture was concentrated under vacuum. The crude product was then dissolved in dichloromethane and a saturated solution of aqueous $NaHCO_3$ was added. The solution was then stirred 15 min, the layers were partitioned and the aqueous phase was extracted 3 times with dichloromethane. The combined organic layers were dried over anhydrous sodium sulfate, filtered and concentrated under vacuum to afford the title compound (770.4 mg, 98% yield). $^1H$ NMR (400 MHz, Chloroform-d) δ 8.23 (s, 1H), 6.89 (s, 1H), 4.03-3.95 (m, 2H), 3.73-3.53 (m, 2H), 3.21-3.12 (m, 2H), 2.89 (s, 2H), 1.59 (s, 6H), 1.40 (d, J=6.9 Hz, 6H).

LCMS: m/z=336.38 ($M+H^+$)

Step VII: (6-Chloro-8-isopropyl-imidazo[1,2-b]pyridazine-2-yl)-[4-(1-hydroxycyclo-butanecarbonyl)-2,2-dimethyl-piperazin-1-yl]methanone Scheme 30

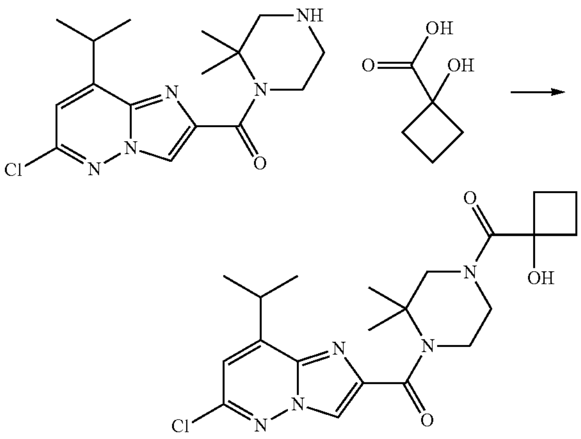

(6-Chloro-8-isopropyl-imidazo[1,2-b]pyridazin-2-yl)-(2,2-dimethylpiperazin-1-yl)methanone (740 mg, 2.2 mmol) was solubilized in N,N-dimethylformamide (11 mL) and DIPEA (711.7 mg, 959 μL, 5.51 mmol). 1-Hydroxycyclobutanecarboxylic acid (268.6 mg, 2.31 mmol) was added, followed by HATU (921.3 mg, 2.42 mmol). The resulting solution was allowed to stir for 3 h. Upon completion, dichloromethane and a saturated aqueous solution of $NaHCO_3$ were added to the reaction mixture. The layers were separated and the aqueous layer was extracted 3 times with dichloromethane. The combined organic layers were washed with brine, dried over anhydrous sodium sulfate, filtered and concentrated under vacuum. The crude product was purified by flash chromatography using 0-100% ethyl acetate: hexanes, followed by trituration with diethyl ether to afford the title compound (583 mg, 58% yield).

$^1H$ NMR (400 MHz, DMSO-$d_6$) δ 8.55 (d, J=5.0 Hz, 1H), 7.31 (s, 1H), 6.03-5.87 (m, 1H), 4.10-4.04 (m, 1H), 3.97 (t, J=5.6 Hz, 1H), 3.76 (t, J=5.6 Hz, 1H), 3.71 (s, 1H), 3.59 (s, 1H), 3.55-3.47 (m, 1H), 3.46-3.40 (m, 1H), 2.57 (ddt, J=14.0, 8.8, 4.8 Hz, 3H), 2.09-1.97 (m, 2H), 1.82-1.72 (m, 1H), 1.52-1.47 (m, 6H), 1.37 (d, 6H). LCMS: m/z=435.42 ($M+H^+$).

Step VIII (I-19): [6-(4-Fluorophenyl)-8-isopropyl-imidazo[1,2-b]pyridazin-2-yl]-[4-(1-hydroxycyclobutanecarbonyl)-2,2-dimethyl-piperazin-1-yl]methanone Scheme 31

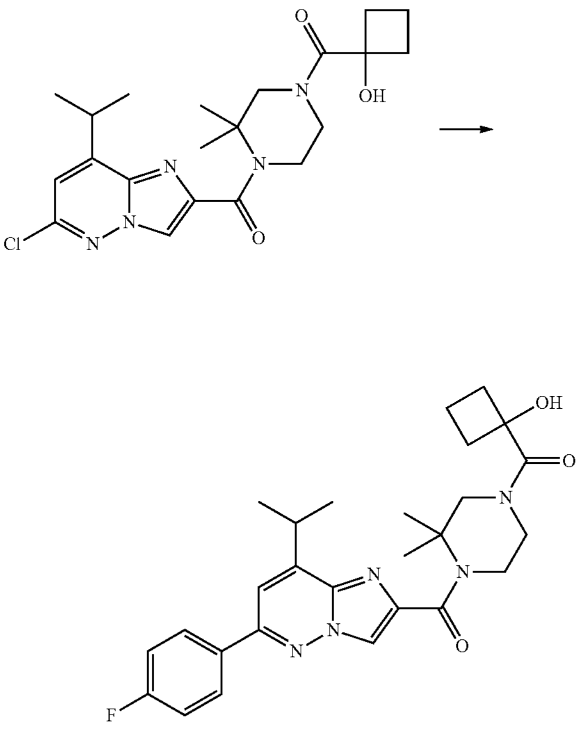

To a rbf containing a solution of (6-chloro-8-isopropyl-imidazo[1,2-b]pyridazin-2-yl)-[4-(1-hydroxycyclobutanecarbonyl)-2,2-dimethyl-piperazin-1-yl]methanone (88 mg, 0.20 mmol) in dioxane (1.6 mL) was added $Pd_2dba_3$ (1.9 mg, 0.0020 mmol) and S-Phos (3.16 mg, 0.0077 mmol). The resulting solution was degassed with nitrogen for 5 min prior to addition of aqueous $K_3PO_4$ solution (304 μL of a 2 M aqueous solution, 0.608 mmol) and 4-fluorophenylboronic acid (31.2 mg, 0.22 mmol). The solution was heated at 110° C. for 90 min. Upon completion, dichloromethane and water were added to the mixture. The layers were partitioned and the aqueous phase was extracted with dichloromethane twice. The combined organic layers were dried over anhydrous sodium sulfate, filtered and concentrated under vacuum. The crude residue obtained was purified by flash chromatography using a gradient of 0-100% ethyl acetate: hexanes to afford the title compound (51 mg, 48% yield). $^1H$ NMR (400 MHz, Chloroform-d) δ 8.36 (s, 1H), 8.00-7.89 (m, 2H), 7.26 (s, 1H), 7.25-7.17 (m, 2H), 4.48-4.24 (m, 2H), 3.97-3.58 (m, 4H), 2.85 (s, 1H), 2.83-2.68 (m, 3H), 2.22-2.10 (m, 2H), 2.00 (dtd, J=11.3, 9.6, 9.0, 5.1 Hz, 1H), 1.81-1.71 (m, 1H), 1.71-1.59 (m, 6H), 1.54-1.39 (m, 6H). LCMS: m/z=494.54 (M+H$^+$), retention time: 1.7 minutes using Method C.

Example 14 (I-20): 1-[4-[8-cyclopropyl-6-(4-fluorophenyl)imidazo[1,2-b]pyridazine-2-carbonyl]-3,3-dimethyl-piperazin-1-yl]-2-hydroxy-2-methyl-propan-1-one Step I: Methyl 8-bromo-6-chloro-imidazo[1,2-b]pyridazine-2-carboxylate Scheme 32

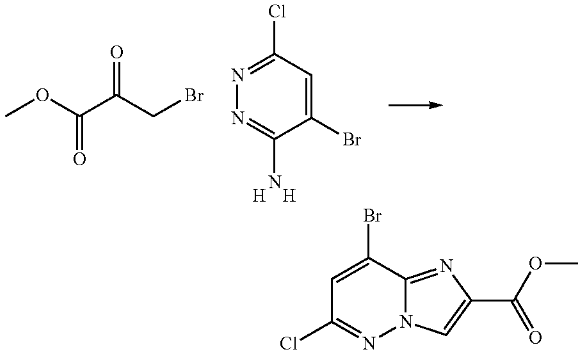

To a solution of 4-bromo-6-chloro-pyridazin-3-amine (250 mg, 1.2 mmol) in DMF (1 mL) and dimethylacetamide (2 mL) were added methyl 3-bromo-2-oxo-propanoate (347.1 mg, 1.92 mmol). The reaction mixture was heated at 70 C for 18 h. At this time, the reaction mixture was cooled, water was added along with EtOAc and the resulting phases were separated. The organic phase was dried over anhydrous $MgSO_4$, filtered and evaporated under reduced pressure. The crude reaction mixture was purified by flash chromatography using a gradient of 0 to 45% EtOAc/Hexanes in 12 CV followed by 45 to 50% EtOAc/Hexanes in 5 CV to afford methyl 8-bromo-6-chloro-imidazo[1,2-b]pyridazine-2-carboxylate (218 mg, 62% yield) as a light yellow solid. $^1H$ NMR (400 MHz, DMSO-$d_6$) δ 9.03 (s, 1H), 8.08 (s, 1H), 3.88 (s, 3H). LC-MS: m/z=291.18 (M+H$^+$).

Step II: Methyl 6-chloro-8-cyclopropyl-imidazo[1,2-b]pyridazine-2-carboxylate

Scheme 33

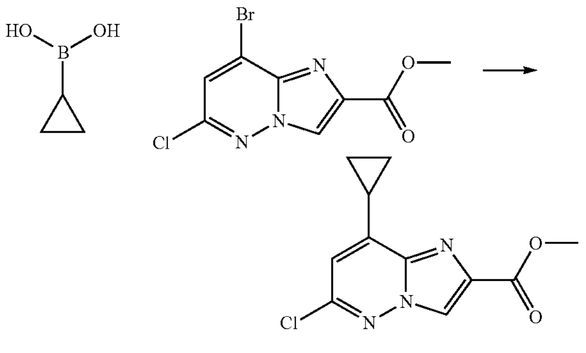

To a solution of methyl 8-bromo-6-chloro-imidazo[1,2-b]pyridazine-2-carboxylate (50 mg, 0.15 mmol) in toluene (1.463 mL) was added cyclopropylboronic acid (12.6 mg, 0.15 mmol), $Pd(PPh_3)_4$ (16.9 mg, 0.015 mmol) and $K_2CO_3$ (30.3 mg, 0.22 mmol). The mixture was degassed for 10 min and heated at 100° C. for 5 h under nitrogen. The reaction mixture was cooled and water was added along with EtOAc and the phases were separated. The aqueous phase was extracted again with EtOAc and the organic phases were combined before being dried over anhydrous $MgSO_4$, filtered and evaporated under reduced pressure. The resulting material was used in the subsequent step without further purification. LC-MS: m/z=253.28 ($M+H^+$).

Step III: Methyl 8-cyclopropyl-6-(4-fluorophenyl) imidazo[1,2-b]pyridazine-2-carboxylate Scheme 34

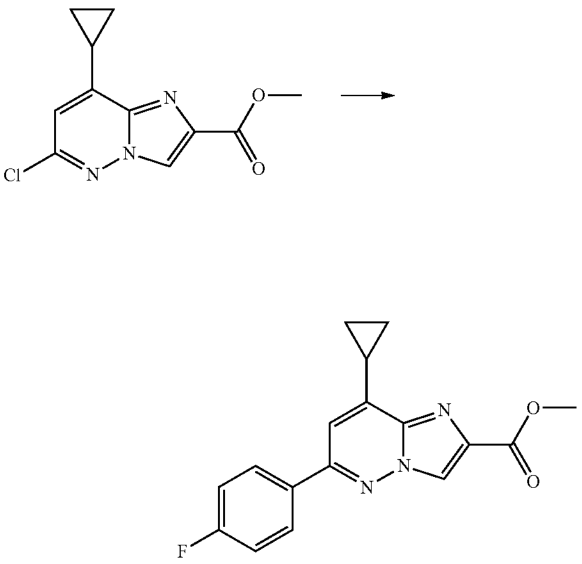

To a rbf containing a solution of methyl 6-chloro-8-cyclopropyl-imidazo[1,2-b]pyridazine-2-carboxylate (160 mg, 0.64 mmol) in dioxane (5.1 mL) was added $Pd_2dba_3$ (5.8 mg, 0.0064 mmol) and S-Phos (9.9 mg, 0.024 mmol) and the solution was degassed with nitrogen for 5 min. An aqueous solution of $K_3PO_4$ (953.5 μL of 2 M, 1.907 mmol) and 4-fluorophenylboronic acid (115.6 mg, 0.83 mmol) were added and the solution was stirred at 110° C. for 2 h. The reaction was cooled to r. t. and water was added along with EtOAc and the phases were separated. The organic phase was washed with water and dried over anhydrous $MgSO_4$, filtered and evaporated under reduced pressure. The resulting crude reaction mixture was purified by flash chromatography using a gradient of 0 to 75% EtOAc/Hexanes in 12 CV to afford methyl 8-cyclopropyl-6-(4-fluorophenyl)imidazo[1,2-b]pyridazine-2-carboxylate (85 mg, 43% yield) as a light yellow solid. $^1H$ NMR (400 MHz, DMSO-$d_6$) δ 8.84 (s, 1H), 8.20-8.10 (m, 2H), 7.46-7.35 (m, 3H), 3.88 (s, 3H), 2.58 (tt, J=8.4, 5.1 Hz, 1H), 1.44-1.36 (m, 2H), 1.30-1.21 (m, 2H). LC-MS: m/z=312.12 ($M+H^+$).

Step IV: 8-cyclopropyl-6-(4-fluorophenyl)imidazo [1,2-b]pyridazine-2-carboxylic acid Scheme 35

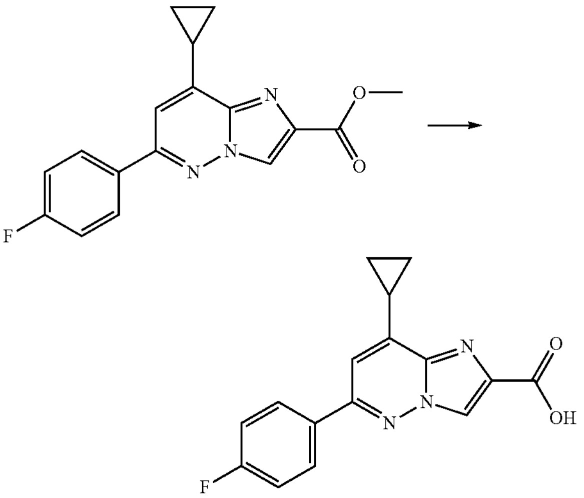

Methyl 8-cyclopropyl-6-(4-fluorophenyl)imidazo[1,2-b] pyridazine-2-carboxylate (85 mg, 0.2730 mmol) was dissolved in MeOH (4 mL) and a solution of NaOH (1.35 mL of a 2 M aqueous solution, 2.7 mmol) was added. The reaction mixture was stirred at r.t. ON. To the resulting reaction mixture was added 1 mL of a 6N HCl solution and then stirred for 1 h. MeOH was removed under vacuum and DCM was added. The resulting aqueous phase was extracted with DCM and twice with EtOAc. The combined organic phases were dried over anhydrous $MgSO_4$, filtered and evaporated under reduced pressure to afford 8-cyclopropyl-6-(4-fluorophenyl)imidazo[1,2-b]pyridazine-2-carboxylic acid (80 mg, 98% yield) as a light yellow solid. $^1H$ NMR (400 MHz, DMSO-$d_6$) δ 12.96 (s, 1H), 8.73 (s, 1H), 8.20-8.09 (m, 2H), 7.46-7.34 (m, 3H), 2.58 (tt, J=8.4, 5.1 Hz, 1H), 1.45-1.37 (m, 2H), 1.32-1.21 (m, 2H). LC-MS: m/z=298.12 ($M+H^+$).

Step V: 4-[8-cyclopropyl-6-(4-fluorophenyl)imidazo [1,2-b]pyridazine-2-carbonyl]-3,3-dimethyl-piperazine-1-carboxylate Scheme 36

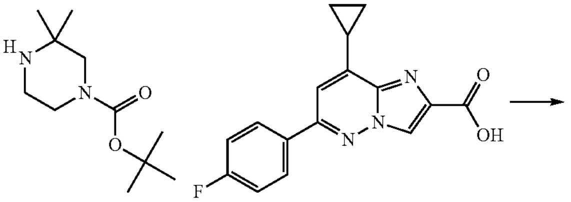

-continued

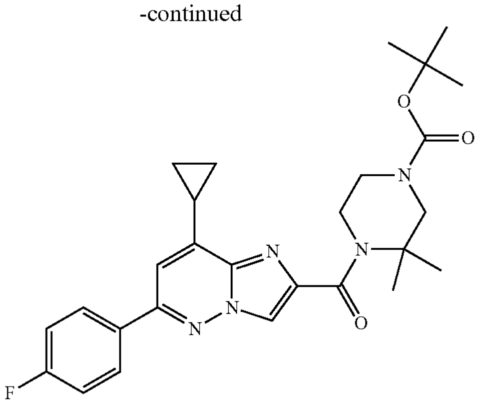

8-Cyclopropyl-6-(4-fluorophenyl)imidazo[1,2-b]pyridazine-2-carboxylic acid (80 mg, 0.27 mmol) was dissolved in DMF (3.4 mL) and DIPEA (121.7 mg, 164 μL, 0.94 mmol) followed by tert-butyl 3,3-dimethylpiperazine-1-carboxylate (69.20 mg, 0.3229 mmol) were successively added at r. t. After 2 min, HATU (153.5 mg, 0.40 mmol) was added and the reaction mixture was stirred at r.t. ON. Water was added and the reaction mixture and the mixture was extracted with EtOAc. The resulting organic phase was washed twice with a 1:1 mixture of water and brine, dried over anhydrous $MgSO_4$, filtered and evaporated under reduced pressure. The resulting crude product was used as such in the next reaction. LC-MS: m/z=494.26 ($M+H^+$).

Step VI: [8-cyclopropyl-6-(4-fluorophenyl)imidazo[1,2-b]pyridazin-2-yl]-(2,2-dimethylpiperazin-1-yl)methanone Scheme 37

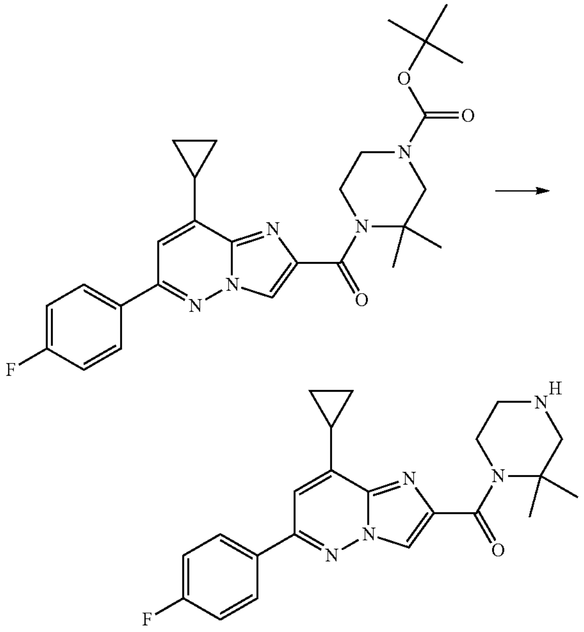

tert-Butyl 4-[8-cyclopropyl-6-(4-fluorophenyl)imidazo[1,2-b]pyridazine-2-carbonyl]-3,3-dimethyl-piperazine-1-carboxylate (132.8 mg, 0.269 mmol) was dissolved in DCM (2.5 mL) and TFA (1.0 mL, 13 mmol) was added. The reaction was then stirred at r.t. for 1 h. The volatiles were evaporated under reduced pressure and dissolved in DCM, and then a saturated aqueous $NaHCO_3$ solution was carefully added until a basic (pH) solution was obtained. The phases were separated and the organic phase was washed with saturated aqueous $NaHCO_3$. The organic phase was dried over anhydrous $MgSO_4$, filtered and evaporated under reduced pressure to afford [8-cyclopropyl-6-(4-fluorophenyl)imidazo[1,2-b]pyridazin-2-yl]-(2,2-dimethylpiperazin-1-yl)methanone (105.9 mg, quantitative yield) as a free base. This material was used in the next reaction without further purification. LC-MS: m/z=394.20 ($M+H^+$).

Step VII (I-20): 1-[4-[8-cyclopropyl-6-(4-fluorophenyl)imidazo[1,2-b]pyridazine-2-carbonyl]-3,3-dimethyl-piperazin-1-yl]-2-hydroxy-2-methyl-propan-1-one Scheme 38

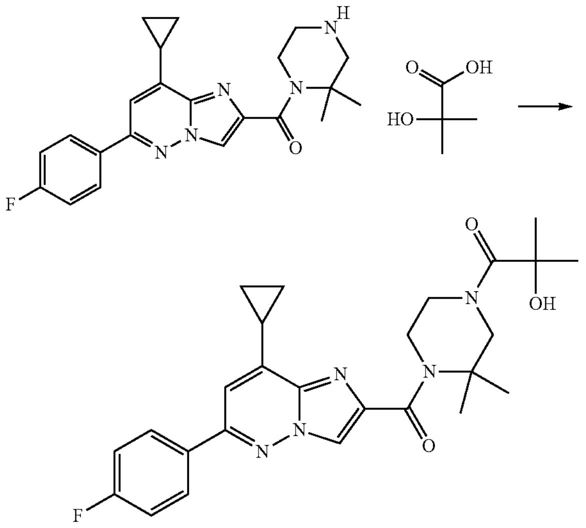

In a rbf under nitrogen was added [8-cyclopropyl-6-(4-fluorophenyl)imidazo[1,2-b]pyridazin-2-yl]-(2,2-dimethylpiperazin-1-yl)methanone (33 mg, 0.084 mmol) in DMF (1.3 mL) and DIPEA (37.9 mg, 51 μL, 0.29 mmol) followed by 2-hydroxy-2-methyl-propanoic acid (10.5 mg, 0.10 mmol) at r. t. After 2 min, HATU (47.8 mg, 0.13 mmol) was added and the reaction mixture was stirred at r.t. ON. At this time water was added and the reaction mixture and then extracted with EtOAc. The resulting organic phase was washed twice with a 1:1 mixture of water and brine, then was dried over anhydrous $MgSO_4$, filtered and evaporated under reduced pressure. The crude mixture was purified by flash chromatography eluting with 75 to 100% EtOAc/Hexanes in 12 CV. The resulting product was dissolved in ACN and water, frozen and lyophilized to give a white powder. This material was further triturated in $Et_2O$ for 2 h, filtered and dried to afford 1-[4-[8-cyclopropyl-6-(4-fluorophenyl)imidazo[1,2-b]pyridazine-2-carbonyl]-3,3-dimethyl-piperazin-1-yl]-2-hydroxy-2-methyl-propan-1-one (9.1 mg, 22% yield). $^1H$ NMR (400 MHz, DMSO-$d_6$) δ 8.51 (s, 1H), 8.14 (ddd, J=10.3, 5.3, 2.6 Hz, 2H), 7.47-7.34 (m, 3H), 5.38 (d, J=34.8 Hz, 1H), 4.10 (d, J=17.3 Hz, 4H), 3.53 (d, J=62.7 Hz, 2H), 1.60-1.40 (m, 9H), 1.35 (s, 6H), 1.29-

1.22 (m, 2H). LC-MS: m/z=480.26 (M+H+), retention time: 3.48 minutes using Method A.

Example 15 (I-21): [8-cyclopropyl-6-(4-fluorophenyl)imidazo[1,2-b]pyridazin-2-yl]-[4-(1-hydroxycyclobutanecarbonyl)-2,2-dimethyl-piperazin-1-yl] methanone Scheme 39

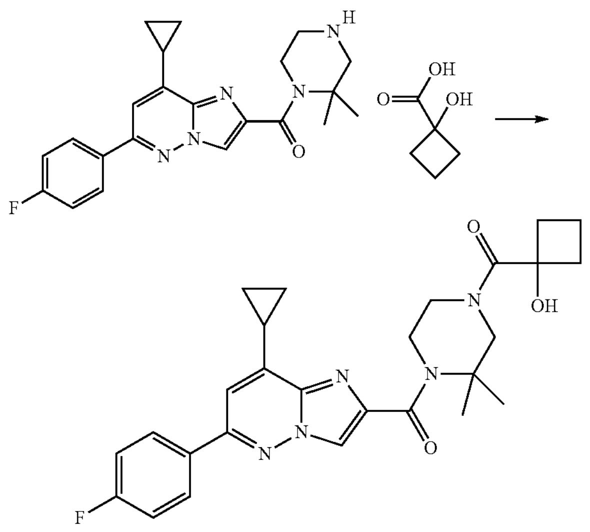

In a rbf under nitrogen, [8-cyclopropyl-6-(4-fluorophenyl)imidazo[1,2-b]pyridazin-2-yl]-(2,2-dimethylpiperazin-1-yl)methanone (33 mg, 0.084 mmol) was dissolved in DMF (1.3 mL) and DIPEA (37.9 mg, 51 μL, 0.29 mmol) followed by 1-hydroxycyclobutanecarboxylic acid (11.7 mg, 0.10 mmol) were successively added at r. t. After 2 min, HATU (48 mg, 0.13 mmol) was added and the reaction mixture was stirred at r.t. ON. Water was added and the reaction mixture was extracted with EtOAc. The resulting organic phase was washed twice with a 1:1 mixture of water and brine, then was dried over anhydrous $MgSO_4$, filtered and evaporated under reduced pressure. The resulting crude mixture was purified by flash chromatography eluting with 50 to 100% EtOAc/Hexanes in 15 CV. The isolated product was then dissolved in ACN and water, frozen and lyophilized to give a white powder which was further triturated with $Et_2O$ for 2 h, filtered dried to afford [8-cyclopropyl-6-(4-fluorophenyl)imidazo[1,2-b]pyridazin-2-yl]-[4-(1-hydroxycyclobutanecarbonyl)-2,2-dimethyl-piperazin-1-yl]methanone (17 mg, 41% yield). $^1$H NMR (400 MHz, DMSO-$d_6$) δ 8.51 (d, J=5.3 Hz, 1H), 8.19-8.09 (m, 2H), 7.45 (d, J=5.9 Hz, 1H), 7.43-7.36 (m, 2H), 5.95 (d, J=28.2 Hz, 1H), 4.10 (dt, J=38.9, 5.7 Hz, 2H), 3.78 (t, J=5.6 Hz, 1H), 3.66 (d, J=48.3 Hz, 2H), 3.50-3.44 (m, 1H), 2.63-2.51 (m, 2H), 2.11-1.98 (m, 2H), 1.83-1.71 (m, 1H), 1.51 (d, J=12.3 Hz, 6H), 1.45 (tt, J=6.2, 3.7 Hz, 2H), 1.26 (dq, J=8.4, 3.6 Hz, 2H). LC-MS: m/z=492.27 (M+H$^+$), retention time: 3.62 minutes using Method A.

Example 16 (I-22): 1-[4-[8-cyclopropyl-6-(4-fluorophenyl)imidazo[1,2-b]pyridazine-2-carbonyl]-3,3-dimethyl-piperazin-1-yl]-2-hydroxy-3-methyl-butan-1-one Scheme 40

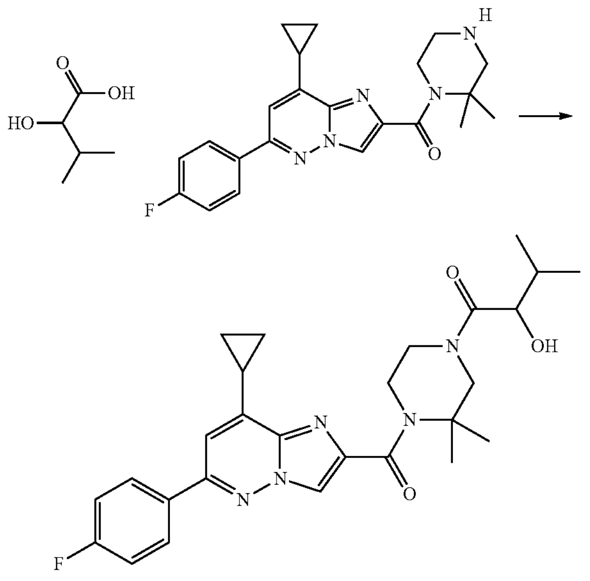

In a rbf under nitrogen, [8-cyclopropyl-6-(4-fluorophenyl)imidazo[1,2-b]pyridazin-2-yl]-(2,2-dimethylpiperazin-1-yl)methanone (33 mg, 0.084 mmol) was dissolved in DMF (1.3 mL) and DIPEA (38 mg, 52 μL, 0.29 mmol) followed by 2-hydroxy-3-methyl-butanoic acid (11.89 mg, 0.10 mmol) was successively added at r. t. After 2 min, HATU (47.8 mg, 0.13 mmol) was added and the reaction mixture was stirred at r.t. ON. Water was then added and the reaction mixture extracted with EtOAc. The resulting organic phase was washed twice with a 1:1 mixture of water and brine, then dried over anhydrous $MgSO_4$, filtered and evaporated under reduced pressure. The crude was purified by flash chromatography eluting with 40% to 90% EtOAc/Hexanes in 12 CV. The resulting product was dissolved in ACN and water, frozen and lyophilized to give a white powder which was further triturated in $Et_2O$ for 2 h, filtered and dried to afford 1-[4-[8-cyclopropyl-6-(4-fluorophenyl)imidazo[1,2-b]pyridazine-2-carbonyl]-3,3-dimethyl-piperazin-1-yl]-2-hydroxy-3-methyl-butan-1-one (10.3 mg, 24% yield). $^1$H NMR (400 MHz, DMSO-$d_6$) δ 8.52 (d, J=4.6 Hz, 1H), 8.18-8.09 (m, 2H), 7.45 (d, J=7.3 Hz, 1H), 7.39 (t, J=8.7 Hz, 2H), 4.75 (t, J=7.4 Hz, 1H), 4.29-4.17 (m, 1H), 4.15-3.95 (m, 2H), 3.86-3.40 (m, 4H), 1.92 (dt, J=13.4, 7.0 Hz, 1H), 1.60-1.40 (m, 8H), 1.25 (dd, J=8.3, 5.5 Hz, 2H), 0.96-0.79 (m, 6H). LC-MS: m/z=494.30 (M+H$^+$), retention time: 3.88 minutes using Method A.

Example 17 (I-23): tert-butyl 5-[6-(4-fluorophenyl)-8-isopropyl-imidazo[1,2-b]pyridazine-2-carbonyl]-2-oxa-5,8-diazaspiro[3.5]nonane-8-carboxylate Scheme 41

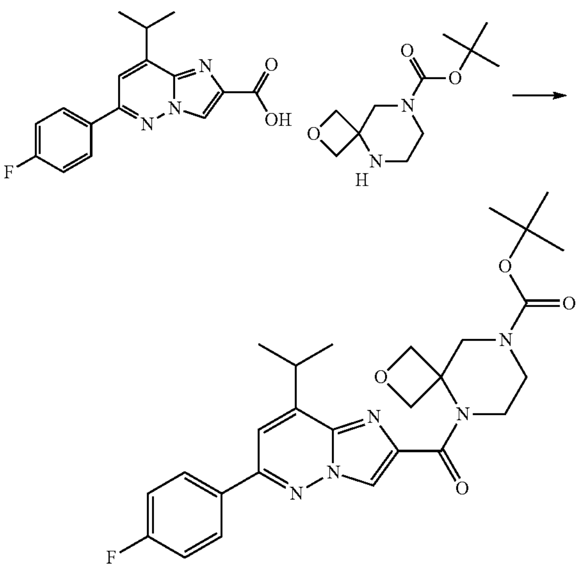

6-(4-Fluorophenyl)-8-isopropyl-imidazo[1,2-b]pyridazine-2-carboxylic acid (50 mg, 0.17 mmol) was dissolved in DMF (1 mL) and DIPEA (75.6 mg, 102 μL, 0.58 mmol) followed by tert-butyl 2-oxa-5,8-diazaspiro[3.5]nonane-8-carboxylate (42 mg, 0.18 mmol) were successively added at r. t. After 2 min, HATU (95.3 mg, 0.25 mmol) were added and the reaction mixture was stirred at r.t. ON. Water was added to the reaction and a brown solid precipitated from the reaction mixture. The resulting mixture was stirred vigorously for 10 min and the precipitate was collected via filtration with a Büchner funnel. The collected material was washed with water several times and then dried under vacuum for 1 h to afford tert-butyl 5-[6-(4-fluorophenyl)-8-isopropyl-imidazo[1,2-b]pyridazine-2-carbonyl]-2-oxa-5,8-diazaspiro[3.5]nonane-8-carboxylate (54.8 mg, 61%). $^1H$ NMR (400 MHz, DMSO-$d_6$) δ 8.64 (s, 1H), 8.20-8.14 (m, 2H), 7.71 (d, J=0.8 Hz, 1H), 7.46-7.38 (m, 2H), 4.74-4.68 (m, 2H), 4.29 (d, J=6.6 Hz, 2H), 3.98 (s, 2H), 3.85 (s, 2H), 3.57 (dt, J=13.9, 6.9 Hz, 1H), 3.24 (s, 2H), 1.49-1.35 (m, 15H). LC-MS: m/z=510.22 ($M+H^+$), retention time: 4.71 minutes using Method A.

Example 18 (I-24): 8-[6-(4-fluorophenyl)-8-isopropyl-imidazo[1,2-b]pyridazine-2-carbonyl]-1-oxa-3,8-diazaspiro[4.5]decan-2-

Scheme 42

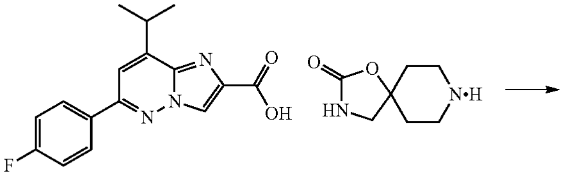

-continued

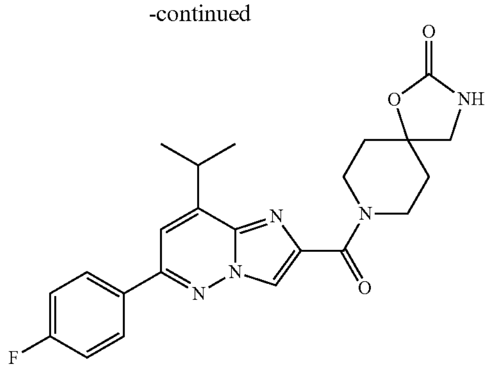

6-(4-Fluorophenyl)-8-isopropyl-imidazo[1,2-b]pyridazine-2-carboxylic acid (25 mg, 0.084 mmol) was dissolved in DMF (1 mL) and DIPEA (37.8 mg, 51 μL, 0.29 mmol) followed by 1-oxa-3,8-diazaspiro[4.5]decan-2-one (hydrochloric acid salt) (17.7 mg, 0.092 mmol) were successively added at r. t. After 2 min, HATU (47.6 mg, 0.13 mmol) were added and the reaction mixture was stirred at rt ON. After the addition of water to the reaction a solid material precipitated. The mixture was stirred for an additional 30 min and the solid material was collected by filtration with a Büchner funnel. The solid material was washed with water twice and dried under vacuum for 5 h to afford 8-[6-(4-fluorophenyl)-8-isopropyl-imidazo[1,2-b]pyridazine-2-carbonyl]-1-oxa-3,8-diazaspiro[4.5]decan-2-one (20.4 mg, 53% yield). LC-MS: m/z=438.12 ($M+H^+$), retention time: 3.2 minutes using Method A.

Example 19 (I-25): 4-[6-(4-fluorophenyl)-8-isopropyl-imidazo[1,2-b]pyridazine-2-carbonyl]-3,3-dimethyl-piperazin-2-one Scheme 43

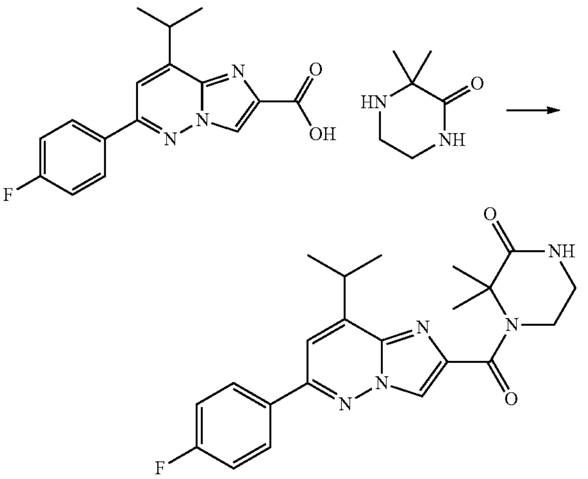

6-(4-Fluorophenyl)-8-isopropyl-imidazo[1,2-b]pyridazine-2-carboxylic acid (25 mg, 0.084 mmol) was dissolved in DMF (1 mL) and DIPEA (37.8 mg, 51 μL, 0.29 mmol) followed by 3,3-dimethylpiperazin-2-one (11.8 mg, 0.092 mmol) were successively added at r. t. After 2 min, HATU (47.6 mg, 0.13 mmol) was added and the reaction mixture as stirred at rt ON. Water was then added and the reaction mixture was extracted with EtOAc. The organic phase was washed twice with a 1:1 mixture of water and brine then dried over anhydrous MgSO4, filtered and evaporated under reduced pressure. The crude mixture was further purified by HPLC and the isolated product in ACN/water was frozen and lyophilized to afford 4-[6-(4-fluorophenyl)-8-isopropyl-imidazo[1,2-b]pyridazine-2-carbonyl]-3,3-dimethyl-piperazin-2-one (10.4 mg, 30% yield). $^1$H NMR (400 MHz, DMSO-$d_6$) δ 8.57 (s, 1H), 8.16 (ddd, J=10.4, 5.4, 2.6 Hz, 2H), 8.11 (s, 1H), 7.69 (d, J=0.8 Hz, 1H), 7.47-7.36 (m, 2H), 3.97-3.89 (m, 2H), 3.54 (p, J=6.9 Hz, 1H), 3.36 (t, J=6.5 Hz, 2H), 1.70 (s, 6H), 1.44 (d, J=6.9 Hz, 6H). LC-MS: m/z=410.12 (M+H$^+$), retention time: 3.43 minutes using Method A.

Example 20 (I-26): [6-(4-fluorophenyl)-8-isopropyl-imidazo[1,2-b]pyridazin-2-yl]-[8-(4-hydroxytetrahydropyran-4-carbonyl)-2-oxa-5,8-diazaspiro[3.5]nonan-5-yl]methanone Step I: [6-(4-fluorophenyl)-8-isopropyl-imidazo[1,2-b]pyridazin-2-yl]-(2-oxa-5,8-diazaspiro[3.5]nonan-5-yl)methanone Scheme 44

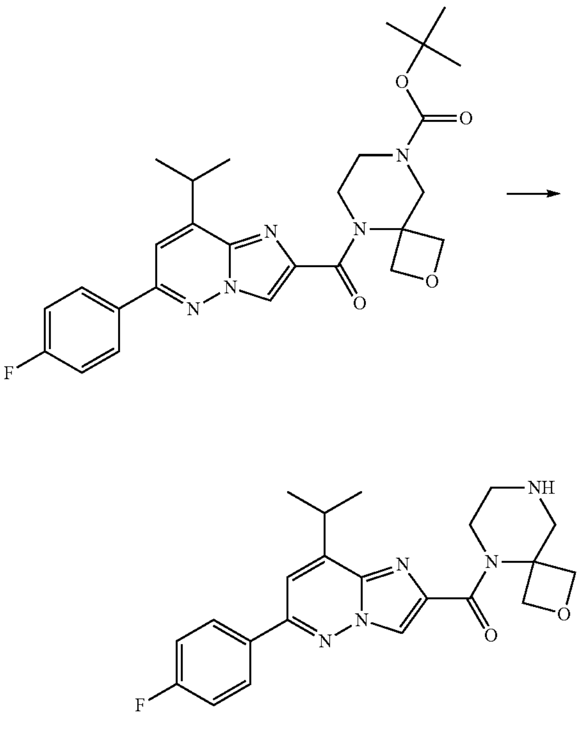

In a rbf under argon, tert-butyl 5-[6-(4-fluorophenyl)-8-isopropyl-imidazo[1,2-b]pyridazine-2-carbonyl]-2-oxa-5,8-diazaspiro[3.5]nonane-8-carboxylate (22.8 mg, 0.045 mmol) was dissolved in DCM (4.5 mL) and $ZnBr_2$ (151 mg, 0.67 mmol) was then added. The mixture was stirred at r. t. ON. The solvent was removed and placed under vacuum for several h to yield [6-(4-fluorophenyl)-8-isopropyl-imidazo[1,2-b]pyridazin-2-yl]-(2-oxa-5, 8-diazaspiro[3.5]nonan-5-yl)methanone (18 mg) as a brown solid. This material was used directly in the next reaction without further purification. LC-MS: m/z=410.41 (M+H$^+$).

Step II (I-26): [6-(4-fluorophenyl)-8-isopropyl-imidazo[1,2-b]pyridazin-2-yl]-[8-(4-hydroxytetrahydropyran-4-carbonyl)-2-oxa-5,8-diazaspiro[3.5]nonan-5-yl]methanone Scheme 45

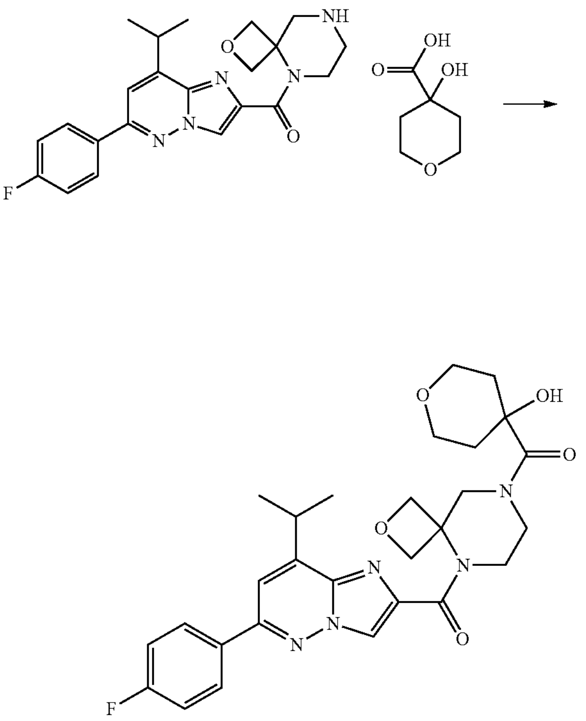

[6-(4-Fluorophenyl)-8-isopropyl-imidazo[1,2-b]pyridazin-2-yl]-(2-oxa-5,8-diazaspiro[3.5]nonan-5-yl)methanone (18 mg, 0.044 mmol) was dissolved in DMF (1 mL) and DIPEA (18 mg, 24 μL, 0.14 mmol) followed by 4-hydroxytetrahydropyran-4-carboxylic acid (7.1 mg, 0.048 mmol) were successively added at r. t. After 2 min, HATU (25 mg, 0.066 mmol) was added and the reaction mixture was stirred at r.t. ON. Water was added and the reaction mixture was extracted with EtOAc. The organic phase was washed twice with a 1:1 mixture of water and brine, dried over anhydrous $MgSO_4$, filtered and evaporated under reduced pressure. The crude mixture was purified by HPLC and the pure fractions in ACN and water were frozen and lyophilized to afford [6-(4-fluorophenyl)-8-isopropyl-imidazo[1,2-b]pyridazin-2-yl]-[8-(4-hydroxytetrahydropyran-4-carbonyl)-2-oxa-5,8-diazaspiro[3.5]nonan-5-yl]methanone (8 mg, 31% yield). LC-MS: m/z=538.55 (M+H$^+$), retention time: 2.82 minutes using Method A.

Example 21 (I-27): [6-(4-fluorophenyl)-8-isopropyl-imidazo[1,2-b]pyridazin-2-yl]-[4-(4-hydroxytetrahydropyran-4-carbonyl)-2,2-dimethyl-piperazin-1-yl]methanone Step I. (6-chloro-8-isopropyl-imidazo[1,2-b]pyridazin-2-yl)-[4-(4-hydroxytetrahydropyran-4-carbonyl)-2,2-dimethyl-piperazin-1-yl]methanone Scheme 46

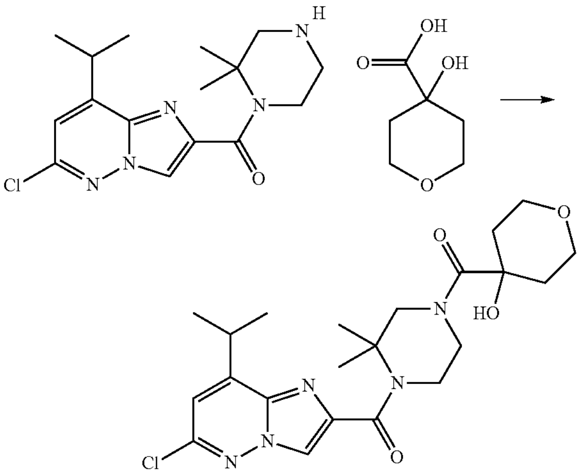

In a rbf under nitrogen, (6-chloro-8-isopropyl-imidazo[1,2-b]pyridazin-2-yl)-(2,2-dimethylpiperazin-1-yl)methanone (54.1 mg, 0.16 mmol) was dissolved in DMF (1.5 mL) and DIPEA (71.7 mg, 97 μL, 0.55 mmol) followed by 4-hydroxytetrahydropyran-4-carboxylic acid (28 mg, 0.19 mmol) were successively added at r. t. After 2 min, HATU (90 mg, 0.24 mmol) was added and the reaction mixture was stirred at rt ON. Water was added and the reaction mixture was extracted with EtOAc. The organic phase was washed twice with a 1:1 water and brine mixture, dried over anhydrous $MgSO_4$, filtered and evaporated under reduced pressure. The crude mixture was purified by flash chromatography eluting with 0 to 10% MeOH/DCM in 15 CV. The isolated material was then dissolved in ACN and water, frozen and lyophilized to afford (6-chloro-8-isopropyl-imidazo[1,2-b]pyridazin-2-yl)-[4-(4-hydroxytetrahydropyran-4-carbonyl)-2,2-dimethyl-piperazin-1-yl]methanone (50 mg, 62% yield) as a white powder. LC-MS: m/z=464.46 ($M+H^+$).

Step II (I-27): [6-(4-fluorophenyl)-8-isopropyl-imidazo[1,2-b]pyridazin-2-yl]-[4-(4-hydroxytetrahydropyran-4-carbonyl)-2,2-dimethyl-piperazin-1-yl]methanone Scheme 47

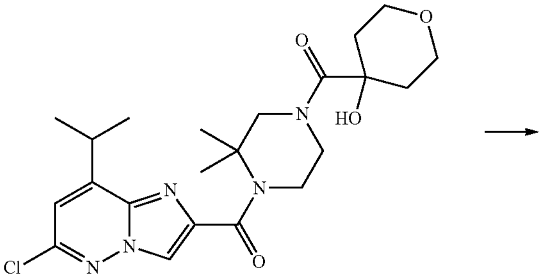

-continued

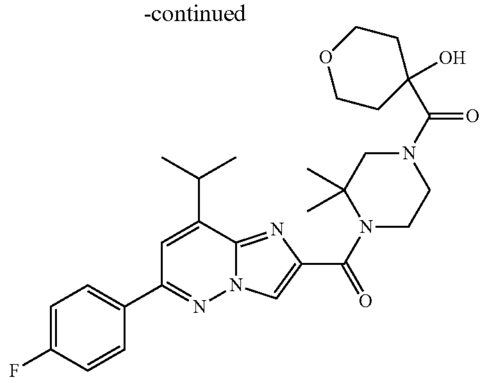

To a rbf containing a solution of (6-chloro-8-isopropyl-imidazo[1,2-b]pyridazin-2-yl)-[4-(4-hydroxytetrahydropyran-4-carbonyl)-2,2-dimethyl-piperazin-1-yl]methanone (40 mg, 0.078 mmol) in dioxane (1 mL) was added $Pd_2dba_3$ (0.7 mg, 0.00077 mmol) and S-Phos (1.2 mg, 0.0030 mmol). The resulting solution was degassed with nitrogen for 5 min prior to the addition of $K_3PO_4$ (116 μL of a 2 M aqueous solution, 0.23 mmol) and 4-fluorophenylboronic acid (12 mg, 0.085 mmol). The mixture was then heated to 110° C. for 18 h. At this time additional S-Phos, $Pd_2dba_3$ and boronic acid were added to the mixture and stirred for a further 5 h at 110° C. The reaction mixture was cooled, DCM and water were then added to the mixture. The layers were separated and the aqueous phase was extracted with DCM twice. The combined organic layers were dried over anhydrous sodium sulfate, filtered and concentrated under vacuum. The crude mixture was purified by HPLC and the pure fractions in ACN/water were frozen and lyophilized to afford [6-(4-fluorophenyl)-8-isopropyl-imidazo[1,2-b]pyridazin-2-yl]-[4-(4-hydroxytetrahydropyran-4-carbonyl)-2,2-dimethyl-piperazin-1-yl]methanone (34.6 mg, 78% yield). $^1H$ NMR (400 MHz, DMSO-$d_6$) δ 8.53 (s, 1H), 8.19-8.13 (m, 2H), 7.68 (s, 1H), 7.45-7.37 (m, 2H), 5.55 (d, J=30.2 Hz, 1H), 4.19-3.98 (m, 4H), 3.73-3.58 (m, 5H), 3.59-3.50 (m, 1H), 3.50-3.41 (m, 1H), 2.05-1.90 (m, 2H), 1.62 (d, J=13.5 Hz, 2H), 1.58-1.47 (m, 6H), 1.44 (d, J=6.9 Hz, 6H).

LC-MS: m/z=524.22 ($M+H^+$), retention time: 3.48 minutes using Method A.

Example 22 (I-28): [6-(4-fluorophenyl)-8-isopropyl-imidazo[1,2-b]pyridazin-2-yl]-[(2S)-4-(1-hydroxycyclobutanecarbonyl)-2-methyl-piperazin-1-yl]methanone Step I: (3S)-4-[6-(4-fluorophenyl)-8-isopropyl-imidazo[1,2-b]pyridazine-2-carbonyl]-3-methyl-piperazine-1-carboxylate Scheme 48

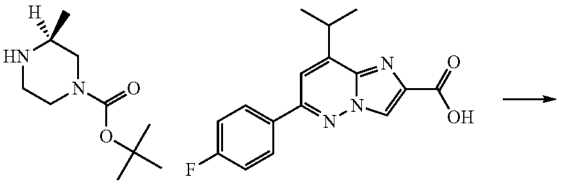

-continued

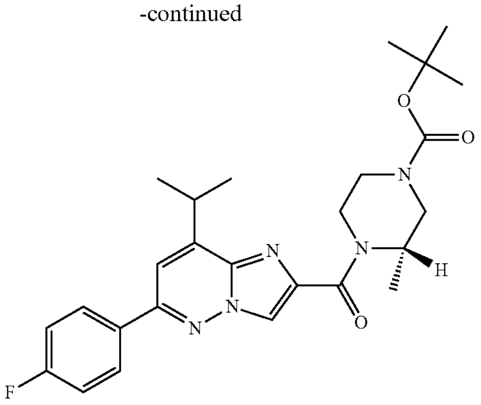

6-(4-Fluorophenyl)-8-isopropyl-imidazo[1,2-b]pyridazine-2-carboxylic acid (43 mg, 0.14 mmol) was dissolved in DMF (1 mL) and DIPEA (65 mg, 87 μL, 0.50 mmol) followed by tert-butyl (3S)-3-methylpiperazine-1-carboxylate (32 mg, 0.16 mmol) were successively added at r. t. After 2 min, HATU (82 mg, 0.22 mmol) were added and the reaction mixture was at rt ON. Water was added and the reaction mixture was extracted with EtOAc. The organic layers were washed twice with a 1:1 brine and water mixture, dried over anhydrous $MgSO_4$, filtered and evaporated under reduced pressure. The resulting material was used directly in the next reaction without further purification. LC-MS: m/z=482.18 (M+H$^+$).

Step II: [6-(4-fluorophenyl)-8-isopropyl-imidazo[1,2-b]pyridazin-2-yl]-[(2S)-2-methylpiperazin-1-yl]methanone Scheme 49

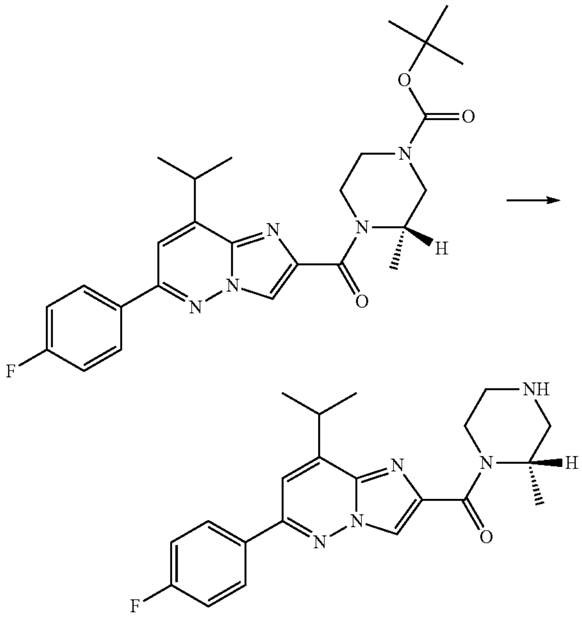

tert-Butyl (3S)-4-[6-(4-fluorophenyl)-8-isopropyl-imidazo[1,2-b]pyridazine-2-carbonyl]-3-methyl-piperazine-1-carboxylate (69 mg, 0.14 mmol) was dissolved in DCM (2.7 mL) and TFA (163 mg, 110 μL, 1.43 mmol) was added. The reaction was stirred at r.t. for 1.5 h. The volatiles were evaporated under reduced pressure and the resulting residue placed under vacuum for 30 min. At this time, DCM was added and a saturated $NaHCO_3$ solution was carefully added to the mixture until the aqueous layer was basic (pH). The phases were separated and the organic layer was washed with a saturated aqueous $NaHCO_3$ solution. The organic layer was dried over anhydrous $MgSO_4$, filtered and evaporated under reduced pressure to afford [6-(4-fluorophenyl)-8-isopropyl-imidazo[1,2-b]pyridazin-2-yl]-[(2S)-2-methyl-piperazin-1-yl]methanone (54.7 mg, quantitative). LC-MS: m/z=382.41 (M+H$^+$).

Step III (I-28): [6-(4-fluorophenyl)-8-isopropyl-imidazo[1,2-b]pyridazin-2-yl]-[(2S)-4-(1-hydroxy-cyclobutanecarbonyl)-2-methyl-piperazin-1-yl]methanone Scheme 50

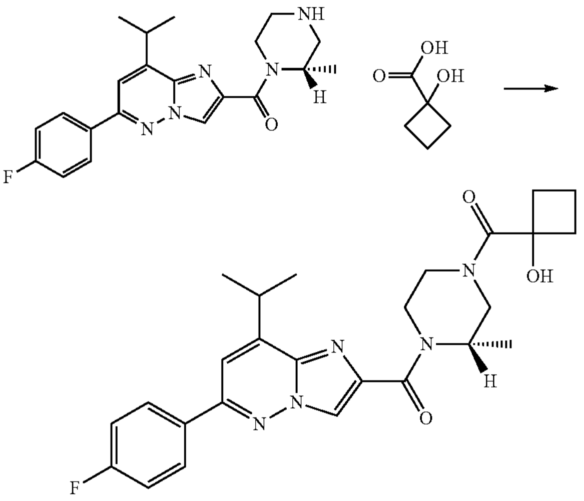

[6-(4-Fluorophenyl)-8-isopropyl-imidazo[1,2-b]pyridazin-2-yl]-[(2S)-2-methylpiperazin-1-yl]methanone (55 mg, 0.14 mmol) was dissolved in DMF (2 mL) and DIPEA (186.4 mg, 251 μL, 1.44 mmol) followed by 1-hydroxycyclobutanecarboxylic acid (20 mg, 0.173 mmol) were successively added at r. t. After 2 min, HATU (82 mg, 0.22 mmol) was added and the reaction mixture was stirred at r. t. ON. Water was added and the reaction mixture was extracted with EtOAc. The organic layer was washed twice with a 1:1 brine water mixture, dried over anhydrous $MgSO_4$, filtered and evaporated under reduced pressure. The crude reaction mixture was purified by flash chromatography eluting with a gradient of 60 to 100% EtOAc/Hexanes in 15 CV. The organic solvent was evaporated under reduced pressure and the resulting oily product was dissolved in ACN and water, frozen and lyophilized to afford [6-(4-fluorophenyl)-8-isopropyl-imidazo[1,2-b]pyridazin-2-yl]-[(2S)-4-(1-hydroxycyclobutanecarbonyl)-2-methyl-piperazin-1-yl]methanone (10.6 mg, 14% yield). LC-MS: m/z=480.23 (M+H$^+$), retention time: 3.72 minutes using Method A.

Example 23 (I-29): 4-[6-(4-fluorophenyl)-8-tetrahydropyran-4-yl-imidazo[1,2-b]pyridazine-2-carbonyl]-3,3-dimethyl-piperazin-2-one Step I: Methyl 8-(3,6-dihydro-2H-pyran-4-yl)-6-(4-fluorophenyl)imidazo[1,2-b]pyridazine-2-carboxylate Scheme 51

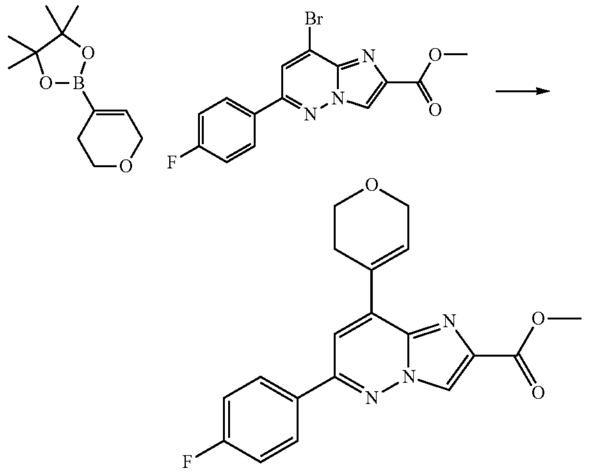

Methyl 8-bromo-6-(4-fluorophenyl)imidazo[1,2-b]pyridazine-2-carboxylate (1.2 g, 3.43 mmol) was dissolved in THF (28.8 mL) and treated with $Na_2CO_3$ (5.14 mL of a 2 M aqueous solution, 10.28 mmol). The reaction mixture was degassed with nitrogen for 5 min, then 2-(3,6-dihydro-2H-pyran-4-yl)-4,4,5,5-tetramethyl-1,3,2-dioxaborolane (1.08 g, 5.14 mmol) was added followed by $Pd(PPh_3)_4$ (396 mg, 0.343 mmol). The reaction mixture was stirred at 75° C. for 18 h. The reaction mixture was cooled, water and EtOAc were added and the phases were then separated. The aqueous phase was extracted with EtOAc and the combined organic phases were washed with brine, dried over anhydrous $MgSO_4$, filtered and evaporated under reduced pressure affording the title compound, methyl 8-(3,6-dihydro-2H-pyran-4-yl)-6-(4-fluorophenyl)imidazo[1,2-b]pyridazine-2-carboxylate (1.21 g) as a light brown solid which was used in the next step without further purification. LC-MS: m/z=354.37 $(M+H^+)$ Step II: Methyl 6-(4-fluorophenyl)-8-tetrahydropyran-4-yl-imidazo[1,2-b]pyridazine-2-carboxylate Scheme 52

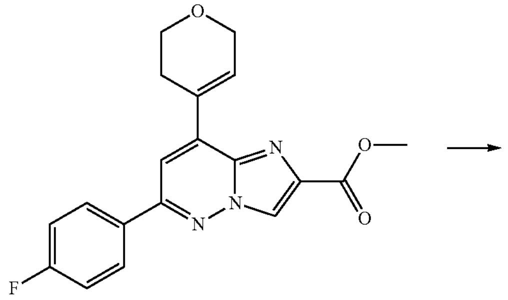

-continued

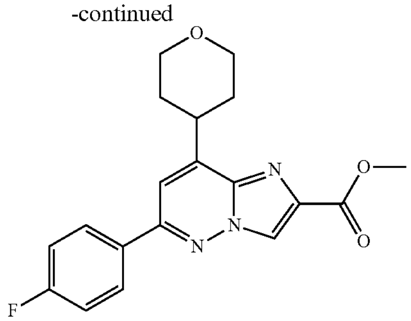

To a Parr shaker flask containing palladium on carbon (903.5 mg, 0.8490 mmol) under a nitrogen atmosphere was added a solution of methyl 8-(3,6-dihydro-2H-pyran-4-yl)-6-(4-fluorophenyl)imidazo[1,2-b]pyridazine-2-carboxylate (1.2 g, 3.40 mmol) in MeOH (70 mL) and DCM (35 mL). The flask was placed in a Parr shaker and the air was removed under vacuum and replaced with nitrogen twice. The flask was then evacuated under reduced pressure and re-filled with hydrogen 3 times and the resulting suspension was shaken under 40 psi of hydrogen for 5 days. Hydrogen was then evacuated and the flask backfilled with nitrogen. The catalyst was removed by filtration on Celite, washed with DCM and the filtrate was evaporated under reduced pressure affording the title compound methyl 6-(4-fluorophenyl)-8-tetrahydropyran-4-yl-imidazo [1,2-b]pyridazine-2-carboxylate (1.2 g, 99% yield) as a brownish solid which was used in the subsequent step without further purification. LC-MS: m/z=356.33 $(M+H^+)$ Step III: 6-(4-fluorophenyl)-8-tetrahydropyran-4-yl-imidazo[1,2-b]pyridazine-2-carboxylic acid Scheme 53

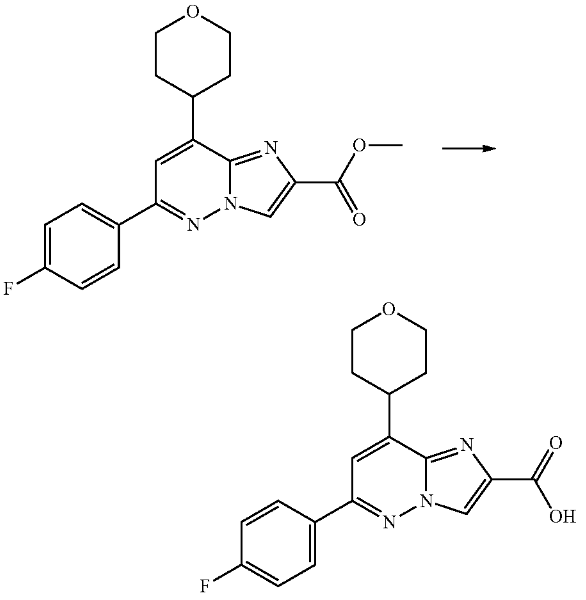

To a rbf containing a solution of methyl 6-(4-fluorophenyl)-8-tetrahydropyran-4-yl-imidazo [1,2-b]pyridazine-2-carboxylate (1.2 g, 3.38 mmol) in dioxane (16.9 mL) were added LiOH (4 mL of a 2 M aqueous solution, 8.0 mmol)

and the solution was stirred for 3 h at r. t. Water and ethyl acetate were then added and the phases were separated. The organic phase was washed twice with an aqueous $NaHCO_3$ solution and the combined aqueous phases were acidified to pH 1 using a 12N HCl aqueous solution. The precipitate formed was collected by filtration, washed with water and dried under reduced pressure. The filtrate was concentrated to approximately 50 mL and cooled to 0° C. The resulting precipitate was filtered, washed with cold water, dried under reduced pressure and mixed with the solid from above affording the title compound 6-(4-fluorophenyl)-8-tetrahydropyran-4-yl-imidazo[1,2-b]pyridazine-2-carboxylic acid (903 mg, 78% yield) as a light yellow solid. NMR: $^1H$ NMR (400 MHz, DMSO-$d_6$) δ 8.74 (s, 1H), 8.16 (dd, J=8.8, 5.5 Hz, 2H), 7.71 (s, 1H), 7.39 (t, J=8.8 Hz, 2H), 4.00 (dd, J=11.1, 4.2 Hz, 2H), 3.59-3.50 (m, 2H), 2.03 (qd, J=12.5, 4.4 Hz, 2H), 1.93-1.82 (m, 2H). LC-MS: m/z=342.33 (M+H$^+$).

Step IV (I-29): 4-[6-(4-fluorophenyl)-8-tetrahydropyran-4-yl-imidazo[1,2-b]pyridazine-2-carbonyl]-3,3-dimethyl-piperazin-2-one Scheme 54

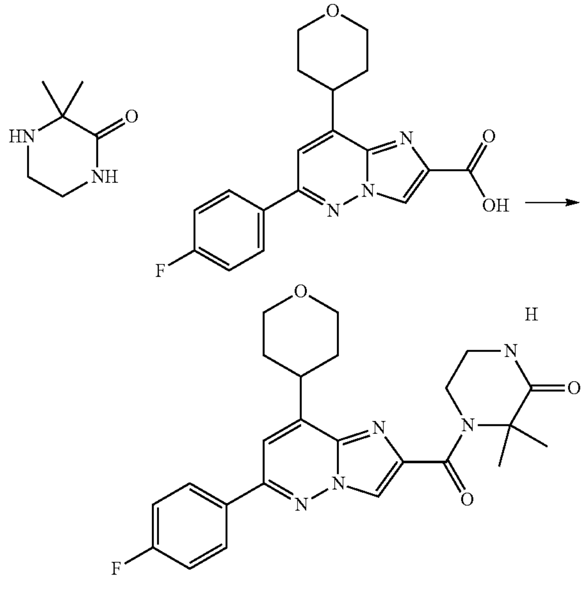

6-(4-Fluorophenyl)-8-tetrahydropyran-4-yl-imidazo[1,2-b]pyridazine-2-carboxylic acid (30 mg, 0.088 mmol) was dissolved in DMF (938 μL) before HATU (43.5 mg, 0.11 mmol), 3,3-dimethylpiperazin-2-one (11.8 mg, 0.092 mmol) and DIPEA (45 mg, 61 μL, 0.35 mmol) were added. The solution was stirred at r. t. for 16 h before aq. $NH_4Cl$ was added. The mixture was cooled to 0° C. and the resulting precipitate was collected by filtration. The solid was washed with water and dried under reduced pressure, affording the title compound 4-[6-(4-fluorophenyl)-8-tetrahydropyran-4-yl-imidazo[1,2-b]pyridazine-2-carbonyl]-3,3-dimethyl-piperazin-2-one (26 mg, 64% yield). $^1H$ NMR (400 MHz, DMSO-$d_6$) δ 8.55 (s, 1H), 8.20-8.11 (m, 2H), 8.08 (s, 1H), 7.68 (d, J=0.7 Hz, 1H), 7.38 (t, J=8.9 Hz, 2H), 3.99 (dd, J=11.3, 4.0 Hz, 2H), 3.90-3.77 (m, 2H), 3.57-3.47 (m, 2H), 3.34 (d, J=3.6 Hz, 2H), 2.11-1.97 (m, 2H), 1.88 (d, J=12.8 Hz, 2H), 1.67 (s, 6H). LC-MS: m/z=452.45 (M+H$^+$), retention time: 1.39 minutes using Method C.

Example 24 (I-30): 4-[6-(4-fluorophenyl)-8-(1-methylcyclopropyl)imidazo[1,2-b]pyridazine-2-carbonyl]-3,3-dimethyl-piperazin-2-one Step I: Methyl 6-(4-fluorophenyl)-8-(1-methylcyclopropyl)imidazo[1,2-b]pyridazine-2-carboxylate Scheme 55

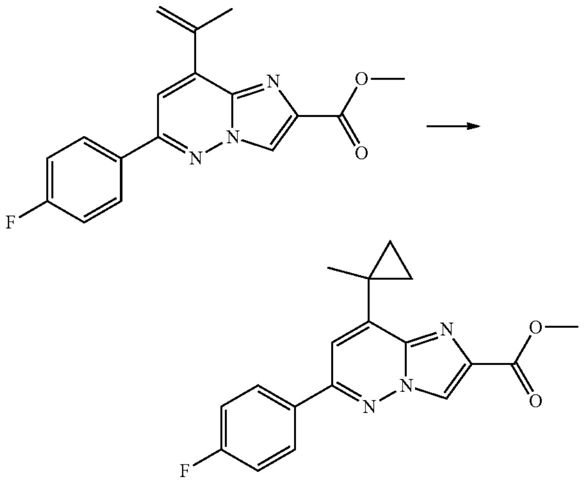

To a solution of methyl 6-(4-fluorophenyl)-8-isopropenyl-imidazo[1,2-b]pyridazine-2-carboxylate (889 mg, 2.86 mmol) and palladium acetate (64 mg, 0.286 mmol) in DCM (22.31 mL) at 0° C. was added dropwise an ethereal solution of diazomethane (171.4 mL of a 1 M solution, 171.4 mmol) over 1 h. The mixture was filtered over Celite and the filtrate concentrated under reduced pressure. The residue was purified by flash chromatography eluting with 0 to 50% EtOAc/hexanes to afford the title compound methyl 6-(4-fluorophenyl)-8-(1-methylcyclopropyl)imidazo[1,2-b]pyridazine-2-carboxylate (340 mg, 37% yield) as a solid. $^1H$ NMR (400 MHz, Methanol-$d_4$) δ 8.55 (s, 1H), 8.10-7.99 (m, 2H), 7.55 (s, 1H), 7.24 (t, J=8.8 Hz, 2H), 3.93 (s, 3H), 1.59 (s, 3H), 1.44 (d, J=2.1 Hz, 2H), 0.98-0.93 (m, 2H). LC-MS: m/z=326.04 (M+H$^+$).

Step II: 6-(4-fluorophenyl)-8-(1-methylcyclopropyl)imidazo[1,2-b]pyridazine-2-carboxylic acid Scheme 56

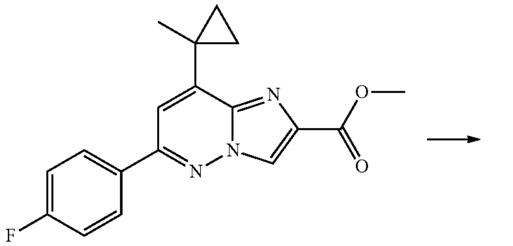

-continued

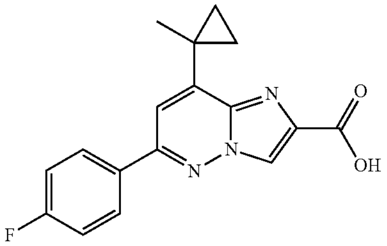

To a solution of methyl 6-(4-fluorophenyl)-8-(1-methylcyclopropyl)imidazo[1,2-b]pyridazine-2-carboxylate (340 mg, 1.05 mmol) in dioxane (5.9 mL) was added LiOH (1.05 mL of a 2 M aqueous solution, 2.1 mmol) and the solution was stirred at r. t. for 2 h. Water (10 mL) was added and the solution was acidified using a 12N HCl aqueous solution. The precipitate formed was collected by filtration, washed with water and dried under reduced pressure affording the title compound 6-(4-fluorophenyl)-8-(1-methylcyclopropyl)imidazo[1,2-b]pyridazine-2-carboxylic acid (265 mg, 81% yield) as an off-white solid. LC-MS: m/z=312.51 (M+H$^+$).

Step III (I-30): 4-[6-(4-fluorophenyl)-8-(1-methylcyclopropyl)imidazo[1,2-b]pyridazine-2-carbonyl]-3,3-dimethyl-piperazin-2-one Scheme 57

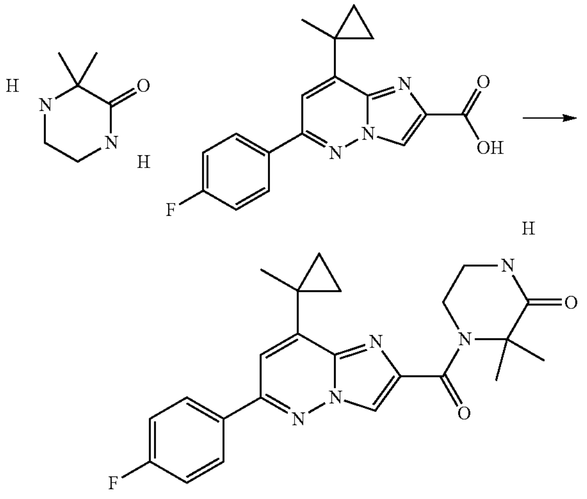

6-(4-Fluorophenyl)-8-(1-methylcyclopropyl)imidazo[1,2-b]pyridazine-2-carboxylic acid (50 mg, 0.16 mmol) was dissolved in DMF (803 μL) and HATU (79 mg, 0.21 mmol), 3,3-dimethylpiperazin-2-one (22.7 mg, 0.177 mmol) and DIPEA (83 mg, 112 μL, 0.64 mmol) were added. The solution was stirred at r. t. for 16 h before water was added and the precipitate formed collected by filtration. The solid was washed with water and dried under reduced pressure affording the title compound 4-[6-(4-fluorophenyl)-8-(1-methylcyclopropyl)imidazo[1,2-b]pyridazine-2-carbonyl]-3,3-dimethyl-piperazin-2-one (57 mg, 80% yield). $^1$H NMR (400 MHz, DMSO-d$_6$) δ 8.51 (s, 1H), 8.12 (dd, J=8.8, 5.5 Hz, 2H), 8.07 (s, 1H), 7.54 (s, 1H), 7.37 (t, J=8.8 Hz, 2H), 3.93-3.85 (m, 2H), 3.34 (m, 2H), 1.75-1.69 (m, 2H), 1.66 (s, 6H), 1.58 (s, 3H), 0.93 (q, J=3.8 Hz, 2H).

LC-MS: m/z=422.4 (M+H$^+$), retention time: 1.65 minutes using Method C.

Example 25 (I-31): [6-(4-fluorophenyl)-8-(1-methylcyclopropyl)imidazo[1,2-b]pyridazin-2-yl]-[4-(4-hydroxytetrahydropyran-4-carbonyl)-2,2-dimethyl-piperazin-1-yl]methanone Step I: tert-butyl 4-[6-(4-fluorophenyl)-8-(1-methylcyclopropyl)imidazo[1,2-b]pyridazine-2-carbonyl]-3,3-dimethyl-piperazine-1-carboxylate Scheme 58

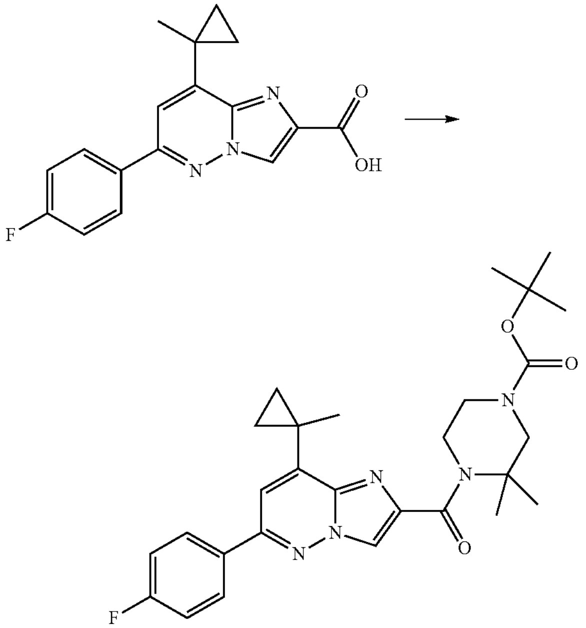

6-(4-Fluorophenyl)-8-(1-methylcyclopropyl)imidazo[1,2-b]pyridazine-2-carboxylic acid (150 mg, 0.48 mmol) was dissolved in DMF (4.5 mL) and HATU (238 mg, 0.63 mmol), tert-butyl 3,3-dimethylpiperazine-1-carboxylate (113.6 mg, 0.53 mmol) and DIPEA (249 mg, 336 μL, 1.93 mmol) were added. The solution was stirred at r. t. for 3 h and then aqueous $NH_4Cl$ was added and the aqueous phase was extracted twice with EtOAc. The combined organic layers were washed with 1N HCl aqueous, saturated aqueous $NaHCO_3$ and brine, dried over anhydrous $MgSO_4$, filtered and the filtrate evaporated under reduced pressure affording the title compound (245 mg, quantitative) as a yellow solid which was used in the subsequent step without further purification. LC-MS: m/z=508.17 (M+H$^+$).

Step II: (2,2-dimethylpiperazin-1-yl)-[6-(4-fluorophenyl)-8-(1-methylcyclopropyl)-imidazo[1,2-b]pyridazin-2-yl]methanone Scheme 59

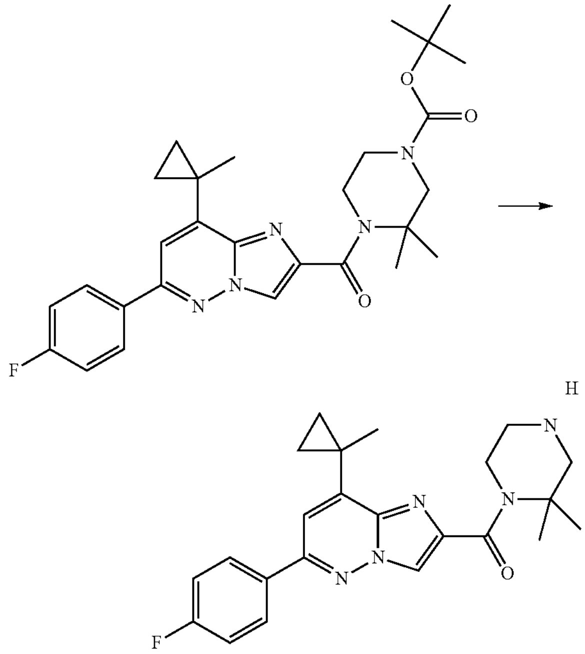

To a solution of tert-butyl 4-[6-(4-fluorophenyl)-8-(1-methylcyclopropyl)imidazo[1,2-b]pyridazine-2-carbonyl]-3,3-dimethyl-piperazine-1-carboxylate (245 mg, 0.483 mmol) in DCM (5.4 mL) was added HCl in dioxane (2.4 mL of a 4 M solution, 9.6 mmol) and the solution was stirred for 3 h. The volatiles were removed under reduced pressure affording the title compound (2,2-dimethylpiperazin-1-yl)-[6-(4-fluorophenyl)-8-(1-methylcyclopropyl)-imidazo[1,2-b]pyridazin-2-yl]methanone hydrochloride (219 mg, quantitative) as a brown solid which was used in the subsequent step without further purification. LC-MS: m/z=408.4 ($M+H^+$).

Step III (I-31): [6-(4-fluorophenyl)-8-(1-methylcyclopropyl)imidazo[1,2-b]pyridazin-2-yl]-[4-(4-hydroxytetrahydropyran-4-carbonyl)-2,2-dimethyl-piperazin-1-yl]methanone Scheme 60

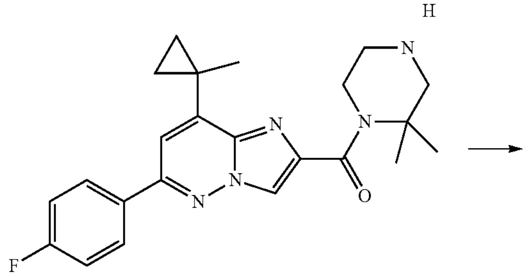

-continued

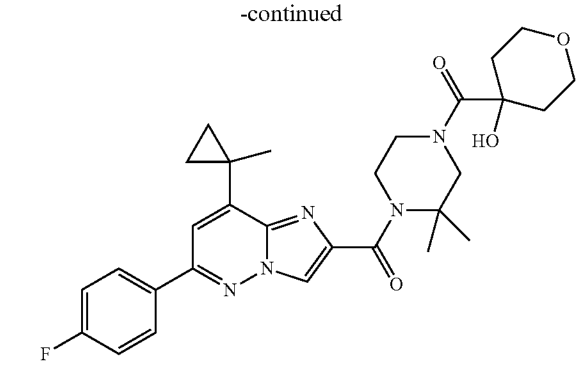

(2,2-Dimethylpiperazin-1-yl)-[6-(4-fluorophenyl)-8-(1-methylcyclopropyl)imidazo[1,2-b]pyridazin-2-yl]methanone (hydrochloride salt) (55 mg, 0.12 mmol) was dissolved in DMF (619 μL) and HATU (66 mg, 0.17 mmol), 4-hydroxytetrahydropyran-4-carboxylic acid (23.5 mg, 0.161 mmol) and DIPEA (96 mg, 130 μL, 0.74 mmol) were added and the solution was stirred at r. t. for 16 h. The product was purified by reverse phase chromatography to afford the title compound [6-(4-fluorophenyl)-8-(1-methylcyclopropyl)imidazo[1,2-b]pyridazin-2-yl]-[4-(4-hydroxytetrahydropyran-4-carbonyl)-2,2-dimethyl-piperazin-1-yl]methanone (39.1 mg, 59% yield).

$^1H$ NMR (400 MHz, DMSO-$d_6$) δ 8.46 (s, 1H), 8.17-8.07 (m, 2H), 7.53 (s, 1H), 7.37 (t, J=8.8 Hz, 2H), 5.60-5.41 (m, 1H), 4.20-3.37 (m, 10H), 1.96 (d, J=14.1 Hz, 2H), 1.70 (s, 2H), 1.65-1.40 (m, 12H), 0.93 (q, J=3.9 Hz, 2H). LC-MS: m/z=536.42 ($M+H^+$), retention time: 4.3 minutes using Method D.

Example 26 (I-32): 1-[4-[6-(4-fluorophenyl)-8-(1-methylcyclopropyl)imidazo[1,2-b]pyridazine-2-carbonyl]-3,3-dimethyl-piperazin-1-yl]-2-hydroxy-2-methyl-propan-1-one Scheme 61

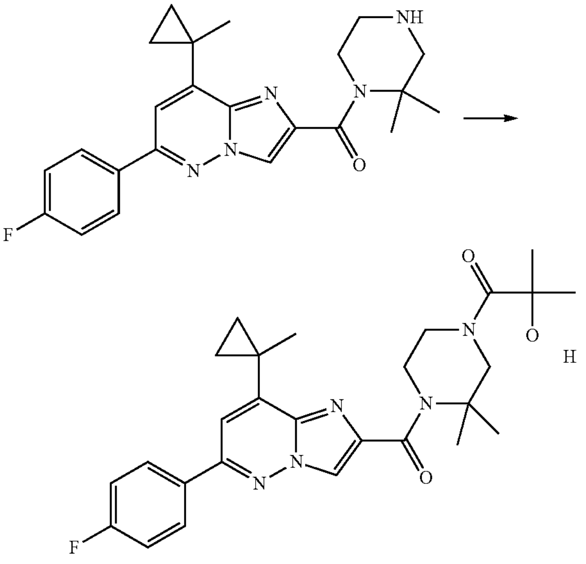

(2,2-Dimethylpiperazin-1-yl)-[6-(4-fluorophenyl)-8-(1-methylcyclopropyl)imidazo[1,2-b]pyridazin-2-yl]methanone (hydrochloride salt) (55 mg, 0.124 mmol) was dissolved in DMF (620 μL) before HATU (66 mg, 0.17 mmol), 2-hydroxy-2-methyl-propanoic acid (17 mg, 0.16 mmol) and DIPEA (96 mg, 130 μL, 0.74 mmol) were added and the solution was stirred at r. t. for 16 h. The product was purified by reverse phase chromatography to afford the title compound 1-[4-[6-(4-fluorophenyl)-8-(1-methylcyclopropyl)imidazo[1,2-b]pyridazine-2-carbonyl]-3,3-dimethyl-piperazin-1-yl]-2-hydroxy-2-methyl-propan-1-one (32 mg, 51% yield). $^1$H NMR (400 MHz, DMSO-$d_6$) δ 8.46 (s, 1H), 8.12 (dd, J=8.8, 5.5 Hz, 2H), 7.54 (s, 1H), 7.37 (t, J=8.8 Hz, 2H), 5.44-5.24 (m, 1H), 4.05 (d, J=35.4 Hz, 5H), 3.64-3.38 (m, 2H), 1.69 (s, 2H), 1.59 (s, 3H), 1.55-1.40 (m, 7H), 1.32 (s, 6H), 0.95-0.91 (m, 2H). LC-MS: m/z=494.39 (M+H$^+$), retention time: 4.58 minutes using Method D.

Example 27 (I-33): [6-(4-fluorophenyl)-8-(1-methylcyclopropyl)imidazo[1,2-b]pyridazin-2-yl]-[4-(1-hydroxycyclobutanecarbonyl)-2,2-dimethyl-piperazin-1-yl]methanone Scheme 62

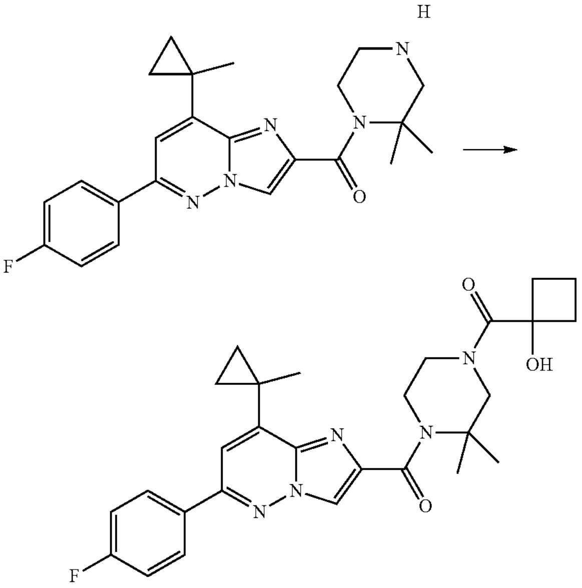

(2,2-dimethylpiperazin-1-yl)-[6-(4-fluorophenyl)-8-(1-methylcyclopropyl)imidazo[1,2-b]pyridazin-2-yl]methanone (hydrochloride salt) (55 mg, 0.12 mmol) was dissolved in DMF (619 μL) before HATU (66 mg, 0.17 mmol), 1-hydroxycyclobutanecarboxylic acid (19 mg, 0.16 mmol) and DIPEA (96.08 mg, 129.5 μL, 0.7434 mmol) were added and the solution was stirred at r. t. for 16 h. The product was purified by reverse phase chromatography to furnish the title compound [6-(4-fluorophenyl)-8-(1-methylcyclopropyl)imidazo[1,2-b]pyridazin-2-yl]-[4-(1-hydroxycyclobutanecarbonyl)-2,2-dimethyl-piperazin-1-yl]methanone (19 mg, 31% yield).

$^1$H NMR (400 MHz, DMSO-$d_6$) δ 8.48-8.44 (m, 1H), 8.12 (dd, J=8.7, 5.6 Hz, 2H), 7.53 (s, 1H), 7.37 (t, J=8.8 Hz, 2H), 5.99-5.86 (m, 1H), 4.16-3.93 (m, 2H), 3.83-3.41 (m, 4H), 2.63-2.50 (m, 2H), 2.11-1.93 (m, 2H), 1.81-1.67 (m, 3H), 1.59 (d, J=2.0 Hz, 3H), 1.47 (d, J=13.1 Hz, 6H), 0.93 (q, J=4.0 Hz, 2H). LC-MS: m/z=506.61 (M+H$^+$), retention time: 4.7 minutes using Method D.

Example 28 (I-34): (2S)-1-[4-[6-(4-fluorophenyl)-8-(1-methylcyclopropyl)imidazo[1,2-b]pyridazine-2-carbonyl]-3,3-dimethyl-piperazin-1-yl]-2-hydroxy-propan-1-one Scheme 63

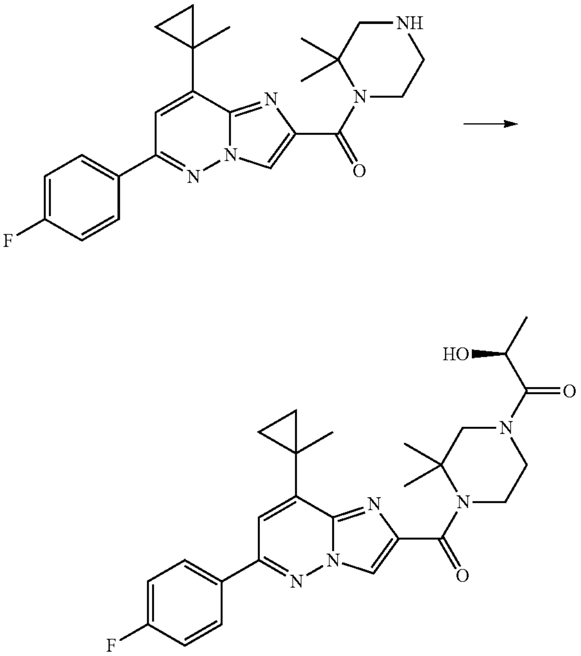

(2,2-Dimethylpiperazin-1-yl)-[6-(4-fluorophenyl)-8-(1-methylcyclopropyl)imidazo[1,2-b]pyridazin-2-yl]methanone (hydrochloride salt) (55 mg, 0.12 mmol) was dissolved in DMF (619 μL) before HATU (75 mg, 0.20 mmol), (2S)-2-hydroxypropanoic acid (17 mg, 0.19 mmol) and DIPEA (96 mg, 130 μL, 0.74 mmol) were added and the solution was stirred at r. t. for 16 h. The product was purified by reverse phase chromatography to afford the title compound (42 mg, 70% yield).

$^1$H NMR (400 MHz, DMSO-$d_6$) δ 8.47 (d, J=4.6 Hz, 1H), 8.12 (dd, J=8.7, 5.5 Hz, 2H), 7.54 (d, J=2.7 Hz, 1H), 7.37 (t, J=8.8 Hz, 2H), 4.94 (dd, J=19.4, 7.1 Hz, 1H), 4.40 (dp, J=30.2, 6.6 Hz, 1H), 4.23-3.39 (m, 6H), 1.73-1.66 (m, 2H), 1.59 (s, 3H), 1.50 (s, 3H), 1.46 (d, J=6.2 Hz, 3H), 1.19 (t, J=6.4 Hz, 3H), 0.94 (dd, J=3.8, 2.6 Hz, 2H). LC-MS: m/z=480.56 (M+H$^+$), retention time: 4.3 minutes using Method D.

Example 29 (I-35): 4-[6-(4-Fluorophenyl)-8-(trifluoromethyl)imidazo[1,2-b]pyridazine-2-carbonyl]-3,3-dimethyl-piperazin-2-one Step I: Methyl 6-(4-fluorophenyl)-8-(trifluoromethyl)imidazo[1,2-b]pyridazine-2-carboxylate Scheme 64

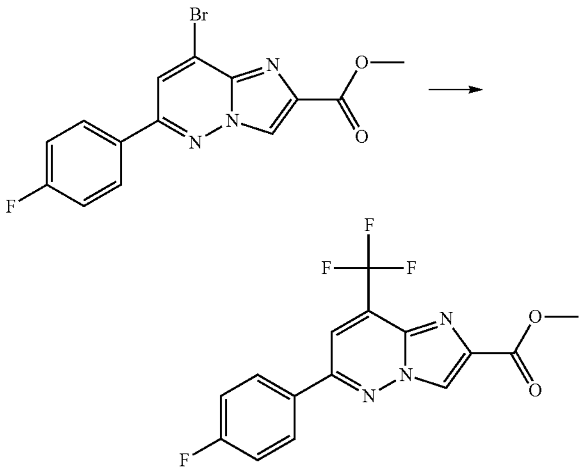

In an oven-dried flask under nitrogen were added CuCl (170 mg, 1.714 mmol), KO$^t$Bu (192 mg, 1.71 mmol) and 1,10-phenanthroline (309 mg, 1.71 mmol) and the flask was purged again. To this mixture was added DMF (3.4 mL) and the resulting solution was stirred at r. t. for 30 min. Trimethyl-(trifluoromethyl)silane (857 μL of a 2 M solution in THF, 1.714 mmol) was slowly added to the reaction mixture, which was then allowed to stir for 1 h at r. t. The stirring was then stopped and methyl 8-bromo-6-(4-fluorophenyl)imidazo[1,2-b]pyridazine-2-carboxylate (300 mg, 0.86 mmol) was added rapidly. The stirring was started again under a nitrogen atmosphere and the resulting solution was heated to 50° C. for 18 h. Upon completion, the reaction mixture was cooled, diluted with $Et_2O$ and filtered through Celite. The Celite was washed with $Et_2O$ and the combined organic phases were washed successively with 1N aqueous HCl, saturated aqueous $NaHCO_3$ solution and brine, and dried over anhydrous $Na_2SO_4$. After filtration and evaporation of the solvent, the crude mixture was purified by flash chromatography eluting with 0-50% EtOAc: hexanes to afford the title compound (291 mg, 34% yield). LCMS: m/z=340.23 (M+H$^+$)

Step II: 6-(4-Fluorophenyl)-8-(trifluoromethyl)imidazo[1,2-b]pyridazine-2-carboxylic acid Scheme 65

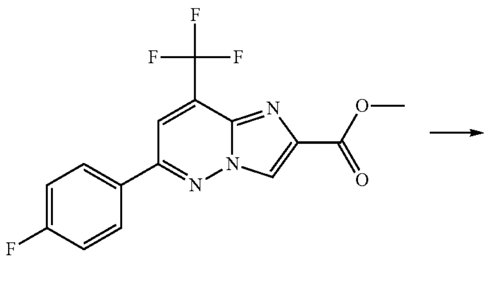

-continued

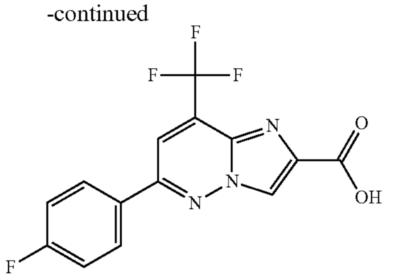

Methyl 6-(4-fluorophenyl)-8-(trifluoromethyl)imidazo[1,2-b]pyridazine-2-carboxylate (100 mg, 0.295 mmol) was dissolved in a mixture of THF (1.1 mL), dioxane (1.1 mL), water (737 μL) and LiOH (14.8 mg, 0.62 mmol). The reaction mixture was allowed to stir at r. t. for 1 h. Upon completion, 1N aqueous HCl was added to the reaction mixture and a precipitate formed. The solid was filtered on a Büchner funnel and rinsed with cold water to afford 6-(4-fluorophenyl)-8-(trifluoromethyl)imidazo[1,2-b]pyridazine-2-carboxylic acid which was used in the next reaction without further purification (91 mg, 95% yield). LCMS: m/z=326.28 (M+H$^+$)

Step III (I-35): 4-[6-(4-Fluorophenyl)-8-(trifluoromethyl)imidazo[1,2-b]pyridazine-2-carbonyl]-3,3-dimethyl-piperazin-2-one Scheme 66

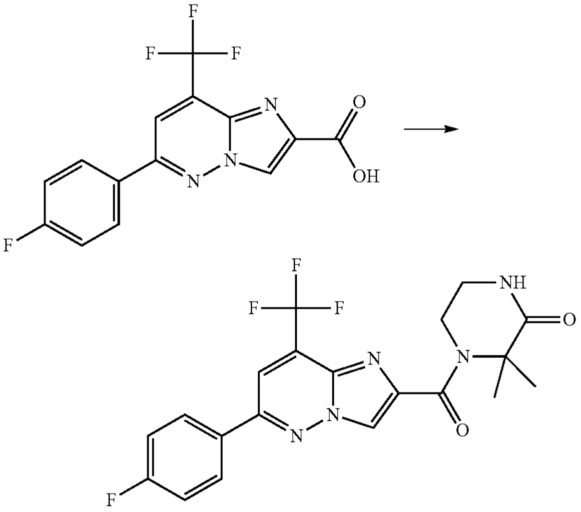

The product were prepared according to General Procedure 1 using 6-(4-Fluorophenyl)-8-(trifluoromethyl)imidazo[1,2-b]pyridazine-2-carboxylic acid (30 mg, 0.092 mmol), DMF (923 μL), DIPEA (41.7 mg, 56 μL, 0.32 mmol), 3,3-dimethylpiperazin-2-one (13.01 mg, 0.1015 mmol) and HATU (53 mg, 0.14 mmol) to afford 4-[6-(4-fluorophenyl)-8-(trifluoromethyl)imidazo[1,2-b]pyridazine-2-carbonyl]-3,3-dimethyl-piperazin2-2-one (21 mg, 52% yield). $^1$H NMR (400 MHz, DMSO-$d_6$) δ 8.83 (s, 1H), 8.32-8.29 (m, 1H), 8.27-8.20 (m, 2H), 8.14-8.10 (m, 1H), 7.49-7.40 (m, 2H), 3.88-3.81 (m, 2H), 3.36-3.31 (m, 2H), 1.71 (s, 6H). Note that in the $^1$H NMR spectrum the multiplet at 3.36-3.31 ppm was covered by the water signal in DMSO-$d_6$. LCMS: m/z=436.31 (M+H$^+$), retention time: 1.49 minutes using Method C.

Example 30 (I-36): 1-[4-[6-(4-Fluorophenyl)-8-(trifluoromethyl)imidazo[1,2-b]pyridazine-2-carbonyl]-3,3-dimethyl-piperazin-1-yl]-2-hydroxy-2-methyl-propan-1-one Step I: tert-Butyl 4-[6-(4-fluorophenyl)-8-(trifluoromethyl)imidazo[1,2-b]pyridazine-2-carbonyl]-3,3-dimethyl-piperazine-1-carboxylate Scheme 67

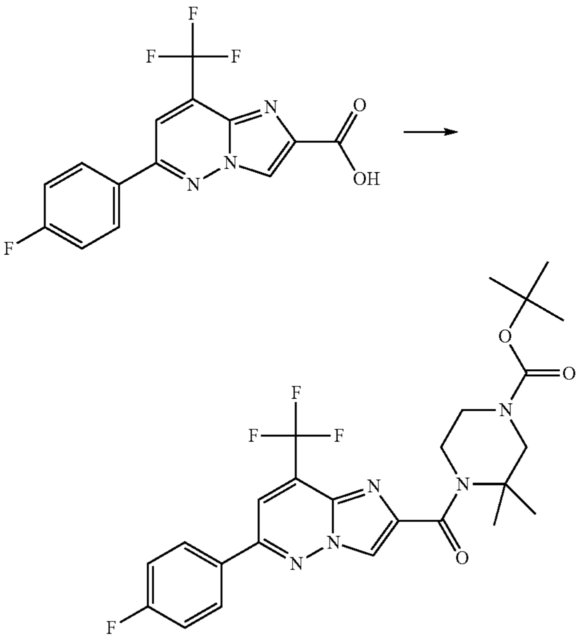

The product were prepared according to General Procedure 1 using 6-(4-Fluorophenyl)-8-(trifluoromethyl)imidazo[1,2-b]pyridazine-2-carboxylic acid (91 mg, 0.28 mmol), DMF (1.9 mL), DIPEA (127 mg, 171 μL, 0.98 mmol), tert-butyl 3,3-dimethylpiperazine-1-carboxylate (69 mg, 0.32 mmol) and HATU (160 mg, 0.42 mmol) to afford tert-Butyl 4-[6-(4-fluorophenyl)-8-(trifluoromethyl)imidazo[1,2-b]pyridazine-2-carbonyl]-3,3-dimethyl-piperazine-1-carboxylate (145 mg, 99% yield) was used as such in the next step. LCMS: m/z=522.45 (M+H$^+$)

Step II: (2,2-Dimethylpiperazin-1-yl)-[6-(4-fluorophenyl)-8-(trifluoromethyl)imidazo-[1,2-b]pyridazin-2-yl]methanone Scheme 68

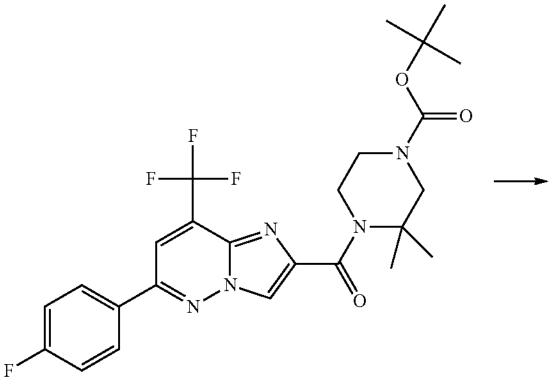

-continued

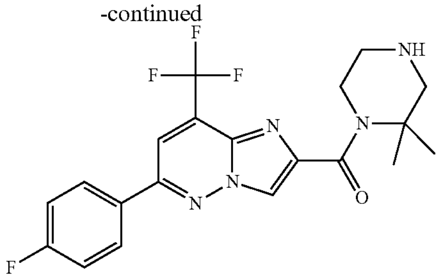

tert-Butyl 4-[6-(4-fluorophenyl)-8-(trifluoromethyl)imidazo[1,2-b]pyridazine-2-carbonyl]-3,3-dimethyl-piperazine-1-carboxylate (145 mg, 0.28 mmol) was dissolved in DCM (1 mL) and TFA (1 mL, 13 mmol) was added to the reaction mixture which was stirred at r. t. for 1 h. Upon completion, the reaction mixture was concentrated under vacuum. The residue obtained was diluted with DCM and a saturated solution of sodium bicarbonate was added, the resulting mixture was stirred for 15 min. The layers were partitioned and the aqueous layer was extracted with DCM 3 times. The combined organic extracts were dried over anhydrous sodium sulfate, filtered and concentrated under vacuum. The crude product (117 mg, 99% yield) was used as such in the next step. LCMS: m/z=422.12 (M+H$^+$)

Step III (I-36): 1-[4-[6-(4-Fluorophenyl)-8-(trifluoromethyl)imidazo[1,2-b]pyridazine-2-carbonyl]-3,3-dimethyl-piperazine-1-yl]-2-hydroxy-2-methyl-propan-1-one Scheme 69

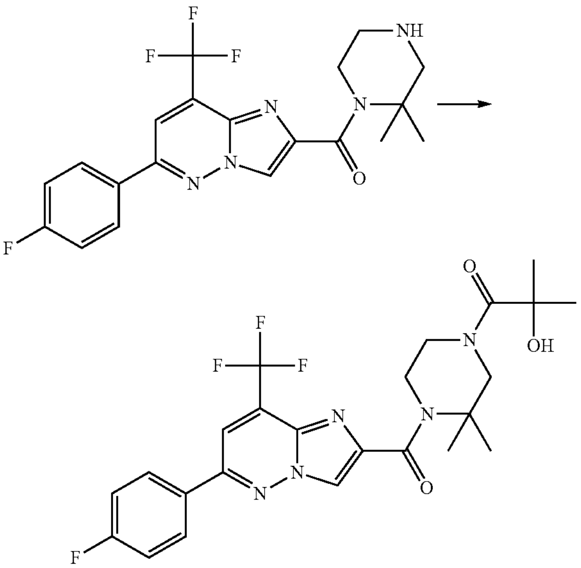

The product were prepared according to General Procedure 3 using (2,2-Dimethylpiperazin-1-yl)-[6-(4-fluorophenyl)-8-(trifluoromethyl)imidazo[1,2-b]pyridazin-2-yl]methanone (36 mg, 0.086 mmol), 2-hydroxy-2-methyl-propanoic acid (9.9 mg, 0.095 mmol), DIPEA (12 mg, 17 μL, 0.095 mmol), DMF (861 μL) and HATU (36 mg, 0.095 mmol) to afford 1-[4-[6-(4-fluorophenyl)-8-(trifluoromethyl)imidazo[1,2-b]pyridazine-2-carbonyl]-3,3-dimethylpiperazin-1-yl]-2-hydroxy-2-methyl-propan-1-one (16 mg, 35% yield). $^1H$ NMR (400 MHz, DMSO-$d_6$) δ 8.80 (s, 1H), 8.29 (s, 1H), 8.27-8.21 (m, 2H), 7.48-7.41 (m, 2H), 5.46-5.27 (m, 1H), 4.19-3.91 (m, 4H), 3.67-3.58 (m, 1H), 3.47-3.38 (m, 1H), 1.59-1.46 (m, 6H), 1.34 (s, 6H). LCMS: m/z=508.49 (M+H$^+$), retention time: 1.5 minutes using Method C.

Example 31 (I-37): [6-(4-Fluorophenyl)-8-(trifluoromethyl)imidazo[1,2-b]pyridazin-2-yl]-[4-(1-hydroxycyclobutanecarbonyl)-2,2-dimethyl-piperazin-1-yl]methanone Scheme 70

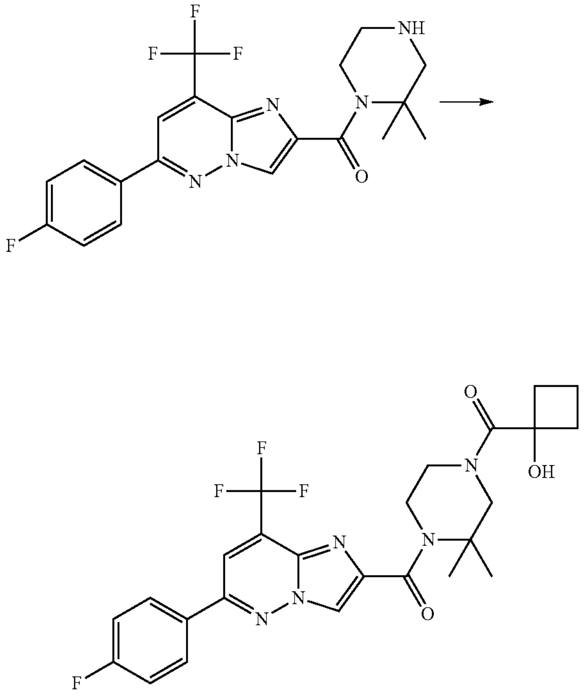

The product were prepared according to General Procedure 3 using (2,2-Dimethylpiperazin-1-yl)-[6-(4-fluorophenyl)-8-(trifluoromethyl)imidazo[1,2-b]pyridazin-2-yl] methanone (39 mg, 0.093 mmol), 1-hydroxycyclobutanecarboxylic acid (12 mg, 0.10 mmol), DIPEA (25 mg, 34 μL, 0.19 mmol), DMF (617 μL) and HATU (42.24 mg, 0.1111 mmol) to afford [6-(4-fluorophenyl)-8-(trifluoromethyl)imidazo[1,2-b]pyridazin-2-yl]-[4-(1-hydroxycyclobutanecarbonyl)-2,2-dimethyl-piperazin-1-yl]methanone (26 mg, 53% yield). $^1H$ NMR (400 MHz, DMSO-$d_6$) δ 8.82-8.76 (m, 1H), 8.29 (s, 1H), 8.27-8.20 (m, 2H), 7.48-7.41 (m, 2H), 6.00-5.91 (m, 1H), 4.09-4.00 (m, 1H), 3.95 (t, J=5.5 Hz, 1H), 3.81-3.70 (m, 2H), 3.63-3.58 (m, 1H), 3.47-3.42 (m, 1H), 2.62-2.53 (m, 2H), 2.10-1.99 (m, 2H), 1.83-1.71 (m, 1H), 1.56-1.42 (m, 7H). LCMS: m/z=520.45 (M+H$^+$), retention time: 1.62 minutes using Method C.

Example 32 (I-38): [6-(4-Fluorophenyl)-8-(trifluoromethyl)imidazo[1,2-b]pyridazin-2-yl]-[4-(4-hydroxytetrahydropyran-4-carbonyl)-2,2-dimethyl-piperazin-1-yl]methanone Scheme 71

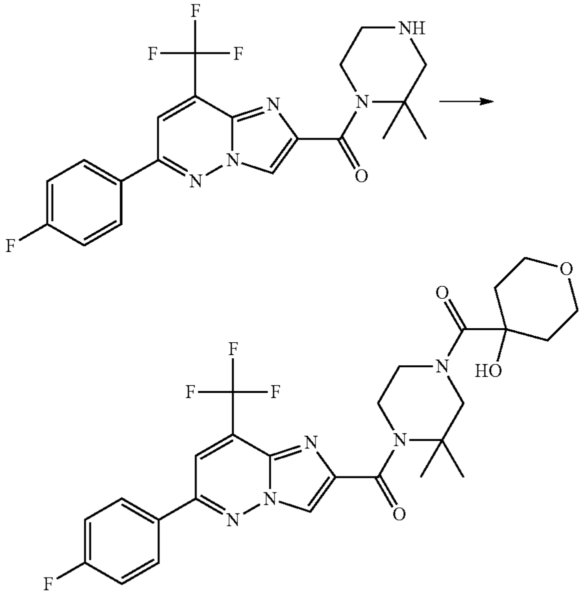

The product were prepared according to General Procedure 3 using (2,2-Dimethylpiperazin-1-yl)-[6-(4-fluorophenyl)-8-(trifluoromethyl)imidazo[1,2-b]pyridazin-2-yl] methanone (39 mg, 0.093 mmol), 4-hydroxytetrahydropyran-4-carboxylic acid (15 mg, 0.10 mmol), DIPEA (25 mg, 34 μL, 0.19 mmol), DMF (617 μL) and HATU (42 mg, 0.11 mmol) to afford [6-(4-fluorophenyl)-8-(trifluoromethyl)imidazo[1,2-b]pyridazin-2-yl]-[4-(4-hydroxytetrahydropyran-4-carbonyl)-2,2-dimethyl-piperazin-1-yl]methanone (26 mg, 47% yield). $^1H$ NMR (400 MHz, DMSO-$d_6$) δ 8.79 (s, 1H), 8.29 (d, J=1.1 Hz, 1H), 8.27-8.20 (m, 2H), 7.49-7.40 (m, 2H), 5.64-5.45 (m, 1H), 4.17-3.88 (m, 4H), 3.74-3.57 (m, 5H), 3.50-3.39 (m, 1H), 2.04-1.91 (m, 2H), 1.68-1.42 (m, 8H). LCMS: m/z=550.50 (M+H$^+$), retention time: 1.51 minutes using Method C.

Example 33 (I-39): (2S)-1-[4-[6-(4-Fluorophenyl)-8-(trifluoromethyl)imidazo[1,2-b]pyridazine-2-carbonyl]-3,3-dimethyl-piperazin-1-yl]-2-hydroxy-propan-1-one Scheme 72

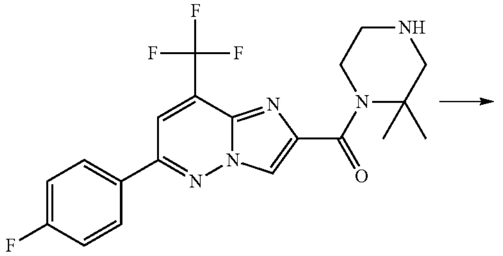

-continued

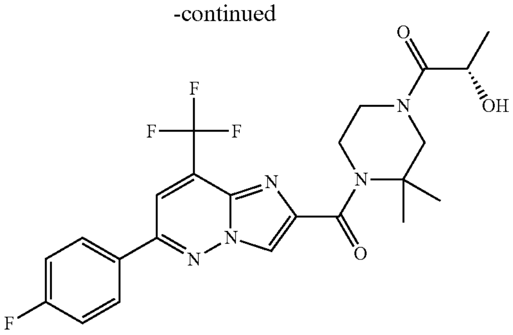

The product were prepared according to General Procedure 3 using (2,2-Dimethylpiperazin-1-yl)-[6-(4-fluorophenyl)-8-(trifluoromethyl)imidazo[1,2-b]pyridazin-2-yl]methanone (39 mg, 0.093 mmol), (2S)-2-hydroxypropanoic acid (9.2 mg, 0.10 mmol), DIPEA (25 mg, 34 μL, 0.19 mmol), DMF (617 μL) and HATU (42 mg, 0.11 mmol) to afford (2S)-1-[4-[6-(4-fluorophenyl)-8-(trifluoromethyl)imidazo[1,2-b]pyridazine-2-carbonyl]-3,3-dimethyl-piperazin-1-yl]-2-hydroxy-propan-1-one (28 mg, 57% yield).

$^1$H NMR (400 MHz, DMSO-$d_6$) δ 8.80 (d, J=4.1 Hz, 1H), 8.30 (s, 1H), 8.27-8.21 (m, 2H), 7.48-7.41 (m, 2H), 4.98 (dd, J=22.7, 7.2 Hz, 1H), 4.43 (dp, J=33.1, 6.7 Hz, 1H), 4.12-3.96 (m, 2H), 3.88-3.60 (m, 3H), 3.54-3.41 (m, 1H), 1.54 (s, 3H), 1.50 (d, J=4.9 Hz, 3H), 1.21 (dd, J=6.6, 1.7 Hz, 3H). LCMS: m/z=494.41 (M+H$^+$), retention time: 1.5 minutes using Method C.

Example 34 (I-40): [6-(Cyclohexen-1-yl)-8-isopropyl-imidazo[1,2-b]pyridazin-2-yl]-[4-(1-hydroxycyclobutanecarbonyl)-2,2-dimethyl-piperazin-1-yl]methanone Scheme 73

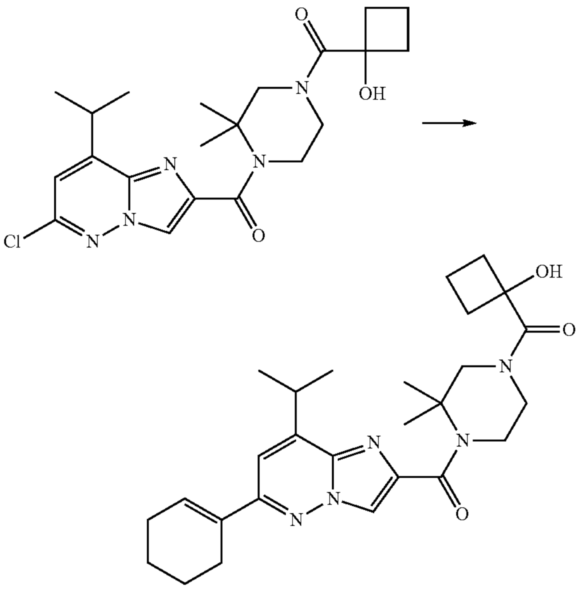

The product were prepared according to General Procedure 6 using (6-chloro-8-isopropyl-imidazo[1,2-b]pyridazin-2-yl)-[4-(1-hydroxycyclobutanecarbonyl)-2,2-dimethyl-piperazin-1-yl]methanone (100 mg, 0.22 mmol), dioxane (1.8 mL), $Pd_2dba_3$ (8.0 mg, 0.0088 mmol), S-Phos (13.7 mg, 0.033 mmol), aqueous solution of $K_3PO_4$ (330 μL of a 2 M aqueous solution, 0.66 mmol) and 1-cyclohexenylboronic acid (30.5 mg, 0.24 mmol) to afford [6-(cyclohexen-1-yl)-8-isopropyl-imidazo[1,2-b]pyridazin-2-yl]-[4-(1-hydroxycyclobutanecarbonyl)-2,2-dimethyl-piperazin-1-yl]methanone (106 mg, 95% yield). $^1$H NMR (400 MHz, Chloroform-d) δ 8.22 (s, 1H), 7.07 (d, J=0.8 Hz, 1H), 6.58 (dq, J=4.0, 2.0, 1.6 Hz, 1H), 4.42-4.21 (m, 2H), 3.92-3.62 (m, 3H), 3.54 (p, J=6.9 Hz, 1H), 2.82-2.70 (m, 2H), 2.59-2.49 (m, 2H), 2.35-2.22 (m, 3H), 2.19-2.07 (m, 2H), 2.02-1.91 (m, 1H), 1.86-1.66 (m, 4H), 1.65-1.57 (m, 7H), 1.39 (d, J=6.9 Hz, 6H). LCMS: m/z=480.55 (M+H$^+$), retention time: 1.86 minutes using Method C.

Example 35 (I-41): (6-Cyclohexyl-8-isopropyl-imidazo[1,2-b]pyridazin-2-yl)-[4-(1-hydroxycyclobutanecarbonyl)-2,2-dimethyl-piperazin-1-yl]methanone Scheme 74

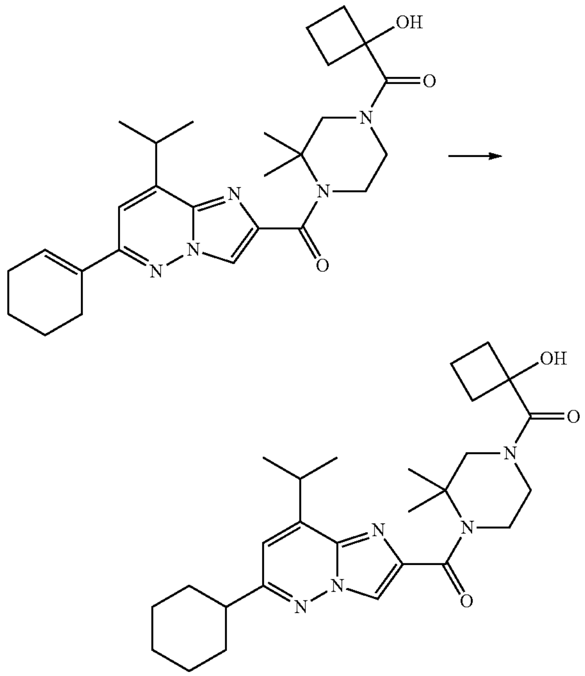

[6-(Cyclohexen-1-yl)-8-isopropyl-imidazo[1,2-b]pyridazin-2-yl]-[4-(1-hydroxycyclo-butanecarbonyl)-2,2-dimethyl-piperazin-1-yl]methanone (100 mg, 0.198 mmol) was dissolved in MeOH (2.0 mL) and the resulting solution was degassed for 5 min with nitrogen. Then palladium on charcoal 10% w/w (21 mg, 0.020 mmol) was added and the solution was stirred under a $H_2$ atmosphere at r. t. for 4 h, at which point the reaction was complete. The solution was purged with nitrogen for several min, then Celite was added and the resulting mixture was filtered over Celite and the residue was rinsed with MeOH. The filtrate was concentrated under vacuum to afford (6-cyclohexyl-8-isopropyl-imidazo[1,2-b]pyridazin-2-yl)-[4-(1-hydroxycyclobutanecarbonyl)-2,2-dimethyl-piperazin-1-yl]methanone (76 mg, 70% yield). $^1$H NMR (400 MHz, DMSO-$d_6$) δ 8.38-8.32 (m, 1H), 7.10 (s, 1H), 5.98 (s, 1H), 4.16-3.96 (m, 2H), 3.81-3.68 (m, 2H), 3.58 (s, 1H), 3.51-3.39 (m, 2H), 3.16 (s, 1H), 2.83-2.73 (m, 1H), 2.63-2.53 (m, 2H), 2.10-1.98 (m, 2H), 1.96-1.64 (m, 7H), 1.62-1.44 (m, 8H), 1.43-1.19 (m, 8H). LCMS: m/z=482.62 (M+H$^+$), retention time: 1.8 minutes using Method C.

Example 36 (I-42): [6-(2-Cyclopropylethynyl)-8-isopropyl-imidazo[1,2-b]pyridazin-2-yl]-[4-(1-hydroxycyclobutanecarbonyl)-2,2-dimethyl-piperazin-1-yl]methanone Scheme 75

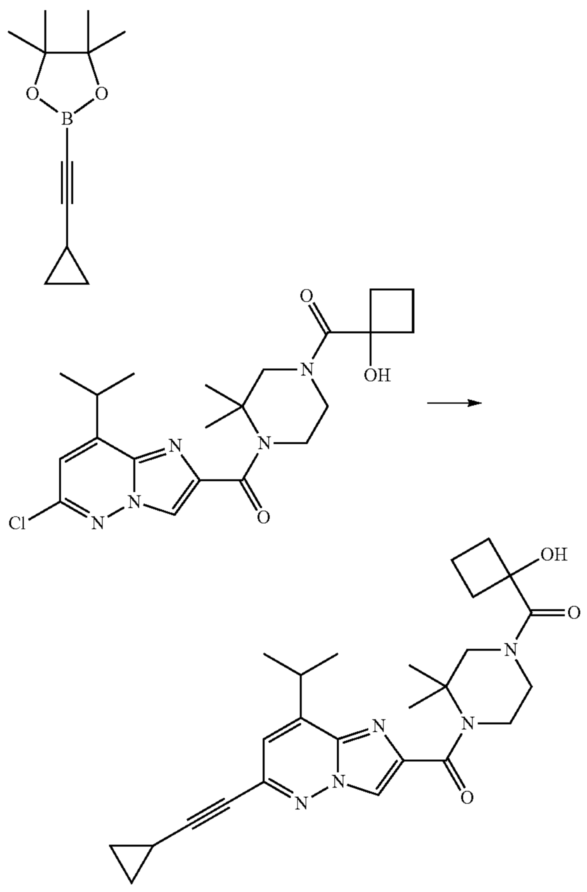

The product were prepared according to General Procedure 6 using 6-chloro-8-isopropyl-imidazo[1,2-b]pyridazin-2-yl)-[4-(1-hydroxycyclobutanecarbonyl)-2,2-dimethyl-piperazin-1-yl]methanone (60 mg, 0.14 mmol), dioxane (1.1 mL), $Pd_2dba_3$ (5.0 mg, 0.0055 mmol), S-Phos (8.6 mg, 0.021 mmol), aqueous solution of $K_3PO_4$ (207 μL of a 2 M solution, 0.41 mmol) and 2-(2-cyclopropylethynyl)-4,4,5,5-tetramethyl-1,3,2-dioxaborolane (29 mg, 0.15 mmol) to afford [6-(2-cyclopropylethynyl)-8-isopropyl-imidazo[1,2-b]pyridazin-2-yl]-[4-(1-hydroxycyclobutanecarbonyl)-2,2-dimethyl-piperazin-1-yl]methanone (18.9 mg, 27% yield). $^1$H NMR (400 MHz, DMSO-d$_6$) δ 8.46-8.43 (m, 1H), 7.14-7.13 (m, 1H), 5.99-5.90 (m, 1H), 4.12-3.96 (m, 2H), 3.79-3.70 (m, 2H), 3.59 (s, 1H), 3.50-3.40 (m, 2H), 2.61-2.53 (m, 2H), 2.09-1.97 (m, 2H), 1.84-1.60 (m, 1H), 1.55-1.44 (m, 7H), 1.35 (d, J=6.9 Hz, 6H), 1.09 (t, J=7.0 Hz, 1H), 1.03-0.93 (m, 2H), 0.91-0.82 (m, 2H). LCMS: m/z=464.49 (M+H$^+$), retention time: 1.63 minutes using Method C.

Example 37 (I-43): [6-(Cyclopenten-1-yl)-8-isopropyl-imidazo[1,2-b]pyridazin-2-yl]-[4-(1-hydroxycyclobutanecarbonyl)-2,2-dimethyl-piperazin-1-yl]methanone Scheme 76

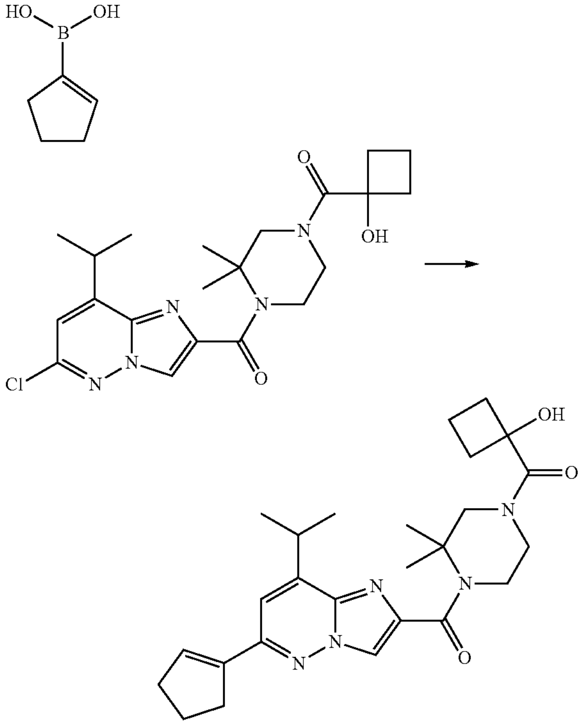

The product were prepared according to General Procedure 6 using (6-chloro-8-isopropyl-imidazo[1,2-b]pyridazin-2-yl)-[4-(1-hydroxycyclobutanecarbonyl)-2,2-dimethyl-piperazin-1-yl]methanone (60 mg, 0.13 mmol), dioxane (1.1 mL), $Pd_2dba_3$ (4.8 mg, 0.0052 mmol), S-Phos (8.2 mg, 0.020 mmol), aqueous solution of $K_3PO_4$ (198 μL of a 2 M solution, 0.40 mmol) and cyclopenten-1-ylboronic acid (16 mg, 0.15 mmol) to afford [6-(cyclopenten-1-yl)-8-isopropyl-imidazo[1,2-b]pyridazin-2-yl]-[4-(1-hydroxycyclobutanecarbonyl)-2,2-dimethyl-piperazin-1-yl]methanone. (7 mg, 11% yield). $^1$H NMR (400 MHz, DMSO-d$_6$) δ 8.40-8.36 (m, 1H), 7.51 (s, 1H), 6.94 (s, 1H), 6.01-5.88 (m, 1H), 4.17-4.08 (m, 1H), 4.02 (t, J=5.6 Hz, 1H), 3.81-3.76 (m, 1H), 3.70 (s, 1H), 3.58 (s, 1H), 3.53-3.41 (m, 2H), 2.83-2.70 (m, 2H), 2.64-2.54 (m, 4H), 2.10-1.93 (m, 4H), 1.84-1.69 (m, 1H), 1.55-1.45 (m, 7H), 1.39 (d, J=6.9 Hz, 6H). LCMS: m/z=466.5 (M+H$^+$), retention time: 1.75 minutes using Method C.

Example 38 (I-44): [6-(3,6-dihydro-2H-pyran-4-yl)-8-isopropyl-imidazo[1,2-b]pyridazin-2-yl]-[4-(1-hydroxycyclobutanecarbonyl)-2,2-dimethyl-piperazin-1-yl]methanone Scheme 77

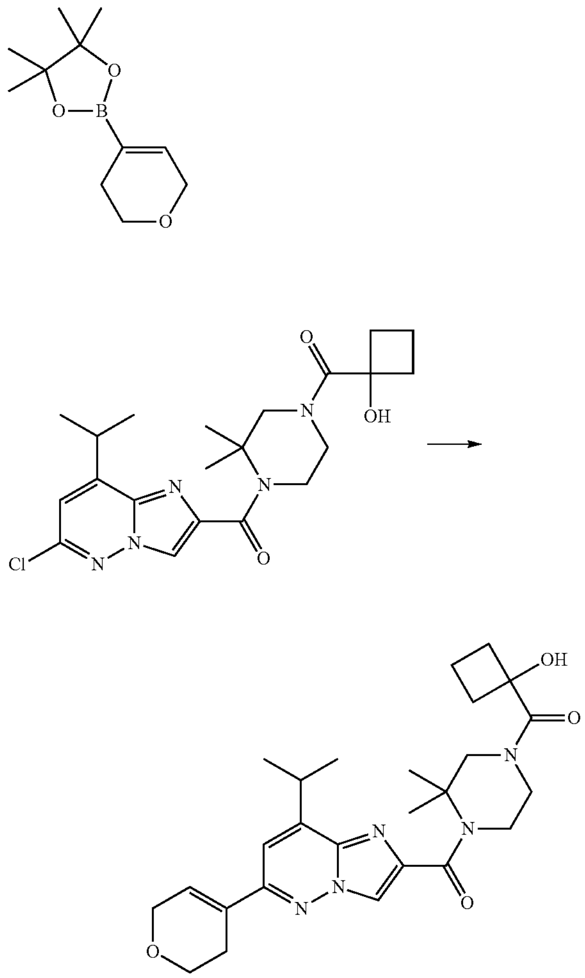

The product were prepared according to General Procedure 6 using (6-chloro-8-isopropyl-imidazo[1,2-b]pyridazin-2-yl)-[4-(1-hydroxycyclobutanecarbonyl)-2,2-dimethyl-piperazin-1-yl]methanone (60 mg, 0.13 mmol), dioxane (1.1 mL), $Pd_2dba_3$ (4.8 mg, 0.0053 mmol), S-Phos (8.3 mg, 0.020 mmol), aqueous solution of $K_3PO_4$ (198 μL of a 2 M solution, 0.40 mmol) and 2-(3,6-dihydro-2H-pyran-4-yl)-4,4,5,5-tetramethyl-1,3,2-dioxaborolane (30 mg, 0.15 mmol) to afford [6-(3,6-dihydro-2H-pyran-4-yl)-8-isopropyl-imidazo[1,2-b]pyridazin-2-yl]-[4-(1-hydroxycyclobutanecarbonyl)-2,2-dimethyl-piperazin-1-yl]methanone (25 mg, 38% yield). $^1H$ NMR (400 MHz, DMSO-$d_6$) δ 8.42-8.37 (m, 1H), 7.47 (s, 1H), 6.96 (s, 1H), 6.01-5.89 (m, 1H), 4.36-4.29 (m, 2H), 4.16-4.08 (m, 1H), 4.01 (t, J=5.5 Hz, 1H), 3.87-3.80 (m, 2H), 3.77 (t, J=5.7 Hz, 1H), 3.71 (s, 1H), 3.59 (s, 1H), 3.54-3.41 (m, 2H), 2.63-2.52 (m, 4H), 2.10-1.97 (m, 2H), 1.83-1.68 (m, 1H), 1.54-1.43 (m, 7H), 1.39 (d, J=6.9 Hz, 6H). LCMS: m/z=482.51 (M+H$^+$), retention time: 1.39 minutes using Method C.

Example 39 (I-45): [4-(1-hydroxycyclobutanecarbonyl)-2,2-dimethyl-piperazin-1-yl]-(8-iso-propyl-6-tetrahydropyran-4-yl-imidazo[1,2-b]pyridazin-2-yl)methanone Scheme 78

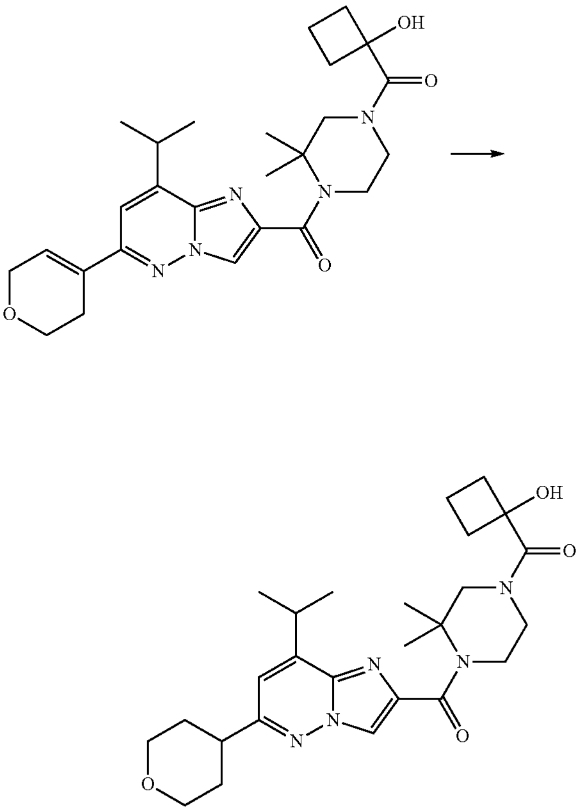

[6-(3,6-Dihydro-2H-pyran-4-yl)-8-isopropyl-imidazo[1,2-b]pyridazin-2-yl]-[4-(1-hydroxycyclobutanecarbonyl)-2,2-dimethyl-piperazin-1-yl]methanone (20 mg, 0.041 mmol) was dissolved in MeOH (2 mL) and the resulting solution was degassed for 5 min with nitrogen. Then palladium on charcoal 10% w/w (4.3 mg, 0.0041 mmol) was added and the solution was stirred under a $H_2$ atmosphere at r. t. for 1 hour, at which point the reaction was complete. The solution was purged with nitrogen for several min, then Celite was added and the resulting solution was filtered over Celite and rinsed with MeOH. The filtrate was concentrated under vacuum to afford [4-(1-hydroxycyclobutanecarbonyl)-2,2-dimethyl-piperazin-1-yl]-(8-isopropyl-6-tetrahydropyran-4-yl-imidazo[1,2-b]pyridazin-2-yl)methanone (20 mg, 95% yield). $^1H$ NMR (400 MHz, DMSO-$d_6$) δ 8.42-8.36 (m, 1H), 7.16 (s, 1H), 6.00 (s, 1H), 4.10 (t, J=5.7 Hz, 1H), 4.04-3.92 (m, 3H), 3.76 (t, J=5.6 Hz, 1H), 3.70 (s, 1H), 3.58 (s, 1H), 3.53-3.42 (m, 4H), 3.17 (s, 1H), 3.12-2.99 (m, 1H), 2.62-2.54 (m, 2H), 2.08-1.98 (m, 2H), 1.91-1.69 (m, 5H), 1.55-1.44 (m, 6H), 1.37 (d, J=6.9 Hz, 6H). LCMS: m/z=484.56 (M+H$^+$).

Example 40 (I-184): 4-[6-(4-fluorophenyl)-8-(1-hydroxy-1-methyl-ethyl)imidazo[1,2-b]pyridazine-2-carbonyl]-3,3-dimethyl-piperazin-2-one Scheme 79

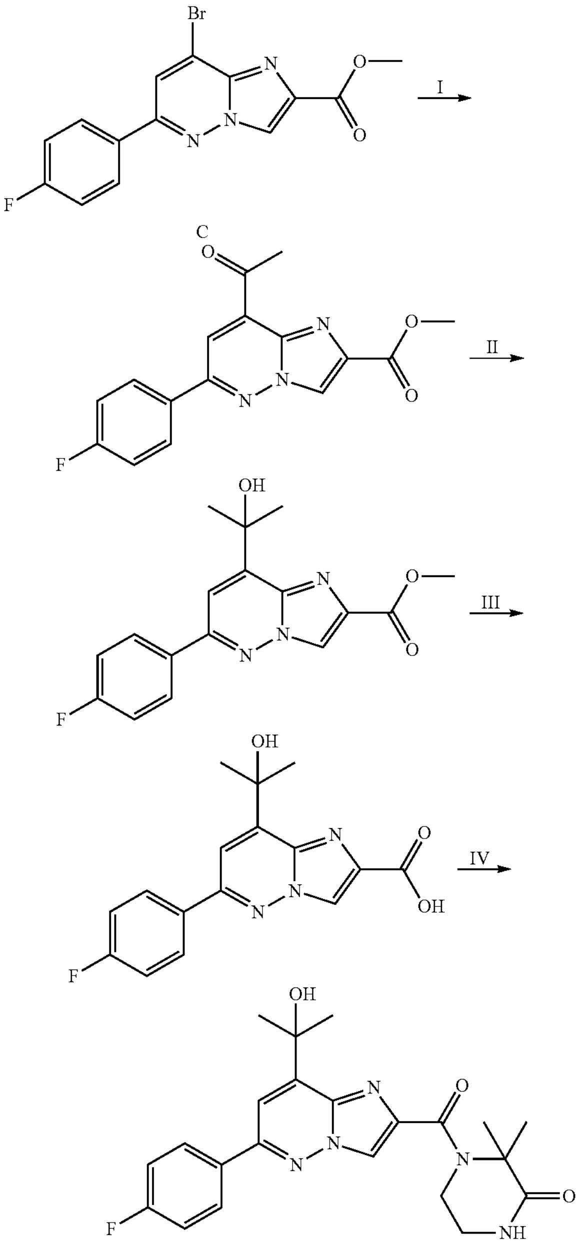

Step I: methyl 8-acetyl-6-(4-fluorophenyl)imidazo[1,2-b]pyridazine-2-carboxylate In a dry and under nitrogen seal tube was dissolved intermediate C (2 g, 5.712 mmol) in toluene (11.42 mL). To the solution was added 1-ethoxyvinyltributyltin (2.269 g, 2.123 mL, 6.283 mmol) and dichloropalladium; triphenylphosphane (40.09 mg, 0.05712 mmol). The reaction mixture was stirred at 100° C. for 24 h.

The reaction mixture was cooled down to rt and HCl (2.855 mL of 4 M in dioxane, 11.42 mmol) was added. The reaction mixture was stirred at rt for 72 h (OWE). Water was added along with EtOAc and the phases were separated. The organic phase was washed 2 other times with sat. brine and water (1:1). It was then dried over MgSO4, filtered and evaporated under reduced pressure. Purification by flash chromatography on silica gel was carried out under standard condition to afford methyl 8-acetyl-6-(4-fluorophenyl)imidazo[1,2-b]pyridazine-2-carboxylate (855 mg, 2.729 mmol, 47.79%) as a yellow solid. $^1$H NMR (400 MHz, DMSO-$d_6$) δ 9.05 (s, 1H), 8.23-8.15 (m, 2H), 8.12 (s, 1H), 7.49-7.39 (m, 2H), 3.91 (s, 3H), 2.98 (s, 3H). LC-MS: 313.91 (M+H$^+$).

Step II: methyl 6-(4-fluorophenyl)-8-(1-hydroxy-1-methyl-ethyl)imidazo[1,2-b]pyridazine-2-carboxylate A solution of $TiCl_4$ (317.9 mg, 142.8 μL, 1.676 mmol) in DCM (5 mL), in an oven-dry 10 ml flask equipped with an N2-inlet, was cool to −42° C. Upon cooling, dimethylzinc (838.0 μL of 2 M, 1.676 mmol) (in toluene) was slowly added via a syringe, the mixture being agitated with a magnetic stirrer. Stirring was continued for 10 minutes. A solution of methyl 8-acetyl-6-(4-fluorophenyl)imidazo[1,2-b]pyridazine-2-carboxylate (250 mg, 0.7980 mmol) in 1.5 mL of DCM was added dropwise to the above reaction mixture at −42° C. and stirred 1 h. The mixture was slowly allowed to come to room temperature during a period of about 2 h. To the complete reaction was added water along with EtOAc and the phases were separated. The organic phase was washed once with NaHCO3 and separated again. The organic phase was dried over MgSO4, filtered and evaporated under reduced pressure. Purification by flash chromatography on silica gel was carried out under standard condition to afford methyl 6-(4-fluorophenyl)-8-(1-hydroxy-1-methyl-ethyl)imidazo[1,2-b]pyridazine-2-carboxylate (235 mg, 0.7136 mmol, 89.42%) as a brown solid. $^1$H NMR (400 MHz, DMSO-$d_6$) δ 8.86 (s, 1H), 8.13-8.05 (m, 2H), 7.83 (s, 1H), 7.49-7.38 (m, 2H), 5.71 (s, 1H), 3.88 (s, 3H), 1.75 (s, 6H). LC-MS: 329.92 (M+H$^+$).

Step III: 6-(4-fluorophenyl)-8-(1-hydroxy-1-methyl-ethyl)imidazo[1,2-b]pyridazine-2-carboxylic acid Methyl 6-(4-fluorophenyl)-8-(1-hydroxy-1-methyl-ethyl)imidazo[1,2-b]pyridazine-2-carboxylate (24 mg, 0.07288 mmol) was dissolved in MeOH (1.171 mL) and NaOH (728.8 μL of 1 M, 0.7288 mmol) was added. The solution was stirred at rt for 2 h. HCl 6N was added until acidic pH was reached. Water was added along with EtOAc and the phases were separated. The organic phase was dried over MgSO4, filtered and evaporated under reduced pressure to afford 6-(4-fluorophenyl)-8-(1-hydroxy-1-methyl-ethyl)imidazo[1,2-b]pyridazine-2-carboxylic acid (22.98 mg, 0.07288 mmol, 100.0%) as a yellowish solid. LC-MS: 315.97 (M+H$^+$).

Step IV: 4-[6-(4-fluorophenyl)-8-(1-hydroxy-1-methyl-ethyl)imidazo[1,2-b]pyridazine-2-carbonyl]-3,3-dimethyl-piperazin-2-one The product were prepared according to General Procedure 1 using 6-(4-fluorophenyl)-8-(1-hydroxy-1-methyl-ethyl)imidazo[1,2-b]pyridazine-2-carboxylic acid (23 mg, 0.07295 mmol), DMF (1000 μL), DIPEA (33.01 mg, 44.49 μL, 0.2554 mmol), 3,3-dimethylpiperazin-2-one (10.29 mg, 0.08025 mmol) and HATU (41.60 mg, 0.1094 mmol) to afford 4-[6-(4-fluorophenyl)-8-(1-hydroxy-1-methyl-ethyl)

imidazo[1,2-b]pyridazine-2-carbonyl]-3,3-dimethyl-piperazin-2-one (10.6 mg, 0.02467 mmol, 33.81%). $^1$H NMR (400 MHz, DMSO-$d_6$) δ 8.59 (s, 1H), 8.14-8.04 (m, 3H), 7.80 (s, 1H), 7.47-7.39 (m, 2H), 5.70 (s, 1H), 3.97-3.89 (m, 2H), 3.58-3.23 (m, 2H), 1.73 (s, 6H), 1.70 (s, 6H). LC-MS: 426.41 (M+H$^+$), retention time: 2.45 minutes using Method A Example 41 (I-191): 4-(8-(tert-butyl)-6-(4-fluorophenyl)imidazo[1,2-b]pyridazine-2-carbonyl)-3,3-dimethylpiperazin-2-one Scheme 80

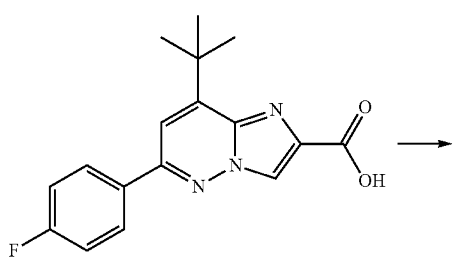

P

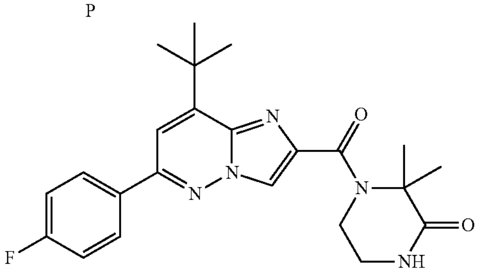

The product were prepared according to General Procedure 1 using intermediate P (14.0 g, 44.26 mmol), DMF (138.7 mL), DIPEA (14.29 g, 19.26 mL, 110.6 mmol), 3,3-dimethylpiperazin-2-one (6.241 g, 48.69 mmol) and [dimethylamino-(triazolo[5,4-b]pyridin-3-yloxy)methylene]-dimethyl-ammonium (Phosphorus Hexafluoride Ion) (18.51 g, 48.69 mmol) affording 4-(8-(tert-butyl)-6-(4-fluorophenyl)imidazo[1,2-b]pyridazine-2-carbonyl)-3,3-dimethylpiperazin-2-one (14.73 g, 34.23 mmol, 77.36%). $^1$H NMR (400 MHz, DMSO-d6) δ 8.57 (s, 1H), 8.18-8.10 (m, 2H), 8.08-8.02 (m, 1H), 7.49 (s, 1H), 7.46-7.35 (m, 2H), 4.03-3.95 (m, 2H), 3.43-3.34 (m, 2H), 2.35-2.24 (m, 2H), 2.19-1.99 (m, 4H), 1.86-1.70 (m, 2H), 1.58 (s, 9H). 424.69 (M+1), retention time: 3.18 minutes using Method A.

Example 42 (I-244): 4-[6-(4-fluoro-3-methyl-phenyl)-8-isopropyl-imidazo[1,2-b]pyridazine-2-carbonyl]-3,3-dimethyl-piperazin-2-one Scheme 81

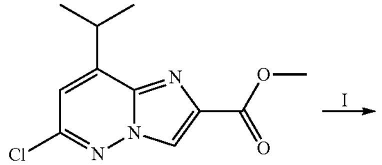

-continued

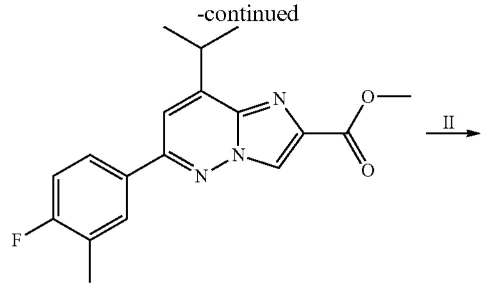

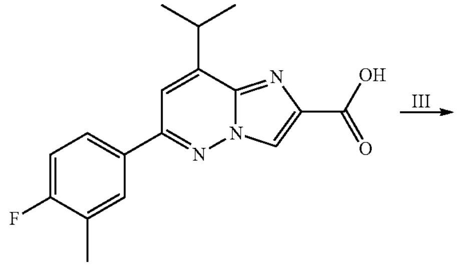

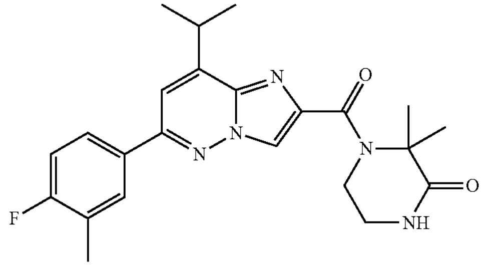

Step I: methyl 6-(4-fluoro-3-methyl-phenyl)-8-isopropyl-imidazo[1,2-b]pyridazine-2-carboxylate The product was prepared according to General Procedure 5 using DMF (10.00 mL), methyl 6-chloro-8-isopropyl-imidazo[1,2-b]pyridazine-2-carboxylate (described in example 13, scheme 26) (1 g, 3.942 mmol), (4-fluoro-3-methyl-phenyl)boronic acid (667.5 mg, 4.336 mmol), $PdCl_2(dppf)_2$-DCM (16.10 mg, 0.01971 mmol) and $Na_2CO_3$ (3.942 mL of 2 M, 7.884 mmol) to afford methyl 6-(4-fluoro-3-methyl-phenyl)-8-isopropyl-imidazo[1,2-b]pyridazine-2-carboxylate (1.169 g, 3.543 mmol, 89.90%) as a beige solid. $^1$H NMR (400 MHz, DMSO-$d_6$) δ 8.82 (s, 1H), 8.05 (ddd, J=7.5, 2.3, 0.9 Hz, 1H), 8.01-7.91 (m, 1H), 7.69 (d, J=0.8 Hz, 1H), 7.33 (dd, J=9.5, 8.6 Hz, 1H), 3.88 (s, 3H), 3.65-3.52 (m, 1H), 2.35 (d, J=2.1 Hz, 3H), 1.43 (d, J=6.9 Hz, 6H). LC-MS: 328.30 (M+H$^+$).

Step II: 6-(4-fluoro-3-methyl-phenyl)-8-isopropyl-imidazo[1,2-b]pyridazine-2-carboxylic acid To a 100 mL rbf equipped with a temperature probe and a $N_2$ inlet was added methyl 6-(4-fluoro-3-methyl-phenyl)-8-isopropyl-imidazo[1,2-b]pyridazine-2-carboxylate (1.0 g, 3.029 mmol) and MeOH (9.916 mL). NaOH (7.575 mL of 2 M, 15.15 mmol) was then added dropwise over 2 min and the reaction mixture (beige slurry, SM not completely soluble in MeOH) was stirred at rt for 2 days (OWE). HCl 12N was added until pH 1-2 was obtained and everything became soluble. The mixture was concentrated to remove MeOH then diluted in 15 mL of ethyl acetate. The layers were separated and the aqueous was back-extracted with 15 ml of ethyl acetate. The combined organic phases were dried over $MgSO_4$, filtered and concentrated under reduced pressure to afford 6-(4-fluoro-3-methyl-phenyl)-8-isopropyl-imidazo[1,2-b]pyridazine-2-carboxylic acid (960 mg, 3.064 mmol, 101.1%) as a light yellow foamy solid. $^1$H NMR (400 MHz, DMSO-$d_6$) δ 12.95 (s, 1H), 8.73 (s, 1H), 8.06 (ddd, J=7.5, 2.4, 0.9 Hz, 1H), 8.00-7.94 (m, 1H), 7.68 (d, J=0.8 Hz, 1H), 7.38-7.29 (m, 1H), 3.67-3.53 (m, 1H), 2.35 (d, J=1.9 Hz, 3H), 1.43 (d, J=6.9 Hz, 6H). LC-MS: 314.3 (M+H$^+$).

Step III: 4-[6-(4-fluoro-3-methyl-phenyl)-8-isopropyl-imidazo[1,2-b]pyridazine-2-carbonyl]-3,3-dimethyl-piperazin-2-one The product was prepared according to General Procedure 1 using 6-(4-fluoro-3-methyl-phenyl)-8-isopropyl-imidazo[1,2-b]pyridazine-2-carboxylic acid (1.0 g, 3.192 mmol), DMF (10.00 mL), DIPEA (1.031 g, 1.389 mL, 7.980 mmol), 3,3-dimethylpiperazin-2-one (450.0 mg, 3.511 mmol) and [dimethylamino-(triazolo[5,4-b]pyridin-3-yloxy)methylene]-dimethyl-ammonium (Phosphorus Hexafluoride Ion) (1.335 g, 3.511 mmol) to afford 4-[6-(4-fluoro-3-methyl-phenyl)-8-isopropyl-imidazo[1,2-b]pyridazine-2-carbonyl]-3,3-dimethyl-piperazin-2-one (1.175 g, 2.724 mmol, 85.31%). $^1$H NMR (400 MHz, DMSO-$d_6$) δ 8.52 (s, 1H), 8.11-7.98 (m, 2H), 7.98-7.84 (m, 1H), 7.64 (s, 1H), 7.30 (t, J=9.1 Hz, 1H), 3.98-3.84 (m, 2H), 3.51 (p, J=6.9 Hz, 1H), 3.38-3.29 (m, 2H), 2.32 (s, 3H), 1.67 (s, 6H), 1.41 (d, J=6.9 Hz, 6H). LC-MS: 424.49 (M+H$^+$). retention time: 1.87 minutes using Method C Example 43 (I-283): 4-[8-tert-butyl-6-[4-(trifluoromethyl)phenyl]imidazo[1,2-b]pyridazine-2-carbonyl]-3,3-dimethyl-piperazin-2-one Scheme 82

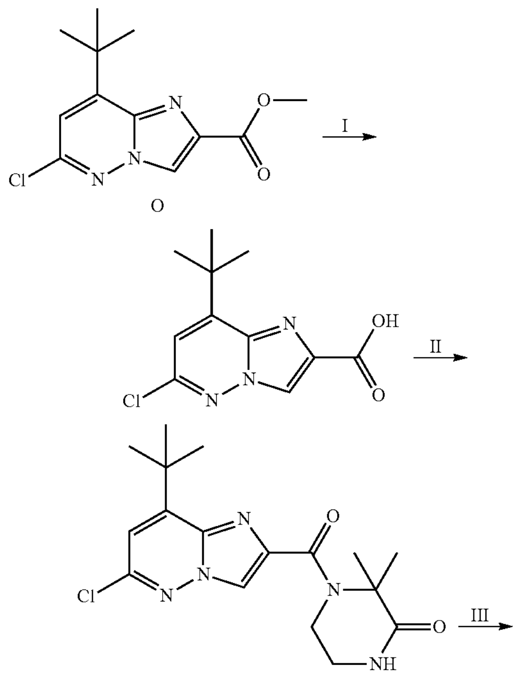

-continued

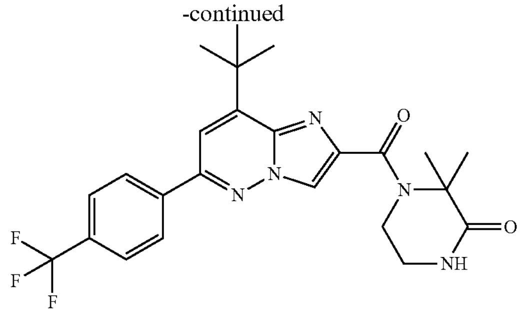

Step I: 8-tert-butyl-6-chloro-imidazo[1,2-b]pyridazine-2-carboxylic acid

The product was prepared according to General Procedure 4 using intermediate O (106 mg, 0.3959 mmol), dioxane (2.639 mL), water (1.320 mL) and LiOH (19.91 mg, 0.8314 mmol) to afford crude 8-tert-butyl-6-chloro-imidazo[1,2-b]pyridazine-2-carboxylic acid (100.4 mg, 0.3958 mmol, 100.0%). $^1$H NMR (400 MHz, DMSO-d6) δ 13.07 (s, 1H), 8.74 (s, 1H), 7.15 (s, 1H), 1.53 (s, 9H). LC-MS: 254.14 (M+H$^+$).

Step II: 4-(8-tert-butyl-6-chloro-imidazo[1,2-b]pyridazine-2-carbonyl)-3,3-dimethyl-piperazin-2-one The product was prepared according to General Procedure 1 using 8-tert-butyl-6-chloro-imidazo[1,2-b]pyridazine-2-carboxylic acid (558 mg, 2.200 mmol)), HATU (1.004 g, 2.640 mmol), DMF (11.00 mL), Hünig's base (853.0 mg, 1.150 mL, 6.600 mmol) and 3,3-dimethylpiperazin-2-one (338.4 mg, 2.640 mmol). Water was added and the desired product precipitated. The solid was filtered on Buchner affording the title compound 4-(8-tert-butyl-6-chloro-imidazo[1,2-b]pyridazine-2-carbonyl)-3,3-dimethyl-piperazin-2-one (710 mg, 1.951 mmol, 88.69%). $^1$H NMR (400 MHz, DMSO-$d_6$) δ 8.58 (s, 1H), 8.09 (t, J=3.1 Hz, 1H), 7.15 (s, 1H), 3.98-3.84 (m, 2H), 3.41-3.32 (m, 2H), 1.69 (s, 6H), 1.51 (s, 9H). LC-MS: 364.54 (M+H$^+$).

Step III: 4-[8-tert-butyl-6-[4-(trifluoromethyl)phenyl]imidazo[1,2-b]pyridazine-2-carbonyl]-3,3-dimethyl-piperazin-2-one The product was prepared according to General Procedure 6 using 4-(8-tert-butyl-6-chloro-imidazo[1,2-b]pyridazine-2-carbonyl)-3,3-dimethyl-piperazin-2-one (69 mg, 0.1669 mmol), dioxane (1.669 mL), $Pd_2(DBA)_3.CHCl_3$ (6.910 mg, 0.006676 mmol), S-Phos (10.42 mg, 0.02537 mmol), $K_3PO_4$ (250.4 μL of 2 M, 0.5007 mmol) and [4-(trifluoromethyl)phenyl]boronic acid (63.40 mg, 0.3338 mmol). The crude oil was triturated with $Et_2O$ and the solid was filtered over Buchner to afford the title compound 4-[8-tert-butyl-6-[4-(trifluoromethyl)phenyl]imidazo[1,2-b]pyridazine-2-carbonyl]-3,3-dimethyl-piperazin-2-one (37.06 mg, 0.06888 mmol, 41.27%). $^1$H NMR (400 MHz, DMSO-$d_6$) δ 8.63 (s, 1H), 8.34-8.28 (m, 2H), 8.13-8.08 (m, 1H), 7.98-7.92 (m, 2H), 7.57 (s, 1H), 4.00-3.94 (m, 2H), 3.44-3.37 (m, 2H), 1.71 (s, 6H), 1.60 (s, 9H). LC-MS: 474.71 (M+H$^+$), retention time: 1.89 minutes using Method C Example 44 (I-316): [6-(4-fluorophenyl)-8-isopropyl-imidazo[1,2-b]pyridazin-2-yl]-[4-(3-hydroxy-3-methyl-cyclobutanecarbonyl)-2,2-dimethyl-piperazin-1-yl]methanone Scheme 83

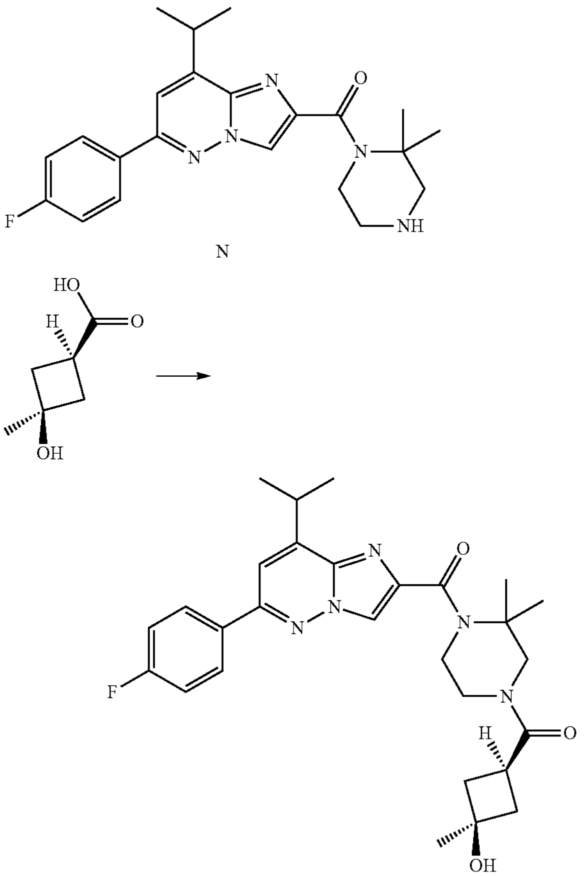

N

The product was prepared according to General Procedure 3 using Intermediate N (83.05 mg, 0.1923 mmol), HATU (87.76 mg, 0.2308 mmol), DMF (641.0 μL), Hünig's base (99.41 mg, 134.0 μL, 0.7692 mmol) and (1S,3S)-3-hydroxy-3-methylcyclobutane-1-carboxylic acid (27.52 mg, 0.2115 mmol) affording the title compound [6-(4-fluorophenyl)-8-isopropyl-imidazo [1,2-b]pyridazin-2-yl]-[4-(3-hydroxy-3-methyl-cyclobutanecarbonyl)-2,2-dimethyl-piperazin-1-yl] methanone (48.83 mg, 0.09620 mmol, 50.03%). $^1$H NMR (400 MHz, DMSO-$d_6$) δ 8.55-8.51 (m, 1H), 8.19-8.13 (m, 2H), 7.70-7.66 (m, 1H), 7.44-7.37 (m, 2H), 4.98 (d, J=14.7 Hz, 1H), 4.17-4.07 (m, 2H), 3.66-3.60 (m, 2H), 3.59-3.51 (m, 2H), 3.49-3.42 (m, 1H), 2.94-2.77 (m, 1H), 2.24-2.14 (m, 2H), 2.14-2.04 (m, 2H), 1.58-1.36 (m, 12H), 1.33-1.22 (m, 3H). LC-MS: 508.73 (M+H$^+$), retention time: 1.57 minutes using Method C.

Example 45 (I-343): (8-(tert-butyl)-6-(4-fluorophenyl)imidazo[1,2-b]pyridazin-2-yl)(2,2-dimethyl-4-(5-methyl-1H-1,2,4-triazole-3-carbonyl)piperazin-1-yl)methanone Scheme 84

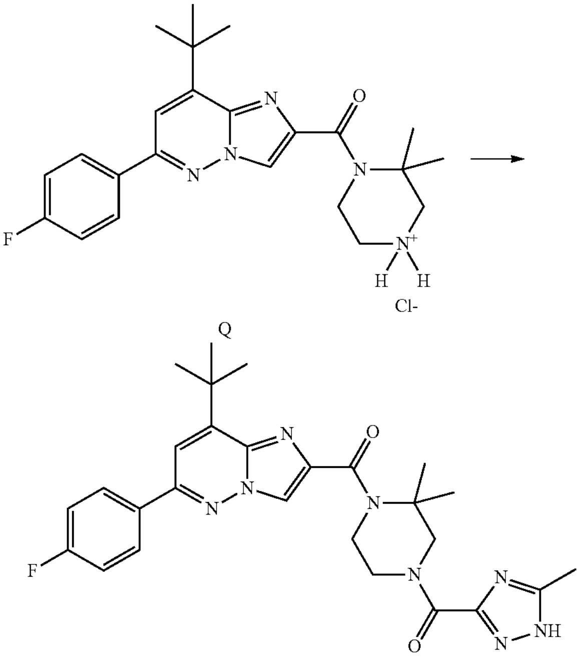

Q

The product were prepared according to General Procedure 3 using intermediate Q (55 g, 122.2 mmol), DMF (545 mL), DIPEA (55.28 g, 74.50 mL, 427.7 mmol), 5-methyl-1H-1,2,4-triazole-3-carboxylic acid (16.31 g, 128.3 mmol) and HATU (Phosphorus Hexafluoride Ion) (48.78 g, 128.3 mmol) affording (8-(tert-butyl)-6-(4-fluorophenyl)imidazo [1,2-b]pyridazin-2-yl)(2,2-dimethyl-4-(5-methyl-1H-1,2,4-triazole-3-carbonyl)piperazin-1-yl)methanone (49.76 g, 95.69 mmol, 78.31%). $^1$H NMR (400 MHz, DMSO-d6) δ 8.48 (d, J=6.3 Hz, 1H), 8.17-8.04 (m, 2H), 7.45 (d, J=9.7 Hz, 1H), 7.38 (td, J=8.9, 3.0 Hz, 2H), 4.27 (t, J=5.9 Hz, 1H), 4.13 (t, J=5.6 Hz, 1H), 4.02 (d, J=16.9 Hz, 2H), 3.78 (s, 1H), 3.71 (dd, J=6.6, 4.8 Hz, 2H), 2.37 (d, J=6.4 Hz, 3H), 1.58 (s, 6H), 1.54 (s, 3H), 1.51 (s, 4H), 1.46 (s, 4H). LC-MS: 519.47 (M+1), retention time: 1.58 minutes using Method C.

Example 46 (I-436) [8-tert-butyl-6-(4-chlorophenyl) imidazo[1,2-b]pyridazin-2-yl]-[2,2-dimethyl-4-(5-methyl-1H-1,2,4-triazole-3-carbonyl)piperazin-1-yl] methanone Scheme 85

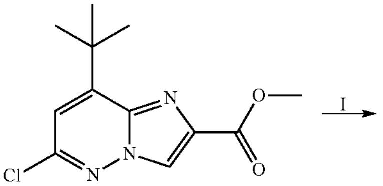

O

-continued

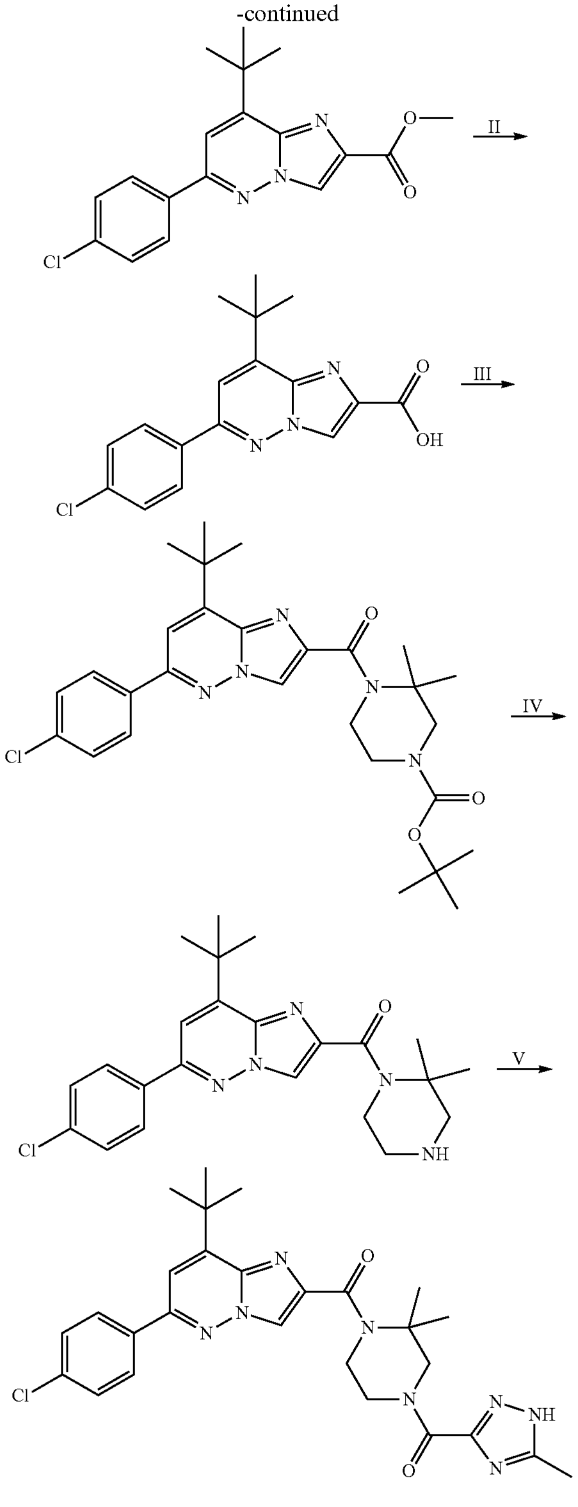

Step I: methyl 8-tert-butyl-6-(4-chlorophenyl)imidazo[1,2-b]pyridazine-2-carboxylate The product were prepared according to General Procedure using methyl 8-tert-butyl-6-chloro-imidazo[1,2-b]pyridazine-2-carboxylate (300 mg, 1.121 mmol), DMF (2.802 mL), cyclopentyl(diphenyl)phosphane;dichloropalladium;iron (8.202 mg, 0.01121 mmol), (4-chlorophenyl)boronic acid (192.8 mg, 1.233 mmol) and $Na_2CO_3$ (1.121 mL of 2 M, 2.242 mmol) to afford methyl 8-tert-butyl-6-(4-chlorophenyl)imidazo[1,2-b]pyridazine-2-carboxylate (371 mg, 1.079 mmol, 96.26%). $^1H$ NMR (400 MHz, DMSO-$d_6$) δ 8.85 (s, 1H), 8.16-8.09 (m, 2H), 7.69-7.62 (m, 2H), 7.53 (s, 1H), 3.89 (s, 3H), 1.60 (s, 9H). LC-MS: 344.24 (M+$H^+$).

Step II: 8-tert-butyl-6-(4-chlorophenyl)imidazo[1,2-b]pyridazine-2-carboxylic acid methyl 8-tert-butyl-6-(4-chlorophenyl)imidazo[1,2-b]pyridazine-2-carboxylate (4.64 g, 13.50 mmol) was dissolved in dioxane (33.76 mL), MeOH (16.87 mL) and water (16.87 mL). LiOH (678.9 mg, 28.35 mmol) was added and the resulting solution was stirred for 18 hours at rt. 1N HCl was added to acidify to pH2-3. A precipitate was formed and filtered over Buchner to afford the title compound 8-tert-butyl-6-(4-chlorophenyl)imidazo[1,2-b]pyridazine-2-carboxylic acid (4.21 g, 12.77 mmol, 94.56%). LC-MS: 330.29 (M+$H^+$).

Step III: tert-butyl-4-[8-tert-butyl-6-(4-chlorophenyl)imidazo[1,2-b]pyridazine-2-carbonyl]-3,3-dimethyl-piperazine-1-carboxylate The product was prepared according to General Procedure 1 using 8-tert-butyl-6-(4-chlorophenyl)imidazo[1,2-b]pyridazine-2-carboxylic acid (482 mg, 1.184 mmol), DMF (5.920 mL), HATU (540.3 mg, 1.421 mmol), Hünig's base (459.1 mg, 618.7 μL, 3.552 mmol) and tert-butyl 3,3-dimethylpiperazine-1-carboxylate (304.5 mg, 1.421 mmol) to afford tert-butyl 4-[8-tert-butyl-6-(4-chlorophenyl)imidazo[1,2-b]pyridazine-2-carbonyl]-3,3-dimethyl-piperazine-1-carboxylate (533 mg, 1.013 mmol, 85.57%). LC-MS: 527.4 (M+$H^+$).

Step IV: [8-tert-butyl-6-(4-chlorophenyl)imidazo[1,2-b]pyridazin-2-yl]-(2,2-dimethylpiperazin-1-yl)methanone The product was prepared according to General Procedure 2 using tert-butyl-4-[8-tert-butyl-6-(4-chlorophenyl)imidazo[1,2-b]pyridazine-2-carbonyl]-3,3-dimethyl-piperazine-1-carboxylate (532 mg, 1.011 mmol) to afford title compound [8-tert-butyl-6-(4-chlorophenyl)imidazo[1,2-b]pyridazin-2-yl]-(2,2-dimethylpiperazin-1-yl)methanone (Hydrochloric Acid (1)) (467.5 mg, 1.011 mmol, 100.0%). $^1H$ NMR (400 MHz, DMSO-$d_6$) δ 8.59 (s, 1H), 8.15-8.09 (m, 2H), 7.67-7.61 (m, 2H), 7.51 (s, 1H), 4.16-4.04 (m, 2H), 3.36-3.28 (m, 2H), 3.23-3.15 (m, 2H), 1.67-1.55 (m, 15H). LC-MS: 427.35 (M+$H^+$).

Step V: [8-tert-butyl-6-(4-chlorophenyl)imidazo[1,2-b]pyridazin-2-yl]-[2,2-dimethyl-4-(5-methyl-1H-1,2,4-triazole-3-carbonyl)piperazin-1-yl]methanone The product was prepared according to General Procedure 3 using [8-tert-butyl-6-(4-chlorophenyl)imidazo[1,2-b]pyridazin-2-yl]-(2,2-dimethylpiperazin-1-yl)methanone (Hydrochloric Acid (1)) (1.33 g, 2.876 mmol), HATU (1.640 g, 4.314 mmol), DMF (10 mL), Hünig's base (1.486 g, 2.003 mL, 11.50 mmol) and 5-methyl-1H-1,2,4-triazole-3-carboxylic acid (402.1 mg, 3.164 mmol) to afford the title compound. [8-tert-butyl-6-(4-chlorophenyl)imidazo[1,2-b]pyridazin-2-yl]-[2,2-dimethyl-4-(5-methyl-1H-1,2,4-triazole-3-carbonyl)piperazin-1-yl]methanone (675.01 mg, 1.217 mmol, 42.32%). $^1H$ NMR (400 MHz, DMSO-$d_6$) δ 13.97 (s, 1H), 8.59-8.49 (m, 1H), 8.17-8.06 (m, 2H), 7.68-

7.60 (m, 2H), 7.55-7.44 (m, 1H), 4.65-4.09 (m, 3H), 3.94-3.66 (m, 3H), 2.44-2.30 (m, 3H), 1.66-1.43 (m, 15H). LC-MS: 535.47 (M+H$^+$), retention time: 3.49 minutes using Method A Example 47 (I-442) 3-benzyl-1-[6-(4-fluoro-3-methyl-phenyl)-8-isopropyl-imidazo[1,2-b]pyridazine-2-carbonyl]-5,5-dimethyl-imidazolidin-4-one Scheme 86

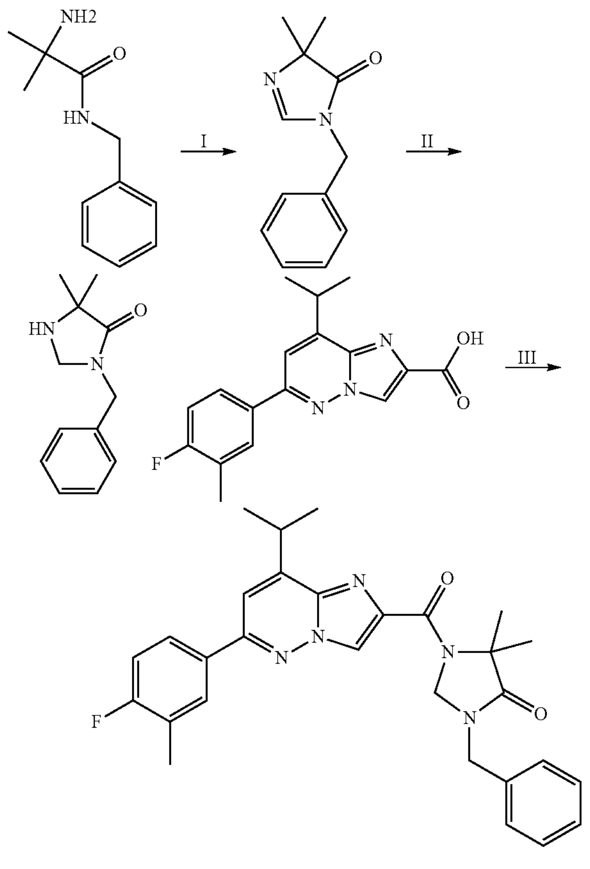

Step I: 3-benzyl-5,5-dimethyl-imidazol-4-one

To a solution of 2-amino-N-benzyl-2-methyl-propanamide (50 mg, 0.2601 mmol) in toluene (3.251 mL) under $N_2$ was added triethylorthoformate (46.25 mg, 51.91 μL, 0.3121 mmol) followed by AcOH (21.08 mg, 19.96 μL, 0.3511 mmol). The solution was refluxed for 5 h. The reaction mixture was allowed to cool to room temperature and was quenched with water. The solution was diluted with EtOAc, washed once with NaHCO3 sat. and then brine, dried over MgSO4, filtered, and concentrated in vacuo to afford 3-benzyl-5,5-dimethyl-imidazol-4-one (52.6 mg, 0.2601 mmol, 99.98%) as a yellow oil. $^1$H NMR (400 MHz, DMSO-d6) δ 8.00 (s, 1H), 7.40-7.33 (m, 2H), 7.33-7.26 (m, 1H), 7.26-7.20 (m, 2H), 4.62 (s, 2H), 1.19 (s, 6H). LC-MS: 202.96 (M+H$^+$)

Step II: 3-benzyl-5,5-dimethyl-imidazolidin-4-one

To a solution of 3-benzyl-5,5-dimethyl-imidazol-4-one (53 mg, 0.2620 mmol) in MeOH (1.541 mL) under $N_2$ was added $NaBH_4$ (19.82 mg, 20.97 μL, 0.5240 mmol). After 1 h, the complete reaction was neutralized with AcOH and concentrated in vacuo. The residue was dissolved with EtOAc, washed once with a saturated sodium bicarbonate solution followed by then brine, dried over MgSO4, filtered, and concentrated in vacuo to afford 3-benzyl-5,5-dimethyl-imidazolidin-4-one (26 mg, 0.1273 mmol, 48.58%) as a pale yellow sticky oil. $^1$H NMR (400 MHz, DMSO-d6) δ 7.39-7.32 (m, 2H), 7.31-7.19 (m, 3H), 4.34 (s, 2H), 4.05 (s, 2H), 3.28-3.03 (m, 1H), 1.11 (s, 6H). LC-MS: 205.29 (M+H$^+$)

Step III: 3-benzyl-1-[6-(4-fluoro-3-methyl-phenyl)-8-isopropyl-imidazo[1,2-b]pyridazine-2-carbonyl]-5,5-dimethyl-imidazolidin-4-one The product was prepared according to General Procedure 1 using 6-(4-fluoro-3-methyl-phenyl)-8-isopropyl-imidazo[1,2-b]pyridazine-2-carboxylic acid (35 mg, 0.1111 mmol) (describe in Example 42, scheme 81), DMF (2 mL), HATU (50.68 mg, 0.1333 mmol), Hünig's base (57.44 mg, 77.41 μL, 0.4444 mmol) and 3-benzyl-5,5-dimethyl-imidazolidin-4-one (24.96 mg, 0.1222 mmol). to afford 3-benzyl-1-[6-(4-fluoro-3-methyl-phenyl)-8-isopropyl-imidazo [1,2-b] pyridazine-2-carbonyl]-5,5-dimethyl-imidazolidin-4-one (38.8 mg, 0.07650 mmol, 68.86%). $^1$H NMR (400 MHz, DMSO-d6) δ 8.64 (s, 1H), 8.07-8.00 (m, 1H), 7.99-7.90 (m, 1H), 7.67 (s, 1H), 7.44-7.37 (m, 2H), 7.37-7.27 (m, 4H), 5.40 (s, 2H), 4.58 (s, 2H), 3.44-3.24 (m, 1H), 2.38-2.30 (m, 3H), 1.64 (s, 6H), 1.37 (d, J=6.9 Hz, 6H). LC-MS: 500.10 (M+H$^+$), retention time: 4.50 minutes using Method A Example 48 (I-448): [8-tert-butyl-6-(4,4-difluorocyclohexyl)imidazo[1,2-b]pyridazin-2-yl]-[2,2-dimethyl-4-(5-methyl-4H-1,2,4-triazole-3-carbonyl)piperazin-1-yl]

Scheme 87

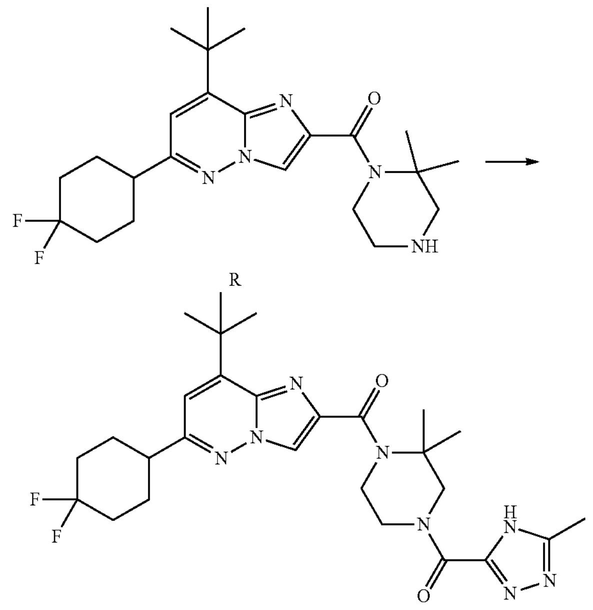

The product was prepared according to General Procedure 3 using Intermediate R (10.99 g, 25.35 mmol), DMF (125 mL), HATU (11.08 g, 29.15 mmol), Hünig's base (10.6 mL, 76.05 mmol) and 5-methyl-4H-1,2,4-triazole-3-carboxylic acid (3.222 g, 25.35 mmol to obtain [8-tert-butyl-6-(4,4-difluorocyclohexyl)imidazo[1,2-b]pyridazin-2-yl]-[2,2-dimethyl-4-(5-methyl-4H-1,2,4-triazole-3-carbonyl)piperazin-1-yl]methanone (Hydrochloric Acid (1)) (8.45 g, 14.20 mmol, 56.00%). $^1$H NMR (400 MHz, Methanol-d4) δ 8.39 (d, J=7.9 Hz, 1H), 7.18 (dd, J=7.1, 1.1 Hz, 1H), 4.34 (dd, J=15.5, 7.3 Hz, 4H), 3.95 (s, 1H), 3.87-3.72 (m, 1H), 3.03 (tt, J=7.4, 3.4 Hz, 1H), 2.68 (d, J=7.1 Hz, 3H), 2.24-1.85 (m, 8H), 1.66 (s, 3H), 1.63 (s, 3H), 1.57 (s, 5H), 1.55 (s, 4H). LC-MS: 543.59 (M+H$^+$), retention time: 3.08 minutes using Method A Example 49 (I-452): [8-tert-butyl-6-(4,4-difluorocyclohexyl)imidazo[1,2-b]pyridazin-2-yl]-[4-(3-hydroxy-3-methyl-cyclobutanecarbonyl)-2,2-dimethyl-piperazin-1-yl]methanone Scheme 88

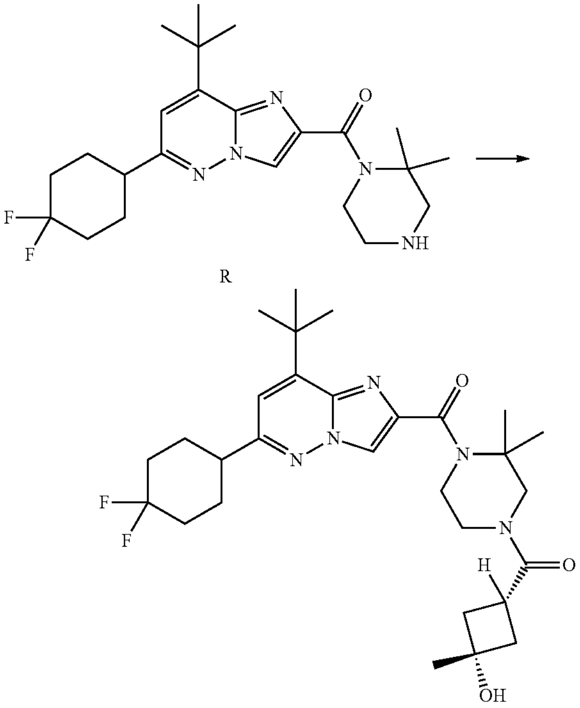

R

The product was prepared according to General Procedure 3 using intermediate R (90 mg, 0.2076 mmol), DMF (5 mL), HATU (118 mg, 0.3103 mmol), Hünig's base (145 μL, 0.8325 mmol) and (1S,3S)-3-hydroxy-3-methylcyclobutane-1-carboxylic acid (30 mg, 0.2305 mmol). to obtain 8-tert-butyl-6-(4,4-difluorocyclohexyl)imidazo[1,2-b]pyridazin-2-yl]-[4-(3-hydroxy-3-methyl-cyclobutanecarbonyl)-2,2-dimethyl-piperazin-1-yl]methanone (92 mg, 0.1543 mmol, 74.30%). $^1$H NMR (400 MHz, Methanol-d4) δ 8.40 (d, J=10.2 Hz, 1H), 7.21 (d, J=18.2 Hz, 1H), 4.20 (t, J=5.7 Hz, 2H), 3.82-3.68 (m, 2H), 3.62 (d, J=9.2 Hz, 2H), 3.08-2.89 (m, 2H), 2.35-1.88 (m, 12H), 1.64-1.53 (m, 15H), 1.38 (d, J=10.2 Hz, 3H). LC-MS: 546.25 (M+H$^+$), retention time: 3.35 minutes using Method A Example 50 (I-462): 6-(8-(tert-butyl)-6-(4-fluorophenyl)imidazo[1,2-b]pyridazine-2-carbonyl)-6,9-diazaspiro[4.5]decan-10-one Scheme 89

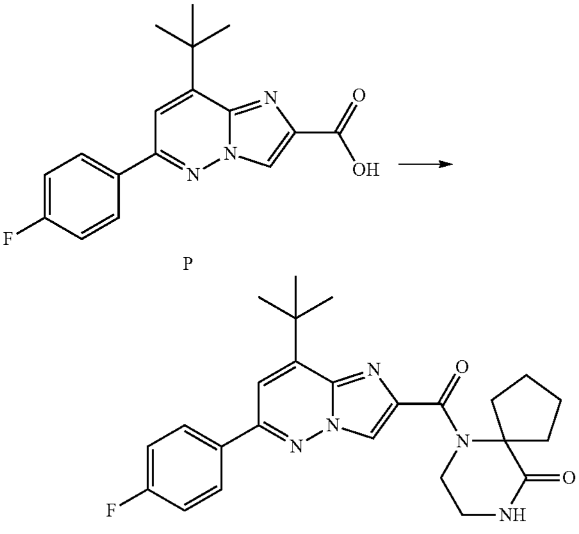

P

The product were prepared according to General Procedure 1 using 8-tert-butyl-6-(4-fluorophenyl)imidazo[1,2-b]pyridazine-2-carboxylic acid (50 mg, 0.1596 mmol), DMF (1 mL), DIPEA (72.20 mg, 97.30 μL, 0.5586 mmol), 8-(tert-butyl)-6-(4-fluorophenyl)imidazo[1,2-b]pyridazine-2-carboxylic acid (29.53 mg, 0.1915 mmol) and HATU (Phosphorus Hexafluoride Ion) (91.03 mg, 0.2394 mmol) affording 6-(8-(tert-butyl)-6-(4-fluorophenyl)imidazo[1,2-b]pyridazine-2-carbonyl)-6,9-diazaspiro[4.5]decan-10-one (58.8 mg, 0.1181 mmol, 74.01%). $^1$H NMR (400 MHz, DMSO-d6) δ 8.57 (s, 1H), 8.18-8.10 (m, 2H), 8.08-8.02 (m, 1H), 7.49 (s, 1H), 7.46-7.35 (m, 2H), 4.03-3.95 (m, 2H), 3.43-3.34 (m, 2H), 2.35-2.24 (m, 2H), 2.19-1.99 (m, 4H), 1.86-1.70 (m, 2H), 1.58 (s, 9H). LC-MS: 450.07 (M+1), retention time: 3.71 minutes using Method A.

Example 51 (I-493): (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylic acid Scheme 90

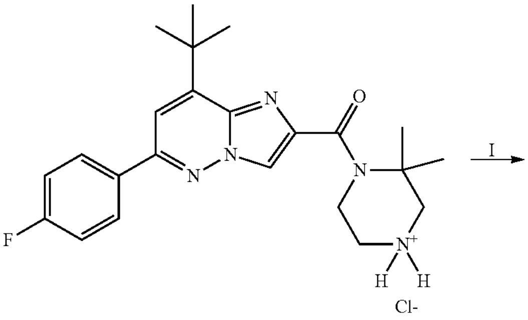

Q

-continued

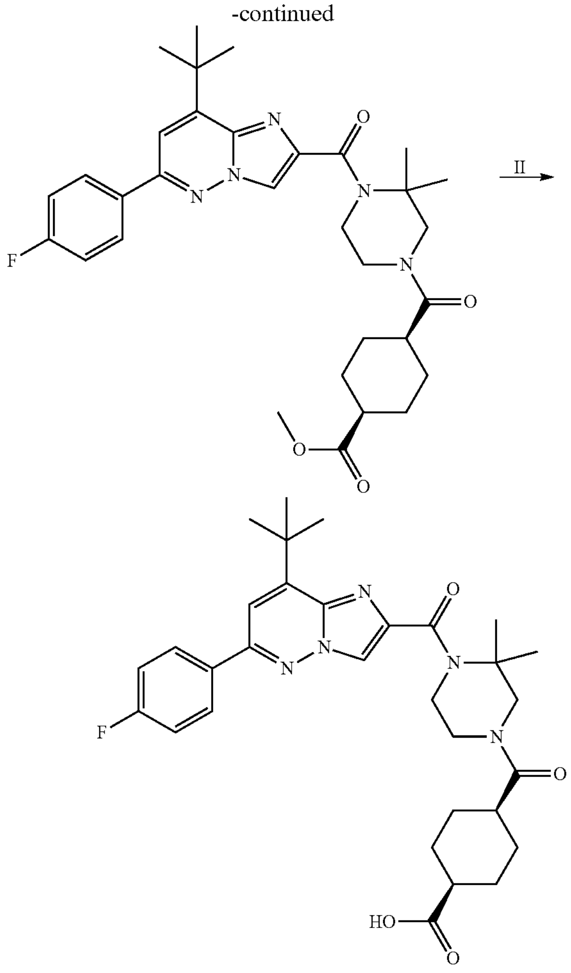

Step I: methyl (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate The product were prepared according to General Procedure 3 Intermediate Q (95 mg, 0.234 mmoL), cis-4-methoxycarbonyl-cyclohexanecarboxylic acid (45.6 mg, 1.05 eq, 0.245 mmoL), HATU (93 mg, 0.245 mmol), DIPEA (163 uL, 0.936 mmol) and DMF (0.7 mL) affording methyl (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate. LC-MS: 579.75 (M+1), retention time: 2.05 minutes using Method A.

Step II: (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-bonyl)cyclohexane-1-carboxylic acid The product were prepared according to General Procedure 4 using methyl (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate, dioxane (0.4 mL) and 2M LiOH (234 uL, 2 eq) affording (1S,4S)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylic acid (2.28 mg, 0.004 mmol, 2%). $^{1}$H NMR (400 MHz, dmso) δ 12.12 (s, 1H), 8.49 (d, J=8.4 Hz, 1H), 8.23-8.02 (m, 2H), 7.52-7.46 (m, 1H), 7.38 (td, J=8.8, 1.7 Hz, 2H), 4.22-3.96 (m, 2H), 3.77 (t, J=5.6 Hz, 1H), 3.61 (d, J=21.2 Hz, 2H), 3.45 (t, J=5.7 Hz, 1H), 2.06-1.84 (m, 2H), 1.62-1.27 (m, 23H). 564.4 (M+1), retention time: 5.43 minutes using Method D.

Example 52 (I-494): (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylic acid Scheme 91

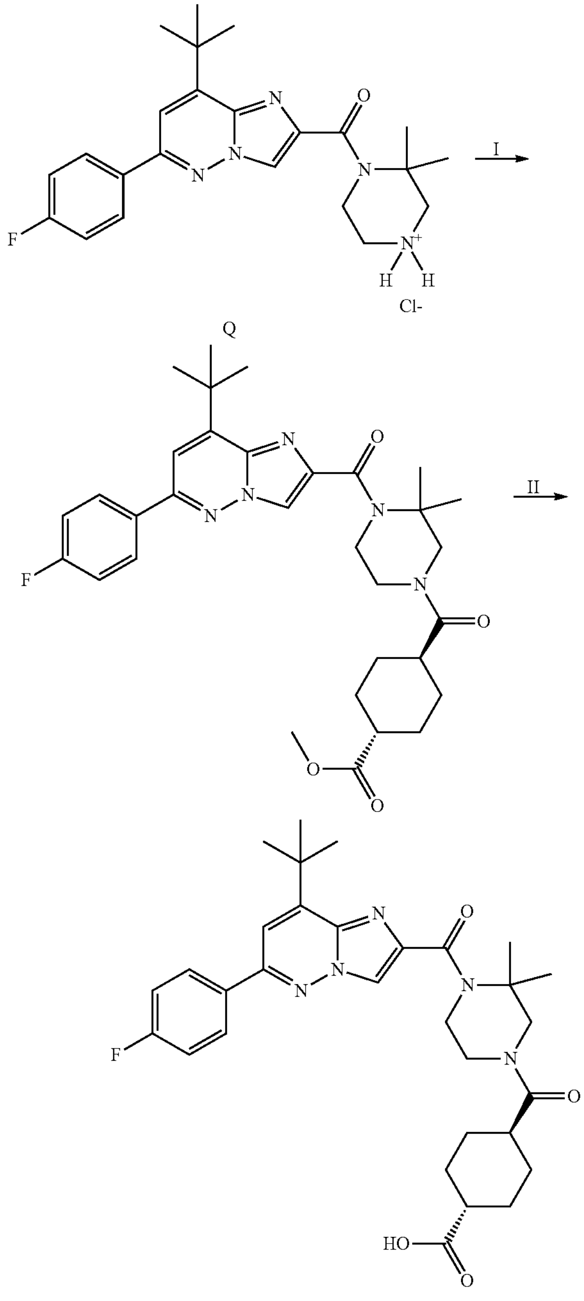

Step I: methyl (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate The product were prepared according to General Procedure 3 using Intermediate Q (95 mg, 0.234 mmoL), trans-4-methoxycarbonyl-cyclohexanecarboxylic acid (45.6 mg, 1.05 eq, 0.245 mmoL), HATU (93 mg, 0.245 mmol), DIPEA (163 uL, 0.936 mmol) and DMF (0.7 mL) affording methyl (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate. LC-MS: 579.57 (M+1), retention time: 2.01 minutes using Method C.

Step II: (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylic acid The product were prepared according to General Procedure 4 methyl (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylate, dioxane (0.4 mL) and 2M LiOH (234 uL, 2 eq) affording (1R,4R)-4-(4-(8-(tert-butyl)-6-(4-fluorophenyl)imidazo[1,2-b]pyridazine-2-carbonyl)-3,3-dimethylpiperazine-1-carbonyl)cyclohexane-1-carboxylic acid (48.15 mg, 0.085 mmol, 37%). $^1$H NMR (400 MHz, dmso) δ 8.49 (d, J=8.6 Hz, 1H), 8.15-8.03 (m, 2H), 7.46-7.41 (m, 1H), 7.38 (td, J=8.8, 1.4 Hz, 2H), 4.19-4.06 (m, 2H), 3.78 (t, J=5.7 Hz, 1H), 3.63 (d, J=25.4 Hz, 2H), 3.46 (d, J=5.8 Hz, 1H), 2.20-2.07 (m, 1H), 1.94-1.80 (m, 2H), 1.80-1.61 (m, 2H), 1.61-1.25 (m, 20H). LC-MS: 564.4 (M+1), retention time: 5.25 minutes using Method D.

Example 53 (I-551): 4-[4-(6,8-diisopropylimidazo[1,2-b]pyridazine-2-carbonyl)-3,3-dimethyl-piperazine-1-carbonyl]cyclohexanecarboxylic acid Scheme 92

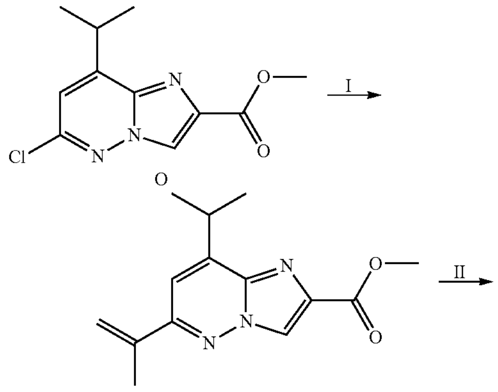

-continued

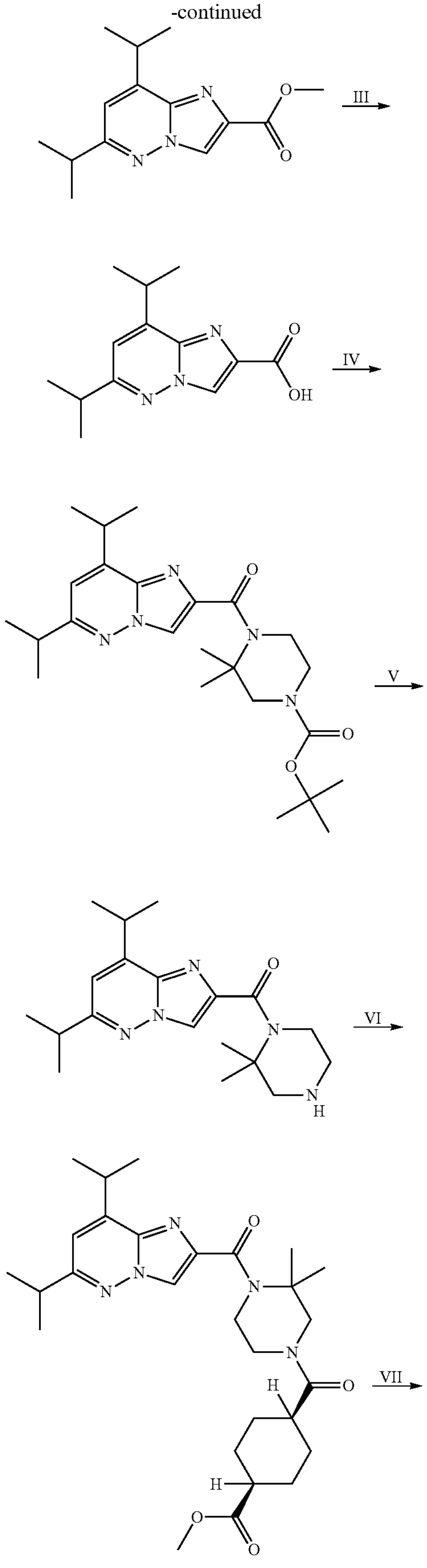

-continued

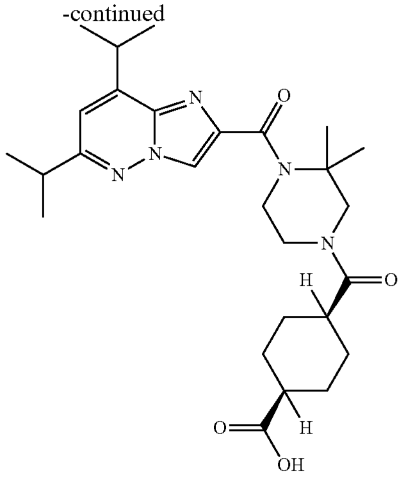

Step I: methyl 6-isopropenyl-8-isopropyl-imidazo[1,2-b]pyridazine-2-carboxylate

The product were prepared according to General Procedure 7 using intermediate 0 (500 mg, 1.971 mmol), THF (12 mL), $Na_2CO_3$ 2M (2.96 mL of 2 M, 5.920 mmol), 2-isopropenyl-4,4,5,5-tetramethyl-1,3,2-dioxaborolane (556 μL, 2.958 mmol) and $Pd(PPh_3)_4$ (228 mg, 0.1973 mmol) To afford crude methyl 6-isopropenyl-8-isopropyl-imidazo[1,2-b]pyridazine-2-carboxylate. LC-MS: 260.01 ($M+H^+$).

Step II: methyl 6,8-diisopropylimidazo[1,2-b]pyridazine-2-carboxylate

To a suspension of the crude methyl 6-isopropenyl-8-isopropyl-imidazo[1,2-b]pyridazine-2-carboxylate (511 mg, 1.971 mmol) and 10% Pd/C (419.5 mg, 3.942 mmol) in EtOH (10 mL) and AcOH (0.5 mL) was bubbled $H_2$ for 6 days. Celite was added and the mixture was filtered. The filtrate was concentrated and the residue was purified by silica gel chromatography to afford methyl 6,8-diisopropylimidazo[1,2-b]pyridazine-2-carboxylate (434 mg, 1.661 mmol, 84.26%) as a pale yellow oil. $^1$H NMR (400 MHz, Chloroform-d) δ 8.40 (d, J=0.8 Hz, 1H), 6.81 (s, 1H), 3.97 (d, J=0.7 Hz, 3H), 3.79 (p, J=6.9 Hz, 1H), 3.07 (p, J=6.9 Hz, 1H), 1.38 (s, 3H), 1.36 (s, 3H), 1.34 (s, 3H), 1.33 (s, 3H). LC-MS: 261.97 ($M+H^+$).

Step III: 6,8-diisopropylimidazo[1,2-b]pyridazine-2-carboxylic acid

The product was prepared according to General Procedure 4 using methyl 6,8-diisopropylimidazo[1,2-b]pyridazine-2-carboxylate (433 mg, 1.657 mmol), Dioxane (15 mL), THF (7.5 mL) and LiOH 2M (6.6 mL of 2 M, 13.20 mmol to afford 6,8-diisopropylimidazo[1,2-b]pyridazine-2-carboxylic acid (409 mg, 1.654 mmol, 99.80%) as a pale yellow oil which was used in the subsequent step without further purification. LC-MS: 248.29 ($M+H^+$).

Steps IV: tert-butyl 4-(6,8-diisopropylimidazo[1,2-b]pyridazine-2-carbonyl)-3,3-dimethyl-piperazine-1-carboxylate The product was prepared according to General Procedure 1 using crude 6,8-diisopropylimidazo[1,2-b]pyridazine-2- carboxylic acid (369 mg, 1.492 mmol), DMF (6.5 mL), HATU (680 mg, 1.788 mmol), Hünig's base (910 μL, 5.224 mmol) and tert-butyl 3,3-dimethylpiperazine-1-carboxylate (377 μL, 1.719 mmol. The residue was purified by silica gel chromatography to afford tert-butyl 4-(6,8-diisopropylimidazo[1,2-b]pyridazine-2-carbonyl)-3,3-dimethyl-piperazine-1-carboxylate (510.6 mg, 1.151 mmol, 77.15%) as a pale yellow solid. $^1$H NMR (400 MHz, Chloroform-d) δ 8.21 (s, 1H), 6.74 (s, 1H), 4.25 (s, 2H), 3.53 (ddd, J=24.0, 16.7, 8.4 Hz, 5H), 3.06 (p, J=7.0 Hz, 1H), 1.59 (s, 6H), 1.47 (s, 9H), 1.39 (s, 3H), 1.38 (s, 3H), 1.33 (s, 3H), 1.31 (s, 3H). LC-MS: 444.46 ($M+H^+$).

Step V: (6,8-diisopropylimidazo[1,2-b]pyridazin-2-yl)-(2,2-dimethylpiperazin-1-yl)methanone The product was prepared according to General Procedure 2 using tert-butyl 4-(6,8-diisopropylimidazo[1,2-b]pyridazine-2-carbonyl)-3,3-dimethyl-piperazine-1-carboxylate (509 mg, 1.147 mmol), DCM (14 mL) and TFA (1.77 mL, 22.97 mmol to afford (6,8-diisopropylimidazo[1,2-b]pyridazin-2-yl)-(2,2-dimethylpiperazin-1-yl)methanone (394 mg, 1.147 mmol, 100.0%) as a yellow solid which was used in the subsequent step without further purification. LC-MS: 344.46 ($M+H^+$).

Step VI: methyl 4-[4-(6,8-diisopropylimidazo[1,2-b]pyridazine-2-carbonyl)-3,3-dimethyl-piperazine-1-carbonyl]cyclohexanecarboxylate The product was prepared according to General Procedure 3 using (6,8-diisopropylimidazo[1,2-b]pyridazin-2-yl)-(2,2-dimethylpiperazin-1-yl)methanone (50 mg, 0.1456 mmol), DMF (700.0 μL), HATU (67 mg, 0.1762 mmol), DIPEA (89 μL, 0.5110 mmol) and 4-methoxycarbonylcyclohexane-1-carboxylic acid (31 mg, 0.1665 mmol). The residue was purified by silica gel chromatography to afford methyl 4-[4-(6,8-diisopropylimidazo[1,2-b]pyridazine-2-carbonyl)-3,3-dimethyl-piperazine-1-carbonyl]cyclohexanecarboxylate (64 mg, 0.1138 mmol, 78.17%) as a white solid. $^1$H NMR (400 MHz, Chloroform-d) δ 8.22 (dd, J=12.6, 3.9 Hz, 1H), 6.75 (d, J=3.4 Hz, 1H), 4.34 (d, J=27.2 Hz, 2H), 3.77 (d, J=5.7 Hz, 1H), 3.72-3.64 (m, 4H), 3.52 (s, 1H), 3.12-3.00 (m, 1H), 2.83-2.40 (m, 2H), 2.35-2.00 (m, 2H), 1.75 (s, 2H), 1.63 (d, J=2.7 Hz, 6H), 1.61-1.51 (m, 6H), 1.45-1.36 (m, 6H), 1.33 (d, J=2.0 Hz, 6H). LC-MS: 512.56 ($M+H^+$).

Step VII: 4-[4-(6,8-diisopropylimidazo[1,2-b]pyridazine-2-carbonyl)-3,3-dimethyl-piperazine-1-carbonyl]cyclohexanecarboxylic acid The product was prepared according to General Procedure 4 using methyl 4-[4-(6,8-diisopropylimidazo[1,2-b]pyridazine-2-carbonyl)-3,3-dimethyl-piperazine-1-carbonyl]cyclohexanecarboxylate (60 mg, 0.1173 mmol), Dioxane (1 mL), THE (500 μL), MeOH (500 μL) and LiOH 3N (391 μL of 3 M, 1.173 mmol to afford 4-[4-(6,8-diisopropylimidazo[1,2-b]pyridazine-2-carbonyl)-3,3-dimethyl-piperazine-1-carbonyl]cyclohexanecarboxylic acid (54 mg, 0.09432 mmol, 64.79%). $^1$H NMR (400 MHz, Chloroform-d) δ 8.23 (d, J=12.2 Hz, 1H), 6.75 (d, J=4.1 Hz, 1H), 4.36 (dt, J=29.2, 5.7 Hz, 2H), 3.79 (t, J=6.0 Hz, 1H), 3.73-3.64 (m, 2H), 3.57-3.47 (m, 2H), 3.13-3.00 (m, 1H), 2.71-2.63 (m, 1H), 2.60-2.46 (m, 1H), 2.36-2.24 (m, 2H), 1.93-1.78 (m, 2H), 1.72-1.62 (m, 5H), 1.61-1.53 (m, 6H), 1.40 (d, J=6.9 Hz, 3H), 1.38 (d, J=6.9 Hz, 3H), 1.33 (d, J=2.5 Hz, 3H), 1.31 (d, J=2.5 Hz, 3H). LC-MS: 498.51 (M+H$^+$), retention time: 1.50 minutes using Method C.

Example 54 (I-555 and I-556): (1S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid and (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid Scheme 93

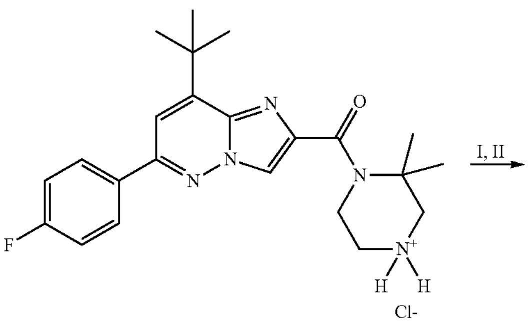

Q

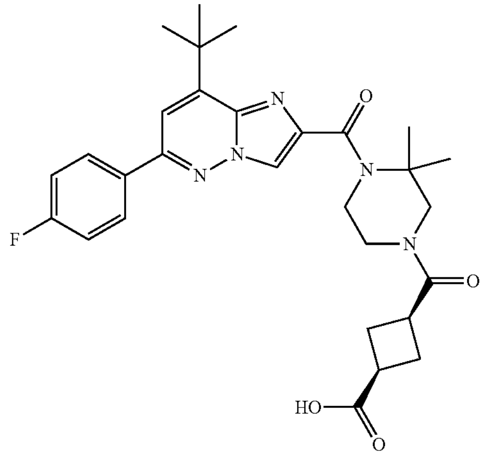

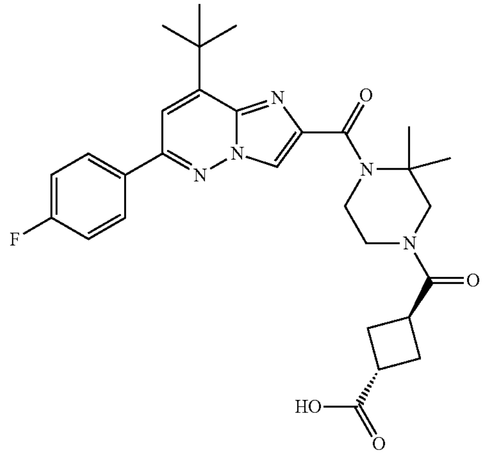

Step I: Synthesis methyl (1S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate and methyl (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate The product were prepared according to General Procedure 3 using intermediate Q (200 mg, 0.4485 mmoL), 3-methoxycarbonylcyclobutanecarboxylic acid (78.03 mg, 0.4934 mmol), HATU (255.8 mg, 0.673 mmol), DIPEA (313 uL, 1.794 mmol) and DMF (0.7 mL). The diastereomers were purified by Prep HPLC to afford methyl (1S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate (21.2 mg, 0.039 mmol, 17%)$^1$H NMR (400 MHz, DMSO-d6) δ 8.53-8.49 (m, 1H), 8.18-8.11 (m, 2H), 7.50-7.47 (m, 1H), 7.45-7.37 (m, 2H), 4.22-4.12 (m, 2H), 3.66-3.56 (m, 5H), 3.55-3.46 (m, 2H), 3.36-3.24 (m, 1H), 3.19-3.03 (m, 1H), 2.41-2.30 (m, 4H), 1.64-1.57 (m, 9H), 1.54-1.45 (m, 6H). LC-MS: 550.87 (M+1), retention time: 3.86 minutes using Method A and methyl (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate (22.7 mmg, 0.041 mmol, 18%). $^1$H NMR (400 MHz, DMSO-d6) δ 8.54-8.51 (m, 1H), 8.17-8.11 (m, 2H), 7.50-7.47 (m, 1H), 7.47-7.35 (m, 2H), 4.21-4.10 (m, 2H), 3.69-3.56 (m, 5H), 3.57-3.50 (m, 1H), 3.49-3.45 (m, 1H), 3.46-3.35 (m, 1H), 3.16-3.02 (m, 1H), 2.48-2.29 (m, 4H), 1.66-1.55 (m, 9H), 1.54-1.43 (m, 6H). 550.22 (M+1), retention time: 3.91 minutes using Method A Step IIa: (1S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid (I-555)

The product were prepared according to General Procedure 4 methyl (1 S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate (17.4 mg, 0.032 mmol), dioxane (0.4 mL) and 2M LiOH (234 uL, 0.468 mmol) affording (1S,3S)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid (15.7 mg, 0.029 mmol, 78.5%). $^1$H NMR (400 MHz, dmso) δ 12.09 (s, 1H), 8.49 (d, J=6.4 Hz, 1H), 8.16-8.07 (m, 2H), 7.45 (d, J=2.7 Hz, 1H), 7.42-7.30 (m, 2H), 4.25-4.05 (m, 2H), 3.72-3.37 (m, 4H), 3.30-3.08 (m, 1H), 3.05-2.86 (m, 1H), 2.40-2.18 (m, 4H), 1.63-1.36 (m, 15H). 536.5 (M+1), retention time: 1.69 minutes using Method C Step IIb: (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid (I-556)

The product were prepared according to General Procedure 4 using methyl (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylate (19.1 mg, 0.035 mmol), dioxane (0.4 mL) and 2M LiOH (234 uL, 0.468 mmol) affording (1R,3R)-3-(4-(8-(tert-butyl)-6-(4-fluorophenyl)imidazo[1,2-b]pyridazine-2-carbonyl)-3,3-dimethylpiperazine-1-carbonyl)cyclobutane-1-carboxylic acid (48.15 mg, 0.085 mmol, 37%). $^1$H NMR (400

MHz, dmso) δ 12.13 (s, 1H), 8.49 (d, J=4.6 Hz, 1H), 8.11 (ddd, J=8.9, 5.5, 1.1 Hz, 2H), 7.45 (d, J=1.8 Hz, 1H), 7.38 (t, J=8.8 Hz, 2H), 4.20-3.99 (m, 2H), 3.66-3.32 (m, 5H), 2.94 (dd, J=9.8, 4.6 Hz, 1H), 2.46-2.24 (m, 4H), 1.56 (d, J=2.4 Hz, 9H), 1.47 (d, J=9.5 Hz, 6H). 536.5 (M+1), retention time: 1.69 minutes using Method C.

Example 55 (I-560): 4-(4-(8-(tert-butyl)-6-(4-fluorophenyl)imidazo[1,2-b]pyridazine-2-carbonyl)-3,3-dimethylpiperazin-1-yl)-4-oxobutanoic acid Scheme 94

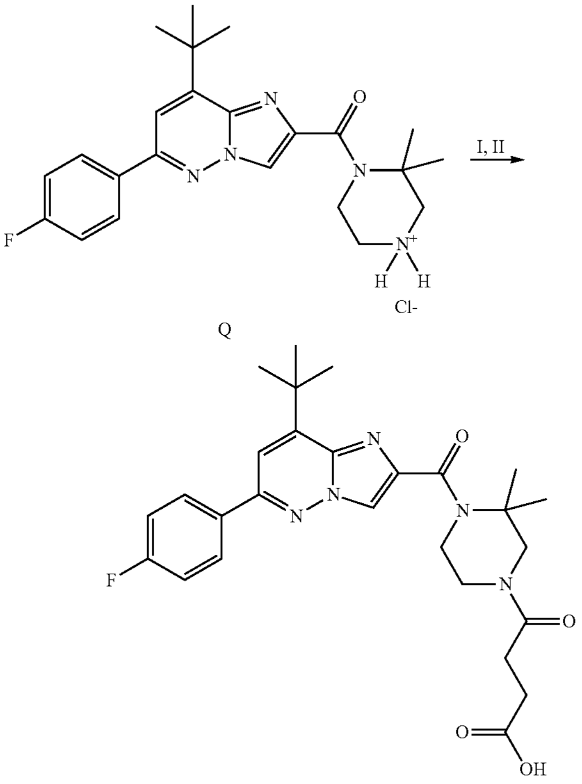

Step I: methyl 4-(4-(8-(tert-butyl)-6-(4-fluorophenyl)imidazo[1,2-b]pyridazine-2-carbonyl)-3,3-dimethylpiperazin-1-yl)-4-oxobutanoate The product was prepared according to General Procedure 3 using intermediate Q (100 mg, 0.244 mmol), 4-methoxy-4-oxobutanoic acid (45.6 mg, 0.293 mmoL), HATU (120.7 mg, 0.318 mmol), DIPEA (170 uL, 0.977 mmol) and DMF (1.0 mL) affording methyl 4-(4-(8-(tert-butyl)-6-(4-fluorophenyl)imidazo[1,2-b]pyridazine-2-carbonyl)-3,3-dimethylpiperazin-1-yl)-4-oxobutanoate (65.75, 0.126 mmol, 51.4%). $^1$H NMR (400 MHz, DMSO-d6) δ 8.56-8.49 (m, 1H), 8.18-8.11 (m, 2H), 7.50-7.47 (m, 1H), 7.45-7.37 (m, 2H), 4.25 (t, J=5.5 Hz, 1H), 4.17 (t, J=5.8 Hz, 1H), 3.72 (t, J=5.6 Hz, 1H), 3.67-3.62 (m, 2H), 3.61-3.55 (m, 3H), 3.51 (t, J=5.8 Hz, 1H), 2.68-2.53 (m, 4H), 1.65-1.46 (m, 15H). 524.78 (M+1), retention time: 1.86 minutes using Method C.

Step II: 4-(4-(8-(tert-butyl)-6-(4-fluorophenyl)imidazo[1,2-b]pyridazine-2-carbonyl)-3,3-dimethylpiperazin-1-yl)-4-oxobutanoic acid The product was prepared according to General Procedure 4 using methyl 4-(4-(8-(tert-butyl)-6-(4-fluorophenyl)imidazo[1,2-b]pyridazine-2-carbonyl)piperazin-1-yl)-4-oxobutanoate (61 mg, 0.1165 mmol), dioxane (1.0 mL) and 2M LiOH (350 uL, 0.70 mmol) affording 4-(4-(8-(tert-butyl)-6-(4-fluorophenyl)imidazo[1,2-b]pyridazine-2-carbonyl)-3,3-dimethylpiperazin-1-yl)-4-oxobutanoic acid (59.3 mg, 0.1164 mmol, 95%). 510.5 (M+1), retention time: 1.65 minutes using Method C.

Example 56 (I-561): 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoic acid Scheme 95

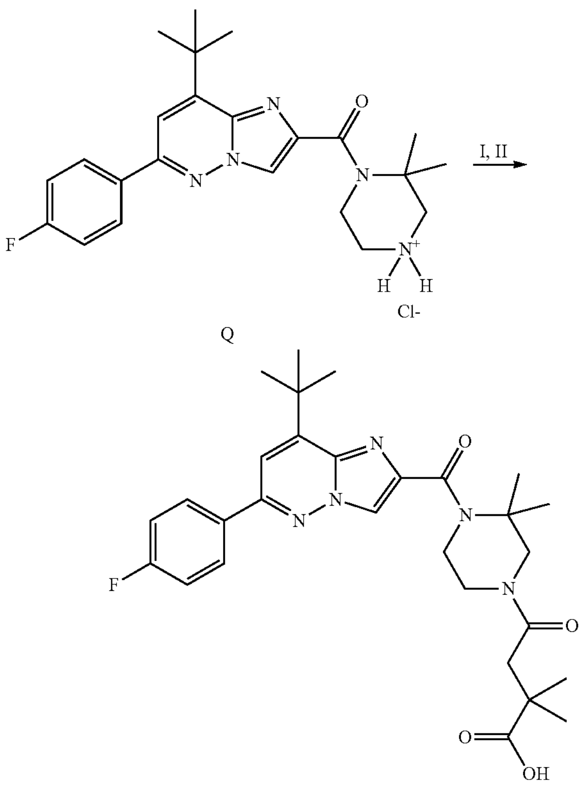

Step I: methyl 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoate The product was prepared according to General Procedure 3 using intermediate Q (100 mg, 0.244 mmoL), 4-methoxy-3,3-dimethyl-4-oxobutanoic acid (45.6 mg, 0.293 mmoL), HATU (120.7 mg, 0.318 mmol), DIPEA (170 uL, 0.977 mmol) and DMF (1.0 mL) affording methyl 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoate (69.7 mg, 0.126 mmol, 51.4%). $^1$H NMR (400 MHz, DMSO-d6) δ 8.56-8.49 (m, 1H), 8.17-8.11 (m, 2H), 7.51-7.47 (m, 1H), 7.45-7.37 (m, 2H), 4.23 (t, J=5.6 Hz, 1H), 4.16 (t, J=5.8 Hz, 1H), 3.74-3.67 (m, 1H), 3.64-3.58 (m, 2H), 3.56-3.51 (m, 3H), 3.51-3.44 (m, 1H), 2.68 (s, 1H), 2.62 (s, 1H), 1.65-1.45 (m, 15H), 1.18 (s, 6H). 552.83. (M+1), retention time: 2.02 minutes using Method C.

Step II: 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoic acid The product was prepared according to General Procedure 4 methyl 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoate. (64.5 mg, 0.1169 mmol), dioxane (1.0 mL) and 2M LiOH (351 uL, 0.702 mmol) affording 4-(4-(8-(tert-butyl)-6-(4-fluorophenyl)imidazo[1,2-b]pyridazine-2-carbonyl)-3,3-dimethylpiperazin-1-yl)-2,2-dimethyl-4-oxobutanoic acid (63 mg, 0.1112 mmol, 95%). $^1$H NMR (400 MHz, dmso) δ 11.76 (s, 1H), 8.49 (d, J=9.3 Hz, 1H), 8.11 (ddd, J=8.9, 5.3, 2.2 Hz, 2H), 7.45 (d, J=3.8 Hz, 1H), 7.38 (td, J=8.8, 1.8 Hz, 2H), 4.16 (dt, J=23.4, 5.9 Hz, 2H), 3.67 (t, J=5.6 Hz, 1H), 3.58 (d, J=1.9 Hz, 2H), 3.46 (t, J=5.8 Hz, 1H), 2.56 (d, J=24.0 Hz, 2H), 1.65-1.37 (m, 15H), 1.14 (s, 6H). 538.8. (M+1), retention time: 1.98 minutes using Method C.

Example 57 (I-563): (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylic acid Scheme 96

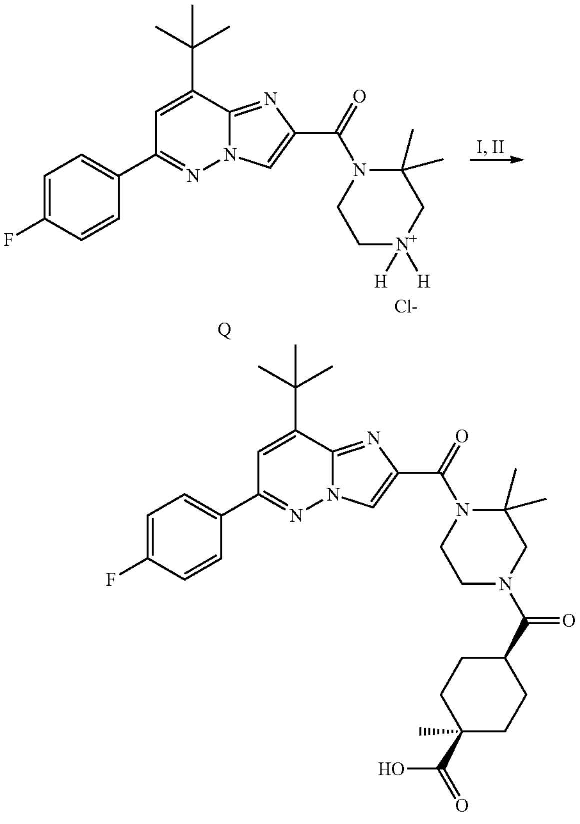

Step I: methyl (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylate The product was prepared according to General Procedure 3 using intermediate Q (100 mg, 0.244 mmoL), (1S,4S)-4-(methoxycarbonyl)-4-methylcyclohexane-1-carboxylic acid (58.7 mg, 0.293 mmol), HATU (120.7 mg, 0.318 mmol) and DIPEA (170 uL, 0.977 mmol) in DMF (1.0 mL). Purification by Prep HPLC afford methyl methyl (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylate (55.6 mg, 0.094 mmol, 38.3%). $^1$H NMR (400 MHz, DMSO-d6) δ 8.56-8.49 (m, 1H), 8.18-8.10 (m, 2H), 7.51-7.47 (m, 1H), 7.44-7.37 (m, 2H), 4.23-4.11 (m, 2H), 3.84-3.76 (m, 1H), 3.63 (s, 5H), 3.51-3.43 (m, 1H), 2.72-2.59 (m, 1H), 2.17-2.07 (m, 2H), 1.67-1.44 (m, 17H), 1.44-1.16 (m, 4H), 1.13-1.07 (m, 3H). 592.31. (M+1), retention time: 2.14 minutes using Method C.

Step II: (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylic acid The product was prepared according to General Procedure 4 using methyl (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylate (48.5 mg, 0.082 mmol), dioxane (1.0 mL) and 2M LiOH (246 uL, 0.492 mmol) affording (1S,4S)-4-(4-(8-(tert-butyl)-6-(4-fluorophenyl)imidazo[1,2-b]pyridazine-2-carbonyl)-3,3-dimethylpiperazine-1-carbonyl)-1-methylcyclohexane-1-carboxylic acid (47 mg, 0.0813 mmol, 99%). $^1$H NMR (400 MHz, dmso) δ 12.11 (s, 1H), 8.49 (d, J=9.2 Hz, 1H), 8.11 (ddd, J=8.8, 5.5, 3.1 Hz, 2H), 7.45 (d, J=5.6 Hz, 1H), 7.38 (td, J=8.8, 2.1 Hz, 2H), 4.22-4.06 (m, 2H), 3.81-3.71 (m, 1H), 3.61 (d, J=24.0 Hz, 2H), 3.49-3.38 (m, 1H), 2.15-1.89 (m, 2H), 1.66-1.28 (m, 19H), 1.28-0.97 (m, 6H). 578.6. (M+1), retention time: 1.90 minutes using Method C.

Example 58 (I-567): 4-(6-(4-fluorophenyl)-8-(thiophen-3-yl)imidazo[1,2-b]pyridazine-2-carbonyl)-3,3-dimethylpiperazin-2-one Scheme 97

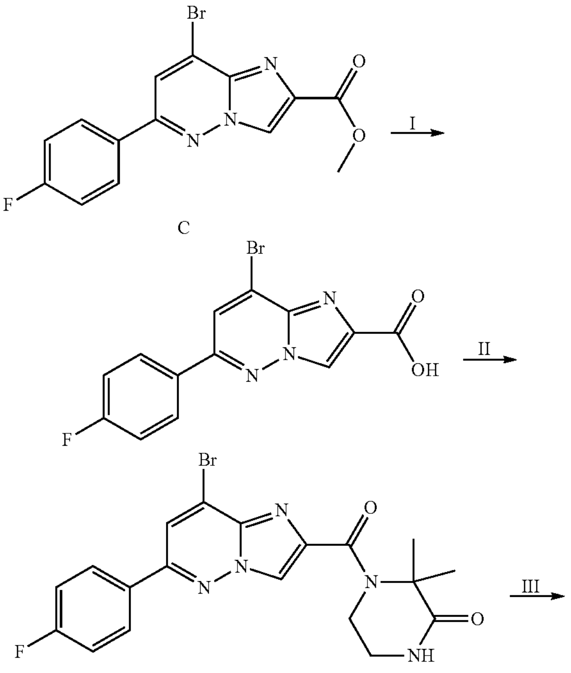

-continued

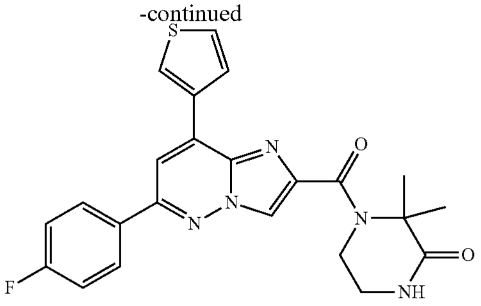

Step I: 8-bromo-6-(4-fluorophenyl)imidazo[1,2-b]pyridazine-2-carboxylic acid

The product was prepared according to General Procedure 4 using intermediate C (1.5 g, 4.284 mmol), 1,4-dioxane (15 mL), THF (6 mL), LiOH 3M (10 mL of 3 M, 30.00 mmol) to afford 8-bromo-6-(4-fluorophenyl)imidazo[1,2-b]pyridazine-2-carboxylic acid (1.19 g, 3.540 mmol, 82.64%). 336.15 $(M+1)^+$, 1.24 minutes using Method C.

Step II: 4-(8-bromo-6-(4-fluorophenyl)imidazo[1,2-b]pyridazine-2-carbonyl)-3,3-dimethylpiperazin-2-one The product was prepared according to General Procedure 1 using 8-bromo-6-(4-fluorophenyl)imidazo[1,2-b]pyridazine-2-carboxylic acid (1 g, 2.975 mmol), 3,3-dimethylpiperazin-2-one (439 mg, 3.425 mmol), DMF (10 mL), HATU (1.36 g, 3.577 mmol) and DIPEA (1.81 mL, 10.39 mmol) affording: 4-(8-bromo-6-(4-fluorophenyl)imidazo[1,2-b]pyridazine-2-carbonyl)-3,3-dimethylpiperazin-2-one (1.1 g, 2.465 mmol, 82.83%). 446.28 $(M+1)^+$, 1.30 minutes using Method C.

Step III: 4-(6-(4-fluorophenyl)-8-(thiophen-3-yl)imidazo[1,2-b]pyridazine-2-carbonyl)-3,3-dimethylpiperazin-2-one The product was prepared according to General Procedure 8 using 4-[8-bromo-6-(4-fluorophenyl)imidazo[1,2-b]pyridazine-2-carbonyl]-3,3-dimethyl-piperazin-2-one (60 mg, 0.1344 mmol), DMF (700 μL), $Na_2CO_3$ in water (200 μL of 2 M, 0.4000 mmol), 3-thienylboronic acid (21 mg, 0.1641 mmol) and $Pd(PPh_3)_4$ (16 mg, 0.01385 mmol) affording 4-(6-(4-fluorophenyl)-8-(thiophen-3-yl)imidazo[1,2-b]pyridazine-2-carbonyl)-3,3-dimethylpiperazin-2-one (56 mg, 0.1072 mmol, 77.52%). $^1H$ NMR (400 MHz, Chloroform-d) δ 8.87-8.81 (m, 1H), 8.49-8.43 (m, 1H), 7.99 (dd, J=8.5, 5.3 Hz, 2H), 7.86 (d, J=5.1 Hz, 1H), 7.67 (s, 1H), 7.51 (dd, J=5.1, 3.0 Hz, 1H), 7.50-7.42 (m, 1H), 7.22 (d, J=8.8 Hz, 1H), 6.08 (s, 1H), 4.32-4.23 (m, 2H), 3.72-3.63 (m, 2H), 1.90 (s, 6H). 450.34 (M+1)+, 1.58 minutes using Method C.

Example 59 (I-484): (8-(tert-butyl)-6-(4-fluorophenyl)imidazo[1,2-b]pyridazin-2-yl)(4-hydroxy-2,2-dimethylpiperidin-1-yl)methanone Scheme 98

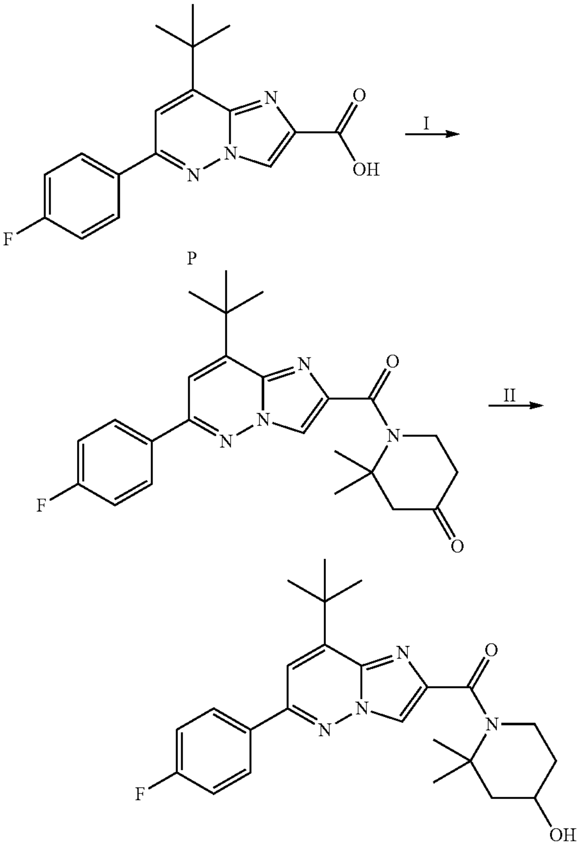

Step I: 1-[8-tert-butyl-6-(4-fluorophenyl)imidazo[1,2-b]pyridazine-2-carbonyl]-2,2-dimethyl-piperidin-4-one The product was prepared according to General Procedure 1 using intermediate P (50 mg, 0.1596 mmol), DMF (1.000 mL), DIPEA (82.51 mg, 111.2 μL, 0.6384 mmol), 2,2-dimethylpiperidin-4-one (Hydrochloric Acid (1)) (31.34 mg, 0.1915 mmol) and HATU (Phosphorus Hexafluoride Ion) (91.03 mg, 0.2394 mmol) affording 1-[8-tert-butyl-6-(4-fluorophenyl)imidazo[1,2-b]pyridazine-2-carbonyl]-2,2-dimethyl-piperidin-4-one (67.4 mg, 0.03350 mmol, 20.99%) 423.17 (M+1)+, Retention time: 2.31 minutes retention time: 3.44 minutes using Method C.

Step II: [8-tert-butyl-6-(4-fluorophenyl)imidazo[1,2-b]pyridazin-2-yl]-(4-hydroxy-2,2-dimethyl-1-piperidyl)methanone The product was prepared according to General Procedure X using 1-[8-tert-butyl-6-(4-fluorophenyl)imidazo[1,2-b]pyridazine-2-carbonyl]-2,2-dimethyl-piperidin-4-one (67.4 mg, 0.1595 mmol), MeOH (2 mL) and $NaBH_4$ (12.07 mg, 12.77 μL, 0.3190 mmol). Purification by reverse phase HPLC was carried out under standard conditions to afford

[8-tert-butyl-6-(4-fluorophenyl)imidazo[1,2-b]pyridazin-2-yl]-(4-hydroxy-2,2-dimethyl-1-piperidyl)methanone (20.6 mg, 0.04741 mmol, 29.72%). $^1$H NMR (400 MHz, DMSO-d6) δ 8.45 (s, 1H), 8.17-8.10 (m, 2H), 7.47 (s, 1H), 7.44-7.36 (m, 2H), 4.72 (d, J=4.5 Hz, 1H), 4.12-4.01 (m, 1H), 3.84 (dt, J=13.4, 5.1 Hz, 1H), 3.50-3.38 (m, 1H), 2.06-1.93 (m, 1H), 1.80-1.71 (m, 1H), 1.65-1.47 (m, 14H), 1.44 (s, 3H). 425.4. (M+1), retention time: 3.44 minutes using Method A.

Example 60: Protocol for Testing PAR2 Compounds in ANTAGONIST Mode Using the Ca FLIPR$^{TETRA}$ Assay (384 Well)

23000 HT-29 cells (ATCC#HTB-38) were plated in 384-well black, transparent-flat bottom plates and incubated in 25 uL of 1% FBS/McCoy's media ON at 37° C. under an atmosphere of 5% $CO_2$. The following day, 25 uL FLIPR calcium 5 Molecular Devices assay reagent (Cat: R-8186) was added. Plates were incubated at 37° C. and r. t. for 45 min and 15 min, respectively. Compounds dilutions were prepared in 100% DMSO using a Biomek FX and diluted 20-fold in HBSS and then 5.5 uL was added directly to the cells by the FLIPR$^{TA}$ (10× dilution) using FLIPR Tetra Pipette tips, black, non-sterile, 384 Molecular Devices (Cat: 9000-0764).

A first read was performed to determine whether the test compounds on their own can activate Ca2+ responses.

The cells were incubated with the compounds for 30 min at r. t. and then read in ANTAGONIST mode in the same plate by stimulating with 6.2 uL of a fixed concentration of the activator: final concentrations: 8 μM SLIGKV, 1 U/mL Thrombin, 3.1 U/mL trypsin, or 0.6 μM UTP.

TABLE 1

Compound analytical data

| Compound Number | LCMS M + H | LCMS (Rt time) (method) | $^1$H NMR |
|---|---|---|---|
| I-1 | 508.4 | 4.7 (A) | (400 MHz, Chloroform-d) δ 8.62 (d, J = 4.0 Hz, 1H), 8.11-7.97 (m, 2H), 7.76 (s, 1H), 7.27-7.13 (m, 3H), 5.34 (d, J = 13.0 Hz, 1H), 4.78-4.27 (m, 2H), 3.97 (t, J = 14.9 Hz, 1H), 3.57-2.83 (m, 3H), 1.49 (s, 9H), 1.22 (d, J = 6.8 Hz, 3H). |
| I-2 | 455.7 | 4.31 (A) | (400 MHz, Chloroform-d) δ 8.43 (s, 1H), 8.06-7.86 (m, 2H), 7.29 (m, 1H), 7.22-7.00 (m, 2H), 5.26 (d, J = 19.5 Hz, 1H), 4.78-4.19 (m, 2H), 4.03-3.82 (m, 1H), 3.59-2.83 (m, 3H), 2.69 (d, J = 1.1 Hz, 3H), 1.47 (s, 9H), 1.19 (s, 3H). |
| I-3 | 468.2 | 4.68 (A) | (400 MHz, Chloroform-d) δ 8.44 (s, 1H), 8.07-7.80 (m, 2H), 7.28 (t, J = 1.1 Hz, 1H), 7.24-7.12 (m, 2H), 5.29 (d, J = 6.2 Hz, 1H), 4.80-4.27 (m, 2H), 3.93 (s, 1H), 3.59-2.84 (m, 5H), 1.46 (d, J = 10.8 Hz, 12H), 1.22 (d, J = 18.0 Hz, 3H). |
| I-4 | 482.5 | 4.80 (A) | (400 MHz, Chloroform-d) δ 8.32 (s, 1H), 8.04-7.86 (m, 2H), 7.26 (s, 1H), 7.22-7.11 (m, 2H), 4.39-3.92 (m, 2H), 3.73-3.40 (m, 4H), 3.09 (m, 2H), 1.65-1.59 (m, 6H), 1.50-1.40 (m, 12H). |
| I-5 | 497.5 | 5.13 (A) | (400 MHz, Chloroform-d) δ 8.33 (s, 1H), 8.11-7.87 (m, 2H), 7.24-7.10 (m, 3H), 4.28 (s, 2H), 3.77-3.43 (m, 5H), 1.61 (s, 6H), 1.51-1.40 (m, 15H). |
| I-6 | 353.3 | 3.94 (B) | (400 MHz, Chloroform-d) δ 8.36 (s, 1H), 8.06-7.86 (m, 2H), 7.28 (d, J = 1.3 Hz, 1H), 7.24-7.15 (m, 2H), 4.05 (t, J = 6.0 Hz, 2H), 3.78-3.48 (m, 2H), 2.70 (d, J = 1.1 Hz, 3H), 2.00-1.80 (m, 4H), 1.64 (h, J = 5.0, 4.1 Hz, 4H). |
| I-7 | 407.3 | 4.49 (A) | (400 MHz, Chloroform-d) δ 8.57 (s, 1H), 8.16-7.88 (m, 2H), 7.73 (d, J = 1.1 Hz, 1H), 7.24 (d, J = 8.6 Hz, 2H), 4.21-4.01 (m, 2H), 3.85-3.69 (m, 2H), 1.87 (m, 4H), 1.76-1.58 (m, 4H). |
| I-8 | 489.4 | 4.36 (A) | (400 MHz, Chloroform-d) δ 8.46 (s, 1H), 8.08-7.88 (m, 2H), 7.51-7.29 (m, 6H), 7.24-7.08 (m, 2H), 5.36 (d, J = 48.5 Hz, 1H), 5.17 (d, J = 2.9 Hz, 2H), 4.83-4.31 (m, 2H), 4.04 (s, 1H), 3.41 (d, J = 83.9 Hz, 2H), 3.03 (d, J = 61.6 Hz, 1H), 2.69 (s, 3H), 1.26 (d, J = 6.5 Hz, 3H). |
| I-9 | 482.1 | 3.94 (A) | (400 MHz, Methanol-$d_4$) δ 8.48 (s, 1H), 8.20-7.97 (m, 2H), 7.65 (d, J = 1.5 Hz, 1H), 7.38-7.15 (m, 2H), 5.02 (s, 1H), 4.78-4.21 (m, 3H), 4.05-3.42 (m, 2H), 3.25-3.04 (m, 2H), 2.69 (d, J = 1.2 Hz, 3H), 1.34-1.13 (m, 3H), 1.09-0.94 (m, 10H), 0.90-0.77 (m, 1H). |
| I-10 | 411.3 | 3.58 (A) | (400 MHz, Chloroform-d) δ 8.37 (s, 1H), 8.05-7.90 (m, 2H), 7.34 (d, J = 1.4 Hz, 1H), 7.25-7.12 (m, 2H), 4.74 (m, 1H), 4.37 (d, J = 85.1 Hz, 1H), 3.71 (m, 4H), 3.34 (d, J = 80.4 Hz, 1H), 2.78 (s, 1H), 2.71 (d, J = 1.1 Hz, 3H), 2.35 (s, 1H), 1.94 (m, 5H), 0.97 (d, J = 19.7 Hz, 3H). |
| I-11 | 543.3 | 3.58 (A) | (400 MHz, Methanol-$d_4$) δ 8.60 (s, 1H), 8.43 (m, 1H), 8.17-8.01 (m, 3H), 7.78 (m, 1H), 7.40 (d, J = 7.9 Hz, 1H), 7.33-7.10 (m, 3H), 5.15 (s, 2H), 5.05 (d, J = 14.5 Hz, 1H), 4.60-4.21 (m, 2H), 3.97 (d, J = 28.8 Hz, |

TABLE 1-continued

| Compound analytical data | | | |
|---|---|---|---|
| Compound Number | LCMS M + H | LCMS (Rt time) (method) | $^1$H NMR |
| | | | 1H), 3.53 (d, J = 13.3 Hz, 1H), 3.43-3.25 (m, 1H), 3.17-2.85 (m, 1H), 1.18 (d, J = 6.8 Hz, 3H). |
| I-12 | 543.4 | 3.25 (A) | (400 MHz, Chloroform-d) δ 8.71-8.62 (m, 2H), 8.60 (m, 1H), 8.04-7.95 (m, 2H), 7.83-7.66 (m, 2H), 7.32 (m, 1H), 7.28 (d, J = 2.1 Hz, 1H), 7.24 (d, J = 2.1 Hz, 1H), 5.44 (d, J = 12.8 Hz, 1H), 5.25-5.14 (m, 2H), 4.74-4.38 (m, 2H), 4.05 (s, 1H), 3.57-2.84 (m, 3H), 1.27 (d, J = 7.0 Hz, 3H). |
| I-13 | 469.4 | 3.61 (A) | (400 MHz, Methanol-$d_4$) δ 8.59 (s, 1H), 8.32-8.08 (m, 3H), 7.90 (d, J = 9.5 Hz, 1H), 7.41-7.23 (m, 2H), 4.92 (s, 1H), 4.47 (d, J = 86.5 Hz, 3H), 4.09-3.39 (m, 2H), 3.28-2.95 (m, 2H), 1.71-1.15 (m, 5H), 1.03 (s, 9H). |
| I-14 | 508.2 | 4.39 (A) | (400 MHz, Chloroform-d) δ 8.46 (s, 1H), 8.05-7.75 (m, 2H), 7.21-7.10 (m, 2H), 7.02 (d, J = 5.6 Hz, 1H), 5.52 (s, 1H), 5.01-4.35 (m, 3H), 3.79-2.82 (m, 5H), 2.49 (d, J = 5.9 Hz, 1H), 1.36-1.21 (m, 7H), 1.07-0.93 (m, 11H). |
| I-15 | 661.5 | 5.39 (A) | (400 MHz, Chloroform-d) δ 8.62 (d, J = 6.6 Hz, 1H), 8.11-7.86 (m, 2H), 7.76 (s, 1H), 7.22 (s, 2H), 5.62-5.36 (m, 1H), 5.20 (m, 1H), 5.02-4.34 (m, 3H), 3.98-2.71 (m, 3H), 1.93 (s, 1H), 1.74-1.60 (m, 4H), 1.51-1.32 (m, 14H), 1.29-1.09 (m, 6H). |
| I-16 | 562.5 | 3.67 (A) | (400 MHz, Methanol-$d_4$) δ 8.71 (s, 1H), 8.18 (m, 3H), 7.42-7.17 (m, 2H), 5.16 (d, J = 32.6 Hz, 1H), 4.54 (d, J = 27.2 Hz, 2H), 4.22 (d, J = 90.6 Hz, 1H), 3.90-3.49 (m, 2H), 3.22-2.99 (m, 1H), 2.02-1.54 (m, 8H), 1.36-1.21 (m, 6H), 1.02 (s, 2H). |
| I-17 | 436.2 | 3.73 (A) | (400 MHz, Chloroform-d) δ 8.48 (s, 1H), 8.02-7.81 (m, 2H), 7.27 (d, J = 0.9 Hz, 1H), 7.23-7.17 (m, 2H), 6.59 (m, 1H), 6.33 (d, J = 16.8 Hz, 1H), 5.73 (m, 1H), 5.51 (s, 1H), 5.10-4.04 (m, 3H), 3.61-2.90 (m, 4H), 1.48-1.45 (m, 6H), 1.30 (d, J = 11.0 Hz, 3H). |
| I-18 | 436.45 | 1.97 (C) | (400 MHz, Chloroform-d) δ 8.27 (s, 1H), 6.89 (s, 1H), 4.31-4.17 (m, 2H), 3.67-3.45 (m, 5H), 1.63-1.58 (m, 6H), 1.51-1.46 (m, 9H), 1.44-1.37 (m, 6H). |
| I-19 | 494.54 | 1.7 (C) | (400 MHz, Chloroform-d) δ 8.36 (s, 1H), 8.00-7.89 (m, 2H), 7.26 (s, 1H), 7.25-7.17 (m, 2H), 4.48-4.24 (m, 2H), 3.97-3.58 (m, 4H), 2.85 (s, 1H), 2.83-2.68 (m, 3H), 2.22-2.10 (m, 2H), 2.00 (dtd, J = 11.3, 9.6, 9.0, 5.1 Hz, 1H), 1.81-1.71 (m, 1H), 1.71-1.59 (m, 6H), 1.54-1.39 (m, 6H). |
| I-20 | 480.26 | 3.48 (A) | (400 MHz, DMSO-$d_6$) δ 8.51 (s, 1H), 8.14 (ddd, J = 10.3, 5.3, 2.6 Hz, 2H), 7.47-7.34 (m, 3H), 5.38 (d, J = 34.8 Hz, 1H), 4.10 (d, J = 17.3 Hz, 4H), 3.53 (d, J = 62.7 Hz, 2H), 1.60-1.40 (m, 9H), 1.35 (s, 6H), 1.29-1.22 (m, 2H). |
| I-21 | 492.27 | 3.62 (A) | (400 MHz, DMSO-$d_6$) δ 8.51 (d, J = 5.3 Hz, 1H), 8.19-8.09 (m, 2H), 7.45 (d, J = 5.9 Hz, 1H), 7.43-7.36 (m, 2H), 5.95 (d, J = 28.2 Hz, 1H), 4.10 (dt, J = 38.9, 5.7 Hz, 2H), 3.78 (t, J = 5.6 Hz, 1H), 3.66 (d, J = 48.3 Hz, 2H), 3.50-3.44 (m, 1H), 2.63-2.51 (m, 2H), 2.11-1.98 (m, 2H), 1.83-1.71 (m, 1H), 1.51 (d, J = 12.3 Hz, 6H), 1.45 (tt, J = 6.2, 3.7 Hz, 2H), 1.26 (dq, J = 8.4, 3.6 Hz, 2H). |
| I-22 | 494.3 | 3.88 (A) | (400 MHz, DMSO-$d_6$) δ 8.52 (d, J = 4.6 Hz, 1H), 8.18-8.09 (m, 2H), 7.45 (d, J = 7.3 Hz, 1H), 7.39 (t, J = 8.7 Hz, 2H), 4.75 (t, J = 7.4 Hz, 1H), 4.29-4.17 (m, 1H), 4.15-3.95 (m, 2H), 3.86-3.40 (m, 4H), 1.92 (dt, J = 13.4, 7.0 Hz, 1H), 1.60-1.40 (m, 8H), 1.25 (dd, J = 8.3, 5.5 Hz, 2H), 0.96-0.79 (m, 6H). |
| I-23 | 510.22 | 4.71 (A) | (400 MHz, DMSO-$d_6$) δ 8.64 (s, 1H), 8.20-8.14 (m, 2H), 7.71 (d, J = 0.8 Hz, 1H), 7.46-7.38 (m, 2H), 4.74-4.68 (m, 2H), 4.29 (d, J = 6.6 Hz, 2H), 3.98 (s, 2H), 3.85 (s, 2H), 3.57 (dt, J = 13.9, 6.9 Hz, 1H), 3.24 (s, 2H), 1.49-1.35 (m, 15H). |
| I-24 | 438.12 | 3.2 (A) | |
| I-25 | 410.12 | 3.43 (A) | (400 MHz, DMSO-$d_6$) δ 8.57 (s, 1H), 8.16 (ddd, J = 10.4, 5.4, 2.6 Hz, 2H), 8.11 (s, 1H), 7.69 (d, J = 0.8 Hz, 1H), 7.47-7.36 (m, 2H), 3.97-3.89 (m, 2H), 3.54 (p, J = 6.9 Hz, 1H), 3.36 (t, J = 6.5 Hz, 2H), 1.70 (s, 6H), 1.44 (d, J = 6.9 Hz, 6H). |

TABLE 1-continued

| Compound analytical data | | | |
|---|---|---|---|
| Compound Number | LCMS M + H | LCMS (Rt time) (method) | $^1$H NMR |
| I-26 | 538.55 | 2.82 (A) | |
| I-27 | 524.22 | 3.48 (A) | (400 MHz, DMSO-$d_6$) δ 8.53 (s, 1H), 8.19-8.13 (m, 2H), 7.68 (s, 1H), 7.45-7.37 (m, 2H), 5.55 (d, J = 30.2 Hz, 1H), 4.19-3.98 (m, 4H), 3.73-3.58 (m, 5H), 3.59-3.50 (m, 1H), 3.50-3.41 (m, 1H), 2.05-1.90 (m, 2H), 1.62 (d, J = 13.5 Hz, 2H), 1.58-1.47 (m, 6H), 1.44 (d, J = 6.9 Hz, 6H). |
| I-28 | 480.23 | 3.72 (A) | |
| I-29 | 452.45 | 1.39 (C) | (400 MHz, DMSO-$d_6$) δ 8.55 (s, 1H), 8.20-8.11 (m, 2H), 8.08 (s, 1H), 7.68 (d, J = 0.7 Hz, 1H), 7.38 (t, J = 8.9 Hz, 2H), 3.99 (dd, J = 11.3, 4.0 Hz, 2H), 3.90-3.77 (m, 2H), 3.57-3.47 (m, 2H), 3.34 (d, J = 3.6 Hz, 2H), 2.11-1.97 (m, 2H), 1.88 (d, J = 12.8 Hz, 2H), 1.67 (s, 6H). |
| I-30 | 422.4 | 1.65 (C) | (400 MHz, DMSO-$d_6$) δ 8.51 (s, 1H), 8.12 (dd, J = 8.8, 5.5 Hz, 2H), 8.07 (s, 1H), 7.54 (s, 1H), 7.37 (t, J = 8.8 Hz, 2H), 3.93-3.85 (m, 2H), 3.34 (m, 2H), 1.75-1.69 (m, 2H), 1.66 (s, 6H), 1.58 (s, 3H), 0.93 (q, J = 3.8 Hz, 2H). |
| I-31 | 536.42 | 4.3 (D) | (400 MHz, DMSO-$d_6$) δ 8.46 (s, 1H), 8.17-8.07 (m, 2H), 7.53 (s, 1H), 7.37 (t, J = 8.8 Hz, 2H), 5.60-5.41 (m, 1H), 4.20-3.37 (m, 10H), 1.96 (d, J = 14.1 Hz, 2H), 1.70 (s, 2H), 1.65-1.40 (m, 12H), 0.93 (q, J = 3.9 Hz, 2H). |
| I-32 | 494.39 | 4.58 (D) | (400 MHz, DMSO-$d_6$) δ 8.46 (s, 1H), 8.12 (dd, J = 8.8, 5.5 Hz, 2H), 7.54 (s, 1H), 7.37 (t, J = 8.8 Hz, 2H), 5.44-5.24 (m, 1H), 4.05 (d, J = 35.4 Hz, 5H), 3.64-3.38 (m, 2H), 1.69 (s, 2H), 1.59 (s, 3H), 1.55-1.40 (m, 7H), 1.32 (s, 6H), 0.95-0.91 (m, 2H). |
| I-33 | 506.61 | 4.7 (D) | (400 MHz, DMSO-$d_6$) δ 8.48-8.44 (m, 1H), 8.12 (dd, J = 8.7, 5.6 Hz, 2H), 7.53 (s, 1H), 7.37 (t, J = 8.8 Hz, 2H), 5.99-5.86 (m, 1H), 4.16-3.93 (m, 2H), 3.83-3.41 (m, 4H), 2.63-2.50 (m, 2H), 2.11-1.93 (m, 2H), 1.81-1.67 (m, 3H), 1.59 (d, J = 2.0 Hz, 3H), 1.47 (d, J = 13.1 Hz, 6H), 0.93 (q, J = 4.0 Hz, 2H). |
| I-34 | 480.56 | 4.3 (D) | (400 MHz, DMSO-$d_6$) δ 8.47 (d, J = 4.6 Hz, 1H), 8.12 (dd, J = 8.7, 5.5 Hz, 2H), 7.54 (d, J = 2.7 Hz, 1H), 7.37 (t, J = 8.8 Hz, 2H), 4.94 (dd, J = 19.4, 7.1 Hz, 1H), 4.40 (dp, J = 30.2, 6.6 Hz, 1H), 4.23-3.39 (m, 6H), 1.73-1.66 (m, 2H), 1.59 (s, 3H), 1.50 (s, 3H), 1.46 (d, J = 6.2 Hz, 3H), 1.19 (t, J = 6.4 Hz, 3H), 0.94 (dd, J = 3.8, 2.6 Hz, 2H). |
| I-35 | 436.31 | 1.49 (C) | (400 MHz, DMSO-$d_6$) δ 8.83 (s, 1H), 8.32-8.29 (m, 1H), 8.27-8.20 (m, 2H), 8.14-8.10 (m, 1H), 7.49-7.40 (m, 2H), 3.88-3.81 (m, 2H), 3.36-3.31 (m, 2H), 1.71 (s, 6H). |
| I-36 | 508.49 | 1.5 (C) | (400 MHz, DMSO-$d_6$) δ 8.80 (s, 1H), 8.29 (s, 1H), 8.27-8.21 (m, 2H), 7.48-7.41 (m, 2H), 5.46-5.27 (m, 1H), 4.19-3.91 (m, 4H), 3.67-3.58 (m, 1H), 3.47-3.38 (m, 1H), 1.59-1.46 (m, 6H), 1.34 (s, 6H). |
| I-37 | 520.45 | 1.62 (C) | (400 MHz, DMSO-$d_6$) δ 8.82-8.76 (m, 1H), 8.29 (s, 1H), 8.27-8.20 (m, 2H), 7.48-7.41 (m, 2H), 6.00-5.91 (m, 1H), 4.09-4.00 (m, 1H), 3.95 (t, J = 5.5 Hz, 1H), 3.81-3.70 (m, 2H), 3.63-3.58 (m, 1H), 3.47-3.42 (m, 1H), 2.62-2.53 (m, 2H), 2.10-1.99 (m, 2H), 1.83-1.71 (m, 1H), 1.56-1.42 (m, 7H). |
| I-38 | 550.5 | 1.51 (C) | (400 MHz, DMSO-$d_6$) δ 8.79 (s, 1H), 8.29 (d, J = 1.1 Hz, 1H), 8.27-8.20 (m, 2H), 7.49-7.40 (m, 2H), 5.64-5.45 (m, 1H), 4.17-3.88 (m, 4H), 3.74-3.57 (m, 5H), 3.50-3.39 (m, 1H), 2.04-1.91 (m, 2H), 1.68-1.42 (m, 8H). |
| I-39 | 494.41 | 1.5 (C) | (400 MHz, DMSO-$d_6$) δ 8.80 (d, J = 4.1 Hz, 1H), 8.30 (s, 1H), 8.27-8.21 (m, 2H), 7.48-7.41 (m, 2H), 4.98 (dd, J = 22.7, 7.2 Hz, 1H), 4.43 (dp, J = 33.1, 6.7 Hz, 1H), 4.12-3.96 (m, 2H), 3.88-3.60 (m, 3H), 3.54-3.41 (m, 1H), 1.54 (s, 3H), 1.50 (d, J = 4.9 Hz, 3H), 1.21 (dd, J = 6.6, 1.7 Hz, 3H). |
| I-40 | 480.55 | 1.86 (C) | (400 MHz, Chloroform-d) δ 8.22 (s, 1H), 7.07 (d, J = 0.8 Hz, 1H), 6.58 (dq, J = 4.0, 2.0, 1.6 Hz, 1H), 4.42-4.21 (m, 2H), 3.92-3.62 (m, 3H), 3.54 (p, J = 6.9 Hz, 1H), 2.82-2.70 (m, 2H), 2.59-2.49 (m, 2H), 2.35-2.22 (m, 3H), 2.19-2.07 (m, 2H), 2.02-1.91 (m, 1H), 1.86-1.66 (m, 4H), 1.65-1.57 (m, 7H), 1.39 (d, J = 6.9 Hz, 6H). |

TABLE 1-continued

| Compound analytical data | | | |
|---|---|---|---|
| Compound Number | LCMS M + H | LCMS (Rt time) (method) | $^1$H NMR |
| I-41 | 482.62 | 1.8 (C) | (400 MHz, DMSO-$d_6$) δ 8.38-8.32 (m, 1H), 7.10 (s, 1H), 5.98 (s, 1H), 4.16-3.96 (m, 2H), 3.81-3.68 (m, 2H), 3.58 (s, 1H), 3.51-3.39 (m, 2H), 3.16 (s, 1H), 2.83-2.73 (m, 1H), 2.63-2.53 (m, 2H), 2.10-1.98 (m, 2H), 1.96-1.64 (m, 7H), 1.62-1.44 (m, 8H), 1.43-1.19 (m, 8H). |
| 3 I-42 | 464.49 | 1.63 (C) | (400 MHz, DMSO-$d_6$) δ 8.46-8.43 (m, 1H), 7.14-7.13 (m, 1H), 5.99-5.90 (m, 1H), 4.12-3.96 (m, 2H), 3.79-3.70 (m, 2H), 3.59 (s, 1H), 3.50-3.40 (m, 2H), 2.61-2.53 (m, 2H), 2.09-1.97 (m, 2H), 1.84-1.60 (m, 1H), 1.55-1.44 (m, 7H), 1.35 (d, J = 6.9 Hz, 6H), 1.09 (t, J = 7.0 Hz, 1H), 1.03-0.93 (m, 2H), 0.91-0.82 (m, 2H). |
| I-43 | 466.5 | 1.75 (C) | (400 MHz, DMSO-$d_6$) δ 8.40-8.36 (m, 1H), 7.51 (s, 1H), 6.94 (s, 1H), 6.01-5.88 (m, 1H), 4.17-4.08 (m, 1H), 4.02 (t, J = 5.6 Hz, 1H), 3.81-3.76 (m, 1H), 3.70 (s, 1H), 3.58 (s, 1H), 3.53-3.41 (m, 2H), 2.83-2.70 (m, 2H), 2.64-2.54 (m, 4H), 2.10-1.93 (m, 4H), 1.84-1.69 (m, 1H), 1.55-1.45 (m, 7H), 1.39 (d, J = 6.9 Hz, 6H). |
| I-44 | 482.51 | 1.39 (C) | (400 MHz, DMSO-$d_6$) δ 8.42-8.37 (m, 1H), 7.47 (s, 1H), 6.96 (s, 1H), 6.01-5.89 (m, 1H), 4.36-4.29 (m, 2H), 4.16-4.08 (m, 1H), 4.01 (t, J = 5.5 Hz, 1H), 3.87-3.80 (m, 2H), 3.77 (t, J = 5.7 Hz, 1H), 3.71 (s, 1H), 3.59 (s, 1H), 3.54-3.41 (m, 2H), 2.63-2.52 (m, 4H), 2.10-1.97 (m, 2H), 1.83-1.68 (m, 1H), 1.54-1.43 (m, 7H), 1.39 (d, J = 6.9 Hz, 6H). |
| I-45 | 484.56 | 1.32 (C) | (400 MHz, DMSO-$d_6$) δ 8.42-8.36 (m, 1H), 7.16 (s, 1H), 6.00 (s, 1H), 4.10 (t, J = 5.7 Hz, 1H), 4.04-3.92 (m, 3H), 3.76 (t, J = 5.6 Hz, 1H), 3.70 (s, 1H), 3.58 (s, 1H), 3.53-3.42 (m, 4H), 3.17 (s, 1H), 3.12-2.99 (m, 1H), 2.62-2.54 (m, 2H), 2.08-1.98 (m, 2H), 1.91-1.69 (m, 5H), 1.55-1.44 (m, 6H), 1.37 (d, J = 6.9 Hz, 6H). |
| I-46 | 542.3 | 4.71 (A) | (400 MHz, Chloroform-d) δ 8.63 (d, J = 2.5 Hz, 1H), 8.00 (dd, J = 8.7, 5.2 Hz, 2H), 7.76 (s, 1H), 7.40-7.31 (m, 5H), 7.28 (d, J = 2.0 Hz, 1H), 7.24 (d, J = 2.1 Hz, 1H), 5.41 (d, J = 12.7 Hz, 1H), 5.17 (d, J = 3.3 Hz, 2H), 4.79-4.35 (m, 2H), 4.07 (s, 1H), 3.59-3.22 (m, 2H), 3.17-2.84 (m, 1H), 1.26 (d, J = 6.7 Hz, 3H). |
| I-47 | 424.4 | 3.46 (A) | N/A |
| I-48 | 438.3 | 4.07 (G) | N/A |
| I-49 | 465 | 4.19 (A) | N/A |
| I-50 | 505.3 | 3.96 (A) | N/A |
| I-51 | 467.3 | 3.9 (A) | N/A |
| I-52 | 522.4 | 4.08 (A) | N/A |
| I-53 | 528.3 | 4.49 (A) | N/A |
| I-54 | 509.3 | 3.23 (A) | N/A |
| I-55 | 505.2 | 2.49 (A) | N/A |
| I-56 | 488.3 | 2.14 (A) | N/A |
| I-57 | 486.3 | 3.61 (A) | N/A |
| I-58 | 463.3 | 2.57 (A) | N/A |
| I-59 | 450.3 | 3.31 (A) | N/A |
| I-60 | 365.3 | 3.11 (A) | N/A |
| I-61 | 381.3 | 3.06 (A) | N/A |
| I-62 | 383.6 | 3.51 (A) | N/A |
| I-63 | 426.3 | 3.2 (A) | N/A |
| I-64 | 465.3 | 4.09 (A) | N/A |
| I-65 | 407.3 | 4.4 (A) | N/A |
| I-66 | 407.5 | 3.29 (A) | N/A |
| I-67 | 471.3 | 3.2 (A) | N/A |
| I-68 | 423.3 | 3.2 (A) | N/A |
| I-69 | 451.4 | 3.72 (A) | N/A |
| I-70 | 463.3 | 3.76 (A) | N/A |
| I-71 | 470 | 5.81 (A) | N/A |
| I-72 | 475.3 | 4.31 (A) | N/A |
| I-73 | 476.3 | 4.41 (A) | N/A |
| I-74 | 508.4 | 4.22 (A) | N/A |
| I-75 | 479.3 | 4.47 (A) | N/A |
| I-76 | 479.3 | 4.41 (A) | N/A |
| I-77 | 522.4 | 4.61 (E) | N/A |
| I-78 | 459.3 | 3.49 (A) | N/A |
| I-79 | 470.3 | 3.83 (A) | N/A |
| I-80 | 551.4 | 3.78 (A) | N/A |

TABLE 1-continued

| Compound analytical data | | | |
|---|---|---|---|
| Compound Number | LCMS M + H | LCMS (Rt time) (method) | $^1$H NMR |
| I-81 | 436.3 | 3.23 (A) | N/A |
| I-82 | 522.7 | 4.91 (A) | N/A |
| I-83 | 528.3 | 4.57 (A) | N/A |
| I-84 | 508.4 | 4.55 (A) | N/A |
| I-85 | 507.4 | 3.51 (A) | N/A |
| I-86 | 519.1 | 4.45 (A) | N/A |
| I-87 | 578.4 | 4.08 (A) | N/A |
| I-88 | 502.1 | 4.05 (A) | N/A |
| I-89 | 512.7 | 4.05 (A) | N/A |
| I-90 | 527.4 | 4.16 (A) | N/A |
| I-91 | 509.4 | 3.8 (A) | N/A |
| I-92 | 557.4 | 4.02 (A) | N/A |
| I-93 | 537.4 | 4.35 (A) | (400 MHz, Chloroform-d) δ 8.62 (s, 1H), 7.99 (dd, J = 8.8, 5.2 Hz, 2H), 7.76 (s, 1H), 7.23 (d, J = 2.1 Hz, 2H), 5.50 (s, 1H), 5.01-4.34 (m, 3H), 3.80-2.79 (m, 4H), 1.40-1.18 (m, 5H), 1.03 (s, 9H). |
| I-94 | 522.4 | 4.77 (A) | (400 MHz, Chloroform-d) δ 8.71-8.39 (m, 1H), 8.07-7.88 (m, 2H), 7.72 (s, 1H), 7.24-7.20 (m, 2H), 5.61-5.04 (m, 1H), 4.98-4.29 (m, 2H), 3.92 (dd, J = 80.5, 17.5 Hz, 1H), 3.26-2.59 (m, 3H), 1.84 (d, J = 92.9 Hz, 2H), 1.35 (d, J = 44.8 Hz, 9H), 1.15-1.01 (m, 3H). |
| I-95 | 464.1 | 3.12 (A) | (400 MHz, Methanol-$d_4$) δ 8.62 (d, J = 4.4 Hz, 1H), 8.32-8.14 (m, 2H), 8.11 (d, J = 1.3 Hz, 1H), 7.39-7.24 (m, 2H), 4.65 (d, J = 16.4 Hz, 1H), 4.32 (dd, J = 56.9, 14.9 Hz, 1H), 3.82-3.53 (m, 1H), 3.50-3.32 (m, 1H), 2.72 (d, J = 4.3 Hz, 3H), 2.64 (dt, J = 9.1, 4.7 Hz, 1H), 2.23 (s, 1H), 2.07-1.65 (m, 2H), 0.90 (ddd, J = 25.5, 17.6, 6.9 Hz, 3H). |
| I-96 | 482.2 | 5.01 (A) | (400 MHz, Chloroform-d) δ 8.45 (s, 1H), 8.05-7.80 (m, 2H), 7.25 (d, J = 0.8 Hz, 1H), 7.22-7.06 (m, 2H), 5.35 (d, J = 12.8 Hz, 1H), 4.75-4.19 (m, 2H), 3.93 (s, 1H), 3.67-2.82 (m, 4H), 1.52-1.42 (m, 15H), 1.21 (d, J = 6.8 Hz, 3H). |
| I-97 | 511.5 | 4.62 (A) | (400 MHz, Chloroform-d) δ 8.48 (s, 1H), 8.13-7.90 (m, 2H), 7.27 (d, J = 0.8 Hz, 1H), 7.22-7.09 (m, 2H), 5.56 (s, 1H), 4.82 (d, J = 49.5 Hz, 1H), 4.46 (d, J = 32.9 Hz, 1H), 3.75-2.80 (m, 6H), 1.48-1.46 (m, 6H), 1.38-1.22 (m, 5H), 1.04 (d, J = 8.7 Hz, 9H). |
| I-98 | 542.6 | 3.91 (A) | (400 MHz, Chloroform-d) δ 8.57 (d, J = 8.0 Hz, 1H), 8.04-7.89 (m, 2H), 7.74 (s, 1H), 7.41-7.29 (m, 4H), 7.26 (d, J = 3.6 Hz, 1H), 7.24-7.17 (m, 2H), 5.47 (d, J = 15.1 Hz, 1H), 5.22 (dd, J = 28.5, 6.5 Hz, 1H), 5.14-4.81 (m, 1H), 4.78-4.49 (m, 2H), 3.61-2.47 (m, 3H), 1.41-1.20 (m, 3H). |
| I-99 | 508.2 | 4.64 (A) | (400 MHz, Chloroform-d) δ 8.50 (s, 1H), 8.13-7.79 (m, 2H), 7.38 (s, 1H), 7.22-7.08 (m, 2H), 6.84-6.68 (m, 1H), 5.75 (s, 1H), 5.54 (d, J = 12.0 Hz, 1H), 5.02-4.36 (m, 3H), 3.74-2.84 (m, 4H), 2.34 (s, 3H), 1.35-1.21 (m, 5H), 1.06-0.93 (m, 10H). |
| I-100 | 544.4 | 2.79 (A) | (400 MHz, Methanol-$d_4$) δ 8.65 (s, 3H), 8.25-8.06 (m, 3H), 7.94 (d, J = 19.2 Hz, 1H), 7.48 (s, 1H), 7.38-7.17 (m, 2H), 5.64 (d, J = 12.5 Hz, 1H), 4.89 (s, 5H), 4.43 (d, J = 27.9 Hz, 1H), 3.26-2.98 (m, 1H), 1.39-1.11 (m, 3H). |
| I-101 | 517.8 | 2.98 (A) | (400 MHz, Methanol-$d_4$) δ 8.55 (d, J = 76.2 Hz, 3H), 8.19-8.02 (m, 2H), 7.92 (s, 1H), 7.56 (s, 1H), 7.49 (s, 1H), 7.34-7.20 (m, 2H), 5.63 (s, 1H), 4.89 (s, 2H), 4.45 (s, 1H), 4.08-3.37 (m, 2H), 3.27-2.86 (m, 3H), 1.47 (d, J = 6.9 Hz, 6H), 1.20 (dd, J = 36.8, 6.7 Hz, 3H). |
| I-102 | 496.2 | 4.01 (A) | (400 MHz, Methanol-$d_4$) δ 8.37 (d, J = 3.0 Hz, 1H), 8.23-8.00 (m, 2H), 7.65 (q, J = 1.0 Hz, 1H), 7.35-7.16 (m, 2H), 4.63-4.35 (m, 1H), 4.18 (d, J = 14.4 Hz, 2H), 3.91-3.66 (m, 4H), 3.24-3.18 (m, 1H), 2.67 (t, J = 1.0 Hz, 3H), 1.70-1.48 (m, 8H), 1.01 (d, J = 4.0 Hz, 9H). |
| I-103 | 525.8 | 4.01 (A) | (400 MHz, Methanol-$d_4$) δ 8.38 (d, J = 2.6 Hz, 1H), 8.20-8.04 (m, 2H), 7.57 (dd, J = 1.6, 0.8 Hz, 1H), 7.39-7.08 (m, 2H), 4.61-4.44 (m, 1H), 4.38-4.08 (m, 2H), 4.01-3.50 (m, 5H), 1.66 (s, 3H), 1.60 (d, J = 8.5 Hz, 4H), 1.55-1.50 (m, 1H), 1.48 (d, J = 6.9 Hz, 6H), 1.02 (d, J = 0.7 Hz, 9H). |

TABLE 1-continued

| Compound analytical data | | | |
|---|---|---|---|
| Compound Number | LCMS M + H | LCMS (Rt time) (method) | $^1$H NMR |
| I-104 | 496.2 | 4.92 (A) | (400 MHz, Methanol-$d_4$) δ 8.48 (s, 1H), 8.19-8.07 (m, 2H), 7.62 (t, J = 1.1 Hz, 1H), 7.33-7.15 (m, 2H), 5.07 (s, 1H), 4.79-4.22 (m, 3H), 4.02-3.34 (m, 2H), 3.22-2.93 (m, 4H), 1.46 (t, J = 7.5 Hz, 5H), 1.27 (s, 1H), 1.20 (s, 2H), 1.00 (s, 9H). |
| I-105 | 497.8 | 4.3 (A) | N/A |
| I-106 | 550.5 | 4.42 (A) | N/A |
| I-107 | 497.8 | 4.33 (A) | N/A |
| I-108 | 534.8 | 4.18 (A) | N/A |
| I-109 | 497.1 | 4.3 (A) | N/A |
| I-110 | 482.2 | 4 (A) | N/A |
| I-111 | 482.2 | 4.06 (A) | N/A |
| I-112 | 468.5 | 3.65 (A) | N/A |
| I-113 | 531.7 | 4.27 (A) | N/A |
| I-114 | 522.2 | 4.66 (A) | N/A |
| I-115 | 467.8 | 3.52 (A) | N/A |
| I-116 | 482.5 | 4.05 (A) | N/A |
| I-117 | 516.7 | 4.15 (A) | N/A |
| I-118 | 469.1 | 3.72 (A) | N/A |
| I-119 | 454.1 | 3.41 (A) | N/A |
| I-120 | 397.5 | 4.29 (A) | N/A |
| I-121 | 492.2 | 4.76 (A) | N/A |
| I-122 | 467.2 | 4.35 (A) | N/A |
| I-123 | 468.2 | 3.38 (A) | N/A |
| I-124 | 452.5 | 4.13 (A) | N/A |
| I-125 | 506.2 | 4.28 (A) | N/A |
| I-126 | 462.2 | 3.97 (A) | N/A |
| I-127 | 480.2 | 4.68 (A) | N/A |
| I-128 | 506.3 | 5 (A) | N/A |
| I-129 | 468.5 | 3.63 (A) | N/A |
| I-130 | 480.3 | 4.62 (A) | N/A |
| I-131 | 482.2 | 3.68 (A) | N/A |
| I-132 | 530.2 | 4.38 (A) | N/A |
| I-133 | 530.2 | 4.36 (A) | N/A |
| I-134 | 532.3 | 3.88 (A) | N/A |
| I-135 | 504.2 | 3.69 (A) | N/A |
| I-136 | 533.2 | 4.03 (A) | N/A |
| I-137 | 535.2 | 3.5 (A) | N/A |
| I-138 | 506.2 | 4.4 (A) | N/A |
| I-139 | 494.5 | 4.99 (A) | N/A |
| I-140 | 464.2 | 4.09 (A) | N/A |
| I-141 | 508.3 | 3.78 (A) | N/A |
| I-142 | 501.3 | 2.89 (A) | N/A |
| I-143 | 482.2 | 3.9 (A) | N/A |
| I-144 | 492.3 | 4.82 (A) | N/A |
| I-145 | 494.2 | 3.67 (A) | N/A |
| I-146 | 496.3 | 4.03 (A) | N/A |
| I-147 | 466.2 | 4.41 (A) | N/A |
| I-148 | 565.8 | 4.2 (A) | (400 MHz, Chloroform-d) δ 8.46 (s, 1H), 8.00-7.87 (m, 2H), 7.26 (d, J = 0.8 Hz, 1H), 7.23-7.16 (m, 2H), 5.48 (s, 1H), 5.17 (s, 1H), 5.02-4.27 (m, 3H), 3.62 (s, 1H), 3.48-3.14 (m, 2H), 3.11-2.81 (m, 1H), 1.46-1.08 (m, 22H). |
| I-149 | 579.6 | 4.41 (A) | (400 MHz, Methanol-$d_4$) δ 8.48 (s, 1H), 8.20-8.04 (m, 2H), 7.58 (s, 1H), 7.35-7.20 (m, 2H), 5.12 (s, 1H), 4.59 (d, J = 95.7 Hz, 2H), 3.71 (d, J = 79.1 Hz, 2H), 3.22-2.92 (m, 1H), 2.89-2.60 (m, 2H), 2.35-1.69 (m, 4H), 1.49 (d, J = 6.9 Hz, 6H), 1.40 (d, J = 5.0 Hz, 9H), 1.32-1.14 (m, 5H). |
| I-150 | 608.6 | 4.86 (A) | (400 MHz, Chloroform-d) δ 8.44 (s, 1H), 7.98-7.91 (m, 2H), 5.36 (s, 1H), 4.95 (s, 1H), 4.57 (s, 2H), 3.62 (s, 1H), 3.52-2.83 (m, 3H), 1.94 (s, 4H), 1.69 (s, 2H), 1.47-1.24 (m, 22H). |
| I-151 | 602.2 | 4.34 (A) | (400 MHz, Chloroform-d) δ 8.45 (s, 1H), 8.01-7.84 (m, 2H), 7.38-7.25 (m, 6H), 7.20 (dd, J = 9.5, 7.7 Hz, (2H), 5.57-5.14 (m, 2H), 5.06 (s, 2H), 4.68 (d, J = 112.6 Hz, 3H), 3.44 (d, J = 135.1 Hz, 3H), 1.57 (s, 6H), 1.47 (dd, J = 7.0, 1.0 Hz, 6H), 1.23 (d, J = 8.3 Hz, 3H). |
| I-152 | 496.3 | 4.3 (A) | (400 MHz, Methanol-$d_4$) δ 8.49 (s, 1H), 8.21-7.99 (m, 2H), 7.58 (s, 1H), 7.39-6.92 (m, 2H), 5.10 (t, J = 26.2 Hz, 1H), 4.68-4.06 (m, 4H), 3.81-3.43 (m, 2H), 3.24-2.96 (m, 2H), 1.49 (d, J = 6.9 Hz, 6H), 1.39-1.16 (m, 3H), 0.99 (d, J = 20.2 Hz, 9H). |

TABLE 1-continued

Compound analytical data

| Compound Number | LCMS M + H | LCMS (Rt time) (method) | $^1$H NMR |
|---|---|---|---|
| I-153 | 468.2 | 3.59 (A) | (400 MHz, Methanol-$d_4$) δ 8.49 (s, 1H), 8.22-8.06 (m, 2H), 7.67 (s, 1H), 7.36-7.17 (m, 2H), 5.00 (s, 1H), 4.39 (d, J = 74.0 Hz, 3H), 3.77-3.43 (m, 1H), 3.27-3.02 (m, 3H), 2.69 (d, J = 1.2 Hz, 3H), 1.27 (d, J = 44.1 Hz, 3H), 0.99 (d, J = 21.5 Hz, 9H). |
| I-154 | 465.7 | 2.73 (A) | (400 MHz, Methanol-$d_4$) δ 8.62 (d, J = 5.7 Hz, 1H), 8.28-8.03 (m, 2H), 7.75 (s, 1H), 7.29 (t, J = 8.7 Hz, 2H), 4.66 (d, J = 31.5 Hz, 2H), 4.16 (s, 1H), 3.75-3.45 (m, 9H), 1.50 (d, J = 6.9 Hz, 6H), 1.38 (dddd, J = 16.2, 11.2, 7.8, 5.1 Hz, 3H). |
| I-155 | 479.5 | 2.94 (A) | (400 MHz, Methanol-$d_4$) δ 8.54 (d, J = 4.0 Hz, 1H), 8.19-7.97 (m, 2H), 7.62 (s, 1H), 7.36-7.16 (m, 2H), 5.17 (s, 1H), 4.59 (s, 1H), 3.79-3.53 (m, 4H), 3.25-3.09 (m, 1H), 2.89 (d, J = 10.1 Hz, 2H), 2.52-2.28 (m, 3H), 2.12 (s, 1H), 1.50 (d, J = 6.9 Hz, 6H), 1.29 (d, J = 20.1 Hz, 4H). |
| I-156 | 507.4 | 3.11 (A) | (400 MHz, Methanol-$d_4$) δ 8.75-8.49 (m, 1H), 8.20-8.07 (m, 2H), 7.67 (t, J = 11.0 Hz, 1H), 7.38-7.24 (m, 2H), 5.00 (d, J = 17.3 Hz, 1H), 4.55 (s, 1H), 4.32 (s, 1H), 3.71-3.33 (m, 4H), 3.23-3.00 (m, 1H), 2.24 (t, J = 14.2 Hz, 2H), 1.87 (q, J = 15.1, 14.3 Hz, 4H), 1.50 (d, J = 6.9 Hz, 9H), 1.29 (d, J = 14.6 Hz, 4H). |
| I-157 | 467.8 | 2.69 (A) | (400 MHz, Methanol-$d_4$) δ 8.48 (s, 1H), 8.26-7.97 (m, 2H), 7.57 (s, 1H), 7.26 (t, J = 8.6 Hz, 2H), 5.09 (s, 1H), 4.54 (q, J = 23.1, 15.9 Hz, 2H), 3.62 (s, 2H), 3.41 (d, J = 39.7 Hz, 2H), 3.14 (d, J = 22.0 Hz, 1H), 1.53-1.25 (m, 15H). |
| I-158 | 441.5 | 2.95 (A) | N/A |
| I-159 | 453.4 | 3.09 (A) | N/A |
| I-160 | 450.2 | 3.82 (A) | (400 MHz, Chloroform-d) δ 8.36 (d, J = 8.3 Hz, 1H), 7.93 (ddd, J = 8.9, 5.2, 1.4 Hz, 2H), 7.20 (t, J = 8.5 Hz, 2H), 6.80-6.53 (m, 1H), 6.47-6.26 (m, 1H), 5.75 (ddd, J = 12.4, 10.3, 2.1 Hz, 1H), 4.42 (dt, J = 31.7, 5.8 Hz, 2H), 3.97-3.73 (m, 3H), 3.62 (d, J = 6.8 Hz, 2H), 1.64 (d, J = 3.1 Hz, 6H), 1.45 (dd, J = 6.9, 3.3 Hz, 6H). |
| I-161 | 468.3 | 3.34 (A) | N/A |
| I-162 | 480.8 | 3.49 (A) | N/A |
| I-163 | 487.5 | 2.58 (A) | N/A |
| I-164 | 494.3 | 3.45 (A) | N/A |
| I-165 | 510.6 | 3.64 (A) | N/A |
| I-165 | 482.3 | 3.76 (A) | N/A |
| I-167 | 498.6 | 4.02 (A) | N/A |
| I-168 | 470.5 | 3.7 (A) | N/A |
| I-169 | 482.8 | 3.96 (A) | N/A |
| I-170 | 480.3 | 3.67 (A) | N/A |
| I-171 | 494.5 | 3.34 (A) | N/A |
| I-172 | 482.2 | 3.95 (A) | N/A |
| I-173 | 494.2 | 3.73 (A) | (400 MHz, Methanol-$d_4$) δ 8.37 (d, J = 2.2 Hz, 1H), 8.24-8.06 (m, 2H), 7.62 (dt, J = 2.9, 1.0 Hz, 1H), 7.39-7.13 (m, 2H), 4.54 (ddd, J = 26.6, 7.4, 5.4 Hz, 1H), 4.37-4.05 (m, 2H), 4.02-3.45 (m, 4H), 3.10 (qdd, J = 7.5, 2.6, 1.0 Hz, 2H), 1.74-1.59 (m, 7H), 1.44 (td, J = 7.5, 2.7 Hz, 3H), 0.91-0.74 (m, 2H), 0.55-0.38 (m, 2H), 0.23-0.03 (m, 2H). |
| I-174 | 482.51 | 1.65 (F) | (400 MHz, DMSO-$d_6$) δ 8.50 (s, 1H), 8.20-8.08 (m, 2H), 7.65 (d, J = 0.8 Hz, 1H), 7.45-7.33 (m, 2H), 5.44-5.25 (m, 1H), 4.09 (s, 4H), 3.65-3.48 (m, 2H), 3.42 (s, 1H), 1.54-1.38 (m, 12H), 1.32 (s, 6H). |
| I-175 | 468.69 | 1.57 (A) | (400 MHz, DMSO-$d_6$) δ 8.54 (d, J = 4.5 Hz, 1H), 8.20-8.12 (m, 2H), 7.68 (d, J = 2.2 Hz, 1H), 7.45-7.37 (m, 2H), 4.97 (dd, J = 20.2, 7.2 Hz, 1H), 4.44 (dp, J = 30.3, 6.6 Hz, 1H), 4.25-4.05 (m, 2H), 3.88-3.68 (m, 2H), 3.68-3.62 (m, 1H), 3.62-3.43 (m, 2H), 1.54 (s, 3H), 1.50 (d, J = 4.7 Hz, 3H), 1.44 (d, J = 6.9 Hz, 6H), 1.21 (dd, J = 6.5, 2.6 Hz, 3H). |
| I-176 | 496.55 | 1.81 (A) | (400 MHz, DMSO-$d_6$) δ 8.56-8.52 (m, 1H), 8.20-8.13 (m, 2H), 7.70-7.66 (m, 1H), 7.46-7.37 (m, 2H), 4.79-4.71 (m, 1H), 4.27-4.16 (m, 1H), 4.13-3.95 (m, 2H), 3.84-3.41 (m, 5H), 2.00-1.83 (m, 1H), 1.57-1.48 (m, 6H), 1.47-1.41 (m, 6H), 0.91-0.82 (m, 6H). |
| I-177 | 507.75 | 1.44 (A) | (400 MHz, DMSO-$d_6$) δ 8.55 (d, J = 7.7 Hz, 1H), 8.20-8.13 (m, 2H), 7.77 (d, J = 19.1 Hz, 1H), 7.68 (d, J = 3.8 Hz, 1H), 7.46-7.37 (m, 2H), 4.64-4.44 (m, 1H), |

TABLE 1-continued

| Compound analytical data | | | |
|---|---|---|---|
| Compound Number | LCMS M + H | LCMS (Rt time) (method) | $^1$H NMR |
| | | | 4.27-4.03 (m, 2H), 3.86-3.41 (m, 5H), 2.42-2.29 (m, 1H), 2.21-2.06 (m, 2H), 1.98-1.81 (m, 1H), 1.60-1.48 (m, 6H), 1.48-1.40 (m, 6H). |
| I-178 | 480.45 | 1.66 (A) | (400 MHz, DMSO-$d_6$) δ 8.59 (s, 1H), 8.21-8.13 (m, 2H), 7.69 (d, J = 0.8 Hz, 1H), 7.45-7.38 (m, 2H), 6.12-5.93 (m, 1H), 5.21-4.55 (m, 1H), 4.55-3.86 (m, 2H), 3.62-3.49 (m, 1H), 3.21-2.78 (m, 2H), 2.67 (p, J = 1.9 Hz, 2H), 2.21-1.94 (m, 2H), 1.82-1.67 (m, 1H), 1.45 (d, J = 7.0 Hz, 7H), 1.35-1.06 (m, 3H). |
| I-179 | 424.16 | 3.33 (A) | (400 MHz, DMSO-d6) δ 8.58 (s, 1H), 8.26-8.20 (m, 1H), 8.20-8.12 (m, 2H), 7.68 (d, J = 0.7 Hz, 1H), 7.46-7.36 (m, 2H), 4.18 (ddd, J = 13.5, 5.1, 3.0 Hz, 1H), 3.67 (ddd, J = 13.5, 8.5, 2.9 Hz, 1H), 3.54 (p, J = 6.9 Hz, 1H), 3.48-3.18 (m, 2H), 2.77 (dq, J = 14.4, 7.4 Hz, 1H), 1.93 (dq, J = 14.4, 7.3 Hz, 1H), 1.64 (s, 3H), 1.44 (d, J = 6.9 Hz, 6H), 0.80 (t, J = 7.3 Hz, 3H). |
| I-180 | 482.48 | 3.15 (A) | (400 MHz, DMSO-d6) δ 8.58 (s, 1H), 8.20-8.12 (m, 2H), 7.69 (d, J = 0.7 Hz, 1H), 7.46-7.37 (m, 2H), 4.60 (s, 1H), 4.06-3.97 (m, 2H), 3.74-3.66 (m, 2H), 3.55 (p, J = 7.0 Hz, 1H), 3.38 (s, 2H), 1.74 (s, 6H), 1.44 (d, J = 6.9 Hz, 6H), 1.09 (s, 6H). |
| I-181 | 424.44 | 3.21 (A) | NMR (400 MHz, DMSO-d6) δ 8.58 (s, 1H), 8.20-8.13 (m, 2H), 7.69 (d, J = 0.7 Hz, 1H), 7.46-7.37 (m, 2H), 4.04-3.96 (m, 2H), 3.61-3.49 (m, 3H), 2.93 (s, 3H), 1.71 (s, 6H), 1.44 (d, J = 6.9 Hz, 6H). |

N/A = not available

TABLE 2

| Compound analytical data | | | | | |
|---|---|---|---|---|---|
| Compound Number | LCMS Retention Time | M + 1 | LCMS Method | NMR | General Procedure |
| I-182 | 2.89 | 481.17 | A | $^1$H NMR (400 MHz, DMSO-$d_6$) δ 8.38 (s, 1H), 8.16-7.93 (m, 3H), 7.40-7.23 (m, 2H), 6.79 (s, 1H), 4.95 (s, 2H), 4.03-3.90 (m, 2H), 3.74 (ddd, J = 10.6, 6.3, 2.4 Hz, 2H), 3.34 (q, J = 4.8, 4.1 Hz, 2H), 2.73 (dd, J = 13.0, 10.6 Hz, 2H), 1.65 (s, 7H), 1.16 (d, J = 6.1 Hz, 6H). | 19 |
| I-183 | 2.82 | 481.66 | A | $^1$H NMR (400 MHz, DMSO-$d_6$) δ 8.37 (s, 1H), 8.13-7.96 (m, 3H), 7.38-7.17 (m, 2H), 6.75 (s, 1H), 4.39-3.80 (m, 8H), 3.33 (dd, J = 6.4, 3.2 Hz, 2H), 1.66 (s, 3H), 1.65 (s, 3H), 1.18 (s, 3H), 1.17 (s, 3H). | 19 |
| I-184 | 2.39 | 426.41 | A | $^1$H NMR (400 MHz, DMSO-$d_6$) δ 8.60 (s, 1H), 8.14-8.04 (m, 3H), 7.80 (s, 1H), 7.49-7.38 (m, 2H), 5.71 (s, 1H), 3.97-3.89 (m, 2H), 3.40-3.35 (m, 2H), 1.73 (s, 6H), 1.70 (s, 6H). | 18 |
| I-185 | 3.07 | 553.24 | A | $^1$H NMR (400 MHz, Methanol-$d_4$) δ 8.25 (s, 1H), 8.09-7.82 (m, 2H), 7.30-7.05 (m, 2H), 6.70 (s, 1H), 5.47 (s, 5H), 4.29 (m, 4H), 3.97-3.53 (m, 4H), 3.27-3.01 (m, 2H), 2.76 (m, 2H), 1.61 (d, J = 11.6 Hz, 6H), 1.45 (s, 6H), 1.27 (d, J = 6.2 Hz, 6H). | 3 |
| I-186 | 3.36 | 568.5 | A | $^1$H NMR (400 MHz, Methanol-$d_4$) δ 8.26 (d, J = 4.0 Hz, 1H), 8.02 (ddd, J = 8.9, 5.4, 1.2 Hz, 2H), 7.21 (t, J = 8.7 Hz, 2H), 6.70 (d, J = 5.1 Hz, 1H), 4.67-4.07 | 3 |

TABLE 2-continued

Compound analytical data

| Compound Number | LCMS Retention Time | M + 1 | LCMS Method | NMR | General Procedure |
|---|---|---|---|---|---|
| | | | | (m, 3H), 3.96-3.55 (m, 6H), 3.27-3.07 (m, 2H), 2.84-2.66 (m, 2H), 1.99 (dt, J = 13.2, 6.6 Hz, 1H), 1.61 (dd, J = 12.0, 4.7 Hz, 6H), 1.28 (dd, J = 6.3, 3.9 Hz, 6H), 1.04-0.89 (m, 6H). | |
| I-187 | 3.68 | 411.03 | A | $^1$H NMR (400 MHz, DMSO-$d_6$) δ 8.52 (s, 1H), 8.19-8.12 (m, 2H), 7.67 (s, 1H), 7.46-7.35 (m, 2H), 4.46 (dd, J = 13.5, 2.9 Hz, 1H), 3.82 (dqd, J = 9.3, 6.1, 2.9 Hz, 1H), 3.57-3.38 (m, 3H), 3.03 (dd, J = 13.5, 10.1 Hz, 1H), 1.49-1.37 (m, 12H), 1.09 (d, J = 6.2 Hz, 3H). | 1 |
| I-188 | 3.48 | 438.05 | A | $^1$H NMR (400 MHz, DMSO-$d_6$) ä 8.58 (s, 1H), 8.19-8.11 (m, 2H), 7.50 (s, 1H), 7.42 (t, J = 8.8 Hz, 2H), 4.10-4.02 (m, 2H), 3.60-3.52 (m, 2H), 2.93 (s, 3H), 1.71 (s, 6H), 1.59 (s, 9H). | 10 |
| I-189 | 2.46 | 441.31 | A | $^1$H NMR (400 MHz, Methanol-$d_4$) δ 8.40 (s, 1H), 8.15-7.97 (m, 2H), 7.51 (s, 1H), 7.34-6.89 (m, 2H), 4.22-4.13 (m, 2H), 4.10 (s, 2H), 3.54 (dd, J = 5.7, 3.9 Hz, 2H), 1.82 (s, 6H), 1.56 (s, 6H). | 1 |
| I-190 | 4.49 | 510.12 | A | $^1$H NMR (400 MHz, DMSO-$d_6$) δ 8.52 (s, 1H), 8.19-8.09 (m, 2H), 7.49 (s, 1H), 7.47-7.36 (m, 2H), 5.76 (s, 1H), 4.17-4.05 (m, 2H), 3.59-3.52 (m, 1H), 3.52-3.43 (m, 2H), 1.59 (s, 9H), 1.50 (s, 6H), 1.43 (s, 9H). | 1 |
| I-191 | 3.18 | 424.33 | A | $^1$H NMR (400 MHz, DMSO-$d_6$) δ 8.57 (s, 1H), 8.17-8.12 (m, 2H), 8.14-8.09 (m, 1H), 7.49 (s, 1H), 7.45-7.37 (m, 2H), 4.00-3.94 (m, 2H), 3.42-3.36 (m, 2H), 1.70 (s, 6H), 1.58 (s, 9H). | 1 |
| I-192 | 2.44 | 481.63 | A | $^1$H NMR (400 MHz, Methanol-$d_4$) δ 8.48 (s, 1H), 8.24-7.99 (m, 2H), 7.66 (s, 1H), 7.28 (t, J = 8.8 Hz, 2H), 4.28-4.11 (m, 2H), 3.59-3.51 (m, 2H), 2.88 (s, 3H), 2.50 (s, 3H), 1.79 (s, 6H), 1.72 (s, 6H). | 1 |
| I-193 | 2.96 | 454.08 | A | $^1$H NMR (400 MHz, Methanol-$d_4$) δ 8.41 (s, 1H), 8.18-7.92 (m, 2H), 7.47 (s, 1H), 7.35-7.09 (m, 2H), 4.28-4.07 (m, 2H), 3.96 (s, 2H), 3.64-3.47 (m, 2H), 3.24 (s, 3H), 1.83 (s, 6H), 1.58 (s, 6H). | 1 |
| I-194 | 3.43 | 509.47 | A | $^1$H NMR (400 MHz, DMSO-$d_6$) δ 8.58 (s, 1H), 8.18-8.11 (m, 2H), 7.50 (s, 1H), 7.46-7.37 (m, 2H), 4.25 (s, 2H), 4.16-4.06 (m, 2H), 3.58-3.49 (m, 2H), 2.96 (s, 3H), 2.84 (s, 3H), 1.72 (s, 6H), 1.58 (s, 9H). | 10 |
| I-195 | 3.46 | 482.53 | A | $^1$H NMR (400 MHz, DMSO-$d_6$) δ 8.56 (s, 1H), 8.20-8.09 (m, 2H), 7.67 (s, 1H), 7.44-7.32 (m, 2H), 5.23-4.71 (m, 3H), 4.62-3.70 (m, 3H), 3.52 (p, J = 7.0 Hz, 1H), 3.25-2.71 (m, 3H), 1.95-1.72 (m, 1H), 1.42 (d, J = 6.9 Hz, 6H), 1.34-1.05 (m, 2H), 0.93-0.71 (m, 6H). | 3 |
| I-196 | 3.63 | 510.22 | A | $^1$H NMR (400 MHz, DMSO-$d_6$) δ 8.56 (s, 1H), 8.18-8.06 (m, 2H), 7.67 (s, 1H), 7.46-7.27 (m, 2H), 5.18-4.92 (m, 1H), 4.76 (s, 2H), 4.46-4.28 (m, 1H), 3.91 (dd, J = 158.7, 13.4 Hz, 1H), 3.52 (p, J = | 3 |

TABLE 2-continued

| Compound Number | LCMS Retention Time | M + 1 | LCMS Method | NMR | General Procedure |
|---|---|---|---|---|---|
| Compound analytical data | | | | | |
| | | | | 6.9 Hz, 1H), 3.24-2.61 (m, 2H), 1.42 (d, J = 6.9 Hz, 7H), 1.38-1.08 (m, 5H), 1.01-0.80 (m, 9H). | |
| I-197 | 3.92 | 510.54 | A | $^{1}$H NMR (400 MHz, DMSO-$d_6$) δ 8.59 (d, J = 1.7 Hz, 1H), 8.21-8.13 (m, 2H), 7.69 (s, 1H), 7.46-7.36 (m, 2H), 5.24-4.63 (m, 2H), 4.57-3.85 (m, 3H), 3.55 (p, J = 6.9 Hz, 1H), 3.26-2.71 (m, 2H), 1.67-1.05 (m, 12H), 0.94 (d, J = 6.0 Hz, 9H). | 3 |
| I-198 | 3.36 | 496.4 | F | $^{1}$H NMR (400 MHz, DMSO-$d_6$) δ 8.52 (s, 1H), 8.18-8.11 (m, 2H), 7.49 (s, 1H), 7.45-7.37 (m, 2H), 5.47-5.24 (m, 1H), 4.24-4.03 (m, 4H), 3.67-3.43 (m, 2H), 1.59 (s, 9H), 1.57-1.46 (m, 6H), 1.35 (s, 6H). | 3 |
| I-199 | 3.67 | 576.06 | F | $^{1}$H NMR (400 MHz, DMSO-$d_6$) δ 8.53 (d, J = 6.4 Hz, 1H), 8.20-8.09 (m, 2H), 7.49 (d, J = 4.0 Hz, 1H), 7.47-7.36 (m, 2H), 6.61 (d, J = 27.7 Hz, 1H), 4.15 (dt, J = 21.1, 5.6 Hz, 2H), 3.70-3.62 (m, 2H), 3.56-3.46 (m, 2H), 3.09-2.93 (m, 1H), 2.70-2.56 (m, 2H), 2.41 (dd, J = 13.0, 9.2 Hz, 2H), 1.59 (s, 9H), 1.51 (d, J = 12.7 Hz, 6H). | 3 |
| I-200 | 3.44 | 508.4 | A | $^{1}$H NMR (400 MHz, DMSO-$d_6$) δ 8.53 (d, J = 5.2 Hz, 1H), 8.18-8.11 (m, 2H), 7.49 (d, J = 1.9 Hz, 1H), 7.45-7.37 (m, 2H), 4.74-4.62 (m, 1H), 4.28-4.10 (m, 2H), 3.92-3.57 (m, 5H), 3.54-3.47 (m, 1H), 2.10-1.99 (m, 2H), 1.94-1.77 (m, 2H), 1.59 (d, J = 2.1 Hz, 9H), 1.54 (d, J = 2.4 Hz, 3H), 1.49 (d, J = 1.5 Hz, 3H). | 3 |
| I-201 | 3.17 | 504.13 | A | $^{1}$H NMR (400 MHz, DMSO-$d_6$) δ 13.23 (s, 1H), 8.53 (d, J = 7.5 Hz, 1H), 8.19-8.11 (m, 2H), 7.87-7.80 (m, 1H), 7.48 (d, J = 8.7 Hz, 1H), 7.46-7.37 (m, 2H), 6.68-6.62 (m, 1H), 4.32-4.10 (m, 4H), 3.87-3.77 (m, 1H), 3.74-3.66 (m, 1H), 1.63-1.47 (m, 15H). | 3 |
| I-202 | 3.17 | 504.13 | F | $^{1}$H NMR (400 MHz, DMSO-$d_6$) δ 8.80 (t, J = 1.8 Hz, 1H), 8.55 (d, J = 4.7 Hz, 1H), 8.18-8.11 (m, 2H), 7.49 (d, J = 8.3 Hz, 1H), 7.45-7.37 (m, 2H), 7.05 (dd, J = 33.0, 1.9 Hz, 1H), 4.26 (dt, J = 32.4, 5.5 Hz, 2H), 3.95 (t, J = 5.5 Hz, 1H), 3.85-3.71 (m, 3H), 1.64-1.48 (m, 15H). | 3 |
| I-203 | 3.03 | 505.08 | A | $^{1}$H NMR (400 MHz, DMSO-$d_6$) δ 9.13 (dd, J = 7.0, 1.7 Hz, 1H), 8.54 (d, J = 8.2 Hz, 1H), 8.20-8.08 (m, 2H), 7.48 (d, J = 11.4 Hz, 1H), 7.45-7.37 (m, 2H), 6.90 (dd, J = 8.6, 1.7 Hz, 1H), 4.24 (dt, J = 50.3, 5.7 Hz, 2H), 3.87 (t, J = 5.6 Hz, 1H), 3.82 (d, J = 7.0 Hz, 2H), 3.76 (t, 1H), 1.63-1.46 (m, 15H). | 3 |
| I-204 | 4.58 | 604.31 | G | $^{1}$H NMR (400 MHz, cdcl3) δ 8.35 (d, J = 7.6 Hz, 1H), 7.98-7.88 (m, 2H), 7.27 (d, J = 6.2 Hz, 1H), 7.24-7.16 (m, 2H), 4.35 (dt, J = 22.6, 5.8 Hz, 2H), 4.17-4.02 (m, 4H), 3.83-3.42 (m, 5H), 3.22-3.02 (m, 1H), 2.92-2.38 (m, 5H), 2.12-1.87 (m, 4H), 1.62 (d, J = 4.3 Hz, 6H). | 3 |

TABLE 2-continued

Compound analytical data

| Compound Number | LCMS Retention Time | M + 1 | LCMS Method | NMR | General Procedure |
|---|---|---|---|---|---|
| I-205 | 2.4 | 410.05 | A | $^1$H NMR (400 MHz, DMSO-$d_6$) δ 9.04 (s, 2H), 8.59 (s, 1H), 8.19-8.11 (m, 2H), 7.51 (s, 1H), 7.46-7.38 (m, 2H), 4.11 (t, J = 5.2 Hz, 2H), 3.22 (s, 2H), 1.59 (d, J = 2.2 Hz, 15H). | 2 |
| I-206 | 4.06 | 464.46 | A | $^1$H NMR (400 MHz, DMSO-$d_6$) δ 8.57 (s, 1H), 8.18-8.11 (m, 2H), 7.50 (s, 1H), 7.45-7.37 (m, 2H), 4.08-4.00 (m, 2H), 3.51-3.44 (m, 2H), 2.78 (tt, J = 7.4, 4.0 Hz, 1H), 1.68 (s, 6H), 1.59 (s, 9H), 0.77-0.70 (m, 2H), 0.63-0.58 (m, 2H). | 21 |
| I-207 | 3.94 | 466.09 | A | $^1$H NMR (400 MHz, DMSO-$d_6$) δ 8.58 (s, 1H), 8.18-8.12 (m, 2H), 7.50 (s, 1H), 7.45-7.38 (m, 2H), 4.54 (p, J = 6.8 Hz, 1H), 4.07-4.00 (m, 2H), 3.47-3.40 (m, 2H), 1.71 (s, 6H), 1.60 (s, 9H), 1.10 (d, J = 6.8 Hz, 6H). | 10 |
| I-208 | 4.84 | 474.4 | A | $^1$H NMR (400 MHz, DMSO-$d_6$) δ 8.61 (s, 1H), 8.19-8.11 (m, 2H), 7.50 (s, 1H), 7.66-7.25 (m, 3H), 3.93 (t, J = 4.7 Hz, 2H), 3.71-3.64 (m, 2H), 1.76 (s, 6H), 1.59 (s, 9H). | 20 |
| I-209 | 4.48 | 566.52 | A | $^1$H NMR (400 MHz, cdcl3) δ 8.30 (s, 1H), 8.00-7.84 (m, 2H), 7.23-7.14 (m, 3H), 4.20 (t, J = 5.8 Hz, 2H), 3.83-3.68 (m, 2H), 3.68-3.43 (m, 4H), 2.13-1.96 (m, 4H), 1.94-1.74 (m, 1H), 1.60 (s, 6H), 1.26 (d, J = 6.1 Hz, 6H), 1.21 (s, 9H). | 11 |
| I-210 | 3.63 | 480.43 | A | $^1$H NMR (400 MHz, DMSO-$d_6$) δ 8.59 (s, 1H), 8.20-8.10 (m, 2H), 7.51 (s, 1H), 7.47-7.36 (m, 2H), 5.19 (p, J = 7.1 Hz, 1H), 4.70 (t, J = 7.3 Hz, 2H), 4.65 (t, J = 6.8 Hz, 2H), 4.18-4.10 (m, 2H), 3.78-3.71 (m, 2H), 1.71 (s, 6H), 1.61 (s, 9H). | 10 |
| I-211 | 4 | 452.18 | A | $^1$H NMR (400 MHz, DMSO-$d_6$) δ 8.55 (s, 1H), 8.15-8.08 (m, 2H), 7.47 (s, 1H), 7.42-7.34 (m, 2H), 4.07-4.00 (m, 2H), 3.55-3.49 (m, 2H), 3.35 (q, J = 7.1 Hz, 2H), 1.68 (s, 6H), 1.56 (s, 9H), 1.04 (t, J = 7.1 Hz, 3H). | 10 |
| I-212 | 3.37 | 422.39 | A | $^1$H NMR (400 MHz, DMSO-$d_6$) δ 8.63 (s, 1H), 8.24-8.14 (m, 2H), 7.73 (s, 1H), 7.47-7.38 (m, 2H), 6.91-6.87 (m, 1H), 5.84-5.79 (m, 1H), 4.07-4.01 (m, 2H), 3.57-3.50 (m, 2H), 2.93 (s, 3H), 2.39-2.33 (m, 3H), 1.71 (s, 6H). | 10 |
| I-213 | 3.62 | 632.49 | A | $^1$H NMR (400 MHz, cdcl3) δ 8.36 (d, J = 7.6 Hz, 1H), 7.95 (dd, J = 7.5, 5.2 Hz, 2H), 7.22 (t, J = 8.4 Hz, 2H), 4.36 (dt, J = 21.7, 5.7 Hz, 2H), 4.22 (s, 1H), 3.86-3.41 (m, 6H), 3.25-3.04 (m, 1H), 2.87-2.71 (m, 2H), 2.63-2.42 (m, 2H), 2.04 (td, J = 12.0, 3.4 Hz, 2H), 1.70-1.43 (m, 10H), 1.30 (d, J = 6.1 Hz, 6H). | 3 |
| I-214 | 3.09 | 560.45 | A | $^1$H NMR (400 MHz, cdcl3) δ 8.33 (s, 1H), 8.00-7.87 (m, 2H), 7.70-7.55 (m, 1H), 7.28 (s, 1H), 7.20 (s, 2H), 6.76 (s, 1H), 4.47-3.40 (m, 10H), 2.02 (dd, J = 22.5, 13.4 | 3 |

TABLE 2-continued

Compound analytical data

| Compound Number | LCMS Retention Time | M + 1 | LCMS Method | NMR | General Procedure |
|---|---|---|---|---|---|
| | | | | Hz, 2H), 1.63 (d, J = 31.6 Hz, 6H), 1.50 (q, J = 12.2 Hz, 1H), 1.33-1.18 (m, 6H). | |
| I-215 | 1.83 | 532.48 | C | $^1$H NMR (400 MHz, DMSO-$d_6$) δ 8.59 (s, 1H), 8.38-8.26 (m, 2H), 8.00-7.90 (m, 2H), 7.80-7.71 (m, 1H), 5.46-5.30 (m, 1H), 4.19-3.95 (m, 3H), 3.66-3.53 (m, 2H), 3.50-3.39 (m, 1H), 1.59-1.42 (m, 12H), 1.36-1.33 (m, 7H). | 6 |
| I-216 | 1.74 | 478.12 | C | $^1$H NMR (400 MHz, DMSO-$d_6$) δ 8.53 (s, 1H), 7.93-7.90 (m, 1H), 7.90-7.85 (m, 1H), 7.66 (s, 1H), 7.45 (t, J = 7.7 Hz, 1H), 7.39-7.34 (m, 1H), 5.47-5.30 (m, 1H), 4.21-4.01 (m, 4H), 3.66-3.51 (m, 2H), 3.49-3.40 (m, 1H), 2.43 (s, 3H), 1.60-1.41 (m, 12H), 1.35 (s, 6H). | 6 |
| I-217 | 1.79 | 532.02 | C | $^1$H NMR (400 MHz, DMSO-$d_6$) δ 8.60 (s, 1H), 8.45-8.40 (m, 2H), 7.96-7.91 (m, 1H), 7.86-7.79 (m, 2H), 5.46-5.31 (m, 1H), 4.22-3.97 (m, 4H), 3.67-3.52 (m, 2H), 3.53-3.39 (m, 1H), 1.61-1.41 (m, 12H), 1.35 (s, 6H). | 6 |
| I-218 | 4.5 | 478.6 | D | $^1$H NMR (400 MHz, DMSO-$d_6$) δ 8.51 (s, 1H), 8.00 (d, J = 8.2 Hz, 2H), 7.65 (s, 1H), 7.40-7.34 (m, 2H), 5.46-5.29 (m, 1H), 4.21-4.00 (m, 4H), 3.65-3.50 (m, 2H), 3.49-3.39 (m, 1H), 2.40 (s, 3H), 1.60-1.39 (m, 12H), 1.35 (s, 6H). | 6 |
| I-219 | 4.83 | 548.51 | D | $^1$H NMR (400 MHz, DMSO-$d_6$) δ 8.56 (s, 1H), 8.26-8.18 (m, 2H), 7.70 (s, 1H), 7.62-7.53 (m, 2H), 5.46-5.30 (m, 1H), 4.20-4.02 (m, 4H), 3.65-3.51 (m, 2H), 3.45 (s, 1H), 1.64-1.47 (m, 6H), 1.47-1.41 (m, 6H), 1.35 (s, 6H). | 6 |
| I-220 | 1.5 | 489.69 | C | $^1$H NMR (400 MHz, DMSO-$d_6$) δ 8.59 (s, 1H), 8.34-8.29 (m, 2H), 8.09-8.04 (m, 2H), 7.77 (s, 1H), 5.48-5.30 (m, 1H), 4.21-3.96 (m, 4H), 3.67-3.53 (m, 2H), 3.49-3.41 (m, 1H), 1.61-1.41 (m, 12H), 1.35 (s, 6H). | 6 |
| I-221 | 1.68 | 500.1 | C | $^1$H NMR (400 MHz, DMSO-$d_6$) δ 8.55 (s, 1H), 8.21 (ddd, J = 12.1, 7.8, 2.3 Hz, 1H), 8.03-7.97 (m, 1H), 7.72 (s, 1H), 7.65 (dt, J = 10.6, 8.5 Hz, 1H), 5.47-5.30 (m, 1H), 4.18-3.99 (m, 4H), 3.67-3.50 (m, 2H), 3.44 (s, 1H), 1.60-1.39 (m, 12H), 1.35 (s, 6H). | 6 |
| I-222 | 4.75 | 550.55 | D | $^1$H NMR (400 MHz, DMSO-$d_6$) δ 8.60 (s, 1H), 8.52-8.47 (m, 1H), 8.46-8.42 (m, 1H), 7.80 (s, 1H), 7.79-7.71 (m, 1H), 5.46-5.31 (m, 1H), 4.19-3.98 (m, 4H), 3.67-3.52 (m, 2H), 3.45 (s, 1H), 1.65-1.29 (m, 18H). | 6 |
| I-223 | 1.76 | 497.67 | C | $^1$H NMR (400 MHz, DMSO-$d_6$) δ 8.52 (s, 1H), 8.08-8.03 (m, 1H), 7.99-7.93 (m, 1H), 7.66 (s, 1H), 7.37-7.30 (m, 1H), 5.47-5.32 (m, 1H), 4.18-3.98 (m, 4H), 3.69-3.50 (m, 2H), 3.50-3.41 (m, 1H), 2.38-2.33 (m, 3H), 1.60-1.41 (m, 12H), 1.35 (s, 6H). | 6 |
| I-224 | 4.45 | 500.63 | C | $^1$H NMR (400 MHz, DMSO-$d_6$) δ 8.57 (s, 1H), 7.91-7.85 (m, 2H), 7.77 (s, 1H), 7.52-7.44 (m, 1H), 5.48-5.30 (m, 1H), 4.18-3.97 | 6 |

TABLE 2-continued

| Compound analytical data | | | | | |
|---|---|---|---|---|---|
| Compound Number | LCMS Retention Time | M + 1 | LCMS Method | NMR | General Procedure |
| | | | | (m, 4H), 3.66-3.51 (m, 2H), 3.49-3.40 (m, 1H), 1.59-1.41 (m, 12H), 1.35 (s, 6H). | |
| I-225 | 3.75 | 496.44 | A | $^1$H NMR (400 MHz, Methanol-$d_4$) δ 8.40 (s, 1H), 8.19-7.90 (m, 2H), 7.48 (s, 1H), 7.27 (t, J = 8.8 Hz, 2H), 4.33-4.17 (m, 2H), 3.90-3.78 (m, 2H), 3.51 (s, 2H), 1.85 (s, 6H), 1.62 (s, 9H), 1.21 (s, 6H). | 10 |
| I-226 | 2.78 | 437.95 | A | $^1$H NMR (400 MHz, DMSO-$d_6$) δ 8.61 (s, 1H), 8.18-8.11 (m, 2H), 8.04 (d, J = 8.8 Hz, 1H), 7.50 (s, 1H), 7.46-7.37 (m, 2H), 4.44-4.31 (m, 1H), 4.16 (d, J = 5.8 Hz, 2H), 1.62 (s, 9H), 1.25 (d, J = 6.8 Hz, 3H), 1.19 (s, 6H). | 1 |
| I-227 | 3.22 | 505.01 | A | $^1$H NMR (400 MHz, DMSO-$d_6$) δ 8.54 (d, J = 8.6 Hz, 1H), 8.50-8.42 (m, 1H), 8.19-8.10 (m, 2H), 7.48 (d, J = 10.7 Hz, 1H), 7.45-7.36 (m, 2H), 4.31 (t, J = 5.8 Hz, 1H), 4.23-4.13 (m, 2H), 4.10-4.01 (m, 1H), 3.83 (s, 1H), 3.75 (t, J = 6.7, 4.8 Hz, 1H), 1.66-1.43 (m, 15H). | 3 |
| I-228 | 3.28 | 504.47 | A | $^1$H NMR (400 MHz, DMSO-$d_6$) δ 13.25 (s, 1H), 8.54 (s, 1H), 8.23-8.08 (m, 3H), 7.91-7.72 (m, 1H), 7.48 (s, 1H), 7.45-7.36 (m, 2H), 4.33-4.14 (m, 2H), 3.96 (s, 1H), 3.88-3.73 (m, 2H), 3.65 (s, 1H), 1.67-1.40 (m, 15H). | 3 |
| I-229 | 3.53 | 503.99 | A | $^1$H NMR (400 MHz, DMSO-$d_6$) δ 13.04-12.91 (m, 1H), 8.54 (d, J = 6.7 Hz, 1H), 8.20-8.13 (m, 2H), 7.49 (d, J = 4.7 Hz, 1H), 7.46-7.37 (m, 2H), 7.31-7.25 (m, 1H), 7.15-7.08 (m, 1H), 4.76 (s, 1H), 4.45-4.20 (m, 3H), 3.84 (s, 1H), 3.77-3.69 (m, 1H), 1.65-1.50 (m, 15H). | 3 |
| I-230 | 3.53 | 516.47 | A | $^1$H NMR (400 MHz, DMSO-$d_6$) δ 9.31 (d, J = 3.3 Hz, 1H), 9.00 (s, 1H), 8.93 (s, 1H), 8.54 (d, J = 10.7 Hz, 1H), 8.20-8.07 (m, 2H), 7.54-7.34 (m, 3H), 4.33-4.23 (m, 1H), 4.17-4.07 (m, 1H), 3.83-3.66 (m, 3H), 3.61 (s, 1H), 1.67-1.38 (m, 15H). | 3 |
| I-231 | 3.64 | 516.47 | A | $^1$H NMR (400 MHz, DMSO-$d_6$) δ 9.25 (dd, J = 4.3, 1.4 Hz, 1H), 8.97 (dd, J = 5.1, 1.2 Hz, 1H), 8.50 (d, J = 10.9 Hz, 1H), 8.16-8.05 (m, 2H), 7.71 (ddd, J = 7.8, 5.1, 1.5 Hz, 1H), 7.50-7.32 (m, 3H), 4.27 (t, J = 5.7 Hz, 1H), 4.07 (t, J = 5.7 Hz, 1H), 3.78 (s, 1H), 3.76-3.65 (m, 2H), 3.60 (s, 1H), 1.63-1.36 (m, 15H). | 3 |
| I-232 | 2.77 | 504.03 | A | $^1$H NMR (400 MHz, DMSO-$d_6$) δ 12.53 (s, 1H), 8.58-8.48 (m, 1H), 8.21-8.08 (m, 2H), 7.80-7.70 (m, 1H), 7.68 (s, 1H), 7.49 (s, 1H), 7.46-7.36 (m, 2H), 4.59 (s, 1H), 4.23 (d, J = 27.2 Hz, 3H), 3.72 (d, J = 35.8 Hz, 2H), 1.66-1.42 (m, 15H). | 3 |
| I-233 | 3.47 | 484.99 | A | $^1$H NMR (400 MHz, Chloroform-d) δ 8.38 (s, 1H), 8.09-7.84 (m, 2H), 7.25 (s, 1H), 7.23-7.15 (m, 2H), 4.73-4.43 (m, 2H), 4.05 (ddd, J = 13.7, 8.0, 2.8 Hz, 1H), 3.74 (dt, J = 11.6, 3.9 Hz, 1H), 3.69-3.57 (m, 2H), 3.49 (ddd, J = | 15 |

TABLE 2-continued

Compound analytical data

| Compound Number | LCMS Retention Time | M + 1 | LCMS Method | NMR | General Procedure |
|---|---|---|---|---|---|
| | | | | 11.9, 5.6, 2.8 Hz, 1H), 3.05 (dd, J = 7.2, 3.9 Hz, 1H), 1.88 (s, 3H), 1.84 (s, 3H), 1.59 (s, 9H), 1.22 (d, J = 7.0 Hz, 3H). | |
| I-234 | 4.14 | 448.97 | A | $^1$H NMR (400 MHz, Chloroform-d) δ 8.41 (s, 1H), 8.02-7.83 (m, 2H), 7.29 (s, 1H), 7.23-7.12 (m, 2H), 4.37 (dd, J = 5.4, 4.1 Hz, 2H), 4.16 (dd, J = 5.4, 4.2 Hz, 2H), 1.92 (s, 6H), 1.59 (s, 9H). | 10 |
| I-235 | 3.76 | 491.99 | A | $^1$H NMR (400 MHz, Chloroform-d) δ 13.45 (s, 1H), 8.44 (s, 1H), 8.07-7.79 (m, 2H), 7.30 (s, 1H), 7.23-7.13 (m, 2H), 4.65-4.37 (m, 4H), 1.99 (s, 6H), 1.62 (s, 9H). | 14 |
| I-236 | 3.26 | 502.18 | A | $^1$H NMR (400 MHz, DMSO-$d_6$) δ 9.28 (dd, J = 7.3, 1.4 Hz, 1H), 9.00 (dd, J = 5.1, 1.2 Hz, 1H), 8.54 (d, J = 12.1 Hz, 1H), 8.20-8.09 (m, 2H), 7.74 (ddd, J = 9.8, 5.1, 1.5 Hz, 1H), 7.67 (d, J = 17.2, 0.8 Hz, 1H), 7.45-7.36 (m, 2H), 4.30-4.04 (m, 2H), 3.81 (s, 1H), 3.76-3.64 (m, 2H), 3.65-3.38 (m, 2H), 1.62-1.32 (m, 12H). | 3 |
| I-237 | 2.93 | 491.44 | A | $^1$H NMR (400 MHz, DMSO-$d_6$) δ 8.70 (s, 1H), 8.58-8.50 (m, 1H), 8.22-8.10 (m, 2H), 7.71-7.62 (m, 1H), 7.47-7.35 (m, 2H), 4.57-4.06 (m, 3H), 3.94-3.66 (m, 3H), 3.64-3.45 (m, 1H), 1.62-1.33 (m, 12H). | 3 |
| I-238 | 3.19 | 490.46 | A | $^1$H NMR (400 MHz, DMSO-$d_6$) δ 8.57-8.51 (m, 1H), 8.21-8.10 (m, 2H), 7.71-7.65 (m, 1H), 7.46-7.36 (m, 2H), 7.20 (s, 2H), 4.75 (s, 1H), 4.40-4.17 (m, 3H), 3.83 (s, 1H), 3.74-3.66 (m, 1H), 3.62-3.50 (m, 1H), 1.59-1.40 (m, 12H). | 3 |
| I-239 | 3.13 | 490.46 | A | $^1$H NMR (400 MHz, DMSO-$d_6$) δ 13.22 (s, 1H), 8.58-8.49 (m, 1H), 8.21-8.11 (m, 2H), 7.87-7.79 (m, 1H), 7.72-7.63 (m, 1H), 7.47-7.34 (m, 2H), 6.69-6.60 (m, 1H), 4.32-4.04 (m, 4H), 3.80 (s, 1H), 3.72-3.64 (m, 1H), 3.63-3.46 (m, 1H), 1.62-1.37 (m, 12H). | 3 |
| I-240 | 3.7 | 562.46 | A | $^1$H NMR (400 MHz, DMSO-$d_6$) δ 8.53 (d, J = 6.4 Hz, 1H), 8.21-8.12 (m, 2H), 7.68 (d, J = 4.4, 0.7 Hz, 1H), 7.46-7.36 (m, 2H), 6.59 (d, J = 21.1 Hz, 1H), 4.16-4.06 (m, 2H), 3.67-3.46 (m, 5H), 3.01 (p, J = 8.6 Hz, 1H), 2.66-2.57 (m, 2H), 2.46-2.37 (m, 2H), 1.51 (d, J = 11.5 Hz, 6H), 1.44 (dd, J = 6.9, 1.4 Hz, 6H). | 3 |
| I-241 | 4.75 | 460.11 | D | $^1$H NMR (400 MHz, DMSO-d6) δ 8.60 (s, 1H), 8.29 (d, J = 8.2 Hz, 2H), 8.07 (s, 1H), 7.91 (d, J = 8.3 Hz, 2H), 7.73 (s, 1H), 3.89 (t, J = 4.8 Hz, 2H), 3.54 (p, J = 6.9 Hz, 1H), 3.30 (m, 2H), 1.68 (s, 6H), 1.42 (d, J = 6.9 Hz, 6H). | 6 |
| I-242 | 4.48 | 406.16 | D | $^1$H NMR (400 MHz, DMSO-d6) δ 8.51 (s, 1H), 8.06 (s, 1H), 7.96 (d, J = 8.2 Hz, 2H), 7.62 (s, 1H), 7.34 (d, 2H), 3.98-3.81 (m, 2H), 3.61-3.43 (m, 1H), 3.36-3.31 (m, 2H), 2.36 (s, 3H), 1.67 (s, 6H), 1.41 (d, J = 6.9 Hz, 6H). | 6 |
| I-243 | 4.4 | 428.13 | D | $^1$H NMR (400 MHz, DMSO-d6) δ 8.55 (s, 1H), 8.22-8.11 (m, | 6 |

TABLE 2-continued

| Compound analytical data | | | | | |
|---|---|---|---|---|---|
| Compound Number | LCMS Retention Time | M + 1 | LCMS Method | NMR | General Procedure |
| | | | | 1H), 8.11-8.03 (m, 1H), 7.99-7.92 (m, 1H), 7.69 (s, 1H), 7.66-7.53 (m, 1H), 3.89 (d, J = 9.8 Hz, 2H), 3.56-3.45 (m, 1H), 3.30 (m, 2H), 1.67 (s, 6H), 1.41 (d, J = 6.9 Hz, 6H). | |
| I-244 | 4.6 | 424.17 | D | $^1$H NMR (400 MHz, DMSO-d6) δ 8.57-8.45 (m, 1H), 8.12-7.98 (m, 2H), 7.96-7.88 (m, 1H), 7.64 (s, 1H), 7.35-7.20 (m, 1H), 3.90 (t, J = 4.8 Hz, 2H), 3.50 (q, J = 6.9 Hz, 1H), 3.30 (m, 2H), 2.32 (d, J = 1.8 Hz, 3H), 1.67 (s, 6H), 1.41 (d, J = 6.9 Hz, 6H). 7.2, 6.5 Hz, 1H), 3.36 (dt, J = 6.2, 3.4 Hz, 2H), 2.35 (d, J = 2.0 Hz, 3H), 1.70 (s, 6H), 1.44 (d, J = 6.9 Hz, 6H). [5] | 6 |
| I-245 | 5.33 | 612.17 | D | $^1$H NMR (400 MHz, DMSO-d6) δ 8.56 (d, J = 6.6 Hz, 1H), 8.28 (d, J = 1.4 Hz, 2H), 7.91 (d, J = 8.2 Hz, 2H), 7.73 (d, J = 4.5 Hz, 1H), 6.56 (d, J = 21.7 Hz, 1H), 4.07 (q, J = 6.4 Hz, 2H), 3.67-3.39 (m, 6H), 2.98 (td, J = 8.9, 1.9 Hz, 1H), 2.71-2.51 (m, 2H), 2.38 (t, J = 10.8 Hz, 2H), 1.48 (d, J = 11.6 Hz, 6H), 1.42 (d, J = 6.9, 1.5 Hz, 6H). | 3 |
| I-246 | 4.7 | 540.19 | D | $^1$H NMR (400 MHz, DMSO-d6) δ 13.19 (s, 1H), 8.57 (d, J = 7.5 Hz, 1H), 8.29 (dd, J = 8.3, 3.5 Hz, 2H), 7.91 (d, J = 7.9 Hz, 2H), 7.79 (d, J = 8.4 Hz, 1H), 7.73 (d, J = 7.8 Hz, 1H), 6.68-6.51 (m, 1H), 4.30-3.98 (m, 4H), 3.78 (s, 1H), 3.67-3.41 (m, 2H), 1.47-1.26 (m, 9H). | 3 |
| I-247 | 4.87 | 552.25 | D | $^1$H NMR (400 MHz, DMSO-d6) δ 9.25 (dd, J = 7.1, 1.4 Hz, 1H), 8.97 (dd, J = 5.2, 0.9 Hz, 1H), 8.57 (d, J = 12.3 Hz, 1H), 8.29 (dd, J = 10.8, 8.2 Hz, 2H), 7.91 (dd, J = 8.3, 6.3 Hz, 2H), 7.78-7.64 (m, 2H), 4.20 (t, J = 5.8 Hz, 1H), 4.05 (t, J = 5.6 Hz, 1H), 3.78 (s, 1H), 3.73-3.49 (m, 4H), 3.46-3.40 (m, 1H), 1.58 (s, 3H), 1.48-1.39 (m, 9H), 1.33 (d, J = 6.9 Hz, 3H). | 3 |
| I-248 | 4.07 | 506.48 | A | $^1$H NMR (400 MHz, Chloroform-d) δ 8.43 (s, 1H), 8.05-7.70 (m, 2H), 7.28 (s, 1H), 7.23-7.10 (m, 2H), 4.53 (dd, J = 5.7, 3.9 Hz, 2H), 4.43 (dd, J = 5.4, 3.9 Hz, 2H), 3.89 (s, 3H), 1.98 (s, 6H), 1.58 (s, 9H). | 10 |
| I-249 | 4 | 506.48 | B | $^1$H NMR (400 MHz, Chloroform-d) δ 8.42 (s, 1H), 8.05-7.82 (m, 2H), 7.27 (s, 1H), 7.20 (dd, J = 8.9, 8.3 Hz, 2H), 4.60-4.47 (m, 2H), 4.37 (s, 5H), 1.99 (s, 6H), 1.60 (s, 9H). | 10 |
| I-250 | 1.72 | 482.48 | C | $^1$H NMR (400 MHz, DMSO-$d_6$) δ 8.55 (s, 1H), 7.99-7.91 (m, 2H), 7.72 (s, 1H), 7.66-7.59 (m, 1H), 7.45-7.37 (m, 1H), 5.45-5.29 (m, 1H), 4.19-3.98 (m, 4H), 3.69-3.49 (m, 2H), 3.50-3.37 (m, 1H), 1.60-1.41 (m, 12H), 1.35 (s, 6H). | 6 |
| I-251 | 1.83 | 496.72 | C | $^1$H NMR (400 MHz, DMSO-$d_6$) δ 8.53 (s, 1H), 7.93-7.86 (m, 2H), 7.70 (s, 1H), 7.52-7.45 (m, 1H), | 6 |

TABLE 2-continued

Compound analytical data

| Compound Number | LCMS Retention Time | M + 1 | LCMS Method | NMR | General Procedure |
|---|---|---|---|---|---|
| | | | | 5.43-5.29 (m, 1H), 4.18-3.98 (m, 4H), 3.70-3.48 (m, 2H), 3.50-3.40 (m, 1H), 2.37-2.28 (m, 3H), 1.59-1.40 (m, 12H), 1.38-1.32 (m, 6H). | |
| I-252 | 1.83 | 550.73 | C | $^1$H NMR (400 MHz, DMSO-d$_6$) δ 8.57 (s, 1H), 8.24 (d, J = 12.1 Hz, 1H), 8.17-8.11 (m, 1H), 7.96 (t, J = 7.9 Hz, 1H), 7.78 (s, 1H), 5.42-5.24 (m, 1H), 4.16-3.93 (m, 4H), 3.66-3.47 (m, 2H), 3.47-3.35 (m, 1H), 1.58-1.38 (m, 12H), 1.35-1.29 (m, 6H). | 6 |
| I-253 | 1.67 | 464.5 | C | $^1$H NMR (400 MHz, DMSO-d$_6$) δ 8.53 (s, 1H), 8.12-8.06 (m, 2H), 7.67 (s, 1H), 7.61-7.53 (m, 3H), 5.44-5.27 (m, 1H), 4.20-3.98 (m, 4H), 3.70-3.49 (m, 2H), 3.50-3.40 (m, 1H), 1.61-1.40 (m, 12H), 1.38-1.32 (m, 6H). | 6 |
| I-254 | 5.18 | 558.19 | D | $^1$H NMR (400 MHz, DMSO-d6) δ 8.48 (d, J = 6.6 Hz, 1H), 7.96 (dd, J = 8.4, 1.5 Hz, 2H), 7.62 (d, J = 4.2 Hz, 1H), 7.35 (d, J = 7.9 Hz, 2H), 6.56 (d, J = 20.9 Hz, 1H), 4.15-4.01 (m, 2H), 3.65-3.41 (m, 5H), 3.07-2.85 (m, 1H), 2.68-2.53 (m, 2H), 2.43-2.29 (m, 5H), 1.47 (d, J = 11.6 Hz, 6H), 1.41 (dd, J = 7.0, 1.5 Hz, 6H). | 3 |
| I-255 | 4.48 | 486.24 | D | $^1$H NMR (400 MHz, DMSO-d6) δ 13.19 (s, 1H), 8.48 (d, J = 7.3 Hz, 1H), 8.02-7.87 (m, 2H), 7.84-7.72 (m, 1H), 7.61 (d, J = 7.8 Hz, 1H), 7.35 (dd, J = 8.4, 2.0 Hz, 2H), 6.67-6.54 (m, 1H), 4.30-3.99 (m, 4H), 3.77 (s, 1H), 3.64 (t, J = 5.7 Hz, 1H), 3.60-3.42 (m, 1H), 2.37 (s, 3H), 1.54 (s, 3H), 1.49-1.30 (m, 9H). | 3 |
| I-256 | 4.63 | 498.2 | D | $^1$H NMR (400 MHz, DMSO-d6) δ 9.25 (dd, J = 7.2, 1.4 Hz, 1H), 8.97 (dd, J = 5.1, 1.2 Hz, 1H), 8.48 (d, J = 12.0 Hz, 1H), 7.96 (dd, J = 10.9, 8.2 Hz, 2H), 7.71 (ddd, J = 9.4, 5.1, 1.5 Hz, 1H), 7.61 (dd, J = 17.3, 0.8 Hz, 1H), 7.41-7.24 (m, 2H), 4.22 (t, J = 5.8 Hz, 1H), 4.07 (t, J = 5.7 Hz, 1H), 3.80-3.47 (m, 6H), 3.45-3.33 (m, 1H), 2.36 (d, J = 4.6 Hz, 3H), 1.57 (s, 3H), 1.48-1.38 (m, 9H), 1.32 (d, J = 6.9 Hz, 3H). | 3 |
| I-257 | 5.06 | 580.16 | D | $^1$H NMR (400 MHz, DMSO-d6) δ 8.51 (d, J = 6.3 Hz, 1H), 8.23-8.09 (m, 1H), 7.96 (d, J = 4.5 Hz, 1H), 7.69 (d, J = 4.3 Hz, 1H), 7.62 (dt, J = 10.5, 8.5 Hz, 1H), 6.56 (d, J = 21.3 Hz, 1H), 4.07 (q, J = 6.0 Hz, 2H), 3.65-3.41 (m, 6H), 3.03-2.90 (m, 1H), 2.68-2.52 (m, 2H), 2.44-2.31 (m, 2H), 1.47 (d, J = 11.5 Hz, 6H), 1.41 (dd, J = 7.0, 1.4 Hz, 6H). | 3 |
| I-258 | 4.38 | 508.18 | D | $^1$H NMR (400 MHz, DMSO-d6) δ 8.52 (d, J = 6.3 Hz, 1H), 8.27-8.12 (m, 1H), 7.97 (dd, J = 7.2, 3.8 Hz, 1H), 7.85-7.50 (m, 3H), 6.62 (dd, J = 16.2, 2.3 Hz, 1H), 4.30-3.95 (m, 5H), 3.78 (s, 1H), 3.58-3.43 (m, 3H), 1.54 (m, 3H), 1.49-1.30 (m, 12H). | 3 |
| I-259 | 4.52 | 520.17 | D | $^1$H NMR (400 MHz, DMSO-d6) δ 9.25 (dd, J = 7.4, 1.4 Hz, 1H), | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 8.97 (dd, J = 5.1, 1.1 Hz, 1H), 8.52 (d, J = 12.3 Hz, 1H), 8.23-8.07 (m, 1H), 7.96 (d, J = 3.4 Hz, 1H), 7.76-7.51 (m, 3H), 4.21 (t, J = 5.7 Hz, 1H), 4.06 (t, J = 5.7 Hz, 1H), 3.78 (s, 1H), 3.73-3.50 (m, 5H), 3.44-3.35 (m, 1H), 1.57 (s, 3H), 1.46-1.37 (m, 9H), 1.32 (d, J = 6.9 Hz, 3H). | |
| I-260 | 5.26 | 576.2 | D | $^1$H NMR (400 MHz, DMSO-d6) δ 8.49 (d, J = 6.6 Hz, 1H), 8.02 (d, J = 8.0 Hz, 1H), 7.97-7.88 (m, 1H), 7.64 (d, J = 4.2 Hz, 1H), 7.30 (t, J = 9.1 Hz, 1H), 6.56 (d, J = 21.3 Hz, 1H), 4.15-4.01 (m, 2H), 3.67-3.40 (m, 5H), 3.06-2.86 (m, 1H), 2.70-2.50 (m, 2H), 2.44-2.26 (m, 5H), 1.47 (d, J = 11.5 Hz, 6H), 1.44-1.37 (m, 6H). | 3 |
| I-261 | 4.62 | 504.21 | D | $^1$H NMR (400 MHz, DMSO-d6) δ 13.19 (s, 1H), 8.56-8.43 (m, 1H), 8.07-7.96 (m, 1H), 7.96-7.89 (m, 1H), 7.86-7.75 (m, 1H), 7.68-7.53 (m, 1H), 7.30 (t, J = 9.1 Hz, 1H), 6.70-6.53 (m, 1H), 4.34-3.99 (m, 3H), 3.77 (s, 1H), 3.64 (t, J = 5.7 Hz, 1H), 3.61-3.39 (m, 1H), 2.33 (d, J = 2.1 Hz, 3H), 1.54 (s, 3H), 1.48-1.28 (m, 9H). | 3 |
| I-262 | 4.73 | 516.21 | D | $^1$H NMR (400 MHz, DMSO-d6) δ 9.25 (dd, J = 7.2, 1.4 Hz, 1H), 8.97 (dd, J = 5.1, 1.0 Hz, 1H), 8.49 (d, J = 12.1 Hz, 1H), 8.01 (ddd, J = 10.7, 7.6, 2.3 Hz, 1H), 7.93 (ddt, J = 8.1, 5.6, 2.8 Hz, 1H), 7.71 (ddd, J = 9.8, 5.1, 1.5 Hz, 1H), 7.62 (d, J = 17.3 Hz, 1H), 7.30 (td, J = 9.1, 6.3 Hz, 1H), 4.22 (t, J = 5.8 Hz, 1H), 4.07 (t, J = 5.6 Hz, 1H), 3.78 (s, 1H), 3.74-3.48 (m, 5H), 3.43-3.34 (m, 1H), 2.32 (dd, J = 6.0, 1.9 Hz, 3H), 1.57 (s, 3H), 1.46-1.37 (m, 9H), 1.32 (d, J = 6.9 Hz, 3H). | 3 |
| I-263 | 5.03 | 558.29 | D | $^1$H NMR (400 MHz, DMSO-d6) δ 8.48 (d, J = 8.1 Hz, 1H), 7.97 (dd, J = 8.4, 2.0 Hz, 2H), 7.62 (d, J = 3.9 Hz, 1H), 7.35 (d, J = 8.3 Hz, 2H), 6.51 (d, J = 8.5 Hz, 1H), 4.09 (dd, J = 12.9, 6.2 Hz, 2H), 3.65-3.37 (m, 6H), 2.51 (s, 1H), 2.37 (s, 3H), 2.19 (q, J = 10.8 Hz, 2H), 1.47 (d, J = 13.8 Hz, 6H), 1.41 (dd, J = 6.9, 3.9 Hz, 6H). | 3 |
| I-264 | 4.9 | 580.19 | D | $^1$H NMR (400 MHz, DMSO-d6) δ 8.51 (d, J = 7.9 Hz, 1H), 8.22-8.09 (m, 1H), 7.97 (ddd, J = 8.5, 3.9, 1.9 Hz, 1H), 7.63 (ddd, J = 10.5, 8.5, 1.9 Hz, 1H), 6.51 (d, J = 8.1 Hz, 1H), 4.18-4.00 (m, 2H), 3.67-3.38 (m, 6H), 2.50-2.52 (m, 2H), 2.27-2.13 (m, 2H), 1.54-1.33 (m, 12H). | 3 |
| I-265 | 5.1 | 576.75 | D | $^1$H NMR (400 MHz, DMSO-d6) δ 8.49 (dd, J = 8.2, 1.7 Hz, 1H), 8.02 (d, J = 7.9 Hz, 1H), 7.97-7.89 (m, 1H), 7.63 (d, J = 3.9 Hz, 1H), 7.30 (t, J = 9.1 Hz, 1H), 6.51 (dd, J = 8.4, 1.7 Hz, 1H), 4.10 (dt, J = 12.5, 5.4 Hz, 2H), 3.65-3.39 (m, 6H), 2.32 (s, 3H), 2.19 (d, J = 10.8 Hz, 2H), 1.55-1.32 (m, 12H). | 3 |

TABLE 2-continued

| Compound analytical data | | | | | |
|---|---|---|---|---|---|
| Compound Number | LCMS Retention Time | M + 1 | LCMS Method | NMR | General Procedure |
| I-266 | 4.41 | 507.32 | A | $^1$H NMR (400 MHz, Chloroform-d) δ 8.65 (d, J = 2.3 Hz, 1H), 8.42 (s, 1H), 8.00 (d, J = 2.3 Hz, 1H), 7.96-7.86 (m, 2H), 7.26 (s, 1H), 7.23-7.17 (m, 2H), 4.61-4.50 (m, 2H), 4.44-4.28 (m, 2H), 1.98 (s, 6H), 1.62 (s, 9H). | 9 |
| I-267 | 3.93 | 463.43 | A | $^1$H NMR (400 MHz, Chloroform-d) δ 8.40 (s, 1H), 8.02-7.87 (m, 2H), 7.27 (s, 1H), 7.23-7.17 (m, 2H), 4.44 (s, 2H), 4.38-4.23 (m, 2H), 3.83-3.68 (m, 2H), 1.88 (s, 6H), 1.60 (s, 9H). | 10 |
| I-268 | 2.95 | 527.97 | A | $^1$H NMR (400 MHz, DMSO-$d_6$) δ 9.25 (dd, J = 10.5, 1.4 Hz, 1H), 8.97 (dd, J = 5.1, 2.1 Hz, 1H), 8.77 (d, J = 13.7 Hz, 1H), 8.31-8.14 (m, 3H), 7.70 (ddd, J = 9.0, 5.1, 1.5 Hz, 1H), 7.41 (td, J = 8.8, 6.5 Hz, 2H), 4.16-3.94 (m, 2H), 3.82-3.54 (m, 4H), 1.50 (d, J = 6 1.4 Hz, 6H). | 3 |
| I-269 | 2.66 | 517.29 | A | $^1$H NMR (400 MHz, DMSO-$d_6$) δ 8.80 (d, J = 10.4 Hz, 1H), 8.47 (s, 1H), 8.34-8.18 (m, 3H), 7.50-7.38 (m, 2H), 4.33-3.90 (m, 4H), 3.84 (s, 1H), 3.75-3.63 (m, 1H), 1.54 (d, J = 33.6 Hz, 6H). | 3 |
| I-270 | 3.03 | 516.1 | A | $^1$H NMR (400 MHz, DMSO-$d_6$) δ 12.96 (s, 1H), 8.80 (d, J = 8.7 Hz, 1H), 8.31-8.27 (m, 1H), 8.27-8.20 (m, 2H), 7.49-7.40 (m, 2H), 7.28 (d, J = 4.1 Hz, 1H), 7.11 (d, J = 10.1, 1.1 Hz, 1H), 4.77 (s, 1H), 4.33 (dd, J = 6.9, 4.4 Hz, 1H), 4.13 (dt, J = 14.0, 5.3 Hz, 2H), 3.84 (s, 1H), 3.67 (dd, J = 6.8, 4.7 Hz, 1H), 1.55 (d, J = 16.2 Hz, 6H). | 3 |
| I-271 | 2.86 | 515.93 | A | $^1$H NMR (400 MHz, DMSO-$d_6$) δ 13.23 (s, 1H), 8.83-8.75 (m, 1H), 8.31-8.17 (m, 3H), 7.88-7.77 (m, 1H), 7.49-7.37 (m, 2H), 6.71-6.60 (m, 1H), 4.28 (s, 1H), 4.19-4.02 (m, 3H), 3.82 (s, 1H), 3.71-3.58 (m, 1H), 1.53 (d, J = 31.1 Hz, 6H). | 3 |
| I-272 | 3.38 | 587.92 | A | $^1$H NMR (400 MHz, DMSO-$d_6$) δ 8.80 (d, J = 6.4 Hz, 1H), 8.30-8.28 (m, 1H), 8.27-8.20 (m, 2H), 7.48-7.40 (m, 2H), 6.59 (d, J = 17.3 Hz, 1H), 4.08-3.96 (m, 2H), 3.69-3.57 (m, 2H), 3.52 (s, 1H), 3.50-3.44 (m, 1H), 3.01 (p, J = 8.9 Hz, 1H), 2.70-2.56 (m, 2H), 2.46-2.3 5 (m, 2H), 1.51 (d, J = 12.3 Hz, 6H). | 3 |
| I-273 | 4.85 | 478.12 | D | $^1$H NMR (400 MHz, DMSO-d6) δ 8.61 (s, 1H), 8.29-8.20 (m, 1H), 8.17-8.09 (m, 1H), 8.09-8.04 (m, 1H), 7.96 (t, J = 7.9 Hz, 1H), 7.78 (d, J = 0.7 Hz, 1H), 3.88 (dd, J = 6.2, 3.5 Hz, 2H), 3.62-3.48 (m, 1H), 3.36-3.30 (m, 2H), 1.68 (s, 6H), 1.42 (d, J = 6.9 Hz, 6H). | 6 |
| I-274 | 3.79 | 434.97 | A | $^1$H NMR (400 MHz, Chloroform-d) δ 8.42 (s, 1H), 8.02-7.85 (m, 2H), 7.29 (d, J = 0.8 Hz, 1H), 7.23-7.12 (m, 2H), 4.35 (dd, J = 5.4, 4.2 Hz, 2H), 4.19-4.00 (m, 2H), 3.66-3.49 (m, 1H), 1.92 (s, 6H), 1.46 (d, J = 6.9 Hz, 6H). | 10 |
| I-275 | 3.39 | 478.02 | A | $^1$H NMR (400 MHz, DMSO-$d_6$) δ 8.59 (s, 1H), 8.28-8.04 (m, 2H), | 14 |

TABLE 2-continued

| Compound analytical data | | | | | |
|---|---|---|---|---|---|
| Compound Number | LCMS Retention Time | M + 1 | LCMS Method | NMR | General Procedure |
| | | | | 7.66 (d, J = 0.8 Hz, 1H), 7.46-7.20 (m, 2H), 4.15 (s, 4H), 3.54 (p, J = 6.8 Hz, 1H), 1.73 (s, 6H), 1.42 (d, J = 6.9 Hz, 6H). | |
| I-276 | 5.43 | 630.17 | D | $^1$H NMR (400 MHz, DMSO-d6) δ 8.57 (d, J = 6.5 Hz, 1H), 8.23 (d, J = 12.1 Hz, 1H), 8.13 (d, J = 8.1 Hz, 1H), 7.96 (t, J = 8.0 Hz, 1H), 7.78 (d, J = 4.3 Hz, 1H), 6.56 (d, J = 22.1 Hz, 1H), 4.06 (q, J = 5.8 Hz, 2H), 3.65-3.41 (m, 5H), 3.03-2.89 (m, 1H), 2.68-2.52 (m, 2H), 2.38 (t, J = 10.8 Hz, 2H), 1.48 (d, J = 11.5 Hz, 6H), 1.42 (dd, J = 6.8, 1.3 Hz, 6H). | 3 |
| I-277 | 4.82 | 558.19 | D | $^1$H NMR (400 MHz, DMSO-d6) δ 13.19 (s, 1H), 8.70-8.45 (m, 1H), 8.24 (dd, J = 12.5, 3.6 Hz, 1H), 8.17-8.05 (m, 1H), 7.96 (t, J = 7.9 Hz, 1H), 7.83-7.71 (m, 2H), 6.68-6.53 (m, 1H), 4.30-3.97 (m, 4H), 3.78 (s, 1H), 3.68-3.42 (m, 2H), 1.54 (s, 3H), 1.48-1.28 (m, 9H). | 3 |
| I-278 | 4.95 | 570.19 | D | $^1$H NMR (400 MHz, DMSO-d6) δ 9.25 (dd, J = 7.2, 1.4 Hz, 1H), 8.97 (dd, J = 5.2, 0.9 Hz, 1H), 8.58 (d, J = 12.5 Hz, 1H), 8.23 (dd, J = 12.5, 11.1 Hz, 1H), 8.13 (t, J = 9.6 Hz, 1H), 7.98-7.89 (m, 1H), 7.82-7.63 (m, 2H), 4.19 (t, J = 5.9 Hz, 1H), 4.04 (t, J = 5.7 Hz, 1H), 3.82-3.49 (m, 4H), 3.46-3.38 (m, 1H), 1.57 (s, 3H), 1.48-1.37 (m, 9H), 1.33 (d, J = 6.9 Hz, 3H). | 3 |
| I-279 | 4.35 | 541.49 | D | $^1$H NMR (400 MHz, DMSO-d6) δ 8.57 (d, J = 9.5 Hz, 1H), 8.47-8.37 (m, 1H), 8.29 (dd, J = 8.0, 5.5 Hz, 2H), 7.91 (dd, J = 8.6, 3.1 Hz, 2H), 7.73 (d, J = 9.9 Hz, 1H), 4.24-4.15 (m, 2H), 4.18-4.08 (m, 2H), 4.07-3.94 (m, 1H), 3.80 (s, 1H), 3.69 (t, J = 5.7 Hz, 1H), 3.61-3.46 (m, 1H), 1.55 (s, 3H), 1.49-1.32 (m, 9H). rotamers | 3 |
| I-280 | 4.93 | 556.57 | D | $^1$H NMR (400 MHz, DMSO-d6) δ 8.58 (d, J = 6.3 Hz, 1H), 8.29 (dd, J = 8.3, 2.6 Hz, 2H), 7.91 (dd, J = 8.5, 2.1 Hz, 2H), 7.73 (d, J = 5.2 Hz, 1H), 4.22 (dt, J = 10.9, 5.7 Hz, 2H), 4.12 (d, J = 12.4 Hz, 2H), 3.82 (s, 1H), 3.69 (dd, J = 6.7, 4.8 Hz, 1H), 3.55 (dt, J = 13.3, 6.7 Hz, 1H), 2.56 (d, J = 4.9 Hz, 3H), 1.53 (d, J = 14.0 Hz, 6H), 1.42 (dd, J = 9.6, 6.9 Hz, 6H). | 3 |
| I-281 | 4.85 | 551.2 | D | $^1$H NMR (400 MHz, DMSO-d6) δ 8.65-8.50 (m, 2H), 8.29 (dd, J = 11.8, 8.2 Hz, 2H), 7.97-7.85 (m, 3H), 7.72 (d, J = 19.6 Hz, 1H), 7.61 (d, J = 7.7 Hz, 1H), 7.49 (ddd, J = 7.8, 5.0, 1.3 Hz, 1H), 4.20 (t, J = 5.8 Hz, 1H), 4.03 (t, J = 5.7 Hz, 1H), 3.78 (s, 1H), 3.75-3.63 (m, 3H), 3.60-3.48 (m, 1H), 1.57 (s, 3H), 1.49-1.37 (m, 6H), 1.33 (d, J = 6.9 Hz, 3H). rotamers | 3 |
| I-282 | 4.52 | 552.57 | D | $^1$H NMR (400 MHz, DMSO-d6) δ 9.39-9.25 (m, 1H), 8.57 (dd, J = 15.2, 1.3 Hz, 1H), 8.29 (dd, J = 12.8, 8.1 Hz, 2H), 7.96-7.78 (m, | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 4H), 7.72 (d, J = 20.9 Hz, 1H), 4.24 (t, J = 5.8 Hz, 1H), 4.08 (t, J = 5.4 Hz, 1H), 3.84 (s, 1H), 3.79-3.63 (m, 3H), 3.57 (q, J = 6.9 Hz, 1H), 1.60 (d, J = 1.4 Hz, 3H), 1.49-1.36 (m, 6H), 1.33 (dd, J = 6.9, 1.3 Hz, 3H). rotamers | |
| I-283 | 1.89 | 474.71 | C | $^1$H NMR (400 MHz, DMSO-$d_6$) δ 8.63 (s, 1H), 8.34-8.28 (m, 2H), 8.13-8.08 (m, 1H), 7.98-7.92 (m, 2H), 7.57 (s, 1H), 4.00-3.94 (m, 2H), 3.44-3.37 (m, 2H), 1.71 (s, 6H), 1.60 (s, 9H). | 3 |
| I-284 | 3.79 | 515.02 | A | $^1$H NMR (400 MHz, DMSO-$d_6$) δ 8.62 (dddd, J = 9.9, 4.8, 1.7, 0.9 Hz, 1H), 8.52 (d, J = 13.5 Hz, 1H), 8.19-8.08 (m, 2H), 8.00-7.90 (m, 1H), 7.68-7.60 (m, 1H), 7.54.7.47 (m, 2H), 7.46-7.35 (m, 2H), 4.34-4.26 (m, 1H), 4.13-4.03 (m, 1H), 3.82 (s, 1H), 3.79-3.72 (m, 2H), 3.70 (s, 1H), 1.71-1.33 (m, 15H). | 3 |
| I-285 | 3.45 | 516 | A | $^1$H NMR (400 MHz, DMSO-$d_6$) δ 8.93 (d, J = 5.0 Hz, 2H), 8.52 (d, J = 12.6 Hz, 1H), 8.19-8.07 (m, 2H), 7.63 (q, J = 4.9 Hz, 1H), 7.51-7.35 (m, 3H), 4.33-4.26 (m, 1H), 4.12-4.05 (m, 1H), 3.82 (s, 1H), 3.79-3.72 (m, 1H), 3.53-3.47 (m, 1H), 3.39 (s, 1H), 1.69-1.34 (m, 15H). | 3 |
| I-286 | 3.55 | 515.44 | A | $^1$H NMR (400 MHz, DMSO-$d_6$) δ 8.73-8.65 (m, 2H), 8.52 (d, J = 14.4 Hz, 1H), 8.19-8.08 (m, 2H), 7.52-7.34 (m, 5H), 4.32-4.23 (m, 1H), 4.10-4.02 (m, 1H), 3.78 (s, 1H), 3.77-3.69 (m, 1H), 3.61-3.54 (m, 1H), 3.48 (s, 1H), 1.67-1.37 (m, 15H). | 3 |
| I-287 | 3.62 | 515.44 | A | $^1$H NMR (400 MHz, DMSO-$d_6$) δ 8.72-8.62 (m, 2H), 8.53 (d, J = 13.6 Hz, 1H), 8.20-8.07 (m, 2H), 7.97-7.84 (m, 1H), 7.56-7.33 (m, 4H), 4.33-4.24 (m, 1H), 4.14-4.03 (m, 1H), 3.82-3.69 (m, 2H), 3.69-3.61 (m, 1H), 3.55 (s, 1H), 1.66-1.37 (m, 15H). | 3 |
| I-288 | 4.22 | 520.22 | A | $^1$H NMR (400 MHz, DMSO-$d_6$) δ 8.54 (d, J = 5.1 Hz, 1H), 8.18-8.11 (m, 2H), 7.49 (d, J = 5.0 Hz, 1H), 7.46-7.36 (m, 2H), 4.37-4.25 (m, 2H), 4.20-4.13 (m, 2H), 3.85 (s, 1H), 3.80-3.71 (m, 1H), 2.59 (d, J = 4.6 Hz, 3H), 1.64-1.50 (m, 15H). | 3 |
| I-289 | 4.21 | 510.25 | A | $^1$H NMR (400 MHz, DMSO-$d_6$) δ 8.52 (d, J = 4.8 Hz, 1H), 8.17-8.11 (m, 2H), 7.49 (d, J = 2.0 Hz, 1H), 7.45-7.37 (m, 2H), 4.90 (d, J = 7.7 Hz, 1H), 4.27-4.13 (m, 2H), 3.77 (t, J = 5.6 Hz, 1H), 3.68 (d, J = 6.0 Hz, 2H), 3.58-3.51 (m, 1H), 2.44 (s, 1H), 1.59 (d, J = 2.3 Hz, 9H), 1.52 (d, J = 11.1 Hz, 6H), 1.22-1.15 (m, 6H). | 3 |
| I-290 | 3.49 | 518.03 | A | $^1$H NMR (400 MHz, DMSO-$d_6$) δ 12.92-12.82 (m, 1H), 8.55-8.49 (m, 1H), 8.19-8.10 (m, 2H), 7.64-7.57 (m, 1H), 7.51-7.45 (m, 1H), 7.41 (ddt, J = 10.5, 8.7, 2.8 Hz, 2H), 4.32-4.24 (m, 1H), 4.16-4.07 (m, 1H), 3.98 (s, 1H), 3.94-3.86 (m, 1H), 3.78 (s, 1H), 3.74- | 3 |

TABLE 2-continued

Compound analytical data

| Compound Number | LCMS Retention Time | M + 1 | LCMS Method | NMR | General Procedure |
|---|---|---|---|---|---|
| | | | | 3.66 (m, 1H), 2.09 (s, 3H), 1.66-1.40 (m, 15H). | |
| I-291 | 3.99 | 518.26 | A | $^1$H NMR (400 MHz, DMSO-$d_6$) δ 12.89 (s, 1H), 8.55-8.49 (m, 1H), 8.19-8.09 (m, 2H), 7.52-7.46 (m, 1H), 7.45-7.36 (m, 2H), 6.40-6.32 (m, 1H), 4.32-4.23 (m, 2H), 4.22-4.06 (m, 2H), 3.78 (s, 1H), 3.71-3.63 (m, 1H), 2.30-2.23 (m, 3H), 1.67-1.43 (m, 15H). | 3 |
| I-292 | 3.76 | 518.23 | A | | 3 |
| I-293 | 4.15 | 522.54 | D | $^1$H NMR (400 MHz, DMSO-d6) δ 13.19 (s, 1H), 8.62-8.47 (m, 1H), 8.27-8.14 (m, 2H), 7.90-7.62 (m, 3H), 7.12 (t, J = 55.8 Hz, 1H), 6.69-6.55 (m, 1H), 4.31-3.96 (m, 4H), 3.78 (s, 1H), 3.68-3.60 (m, 1H), 3.57-3.46 (m, 1H), 1.54 (s, 3H), 1.50-1.32 (m, 9H). rotamers | 3 |
| I-294 | 3.97 | 523.22 | D | $^1$H NMR (400 MHz, DMSO-d6) δ 8.62-8.50 (m, 1H), 8.48-8.38 (m, 1H), 8.21 (dd, J = 8.0, 5.6 Hz, 2H), 7.80-7.62 (m, 3H), 7.12 (t, J = 55.8, 2.2 Hz, 1H), 4.22 (t, J = 5.9 Hz, 2H), 4.17-4.08 (m, 2H), 4.05-3.93 (m, 1H), 3.80 (s, 1H), 3.73-3.63 (m, 1H), 3.53 (dt, J = 27.0, 6.9 Hz, 1H), 1.55 (s, 3H), 1.49-1.40 (m, 9H), 1.39 (d, J = 6.9 Hz, 3H). rotamers | 3 |
| I-295 | 3.95 | 522.21 | D | $^1$H NMR (400 MHz, DMSO-d6) δ 13.20 (s, 1H), 8.55 (s, 1H), 8.21 (d, J = 8.1 Hz, 3H), 7.87-7.57 (m, 4H), 7.12 (t, J = 55.8 Hz, 1H), 4.16 (t, J = 5.7 Hz, 2H), 3.82 (d, J = 48.3 Hz, 3H), 3.54 (s, 2H), 1.63-1.24 (m, 12H). rotamers | 3 |
| I-296 | 3.34 | 506.02 | A | $^1$H NMR (400 MHz, Methanol-$d_4$) δ 8.39 (d, J = 8.3 Hz, 1H), 8.14-8.05 (m, 3H), 7.48 (d, J = 14.2 Hz, 1H), 7.33-7.22 (m, 2H), 4.55-4.47 (m, 1H), 4.39-4.32 (m, 1H), 4.16-4.05 (m, 2H), 3.99-3.88 (m, 2H), 1.74-1.54 (m, 15H). | 3 |
| I-297 | 3.57 | 494.02 | A | $^1$H NMR (400 MHz, Chloroform-d) δ 8.38 (s, 1H), 8.03-7.80 (m, 2H), 7.26 (s, 1H), 7.23-7.16 (m, 2H), 4.30 (dd, J = 6.6, 3.1 Hz, 2H), 4.07 (t, J = 4.4 Hz, 1H), 3.78-3.52 (m, 4H), 1.81 (s, 6H), 1.60 (s, 9H), 1.06-0.99 (m, 2H), 0.97-0.90 (m, 2H). | 15 |
| I-298 | 1.86 | 438.69 | C | $^1$H NMR (400 MHz, DMSO-$d_6$) δ 8.56 (s, 1H), 8.09 (t, J = 3.1 Hz, 1H), 7.91-7.82 (m, 2H), 7.53-7.45 (m, 2H), 4.01-3.93 (m, 2H), 3.43-3.36 (m, 2H), 2.36-2.29 (m, 3H), 1.70 (s, 6H), 1.58 (s, 9H). | 6 |
| I-299 | 4.47 | 538.5 | D | $^1$H NMR (400 MHz, DMSO-d6) δ 8.56 (d, J = 6.2 Hz, 1H), 8.21 (dd, J = 8.6, 2.6 Hz, 2H), 7.76-7.66 (m, 3H), 7.12 (t, J = 55.7, 1.4 Hz, 1H), 4.23 (dt, J = 11.0, 5.6 Hz, 2H), 4.17-4.02 (m, 2H), 3.82 (s, 1H), 3.69 (dd, J = 6.8, 4.7 Hz, 1H), 3.62-3.45 (m, 1H), 2.56 (d, J = 4.9 Hz, 3H), 1.53 (d, J = 14.1 Hz, 6H), 1.42 (dd, J = 9.7, 6.9 Hz, 6H). | 3 |
| I-300 | 4.13 | 442.55 | D | $^1$H NMR (400 MHz, DMSO-d6) δ 8.58 (s, 1H), 8.21 (d, J = 8.1 Hz, 2H), 8.07 (s, 1H), 7.78-7.68 (m, 3H), 7.12 (t, J = 55.8 Hz, 1H), | 6 |

TABLE 2-continued

| Compound analytical data | | | | | |
|---|---|---|---|---|---|
| Compound Number | LCMS Retention Time | M + 1 | LCMS Method | NMR | General Procedure |
| | | | | 3.96-3.80 (m, 2H), 3.53 (p, J = 6.9 Hz, 1H), 3.37-3.29 (m, 2H), 1.68 (s, 6H), 1.42 (d, J = 6.9 Hz, 6H). | |
| I-301 | 4.47 | 424.58 | D | $^1$H NMR (400 MHz, DMSO-d6) δ 8.54 (s, 1H), 8.06 (t, J = 3.2 Hz, 1H), 7.92-7.79 (m, 2H), 7.67 (s, 1H), 7.53-7.39 (m, 1H), 3.93-3.82 (m, 2H), 3.56-3.46 (m, 1H), 3.27 (m, 2H), 2.29 (d, J = 1.9 Hz, 3H), 1.67 (s, 6H), 1.41 (d, J = 6.9 Hz, 6H). | 6 |
| I-302 | 3.11 | 504.03 | A | $^1$H NMR (400 MHz, DMSO-$d_6$) δ 12.91-12.84 (m, 1H), 8.56-8.49 (m, 1H), 8.20-8.10 (m, 2H), 7.70-7.64 (m, 1H), 7.64-7.58 (m, 1H), 7.45-7.35 (m, 2H), 4.27-4.06 (m, 2H), 3.98 (s, 1H), 3.91-3.83 (m, 1H), 3.78 (s, 1H), 3.71-3.64 (m, 1H), 3.63-3.45 (m, 1H), 2.14-2.01 (m, 3H), 1.60-1.33 (m, 12H). | 3 |
| I-303 | 3.12 | 504.03 | A | $^1$H NMR (400 MHz, DMSO-$d_6$) δ 12.89 (s, 1H), 8.53 (d, J = 6.6 Hz, 1H), 8.16 (ddd, J = 8.6, 5.5, 2.6 Hz, 2H), 7.67 (d, J = 6.5 Hz, 1H), 7.41 (td, J = 8.9, 1.4 Hz, 2H), 6.41-6.33 (m, 1H), 4.30-4.03 (m, 4H), 3.78 (s, 1H), 3.64 (dd, J = 6.8, 4.7 Hz, 1H), 3.63-3.47 (m, 1H), 2.26 (d, J = 5.5 Hz, 3H), 1.59-1.37 (m, 12H). | 3 |
| I-304 | 2.89 | 504.06 | A | | 3 |
| I-305 | 3.28 | 496.05 | A | $^1$H NMR (400 MHz, DMSO-$d_6$) δ 8.53 (d, J = 4.9 Hz, 1H), 8.20-8.12 (m, 2H), 7.68 (d, J = 3.0, 0.8 Hz, 1H), 7.45-7.37 (m, 2H), 4.90 (d, J = 9.9 Hz, 1H), 4.23-4.07 (m, 2H), 3.77-3.71 (m, 1H), 3.68 (d, J = 7.0 Hz, 2H), 3.61-3.48 (m, 2H), 2.44 (s, 2H), 1.52 (d, J = 10.5 Hz, 6H), 1.44 (d, J = 6.9, 0.8 Hz, 6H), 1.23-1.16 (m, 6H). | 3 |
| I-306 | 3.44 | 502.2 | A | $^1$H NMR (400 MHz, DMSO-$d_6$) δ 9.41-9.27 (m, 2H), 8.54 (d, J = 12.8 Hz, 1H), 8.21-8.09 (m, 2H), 7.81 (ddd, J = 35.3, 4.9, 2.5 Hz, 1H), 7.66 (dd, J = 18.9, 0.8 Hz, 1H), 7.46-7.34 (m, 2H), 4.28-4.05 (m, 2H), 3.78 (s, 1H), 3.76-3.69 (m, 1H), 3.62-3.37 (m, 3H), 1.68-1.30 (m, 12H). | 3 |
| I-307 | 3.51 | 502.2 | A | $^1$H NMR (400 MHz, DMSO-$d_6$) δ 9.38-9.31 (m, 1H), 8.54 (d, J = 14.9 Hz, 1H), 8.21-8.08 (m, 2H), 7.96-7.91 (m, 1H), 7.91-7.83 (m, 1H), 7.72-7.62 (m, 1H), 7.45-7.35 (m, 2H), 4.32-4.08 (m, 2H), 3.86 (s, 1H), 3.82-3.76 (m, 1H), 3.75-3.65 (m, 2H), 3.65-3.39 (m, 1H), 1.66-1.30 (m, 12H). | 3 |
| I-308 | 1.54 | 501.03 | C | $^1$H NMR (400 MHz, DMSO-$d_6$) δ 8.66 (dd, J = 10.6, 4.7 Hz, 2H), 8.51 (d, 1H), 8.18-8.07 (m, 2H), 7.63 (d, 1H), 7.47-7.31 (m, 4H), 4.11 (dt, J = 66.0, 5.5 Hz, 2H), 3.77-3.63 (m, 2H), 3.59-3.35 (m, 3H), 1.57 (s, 2H), 1.43 (d, J = 6.9 Hz, 4H), 1.39 (s, 4H), 1.29 (d, J = 6.9 Hz, 2H). | 3 |
| I-309 | 1.55 | 501.03 | C | $^1$H NMR (400 MHz, DMSO-$d_6$) δ 8.70-8.59 (m, 2H), 8.50 (d, J = 14.2 Hz, 1H), 8.12 (dt, J = 11.3, 7.0 Hz, 2H), 7.87 (dd, J = 23.7, | 3 |

TABLE 2-continued

Compound analytical data

| Compound Number | LCMS Retention Time | M + 1 | LCMS Method | NMR | General Procedure |
|---|---|---|---|---|---|
| | | | | 7.9 Hz, 1H), 7.63 (d, J = 19.7 Hz, 1H), 7.49 (dd, J = 7.9, 5.0 Hz, 1H), 7.37 (q, J = 7.9, 7.4 Hz, 2H), 4.26-4.00 (m, 2H), 3.79-3.64 (m, 2H), 3.54 (d, J = 18.4 Hz, 3H), 1.58 (s, 2H), 1.43 (d, J = 6.9 Hz, 4H), 1.40 (s, 4H), 1.30 (d, J = 6.9 Hz, 2H). | |
| I-310 | 3.45 | 491.32 | A | $^1$H NMR (400 MHz, Chloroform-d) δ 8.42 (s, 1H), 8.06-7.90 (m, 4H), 7.41-6.87 (m, 4H), 4.46 (dd, J = 5.5, 4.1 Hz, 2H), 4.05-3.94 (m, 2H), 1.94 (s, 6H), 1.63 (s, 9H). | 1 |
| I-311 | 2.88 | 518.1 | A | $^1$H NMR (400 MHz, DMSO-$d_6$) δ 8.52 (s, 1H), 8.18-8.10 (m, 2H), 7.89-7.58 (m, 1H), 7.49 (s, 1H), 7.45-7.36 (m, 2H), 4.40-3.98 (m, 4H), 3.79-3.60 (m, 2H), 2.36 (s, 3H), 1.68-1.40 (m, 15H). | 3 |
| I-312 | 2.85 | 518.41 | A | $^1$H NMR (400 MHz, DMSO-$d_6$) δ 8.53 (s, 1H), 8.18-8.10 (m, 2H), 7.56 (s, 1H), 7.49 (s, 1H), 7.46-7.36 (m, 2H), 4.52-3.97 (m, 4H), 3.89-3.58 (m, 2H), 2.34 (s, 3H), 1.68-1.44 (m, 15H). | 3 |
| I-313 | 1.8 | 535.98 | C | $^1$H NMR (400 MHz, DMSO-$d_6$) δ 8.53 (s, 1H), 8.22-8.10 (m, 2H), 7.67 (s, 1H), 7.41 (t, J = 8.8 Hz, 2H), 7.21-6.97 (m, 1H), 4.28-3.98 (m, 4H), 3.75-3.43 (m, 3H), 1.64-1.48 (m, 9H), 1.44 (d, J = 6.9 Hz, 6H). | 3 |
| I-314 | 1.81 | 535.75 | C | $^1$H NMR (400 MHz, DMSO-$d_6$) δ 8.50 (s, 1H), 8.22-8.06 (m, 2H), 7.64 (s, 1H), 7.46-7.29 (m, 2H), 4.83-3.81 (m, 5H), 3.82-3.32 (m, 2H), 2.61-2.56 (m, 2H), 1.65-1.34 (m, 15H). | 3 |
| I-315 | 4.33 | 405.89 | D | $^1$H NMR (400 MHz, DMSO-d6) δ 8.53 (s, 1H), 8.09-8.03 (m, 1H), 7.92-7.79 (m, 2H), 7.63 (s, 1H), 7.46-7.37 (m, 1H), 7.38-7.29 (m, 1H), 3.96-3.84 (m, 2H), 3.58-3.45 (m, 1H), 3.38-3.31 (m, 1H), 2.40 (s, 3H), 1.67 (s, 6H), 1.41 (d, J = 6.9 Hz, 6H). | 6 |
| I-316 | 1.57 | 508.03 | C | $^1$H NMR (400 MHz, DMSO-$d_6$) δ 8.55-8.51 (m, 1H), 8.19-8.13 (m, 2H), 7.70-7.66 (m, 1H), 7.44-7.37 (m, 2H), 4.98 (d, J = 14.7 Hz, 1H), 4.17-4.07 (m, 2H), 3.66-3.60 (m, 2H), 3.59-3.51 (m, 2H), 3.49-3.42 (m, 1H), 2.94-2.77 (m, 1H), 2.24-2.14 (m, 2H), 2.14-2.04 (m, 2H), 1.58-1.36 (m, 12H), 1.33-1.22 (m, 3H). | 3 |
| I-317 | 1.97 | 550.4 | C | $^1$H NMR (400 MHz, DMSO-$d_6$) δ 8.52 (s, 1H), 8.19-8.09 (m, 2H), 7.48 (s, 1H), 7.45-7.37 (m, 2H), 7.18-6.99 (m, 1H), 4.34-3.93 (m, 4H), 3.77-3.60 (m, 1H), 3.60-3.44 (m, 1H), 1.66-1.44 (m, 18H). | 3 |
| I-318 | 1.99 | 549 | C | $^1$H NMR (400 MHz, DMSO-$d_6$) δ 8.53-8.52 (m, 1H), 8.18-8.11 (m, 2H), 7.48 (s, 1H), 7.46-7.23 (m, 2H), 4.74-3.36 (m, 5H), 2.84-2.55 (m, 2H), 1.78-1.32 (m, 19H). | 3 |
| I-319 | 1.75 | 522.73 | C | $^1$H NMR (400 MHz, DMSO-$d_6$) δ 8.52-8.46 (m, 1H), 8.14-8.08 (m, 2H), 7.47-7.44 (m, 1H), 7.41-7.34 (m, 2H), 4.95 (d, J = 19.3 | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | Hz, 1H), 4.18-4.08 (m, 2H), 3.68-3.44 (m, 4H), 2.90-2.76 (m, 1H), 2.20-2.11 (m, 2H), 2.11-2.01 (m, 2H), 1.56 (d, J = 4.4 Hz, 9H), 1.47 (d, J = 15.4 Hz, 6H), 1.25 (d, J = 10.9 Hz, 3H). | |
| I-320 | 1.8 | 501.46 | C | $^1$H NMR (400 MHz, DMSO-$d_6$) δ 8.58 (dddd, J = 11.8, 4.8, 1.7, 0.9 Hz, 1H), 8.50 (d, J = 14.9 Hz, 1H), 8.12 (tdd, J = 8.9, 5.4, 2.2 Hz, 2H), 7.92 (tdd, J = 7.7, 7.0, 1.7 Hz, 1H), 7.68-7.58 (m, 2H), 7.48 (dddd, J = 7.9, 6.8, 4.8, 1.2 Hz, 1H), 7.43-7.32 (m, 2H), 4.22 (t, J = 5.8 Hz, 1H), 4.04 (t, J = 5.6 Hz, 1H), 3.78 (s, 1H), 3.73-3.63 (m, 3H), 1.57 (s, 2H), 1.46-1.38 (m, 8H), 1.32 (d, J = 6.9 Hz, 2H). | 3 |
| I-321 | 1.88 | 491.43 | C | $^1$H NMR (400 MHz, DMSO-$d_6$) δ 9.09 (dd, J = 9.7, 1.7 Hz, 1H), 8.51 (d, J = 8.9 Hz, 1H), 8.17-8.07 (m, 2H), 7.64 (dd, J = 10.6, 0.8 Hz, 1H), 7.42-7.33 (m, 2H), 6.86 (dd, J = 11.8, 1.7 Hz, 1H), 4.18 (dt, J = 35.6, 5.7 Hz, 2H), 3.83-3.75 (m, 3H), 3.70 (dd, J = 6.5, 5.0 Hz, 1H), 3.59-3.42 (m, 1H), 1.55 (s, 2H), 1.47-1.41 (m, 8H), 1.37 (d, J = 6.9 Hz, 2H). | 3 |
| I-322 | 1.67 | 502.46 | C | $^1$H NMR (400 MHz, DMSO-$d_6$) δ 9.32-9.22 (m, 1H), 9.00-8.85 (m, 2H), 8.55-8.45 (m, 1H), 8.21-8.05 (m, 2H), 7.64 (d, J = 16.6 Hz, 1H), 7.37 (q, J = 7.8, 7.3 Hz, 2H), 4.20 (t, J = 5.6 Hz, 1H), 4.07 (t, J = 5.6 Hz, 1H), 3.79-3.47 (m, 5H), 1.59 (s, 3H), 1.48-1.39 (m, 8H), 1.32 (d, J = 6.9 Hz, 3H). | 3 |
| I-323 | 1.67 | 502.46 | C | $^1$H NMR (400 MHz, DMSO-$d_6$) δ 8.89 (dd, J = 5.0, 0.9 Hz, 2H), 8.50 (d, J = 14.7 Hz, 1H), 8.18-8.05 (m, 2H), 7.69-7.57 (m, 2H), 7.37 (td, J = 8.9, 7.2 Hz, 2H), 4.21 (dd, J = 7.0, 4.5 Hz, 1H), 4.04 (t, J = 5.6 Hz, 1H), 3.81-3.66 (m, 2H), 3.48-3.34 (m, 3H), 1.57 (s, 2H), 1.46-1.38 (m, 8H), 1.30 (d, J = 6.9 Hz, 2H). | 3 |
| I-324 | 1.81 | 506.48 | C | $^1$H NMR (400 MHz, DMSO-$d_6$) δ 8.52 (d, J = 5.9 Hz, 1H), 8.19-8.06 (m, 2H), 7.65 (d, J = 5.3 Hz, 1H), 7.38 (td, J = 8.9, 2.2 Hz, 2H), 4.31-4.18 (m, 2H), 4.19-4.06 (m, 2H), 3.82 (s, 1H), 3.69 (t, J = 5.7 Hz, 1H), 3.53 (dp, J = 13.7, 6.8 Hz, 1H), 2.56 (d, J = 4.9 Hz, 3H), 1.53 (d, J = 14.2 Hz, 6H), 1.41 (dd, J = 9.7, 6.9 Hz, 6H). | 3 |
| I-325 | 1.6 | 432.38 | H | $^1$H NMR (400 MHz, DMSO-$d_6$) δ 8.72 (s, 1H), 8.22-8.12 (m, 2H), 8.07 (t, J = 3.1 Hz, 1H), 7.90 (t, J = 1.1 Hz, 1H), 7.45-7.36 (m, 2H), 3.85 (t, J = 4.8 Hz, 2H), 3.37-3.31 (m, 2H), 2.25 (t, J = 19.5 Hz, 3H), 1.68 (s, 6H). | 1 |
| I-326 | 1.48 | 490.42 | C | $^1$H NMR (400 MHz, DMSO-$d_6$) δ 8.51 (s, 1H), 8.18-8.06 (m, 2H), 7.75 (s, 1H), 7.64 (d, J = 7.1 Hz, 2H), 7.44-7.33 (m, 2H), 4.49 (s, 1H), 4.23-4.05 (m, 3H), 3.76 (s, 1H), 3.58 (d, J = 34.6 Hz, 2H), 1.61-1.45 (m, 6H), 1.42 (d, J = 6.7 Hz, 6H). | 3 |

TABLE 2-continued

| Compound Number | LCMS Retention Time | M + 1 | LCMS Method | NMR | General Procedure |
|---|---|---|---|---|---|
| Compound analytical data | | | | | |
| I-327 | 1.58 | 490.46 | C | $^1$H NMR (400 MHz, DMSO-$d_6$) δ 8.51 (s, 1H), 8.22-8.03 (m, 3H), 7.81 (s, 1H), 7.64 (s, 1H), 7.38 (t, J = 8.8 Hz, 2H), 4.17 (t, J = 5.5 Hz, 2H), 3.82 (d, J = 48.7 Hz, 3H), 3.69-3.44 (m, 2H), 1.49 (d, J = 22.9 Hz, 6H), 1.40 (d, J = 6.7 Hz, 7H). | 3 |
| I-328 | 3.09 | 491.08 | A | $^1$H NMR (400 MHz, Methanol-$d_4$) δ 8.45 (s, 1H), 8.14-8.04 (m, 2H), 7.50 (s, 1H), 7.31-7.22 (m, 2H), 4.44 (bs, 2H), 4.07 (bs, 2H), 2.30-1.78 (bs, 6H), 1.63 (s, 9H). | 9, 11 |
| I-329 | 1.86 | 438.69 | C | $^1$H NMR (400 MHz, DMSO-$d_6$) δ 8.55 (s, 1H), 8.12-8.07 (m, 1H), 8.06-8.01 (m, 1H), 7.98-7.89 (m, 1H), 7.48 (s, 1H), 7.39-7.29 (m, 1H), 4.02-3.92 (m, 2H), 3.43-3.35 (m, 2H), 2.40-2.34 (m, 3H), 1.70 (s, 6H), 1.58 (s, 9H). | 6 |
| I-330 | 4.43 | 500.27 | D | $^1$H NMR (400 MHz, DMSO-d6) δ 12.86 (s, 1H), 8.53-8.43 (m, 1H), 7.96 (dd, J = 8.3, 2.8 Hz, 2H), 7.61 (d, J = 6.4 Hz, 1H), 7.35 (d, J = 7.8 Hz, 2H), 6.34 (d, J = 9.2 Hz, 1H), 4.27-3.93 (m, 4H), 3.75 (s, 1H), 3.68-3.57 (m, 1H), 3.57-3.39 (m, 1H), 2.37 (s, 3H), 1.52 (s, 3H), 1.42 (dd, J = 13.2, 6.4 Hz, 9H). | 3 |
| I-331 | 4.15 | 487.57 | D | $^1$H NMR (400 MHz, DMSO-d6) δ 8.49 (d, J = 9.1 Hz, 1H), 7.96 (dd, J = 8.0, 5.8 Hz, 2H), 7.61 (d, J = 10.0 Hz, 1H), 7.39-7.27 (m, 2H), 4.22 (d, J = 5.9 Hz, 2H), 4.18-4.10 (m, 1H), 3.79 (s, 1H), 3.69 (t, J = 5.8 Hz, 2H), 3.63-3.43 (m, 1H), 2.36 (s, 3H), 1.55 (s, 3H), 1.50-1.40 (m, 9H), 1.37 (d, J = 6.9 Hz, 3H). | 3 |
| I-332 | 4.72 | 502.62 | D | $^1$H NMR (400 MHz, DMSO-d6) δ 8.50 (d, J = 5.8 Hz, 1H), 7.97 (dd, J = 8.3, 2.8 Hz, 2H), 7.61 (d, J = 0.7 Hz, 1H), 7.36-7.28 (m, 2H), 4.29-4.20 (m, 2H), 4.15-4.06 (m, 2H), 3.81 (s, 1H), 3.72-3.65 (m, 1H), 3.59-3.41 (m, 1H), 2.56 (d, J = 4.9 Hz, 3H), 2.37 (s, 3H), 1.53 (d, J = 14.1 Hz, 6H), 1.41 (dd, J = 9.8, 6.9 Hz, 6H). | 3 |
| I-333 | 4.37 | 504.7 | D | $^1$H NMR (400 MHz, DMSO-d6) δ 8.47 (d, J = 6.2 Hz, 1H), 7.96 (dd, J = 8.4, 1.9 Hz, 2H), 7.62 (d, J = 4.7 Hz, 1H), 7.35 (d, J = 7.9 Hz, 2H), 4.95 (d, J = 14.6 Hz, 1H), 4.13-4.02 (m, 2H), 3.61-3.47 (m, 4H), 3.43 (t, J = 5.7 Hz, 1H), 2.89-2.70 (m, 1H), 2.37 (s, 3H), 2.21-1.95 (m, 4H), 1.52-1.35 (m, 12H), 1.25 (d, J = 13.2 Hz, 3H). | 3 |
| I-334 | 4.13 | 501.25 | D | $^1$H NMR (400 MHz, DMSO-d6) δ 8.48 (d, J = 8.1 Hz, 1H), 7.96 (dd, J = 8.3, 4.7 Hz, 2H), 7.61 (d, J = 8.4 Hz, 1H), 7.35 (dd, J = 8.4, 2.7 Hz, 2H), 4.28-4.18 (m, 2H), 4.11 (s, 1H), 3.77 (s, 1H), 3.72-3.64 (m, 2H), 3.62-3.37 (m, 1H), 2.41-2.28 (m, 3H), 1.53 (s, 3H), 1.49-1.29 (m, 9H). | 3 |
| I-335 | 4.53 | 518.57 | D | $^1$H NMR (400 MHz, DMSO-d6) δ 12.86 (s, 1H), 8.55-8.44 (m, 1H), 7.91-7.80 (m, 2H), 7.71-7.61 (m, 1H), 7.45 (t, J = 8.1 Hz, | 3 |

TABLE 2-continued

Compound analytical data

| Compound Number | LCMS Retention Time | M + 1 | LCMS Method | NMR | General Procedure |
| --- | --- | --- | --- | --- | --- |
| | | | | 1H), 6.38-6.26 (m, 1H), 4.25-3.97 (m, 4H), 3.75 (s, 1H), 3.61 (t, J = 5.7 Hz, 1H), 3.57-3.41 (m, 1H), 2.29 (d, J = 1.8 Hz, 3H), 2.23 (d, J = 5.3 Hz, 3H), 1.52 (s, 3H), 1.42 (dd, J = 13.2, 6.3 Hz, 12H). | |
| I-336 | 4.23 | 505.48 | D | $^1$H NMR (400 MHz, DMSO-d6) δ 8.58-8.45 (m, 1H), 8.44 (s, 1H), 7.91-7.76 (m, 2H), 7.71-7.60 (m, 1H), 7.52-7.38 (m, 1H), 4.29-4.07 (m, 3H), 4.00 (s, 1H), 3.79 (s, 1H), 3.69 (dd, J = 6.8, 4.6 Hz, 1H), 3.60-3.41 (m, 1H), 2.29 (s, 3H), 1.55 (s, 3H), 1.48-1.39 (m, 6H), 1.38 (d, J = 6.9 Hz, 3H). | 3 |
| I-337 | 4.83 | 520.56 | D | $^1$H NMR (400 MHz, DMSO-d6) δ 8.52 (d, J = 6.0 Hz, 1H), 7.93-7.81 (m, 2H), 7.68 (dd, J = 5.3, 0.8 Hz, 1H), 7.51-7.39 (m, 1H), 4.30-4.16 (m, 2H), 4.16-4.06 (m, 2H), 3.81 (s, 1H), 3.69 (t, J = 5.8 Hz, 1H), 3.57-3.45 (m, 1H), 2.56 (d, J = 4.9 Hz, 3H), 2.30 (s, 3H), 1.53 (d, J = 14.2 Hz, 6H), 1.41 (dd, J = 9.8, 6.9 Hz, 6H). | 3 |
| I-338 | 4.45 | 522.67 | D | $^1$H NMR (400 MHz, DMSO-d6) δ 8.49 (d, J = 6.1 Hz, 1H), 7.89-7.80 (m, 2H), 7.67 (d, J = 4.6 Hz, 1H), 7.51-7.31 (m, 1H), 4.95 (d, J = 14.8 Hz, 1H), 4.08 (q, J = 5.4 Hz, 2H), 3.64-3.47 (m, 4H), 3.47-3.37 (m, 1H), 2.89-2.70 (m, 1H), 2.29 (d, J = 1.9 Hz, 3H), 2.20-2.00 (m, 4H), 1.51-1.34 (m, 12H), 1.25 (d, J = 13.3 Hz, 3H). | 3 |
| I-339 | 4.22 | 519.48 | D | $^1$H NMR (400 MHz, DMSO-d6) δ 8.50 (d, J = 8.2 Hz, 1H), 7.90-7.79 (m, 2H), 7.67 (d, J = 8.5 Hz, 1H), 7.45 (td, J = 8.9, 8.4, 2.6 Hz, 1H), 4.24-4.16 (m, 2H), 4.15-3.92 (m, 2H), 3.77 (s, 1H), 3.70-3.61 (m, 1H), 3.60-3.43 (m, 1H), 2.39-2.26 (m, 6H), 1.53 (s, 3H), 1.48-1.31 (m, 9H). | 3 |
| I-340 | 4.28 | 518.26 | A | $^1$H NMR (400 MHz, DMSO-$d_6$) δ 12.75-12.60 (m, 1H), 8.56-8.49 (m, 1H), 8.19-8.09 (m, 2H), 7.52-7.46 (m, 1H), 7.46-7.36 (m, 2H), 7.01-6.75 (m, 1H), 4.75 (s, 1H), 4.46-4.35 (m, 1H), 4.34-4.16 (m, 2H), 3.82 (s, 1H), 3.76-3.67 (m, 1H), 2.24-2.12 (m, 3H), 1.66-1.47 (m, 15H). | 3 |
| I-341 | 4.52 | 518.54 | D | $^1$H NMR (400 MHz, DMSO-d6) δ 12.86 (s, 1H), 8.55-8.40 (m, 1H), 8.06-7.97 (m, 1H), 7.97-7.86 (m, 1H), 7.63 (d, J = 6.5 Hz, 1H), 7.30 (t, J = 9.1 Hz, 1H), 6.34 (d, J = 9.1 Hz, 1H), 4.27-3.95 (m, 4H), 3.75 (s, 1H), 3.61 (t, J = 5.6 Hz, 1H), 3.58-3.43 (m, 1H), 2.32 (s, 3H), 2.23 (s, 3H), 1.52 (s, 3H), 1.47-1.27 (m, 9H). | 3 |
| I-342 | 4.22 | 505.54 | D | $^1$H NMR (400 MHz, DMSO-d6) δ 8.49 (d, J = 9.2 Hz, 2H), 8.05-7.99 (m, 1H), 7.98-7.86 (m, 1H), 7.63 (d, J = 10.0 Hz, 1H), 7.40-7.21 (m, 1H), 4.26-4.19 (m, 2H), 4.19-4.07 (m, 1H), 3.79 (s, 1H), 3.73-3.62 (m, 1H), 3.61-3.43 (m, 1H), 2.32 (t, J = 2.4 Hz, 3H), 1.54 (s, 3H), 1.50-1.28 (m, 9H). | 3 |
| I-343 | 3.21 | 519.04 | A | $^1$H NMR (400 MHz, DMSO-$d_6$) δ 13.97 (s, 1H), 8.53 (dd, J = 7.2, | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 4.7 Hz, 1H), 8.14 (ddq, J = 8.3, 5.7, 2.9, 2.5 Hz, 2H), 7.48 (d, J = 11.0 Hz, 1H), 7.41 (td, J = 8.8, 2.6 Hz, 2H), 4.56-3.63 (m, 6H), 2.46-2.25 (m, 3H), 1.66-1.43 (m, 15H). | |
| I-344 | 4.78 | 520.59 | D | $^1$H NMR (400 MHz, DMSO-d6) δ 8.51 (d, J = 5.9 Hz, 1H), 8.05-7.99 (m, 1H), 7.97-7.83 (m, 1H), 7.64 (dd, J = 5.3, 0.8 Hz, 1H), 7.32-7.24 (m, 1H), 4.31-4.18 (m, 2H), 4.17-4.05 (m, 2H), 3.81 (s, 1H), 3.74-3.66 (m, 1H), 3.59-3.44 (m, 1H), 2.56 (d, J = 4.8 Hz, 3H), 2.33 (d, J = 1.9 Hz, 3H), 1.53 (d, J = 14.1 Hz, 6H), 1.41 (dd, J = 9.8, 6.9 Hz, 6H). | 3 |
| I-345 | 1.57 | 519.3 | C | $^1$H NMR (400 MHz, DMSO-d6) δ 8.49 (d, J = 8.1 Hz, 1H), 8.05-7.97 (m, 1H), 7.97-7.89 (m, 1H), 7.63 (d, J = 8.6 Hz, 1H), 7.30 (td, J = 9.1, 2.6 Hz, 1H), 4.21 (t, J = 5.7 Hz, 2H), 4.11 (s, 3H), 3.77 (s, 1H), 3.66 (dd, J = 6.8, 4.6 Hz, 1H), 3.59-3.42 (m, 1H), 2.40-2.26 (m, 6H), 1.53 (s, 3H), 1.48-1.31 (m, 9H). | 3 |
| I-346 | 3.32 | 506.02 | A | $^1$H NMR (400 MHz, Methanol-$d_4$) δ 8.45 (s, 1H), 8.22-7.94 (m, 2H), 7.53 (s, 1H), 7.27 (dd, J = 9.0, 8.5 Hz, 2H), 4.94 (s, 2H), 4.43-4.19 (m, 2H), 4.04-3.75 (m, 2H), 1.83 (s, 6H), 1.62 (s, 9H). | 24 |
| I-347 | 1.83 | 420.68 | C | $^1$H NMR (400 MHz, DMSO-$d_6$) δ 8.57-8.49 (m, 1H), 8.13-8.07 (m, 1H), 7.97 (d, J = 8.2 Hz, 2H), 7.47 (s, 1H), 7.40-7.32 (m, 2H), 4.04-3.92 (m, 2H), 3.63-3.32 (m, 2H), 2.44-2.35 (m, 3H), 1.76-1.64 (m, 6H), 1.63-1.51 (m, 9H). | 6 |
| I-348 | 1.7 | 406.58 | C | $^1$H NMR (400 MHz, DMSO-$d_6$) δ 8.57 (s, 1H), 8.12-8.05 (m, 3H), 7.60-7.55 (m, 3H), 7.50 (s, 1H), 4.01-3.94 (m, 2H), 3.43-3.36 (m, 2H), 1.71 (s, 6H), 1.59 (s, 9H). | 6 |
| I-349 | 1.71 | 456.7 | C | $^1$H NMR (400 MHz, DMSO-$d_6$) δ 8.60 (s, 1H), 8.25-8.19 (m, 2H), 8.12-8.07 (m, 1H), 7.81-7.72 (m, 2H), 7.54 (s, 1H), 7.15 (t, J = 55.8 Hz, 1H), 4.01-3.91 (m, 2H), 3.44-3.37 (m, 2H), 1.71 (s, 6H), 1.59 (s, 9H). | 6 |
| I-350 | 1.83 | 420.68 | C | $^1$H NMR (400 MHz, DMSO-$d_6$) δ 8.56 (s, 1H), 8.12-8.06 (m, 1H), 7.91-7.88 (m, 1H), 7.88-7.83 (m, 1H), 7.50-7.42 (m, 2H), 7.40-7.35 (m, 1H), 4.01-3.94 (m, 2H), 3.44-3.36 (m, 2H), 2.43 (s, 3H), 1.70 (s, 6H), 1.59 (s, 9H). | 6 |
| I-351 | 3.33 | 486.04 | A | $^1$H NMR (400 MHz, Methanol-$d_4$) δ 8.79 (dd, J = 1.6, 0.7 Hz, 1H), 8.57-8.34 (m, 1H), 8.12-7.81 (m, 2H), 7.61 (d, J = 1.5 Hz, 1H), 7.54-7.45 (m, 1H), 7.35 (d, J = 8.0 Hz, 2H), 4.47 (d, J = 5.1 Hz, 2H), 4.21-3.98 (m, 2H), 2.41 (s, 3H), 1.94 (s, 6H), 1.63 (s, 9H). | 12 |
| I-352 | 1.76 | 442.7 | C | $^1$H NMR (400 MHz, DMSO-$d_6$) δ 8.58 (s, 1H), 8.20 (ddd, J = 12.0, 7.8, 2.3 Hz, 1H), 8.13-8.07 (m, 1H), 8.01-7.95 (m, 1H), 7.65 (dt, J = 10.6, 8.5 Hz, 1H), 7.52 (s, 1H), 4.00-3.93 (m, 2H), 3.42- | 6 |

TABLE 2-continued

| Compound analytical data | | | | | |
|---|---|---|---|---|---|
| Compound Number | LCMS Retention Time | M + 1 | LCMS Method | NMR | General Procedure |
| | | | | 3.36 (m, 2H), 1.70 (s, 6H), 1.58 (s, 9H). | |
| I-353 | 4.5 | 425.91 | D | $^1$H NMR (400 MHz, DMSO-d6) δ 8.55 (s, 1H), 8.11 (d, 2H), 8.06 (s, 1H), 7.67 (s, 1H), 7.61 (d, J = 8.5 Hz, 2H), 3.95-3.81 (m, 2H), 3.55-3.45 (m, 1H), 3.27 (m, 2H), 1.67 (s, 6H), 1.41 (d, J = 6.9 Hz, 6H). | 6 |
| I-354 | 4.58 | 444.47 | D | $^1$H NMR (400 MHz, DMSO-d6) δ 8.56 (s, 1H), 8.15 (dd, J = 10.7, 2.0 Hz, 1H), 8.06 (s, 1H), 8.04-7.95 (m, 1H), 7.84-7.74 (m, 1H), 7.72 (s, 1H), 3.95-3.82 (m, 2H), 3.53 (p, J = 6.8 Hz, 1H), 3.27 (m, 2H), 1.67 (s, 6H), 1.41 (d, J = 6.9 Hz, 6H). | 6 |
| I-355 | 1.66 | 526.51 | C | $^1$H NMR (400 MHz, DMSO-$d_6$) δ 8.68 (d, J = 6.4 Hz, 1H), 8.17 (ddd, J = 8.6, 5.4, 2.7 Hz, 2H), 7.90 (d, J = 5.2 Hz, 1H), 7.40 (t, J = 8.6 Hz, 2H), 6.39-6.29 (m, 1H), 4.23 (s, 1H), 4.13 (t, J = 5.8 Hz, 1H), 4.05 (s, 1H), 3.76 (s, 1H), 3.60 (t, J = 5.7 Hz, 1H), 2.36-2.15 (m, 7H), 1.53 (s, 3H), 1.45 (s, 4H). | 3 |
| I-356 | 1.57 | 532.06 | A | $^1$H NMR (400 MHz, DMSO-$d_6$) δ 13.44-13.35 (m, 1H), 8.52 (d, J = 8.1 Hz, 1H), 8.18-8.10 (m, 2H), 7.97 (dd, J = 3.9, 1.9 Hz, 1H), 7.51-7.45 (m, 2H), 7.45-7.37 (m, 2H), 4.28-4.20 (m, 1H), 4.16-4.09 (m, 1H), 3.74 (s, 1H), 3.71-3.64 (m, 1H), 3.60-3.53 (m, 1H), 3.43 (s, 1H), 1.64-1.42 (m, 15H). | 3 |
| I-357 | 1.57 | 521.75 | A | $^1$H NMR (400 MHz, DMSO-$d_6$) δ 12.05-11.88 (m, 1H), 8.50 (d, J = 5.2 Hz, 1H), 8.16-8.07 (m, 2H), 7.46 (d, J = 4.2 Hz, 1H), 7.42-7.34 (m, 2H), 4.32-4.03 (m, 4H), 3.76 (s, 1H), 3.71-3.60 (m, 1H), 1.65-1.39 (m, 15H). | 3 |
| I-358 | 3.57 | 540.04 | A | $^1$H NMR (400 MHz, Methanol-$d_4$) δ 8.75 (d, J = 1.6 Hz, 1H), 8.52 (s, 1H), 8.35-8.10 (m, 2H), 7.85 (d, J = 8.2 Hz, 2H), 7.65-7.40 (m, 2H), 4.56-4.32 (m, 2H), 4.22-3.98 (m, 2H), 1.94 (s, 6H), 1.66 (s, 9H). | 12 |
| I-359 | 3.67 | 491.71 | A | $^1$H NMR (400 MHz, Methanol-$d_4$) δ 8.44 (d, J = 0.7 Hz, 1H), 8.29-7.89 (m, 3H), 7.49 (s, 1H), 7.39-7.19 (m, 2H), 4.60-4.39 (m, 2H), 4.27 (s, 2H), 1.92 (s, 6H), 1.66 (s, 9H). | 9, 16, 17 |
| I-360 | 3.48 | 504.69 | A | $^1$H NMR (400 MHz, Methanol-$d_4$) δ 8.78 (d, J = 1.6 Hz, 1H), 8.48 (s, 1H), 7.89-7.72 (m, 2H), 7.61 (d, J = 1.6 Hz, 1H), 7.50 (s, 1H), 7.48-7.14 (m, 1H), 4.60-4.40 (m, 2H), 4.20-3.95 (m, 2H), 2.48-2.30 (m, 3H), 1.94 (s, 6H), 1.64 (s, 9H). | 12 |
| I-361 | 1.87 | 440.6 | C | $^1$H NMR (400 MHz, DMSO-$d_6$) δ 8.58 (s, 1H), 8.14-8.07 (m, 3H), 7.67-7.61 (m, 2H), 7.51 (s, 1H), 4.00-3.94 (m, 2H), 3.44-3.35 (m, 2H), 1.70 (s, 6H), 1.58 (s, 9H). | 6 |
| I-362 | 3.13 | 428.01 | A | $^1$H NMR (400 MHz, DMSO-$d_6$) δ 8.66 (s, 1H), 8.18-8.07 (m, 3H), 7.69 (s, 1H), 7.45-7.37 (m, 2H), | 1 |

TABLE 2-continued

Compound analytical data

| Compound Number | LCMS Retention Time | M + 1 | LCMS Method | NMR | General Procedure |
|---|---|---|---|---|---|
| | | | | 3.93-3.87 (m, 2H), 3.41-3.34 (m, 2H), 1.95 (d, J = 22.8 Hz, 6H), 1.70 (s, 6H). | |
| I-363 | 1.69 | 444.3 | C | $^1$H NMR (400 MHz, DMSO-d6) δ 8.56 (s, 1H), 8.32 (dd, J = 7.1, 2.3 Hz, 1H), 8.17-8.10 (m, 1H), 8.07-8.00 (m, 1H), 7.72 (s, 1H), 7.60 (t, J = 8.9 Hz, 1H), 3.94-3.84 (m, 2H), 3.56-3.45 (m, 1H), 3.37-3.30 (m, 2H), 1.67 (s, 6H), 1.41 (d, J = 6.9 Hz, 6H). | 6 |
| I-364 | 3.69 | 486.11 | A | $^1$H NMR (400 MHz, Methanol-$d_4$) δ 8.44 (s, 1H), 8.04 (s, 2H), 7.96-7.82 (m, 2H), 7.51 (s, 1H), 7.41-7.22 (m, 2H), 4.50-4.29 (m, 2H), 4.16-3.93 (m, 2H), 2.41 (s, 3H), 1.91 (s, 6H), 1.64 (s, 9H). | 12 |
| I-365 | 3.77 | 504.73 | A | $^1$H NMR (400 MHz, Methanol-$d_4$) δ 8.44 (s, 1H), 8.01 (s, 2H), 7.80-7.61 (m, 2H), 7.48 (s, 1H), 7.41-7.05 (m, 1H), 4.50-4.27 (m, 2H), 4.16-3.90 (m, 2H), 2.33 (dd, J = 1.9, 0.8 Hz, 3H), 1.90 (s, 6H), 1.64 (s, 9H). | 12 |
| I-366 | 3.84 | 540.74 | A | $^1$H NMR (400 MHz, Methanol-$d_4$) δ 8.49 (s, 1H), 8.33-8.21 (m, 2H), 8.04 (s, 2H), 7.84 (ddd, J = 8.1, 1.4, 0.7 Hz, 2H), 7.57 (s, 1H), 4.44-4.32 (m, 2H), 4.11-3.98 (m, 2H), 1.90 (s, 6H), 1.66 (s, 9H). | 12 |
| I-367 | 2.86 | 504.06 | F | $^1$H NMR (400 MHz, Methanol-$d_4$) δ 8.49 (s, 1H), 8.18-7.99 (m, 2H), 7.53 (s, 1H), 7.44 (s, 1H), 7.27 (dd, J = 9.0, 8.5 Hz, 2H), 4.52-4.30 (m, 2H), 4.16-3.84 (m, 2H), 2.63 (s, 3H), 1.93 (s, 6H), 1.64 (s, 9H). | 9, 12 |
| I-368 | 3.16 | 500.74 | A | $^1$H NMR (400 MHz, Methanol-$d_4$) δ 8.45 (s, 1H), 8.02-7.85 (m, 2H), 7.49 (s, 1H), 7.43 (s, 1H), 7.38-7.21 (m, 2H), 4.52-4.42 (m, 2H), 4.12-4.02 (m, 2H), 2.62 (s, 3H), 2.41 (s, 3H), 1.93 (s, 6H), 1.63 (s, 9H). | 12 |
| I-369 | 3.36 | 518.12 | A | $^1$H NMR (400 MHz, Methanol-$d_4$) δ 8.47 (s, 1H), 7.89-7.69 (m, 2H), 7.49 (s, 1H), 7.42 (d, J = 11.0 Hz, 2H), 4.52-4.38 (m, 2H), 4.12-3.92 (m, 2H), 2.62 (s, 3H), 2.38-2.24 (m, 3H), 1.93 (s, 6H), 1.63 (s, 9H). | 12 |
| I-370 | 4.55 | 552.6 | D | $^1$H NMR (400 MHz, DMSO-d6) δ 8.90 (d, J = 5.0 Hz, 2H), 8.56 (d, J = 14.9 Hz, 1H), 8.28 (dd, J = 13.1, 8.1 Hz, 2H), 7.90 (t, J = 7.9 Hz, 2H), 7.71 (d, J = 20.2 Hz, 1H), 7.60 (t, J = 5.0 Hz, 1H), 4.24-4.15 (m, 1H), 4.09-3.96 (m, 1H), 3.79 (s, 1H), 3.70 (dd, J = 6.7, 4.8 Hz, 1H), 3.65-3.51 (m, 1H), 3.47-3.40 (m, 1H), 3.37 (s, 1H), 1.57 (s, 3H), 1.47-1.38 (m, 9H), 1.32 (d, J = 6.9 Hz, 3H). | 3 |
| I-371 | 4.55 | 558.68 | D | $^1$H NMR (400 MHz, DMSO-d6) δ 8.56 (d, J = 6.1 Hz, 1H), 8.29 (dd, J = 8.2, 2.1 Hz, 2H), 7.91 (d, J = 7.9 Hz, 2H), 7.73 (d, J = 4.8 Hz, 1H), 4.95 (d, J = 15.2 Hz, 1H), 4.15-4.03 (m, 2H), 3.66-3.47 (m, 4H), 3.44 (t, J = 5.7 Hz, 1H), 2.93-2.70 (m, 1H), 2.22-1.96 (m, 4H), 1.52-1.37 (m, 12H), 1.25 (d, J = 13.3 Hz, 3H). | 3 |

TABLE 2-continued

| Compound analytical data | | | | | |
|---|---|---|---|---|---|
| Compound Number | LCMS Retention Time | M + 1 | LCMS Method | NMR | General Procedure |
| I-372 | 3.25 | 554.26 | D | $^1$H NMR (400 MHz, DMSO-d6) δ 8.60 (s, 1H), 8.30 (d, J = 8.1 Hz, 2H), 7.99-7.87 (m, 3H), 7.75 (s, 1H), 4.33-4.14 (m, 2H), 4.04-3.79 (m, 2H), 3.65 (s, 1H), 3.59-3.50 (m, 1H), 3.50(m, 1H), 1.61-1.47 (m, 6H), 1.42 (d, J = 6.6 Hz, 7H). | 3 |
| I-373 | 4.47 | 516.56 | D | $^1$H NMR (400 MHz, DMSO-d6) δ 8.89 (dd, J = 5.0, 0.9 Hz, 2H), 8.50 (d, J = 14.8 Hz, 1H), 7.91-7.77 (m, 2H), 7.68 (s, 1H), 7.64-7.54 (m, 2H), 7.51-7.38 (m, 1H), 4.21 (t, J = 5.8 Hz, 1H), 4.04 (t, J = 5.6 Hz, 1H), 3.78 (s, 1H), 3.74-3.67 (m, 1H), 3.55 (p, J = 7.0 Hz, 1H), 3.44-3.40 (m, 1H), 3.36 (s, 1H), 2.32-2.22 (m, 3H), 1.57 (s, 3H), 1.48-1.34 (m, 9H), 1.30 (d, J = 6.9 Hz, 3H). | 3 |
| I-374 | 4.43 | 504.6 | D | $^1$H NMR (400 MHz, DMSO-d6) δ 13.20 (s, 1H), 8.50 (d, J = 6.9 Hz, 1H), 7.96-7.73 (m, 3H), 7.66 (d, J = 7.9 Hz, 1H), 7.56-7.33 (m, 1H), 6.68-6.47 (m, 1H), 4.30-3.96 (m, 4H), 3.77 (s, 1H), 3.64 (t, J = 5.6 Hz, 1H), 3.60-3.43 (m, 1H), 2.29 (s, 3H), 1.54 (s, 3H), 1.49-1.24 (m, 9H). | 3 |
| I-375 | 4.75 | 515.65 | D | $^1$H NMR (400 MHz, DMSO-d6) δ 8.61-8.55 (m, 1H), 8.50 (d, J = 15.0 Hz, 1H), 7.98-7.77 (m, 3H), 7.68 (s, 1H), 7.66-7.59 (m, 1H), 7.56-7.37 (m, 2H), 4.21 (t, J = 5.8 Hz, 1H), 4.04 (t, J = 5.7 Hz, 1H), 3.78 (s, 1H), 3.73-3.61 (m, 3H), 3.59-3.45 (m, 1H), 3.44-3.34 (m, 1H), 2.34-2.25 (m, 3H), 1.57 (s, 2H), 1.46-1.35 (m, 9H), 1.31 (d, J = 6.9 Hz, 3H) rotamers | 3 |
| I-376 | 3.12 | 518.28 | D | $^1$H NMR (400 MHz, DMSO-d6) δ 8.53 (s, 1H), 8.00-7.91 (m, 1H), 7.89-7.78 (m, 2H), 7.69 (s, 1H), 7.46 (t, J = 8.1 Hz, 1H), 4.35-4.14 (m, 2H), 4.06-3.88 (m, 2H), 3.82 (s, 1H), 3.65 (s, 1H), 3.59-3.46 (m, 1H), 2.30 (s, 3H), 1.60-1.46 (m, 6H), 1.41 (d, J = 6.7 Hz, 6H). | 3 |
| I-377 | 4.43 | 516.59 | D | $^1$H NMR (400 MHz, DMSO-d6) δ 8.90 (d, J = 5.0 Hz, 2H), 8.49 (d, J = 14.7 Hz, 1H), 8.04-7.85 (m, 2H), 7.64 (s, 1H), 7.63-7.53 (m, 2H), 7.37-7.14 (m, 1H), 4.27-4.14 (m, 1H), 4.04 (t, 1H), 3.78 (s, 1H), 3.69 (dd, J = 6.7, 4.7 Hz, 2H), 3.61-3.50 (m, 1H), 3.45-3.40 (m, 1H), 3.36 (s, 2H), 2.38-2.26 (m, 3H), 1.57 (s, 3H), 1.48-1.35 (m, 9H), 1.30 (d, J = 6.9 Hz, 3H). | 3 |
| I-378 | 4.43 | 522.64 | D | $^1$H NMR (400 MHz, DMSO-d6) δ 8.48 (d, J = 6.2 Hz, 1H), 8.01 (dd, J = 7.4, 2.1 Hz, 1H), 7.97-7.86 (m, 1H), 7.63 (d, J = 4.6 Hz, 1H), 7.39-7.22 (m, 1H), 4.95 (d, J = 14.9 Hz, 1H), 4.15-4.01 (m, 2H), 3.65-3.47 (m, 4H), 3.43 (dd, J = 6.7, 4.8 Hz, 1H), 2.82 (dp, J = 17.6, 8.8 Hz, 1H), 2.32 (s, 3H), 2.21-1.99 (m, 4H), 1.54-1.36 (m, 12H), 1.25 (d, J = 13.2 Hz, 3H). | 3 |
| I-379 | 4.73 | 515.58 | D | $^1$H NMR (400 MHz, DMSO-d6) δ 8.66-8.53 (m, 1H), 8.48 (dd, J = | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 14.9, 0.8 Hz, 1H), 8.08-7.95 (m, 1H), 7.95-7.86 (m, 2H), 7.71-7.55 (m, 2H), 7.54-7.42 (m, 1H), 7.31-7.22 (m, 1H), 4.27-4.16 (m, 1H), 4.09-3.98 (m, 1H), 3.78 (s, 1H), 3.75-3.62 (m, 3H), 3.55 (p, J = 6.8 Hz, 1H), 3.44-3.34 (m, 1H), 2.40-2.20 (m, 3H), 1.57 (s, 3H), 1.45-1.35 (m, 6H), 1.32 (d, J = 6.9 Hz, 6H) rotamers. | |
| I-380 | 3.12 | 518.28 | D | $^1$H NMR (400 MHz, DMSO-d6) δ 8.53 (s, 1H), 8.08-8.00 (m, 2H), 8.00-7.86 (m, 1H), 7.65 (s, 1H), 7.31 (t, J = 9.1 Hz, 1H), 4.38-4.16 (m, 2H), 4.00-3.74 (m, 3H), 3.67 (s, 1H), 3.59-3.47 (m, 1H), 2.42-2.25 (m, 3H), 1.60-1.47 (m, 6H), 1.47-1.32 (m, 6H). | 3 |
| I-381 | 4.9 | 518.64 | D | $^1$H NMR (400 MHz, DMSO-d6) δ 13.19 (s, 1H), 8.48 (d, J = 6.5 Hz, 1H), 8.07-7.69 (m, 2H), 7.44 (d, J = 8.4 Hz, 1H), 7.40-7.17 (m, 1H), 6.71-6.48 (m, 1H), 4.37-3.96 (m, 4H), 3.86-3.60 (m, 2H), 2.32 (s, 3H), 1.62-1.15 (m, 15H). | 3 |
| I-382 | 5.02 | 532.61 | D | $^1$H NMR (400 MHz, DMSO-d6) δ 12.85 (s, 1H), 8.52-8.39 (m, 1H), 8.05-7.95 (m, 1H), 7.95-7.85 (m, 1H), 7.44 (d, J = 6.5 Hz, 1H), 7.30 (t, J = 9.1 Hz, 1H), 6.45-6.25 (m, 1H), 4.30-4.00 (m, 4H), 3.75 (s, 1H), 3.65 (t, J = 5.7 Hz, 1H), 2.32 (d, J = 1.9 Hz, 3H), 2.23 (d, J = 4.5 Hz, 3H), 1.72-1.35 (m, 15H). | 3 |
| I-383 | 3.39 | 532.58 | D | $^1$H NMR (400 MHz, DMSO-d6) δ 8.56-8.44 (m, 1H), 8.06-7.95 (m, 1H), 7.95-7.82 (m, 2H), 7.46 (s, 1H), 7.31 (t, J = 9.1 Hz, 1H), 4.39-4.19 (m, 2H), 4.14-3.94 (m, 2H), 3.91-3.77 (m, 1H), 3.74-3.62 (m, 1H), 2.33 (s, 3H), 1.55 (d, J = 8.4 Hz, 15H). | 3 |
| I-384 | 4.92 | 536.68 | D | $^1$H NMR (400 MHz, DMSO-d6) δ 8.47 (d, J = 6.1 Hz, 1H), 8.03-7.96 (m, 1H), 7.91 (ddt, J = 9.2, 4.7, 2.2 Hz, 1H), 7.44 (d, J = 4.1 Hz, 1H), 7.32-7.24 (m, 1H), 4.95 (d, J = 19.5 Hz, 1H), 4.13 (dt, J = 10.3, 5.4 Hz, 2H), 3.69-3.54 (m, 2H), 3.54-3.40 (m, 2H), 2.82 (dt, J = 20.0, 8.4 Hz, 1H), 2.32 (s, 3H), 2.23-2.00 (m, 4H), 1.56 (d, J = 4.5 Hz, 9H), 1.47 (d, J = 15.5 Hz, 6H), 1.25 (d, J = 10.8 Hz, 3H). | 3 |
| I-385 | 5.33 | 533.95 | D | $^1$H NMR (400 MHz, DMSO-d6) δ 8.50 (d, J = 5.0 Hz, 1H), 8.00 (dt, J = 7.7, 2.6 Hz, 1H), 7.95-7.86 (m, 1H), 7.45 (d, J = 5.2 Hz, 1H), 7.30 (ddd, J = 10.7, 8.8, 2.0 Hz, 1H), 4.35-4.19 (m, 2H), 4.17-4.06 (m, 2H), 3.82 (s, 1H), 3.77-3.66 (m, 1H), 2.56 (d, J = 4.5 Hz, 3H), 2.32 (s, 3H), 1.63-1.45 (m, 15H). | 3 |
| I-386 | 5.28 | 529.62 | D | $^1$H NMR (400 MHz, DMSO-d6) δ 8.63-8.52 (m, 1H), 8.47 (d, J = 13.5 Hz, 1H), 8.03-7.81 (m, 3H), 7.67-7.56 (m, 1H), 7.55-7.45 (m, 1H), 7.40 (s, 1H), 7.34-7.23 (m, 1H), 4.27 (dd, J = 7.1, 4.5 Hz, 1H), 4.06 (t, J = 5.7 Hz, 1H), 3.78 (s, 1H), 3.76-3.68 (m, 2H), 3.67 | 3 |

TABLE 2-continued

| Compound Number | LCMS Retention Time | M + 1 | LCMS Method | NMR | General Procedure |
|---|---|---|---|---|---|
| Compound analytical data | | | | | |
| | | | | (s, 1H), 2.33-2.25 (m, 3H), 1.57 (d, J = 7.0 Hz, 9H), 1.41 (d, J = 9.6 Hz, 6H). | |
| I-387 | 4.95 | 529.95 | D | $^1$H NMR (400 MHz, DMSO-d6) δ 8.90 (d, J = 5.0 Hz, 2H), 8.47 (d, J = 12.7 Hz, 1H), 8.05-7.82 (m, 2H), 7.60 (q, J = 4.9 Hz, 1H), 7.43 (d, J = 23.4 Hz, 1H), 7.29 (td, J = 9.0, 7.5 Hz, 1H), 4.27 (t, J = 5.8 Hz, 1H), 4.05 (t, J = 5.6 Hz, 1H), 3.79 (s, 1H), 3.75-3.66 (m, 1H), 3.47 (t, J = 5.6 Hz, 1H), 3.36 (s, 1H), 2.36-2.26 (m, 3H), 1.57 (d, J = 6.8 Hz, 6H), 1.40 (s, 9H). | 3 |
| I-388 | 3.04 | 490.69 | A | $^1$H NMR (400 MHz, Methanol-d$_4$) δ 8.79 (d, J = 1.6 Hz, 1H), 8.62 (s, 1H), 8.11-7.99 (m, 1H), 7.94 (ddd, J = 7.7, 4.7, 2.4 Hz, 1H), 7.79 (d, J = 0.8 Hz, 1H), 7.60 (d, J = 1.6 Hz, 1H), 7.21 (dd, J = 9.3, 8.7 Hz, 1H), 4.37-4.27 (m, 2H), 4.16-3.89 (m, 2H), 3.72-3.53 (m, 1H), 2.37 (d, J = 1.9 Hz, 3H), 1.95 (s, 6H), 1.50 (d, J = 6.9 Hz, 6H). | 3 |
| I-389 | 2.94 | 504.1 | A | $^1$H NMR (400 MHz, Methanol-d$_4$) δ 8.58 (s, 1H), 8.00 (d, J = 7.6 Hz, 1H), 7.95-7.83 (m, 1H), 7.76 (d, J = 0.8 Hz, 1H), 7.40 (s, 1H), 7.21 (t, J = 9.0 Hz, 1H), 4.36-4.19 (m, 2H), 4.11-3.90 (m, 2H), 3.74-3.51 (m, 1H), 2.62 (s, 3H), 2.40-2.30 (m, 3H), 1.94 (s, 6H), 1.49 (d, J = 6.9 Hz, 6H). | 12 |
| I-390 | 4.62 | 553.97 | D | $^1$H NMR (400 MHz, DMSO-d6) δ 12.86 (s, 1H), 8.65-8.48 (m, 1H), 8.35-8.21 (m, 2H), 7.91 (d, J = 8.2 Hz, 2H), 7.76-7.66 (m, 1H), 6.41-6.25 (m, 1H), 4.31-3.98 (m, 4H), 3.75 (s, 1H), 3.69-3.46 (m, 2H), 2.29-2.12 (m, 3H), 1.57-1.30 (m, 12H). | 3 |
| I-391 | 3.97 | 511.13 | A | $^1$H NMR (400 MHz, DMSO-d$_6$) δ 8.66-8.57 (m, 1H), 8.50 (d, J = 13.5 Hz, 1H), 8.02-7.89 (m, 3H), 7.64 (s, 1H), 7.54-7.49 (m, 1H), 7.45 (d, J = 22.4 Hz, 1H), 7.41-7.34 (m, 2H), 4.36-4.26 (m, 1H), 4.13-4.05 (m, 1H), 3.81 (s, 1H), 3.79-3.72 (m, 2H), 3.70 (s, 1H), 2.39 (d, J = 5.1 Hz, 3H), 1.67-1.40 (m, 15H). | 3 |
| I-392 | 3.68 | 512.11 | A | $^1$H NMR (400 MHz, DMSO-d$_6$) δ 8.93 (d, J = 5.0 Hz, 2H), 8.50 (d, J = 12.6 Hz, 1H), 8.02-7.92 (m, 2H), 7.63 (q, J = 4.9 Hz, 1H), 7.46 (d, J = 23.3 Hz, 1H), 7.42-7.34 (m, 2H), 4.35-4.27 (m, 1H), 4.13-4.04 (m, 1H), 3.82 (s, 1H), 3.79-3.72 (m, 1H), 3.55-3.48 (m, 1H), 3.40 (s, 1H), 2.40 (d, J = 5.4 Hz, 3H), 1.67-1.34 (m, 15H). | 3 |
| I-393 | 3.96 | 516.07 | A | $^1$H NMR (400 MHz, DMSO-d$_6$) δ 8.52 (d, J = 4.9 Hz, 1H), 8.01-7.94 (m, 2H), 7.47 (d, J = 5.1 Hz, 1H), 7.41-7.35 (m, 2H), 4.38-4.26 (m, 2H), 4.21-4.11 (m, 2H), 3.85 (s, 1H), 3.80-3.71 (m, 1H), 2.59 (d, J = 4.6 Hz, 3H), 2.40 (s, 3H), 1.66-1.48 (m, 15H). | 3 |
| I-394 | 3.61 | 500.07 | A | $^1$H NMR (400 MHz, DMSO-d$_6$) δ 13.22 (s, 1H), 8.54-8.47 (m, 1H), 8.02-7.93 (m, 2H), 7.87-7.79 (m, 1H), 7.51-7.44 (m, 1H), | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 7.42-7.34 (m, 2H), 6.68-6.60 (m, 1H), 4.35-4.07 (m, 4H), 3.81 (s, 1H), 3.75-3.66 (m, 1H), 2.40 (s, 3H), 1.66-1.45 (m, 15H). | |
| I-395 | 4.02 | 514.51 | A | $^1$H NMR (400 MHz, DMSO-$d_6$) δ 12.89 (s, 1H), 8.53-8.47 (m, 1H), 8.01-7.92 (m, 2H), 7.50-7.44 (m, 1H), 7.42-7.34 (m, 2H), 6.42-6.33 (m, 1H), 4.33-4.04 (m, 4H), 3.78 (s, 1H), 3.73-3.64 (m, 1H), 2.40 (s, 3H), 2.31-2.19 (m, 3H), 1.66-1.44 (m, 15H). | 3 |
| I-396 | 3.71 | 518.1 | A | $^1$H NMR (400 MHz, DMSO-$d_6$) δ 8.50 (d, J = 6.1 Hz, 1H), 8.01-7.95 (m, 2H), 7.47 (d, J = 4.1 Hz, 1H), 7.42-7.35 (m, 2H), 4.98 (d, J = 19.1 Hz, 1H), 4.21-4.11 (m, 2H), 3.70-3.60 (m, 2H), 3.54 (s, 1H), 3.53-3.45 (m, 1H), 2.91-2.79 (m, 1H), 2.40 (s, 3H), 2.23-2.15 (m, 2H), 2.15-2.05 (m, 2H), 1.59 (d, J = 4.5 Hz, 9H), 1.50 (d, J = 15.4 Hz, 6H), 1.28 (d, J = 10.7 Hz, 3H). | 3 |
| I-397 | 3.68 | 515.54 | A | $^1$H NMR (400 MHz, DMSO-$d_6$) δ 14.01-13.92 (m, 1H), 8.54-8.47 (m, 1H), 8.02-7.93 (m, 2H), 7.51-7.43 (m, 1H), 7.42-7.35 (m, 2H), 4.35-4.10 (m, 2H), 3.96-3.65 (m, 4H), 2.45-2.34 (m, 6H), 1.67-1.41 (m, 15H). | 3 |
| I-398 | 4.43 | 565.09 | A | $^1$H NMR (400 MHz, DMSO-$d_6$) δ 8.66-8.55 (m, 2H), 8.35-8.25 (m, 2H), 8.00-7.89 (m, 3H), 7.68-7.61 (m, 1H), 7.59-7.47 (m, 2H), 4.33-4.25 (m, 1H), 4.12-4.04 (m, 1H), 3.82 (s, 1H), 3.80-3.73 (m, 2H), 3.70 (s, 1H), 1.67-1.39 (m, 15H). | 3 |
| I-399 | 4.17 | 566.1 | A | $^1$H NMR (400 MHz, DMSO-$d_6$) δ 8.96-8.89 (m, 2H), 8.59 (d, J = 12.7 Hz, 1H), 8.35-8.25 (m, 2H), 7.98-7.89 (m, 2H), 7.63 (q, J = 5.0 Hz, 1H), 7.55 (d, J = 23.2 Hz, 1H), 4.33-4.25 (m, 1H), 4.11-4.03 (m, 1H), 3.82 (s, 1H), 3.79-3.72 (m, 1H), 3.55-3.48 (m, 1H), 3.40 (s, 1H), 1.67-1.38 (m, 15H). | 3 |
| I-400 | 4.43 | 570.09 | A | $^1$H NMR (400 MHz, DMSO-$d_6$) δ 8.61 (d, J = 5.3 Hz, 1H), 8.35-8.28 (m, 2H), 7.99-7.90 (m, 2H), 7.57 (d, J = 5.0 Hz, 1H), 4.37-4.24 (m, 2H), 4.22-4.12 (m, 2H), 3.85 (s, 1H), 3.80-3.71 (m, 1H), 2.60 (d, J = 4.5 Hz, 3H), 1.67-1.50 (m, 15H). | 3 |
| I-401 | 4.11 | 554.07 | A | $^1$H NMR (400 MHz, DMSO-$d_6$) δ 13.22 (s, 1H), 8.62-8.55 (m, 1H), 8.34-8.27 (m, 2H), 7.98-7.91 (m, 2H), 7.87-7.79 (m, 1H), 7.59-7.52 (m, 1H), 6.69-6.61 (m, 1H), 4.27 (d, J = 6.0 Hz, 2H), 4.22-4.08 (m, 2H), 3.81 (s, 1H), 3.75-3.64 (m, 1H), 1.68-1.43 (m, 15H). | 3 |
| I-402 | 4.09 | 568.48 | A | $^1$H NMR (400 MHz, DMSO-$d_6$) δ 12.89 (s, 1H), 8.62-8.55 (m, 1H), 8.35-8.27 (m, 2H), 7.97-7.91 (m, 2H), 7.60-7.53 (m, 1H), 6.42-6.32 (m, 1H), 4.31-4.06 (m, 4H), 3.84-3.76 (m, 1H), 3.73-3.63 (m, 1H), 2.30-2.23 (m, 3H), 1.67-1.42 (m, 15H). | 3 |

TABLE 2-continued

| Compound analytical data | | | | | |
|---|---|---|---|---|---|
| Compound Number | LCMS Retention Time | M + 1 | LCMS Method | NMR | General Procedure |
| I-403 | 3.85 | 569.51 | A | $^1H$ NMR (400 MHz, DMSO-$d_6$) δ 14.00-13.94 (m, 1H), 8.62-8.54 (m, 1H), 8.34-8.26 (m, 2H), 7.99-7.90 (m, 2H), 7.59-7.53 (m, 1H), 4.38-4.07 (m, 2H), 3.96-3.66 (m, 4H), 2.44-2.34 (m, 3H), 1.68-1.41 (m, 15H). | 3 |
| I-404 | 4.8 | 500.6 | D | $^1H$ NMR (400 MHz, DMSO-d6) δ 13.20 (s, 1H), 8.57-8.38 (m, 1H), 7.90-7.73 (m, 3H), 7.46-7.37 (m, 2H), 7.38-7.28 (m, 1H), 6.69-6.48 (m, 1H), 4.36-4.03 (m, 4H), 3.86-3.59 (m, 2H), 2.40 (s, 3H), 1.66-1.33 (m, 15H). | 3 |
| I-405 | 3.38 | 490.38 | A | $^1H$ NMR (400 MHz, Chloroform-d) δ 9.99 (s, 1H), 8.41 (s, 1H), 8.00 (bs, 2H), 7.80 (dd, J = 7.2, 2.3 Hz, 1H), 7.73 (ddd, J = 7.8, 4.8, 2.5 Hz, 1H), 7.27 (d, J = 0.8 Hz, 1H), 7.14 (t, J = 8.9 Hz, 1H), 4.60-4.31 (m, 2H), 4.12-3.93 (m, 2H), 3.63 (p, J = 6.9 Hz, 1H), 2.38 (d, J = 1.9 Hz, 3H), 1.94 (s, 7H), 1.49 (d, J = 6.9 Hz, 6H). | 12 |
| I-406 | 4.92 | 514.67 | D | $^1H$ NMR (400 MHz, DMSO-d6) δ 12.86 (s, 1H), 8.57-8.38 (m, 1H), 7.91-7.77 (m, 3H), 7.48-7.39 (m, 2H), 7.38-7.28 (m, 1H), 6.34 (s, 1H), 4.35-4.00 (m, 4H), 3.81-3.54 (m, 2H), 2.40 (s, 3H), 2.23 (s, 3H), 1.65-1.32 (m, 15H). | 3 |
| I-407 | 3.3 | 514.25 | D | $^1H$ NMR (400 MHz, DMSO-d6) δ 8.50 (s, 1H), 7.88-7.78 (m, 2H), 7.56 (s, 1H), 7.49-7.37 (m, 2H), 7.34 (d, J = 7.5 Hz, 1H), 4.40-4.28 (m, 1H), 4.30-4.20 (m, 2H), 4.14-4.00 (m, 1H), 3.86-3.74 (m, 1H), 3.70-3.53 (m, 1H), 2.40 (s, 3H), 2.32 (s, 3H), 1.64-1.40 (m, 15H). | 3 |
| I-408 | 4.52 | 515.58 | D | $^1H$ NMR (400 MHz, DMSO-d6) δ 8.54-8.41 (m, 1H), 7.88-7.74 (m, 2H), 7.51-7.38 (m, 2H), 7.38-7.29 (m, 1H), 4.31-4.22 (m, 2H), 4.16-4.05 (m, 1H), 3.92-3.82 (m, 1H), 3.80-3.62 (m, 2H), 2.44-2.25 (m, 6H), 1.63-1.37 (m, 15H). | 3 |
| I-409 | 4.82 | 518.7 | D | $^1H$ NMR (400 MHz, DMSO-d6) δ 8.48 (d, J = 6.2 Hz, 1H), 7.88-7.75 (m, 2H), 7.47-7.38 (m, 2H), 7.34 (d, J = 7.5 Hz, 1H), 4.96 (d, J = 19.4 Hz, 1H), 4.13 (dt, J = 10.6, 5.4 Hz, 2H), 3.68-3.54 (m, 2H), 3.55-3.42 (m, 2H), 2.82 (dt, J = 20.5, 8.8 Hz, 1H), 2.40 (s, 3H), 2.21-2.00 (m, 4H), 1.57 (d, J = 4.5 Hz, 9H), 1.47 (d, J = 15.5 Hz, 6H), 1.25 (d, J = 10.7 Hz, 3H). | 3 |
| I-410 | 5.25 | 516.66 | D | $^1H$ NMR (400 MHz, DMSO-d6) δ 8.51 (d, J = 4.9 Hz, 1H), 7.92-7.75 (m, 2H), 7.48-7.37 (m, 2H), 7.34 (d, J = 6.3 Hz, 1H), 4.36-4.22 (m, 2H), 4.18-4.09 (m, 2H), 3.82 (s, 1H), 3.72 (dd, J = 6.8, 4.6 Hz, 1H), 2.49-2.42 (m, 3H), 2.40 (d, J = 1.7 Hz, 3H), 1.55 (dd, J = 13.3, 10.9 Hz, 15H). | 3 |
| I-411 | 5.2 | 511.65 | D | $^1H$ NMR (400 MHz, DMSO-d6) δ 8.59 (ddt, J = 9.8, 4.8, 1.4 Hz, 1H), 8.48 (d, J = 13.4 Hz, 1H), 7.99-7.74 (m, 3H), 7.65-7.55 (m, 1H), 7.51-7.37 (m, 3H), 7.37-7.30 (m, 1H), 4.28 (t, J = 5.8 Hz, | 3 |

TABLE 2-continued

Compound analytical data

| Compound Number | LCMS Retention Time | M + 1 | LCMS Method | NMR | General Procedure |
|---|---|---|---|---|---|
| | | | | 1H), 4.06 (t, J = 5.7 Hz, 1H), 3.79 (s, 1H), 3.76-3.69 (m, 2H), 3.67 (s, 1H), 2.44-2.35 (m, 3H), 1.58 (d, J = 7.6 Hz, 9H), 1.41 (d, J = 10.3 Hz, 6H). | |
| I-412 | 4.85 | 512.63 | D | $^1$H NMR (400 MHz, DMSO-d6) δ 8.90 (d, J = 5.0 Hz, 2H), 8.49 (d, J = 12.6 Hz, 1H), 7.89-7.73 (m, 2H), 7.60 (q, J = 4.9 Hz, 1H), 7.50-7.38 (m, 2H), 7.37-7.28 (m, 1H), 4.27 (t, J = 5.8 Hz, 1H), 4.05 (t, J = 5.6 Hz, 1H), 3.79 (s, 1H), 3.73 (dd, J = 6.6, 4.8 Hz, 1H), 3.48 (t, J = 5.6 Hz, 1H), 3.36 (s, 1H), 2.40 (d, J = 6.9 Hz, 3H), 1.58 (d, J = 7.8 Hz, 9H), 1.41 (s, 6H). | 3 |
| I-413 | 4.3 | 555.2 | D | $^1$H NMR (400 MHz, DMSO-d6) δ 8.57 (d, J = 8.4 Hz, 1H), 8.36-8.24 (m, 2H), 7.98-7.85 (m, 2H), 7.73 (d, J = 8.4 Hz, 1H), 4.19 (t, J = 5.8 Hz, 2H), 4.14-4.03 (m, 1H), 3.77 (s, 1H), 3.70-3.62 (m, 1H), 3.60-3.45 (m, 1H), 2.39-2.30 (m, 3H), 1.54 (s, 3H), 1.49-1.32 (m, 9H). | 3 |
| I-414 | 4.6 | 533.23 | D | $^1$H NMR (400 MHz, DMSO-d6) δ 8.48 (d, J = 7.1 Hz, 1H), 8.00 (dt, J = 7.3, 3.5 Hz, 1H), 7.95-7.87 (m, 1H), 7.44 (d, J = 8.9 Hz, 1H), 7.30 (td, J = 9.1, 2.8 Hz, 1H), 4.26 (t, J = 5.8 Hz, 2H), 4.18-4.11 (m, 1H), 4.01 (s, 2H), 3.77 (s, 1H), 3.69 (dd, J = 6.7, 4.6 Hz, 1H), 2.41-2.26 (m, 6H), 1.58 (s, 6H), 1.52 (d, J = 7.9 Hz, 6H), 1.45 (s, 3H). | 3 |
| I-415 | 1.88 | 536.5 | C | $^1$H NMR (400 MHz, DMSO-$d_6$) δ 8.52 (d, J = 6.0 Hz, 1H), 7.91-7.83 (m, 2H), 7.52-7.45 (m, 2H), 4.98 (d, J = 19.4 Hz, 1H), 4.20-4.10 (m, 2H), 3.70-3.46 (m, 4H), 2.68-2.65 (m, 1H), 2.36-2.30 (m, 3H), 2.23-2.15 (m, 2H), 2.15-2.06 (m, 2H), 1.59 (d, J = 4.4 Hz, 9H), 1.50 (d, J = 15.4 Hz, 6H), 1.32-1.21 (m, 3H). | 3 |
| I-416 | 1.75 | 533.46 | C | $^1$H NMR (400 MHz, DMSO-$d_6$) δ 13.93 (s, 1H), 8.54-8.46 (m, 1H), 7.88-7.79 (m, 2H), 7.51-7.43 (m, 2H), 4.47-4.06 (m, 2H), 3.92-3.64 (m, 4H), 2.41-2.27 (m, 6H), 1.61-1.40 (m, 15H). | 3 |
| I-417 | 3.73 | 504.1 | A | $^1$H NMR (400 MHz, Chloroform-d) δ 9.99 (s, 1H), 8.41 (s, 1H), 7.98 (s, 2H), 7.82-7.76 (m, 1H), 7.72 (ddd, J = 7.7, 4.8, 2.4 Hz, 1H), 7.31-7.26 (m, 1H), 7.14 (t, J = 8.9 Hz, 1H), 4.54-4.35 (m, 2H), 4.18-3.78 (m, 2H), 2.46-2.25 (m, 3H), 1.94 (s, 6H), 1.63 (s, 9H). | 12 |
| I-418 | 3.4 | 504.1 | A | $^1$H NMR (400 MHz, Methanol-$d_4$) δ 8.79 (d, J = 1.6 Hz, 1H), 8.46 (s, 1H), 8.07-7.91 (m, 1H), 7.88 (ddd, J = 8.6, 4.8, 2.3 Hz, 1H), 7.61 (d, J = 1.6 Hz, 1H), 7.49 (s, 1H), 7.19 (dd, J = 9.4, 8.6 Hz, 1H), 4.54-4.37 (m, 2H), 4.26-3.94 (m, 2H), 2.37 (d, J = 1.9 Hz, 3H), 1.94 (s, 6H), 1.64 (s, 9H). | 12 |
| I-419 | 1.89 | 458.61 | C | $^1$H NMR (400 MHz, DMSO-$d_6$) δ 8.58 (s, 1H), 8.17 (dd, J = 10.7, 2.1 Hz, 1H), 8.13-8.07 (m, 1H), | 1 |

TABLE 2-continued

| Compound analytical data | | | | | |
|---|---|---|---|---|---|
| Compound Number | LCMS Retention Time | M + 1 | LCMS Method | NMR | General Procedure |
| | | | | 7.98 (ddd, J = 8.5, 2.1, 0.8 Hz, 1H), 7.79 (dd, J = 8.5, 7.7 Hz, 1H), 7.54 (s, 1H), 4.00-3.92 (m, 2H), 3.43-3.37 (m, 2H), 1.70 (s, 6H1 1.58 (s, 9H). | |
| I-420 | 3.27 | 522.12 | A | $^1$H NMR (400 MHz, DMSO-$d_6$) ä 12.89 (s, 1H), 8.66-8.59 (m, 1H), 8.20-8.09 (m, 2H), 7.71-7.64 (m, 1H), 7.47-7.35 (m, 2H), 6.42-6.33 (m, 1H), 4.26 (s, 1H), 4.23-4.15 (m, 1H), 4.09 (dd, J = 10.7, 5.5 Hz, 2H), 3.78 (s, 1H), 3.70-3.60 (m, 1H), 2.31-2.19 (m, 3H), 2.05-1.84 (m, 6H), 1.51 (d, J = 27.5 Hz, 6H). | 3 |
| I-421 | 1.88 | 539.48 | C | $^1$H NMR (400 MHz, DMSO-$d_6$) δ 8.50 (d, J = 6.1 Hz, 1H), 8.14-8.04 (m, 2H), 7.65-7.56 (m, 2H), 7.47 (d, J = 4.2 Hz, 1H), 4.95 (d, J = 19.4 Hz, 1H), 4.19-4.09 (m, 2H), 3.68-3.42 (m, 4H), 2.91-2.73 (m, 1H), 2.21-2.11 (m, 2H), 2.13-2.00 (m, 2H), 1.56 (d, J = 4.4 Hz, 9H), 1.47 (d, J = 15.4 Hz, 6H), 1.25 (d, J = 10.9 Hz, 3H). | 3 |
| I-422 | 3.02 | 514.46 | A | $^1$H NMR (400 MHz, DMSO-$d_6$) δ 12.47-12.03 (m, 1H), 8.55-8.43 (m, 1H), 8.01-7.93 (m, 2H), 7.57-7.43 (m, 1H), 7.38 (d, J = 8.0 Hz, 2H), 4.68-3.53 (m, 6H), 2.40 (s, 3H), 2.35-2.24 (m, 3H), 1.67-1.45 (m, 15H). | 3 |
| I-423 | 3.13 | 568.08 | A | $^1$H NMR (400 MHz, DMSO-$d_6$) δ 8.64-8.57 (m, 1H), 8.35-8.27 (m, 2H), 7.99-7.91 (m, 2H), 7.90-7.78 (m, 1H), 7.61-7.52 (m, 1H), 4.50-3.58 (m, 6H), 2.47 (s, 3H), 1.57 (d, J = 29.9 Hz, 15H). | 3 |
| I-424 | 1.84 | 518.72 | C | $^1$H NMR (400 MHz, DMSO-$d_6$) δ 13.22 (s, 1H), 8.57-8.48 (m, 1H), 7.92-7.79 (m, 3H), 7.54-7.43 (m, 2H), 6.68-6.59 (m, 1H), 4.32-4.08 (m, 4H), 3.86-3.77 (m, 1H), 3.75-3.65 (m, 1H), 2.36-2.30 (m, 3H), 1.65-1.52 (m, 12H1 1.52-1.46 (m, 3H) | 3 |
| I-425 | 2.01 | 529.78 | C | $^1$H NMR (400 MHz, DMSO-$d_6$) δ 8.65-8.59 (m, 1H), 8.55-8.49 (m, 1H), 7.99-7.91 (m, 1H), 7.91-7.81 (m, 2H), 7.67-7.61 (m, 1H), 7.54-7.44 (m, 3H), 4.33-4.26 (m, 1H), 4.08 (t, J = 5.6 Hz, 1H), 3.81 (s, 1H), 3.79-3.72 (m, 2H), 3.70 (s, 1H), 2.35-2.29 (m, 3H), 1.68-1.38 (m, 15H). | 3 |
| I-426 | 1.88 | 530.9 | C | $^1$H NMR (400 MHz, DMSO-$d_6$) δ 8.93 (d, J = 5.0 Hz, 2H), 8.52 (d, J = 12.7 Hz, 1H), 7.91-7.81 (m, 2H), 7.63 (q, J = 4.9 Hz, 1H), 7.53-7.44 (m, 2H), 4.33-4.26 (m, 1H), 4.11-4.04 (m, 1H), 3.82 (s, 1H), 3.75 (dd, J = 6.9, 4.6 Hz, 1H), 3.50 (t, J = 5.6 Hz, 1H), 3.39 (s, 1H), 2.36-2.28 (m, 3H), 1.67-1.38 (m, 15H). | 3 |
| I-427 | 1.89 | 532.86 | C | $^1$H NMR (400 MHz, DMSO-$d_6$) δ 12.88 (s, 1H), 8.56-8.48 (m, 1H), 7.94-7.80 (m, 2H), 7.54-7.43 (m, 2H), 6.41-6.33 (m, 1H), 4.31-4.23 (m, 2H), 4.23-4.06 (m, 2H), 3.78 (s, 1H), 3.72-3.64 (m, 1H), 2.37-2.30 (m, 3H), 2.30-2.20 (m, 3H), 1.65-1.45 (m, 15H). | 3 |

TABLE 2-continued

| Compound analytical data | | | | | |
|---|---|---|---|---|---|
| Compound Number | LCMS Retention Time | M + 1 | LCMS Method | NMR | General Procedure |
| I-428 | 3.26 | 448.06 | A | $^1$H NMR (400 MHz, Chloroform-d) δ 8.27 (s, 1H), 6.74 (s, 1H), 5.95 (s, 1H), 4.33-4.07 (m, 2H), 3.75-3.54 (m, 2H), 2.82 (m, 1H), 2.25 (m, 2H), 1.87 (m, 12H), 1.53 (s, 9H). | 1 |
| I-429 | 1.68 | 514.65 | C | $^1$H NMR (400 MHz, Methanol-$d_4$) δ 8.42 (s, 1H), 8.22 (s, 2H), 7.14 (s, 1H), 4.33 (m, 2H), 4.10-3.84 (m, 2H), 3.00 (m, 1H), 2.30-1.85 (m, 14H), 1.58 (s, 9H). | 12 |
| I-430 | 1.5 | 514.01 | C | $^1$H NMR (400 MHz, Methanol-$d_4$) δ 8.78 (d, J = 1.5 Hz, 1H), 8.38 (s, 1H), 7.59 (d, J = 1.6 Hz, 1H), 7.06 (s, 1H), 4.43 (m, 2H), 4.22-3.97 (m, 2H), 2.97 (m, 1H), 1.92 (m, 14H), 1.57 (s, 9H). | 12 |
| I-431 | 1.54 | 532.16 | C | $^1$H NMR (400 MHz, DMSO-$d_6$) δ 8.54 (s, 1H), 7.91-7.83 (m, 2H), 7.69-7.60 (m, 1H), 7.53-7.45 (m, 2H), 4.50-4.21 (m, 3H), 4.14-3.99 (m, 1H), 3.89-3.61 (m, 2H), 2.44-2.27 (m, 6H), 1.68-1.44 (m, 15H). | 3 |
| I-432 | 2 | 534.77 | C | $^1$H NMR (400 MHz, DMSO-$d_6$) δ 8.56-8.53 (m, 1H), 7.91-7.83 (m, 2H), 7.53-7.46 (m, 2H), 4.37-4.26 (m, 2H), 4.20-4.15 (m, 2H), 3.85 (s, 1H), 3.79-3.72 (m, 1H), 2.63-2.56 (m, 3H), 2.35-2.30 (m, 3H), 1.64-1.51 (m, 15H). | 3 |
| I-433 | 4.41 | 519.16 | A | $^1$H NMR (400 MHz, DMSO-$d_6$) δ 8.56-8.50 (m, 1H), 8.20-8.09 (m, 2H), 7.48 (d, J = 9.4 Hz, 1H), 7.45-7.34 (m, 2H), 6.56-6.46 (m, 1H), 4.34-4.26 (m, 1H), 4.21-3.84 (m, 2H), 3.85-3.78 (m, 2H), 3.77-3.68 (m, 1H), 2.49-2.42 (m, 3H), 1.66-1.45 (m, 15H). | 3 |
| I-434 | 1.9 | 535.42 | C | $^1$H NMR (400 MHz, DMSO-$d_6$) δ 12.95-12.83 (m, 1H), 8.57-8.50 (m, 1H), 8.18-8.06 (m, 2H), 7.70-7.58 (m, 2H), 7.54-7.46 (m, 1H), 6.42-6.32 (m, 1H), 4.32-4.22 (m, 2H), 4.21-4.06 (m, 2H), 3.83-3.76 (m, 1H), 3.68 (t, J = 5.7 Hz, 1H), 2.31-2.18 (m, 3H), 1.67-1.44 (m, 15H). | 3 |
| I-435 | 1.85 | 521.38 | C | $^1$H NMR (400 MHz, DMSO-$d_6$) δ 13.22 (s, 1H), 8.59-8.49 (m, 1H), 8.18-8.05 (m, 2H), 7.87-7.78 (m, 1H), 7.68-7.59 (m, 2H), 7.55-7.44 (m, 1H), 6.68-6.60 (m, 1H), 4.33-4.08 (m, 4H), 3.81 (s, 1H), 3.75-3.67 (m, 1H), 1.67-1.44 (m, 15H). | 3 |
| I-436 | 1.76 | 536.45 | C | $^1$H NMR (400 MHz, DMSO-$d_6$) δ 8.56-8.52 (m, 1H), 8.16-8.09 (m, 2H), 7.67-7.61 (m, 2H), 7.52-7.47 (m, 1H), 4.29 (t, J = 5.7 Hz, 1H), 4.23-3.88 (m, 3H), 3.80 (s, 1H), 3.76-3.67 (m, 1H), 2.42-2.34 (m, 3H), 1.65-1.45 (m, 15H). | 3 |
| I-437 | 3.29 | 542.84 | A | $^1$H NMR (400 MHz, Methanol-$d_4$) δ 8.37 (s, 1H), 8.34 (s, 0H), 7.15 (s, 1H), 7.10 (s, 0H), 6.47 (s, 0H), 6.43 (d, J = 0.9 Hz, 1H), 4.46-4.30 (m, 1H), 4.22 (d, J = 11.4 Hz, 2H), 4.13 (t, J = 5.5 Hz, 1H), 3.88 (s, 1H), 3.81-3.68 (m, 1H), 3.00 (d, J = 10.1 Hz, 1H), 2.32 (dd, J = 5.0, 0.8 Hz, 3H), 2.24-1.87 (m, 8H), 1.65 (s, 2H), 1.56 (d, J = 5.2 Hz, 9H), 1.52 (s, 4H). | 3 |

TABLE 2-continued

| Compound Number | LCMS Retention Time | M + 1 | LCMS Method | NMR | General Procedure |
|---|---|---|---|---|---|
| Compound analytical data | | | | | |
| I-438 | 1.85 | 458.38 | C | $^1$H NMR (400 MHz, DMSO-$d_6$) δ 8.59 (s, 1H), 8.33 (dd, J = 7.1, 2.3 Hz, 1H), 8.16-8.06 (m, 2H), 7.63 (t, J = 8.9 Hz, 1H), 7.54 (s, 1H), 4.00-3.93 (m, 2H), 3.43-3.36 (m, 2H), 1.70 (s, 6H), 1.59 (s, 9H). | 1 |
| I-439 | 1.74 | 438.78 | C | $^1$H NMR (400 MHz, DMSO-$d_6$) δ 8.55 (s, 1H), 8.13-8.06 (m, 1H), 7.57 (dd, J = 8.6, 6.0 Hz, 1H), 7.30-7.24 (m, 1H), 7.23-7.16 (m, 1H), 7.13 (s, 1H), 4.01-3.94 (m, 2H), 3.43-3.36 (m, 2H), 2.37 (s, 3H), 1.70 (s, 6H), 1.55 (s, 9H). | 1 |
| I-440 | 4.88 | 438.56 | D | $^1$H NMR (400 MHz, DMSO-d6) δ 8.53 (d, J = 1.2 Hz, 1H), 8.02 (dd, J = 7.4, 2.3 Hz, 1H), 7.93 (ddd, J = 7.9, 5.0, 2.3 Hz, 1H), 7.64 (s, 1H), 7.30 (t, J = 9.1 Hz, 1H), 3.98 (t, J = 4.8 Hz, 2H), 3.60-3.41 (m, 4H), 2.90 (d, J = 1.0 Hz, 3H), 2.32 (d, J = 1.9 Hz, 3H), 1.68 (d, J = 0.9 Hz, 6H), 1.42 (d, J = 6.9 Hz, 6H). | 10 |
| I-441 | 1.6 | 535.47 | C | $^1$H NMR (400 MHz, DMSO-$d_6$) δ 12.45-12.07 (m, 1H), 8.63-8.48 (m, 1H), 8.19-8.05 (m, 2H), 7.71-7.60 (m, 2H), 7.58-7.26 (m, 2H), 4.65-3.60 (m, 6H), 2.37-2.21 (m, 3H), 1.67-1.44 (m, 15H). | 3 |
| I-442 | 4.50 | 500.10 | A | $^1$H NMR (400 MHz, DMSO-$d_6$) δ 8.64 (s, 1H), 8.07-8.00 (m, 1H), 7.99-7.90 (m, 1H), 7.67 (s, 1H), 7.44-7.37 (m, 2H), 7.37-7.27 (m, 4H), 5.40 (s, 2H), 4.58 (s, 2H), 3.44-3.24 (m, 1H), 2.38-2.30 (m, 3H), 1.64 (s, 6H), 1.37 (d, J = 6.9 Hz, 6H). | 10 |
| I-443 | 1.99 | 536.17 | C | $^1$H NMR (400 MHz, DMSO-$d_6$) δ 8.57-8.54 (m, 1H), 8.15-8.08 (m, 2H), 7.67-7.61 (m, 2H), 7.53-7.48 (m, 1H), 4.37-4.25 (m, 2H), 4.21-4.14 (m, 2H), 3.85 (s, 1H), 3.79-3.71 (m, 1H), 2.62-2.57 (m, 3H), 1.65-1.51 (m, 15H). | 3 |
| I-444 | 1.99 | 531.13 | C | $^1$H NMR (400 MHz, DMSO-$d_6$) δ 8.65-8.59 (m, 1H), 8.56-8.50 (m, 1H), 8.16-8.07 (m, 2H), 8.00-7.91 (m, 1H), 7.67-7.60 (m, 3H), 7.55-7.44 (m, 2H), 4.34-4.26 (m, 1H), 4.09 (t, J = 5.5 Hz, 1H), 3.82 (s, 1H), 3.79-3.72 (m, 2H), 3.70 (s, 1H), 1.66-1.40 (m, 15H). | 3 |
| I-445 | 1.87 | 532.16 | C | $^1$H NMR (400 MHz, DMSO-$d_6$) δ 8.95-8.91 (m, 2H), 8.57-8.51 (m, 1H), 8.15-8.07 (m, 2H), 7.68-7.60 (m, 3H), 7.53-7.44 (m, 1H), 4.33-4.25 (m, 1H), 4.08 (t, J = 5.6 Hz, 1H), 3.82 (s, 1H), 3.79-3.72 (m, 1H), 3.50 (t, J = 5.4 Hz, 1H), 3.39 (s, 1H), 1.68-1.38 (m, 15H). | 3 |
| I-446 | 2.83 | 426.09 | A | $^1$H NMR (400 MHz, DMSO-$d_6$) δ 8.13-7.95 (m, 3H), 7.83 (s, 1H), 7.44-7.21 (m, 2H), 4.06 (m, 3.84 (m, 1H), 3.28-3.20 (m, 2H), 3.14 (m, 2H), 2.97 (m, 1H), 1.62 (s, 3H), 1.61 (s, 3H), 0.94 (s, 9H). | 13 |
| I-447 | 2.91 | 426.04 | A | $^1$H NMR (400 MHz, Methanol-$d_4$) δ 7.88 (ddd, J = 7.4, 2.4, 1.0 Hz, 1H), 7.84-7.79 (m, 1H), 7.75 (s, 0H), 7.20-7.05 (m, 1H), 4.06 (ddd, J = 13.7, 6.1, 3.4 Hz, 1H), 3.96 (ddd, J = 13.7, 6.8, 3.4 Hz, 1H), 3.46 (qdd, J = 12.4, 6.4, 3.4 Hz, 2H), 3.16-3.10 (m, 3H), 2.33 (d, | 13 |

TABLE 2-continued

| Compound analytical data | | | | | |
|---|---|---|---|---|---|
| Compound Number | LCMS Retention Time | M + 1 | LCMS Method | NMR | General Procedure |
| | | | | J = 2.0 Hz, 3H), 2.15 (pd, J = 6.7, 3.9 Hz, 1H), 1.78 (d, J = 4.1 Hz, 6H), 0.96 (dd, J = 9.2, 6.8 Hz, 6H). | |
| I-448 | 3.09 | 543.17 | A | $^1$H NMR (400 MHz, Methanol-$d_4$) δ 8.26 (d, J = 4.3 Hz, 1H), 6.98 (d, J = 9.1 Hz, 1H), 4.44 (dd, J = 7.0, 4.6 Hz, 1H), 4.31 (t, J = 5.7 Hz, 1H), 4.17 (d, J = 21.2 Hz, 2H), 3.90 (s, 1H), 3.86-3.71 (m, 1H), 2.96 (s, 1H), 2.47 (d, J = 6.2 Hz, 3H), 2.22-1.85 (m, 9H), 1.65 (s, 2H), 1.57 (s, 9H), 1.51 (s, 4H). | 3 |
| I-449 | 3.51 | 496.46 | A | $^1$H NMR (400 MHz, DMSO-$d_6$) δ 8.56 (s, 1H), 8.09-8.03 (m, 1H), 8.00-7.93 (m, 1H), 7.68 (d, J = 0.7 Hz, 1H), 7.38-7.29 (m, 1H), 4.58 (s, 1H), 4.06-3.97 (m, 2H), 3.74-3.66 (m, 2H), 3.55 (p, J = 6.9 Hz, 1H), 3.38 (s, 2H), 2.39-2.34 (m, 3H), 1.74 (s, 6H), 1.44 (d, J = 6.9 Hz, 6H), 1.09 (s, 6H). | 10 |
| I-450 | 1.92 | 552.46 | C | $^1$H NMR (400 MHz, DMSO-$d_6$) δ 12.91-12.85 (m, 1H), 8.58-8.50 (m, 1H), 8.20-8.14 (m, 1H), 8.03-7.95 (m, 1H), 7.85-7.74 (m, 1H), 7.57-7.50 (m, 1H), 6.41-6.33 (m, 1H), 4.33-4.09 (m, 4H), 3.91-3.63 (m, 2H), 2.31-2.23 (m, 3H), 1.65-1.44 (m, 15H). | 3 |
| I-451 | 1.78 | 553.44 | C | $^1$H NMR (400 MHz, DMSO-$d_6$) δ 13.97 (s, 1H), 8.62-8.49 (m, 1H), 8.22-8.10 (m, 1H), 8.01-7.93 (m, 1H), 7.83-7.74 (m, 1H), 7.57-7.47 (m, 1H), 4.66-4.08 (m, 3H), 3.99-3.63 (m, 3H), 2.45-2.28 (m, 3H), 1.71-1.40 (m, 15H). | 3 |
| I-452 | 3.35 | 546.25 | A | $^1$H NMR (400 MHz, Methanol-$d_4$) δ 8.40 (d, J = 10.2 Hz, 1H), 7.21 (d, J = 18.2 Hz, 1H), 4.20 (t, J = 5.7 Hz, 2H), 3.82-3.68 (m, 2H), 3.62 (d, J = 9.2 Hz, 2H), 3.08-2.89 (m, 2H), 2.35-1.88 (m, 12H), 1.64-1.53 (m, 15H), 1.38 (d, J = 10.2 Hz, 3H). | 3 |
| I-453 | 1.58 | 552.46 | C | $^1$H NMR (400 MHz, DMSO-$d_6$) δ 8.59 (s, 1H), 8.21-8.16 (m, 1H), 8.10-8.02 (m, 1H), 8.01-7.96 (m, 1H), 7.84-7.78 (m, 1H), 7.55 (s, 1H), 4.38-4.23 (m, 1H), 4.10-3.68 (m, 5H), 2.55 (s, 3H), 1.64-1.49 (m, 15H). | 3 |
| I-454 | 1.87 | 538.69 | C | $^1$H NMR (400 MHz, DMSO-$d_6$) δ 13.23 (s, 1H), 8.59-8.52 (m, 1H), 8.22-8.12 (m, 1H), 8.03-7.95 (m, 1H), 7.86-7.76 (m, 2H), 7.57-7.50 (m, 1H), 6.68-6.61 (m, 1H), 4.31-4.23 (m, 2H), 4.23-4.07 (m, 2H), 3.85-3.79 (m, 1H), 3.74-3.67 (m, 1H), 1.65-1.46 (m, 15H). | 3 |
| I-455 | 2.02 | 549.1 | C | $^1$H NMR (400 MHz, DMSO-$d_6$) δ 8.65-8.59 (m, 1H), 8.57-8.51 (m, 1H), 8.20-8.12 (m, 1H), 8.02-7.92 (m, 2H), 7.84-7.75 (m, 1H), 7.68-7.62 (m, 1H), 7.56-7.47 (m, 2H), 4.33-4.26 (m, 1H), 4.08 (t, J = 5.7 Hz, 1H), 3.82 (s, 1H), 3.79-3.72 (m, 2H), 3.70 (s, 1H), 1.66-1.39 (m, 15H). | 3 |
| I-456 | 1.9 | 550.73 | C | $^1$H NMR (400 MHz, DMSO-$d_6$) δ 8.95-8.91 (m, 2H), 8.58-8.52 (m, 1H), 8.21-8.12 (m, 1H), 8.02-7.94 (m, 1H), 7.84-7.75 (m, 1H), 7.67-7.60 (m, 1H), 7.57- | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 7.48 (m, 1H), 4.28 (t, J = 5.8 Hz, 1H), 4.07 (t, J = 5.6 Hz, 1H), 3.82 (s, 1H), 3.79-3.72 (m, 1H), 3.50 (t, J = 5.6 Hz, 1H), 3.40 (s, 1H), 1.66-1.38 (m, 15H). | |
| I-457 | 2.02 | 554.42 | C | $^{1}$H NMR (400 MHz, DMSO-$d_6$) δ 8.59-8.55 (m, 1H), 8.20-8.13 (m, 1H), 8.02-7.96 (m, 1H), 7.83-7.77 (m, 1H), 7.56-7.52 (m, 1H), 4.30 (s, 2H), 4.22-4.14 (m, 2H), 3.85 (s, 1H), 3.79-3.71 (m, 1H), 2.62-2.57 (m, 3H), 1.66-1.48 (m, 15H). | 3 |
| I-458 | 4.43 | 550.15 | A | $^{1}$H NMR (400 MHz, DMSO-$d_6$) δ 8.66-8.58 (m, 1H), 8.54 (d, J = 13.5 Hz, 1H), 8.32 (ddd, J = 11.8, 7.1, 2.3 Hz, 1H), 8.17-8.06 (m, 1H), 7.95 (s, 1H), 7.68-7.57 (m, 2H), 7.56-7.46 (m, 2H), 4.33-4.25 (m, 1H), 4.12-4.04 (m, 1H), 3.82 (s, 1H), 3.79-3.72 (m, 2H), 3.70 (s, 1H), 1.66-1.36 (m, 15H). | 3 |
| I-459 | 4.09 | 539.13 | A | $^{1}$H NMR (400 MHz, DMSO-$d_6$) δ 13.22 (s, 1H), 8.59-8.52 (m, 1H), 8.37-8.29 (m, 1H), 8.17-8.08 (m, 1H), 7.88-7.79 (m, 1H), 7.68-7.58 (m, 1H), 7.57-7.47 (m, 1H), 6.68-6.60 (m, 1H), 4.34-4.07 (m, 4H), 3.81 (s, 1H), 3.75-3.65 (m, 1H), 1.64-1.45 (m, 15H). | 3 |
| I-460 | 4.16 | 557.14 | A | $^{1}$H NMR (400 MHz, DMSO-$d_6$) δ 8.54 (d, J = 6.0 Hz, 1H), 8.33 (dt, J = 7.1, 2.3 Hz, 1H), 8.16-8.08 (m, 1H), 7.67-7.58 (m, 1H), 7.53 (d, J = 4.2 Hz, 1H), 4.99 (d, J = 19.6 Hz, 1H), 4.19-4.10 (m, 2H), 3.69-3.60 (m, 2H), 3.54 (s, 1H), 3.53-3.46 (m, 1H), 2.93-2.76 (m, 1H), 2.23-2.04 (m, 4H), 1.63-1.56 (m, 9H), 1.50 (d, J = 15.4 Hz, 6H), 1.31-1.25 (m, 3H). | 3 |
| I-461 | 3.6 | 544.2 | A | $^{1}$H NMR (400 MHz, Methanol-$d_4$) δ 8.27 (d, J = 2.5 Hz, 1H), 6.99 (d, J = 4.9 Hz, 1H), 4.58-4.31 (m, 4H), 3.93 (s, 1H), 3.87-3.78 (m, 1H), 3.04-2.87 (m, 1H), 2.61 (d, J = 3.1 Hz, 3H), 2.20-1.83 (m, 8H), 1.65 (d, J = 8.3 Hz, 6H), 1.56 (d, J = 12.1 Hz, 9H). | 3 |
| I-462 | 3.71 | 450.07 | A | $^{1}$H NMR (400 MHz, DMSO-$d_6$) δ 8.57 (s, 1H), 8.18-8.10 (m, 2H), 8.08-8.02 (m, 1H), 7.49 (s, 1H), 7.46-7.35 (m, 2H), 4.03-3.95 (m, 2H), 3.43-3.34 (m, 2H), 2.35-2.24 (m, 2H), 2.19-1.99 (m, 4H), 1.86-1.70 (m, 2H), 1.58 (s, 9H). | 1 |
| I-463 | 3.84 | 572.1 | A | $^{1}$H NMR (400 MHz, DMSO-$d_6$) δ 8.58 (d, J = 6.1 Hz, 1H), 8.33-8.28 (m, 2H), 7.97-7.91 (m, 2H), 7.56 (d, J = 4.2 Hz, 1H), 4.99 (d, J = 19.9 Hz, 1H), 4.20-4.09 (m, 2H), 3.70-3.60 (m, 2H), 3.55 (s, 1H), 3.53-3.46 (m, 1H), 2.92-2.78 (m, 1H), 2.23-2.04 (m, 4H), 1.61 (d, J = 4.4 Hz, 9H), 1.50 (d, J = 15.4 Hz, 6H), 1.28 (d, J = 10.6 Hz, 3H). | 3 |
| I-464 | 3.8 | 550.73 | A | $^{1}$H NMR (400 MHz, DMSO-$d_6$) δ 8.93 (d, J = 5.0 Hz, 2H), 8.55 (d, J = 12.7 Hz, 1H), 8.32 (ddd, J = 12.4, 7.1, 2.3 Hz, 1H), 8.17-8.06 (m, 1H), 7.68-7.45 (m, 3H), 4.33-4.25 (m, 1H), 4.11-4.03 (m, 1H), 3.82 (s, 1H), 3.78-3.71 (m, | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 1H), 3.54-3.47 (m, 1H), 3.40 (s, 1H), 1.66-1.56 (m, 9H), 1.48-1.40 (m, 6H). | |
| I-465 | 4.4 | 555.14 | A | $^1$H NMR (400 MHz, DMSO-$d_6$) δ 8.57 (d, J = 5.1 Hz, 1H), 8.36-8.30 (m, 1H), 8.17-8.09 (m, 1H), 7.63 (td, J = 8.9, 2.1 Hz, 1H), 7.53 (d, J = 5.1 Hz, 1H), 4.37-4.25 (m, 2H), 4.20-4.13 (m, 2H), 3.85 (s, 1H), 3.80-3.72 (m, 1H), 2.59 (d, J = 4.5 Hz, 3H), 1.67-1.48 (m, 15H). | 3 |
| I-466 | 4.18 | 553.13 | A | $^1$H NMR (400 MHz, DMSO-$d_6$) δ 12.90 (s, 1H), 8.57-8.51 (m, 1H), 8.36-8.28 (m, 1H), 8.16-8.07 (m, 1H), 7.66-7.57 (m, 1H), 7.55-7.49 (m, 1H), 6.41-6.33 (m, 1H), 4.32-4.22 (m, 2H), 4.21-4.05 (m, 2H), 3.78 (s, 1H), 3.72-3.63 (m, 1H), 2.30-2.18 (m, 3H), 1.68-1.43 (m, 15H). | 3 |
| I-467 | 3.07 | 553.18 | A | $^1$H NMR (400 MHz, DMSO-$d_6$) δ 12.45-12.09 (m, 1H), 8.58-8.51 (m, 1H), 8.33 (dd, J = 7.1, 2.3 Hz, 1H), 8.18-8.07 (m, 1H), 7.62 (t, J = 8.9 Hz, 1H), 7.57-7.24 (m, 2H), 4.56 (s, 1H), 4.34-4.08 (m, 3H), 4.04-3.56 (m, 2H), 2.36-2.23 (m, 3H), 1.70-1.43 (m, 15H). | 3 |
| I-468 | 3.88 | 554.16 | A | $^1$H NMR (400 MHz, DMSO-$d_6$) δ 8.55 (d, J = 7.1 Hz, 1H), 8.37-8.26 (m, 1H), 8.17-8.06 (m, 1H), 7.63 (td, J = 8.9, 2.9 Hz, 1H), 7.53 (d, J = 8.8 Hz, 1H), 4.33-4.24 (m, 1H), 4.21-3.89 (m, 3H), 3.80 (s, 1H), 3.77-3.66 (m, 1H), 2.38 (d, J = 8.4 Hz, 3H), 1.67-1.42 (m, 15H). | 3 |
| I-469 | 3.84 | 556.47 | A | $^1$H NMR (400 MHz, DMSO-$d_6$) δ 8.57-8.53 (m, 1H), 8.17 (dt, J = 10.4, 2.1 Hz, 1H), 8.02-7.96 (m, 1H), 7.84-7.77 (m, 1H), 7.56-7.52 (m, 1H), 4.98 (d, J = 19.7 Hz, 1H), 4.22-4.07 (m, 2H), 3.71-3.45 (m, 4H), 2.93-2.75 (m, 1H), 2.24-2.04 (m, 4H), 1.64-1.56 (m, 9H), 1.55-1.46 (m, 6H), 1.32-1.22 (m, 3H). | 3 |
| I-470 | 3.2 | 454.04 | A | $^1$H NMR (400 MHz, DMSO-$d_6$) δ 8.57 (s, 1H), 8.13-8.02 (m, 1H), 8.02-7.91 (m, 1H), 7.68 (d, J = 0.7 Hz, 1H), 7.41-7.28 (m, 1H), 5.99 (t, J = 7.2 Hz, 1H), 4.77 (d, J = 7.2 Hz, 2H), 4.05-3.91 (m, 2H), 3.68-3.45 (m, 3H), 2.38-2.34 (m, 3H), 1.72 (s, 6H), 1.45 (d, J = 6.9 Hz, 6H). | 10 |
| I-471 | 3.66 | 490.13 | A | $^1$H NMR (400 MHz, Methanol-$d_4$) δ 8.43 (s, 1H), 8.17-7.98 (m, 2H), 7.60 (d, J = 2.4 Hz, 1H), 7.48 (s, 1H), 7.34-7.18 (m, 2H), 6.69 (s, 1H), 4.49-4.35 (m, 2H), 4.18 (dd, J = 5.9, 3.8 Hz, 2H), 1.91 (s, 6H), 1.64 (s, 9H). | 12 |
| I-472 | 1.73 | 442.65 | C | $^1$H NMR (400 MHz, DMSO-$d_6$) δ 8.60 (s, 1H), 8.13-8.07 (m, 1H), 7.91 (td, J = 8.8, 6.6 Hz, 1H), 7.51 (ddd, J = 11.6, 9.3, 2.5 Hz, 1H), 7.35-7.27 (m, 2H), 3.99-3.92 (m, 2H), 3.43-3.36 (m, 2H), 1.70 (s, 6H), 1.56 (s, 9H). | 1 |
| I-473 | 1.69 | 424.74 | C | $^1$H NMR (400 MHz, DMSO-$d_6$) δ 8.60 (s, 1H), 8.12-8.07 (m, 1H), 7.83 (td, J = 7.8, 2.0 Hz, 1H), | 1 |

TABLE 2-continued

Compound analytical data

| Compound Number | LCMS Retention Time | M + 1 | LCMS Method | NMR | General Procedure |
|---|---|---|---|---|---|
| | | | | 7.66-7.57 (m, 1H), 7.47-7.38 (m, 2H), 7.35 (d, J = 2.1 Hz, 1H), 3.99-3.92 (m, 2H), 3.44-3.36 (m, 2H), 1.71 (s, 6H), 1.56 (s, 9H). | |
| I-474 | 3.53 | 514.1 | A | | 12 |
| I-475 | 1.46 | 505.42 | C | $^1$H NMR (400 MHz, DMSO-d6) δ 8.51 (d, J = 8.2 Hz, 1H), 8.15-8.05 (m, 2H), 7.64 (d, J = 8.4 Hz, 1H), 7.46-7.29 (m, 2H), 4.21 (t, J = 5.9 Hz, 1H), 4.17-3.86 (m, 2H), 3.77 (s, 1H), 3.72-3.61 (m, 1H), 3.62-3.44 (m, 1H), 2.39-2.25 (m, 3H), 1.53 (s, 3H), 1.48-1.32 (m, 9H). | 3 |
| I-476 | 4.89 | 450.26 | D | $^1$H NMR (400 MHz, DMSO-d6) δ 8.52 (s, 1H), 8.10-8.00 (m, 1H), 7.87 (ddd, J = 8.5, 4.9, 2.3 Hz, 1H), 7.67-7.55 (m, 2H), 7.30 (dd, J = 10.1, 8.6 Hz, 1H), 3.94-3.84 (m, 2H), 3.50 (p, J = 6.9 Hz, 1H), 3.34 (m, 2H), 2.16-2.01 (m, 1H), 1.67 (s, 6H), 1.41 (d, J = 6.9 Hz, 6H), 1.09-0.92 (m, 2H), 0.88-0.81 (m, 2H). | 6 |
| I-477 | 4.27 | 428.23 | D | $^1$H NMR (400 MHz, DMSO-d6) δ 8.57 (s, 1H), 8.10-8.01 (m, 1H), 7.86 (td, J = 8.8, 6.5 Hz, 1H), 7.48 (ddd, J = 11.6, 9.3, 2.6 Hz, 1H), 7.39 (dd, J = 2.1, 0.8 Hz, 1H), 7.35-7.22 (m, 1H), 3.95-3.80 (m, 2H), 3.56-3.41 (m, 1H), 3.37-3.31 (m, 2H), 1.67 (s, 6H), 1.38 (d, J = 6.9 Hz, 6H). | 6 |
| I-478 | 4.35 | 424.26 | D | $^1$H NMR (400 MHz, DMSO-d6) δ 8.52 (s, 1H), 8.11-8.00 (m, 1H), 7.52 (dd, J = 8.5, 6.0 Hz, 1H), 7.28-7.21 (m, 2H), 7.16 (td, J = 8.5, 2.7 Hz, 1H), 3.95-3.84 (m, 2H), 3.56-3.45 (m, 1H), 3.32 (s, 2H), 2.34 (s, 3H), 1.67 (s, 6H), 1.38 (d, J = 6.9 Hz, 6H). | 6 |
| I-479 | 4.15 | 410.22 | D | $^1$H NMR (400 MHz, DMSO-d6) δ 8.58 (s, 1H), 8.10-8.00 (m, 1H), 7.79 (td, J = 7.8, 1.8 Hz, 1H), 7.65-7.53 (m, 1H), 7.46-7.31 (m, 3H), 3.93-3.83 (m, 2H), 3.52 (p, J = 6.8 Hz, 1H), 3.36-3.30 (m, 2H), 1.68 (s, 6H), 1.38 (d, J = 6.9 Hz, 6H). | 6 |
| I-480 | 4.27 | 410.22 | D | $^1$H NMR (400 MHz, DMSO-d6) δ 8.56 (s, 1H), 8.06 (t, J = 3.2 Hz, 1H), 7.96-7.85 (m, 2H), 7.69 (s, 1H), 7.59 (td, J = 8.2, 6.3 Hz, 1H), 7.43-7.30 (m, 1H), 3.95-3.85 (m, 2H), 3.57-3.46 (m, 1H), 3.38-3.30 (m, 2H), 1.67 (s, 6H), 1.41 (d, J = 6.9 Hz, 6H). | 6 |
| I-481 | 1.31 | 629.55 | C | $^1$H NMR (400 MHz, DMSO-$d_6$) δ 8.50 (d, J = 8.1 Hz, 1H), 8.17-8.05 (m, 2H), 7.46 (d, J = 7.4 Hz, 1H), 7.38 (t, J = 8.3 Hz, 2H), 5.91 (d, J = 10.0 Hz, 2H), 4.27 (t, J = 5.7 Hz, 1H), 4.16 (t, J = 5.6 Hz, 1H), 3.96-3.86 (m, 2H), 3.80-3.64 (m, 2H), 2.30 (d, J = 14.3 Hz, 3H), 1.64-1.47 (m, 15H). | 22, 23 |
| I-482 | 1.71 | 542.84 | C | $^1$H NMR (400 MHz, DMSO-$d_6$) δ 8.52 (d, J = 6.0 Hz, 1H), 8.32 (dt, J = 7.1, 2.1 Hz, 1H), 8.15-8.08 (m, 1H), 7.72 (dd, J = 4.7, 0.7 Hz, 1H), 7.60 (td, J = 9.0, 1.4 Hz, 1H), 4.95 (d, J = 15.0 Hz, 1H), 4.13-4.02 (m, 2H), 3.64-3.48 (m, 4H), 3.46-3.40 (m, 1H), 2.90- | 3 |

TABLE 2-continued

Compound analytical data

| Compound Number | LCMS Retention Time | M + 1 | LCMS Method | NMR | General Procedure |
|---|---|---|---|---|---|
| | | | | 2.74 (m, 1H), 2.20-2.01 (m, 4H), 1.52-1.36 (m, 12H), 1.25 (d, J = 13.3 Hz, 3H). | |
| I-483 | 1.59 | 539.44 | C | $^1$H NMR (400 MHz, DMSO-$d_6$) δ 13.97 (s, 1H), 8.63-8.52 (m, 1H), 8.39-8.29 (m, 1H), 8.23-8.11 (m, 1H), 7.79-7.71 (m, 1H), 7.69-7.56 (m, 1H), 4.53-4.06 (m, 3H), 3.93-3.78 (m, 2H), 3.77-3.48 (m, 2H), 2.43-2.30 (m, 3H), 1.60-1.36 (m, 12H). | 3 |
| I-484 | 3.44 | 425.41 | A | $^1$H NMR (400 MHz, DMSO-$d_6$) δ 8.45 (s, 1H), 8.17-8.10 (m, 2H), 7.47 (s, 1H), 7.44-7.36 (m, 2H), 4.72 (d, J = 4.5 Hz, 1H), 4.12-4.01 (m, 1H), 3.84 (dt, J = 13.4, 5.1 Hz, 1H), 3.50-3.38 (m, 1H), 2.06-1.93 (m, 1H), 1.80-1.71 (m, 1H), 1.65-1.47 (m, 14H), 1.44 (s, 3H). | 18 |
| I-485 | 1.23 | 629.5 | C | $^1$H NMR (400 MHz, DMSO-$d_6$) δ 8.48 (d, J = 9.3 Hz, 1H), 8.18-8.04 (m, 2H), 7.48-7.32 (m, 3H), 5.78-5.64 (m, 2H), 4.29-4.20 (m, 1H), 4.18-4.07 (m, 1H), 3.94-3.81 (m, 2H), 3.76 (s, 1H), 3.71-3.62 (m, 2H), 2.51 (d, 3H), 1.62-1.39 (m, 15H). | 22, 23 |
| I-486 | 5.5 | 570.54 | D | $^1$H NMR (400 MHz, DMSO-d6) δ 12.16 (bs, 1H), 8.58-8.44 (m, 1H), 8.37-8.24 (m, 1H), 8.20-7.99 (m, 1H), 7.67-7.53 (m, 1H), 7.50 (s, 1H), 4.19-4.03 (m, 2H), 3.66-3.38 (m, 5H), 3.04-2.85 (m, 1H), 2.38-2.18 (m, 4H), 1.56 (d, J = 3.7 Hz, 9H), 1.49-1.36 (m, 6H). | 4 |
| I-487 | 5.85 | 598.59 | D | $^1$H NMR (400 MHz, DMSO-d6) δ 12.13 (bs, 1H), 8.51 (d, J = 8.5 Hz, 1H), 8.34-8.23 (m, 1H), 8.09 (ddd, J = 8.7, 4.6, 2.3 Hz, 1H), 7.59 (td, J = 9.0, 1.6 Hz, 1H), 7.49 (d, J = 4.1 Hz, 1H), 4.19-4.05 (m, 2H), 3.82-3.68 (m, 1H), 3.61 (d, J = 21.5 Hz, 2H), 3.47-3.38 (m, 1H), 2.14-1.88 (m, 2H), 1.69-1.33 (m, 23H). | 4 |
| I-488 | 5.67 | 598.59 | D | $^1$H NMR (400 MHz, DMSO-d6) δ 12.05 (bs, 1H), 8.51 (d, J = 8.5 Hz, 1H), 8.30 (dt, J = 7.0, 2.7 Hz, 1H), 8.16-7.96 (m, 1H), 7.59 (td, J = 9.0, 1.3 Hz, 1H), 7.50 (d, J = 5.1 Hz, 1H), 4.18-4.05 (m, 2H), 3.82-3.72 (m, 1H), 3.63 (d, J = 25.4 Hz, 2H), 3.50-3.38 (m, 1H), 2.24-2.04 (m, 1H), 1.94-1.80 (m, 2H), 1.79-1.60 (m, 2H), 1.63-1.24 (m, 20H). | 4 |
| I-489 | 5.5 | 552.34 | D | $^1$H NMR (400 MHz, DMSO-d6) δ 8.56-8.43 (m, 1H), 8.09 (dd, J = 8.6, 1.4 Hz, 2H), 7.61 (d, J = 8.4 Hz, 2H), 7.47 (d, J = 2.7 Hz, 1H), 4.17-4.06 (m, 2H), 3.67-3.40 (m, 5H), 2.97-2.85 (m, 1H), 2.29 (t, J = 9.0 Hz, 4H), 1.56 (d, J = 3.1 Hz, 9H), 1.47 (dd, J = 11.2, 1.7 Hz, 6H). | 4 |
| I-490 | 5.87 | 580.36 | D | $^1$H NMR (400 MHz, DMSO-d6) δ 12.16 (bs, 1H), 8.50 (d, J = 8.5 Hz, 1H), 8.09 (dd, J = 8.7, 2.2 Hz, 2H), 7.61 (dd, J = 8.6, 1.6 Hz, 2H), 7.47 (d, J = 4.2 Hz, 1H), 4.24-4.04 (m, 2H), 3.81-3.73 (m, 1H), 3.61 (d, J = 21.4 Hz, | 4 |

TABLE 2-continued

| Compound analytical data | | | | | |
|---|---|---|---|---|---|
| Compound Number | LCMS Retention Time | M + 1 | LCMS Method | NMR | General Procedure |
| | | | | 2H), 3.47-3.36 (m, 1H), 2.07-1.90 (m, 2H), 1.64-1.34 (m, 23H). | |
| I-491 | 5.65 | 580.62 | D | $^1$H NMR (400 MHz, DMSO-d6) δ 8.50 (d, J = 8.6 Hz, 1H), 8.09 (dd, J = 8.8, 2.5 Hz, 2H), 7.61 (dd, J = 8.6, 1.3 Hz, 2H), 7.47 (d, J = 4.9 Hz, 1H), 4.20-4.06 (m, 2H), 3.78 (t, J = 5.6 Hz, 1H), 3.68-3.55 (m, 2H), 3.45 (s, 1H), 2.21-2.10 (m, 1H), 1.94-1.81 (m, 2H), 1.80-1.60 (m, 2H), 1.59-1.25 (m, 20H). | 4 |
| I-492 | 5.07 | 536.68 | D | $^1$H NMR (400 MHz, DMSO-d6) δ 12.14 (s, 1H), 8.57-8.37 (m, 1H), 8.26-7.96 (m, 2H), 7.45 (d, J = 2.4 Hz, 1H), 7.38 (td, J = 8.8, 1.0 Hz, 2H), 4.13 (q, J = 7.6, 6.6 Hz, 2H), 3.59 (t, J = 6.2 Hz, 2H), 3.46 (d, J = 18.3 Hz, 2H), 2.95 (ddd, J = 15.0, 10.5, 7.5 Hz, 1H), 2.43-2.14 (m, 5H), 1.56 (d, J = 3.2 Hz, 9H), 1.47 (dd, J = 11.1, 1.7 Hz, 6H). | 4 |
| I-493 | 5.43 | 564.4 | D | $^1$H NMR (400 MHz, DMSO-d6) δ 12.12 (s, 1H), 8.49 (d, J = 8.4 Hz, 1H), 8.23-8.02 (m, 2H), 7.52-7.46 (m, 1H), 7.38 (td, J = 8.8, 1.7 Hz, 2H), 4.22-3.96 (m, 2H), 3.77 (t, J = 5.6 Hz, 1H), 3.61 (d, J = 21.2 Hz, 2H), 3.45 (t, J = 5.7 Hz, 1H), 2.06-1.84 (m, 2H), 1.62-1.27 (m, 23H). | 4 |
| I-494 | 5.25 | 564.4 | D | $^1$H NMR (400 MHz, DMSO-d6) δ 8.49 (d, J = 8.6 Hz, 1H), 8.15-8.03 (m, 2H), 7.46-7.41 (m, 1H), 7.38 (td, J = 8.8, 1.4 Hz, 2H), 4.19-4.06 (m, 2H), 3.78 (t, J = 5.7 Hz, 1H), 3.63 (d, J = 25.4 Hz, 2H), 3.46 (d, J = 5.8 Hz, 1H), 2.20-2.07 (m, 1H), 1.94-1.80 (m, 2H), 1.80-1.61 (m, 2H), 1.61-1.25 (m, 20H). | 4 |
| I-495 | 1.81 | 584.52 | C | $^1$H NMR (400 MHz, DMSO-$d_6$) δ 8.56-8.50 (m, 1H), 8.34-8.29 (m, 1H), 8.15-8.08 (m, 1H), 7.74-7.70 (m, 1H), 7.63-7.56 (m, 1H), 4.18-4.05 (m, 2H), 3.79-3.73 (m, 1H), 3.70-3.64 (m, 1H), 3.63-3.59 (m, 1H), 3.50-3.42 (m, 1H), 2.77-2.43 (m, 2H), 2.10-1.96 (m, 2H), 1.63-1.34 (m, 19H). | 4 |
| I-496 | 1.73 | 584.8 | C | $^1$H NMR (400 MHz, DMSO-$d_6$) δ 8.57-8.52 (m, 1H), 8.35-8.30 (m, 1H), 8.16-8.09 (m, 1H), 7.76-7.71 (m, 1H), 7.64-7.56 (m, 1H), 4.18-4.08 (m, 2H), 3.81-3.74 (m, 1H), 3.69 (s, 1H), 3.62 (s, 1H), 3.50-3.42 (m, 1H), 2.26-2.08 (m, 1H), 1.98-1.83 (m, 3H), 1.83-1.64 (m, 2H), 1.60-1.23 (m, 17H). | 4 |
| I-497 | 1.26 | 430.06 | C | $^1$H NMR (400 MHz, DMSO-$d_6$) δ 8.52 (s, 1H), 8.34 (dd, J = 7.1, 2.3 Hz, 1H), 8.18-8.11 (m, 2H), 7.73 (s, 1H), 7.63 (t, J = 9.0 Hz, 1H), 3.80-3.74 (m, 2H), 3.62-3.51 (m, 1H), 3.00-2.91 (m, 2H), 2.77 (s, 2H), 1.55-1.38 (m, 12H). | 2 |
| I-498 | 1.65 | 528.8 | C | $^1$H NMR (400 MHz, DMSO-$d_6$) δ 8.57-8.53 (m, 1H), 8.37-8.32 (m, 1H), 8.18-8.10 (m, 1H), 7.77-7.72 (m, 1H), 7.66-7.59 (m, 1H), 5.08 (d, J = 7.0 Hz, 1H), 4.18-4.05 (m, 2H), 4.03-3.90 | 3 |

TABLE 2-continued

Compound analytical data

| Compound Number | LCMS Retention Time | M + 1 | LCMS Method | NMR | General Procedure |
|---|---|---|---|---|---|
| | | | | (m, 1H), 3.66-3.50 (m, 4H), 3.50-3.42 (m, 1H), 2.84-2.64 (m, 1H), 2.44-2.30 (m, 2H), 2.04-1.90 (m, 2H), 1.56-1.40 (m, 12H). | |
| I-499 | 1.86 | 542.14 | C | $^1$H NMR (400 MHz, DMSO-$d_6$) δ 8.58-8.53 (m, 1H), 8.37-8.32 (m, 1H), 8.17-8.11 (m, 1H), 7.76-7.72 (m, 1H), 7.66-7.59 (m, 1H), 4.18-4.07 (m, 2H), 3.84-3.71 (m, 1H), 3.65-3.52 (m, 4H), 3.51-3.43 (m, 1H), 3.15-3.09 (m, 3H), 3.00-2.80 (m, 1H), 2.48-2.36 (m, 2H), 2.04-1.92 (m, 2H), 1.55-1.40 (m, 12H). | 3 |
| I-500 | 1.9 | 596.14 | C | $^1$H NMR (400 MHz, DMSO-$d_6$) δ 8.58-8.54 (m, 1H), 8.38-8.32 (m, 1H), 8.17-8.11 (m, 1H), 7.78-7.73 (m, 1H), 7.66-7.59 (m, 1H), 6.65-6.54 (m, 1H), 4.17-4.06 (m, 2H), 3.69-3.45 (m, 5H), 3.08-2.95 (m, 1H), 2.71-2.56 (m, 2H), 2.47-2.37 (m, 2H), 1.56-1.47 (m, 6H), 1.48-1.41 (m, 6H) | 3 |
| I-501 | 1.67 | 556.47 | C | $^1$H NMR (400 MHz, DMSO-$d_6$) δ 12.15-12.07 (m, 1H), 8.52 (d, J = 4.7 Hz, 1H), 8.32 (dd, J = 7.4, 2.3 Hz, 1H), 8.15-8.08 (m, 1H), 7.72 (s, 1H), 7.60 (t, J = 8.9 Hz, 1H), 4.11-4.04 (m, 3H), 3.63-3.42 (m, 3H), 3.02-2.91 (m, 2H), 2.67-2.62 (m, 1H), 2.43-2.19 (m, 4H), 1.51-1.37 (m, 12H). | 4 |
| I-502 | 1.68 | 556.47 | C | $^1$H NMR (400 MHz, DMSO-$d_6$) δ 8.60-8.52 (m, 1H), 8.40-8.30 (m, 1H), 8.20-8.09 (m, 1H), 7.77-7.70 (m, 1H), 7.68-7.58 (m, 1H), 4.19-4.07 (m, 2H), 3.67-3.44 (m, 5H), 3.05-2.93 (m, 1H), 2.70-2.66 (m, 1H), 2.37-2.26 (m, 4H), 1.56-1.38 (m, 12H). | 4 |
| I-503 | 3.82 | 496.13 | A | $^1$H NMR (400 MHz, DMSO-$d_6$) δ 8.59 (s, 1H), 8.18-8.10 (m, 2H), 7.50 (s, 1H), 7.46-7.37 (m, 2H), 4.19 (s, 2H), 4.15-4.09 (m, 2H), 3.67 (s, 3H), 3.66-3.60 (m, 2H), 1.73 (s, 6H), 1.59 (s, 9H). | 10 |
| I-504 | 1.78 | 599.5 | C | $^1$H NMR (400 MHz, DMSO-d6) δ 8.53 (d, J = 7.1 Hz, 1H), 8.44-8.37 (m, 1H), 8.16-8.06 (m, 1H), 7.55 (td, J = 8.6, 2.9 Hz, 1H), 7.49 (d, J = 8.8 Hz, 1H), 4.25 (t, J = 5.9 Hz, 2H), 4.18-3.84 (m, 2H), 3.77 (s, 1H), 3.69 (t, J = 5.8 Hz, 1H), 2.35 (d, J = 8.3 Hz, 3H), 1.64-1.39 (m, 15H). | 3 |
| I-505 | 1.64 | 528.47 | C | $^1$H NMR (400 MHz, DMSO-$d_6$) δ 8.57-8.53 (m, 1H), 8.37-8.32 (m, 1H), 8.17-8.11 (m, 1H), 7.76-7.72 (m, 1H), 7.66-7.58 (m, 1H), 5.19-4.98 (m, 1H), 4.23-4.04 (m, 3H), 3.68-3.43 (m, 5H), 3.23-3.11 (m, 1H), 2.44-2.29 (m, 2H), 2.14-2.00 (m, 2H), 1.57-1.36 (m, 12H). | 3 |
| I-506 | 3.4 | 588.3 | A | $^1$H NMR (400 MHz, Methanol-$d_4$) δ 8.25 (d, J = 4.0 Hz, 1H), 6.99 (d, J = 4.6 Hz, 1H), 4.32 (dt, J = 14.4, 5.7 Hz, 2H), 3.90 (t, J = 5.7 Hz, 1H), 3.74 (d, J = 8.5 Hz, 2H), 3.65-3.51 (m, 1H), 2.96 (s, 1H), 2.60 (d, J = 3.7 Hz, 1H), 2.28 (dt, J = 11.2, 3.6 Hz, 1H), 2.21-1.80 (m, 13H), 1.66-1.51 (m, 18H). | 4 |

TABLE 2-continued

| Compound analytical data | | | | | |
|---|---|---|---|---|---|
| Compound Number | LCMS Retention Time | M + 1 | LCMS Method | NMR | General Procedure |
| I-507 | 1.82 | 440.37 | C | $^1$H NMR (400 MHz, DMSO-$d_6$) δ 8.57 (s, 1H), 8.12-8.07 (m, 2H), 7.97-7.93 (m, 1H), 7.70 (s, 1H), 7.61 (d, J = 8.4 Hz, 1H), 3.97-3.90 (m, 2H), 3.60-3.50 (m, 1H), 3.40-3.32 (m, 2H), 2.46 (s, 3H), 1.70 (s, 6H), 1.44 (d, J = 6.9 Hz, 6H). | 1 |
| I-508 | 1.81 | 440.37 | C | $^1$H NMR (400 MHz, DMSO-$d_6$) δ 8.59 (s, 1H), 8.17 (d, J = 1.9 Hz, 1H), 8.11-8.07 (m, 1H), 8.00 (dd, J = 8.0, 1.9 Hz, 1H), 7.73 (s, 1H), 7.56 (d, J = 8.1 Hz, 1H), 3.97-3.89 (m, 2H), 3.60-3.51 (m, 1H), 3.41-3.34 (m, 2H), 2.42 (s, 3H), 1.70 (s, 6H), 1.44 (d, J = 6.9 Hz, 6H). | 1 |
| I-509 | 4.58 | 482.66 | D | $^1$H NMR (400 MHz, DMSO-d6) δ 8.49 (s, 1H), 8.26-8.20 (m, 1H), 8.11 (dd, J = 8.9, 5.4 Hz, 2H), 7.46 (s, 1H), 7.38 (t, J = 8.8 Hz, 2H), 4.17 (ddd, J = 13.2, 5.1, 3.1 Hz, 1H), 4.06 (ddd, J = 13.2, 8.3, 3.3 Hz, 1H), 3.80 (d, J = 16.6 Hz, 1H), 3.50 (s, 3H), 3.41-3.31 (m, 2H), 3.14 (d, J = 16.6 Hz, 1H), 1.68 (s, 3H), 1.55 (s, 9H). | 1 |
| I-510 | 1.99 | 425.39 | C | $^1$H NMR (400 MHz, DMSO-$d_6$) δ 8.61 (s, 1H), 8.19-8.11 (m, 2H), 7.51 (s, 1H), 7.45-7.38 (m, 2H), 4.61-4.54 (m, 2H), 4.35-4.27 (m, 2H), 1.84 (s, 6H), 1.58 (s, 9H). | 1 |
| I-511 | 1.79 | 411.67 | C | $^1$H NMR (400 MHz, DMSO-$d_6$) δ 8.62 (s, 1H), 8.21-8.13 (m, 2H), 7.70 (s, 1H), 7.45-7.38 (m, 2H), 4.57-4.51 (m, 2H), 4.32-4.25 (m, 2H), 3.62-3.50 (m, 1H), 1.84 (s, 6H), 1.44 (d, J = 6.9 Hz, 6H). | 1 |
| I-512 | 1.56 | 438.13 | C | $^1$H NMR (400 MHz, DMSO-$d_6$) δ 8.53 (d, J = 6.1 Hz, 1H), 8.21-8.09 (m, 2H), 7.70-7.65 (m, 1H), 7.46-7.35 (m, 2H), 4.24-4.16 (m, 1H), 4.15-4.07 (m, 1H), 3.70-3.51 (m, 4H), 3.51-3.44 (m, 1H), 2.03 (d, J = 16.3 Hz, 3H), 1.52 (d, J = 15.7 Hz, 6H), 1.44 (dd, J = 6.9, 1.1 Hz, 6H). | 3 |
| I-513 | 1.76 | 452.13 | C | $^1$H NMR (400 MHz, DMSO-$d_6$) δ 8.52 (d, J = 6.2 Hz, 1H), 8.18-8.09 (m, 2H), 7.51-7.46 (m, 1H), 7.45-7.36 (m, 2H), 4.28-4.12 (m, 2H), 3.72-3.66 (m, 1H), 3.61 (d, J = 8.6 Hz, 2H), 3.55-3.46 (m, 1H), 2.03 (d, J = 16.5 Hz, 3H), 1.62-1.56 (m, 9H), 1.52 (d, J = 16.4 Hz, 6H). | 3 |
| I-514 | 1.71 | 437.33 | C | $^1$H NMR (400 MHz, DMSO-$d_6$) δ 8.84 (s, 1H), 8.29 (s, 1H), 8.25-8.18 (m, 2H), 7.45-7.38 (m, 2H), 4.50 (dd, J = 5.1, 4.0 Hz, 2H), 4.18-4.12 (m, 2H), 1.81 (s, 6H). | 1 |
| I-515 | 3.27 | 560.51 | A | $^1$H NMR (400 MHz, Methanol-$d_4$) δ 8.25 (s, 1H), 6.99 (s, 1H), 4.33 (t, J = 5.8 Hz, 1H), 4.26 (t, J = 5.7 Hz, 1H), 3.78-3.42 (m, 5H), 3.16-3.04 (m, 1H), 2.99-2.86 (m, 1H), 2.52 (dddt, J = 17.9, 12.3, 9.5, 4.8 Hz, 4H), 2.24-1.86 (m, 8H), 1.65-1.51 (m, 15H). | 1 |
| I-516 | 3.28 | 560.25 | A | $^1$H NMR (400 MHz, Methanol-$d_4$) δ 8.38 (t, J = 5.1 Hz, 1H), 7.18 (s, 1H), 4.22 (s, 2H), 3.71 (d, J = 6.4 Hz, 2H), 3.61 (d, J = 5.9 Hz, 2H), 3.47-3.33 (m, 1H), 3.14 (td, J = 9.1, 3.0 Hz, 1H), 3.01 (s, 1H), | 1 |

TABLE 2-continued

| Compound analytical data | | | | | |
|---|---|---|---|---|---|
| Compound Number | LCMS Retention Time | M + 1 | LCMS Method | NMR | General Procedure |
| | | | | 2.47 (dddd, J = 14.8, 12.6, 6.3, 4.3 Hz, 4H), 2.23-1.79 (m, 8H), 1.62-1.49 (m, 15H). | |
| I-517 | 5.15 | 484.28 | D | $^1$H NMR (400 MHz, DMSO-d6) δ 8.55 (s, 1H), 8.06 (s, 1H), 8.02 (d, J = 8.6 Hz, 2H), 7.75 (d, J = 8.5 Hz, 2H), 7.47 (s, 1H), 3.98-3.87 (m, 2H), 3.40-3.32 (m, 2H), 1.67 (s, 6H), 1.55 (s, 9H). | 1 |
| I-518 | 3.72 | 482.15 | A | $^1$H NMR (400 MHz, DMSO-$d_6$) δ 8.58 (s, 1H), 8.19-8.10 (m, 2H), 7.50 (s, 1H), 7.45-7.36 (m, 2H), 4.14-4.07 (m, 2H), 4.05 (s, 2H), 3.65-3.57 (m, 2H), 1.72 (s, 6H), 1.59 (s, 9H). | 25 |
| I-519 | 4.77 | 579.38 | D | $^1$H NMR (400 MHz, DMSO-d6) δ 8.51 (d, J = 7.2 Hz, 1H), 8.01 (dd, J = 8.4, 4.6 Hz, 2H), 7.74 (dd, J = 8.6, 2.8 Hz, 2H), 7.46 (d, J = 8.8 Hz, 1H), 4.31-4.20 (m, 1H), 4.19-3.87 (m, 3H), 3.77 (s, 1H), 3.74-3.63 (m, 1H), 2.35 (d, J = 8.6 Hz, 3H), 1.65-1.36 (m, 15H). | 3 |
| I-520 | 6.1 | 638.44 | D | $^1$H NMR (400 MHz, DMSO-d6) δ 8.50 (d, J = 8.7 Hz, 1H), 8.01 (dd, J = 8.7, 2.1 Hz, 2H), 7.75 (dd, J = 8.6, 1.7 Hz, 2H), 7.46 (d, J = 4.1 Hz, 1H), 4.21-4.07 (m, 2H), 3.84-3.73 (m, 1H), 3.59 (s, 5H), 3.52-3.40 (m, 1H), 2.74-2.52 (m, 2H), 2.09-1.92 (m, 2H), 1.68-1.34 (m, 20H). | 3 |
| I-521 | 1.28 | 413.4 | C | $^1$H NMR (400 MHz, DMSO-$d_6$) δ 9.29-9.20 (m, 1H), 8.61 (s, 1H), 8.16-8.11 (m, 2H), 7.72 (s, 1H), 7.68-7.63 (m, 2H), 4.11-4.03 (m, 2H), 3.63-3.51 (m, 1H), 3.37-3.27 (m, 2H), 3.24-3.17 (m, 2H), 1.60 (s, 6H), 1.44 (d, J = 6.9 Hz, 6H). | 2 |
| I-522 | 4.23 | 557.41 | D | $^1$H NMR (400 MHz, Chloroform-d) δ 8.47 (s, 1H), 8.30-8.19 (m, 2H), 8.00 (dd, J = 8.8, 5.3 Hz, 2H), 7.58 (d, J = 2.0 Hz, 1H), 7.32-7.17 (m, 4H), 4.55 (s, 1H), 4.52-4.42 (m, 3H), 3.90 (d, J = 6.5 Hz, 2H), 2.48 (d, J = 5.8 Hz, 3H), 1.67 (d, J = 13.0 Hz, 6H). | 3 |
| I-523 | 1.62 | 462.43 | C | $^1$H NMR (400 MHz, Chloroform-d) δ 8.49 (s, 1H), 8.23 (dd, J = 8.9, 5.3 Hz, 2H), 8.00 (dd, J = 8.8, 5.2 Hz, 2H), 7.59 (s, 1H), 7.29-7.18 (m, 4H), 5.98 (s, 1H), 4.26-4.17 (m, 2H), 3.67-3.55 (m, 2H), 1.88 (s, 6H). | 1 |
| I-524 | 1.73 | 602.46 | C | $^1$H NMR (400 MHz, Chloroform-d) δ 8.46 (d, J = 9.5 Hz, 1H), 8.22 (dd, J = 7.4, 4.9 Hz, 2H), 8.06-7.95 (m, 2H), 7.57 (s, 1H), 7.34-7.16 (m, 4H), 4.39 (d, J = 23.7 Hz, 2H), 3.83-3.77 (m, 1H), 3.76-3.68 (m, 2H), 3.57 (s, 1H), 2.75-2.65 (m, 1H), 2.53 (d, J = 29.1 Hz, 1H), 2.31 (d, J = 12.7 Hz, 2H), 1.86 (d, J = 9.0 Hz, 3H), 1.74-1.58 (m, 9H). | 4 |
| I-525 | 2.93 | 491.47 | A | $^1$H NMR (400 MHz, DMSO-$d_6$) δ 13.98 (s, 1H), 8.61 (d, J = 3.8 Hz, 1H), 8.19-8.10 (m, 2H), 7.51 (d, J = 2.2 Hz, 1H), 7.42 (t, J = 8.8 Hz, 2H), 4.30 (d, J = 61.9 Hz, 3H), 3.77 (s, 5H), 2.36 (d, J = 29.8 Hz, 3H), 1.61 (s, 9H). | 3 |

TABLE 2-continued

| Compound analytical data | | | | | |
|---|---|---|---|---|---|
| Compound Number | LCMS Retention Time | M + 1 | LCMS Method | NMR | General Procedure |
| I-526 | 2.14 | 592.31 | C | $^1$H NMR (400 MHz, DMSO-d$_6$) δ 8.56-8.49 (m, 1H), 8.18-8.10 (m, 2H), 7.51-7.47 (m, 1H), 7.44-7.37 (m, 2H), 4.23-4.11 (m, 2H), 3.84-3.76 (m, 1H), 3.63 (s, 5H), 3.51-3.43 (m, 1H), 2.72-2.59 (m, 1H), 2.17-2.07 (m, 2H), 1.67-1.44 (m, 17H), 1.44-1.16 (m, 4H), 1.13-1.07 (m, 3H). | 3 |
| I-527 | 1.91 | 536.82 | C | $^1$H NMR (400 MHz, DMSO-d$_6$) δ 8.53 (s, 1H), 8.18-8.11 (m, 2H), 7.49 (s, 1H), 7.45-7.36 (m, 2H), 4.22-4.16 (m, 1H), 4.15-4.09 (m, 1H), 3.76-3.70 (m, 1H), 3.68 (s, 1H), 3.66-3.61 (m, 3H), 3.58 (s, 1H), 3.56-3.51 (m, 1H), 1.64-1.50 (m, 15H), 1.45-1.28 (m, 4H). | 3 |
| I-528 | 2.02 | 552.83 | C | $^1$H NMR (400 MHz, DMSO-d$_6$) δ 8.56-8.49 (m, 1H), 8.17-8.11 (m, 2H), 7.51-7.47 (m, 1H), 7.45-7.37 (m, 2H), 4.23 (t, J = 5.6 Hz, 1H), 4.16 (t, J = 5.8 Hz, 1H), 3.74-3.67 (m, 1H), 3.64-3.58 (m, 2H), 3.56-3.51 (m, 3H), 3.51-3.44 (m, 1H), 2.68 (s, 1H), 2.62 (s, 1H), 1.65-1.45 (m, 15H), 1.18 (s, 6H). | 3 |
| I-529 | 1.86 | 524.78 | C | $^1$H NMR (400 MHz, DMSO-d$_6$) δ 8.56-8.49 (m, 1H), 8.18-8.11 (m, 2H), 7.50-7.47 (m, 1H), 7.45-7.37 (m, 2H), 4.25 (t, J = 5.5 Hz, 1H), 4.17 (t, J = 5.8 Hz, 1H), 3.72 (t, J = 5.6 Hz, 1H), 3.67-3.62 (m, 2H), 3.61-3.55 (m, 3H), 3.51 (t, J = 5.8 Hz, 1H), 2.68-2.53 (m, 4H), 1.65-1.46 (m, 15H). | 3 |
| I-530 | 1.92 | 562.86 | C | $^1$H NMR (400 MHz, DMSO-d$_6$) δ 8.57-8.50 (m, 1H), 8.18-8.10 (m, 2H), 7.52-7.47 (m, 1H), 7.45-7.37 (m, 2H), 4.22-4.11 (m, 2H), 3.87-3.82 (m, 1H), 3.69 (s, 1H), 3.66-3.61 (m, 4H), 3.54-3.46 (m, 1H), 2.40-2.30 (m, 6H), 1.65-1.45 (m, 15H). | 3 |
| I-531 | 2 | 536.22 | C | $^1$H NMR (400 MHz, DMSO-d$_6$) δ 8.56-8.51 (m, 1H), 8.18-8.11 (m, 2H), 7.57-7.35 (m, 4H), 6.70-6.59 (m, 1H), 4.29-4.16 (m, 4H), 3.92-3.86 (m, 1H), 3.79 (s, 1H), 3.73 (s, 1H), 3.69-3.61 (m, 1H), 1.64-1.48 (m, 15H), 1.32-1.19 (m, 3H). | 3 |
| I-532 | 6.25 | 608.5 | D | $^1$H NMR (400 MHz, DMSO-d6) δ 8.50 (d, J = 9.7 Hz, 1H), 8.09 (dd, J = 8.6, 3.1 Hz, 2H), 7.61 (dd, J = 8.6, 2.1 Hz, 2H), 7.47 (d, J = 5.6 Hz, 1H), 4.13 (q, J = 6.5, 5.9 Hz, 2H), 3.83-3.72 (m, 1H), 3.67-3.54 (m, 5H), 3.44 (t, J = 5.8 Hz, 1H), 2.17-2.00 (m, 2H), 1.70-1.48 (m, 15H), 1.43 (s, 3H), 1.39-1.12 (m, 4H), 1.08 (d, J = 1.7 Hz, 3H). | 3 |
| I-533 | 3.57 | 588.3 | A | $^1$H NMR (400 MHz, Methanol-d$_4$) δ 8.25 (d, J = 4.6 Hz, 1H), 6.99 (d, J = 5.6 Hz, 1H), 4.31 (dt, J = 13.9, 5.6 Hz, 2H), 3.88 (t, J = 5.7 Hz, 1H), 3.72 (d, J = 9.5 Hz, 2H), 3.64-3.55 (m, 1H), 3.04-2.90 (m, 1H), 2.81-2.53 (m, 2H), 2.28-1.84 (m, 10H), 1.77-1.51 (m, 21H) | 4 |
| I-534 | 5.62 | 594.49 | D | $^1$H NMR (400 MHz, DMSO-d6) δ 12.25 (bs, 1H), 8.63-8.36 (m, | 4 |

TABLE 2-continued

| Compound analytical data | | | | | |
|---|---|---|---|---|---|
| Compound Number | LCMS Retention Time | M + 1 | LCMS Method | NMR | General Procedure |
| | | | | 1H), 8.09 (dd, J = 8.6, 3.0 Hz, 2H), 7.61 (dd, J = 8.7, 2.0 Hz, 2H), 7.47 (d, J = 5.5 Hz, 1H), 4.25-4.03 (m, 2H), 3.84-3.74 (m, 1H), 3.73-3.54 (m, 2H), 3.53-3.37 (m, 1H), 2.05 (d, J = 12.5 Hz, 2H), 1.65-1.32 (m, 20H), 1.27-0.97 (m, 5H). | |
| I-535 | 1.39 | 590.6 | C | $^1$H NMR (400 MHz, DMSO-d6) δ 12.07 (s, 1H), 8.49 (d, J = 8.6 Hz, 1H), 8.20 (s, 2H), 8.10-7.86 (m, 4H), 7.48 (d, J = 4.2 Hz, 1H), 4.24-4.02 (m, 2H), 3.77 (t, J = 5.7 Hz, 1H), 3.72-3.52 (m, 2H), 3.52-3.39 (m, 1H), 2.63-2.51 (m, 2H), 2.12-1.86 (m, 2H), 1.68-1.33 (m, 21H). | 4 |
| I-536 | 3.63 | 447.46 | A | $^1$H NMR (400 MHz, Chloroform-d) δ 8.40 (d, J = 0.7 Hz, 1H), 8.11-7.87 (m, 2H), 7.28 (s, 1H), 7.23-7.11 (m, 2H), 6.01 (s, 1H), 4.36-4.21 (m, 2H), 3.72-3.61 (m, 2H), 1.90 (s, 6H), 1.60 (s, 9H). | 1 |
| I-537 | 3.86 | 550.87 | A | $^1$H NMR (400 MHz, DMSO-$d_6$) δ 8.53-8.49 (m, 1H), 8.18-8.11 (m, 2H), 7.50-7.47 (m, 1H), 7.45-7.37 (m, 2H), 4.22-4.12 (m, 2H), 3.66-3.56 (m, 5H), 3.55-3.46 (m, 2H), 3.36-3.24 (m, 1H), 3.19-3.03 (m, 1H), 2.41-2.30 (m, 4H), 1.64-1.57 (m, 9H), 1.54-1.45 (m, 6H). | 3 |
| I-538 | 3.91 | 550.22 | A | $^1$H NMR (400 MHz, DMSO-$d_6$) δ 8.54-8.51 (m, 1H), 8.17-8.11 (m, 2H), 7.50-7.47 (m, 1H), 7.47-7.35 (m, 2H), 4.21-4.10 (m, 2H), 3.69-3.56 (m, 5H), 3.57-3.50 (m, 1H), 3.49-3.45 (m, 1H), 3.46-3.35 (m, 1H), 3.16-3.02 (m, 1H), 2.48-2.29 (m, 4H), 1.66-1.55 (m, 9H), 1.54-1.43 (m, 6H). | 3 |
| I-539 | 5.38 | 580.49 | D | $^1$H NMR (400 MHz, DMSO-$d_6$) δ 8.57-8.52 (m, 1H), 8.16-8.10 (m, 2H), 7.72-7.68 (m, 1H), 7.67-7.62 (m, 2H), 4.18-4.06 (m, 2H), 3.80-3.73 (m, 1H), 3.71-3.51 (m, 6H), 3.49-3.42 (m, 1H), 2.79-2.55 (m, 2H), 2.11-1.97 (m, 2H), 1.67-1.40 (m, 18H). | 3 |
| I-540 | 1.62 | 510.18 | C | $^1$H NMR (400 MHz, DMSO-$d_6$) δ 8.56-8.52 (m, 1H), 8.17-8.11 (m, 2H), 7.72-7.68 (m, 1H), 7.67-7.61 (m, 2H), 5.10-5.02 (m, 1H), 4.23-4.05 (m, 3H), 3.63 (s, 1H), 3.61-3.52 (m, 2H), 3.52-3.44 (m, 2H), 3.28-3.12 (m, 1H), 2.44-2.32 (m, 2H), 2.12-1.97 (m, 2H), 1.57-1.40 (m, 12H). | 3 |
| I-541 | 1.71 | 524.22 | C | $^1$H NMR (400 MHz, DMSO-$d_6$) δ 8.56-8.52 (m, 1H), 8.17-8.10 (m, 2H), 7.71-7.67 (m, 1H), 7.66-7.61 (m, 2H), 5.03-4.90 (m, 1H), 4.18-4.07 (m, 2H), 3.68-3.51 (m, 4H), 3.50-3.43 (m, 1H), 2.96-2.79 (m, 1H), 2.24-2.04 (m, 4H), 1.58-1.40 (m, 12H), 1.33-1.24 (m, 3H). | 3 |
| I-542 | 1.9 | 578.5 | C | $^1$H NMR (400 MHz, DMSO-$d_6$) δ 8.57-8.51 (m, 1H), 8.17-8.11 (m, 2H), 7.70-7.68 (m, 1H), 7.67-7.62 (m, 2H), 6.64-6.56 (m, 1H), 4.16-4.06 (m, 2H), 3.69-3.46 (m, 5H), 3.07-2.95 (m, 1H), 2.70-2.57 (m, 2H), 2.47-2.37 | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | (m, 2H), 1.56-1.47 (m, 6H), 1.47-1.40 (m, 6H). | |
| I-543 | 1.63 | 510.18 | C | $^1$H NMR (400 MHz, DMSO-$d_6$) δ 8.56-8.51 (m, 1H), 8.16-8.08 (m, 2H), 7.71-7.67 (m, 1H), 7.66-7.61 (m, 2H), 5.12-5.05 (m, 1H), 4.19-4.05 (m, 2H), 4.03-3.93 (m, 1H), 3.66-3.50 (m, 4H), 3.50-3.43 (m, 1H), 2.84-2.67 (m, 1H), 2.44-2.31 (m, 2H), 2.04-1.86 (m, 2H), 1.57-1.37 (m, 12H). | 3 |
| I-544 | 3.68 | 552.47 | A | $^1$H NMR (400 MHz, DMSO-$d_6$) δ 8.57-8.52 (m, 1H), 8.16-8.10 (m, 2H), 7.72-7.67 (m, 1H), 7.67-7.62 (m, 2H), 4.18-4.05 (m, 2H), 3.68-3.43 (m, 8H), 3.33-3.21 (m, 1H), 3.19-3.03 (m, 1H), 2.41-2.30 (m, 4H), 1.57-1.41 (m, 12H). | 3 |
| I-545 | 3.74 | 552.47 | A | $^1$H NMR (400 MHz, DMSO-$d_6$) δ 8.56-8.53 (m, 1H), 8.16-8.11 (m, 2H), 7.71-7.68 (m, 1H), 7.67-7.62 (m, 2H), 4.15-4.07 (m, 2H), 3.67-3.60 (m, 3H), 3.61-3.52 (m, 2H), 3.52-3.41 (m, 4H), 3.15-3.02 (m, 1H), 2.48-2.28 (m, 4H), 1.55-1.48 (m, 6H), 1.47-1.39 (m, 6H). | 3 |
| I-546 | 5.48 | 580.42 | D | $^1$H NMR (400 MHz, DMSO-$d_6$) δ 8.57-8.51 (m, 1H), 8.17-8.11 (m, 2H), 7.72-7.67 (m, 1H), 7.67-7.62 (m, 2H), 4.18-4.07 (m, 2H), 3.81-3.74 (m, 1H), 3.72-3.51 (m, 7H), 3.50-3.43 (m, 1H), 2.75-2.63 (m, 1H), 2.38-2.26 (m, 1H), 2.01-1.85 (m, 2H), 1.84-1.67 (m, 2H), 1.57-1.32 (m, 15H). | 3 |
| I-547 | 4.47 | 410.32 | D | $^1$H NMR (400 MHz, DMSO-$d_6$) δ 8.63 (s, 1H), 8.19-8.12 (m, 2H), 8.05 (s, 1H), 7.51 (s, 1H), 7.46-7.37 (m, 2H), 5.67-5.05 (m, 1H), 4.82-4.42 (m, 1H), 3.58-3.46 (m, 1H), 3.30-3.19 (m, 2H), 1.71-1.36 (m, 12H). | 1 |
| I-548 | 4.47 | 410.74 | D | $^1$H NMR (400 MHz, DMSO-$d_6$) δ 8.63 (s, 1H), 8.19-8.10 (m, 2H), 8.05 (s, 1H), 7.51 (s, 1H), 7.46-7.37 (m, 2H), 5.69-4.97 (m, 1H), 4.88-4.35 (m, 1H), 3.57-3.44 (m, 1H), 3.29-3.20 (m, 2H), 1.67-1.38 (m, 12H). | 1 |
| I-549 | 1.68 | 566.5 | C | $^1$H NMR (400 MHz, DMSO-d6) δ 11.98 (s, 1H), 8.51 (d, J = 9.1 Hz, 1H), 8.10 (dd, J = 8.5, 2.4 Hz, 2H), 7.76-7.47 (m, 3H), 4.17-4.02 (m, 2H), 3.79-3.35 (m, 4H), 2.21-2.08 (m, 1H), 1.99-1.80 (m, 2H), 1.81-1.60 (m, 2H), 1.60-1.24 (m, 17H). | 4 |
| I-550 | 1.73 | 512.56 | C | $^1$H NMR (400 MHz, Chloroform-d) δ 8.22 (dd, J = 12.6, 3.9 Hz, 1H), 6.75 (d, J = 3.4 Hz, 1H), 4.34 (d, J = 27.2 Hz, 2H), 3.77 (d, J = 5.7 Hz, 1H), 3.72-3.64 (m, 4H), 3.52 (s, 1H), 3.12-3.00 (m, 1H), 2.83-2.40 (m, 2H), 2.35-2.00 (m, 2H), 1.75 (s, 2H), 1.63 (d, J = 2.7 Hz, 6H), 1.61-1.51 (m, 6H), 1.45-1.36 (m, 6H), 1.33 (d, J = 2.0 Hz, 6H). | 3 |
| I-551 | 1.5 | 498.51 | C | $^1$H NMR (400 MHz, Chloroform-d) δ 8.23 (d, J = 12.2 Hz, 1H), 6.75 (d, J = 4.1 Hz, 1H), 4.36 (dt, J = 29.2, 5.7 Hz, 2H), 3.79 (t, J = | 3 |

TABLE 2-continued

| Compound analytical data | | | | | |
|---|---|---|---|---|---|
| Compound Number | LCMS Retention Time | M + 1 | LCMS Method | NMR | General Procedure |
| | | | | 6.0 Hz, 1H), 3.73-3.64 (m, 2H), 3.57-3.47 (m, 2H), 3.13-3.00 (m, 1H), 2.71-2.63 (m, 1H), 2.60-2.46 (m, 1H), 2.36-2.24 (m, 2H), 1.93-1.78 (m, 2H), 1.72-1.62 (m, 5H), 1.61-1.53 (m, 6H), 1.40 (d, J = 6.9 Hz, 3H), 1.38 (d, J = 6.9 Hz, 3H), 1.33 (d, J = 2.5 Hz, 3H), 1.31 (d, J = 2.5 Hz, 3H). | |
| I-552 | 2.59 | 477.14 | A | $^1$H NMR (400 MHz, DMSO-$d_6$) δ 13.98 (s, 1H), 8.61 (s, 1H), 8.21-8.12 (m, 2H), 7.69 (s, 1H), 7.41 (t, J = 8.8 Hz, 2H), 4.28 (d, J = 65.3 Hz, 3H), 3.76 (s, 5H), 3.58 (p, J = 7.7, 6.9 Hz, 1H), 2.45-2.29 (m, 3H), 1.51-1.37 (m, 6H). | 3 |
| I-553 | 1.62 | 538.4 | C | $^1$H NMR (400 MHz, DMSO-d6) δ 12.08 (s, 1H), 8.51 (d, J = 6.9 Hz, 1H), 8.10 (dd, J = 8.6, 1.6 Hz, 2H), 7.68-7.56 (m, 3H), 4.20-3.96 (m, 2H), 3.63-3.37 (m, 5H), 3.22 (s, 1H), 3.02-2.86 (m, 1H), 2.36-2.17 (m, 4H), 1.57-1.32 (m, 12H). | 4 |
| I-554 | 1.62 | 538.5 | C | $^1$H NMR (400 MHz, DMSO-d6) δ 12.17 (s, 1H), 8.51 (d, J = 4.7 Hz, 1H), 8.10 (d, J = 8.6 Hz, 2H), 7.78-7.51 (m, 3H), 4.16-3.96 (m, 2H), 3.65-3.32 (m, 6H), 3.01-2.81 (m, 1H), 2.43-2.21 (m, 4H), 1.56-1.34 (m, 12H). | 4 |
| I-555 | 1.69 | 536.5 | C | $^1$H NMR (400 MHz, DMSO-d6) δ 12.09 (s, 1H), 8.49 (d, J = 6.4 Hz, 1H), 8.16-8.07 (m, 2H), 7.45 (d, J = 2.7 Hz, 1H), 7.42-7.30 (m, 2H), 4.25-4.05 (m, 2H), 3.72-3.37 (m, 4H), 3.30-3.08 (m, 1H), 3.05-2.86 (m, 1H), 2.40-2.18 (m, 4H), 1.63-1.36 (m, 15H). | 4 |
| I-556 | 1.69 | 536.5 | C | $^1$H NMR (400 MHz, DMSO-d6) δ 12.13 (s, 1H), 8.49 (d, J = 4.6 Hz, 1H), 8.11 (ddd, J = 8.9, 5.5, 1.1 Hz, 2H), 7.45 (d, J = 1.8 Hz, 1H), 7.38 (t, J = 8.8 Hz, 2H), 4.20-3.99 (m, 2H), 3.66-3.32 (m, 5H), 2.94 (dd, J = 9.8, 4.6 Hz, 1H), 2.46-2.24 (m, 4H), 1.56 (d, J = 2.4 Hz, 9H), 1.47 (d, J = 9.5 Hz, 6H). | 4 |
| I-557 | 1.79 | 566.5 | C | $^1$H NMR (400 MHz, DMSO-d6) δ 12.06 (s, 1H), 8.51 (d, J = 9.1 Hz, 1H), 8.10 (dd, J = 8.7, 2.1 Hz, 2H), 7.66 (d, J = 6.1 Hz, 1H), 7.61 (dd, J = 8.6, 1.8 Hz, 2H), 4.17-4.00 (m, 2H), 3.80-3.47 (m, 4H), 3.47-3.33 (m, 1H), 2.57-2.50 (m, 2H), 2.10-1.91 (m, 2H), 1.61-1.33 (m, 18H). | 4 |
| I-558 | 1.67 | 508.5 | C | $^1$H NMR (400 MHz, DMSO-d6) δ 8.50 (d, J = 6.4 Hz, 1H), 8.11 (dd, J = 8.7, 5.6 Hz, 2H), 7.45 (d, J = 2.4 Hz, 1H), 7.43-7.33 (m, 3H), 7.28 (d, J = 15.4 Hz, 1H), 6.56 (dd, J = 15.2, 8.2 Hz, 1H), 4.20 (q, J = 5.4 Hz, 2H), 3.84 (t, J = 5.6 Hz, 1H), 3.73 (d, J = 23.4 Hz, 2H), 3.61 (dd, J = 6.8, 4.5 Hz, 1H), 1.53 (dd, J = 25.0, 1.6 Hz, 15H). | 4 |
| I-559 | 1.68 | 548.5 | C | $^1$H NMR (400 MHz, DMSO-d6) δ 8.49 (d, J = 7.4 Hz, 1H), 8.11 (ddd, J = 8.8, 5.5, 3.3 Hz, 2H), 7.46 (d, J = 5.8 Hz, 1H), 7.38 (td, J = 8.8, 2.0 Hz, 2H), 4.23-4.06 (m, 2H), 3.81 (t, J = 5.7 Hz, 1H), | 4 |

TABLE 2-continued

Compound analytical data

| Compound Number | LCMS Retention Time | M + 1 | LCMS Method | NMR | General Procedure |
|---|---|---|---|---|---|
| | | | | 3.69-3.40 (m, 5H), 2.26 (d, J = 12.1 Hz, 6H), 1.68-1.35 (m, 15H). | |
| I-560 | 1.65 | 510.5 | C | | 4 |
| I-561 | 1.98 | 538.83 | C | $^1$H NMR (400 MHz, DMSO-d6) δ 11.76 (s, 1H), 8.49 (d, J = 9.3 Hz, 1H), 8.11 (ddd, J = 8.9, 5.3, 2.2 Hz, 2H), 7.45 (d, J = 3.8 Hz, 1H), 7.38 (td, J = 8.8, 1.8 Hz, 2H), 4.16 (dt, J = 23.4, 5.9 Hz, 2H), 3.67 (t, J = 5.6 Hz, 1H), 3.58 (d, J = 1.9 Hz, 2H), 3.46 (t, J = 5.8 Hz, 1H), 2.56 (d, J = 24.0 Hz, 2H), 1.65-1.37 (m, 15H), 1.14 (s, 6H). | 4 |
| I-562 | 1.68 | 522.5 | C | $^1$H NMR (400 MHz, DMSO-d6) δ 12.80 (s, 1H), 8.49 (d, J = 2.2 Hz, 1H), 8.28-8.00 (m, 2H), 7.45 (d, J = 1.2 Hz, 1H), 7.37 (t, J = 8.8 Hz, 2H), 4.23-4.08 (m, 2H), 3.83-3.68 (m, 1H), 3.60 (d, J = 8.9 Hz, 2H), 3.54-3.45 (m, 1H), 1.64-1.40 (m, 15H), 1.37-1.24 (m, 2H), 1.27-1.13 (m, 2H). | 4 |
| I-563 | 1.9 | 578.6 | C | $^1$H NMR (400 MHz, DMSO-d6) δ 12.11 (s, 1H), 8.49 (d, J = 9.2 Hz, 1H), 8.11 (ddd, J = 8.8, 5.5, 3.1 Hz, 2H), 7.45 (d, J = 5.6 Hz, 1H), 7.38 (td, J = 8.8, 2.1 Hz, 2H), 4.22-4.06 (m, 2H), 3.81-3.71 (m, 1H), 3.61 (d, J = 24.0 Hz, 2H), 3.49-3.38 (m, 1H), 2.15-1.89 (m, 2H), 1.66-1.28 (m, 19H), 1.28-0.97 (m, 6H). | 4 |
| I-564 | 2.25 | 466.45 | B | $^1$H NMR (400 MHz, DMSO-$d_6$) δ 8.69 (s, 1H), 8.21-8.11 (m, 2H), 7.53 (s, 1H), 7.46-7.36 (m, 2H), 5.73 (s, 2H), 1.66-1.51 (m, 15H), 1.46 (s, 9H). | 1 |
| I-565 | 4.88 | 500.21 | A | $^1$H NMR (400 MHz, DMSO-$d_6$) δ 8.65 (s, 1H), 8.17-8.09 (m, 2H), 7.48 (s, 1H), 7.45-7.37 (m, 4H), 7.36-7.28 (m, 3H), 5.41 (s, 2H), 4.58 (s, 2H), 1.65 (s, 6H), 1.47 (s, 9H). | 1 |
| I-566 | 3.57 | 491.19 | A | $^1$H NMR (400 MHz, DMSO-$d_6$) δ 8.53 (d, J = 6.6 Hz, 1H), 8.18-8.10 (m, 2H), 7.51-7.47 (m, 1H), 7.46-7.37 (m, 2H), 4.31-4.23 (m, 1H), 4.22-4.15 (m, 1H), 3.73-3.59 (m, 3H), 3.58-3.52 (m, 1H), 2.80-2.70 (m, 2H), 2.69-2.62 (m, 2H), 1.64-1.56 (m, 9H), 1.53 (d, 6H). | 3 |
| I-567 | 1.58 | 450.34 | C | $^1$H NMR (400 MHz, Chloroform-d) δ 8.87-8.81 (m, 1H), 8.49-8.43 (m, 1H), 7.99 (dd, J = 8.5, 5.3 Hz, 2H), 7.86 (d, J = 5.1 Hz, 1H), 7.67 (s, 1H), 7.51 (dd, J = 5.1, 3.0 Hz, 1H), 7.50-7.42 (m, 1H), 7.22 (d, J = 8.8 Hz, 1H), 6.08 (s, 1H), 4.32-4.23 (m, 2H), 3.72-3.63 (m, 2H), 1.90 (s, 6H). | 8 |
| I-568 | 1.62 | 445.15 | C | $^1$H NMR (400 MHz, Chloroform-d) δ 9.42 (d, J = 2.3 Hz, 1H), 8.77 (dd, J = 4.8, 1.6 Hz, 1H), 8.51 (dt, J = 7.9, 2.2 Hz, 2H), 8.01 (dd, J = 8.7, 5.3 Hz, 2H), 7.66 (s, 1H), 7.50 (dd, J = 7.9, 4.9 Hz, 1H), 7.29-7.20 (m, 1H), 5.97 (s, 1H), 5.28 (s, 1H), 4.27-4.16 (m, 2H), 3.68-3.55 (m, 2H), 1.88 (s, 6H). | 8 |
| I-569 | 1.58 | 445.15 | C | $^1$H NMR (400 MHz, DMSO-d) δ 9.67 (d, J = 5.7 Hz, 2H), 9.58 (s, | 8 |

TABLE 2-continued

| Compound analytical data | | | | | |
|---|---|---|---|---|---|
| Compound Number | LCMS Retention Time | M + 1 | LCMS Method | NMR | General Procedure |
| | | | | 1H), 9.25 (d, J = 5.7 Hz, 2H), 9.17-9.09 (m, 3H), 8.95 (s, 1H), 8.28 (t, J = 8.7 Hz, 2H), 4.84-4.75 (m, 2H), 4.22 (s, 2H), 4.16 (s, 6H). | |
| I-570 | 1.82 | 552.5 | C | $^1$H NMR (400 MHz, DMSO-d6) δ 12.12 (s, 1H), 8.50 (d, J = 4.5 Hz, 1H), 8.22-8.00 (m, 2H), 7.61 (d, J = 8.6 Hz, 2H), 7.47 (d, J = 1.7 Hz, 1H), 4.21-4.02 (m, 2H), 3.64-3.42 (m, 5H), 3.01-2.87 (m, 1H), 2.44-2.24 (m, 4H), 1.56 (d, J = 2.4 Hz, 9H), 1.47 (d, J = 9.5 Hz, 6H). | 4 |
| I-571 | 1.79 | 538.5 | C | $^1$H NMR (400 MHz, DMSO-$d_6$) δ 11.76 (s, 1H), 8.49 (s, 1H), 8.13-8.03 (m, 2H), 7.45 (s, 1H), 7.38 (t, J = 8.8 Hz, 2H), 4.17-4.01 (m, 2H), 3.68 (s, 2H), 3.54 (s, 2H), 2.53 (s, 2H), 1.65-1.41 (m, 15H), 1.30 (s, 6H). | 4 |
| I-572 | 0.59 | 487.45 | H | $^1$H NMR (400 MHz, Chloroform-d) δ 8.50 (s, 1H), 8.00 (dd, J = 8.8, 5.3 Hz, 2H), 7.66 (ddd, J = 11.8, 7.9, 1.1 Hz, 1H), 7.54-7.47 (m, 1H), 7.43-7.34 (m, 2H), 7.23-7.19 (m, 2H), 6.90 (d, J = 7.6 Hz, 1H), 5.95 (s, 1H), 4.35-4.27 (m, 2H), 3.61-3.52 (m, 2H), 3.03 (s, 6H), 1.88 (s, 6H). | 8 |
| I-573 | 1.83 | 459.1 | C | $^1$H NMR (400 MHz, Chloroform-d) δ 8.47 (s, 1H), 8.08-7.92 (m, 2H), 7.60 (s, 1H), 7.58-7.44 (m, 2H), 7.32 (t, J = 7.9 Hz, 1H), 7.24-7.16 (m, 2H), 6.85 (dd, J = 7.2, 1.6 Hz, 1H), 6.01 (s, 1H), 4.33-4.17 (m, 2H), 3.83 (s, 2H), 3.70-3.54 (m, 2H), 1.88 (s, 6H). | 8 |
| I-574 | 1.65 | 434.09 | C | $^1$H NMR (400 MHz, DMSO-d6) δ 8.90 (s, 1H), 8.65 (s, 1H), 8.58 (s, 1H), 8.21 (dd, J = 8.8, 5.4 Hz, 2H), 8.15 (s, 1H), 7.42 (d, J = 8.8 Hz, 2H), 7.21 (s, 2H), 4.06-3.99 (m, 2H), 3.42 (dd, J = 2.8, 1.6 Hz, 2H), 1.70 (s, 6H). | 8 |
| I-575 | 1.71 | 487.4 | C | $^1$H NMR (400 MHz, Chloroform-d) δ 8.43 (s, 1H), 8.27 (d, J = 9.0 Hz, 2H), 7.98 (dd, J = 8.7, 5.2 Hz, 2H), 7.55 (s, 1H), 7.26-7.13 (m, 2H), 6.81 (d, J = 9.1 Hz, 2H), 6.05 (s, 1H), 4.35-4.22 (m, 2H), 3.67 (s, 2H), 3.08 (s, 6H), 1.89 (s, 6H). | 8 |
| I-576 | 1.39 | 459.39 | C | $^1$H NMR (400 MHz, Chloroform-d) δ 8.45 (s, 1H), 8.15 (d, J = 7.9 Hz, 2H), 7.98 (dd, J = 7.7, 5.2 Hz, 2H), 7.54 (s, 1H), 7.26-7.16 (m, 2H), 6.80 (d, J = 7.6 Hz, 2H), 5.94 (s, 1H), 4.30-4.21 (m, 2H), 4.03 (s, 2H), 3.64 (q, J = 4.0, 3.5 Hz, 2H), 1.89 (s, 6H). | 8 |
| I-577 | 3.67 | 434.68 | D | $^1$H NMR (400 MHz, DMSO-d6) δ 13.57 (s, 1H), 8.64 (s, 1H), 8.32-8.19 (m, 1H), 8.14 (dd, J = 7.7, 6.3 Hz, 3H), 7.58-7.50 (m, 2H), 7.49-7.30 (m, 2H), 4.00 (dd, J = 3.9, 1.6 Hz, 2H), 3.41 (dd, J = 5.2, 3.2 Hz, 2H), 1.69 (s, 6H). | 8 |
| I-578 | 1.26 | 448.33 | C | $^1$H NMR (400 MHz, DMSO-d6) δ 8.68 (s, 1H), 8.19 (dd, J = 8.7, 5.5 Hz, 2H), 8.07 (s, 1H), 7.96 (s, 1H), 7.63 (d, J = 1.8 Hz, 1H), 7.41 (t, J = 8.8 Hz, 2H), 6.96 (d, J = 1.9 Hz, 1H), 4.03 (s, 3H), 3.95- | 8 |

TABLE 2-continued

| Compound analytical data | | | | | |
|---|---|---|---|---|---|
| Compound Number | LCMS Retention Time | M + 1 | LCMS Method | NMR | General Procedure |
| | | | | 3.87 (m, 2H), 3.36-3.29 (m, 2H), 1.66 (s, 6H). | |
| I-579 | 1.73 | 448.04 | C | $^1$H NMR (400 MHz, DMSO-d6) δ 8.83 (s, 1H), 8.58 (d, J = 2.9 Hz, 2H), 8.20 (dd, J = 8.5, 5.8 Hz, 2H), 8.12 (s, 2H), 7.41 (t, J = 8.7 Hz, 2H), 4.05-3.98 (m, 2H), 3.97 (s, 3H), 3.43 (dd, J = 3.4, 1.6 Hz, 2H), 1.70 (s, 6H). | 8 |

TABLE 3

| Compound analytical data | | | | | |
|---|---|---|---|---|---|
| Compound Number | LCMS Retention Time | M + 1 | LCMS Method | NMR | General Procedure |
| I-580 | 4.5 | 543.6 | A | $^1$H NMR (400 MHz, Chloroform-d) δ 8.97-8.52 (m, 1H), 8.39 (d, J = 5.0 Hz, 1H), 7.52 (dd, J = 8.5, 5.2 Hz, 2H), 7.40-7.30 (m, 5H), 7.24-7.14 (m, 2H), 5.50-5.03 (m, 3H), 4.83-4.32 (m, 2H), 4.06 (s, 1H), 3.69-2.81 (m, 3H), 1.27-1.10 (m, 3H). | 1 |
| I-581 | 2.48 | 485.3 | A | | 1 |
| I-582 | 4.22 | 497.2 | A | | 1 |
| I-583 | 2.14 | 488.3 | A | | 1 |
| I-584 | 3.31 | 450.3 | A | | 1 |
| I-585 | 2.81 | 367.2 | A | | 1 |
| I-586 | 3.06 | 381.3 | A | | 1 |
| I-587 | 4.65 | 409.5 | A | | 1 |
| I-588 | 2.36 | 464.46 | A | | 3 |
| I-589 | 1.44 | 435.42 | C | $^1$H NMR (400 MHz, DMSO-d6) δ 8.55 (d, J = 5.0 Hz, 1H), 7.31 (s, 1H), 6.03-5.87 (m, 1H), 4.10-4.04 (m, 1H), 3.97 (t, J = 5.6 Hz, 1H), 3.76 (t, J = 5.6 Hz, 1H), 3.71 (s, 1H), 3.59 (s, 1H), 3. 55-3.47 (m, 1H), 3.46-3.40 (m, 1H), 2.57 (ddt, J = 14.0, 8.8, 4.8 Hz, 3H), 2.09-1.97 (m, 2H), 1.82-1.72 (m, 1H), 1.52-1.47 (m, 6H), 1.37 (d, 6H). | 3 |
| I-590 | 1.32 | 484.56 | C | $^1$H NMR (400 MHz, DMSO-d6) δ 8.42-8.36 (m, 1H), 7.16 (s, 1H), 6.00 (s, 1H), 4.10 (t, J = 5.7 Hz, 1H), 4.04-3.92 (m, 3H), 3.76 (t, J = 5.6 Hz, 1H), 3.70 (s, 1H), 3.58 (s, 1H), 3.53-3.42 | 11 |

TABLE 3-continued

| Compound analytical data | | | | | |
|---|---|---|---|---|---|
| Compound Number | LCMS Retention Time | M + 1 | LCMS Method | NMR | General Procedure |
| | | | | (m, 4H), 3.17 (s, 1H), 3.12-2.99 (m, 1H), 2.62-2.54 (m, 2H), 2.08-1.98 (m, 2H), 1.91-1.69 (m, 5H), 1.55-1.44 (m, 6H), 1.37 (d, J = 6.9 Hz, 6H). | |
| I-591 | 2.82 | 382.3 | A | $^1$H NMR (400 MHz, DMSO-d6) δ 8.64 (s, 1H), 8.22-8.09 (m, 3H), 7.71 (s, 1H), 7.47-7.36 (m, 2H), 4.79 (s, 1H), 4.32 (s, 1H), 4.17 (s, 1H), 3.84 (s, 1H), 3.55 (dt, J = 14.0, 7.0 Hz, 1H), 3.33 (s, 2H), 1.45 (d, J = 6.9 Hz, 6H). | 1 |

TABLE 4

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-1 | 0.28 | 1.0 | 3.6 | 3.1 |
| I-2 | 0.86 | 2.4 | 6.1 | 4.7 |
| I-3 | 0.16 | 0.825 | 18 | 16 |
| I-4 | 0.003 | 0.016 | 12 | 17 |
| I-5 | 0.002 | 0.005 | 51 | 97 |
| I-6 | 1.28 | 2.5 | 10 | 11 |
| I-7 | 0.089 | 45% @ 0.62 | >50 | >50 |
| I-8 | 0.18 | 0.69 | 43 | 31 |
| I-9 | 0.009 | 0.11 | >5 | >5 |
| I-10 | 0.43 | 1.1 | 16 | 18 |
| I-11 | 0.065 | 0.30 | 9.6 | >5 |
| I-12 | 0.084 | 0.49 | 7.7 | 9.2 |
| I-13 | 0.48 | 2.4 | 13 | 13 |
| I-14 | 0.0005 | 0.0008 | >5 | >5 |
| I-15 | 0.047 | 0.058 | >50 | >50 |
| I-16 | 0.037 | 0.28 | 11 | 11 |
| I-17 | 0.041 | 0.78 | 20 | 19 |

TABLE 4-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-18 | 2.8 | 6.8 | 20 | 18 |
| I-19 | 0.025 | 0.056 | 62% @ 50 | 50 |
| I-20 | 0.28 | 1.02 | 3.6 | 3.0 |
| I-21 | 0.019 | 0.029 | >50 | 64 |
| I-22 | 0.007 | 0.014 | 21 | 25 |
| I-23 | 0.13 | 0.30 | >50 | >50 |
| I-24 | 0.22 | 0.59 | >50 | >50 |
| I-25 | 0.009 | 0.021 | >50 | >50 |
| I-26 | 4.4 | 9.1 | 28 | 31 |
| I-27 | 0.059 | 0.25 | 35 | 42 |
| I-28 | 8.8 | 15 | 33 | 38 |
| I-29 | 0.24 | 0.39 | >50 | >50 |
| I-30 | 0.002 | 0.003 | 25 | 26 |
| I-31 | 0.031 | 0.042 | 19 | 24 |
| I-32 | 0.017 | 0.021 | >50 | >50 |
| I-33 | 0.045 | 0.014 | >50 | >50 |
| I-34 | 0.054 | 0.059 | 21 | 21 |
| I-35 | 0.023 | 0.062 | 43 | 41 |
| I-36 | 0.071 | 0.24 | >50 | >50 |
| I-37 | 0.20 | 0.25 | >50 | >50 |
| I-38 | 0.39 | 0.48 | >50 | >45 |
| I-39 | 0.83 | 0.86 | >50 | >50 |
| I-40 | 0.072 | 0.37 | 24 | 17 |
| I-41 | 0.061 | 0.28 | 20 | 21 |
| I-42 | 2.2 | 5.2 | 32 | 41 |
| I-43 | 0.48 | 1.1 | 27 | 31 |
| I-44 | 5.0 | 9.5 | >50 | >50 |
| I-45 | 20 | >50 | >50 | >50 |
| I-46 | 0.04 | 0.095 | >5 | >5 |
| I-47 | 3.1 | 7.5 | 16 | 32 |
| I-48 | 51% @ 1.9 | 30% @ 1.9 | >50 | >50 |
| I-49 | 0.53 | 1.5 | 5.2 | 6.0 |
| I-50 | 44% @ 1.9 | 27 | >50 | >50 |
| I-51 | 42% @ 1.9 | 51% @ 1.9 | >50 | >50 |
| I-52 | 0.14 | 0.35 | 47 | 16 |
| I-53 | 55% @ 5.6 | 21 | >50 | >50 |
| I-54 | 0.84 | >50 | >50 | >50 |
| I-55 | 0.95 | 3.1 | >50 | >50 |
| I-56 | 23 | >50 | >50 | >50 |
| I-57 | 0.59 | 48 | >50 | >50 |
| I-58 | 1.3 | 45% @ 5.6 | >50 | >50 |
| I-59 | 22 | 2 | >50 | >50 |
| I-60 | 7.9 | 14 | 32 | 40 |
| I-61 | 13 | 19 | 26 | 38 |
| I-62 | 7.4 | 29 | 38 | 44 |
| I-63 | 1.0 | 4.1 | 35 | 37 |
| I-64 | 0.11 | 0.22 | 5.7 | 42 |
| I-65 | 56% @ 1.9 | 51% @ 1.9 | >50 | >50 |
| I-66 | 5 | 12 | 48 | >50 |
| I-67 | 3.1 | 3.6 | 6.7 | 8.1 |
| I-68 | 5.9 | 13 | 19 | 29 |
| I-69 | 6.0 | 9.3 | 8.5 | 36 |
| I-70 | 3.7 | 5.7 | 12 | 17 |
| I-71 | 0.95 | 0.68 | 43 | >50 |
| I-72 | 1.4 | 1.5 | 50 | >50 |
| I-73 | 0.74 | 0.92 | 1.7 | RND, |
| I-74 | 0.48 | 55% @ 50 | >50 | 62% @ 50 |
| I-75 | 1.1 | 1.2 | 1.6 | 2.2 |
| I-76 | 3.3 | 4.8 | 5.5 | 4.4 |
| I-77 | 0.68 | 32% @ 1.9 | >50 | >50 |
| I-78 | 0.51 | 1.6 | 4.1 | 4.5 |
| I-79 | 1.3 | 1.7 | 2 | 3 |
| I-80 | 0.054 | 0.082 | >5 | >5 |
| I-81 | 6.7 | 12 | 9.2 | 17 |
| I-82 | 0.022 | 0.10 | 14 | 22 |
| I-83 | 46% @ 0.069 | >50 | >50 | >50 |
| I-84 | 0.79 | 1.8 | 6.4 | 5.1 |
| I-85 | 1.6 | 10 | 49 | 40 |
| I-86 | 0.078 | 0.6 | 35 | 37 |
| I-87 | 0.021 | 49% @ 0.069 | >50 | >50 |
| I-88 | 0.68 | 55% @ 5.5 | >50 | >50 |
| I-89 | 0.27 | 0.9 | >50 | >50 |
| I-90 | 0.015 | 0.044 | >5 | >5 |
| I-91 | 0.069 | 1.5 | 26 | 20 |
| I-92 | 0.01 | 0.015 | >5 | >5 |

TABLE 4-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-93 | 0.001 | 0.003 | >5 | >5 |
| I-94 | 3.6 | 12 | >50 | >50 |
| I-95 | 1.6 | 7.2 | >50 | 43 |
| I-96 | 0.044 | 0.15 | 52% @ 50 | 66% @ 50 |
| I-97 | 0.0007 | 0.0006 | >5 | >5 |
| I-98 | 0.005 | 0.007 | >5 | >5 |
| I-99 | 0.003 | 0.01 | >50 | >50 |
| I-100 | 0.2 | 3.0 | 43 | 48 |
| I-101 | 0.007 | 1.4 | 27 | 30 |
| I-102 | 0.003 | 0.008 | 17 | 23 |
| I-103 | 0.0004 | 0.0009 | >5 | >5 |
| I-104 | 0.002 | 0.007 | 15 | 12 |
| I-105 | 0.0004 | 0.0008 | 10 | 8.8 |
| I-106 | 0.0006 | 0.001 | >5 | >5 |
| I-107 | 0.001 | 0.004 | 10 | 9.6 |
| I-108 | 0.0007 | 0.0007 | 8.3 | 16 |
| I-109 | 0.0009 | 0.004 | 11 | 10 |
| I-110 | 0.11 | 1.5 | 19 | 18 |
| I-111 | 0.007 | 0.015 | 20 | 19 |
| I-112 | 2.4 | 1 | 38 | 35 |
| I-113 | 0.0008 | 0.003 | 8.4 | 7.2 |
| I-114 | 0.0005 | 0.0006 | 7.7 | 8.7 |
| I-115 | 0.10 | 0.16 | >50 | >50 |
| I-116 | 0.012 | 0.072 | 19 | 22 |
| I-117 | 0.0003 | 0.0009 | 9.6 | 8.1 |
| I-118 | 0.016 | 1.0 | 31 | 27 |
| I-119 | 0.20 | 2.1 | >50 | >50 |
| I-120 | 0.13 | 1.0 | 20 | 24 |
| I-121 | 0.004 | 0.007 | 9.2 | >0.5 |
| I-122 | 0.007 | 0.023 | 10 | 10 |
| I-123 | 0.20 | 0.34 | >50 | >50 |
| I-124 | 0.026 | 0.16 | 15 | 13 |
| I-125 | 0.002 | 0.005 | >0.5 | >0.5 |
| I-126 | 0.025 | 0.21 | 13 | 13 |
| I-127 | 0.002 | 0.004 | 6.5 | 5.4 |
| I-128 | 0.002 | 0.002 | 30 | 31 |
| I-129 | 0.12 | 0.50 | 41 | 37 |
| I-130 | 0.002 | 0.006 | 4.5 | 5 |
| I-131 | 0.067 | 0.65 | 33 | 32 |
| I-132 | 0.003 | 0.005 | >0.5 | >0.5 |
| I-133 | 0.001 | 0.006 | 36 | >0.5 |
| I-134 | 0.012 | 0.28 | 10 | 7.9 |
| I-135 | 0.022 | 0.22 | 16 | 17 |
| I-136 | 0.007 | 0.034 | >5 | 7.7 |
| I-137 | 0.042 | 0.24 | 43 | 40 |
| I-138 | 0.011 | 0.052 | >5 | >5 |
| I-139 | 0.002 | 0.009 | 25 | >0.5 |
| I-140 | 0.014 | 0.25 | 15 | 14 |
| I-141 | 0.016 | 0.13 | 19 | 24 |
| I-142 | 0.035 | 0.28 | 26 | 24 |
| I-143 | 0.041 | 0.29 | 22 | 21 |
| I-144 | 0.002 | 0.005 | 6.6 | 5.2 |
| I-145 | 0.072 | 0.33 | 24 | 23 |
| I-146 | 0.016 | 1.0 | 20 | 19 |
| I-147 | 0.006 | 0.061 | 8 | 6.6 |
| I-148 | 0.052 | 0.096 | >50 | 39 |
| I-149 | 0.030 | 0.057 | >50 | >50 |
| I-150 | 0.074 | 0.23 | >50 | 84 |
| I-151 | 0.063 | 0.16 | >50 | >50 |
| I-152 | 0.004 | 0.054 | 13 | 10 |
| I-153 | 0.25 | 1.45 | 19 | 22 |
| I-154 | 1.4 | 6.4 | >50 | >50 |
| I-155 | 0.80 | 3.5 | 27 | 25 |
| I-156 | 1.4 | 6.8 | 21 | 17 |
| I-157 | 5.7 | 14 | 40 | 38 |
| I-158 | 9.1 | 26 | 77 | 67 |
| I-159 | 7.3 | 17 | 42 | 36 |
| I-160 | 0.01 | 0.041 | 7.9 | 14 |
| I-161 | 0.20 | 0.33 | 140 | 72 |
| I-162 | 0.11 | 0.16 | 35 | 35 |
| I-163 | 0.64 | 1.7 | 12 | 13 |
| I-164 | 0.20 | 2.0 | 54 | 54 |
| I-165 | 0.001 | 0.002 | 7.4 | 8 |
| I-166 | 0.016 | 0.053 | 23 | 27 |
| I-167 | 0.002 | 0.002 | 8.5 | 9.6 |

TABLE 4-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-168 | 0.067 | 0.35 | 16 | 13 |
| I-169 | 0.01 | 0.017 | 25 | 26 |
| I-170 | 0.014 | 0.038 | 33 | 30 |
| I-171 | 0.003 | 0.005 | 15 | 15 |
| I-172 | 0.022 | 0.33 | 15 | 15 |
| I-173 | 0.008 | 0.013 | 20 | 23 |
| I-174 | 0.028 | 0.055 | 35 | 38 |
| I-175 | 0.023 | 0.06 | 41 | 34 |
| I-176 | 0.006 | 0.011 | 14 | 17 |
| I-177 | 0.048 | 0.082 | 35 | 40 |
| I-178 | 4.8 | 8.3 | 43 | 14 |
| I-179 | 0.003 | 0.011 | 6.9 | 8.5 |
| I-180 | 0.032 | 0.041 | >50 | 18 |
| I-181 | 0.010 | 0.011 | 10 | 5.8 |

TABLE 5

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-182 | 0.0173 | 0.0403 | 1.14 | 1.27 |
| I-183 | 0.015 | 0.0336 | 0.84 | 0.81 |
| I-184 | 0.125 | 0.1825 | 1.45 | 1.95 |
| I-185 | 0.1167 | 0.1567 | >5 | >5 |
| I-186 | 0.0277 | 0.0387 | 1.5 | 1.8 |
| I-187 | 0.0625 | 0.0525 | >50 | 33 |
| I-188 | 0.0018 | 0.004 | 2.5 | 3.9 |
| I-189 | 0.40 | 0.4167 | >1 | >50 |
| I-190 | 0.0042 | 0.0048 | >50 | >50 |
| I-191 | 0.0014 | 0.0023 | 0.32 | 0.44 |
| I-192 | 0.575 | 8.95 | >50 | >50 |
| I-193 | 0.0053 | 0.046 | 10 | 19 |
| I-194 | 0.0413 | 0.0403 | >1 | >1 |
| I-195 | 0.57 | >1 | >1 | >1 |
| I-196 | 0.0205 | 0.020 | >1 | >1 |
| I-197 | 0.15 | 0.43 | >1 | >1 |
| I-198 | 0.0044 | 0.0056 | >1 | >1 |
| I-199 | 0.0001 | 0.0002 | >1 | >1 |
| I-200 | 0.0024 | 0.0029 | >1 | >1 |
| I-201 | 0.0007 | 0.0009 | 0.37 | 0. 56 |
| I-202 | 0.0006 | 0.0009 | >1 | >1 |
| I-203 | 0.0007 | 0.001 | >1 | >1 |
| I-204 | 0.0425 | 0.093 | >1 | >1 |
| I-205 | 0.31 | 0.58 | >1 | >1 |
| I-206 | 0.0008 | 0.0008 | >1 | >1 |
| I-207 | 0.0098 | 0.0083 | >1 | >1 |
| I-208 | 0.085 | 0.1027 | >1 | >1 |
| I-209 | 0.0166 | 0.0166 | >1 | >1 |
| I-210 | 0.004 | 0.0035 | >1 | >1 |
| I-211 | 0.0054 | 0.0045 | >1 | >1 |
| I-212 | 0.0903 | 0.0547 | >1 | >1 |
| I-213 | 0.0035 | 0.0054 | >1 | >1 |
| I-214 | 0.0212 | 0.0268 | 1 | >1 |
| I-215 | 0.012 | 0.0182 | >1 | >1 |
| I-216 | 0.1075 | 0.19 | >1 | >1 |
| I-217 | 0.205 | 0.545 | >1 | >1 |
| I-218 | 0.0248 | 0.0398 | >1 | >1 |
| I-219 | 0.1428 | 0.36 | >1 | >1 |
| I-220 | 0.76 | 0.88 | >1 | >1 |
| I-221 | 0.0233 | 0.0395 | >1 | >1 |
| I-222 | 0.1085 | 0.205 | >1 | >1 |
| I-223 | 0.0163 | 0.0267 | >1 | >1 |
| I-224 | 0.11 | 0.1633 | >1 | >1 |
| I-225 | 0.0013 | 0.0025 | 0.23 | 0.23 |
| I-226 | 0.525 | 0.76 | >1 | >1 |
| I-227 | 0.0007 | 0.0016 | 0.57 | 0.42 |
| I-228 | 0.0006 | 0.0008 | 0.59 | 0.59 |
| I-229 | 0.0005 | 0.0008 | >1 | >1 |
| I-230 | 0.0024 | 0.0055 | 0.73 | >1 |
| I-231 | 0.0011 | 0.0016 | >1 | >1 |

TABLE 5-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-232 | 0.001 | 0.0014 | 0.89 | 0.90 |
| I-233 | 0.005 | 0.0068 | >1 | >1 |
| I-234 | 0.0009 | 0.0013 | >1 | >1 |
| I-235 | 0.0007 | 0.0011 | >1 | 0.93 |
| I-236 | 0.0082 | 0.0186 | >1 | >1 |
| I-237 | 0.0058 | 0.0141 | >1 | >1 |
| I-238 | 0.0025 | 0.0085 | >1 | >1 |
| I-239 | 0.0032 | 0.0064 | >1 | >1 |
| I-240 | 0.0001 | 0.0003 | >1 | >1 |
| I-241 | 0.0017 | 0.002 | >1 | >1 |
| I-242 | 0.005 | 0.0077 | >1 | >1 |
| I-243 | 0.0041 | 0.0085 | >1 | >1 |
| I-244 | 0.0075 | 0.0102 | 3.75 | 3.65 |
| I-245 | 0.0003 | 0.0006 | >1 | >1 |
| I-246 | 0.0017 | 0.002 | >1 | >1 |
| I-247 | 0.0043 | 0.0071 | >1 | >1 |
| I-248 | 0.0566 | 0.0585 | >1 | >1 |
| I-249 | 0.0006 | 0.0007 | >1 | >1 |
| I-250 | 0.057 | 0.128 | >1 | >1 |
| I-251 | 0.0058 | 0.0166 | >1 | >1 |
| I-252 | 0.0026 | 0.0067 | >1 | >1 |
| I-253 | 0.092 | 0.185 | >1 | >1 |
| I-254 | 0.0002 | 0.0003 | >1 | >1 |
| I-255 | 0.0036 | 0.0038 | >1 | >1 |
| I-256 | 0.0061 | 0.0123 | >1 | >1 |
| I-257 | 0.0001 | 0.0002 | >0.1 | >0.1 |
| I-258 | 0.0017 | 0.0019 | >1 | >1 |
| I-259 | 0.0062 | 0.0165 | >1 | >1 |
| I-260 | 0.0007 | 0.0011 | >0.1 | >0.1 |
| I-261 | 0.0035 | 0.0065 | >1 | >1 |
| I-262 | 0.0092 | 0.0145 | >1 | >1 |
| I-263 | 0.0065 | 0.0072 | 0.22 | >1 |
| I-264 | 0.0031 | 0.0052 | >1 | >1 |
| I-265 | 0.0039 | 0.0056 | 0.57 | >1 |
| I-266 | 0.0006 | 0.001 | >0.1 | >1 |
| I-267 | 0.0014 | 0.002 | 0.56 | >1 |
| I-268 | 0.0645 | 0.1035 | >1 | >1 |
| I-269 | 0.0905 | 0.12 | >1 | >1 |
| I-270 | 0.0475 | 0.071 | >1 | >1 |
| I-271 | 0.0133 | 0.0303 | >1 | >1 |
| I-272 | 0.0015 | 0.0025 | >1 | >1 |
| I-273 | 0.0007 | 0.0012 | >1 | >1 |
| I-274 | 0.0026 | 0.0046 | >1 | >1 |
| I-275 | 0.0098 | 0.0167 | >1 | >1 |
| I-276 | 0.0004 | 0.0004 | >1 | >1 |
| I-277 | 0.0013 | 0.0013 | >1 | >1 |
| I-278 | 0.0021 | 0.0028 | >1 | >1 |
| I-279 | 0.0033 | 0.0046 | >1 | >1 |
| I-280 | 0.0096 | 0.006 | >1 | >1 |
| I-281 | 0.0025 | 0.0036 | >1 | >1 |
| I-282 | 0.016 | 0.0142 | >1 | >1 |
| I-283 | 0.0022 | 0.002 | >1 | >1 |
| I-284 | 0.001 | 0.0014 | >1 | >1 |
| I-285 | 0.0018 | 0.0026 | 0.65 | >1 |
| I-286 | 0.0027 | 0.0039 | 0.84 | >1 |
| I-287 | 0.002 | 0.0028 | 0.63 | 0.98 |
| I-288 | 0.0012 | 0.0018 | 0.77 | >1 |
| I-289 | 0.0015 | 0.0025 | 0.43 | 0.54 |
| I-290 | 0.0034 | 0.0031 | 0.53 | 0.73 |
| I-291 | 0.0002 | 0.0003 | 0.75 | 0.67 |
| I-292 | 0.0024 | 0.0022 | >1 | >1 |
| I-293 | 0.0066 | 0.0094 | >1 | >1 |
| I-294 | 0.0088 | 0.0137 | >1 | >1 |
| I-295 | 0.0075 | 0.0083 | >1 | >1 |
| I-296 | 0.032 | 0.0447 | >1 | >1 |
| I-297 | 0.0091 | 0.0127 | 0.3 | >1 |
| I-298 | 0.0023 | 0.0018 | >1 | >1 |
| I-299 | 0.0373 | 0.053 | >1 | >1 |
| I-300 | 0.0277 | 0.0265 | >1 | >1 |
| I-301 | 0.003 | 0.003 | >1 | >1 |
| I-302 | 0.0103 | 0.013 | 1.10 | 0.90 |
| I-303 | 0.002 | 0.002 | >1 | >1 |
| I-304 | 0.0403 | 0.0543 | >1 | >1 |
| I-305 | 0.033 | 0.045 | >1 | >1 |
| I-306 | 0.068 | 0.185 | >1 | >1 |

TABLE 5-continued

| Compound number | SLIGKV IC50 (μM) | Trypsin IC50 (μM) | Thrombin IC50 (μM) | UTP IC50 (μM) |
|---|---|---|---|---|
| | Compound biological data | | | |
| I-307 | 0.0528 | 0.042 | >1 | >1 |
| I-308 | 0.028 | 0.0335 | >1 | >1 |
| I-309 | 0.0175 | 0.019 | >1 | >1 |
| I-310 | 0.0006 | 0.001 | >1 | 0.88 |
| I-311 | 0.0068 | 0.0041 | >1 | >1 |
| I-312 | 0.0013 | 0.0013 | >1 | >1 |
| I-313 | 0.0152 | 0.0114 | >1 | >1 |
| I-314 | 0.0104 | 0.0076 | >1 | >1 |
| I-315 | 0.0575 | 0.034 | >1 | >1 |
| I-316 | 0.0035 | 0.0031 | >1 | >1 |
| I-317 | 0.0034 | 0.0029 | >1 | >1 |
| I-318 | 0.0017 | 0.0022 | >1 | >1 |
| I-319 | 0.0004 | 0.0006 | 0.76 | 0.95 |
| I-320 | 0.0071 | 0.0142 | >1 | >1 |
| I-321 | 0.0015 | 0.0028 | >1 | >1 |
| I-322 | 0.0415 | 0.069 | >1 | >1 |
| I-323 | 0.0205 | 0.0555 | >1 | >1 |
| I-324 | 0.0211 | 0.0225 | >1 | >1 |
| I-325 | 0.0555 | 0.1095 | >1 | >1 |
| I-326 | 0.017 | 0.012 | >1 | >1 |
| I-327 | 0.0056 | 0.0059 | >1 | >1 |
| I-328 | 0.0014 | 0.0017 | >1 | >1 |
| I-329 | 0.0059 | 0.0028 | >1 | >1 |
| I-330 | 0.0017 | 0.0014 | >1 | >1 |
| I-331 | 0.0114 | 0.0069 | >1 | >1 |
| I-332 | 0.0133 | 0.0115 | >1 | >1 |
| I-333 | 0.0032 | 0.0038 | >1 | >1 |
| I-334 | 0.0046 | 0.0048 | >1 | >1 |
| I-335 | 0.0008 | 0.0006 | >1 | >1 |
| I-336 | 0.005 | 0.0028 | >1 | >1 |
| I-337 | 0.0054 | 0.0045 | >1 | >1 |
| I-338 | 0.0022 | 0.0016 | >1 | >1 |
| I-339 | 0.0019 | 0.0019 | >1 | >1 |
| I-340 | 0.0015 | 0.0016 | >1 | >1 |
| I-341 | 0.0021 | 0.0017 | >1 | >1 |
| I-342 | 0.0126 | 0.0082 | >1 | >1 |
| I-343 | 0.0005 | 0.0008 | 1.11 | 1.03 |
| I-344 | 0.0154 | 0.0158 | >1 | >1 |
| I-345 | 0.0056 | 0.0062 | >1 | >1 |
| I-346 | 0.0433 | 0.0465 | >1 | >1 |
| I-347 | 0.0029 | 0.0023 | >1 | >1 |
| I-348 | 0.004 | 0.0051 | 0.6734 | 0.36 |
| I-349 | 0.003 | 0.0026 | >1 | >1 |
| I-350 | 0.0129 | 0.0137 | >1 | >1 |
| I-351 | 0.005 | 0.0034 | >1 | >1 |
| I-352 | 0.0012 | 0.0015 | >1 | >1 |
| I-353 | 0.0024 | 0.003 | >1 | >1 |
| I-354 | 0.0012 | 0.0013 | >1 | >1 |
| I-355 | 0.0096 | 0.007 | >1 | >1 |
| I-356 | 0.028 | 0.015 | >1 | >1 |
| I-357 | 0.0033 | 0.0044 | >1 | 0.89 |
| I-358 | 0.0113 | 0.0044 | >1 | >1 |
| I-359 | 0.001 | 0.0011 | >1 | >1 |
| I-360 | 0.0046 | 0.003 | >1 | >1 |
| I-361 | 0.0027 | 0.0022 | >1 | >1 |
| I-362 | 0.013 | 0.031 | >1 | >1 |
| I-363 | 0.0054 | 0.0028 | >1 | >1 |
| I-364 | 0.0015 | 0.0017 | >1 | >1 |
| I-365 | 0.0011 | 0.0015 | >1 | >1 |
| I-366 | 0.0022 | 0.0025 | >1 | >1 |
| I-367 | 0.0026 | 0.0042 | >1 | >1 |
| I-368 | 0.0052 | 0.0068 | >1 | >1 |
| I-369 | 0.0054 | 0.0073 | >1 | >1 |
| I-370 | 0.0077 | 0.0104 | >1 | >1 |
| I-371 | 0.0013 | 0.0016 | >1 | >1 |
| I-372 | 0.0045 | 0.0056 | >1 | >1 |
| I-373 | 0.0065 | 0.0081 | >1 | >1 |
| I-374 | 0.0014 | 0.0016 | >1 | >1 |
| I-375 | 0.0023 | 0.0038 | >1 | >1 |
| I-376 | 0.002 | 0.0032 | >1 | >1 |
| I-377 | 0.019 | 0.029 | >1 | >1 |
| I-378 | 0.005 | 0.0072 | >1 | >1 |
| I-379 | 0.0094 | 0.0105 | >1 | >1 |
| I-380 | 0.0083 | 0.0074 | >1 | >1 |
| I-381 | 0.0013 | 0.0012 | >1 | >1 |

TABLE 5-continued

| Compound number | SLIGKV IC50 (μM) | Trypsin IC50 (μM) | Thrombin IC50 (μM) | UTP IC50 (μM) |
|---|---|---|---|---|
| | Compound biological data | | | |
| I-382 | 0.0006 | 0.0007 | >1 | >1 |
| I-383 | 0.0019 | 0.0029 | >1 | >1 |
| I-384 | 0.0006 | 0.0008 | >1 | >1 |
| I-385 | 0.0022 | 0.0043 | >1 | >1 |
| I-386 | 0.0017 | 0.0026 | >1 | >1 |
| I-387 | 0.0014 | 0.0031 | >1 | >1 |
| I-388 | 0.0125 | 0.0155 | >1 | >1 |
| I-389 | 0.02 | 0.025 | >1 | >1 |
| I-390 | 0.001 | 0.0013 | >1 | >1 |
| I-391 | 0.0018 | 0.0022 | >1 | >1 |
| I-392 | 0.0014 | 0.0025 | >1 | >1 |
| I-393 | 0.0016 | 0.0015 | >1 | >1 |
| I-394 | 0.0009 | 0.0011 | >1 | >1 |
| I-395 | 0.0006 | 0.0005 | >1 | >1 |
| I-396 | 0.0004 | 0.0007 | >1 | >1 |
| I-397 | 0.0006 | 0.0006 | >1 | >1 |
| I-398 | 0.0031 | 0.0026 | >1 | >1 |
| I-399 | 0.0018 | 0.0015 | >1 | >1 |
| I-400 | 0.0036 | 0.0028 | >1 | >1 |
| I-401 | 0.0021 | 0.0015 | >1 | >1 |
| I-402 | 0.0008 | 0.001 | >1 | >1 |
| I-403 | 0.001 | 0.0015 | >1 | >1 |
| I-404 | 0.0009 | 0.0043 | 0.69 | >1 |
| I-405 | 0.0016 | 0.0018 | >1 | >1 |
| I-406 | 0.0022 | 0.0028 | 0.37 | >1 |
| I-407 | 0.0056 | 0.0051 | >1 | >1 |
| I-408 | 0.0028 | 0.0043 | 0.54 | >1 |
| I-409 | 0.0017 | 0.0017 | 0.83 | >1 |
| I-410 | 0.0063 | 0.0082 | 0.95 | >1 |
| I-411 | 0.0048 | 0.0065 | 0.88 | >1 |
| I-412 | 0.0064 | 0.01 | 0.71 | >1 |
| I-413 | 0.0034 | 0.0043 | >1 | >1 |
| I-414 | 0.001 | 0.0013 | >1 | >1 |
| I-415 | 0.0003 | 0.0005 | >1 | >1 |
| I-416 | 0.0006 | 0.0006 | >1 | >1 |
| I-417 | 0.0025 | 0.0032 | >1 | >1 |
| I-418 | 0.0076 | 0.0071 | >1 | >1 |
| I-419 | 0.0011 | 0.0009 | >1 | >1 |
| I-420 | 0.0017 | 0.0024 | >1 | >1 |
| I-421 | 0.0003 | 0.0002 | >1 | >1 |
| I-422 | 0.0019 | 0.002 | >1 | >1 |
| I-423 | 0.0017 | 0.0022 | >1 | >1 |
| I-424 | 0.0009 | 0.0012 | >1 | >1 |
| I-425 | 0.0015 | 0.0012 | >1 | >1 |
| I-426 | 0.0017 | 0.0018 | >1 | >1 |
| I-427 | 0.0005 | 0.0007 | >1 | >1 |
| I-428 | 0.0307 | 0.0597 | >1 | >1 |
| I-429 | 0.0024 | 0.0033 | >1 | >1 |
| I-430 | 0.0163 | 0.0238 | >1 | >1 |
| I-431 | 0.0014 | 0.0016 | >1 | >1 |
| I-432 | 0.0019 | 0.0021 | >1 | >1 |
| I-433 | 0.0007 | 0.0011 | >1 | >1 |
| I-434 | 0.0005 | 0.0005 | >1 | >1 |
| I-435 | 0.0008 | 0.0007 | >1 | >1 |
| I-436 | 0.0003 | 0.0004 | 11.0 | 3.60 |
| I-437 | 0.0007 | 0.002 | >1 | >1 |
| I-438 | 0.0015 | 0.0026 | >1 | >1 |
| I-439 | 0.081 | 0.125 | >1 | >1 |
| I-440 | 0.0081 | 0.014 | >1 | >1 |
| I-441 | 0.0005 | 0.0006 | >1 | >1 |
| I-442 | 0.109 | 0.15 | >1 | >1 |
| I-443 | 0.0008 | 0.0012 | >1 | >1 |
| I-444 | 0.0008 | 0.0013 | >1 | >1 |
| I-445 | 0.0004 | 0.0009 | >1 | >1 |
| I-446 | 0.056 | 0.104 | >1 | >1 |
| I-447 | 0.17 | 0.18 | >1 | >1 |
| I-448 | 0.0069 | 0.0114 | 17.5 | 14.5 |
| I-449 | 0.0255 | 0.0465 | >1 | >1 |
| I-450 | 0.0001 | 0.0003 | >1 | >1 |
| I-451 | 0.0001 | 0.0003 | >1 | 0.71 |
| I-452 | 0.0033 | 0.0062 | 7.85 | 11.6 |
| I-453 | 0.0007 | 0.0012 | >1 | >1 |
| I-454 | 0.0004 | 0.0007 | >1 | >1 |
| I-455 | 0.0006 | 0.0009 | >1 | >1 |
| I-456 | 0.0005 | 0.0007 | >1 | >1 |

TABLE 5-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-457 | 0.0006 | 0.0008 | >1 | >1 |
| I-458 | 0.0013 | 0.0021 | >1 | >1 |
| I-459 | 0.001 | 0.0015 | >1 | >1 |
| I-460 | 0.0005 | 0.0007 | >1 | >1 |
| I-461 | 0.0148 | 0.0398 | >1 | >1 |
| I-462 | 0.0022 | 0.0037 | >1 | >1 |
| I-463 | 0.0018 | 0.0027 | >1 | >1 |
| I-464 | 0.0012 | 0.0022 | >1 | >1 |
| I-465 | 0.0018 | 0.0037 | >1 | >1 |
| I-466 | 0.0007 | 0.0019 | >1 | >1 |
| I-467 | 0.0009 | 0.002 | >1 | >1 |
| I-468 | 0.0007 | 0.0012 | 3.24 | 2.1225 |
| I-469 | 0.0002 | 0.0002 | 8.84 | 11.025 |
| I-470 | 0.0257 | 0.0317 | >1 | >1 |
| I-471 | 0.0008 | 0.0016 | 0.905 | >1 |
| I-472 | 0.0062 | 0.013 | >1 | 0.82 |
| I-473 | 0.015 | 0.0255 | 0.475 | 0.39 |
| I-474 | 0.0024 | 0.02 | >1 | >1 |
| I-475 | 0.0038 | 0.0071 | 10.3 | 13.7 |
| I-476 | 0.66 | 0.965 | >1 | >1 |
| I-477 | 0.043 | 0.093 | >1 | >1 |
| I-478 | 0.79 | 1.00 | >1 | >1 |
| I-479 | 0.155 | 0.25 | >1 | >1 |
| I-480 | 0.02 | 0.06 | >1 | >1 |
| I-481 | 0.0472 | 0.0445 | >1 | >1 |
| I-482 | 0.0027 | 0.0027 | 2.70 | 6.35 |
| I-483 | 0.0025 | 0.0043 | 6.90 | 6.80 |
| I-484 | 0.0028 | 0.0096 | >1 | N/A |
| I-485 | 0.097 | 0.235 | >1 | >1 |
| I-486 | 0.0017 | 0.0021 | 4.15 | 2.18 |
| I-487 | 0.0003 | 0.0003 | >1 | >1 |
| I-488 | 0.0042 | 0.0042 | >1 | >1 |
| I-489 | 0.001 | 0.0009 | 8.60 | 4.10 |
| I-490 | 0.0001 | 0.0002 | >1 | >1 |
| I-491 | 0.0024 | 0.0032 | >1 | >1 |
| I-492 | 0.004 | 0.0056 | 0.82 | 0.69 |
| I-493 | 0.0005 | 0.0005 | 0.76 | 0.44 |
| I-494 | 0.0124 | 0.0139 | >1 | >1 |
| I-495 | 0.0041 | 0.005 | 21.5 | 11.1 |
| I-496 | 0.0553 | 0.1013 | >1 | >1 |
| I-497 | 0.405 | 0.27 | >1 | >1 |
| I-498 | 0.0056 | 0.0074 | >1 | >1 |
| I-499 | 0.0083 | 0.0096 | >1 | >1 |
| I-500 | 0.0003 | 0.0004 | >1 | >1 |
| I-501 | 0.051 | 0.0595 | >1 | >1 |
| I-502 | 0.021 | 0.02 | >1 | >1 |
| I-503 | 0.0039 | 0.0046 | >1 | >1 |
| I-504 | 0.0012 | 0.0015 | >1 | 0.46 |
| I-505 | 0.012 | 0.023 | >1 | >1 |
| I-506 | 0.1067 | 0.1633 | >1 | >1 |
| I-507 | 0.0031 | 0.0049 | >1 | >1 |
| I-508 | 0.0047 | 0.0041 | >1 | >1 |
| I-509 | 0.0825 | 0.17 | >1 | >1 |
| I-510 | 0.0068 | 0.0088 | >1 | >1 |
| I-511 | 0.023 | 0.087 | >1 | >1 |
| I-512 | 0.0235 | 0.053 | >1 | >1 |
| I-513 | 0.0018 | 0.003 | >1 | >1 |
| I-514 | 0.16 | 0.315 | >1 | >1 |
| I-515 | 0.0625 | 0.11 | >1 | >1 |
| I-516 | 0.0395 | 0.092 | >1 | >1 |
| I-517 | 0.0027 | 0.0021 | >1 | >1 |
| I-518 | 0.057 | 0.0685 | >1 | >1 |
| I-519 | 0.0004 | 0.0004 | >1 | >1 |
| I-520 | 0.001 | 0.001 | >1 | >1 |
| I-521 | 0.625 | 0.48 | >1 | >1 |
| I-522 | 0.0019 | 0.0024 | >1 | >1 |
| I-523 | 0.012 | 0.0096 | >1 | >1 |
| I-524 | 0.0014 | 0.0017 | >1 | >1 |
| I-525 | 0.116 | 0.2465 | >1 | >1 |
| I-526 | 0.0006 | 0.0008 | >1 | >1 |
| I-527 | 0.0043 | 0.003 | >1 | >1 |
| I-528 | 0.0018 | 0.0042 | >1 | >1 |
| I-529 | 0.0022 | 0.0037 | >1 | >1 |
| I-530 | 0.0013 | 0.0022 | 0.41 | 0.50 |
| I-531 | 0.0012 | 0.002 | >1 | >1 |

TABLE 5-continued

| Compound biological data | | | | |
|---|---|---|---|---|
| Compound number | SLIGKV IC50 (μM) | Trypsin IC50 (μM) | Thrombin IC50 (μM) | UTP IC50 (μM) |
| I-532 | 0.0008 | 0.0011 | >1 | >1 |
| I-533 | 0.0047 | 0.0079 | >1 | >1 |
| I-534 | 0.00008 | 0.0001 | >1 | >1 |
| I-535 | 0.8275 | 0.058 | >1 | >1 |
| I-536 | 0.17 | 0.235 | >1 | >1 |
| I-537 | 0.0008 | 0.0012 | >1 | >1 |
| I-538 | 0.0008 | 0.0009 | >1 | >1 |
| I-539 | 0.0008 | 0.0013 | >1 | >1 |
| I-540 | 0.0042 | 0.0082 | >1 | >1 |
| I-541 | 0.001 | 0.0015 | >1 | >1 |
| I-542 | 0.0002 | 0.0003 | >1 | >1 |
| I-543 | 0.0032 | 0.0048 | >1 | >1 |
| I-544 | 0.0015 | 0.0018 | >1 | >1 |
| I-545 | 0.0011 | 0.0019 | >1 | >1 |
| I-546 | 0.0018 | 0.0016 | >1 | >1 |
| I-547 | 0.635 | >1 | >1 | >1 |
| I-548 | 0.545 | >1 | >1 | >1 |
| I-549 | 0.0275 | 0.0575 | >1 | >1 |
| I-550 | 0.7733 | 1.055 | >30 | >30 |
| I-551 | 0.97 | 1.5 | >30 | >30 |
| I-552 | 0.72 | 0.72 | >1 | >1 |
| I-553 | 0.024 | 0.0495 | >1 | >1 |
| I-554 | 0.0093 | 0.0112 | >1 | >1 |
| I-555 | 0.0042 | 0.0078 | >1 | >1 |
| I-556 | 0.009 | 0.021 | >1 | >1 |
| I-557 | 0.0024 | 0.005 | >1 | >1 |
| I-558 | 0.0185 | 0.0435 | >1 | >1 |
| I-559 | 0.02 | 0.0515 | >1 | >1 |
| I-560 | 0.0049 | 0.0093 | >1 | >1 |
| I-561 | 0.0005 | 0.0007 | >1 | >1 |
| I-562 | 0.028 | 0.1285 | >1 | >1 |
| I-563 | 0.0003 | 0.0004 | >1 | >1 |
| I-564 | 0.125 | 0.1935 | >1 | >1 |
| I-565 | 0.043 | 0.042 | >1 | >1 |
| I-566 | 0.003 | 0.0051 | >1 | >1 |
| I-567 | 0.023 | 0.0498 | >1 | >1 |
| I-568 | 0.52 | 0.62 | >1 | >1 |
| I-569 | 0.395 | 0.64 | >1 | >1 |
| I-570 | 0.0016 | 0.0022 | >1 | >1 |
| I-571 | 0.0011 | 0.0033 | 0.98 | >1 |
| I-572 | 0.0054 | 0.059 | >1 | >1 |
| I-573 | 0.1025 | 0.435 | >1 | >1 |
| I-574 | 0.56 | 31% @ 1 μM | >1 | >1 |
| I-575 | 0.084 | 0.12 | >1 | >1 |
| I-576 | 0.15 | 0.26 | >1 | >1 |
| I-577 | 0.70 | 0.84 | >1 | >1 |
| I-578 | 0.37 | 0.65 | >1 | >1 |
| I-579 | 0.14 | 0.28 | 1.1 | >1 |

TABLE 6
| Compound biological data | | | |
|---|---|---|---|
| Compound Number | Structure | SLIGKV $IC_{50}$ (μM) | Trypsin $IC_{50}$ (μM) |
| I-580 | 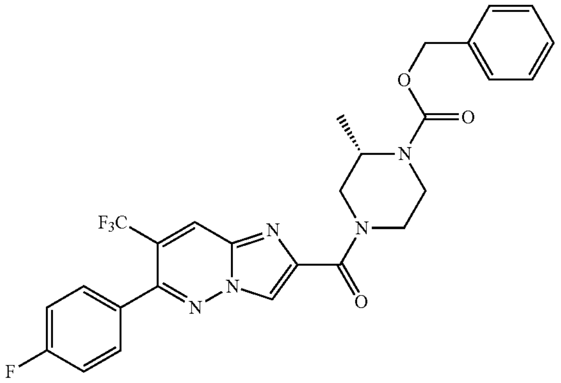 [SMILES: C[C@H]1CN(C(=O)c2cn3nc(-c4ccc(F)cc4)c(C(F)(F)F)cc3n2)CCN1C(=O)OCc1ccccc1] | 23 | 48% @ 50 |
| I-581 | 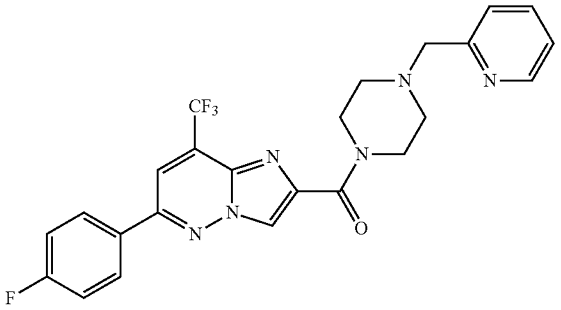 [SMILES: O=C(c1cn2nc(-c3ccc(F)cc3)cc(C(F)(F)F)c2n1)N1CCN(Cc2ccccn2)CC1] | 50 | 46 |
| I-582 | 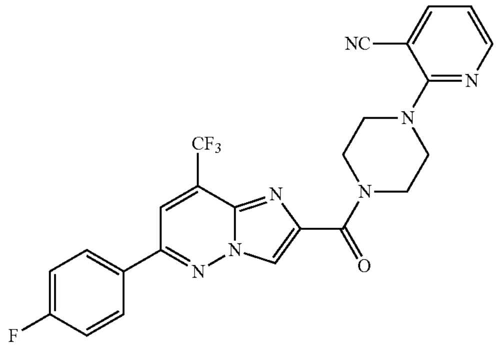 [SMILES: N#Cc1cccnc1N1CCN(C(=O)c2cn3nc(-c4ccc(F)cc4)cc(C(F)(F)F)c3n2)CC1] | 50 | >50 |
| I-583 | 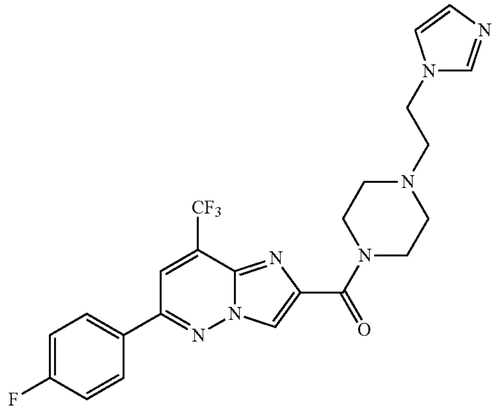 [SMILES: O=C(c1cn2nc(-c3ccc(F)cc3)cc(C(F)(F)F)c2n1)N1CCN(CCn2ccnc2)CC1] | 23 | >50 |

TABLE 6-continued
| Compound biological data | | | |
|---|---|---|---|
| Compound Number | Structure | SLIGKV $IC_{50}$ (μM) | Trypsin $IC_{50}$ (μM) |
| I-584 | 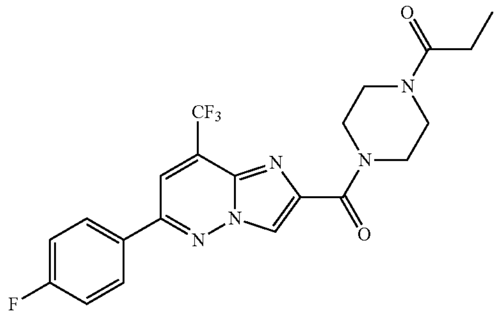 [SMILES: CCC(=O)N1CCN(C(=O)c2cn3nc(-c4ccc(F)cc4)cc(C(F)(F)F)c3n2)CC1] | 22 | 2 |
| I-585 | 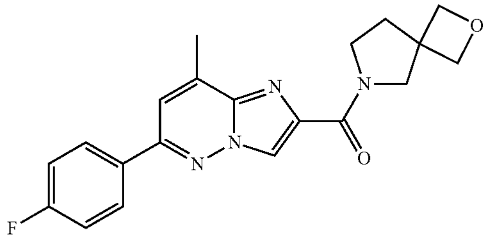 [SMILES: Cc1cc(-c2ccc(F)cc2)nn2cc(C(=O)N3CCC4(COC4)C3)nc12] | 27 | 24 |
| I-586 | 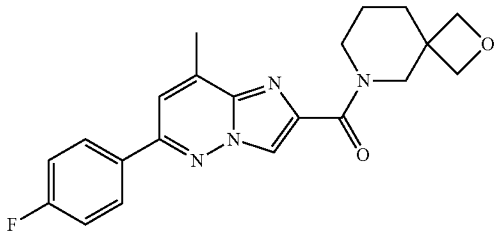 [SMILES: Cc1cc(-c2ccc(F)cc2)nn2cc(C(=O)N3CCCC4(COC4)C3)nc12] | 13 | 19 |
| I-587 | 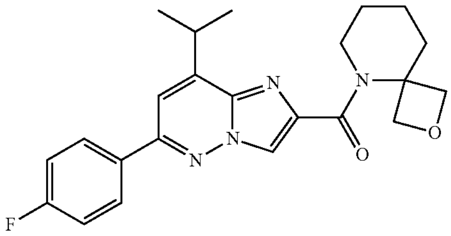 [SMILES: CC(C)c1cc(-c2ccc(F)cc2)nn2cc(C(=O)N3CCCCC34COC4)nc12] | 25 | 19 |
| I-588 | 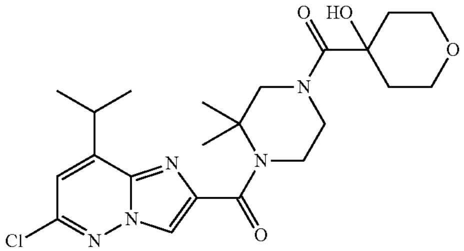 [SMILES: CC(C)c1cc(Cl)nn2cc(C(=O)N3CCN(C(=O)C4(O)CCOCC4)CC3(C)C)nc12] | 37 | >50 |

TABLE 6-continued

| Compound biological data | | | |
|---|---|---|---|
| Compound Number | Structure | SLIGKV $IC_{50}$ (μM) | Trypsin $IC_{50}$ (μM) |
| I-589 | 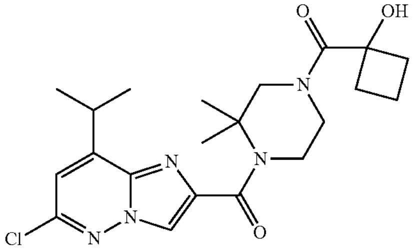 [SMILES: CC(C)c1cc(Cl)nn2cc(C(=O)N3CCN(C(=O)C4(O)CCC4)CC3(C)C)nc12] | 27 | >50 |
| I-590 | 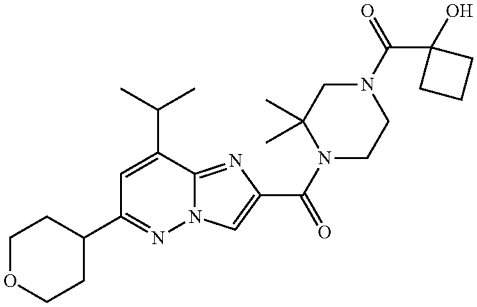 [SMILES: CC(C)c1cc(C2CCOCC2)nn2cc(C(=O)N3CCN(C(=O)C4(O)CCC4)CC3(C)C)nc12] | 20 | >50 |
| I-591 | 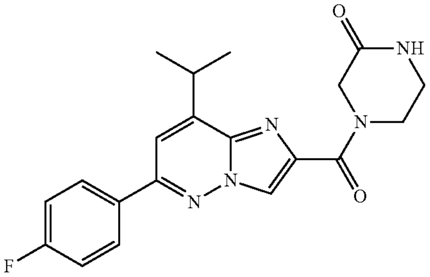 [SMILES: CC(C)c1cc(-c2ccc(F)cc2)nn2cc(C(=O)N3CCNC(=O)C3)nc12] | 17 | 41 |

Example 61: Protocol for Testing PAR2 Compounds In Vivo Rat Pharmacokinetics Experiments Compounds delivered by intravenous route were formulated using a solution formulation consisting of 5% N-methylpyrrolidone 10% Vitamin E-TPGS and 85% water (v/v/) or a solution formulation consisting of 25% N-methylpyrrolidone 35% polyethylene glycol 400 and 40% water (v/v/). Intravenous formulations were administered by a bolus injection (over approximately 10 seconds) using a hypodermic needle attaches to a syringe (tail vein). The dose volume was varied from 1 to 2 mL/kg and the dose was varied from 0.5 to 1 mg/kg. Compounds delivered orally were formulated as a solution formulation consisting of 5% N-methylpyrrolidone 10% Vitamin E-TPGS and 85% water (v/v/) or as fine suspension using a cellulose derivative suspending agent with or without the addition of a wetting agent/surfactant. Milling of large particles was performed as needed to reduce particle size using focused electroacoustic milling, homogenization or low energy media milling. A spray-dried solid dispersion was prepared for key compounds using 1:1 combination with cellulose derivatives. Test compounds were administered orally by gavage using a gavage plastic needle attached to a syringe. The dose volume was varied from 5 to 10 mL/kg and the dose was varied from 1 to 600 mg/kg.

Rats were bled by venipuncture (jugular vein) and the samples were collected into tubes containing $K_3EDTA$. The tubes were placed on wet ice until processed. The samples were centrifuged for approximately 10 minutes (at approximately 4° C.) within approximately 30 minutes of collection to prepare plasma or diluted in citrate buffer (1:3) and stored frozen (approximately −30° C.). Thawed plasma or whole blood samples were extracted by protein precipitation using an organic solvent followed by centrifugation. The supernatants were separated by high-performance liquid chromatography coupled to mass spectrometry detection. A calibration curve was prepared using reference standard compounds spiked into either blank plasma or whole blood matrices and extracted similarly to unknown samples. Pharmacokinetic parameters were calculated using non-compartmental analysis.

TABLE 7

| Compound pharmacokinetic data in rat | | | | |
|---|---|---|---|---|
| Compound number | $Cl_p$ (mL/min/kg) | T 1/2 (h) | Vss | F (%) |
| I-9 | 21.7 | 1.2 | 1.4 | 57 |
| I-29 | 3.6 | 6.7 | 1.8 | 71 |

TABLE 7-continued
| Compound pharmacokinetic data in rat | | | | |
|---|---|---|---|---|
| Compound number | $Cl_p$ (mL/min/kg) | T 1/2 (h) | Vss | F (%) |
| I-32 | 29.3 | 1.4 | 2.2 | 39 |
| I-191 | 0.7 | 56.9 | 3.2 | 66 |
| I-199 | 3.2 | 18.1 | 4.2 | 67 |
| I-201 | 10.9 | 4.3 | 3.3 | 55 |
| I-232 | 16.9 | 2.5 | 3.3 | 75 |
| I-244 | 4.8 | 5.1 | 1.6 | 70 |
| I-252 | 4.17 | 5.85 | 1.49 | 92 |
| I-283 | 1.07 | 77.90 | 6.82 | 76 |
| I-303 | 7.15 | 5.36 | 2.04 | 69 |
| I-343 | 3.39 | 7.03 | 1.65 | 62 |
| I-421 | 6.15 | 9.62 | 3.07 | 189 |
| I-436 | 4.21 | 7.5 | 2.05 | 77 |
| I-448 | 6.44 | 5.14 | 1.84 | 87 |
| I-452 | 7.24 | 3.62 | 1.96 | 67 |
| I-563 | 61.7 | 0.413 | 1.19 | 15 |
TABLE 8
| Reported compounds of WO2005/030773, JP2003286171, & JP2004170323 | | | |
|---|---|---|---|
| Compound number | Structure | SLIGKV $IC_{50}$ (μM) | Trypsin $IC_{50}$ (μM) |
| P-592 | 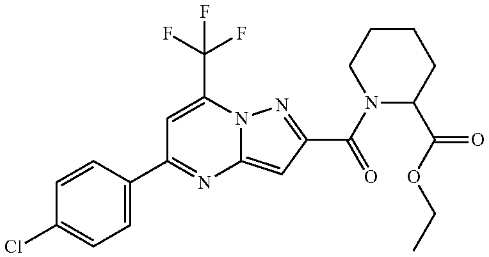 [SMILES: CCOC(=O)C1CCCCN1C(=O)c1cc2nc(-c3ccc(Cl)cc3)cc(C(F)(F)F)n2n1] | 0.057 | 0.13 |
| P-593 | 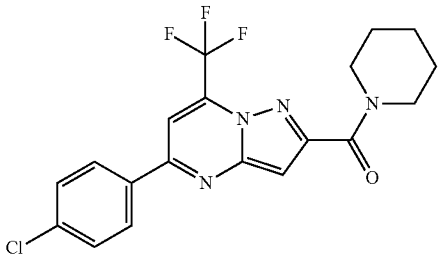 [SMILES: O=C(c1cc2nc(-c3ccc(Cl)cc3)cc(C(F)(F)F)n2n1)N1CCCCC1] | 67% @ 50 μM | >50 |
| P-594 | 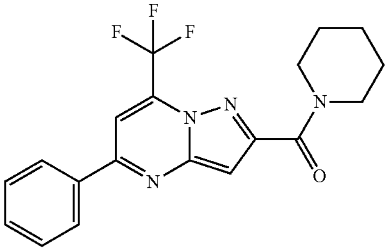 [SMILES: O=C(c1cc2nc(-c3ccccc3)cc(C(F)(F)F)n2n1)N1CCCCC1] | 4.67 | 28 |
| P-595 | 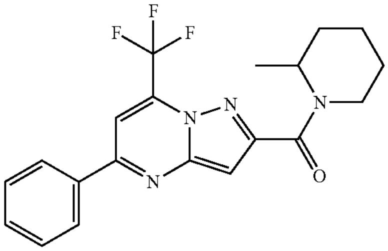 [SMILES: CC1CCCCN1C(=O)c1cc2nc(-c3ccccc3)cc(C(F)(F)F)n2n1] | 1.73 | 19.17 |

TABLE 8-continued
| Reported compounds of WO2005/030773, JP2003286171, & JP2004170323 | | | |
|---|---|---|---|
| Compound number | Structure | SLIGKV $IC_{50}$ (μM) | Trypsin $IC_{50}$ (μM) |
| P-596 | 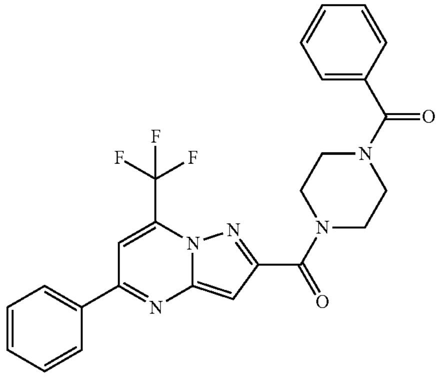 [SMILES: O=C(c1ccccc1)N1CCN(C(=O)c2cc3nc(-c4ccccc4)cc(C(F)(F)F)n3n2)CC1] | 10.79 | >50 |
| P-597 | 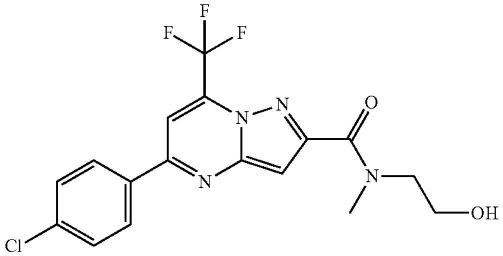 [SMILES: CN(CCO)C(=O)c1cc2nc(-c3ccc(Cl)cc3)cc(C(F)(F)F)n2n1] | 17.4 | 27 |
| P-598 | 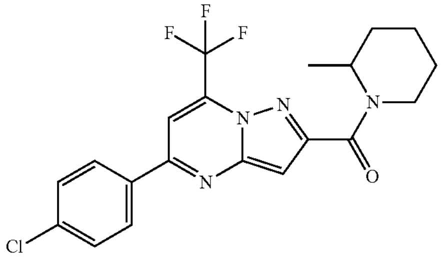 [SMILES: CC1CCCCN1C(=O)c1cc2nc(-c3ccc(Cl)cc3)cc(C(F)(F)F)n2n1] | >50 | >50 |
| P-599 | 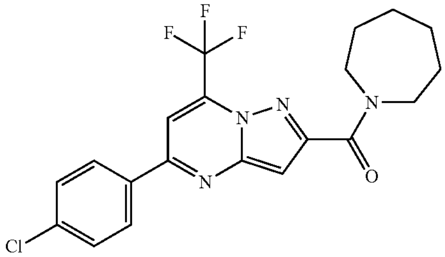 [SMILES: O=C(c1cc2nc(-c3ccc(Cl)cc3)cc(C(F)(F)F)n2n1)N1CCCCCC1] | 9.81 | >50 |
| P-600 | 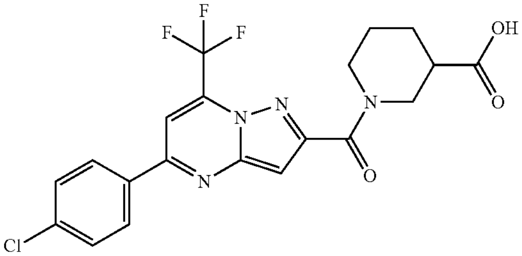 [SMILES: O=C(O)C1CCCN(C(=O)c2cc3nc(-c4ccc(Cl)cc4)cc(C(F)(F)F)n3n2)C1] | 37 | >50 |

TABLE 8-continued
| Reported compounds of WO2005/030773, JP2003286171, & JP2004170323 | | | |
|---|---|---|---|
| Compound number | Structure | SLIGKV $IC_{50}$ (μM) | Trypsin $IC_{50}$ (μM) |
| P-601 | 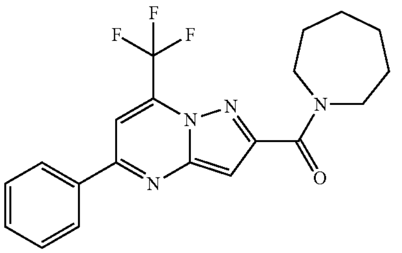 [SMILES: O=C(c1cc2nc(-c3ccccc3)cc(C(F)(F)F)n2n1)N1CCCCCC1] | 0.061 | 0.88 |
| P-602 | 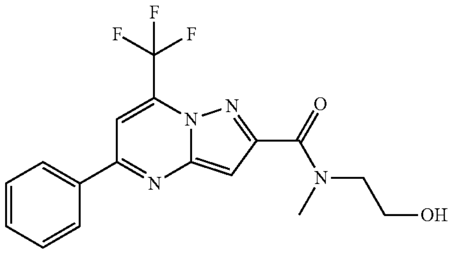 [SMILES: CN(CCO)C(=O)c1cc2nc(-c3ccccc3)cc(C(F)(F)F)n2n1] | 31 | >50 |
| P-603 | 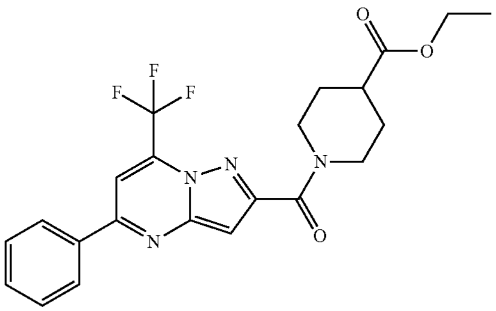 [SMILES: CCOC(=O)C1CCN(C(=O)c2cc3nc(-c4ccccc4)cc(C(F)(F)F)n3n2)CC1] | 0.14 | 17 |
| P-604 | 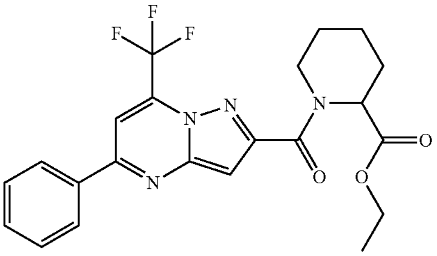 [SMILES: CCOC(=O)C1CCCCN1C(=O)c1cc2nc(-c3ccccc3)cc(C(F)(F)F)n2n1] | 0.64 | 3.85 |
| P-605 | 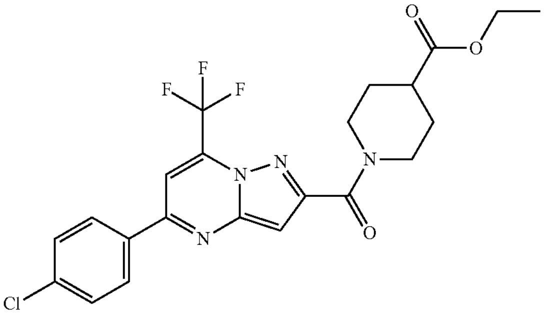 [SMILES: CCOC(=O)C1CCN(C(=O)c2cc3nc(-c4ccc(Cl)cc4)cc(C(F)(F)F)n3n2)CC1] | 0.073 | 50% @ 50 μM |

TABLE 8-continued
| Reported compounds of WO2005/030773, JP2003286171, & JP2004170323 | | | |
|---|---|---|---|
| Compound number | Structure | SLIGKV $IC_{50}$ (μM) | Trypsin $IC_{50}$ (μM) |
| P-606 | 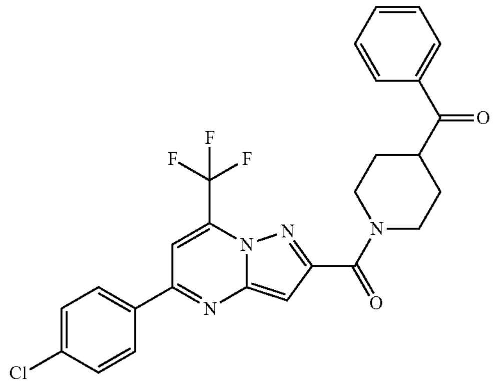 [SMILES: O=C(c1ccccc1)C1CCN(C(=O)c2cc3nc(-c4ccc(Cl)cc4)cc(C(F)(F)F)n3n2)CC1] | 0.37 | >50 |
| P-607 | 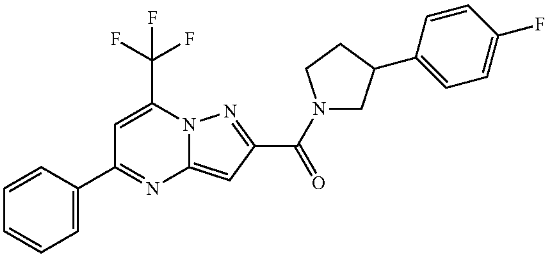 [SMILES: O=C(c1cc2nc(-c3ccccc3)cc(C(F)(F)F)n2n1)N1CCC(c2ccc(F)cc2)C1] | >50 | >50 |
| P-608 | 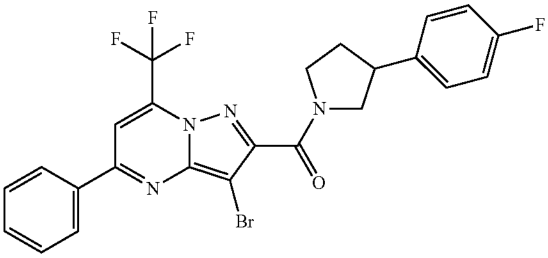 [SMILES: O=C(c1nn2c(C(F)(F)F)cc(-c3ccccc3)nc2c1Br)N1CCC(c2ccc(F)cc2)C1] | 23 | 33 |
| P-609 | 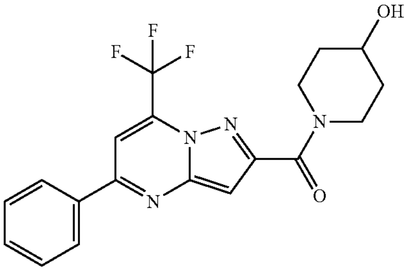 [SMILES: O=C(c1cc2nc(-c3ccccc3)cc(C(F)(F)F)n2n1)N1CCC(O)CC1] | 2.8 | 14 |
| P-610 | 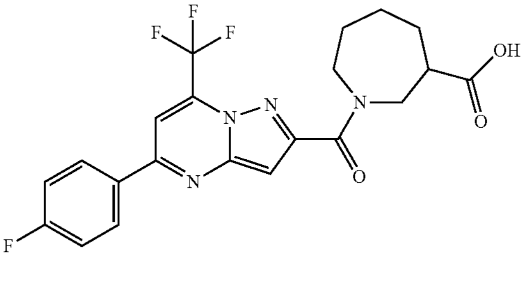 [SMILES: O=C(O)C1CCCCN(C(=O)c2cc3nc(-c4ccc(F)cc4)cc(C(F)(F)F)n3n2)C1] | 0.48 | 63% @ 50 μM |

TABLE 8-continued

| Reported compounds of WO2005/030773, JP2003286171, & JP2004170323 | | | |
|---|---|---|---|
| Compound number | Structure | SLIGKV $IC_{50}$ (μM) | Trypsin $IC_{50}$ (μM) |
| P-611 | 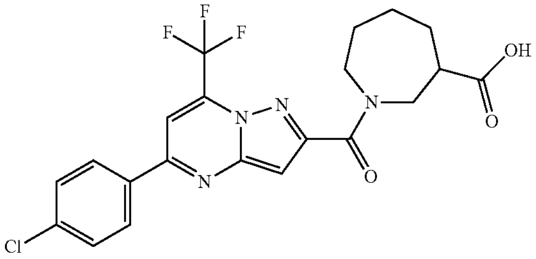 [SMILES: O=C(O)C1CCCCN(C(=O)c2cc3nc(-c4ccc(Cl)cc4)cc(C(F)(F)F)n3n2)C1] | 0.11 | 1.25 |

Example 62: In Vivo Pharmacological Evaluation of PAR2 Pathway Inhibitors Subjects and Housing Male Sprague Dawley rats and BALB/c mice were housed in groups in a temperature controlled room and were acclimatized in the animal facility for at least three days prior to use. Experiments were performed during the light phase of the cycle. Animals have food and water ad libitum.

Example 63: Rat Carrageenan-Induced Paw Edema Model

Peripheral inflammation was induced by intra-plantar administration of 100 ul of a 1% w/volume (in saline) carrageenan solution under isoflurane anesthesia. The degree of swelling was assessed using the plethysmometer at 2-3-4-5-6 h after carrageenan injection. Test compound or vehicle (0.5% MC/0.1% SDS) was systemically administered at the indicated doses in a volume of 5 mL/kg either 1-3 hour before carrageenan challenge (Table 9) or 2 hours post carrageenan challenge (Table 10).

TABLE 9

Inhibition of carrageenan induced paw edema in rats

| Compound | Dose (mg/kg) | % inhibition |
|---|---|---|
| I-27 | 3 | 16 |
| | 6 | 25* |
| | 10 | 30 |
| | 20 | 33** |
| | 30 | 31* |
| | 60 | 30** |
| I-199 | 7.5 | 14 |
| | 20 | 52*** |
| I-201 | 5 | 55** |
| | 20 | 60*** |
| I-213 | 7 | 36* |
| I-227 | 0.3 | 35* |
| | 10 | 64** |
| I-228 | 10 | 48** |
| I-232 | 10 | 19* |
| I-241 | 7 | 17** |
| I-244 | 2 | 42** |
| | 6 | 51** |
| | 20 | 67*** |
| I-288 | 10 | 48*** |
| I-291 | 5 | 37** |
| I-249 | 10 | 49*** |
| | 30 | 26* |
| I-283 | 20 | 19* |
| I-310 | 5 | 25** |
| I-316 | 10 | 39** |

TABLE 9-continued

Inhibition of carrageenan induced paw edema in rats

| Compound | Dose (mg/kg) | % inhibition |
|---|---|---|
| I-343 | 0.3 | 19* |
| | 3 | 28* |
| | 10 | 34* |
| | 30 | 50*** |
| I-417 | 20 | 32** |
| I-436 | 1 | −17* |
| | 30 | 36** |
| I-366 | 20 | 43** |
| I-421 | 1 | 11 |
| | 10 | −32** |
| I-429 | 20 | 43** |
| I-448 | 20 | 15 |
| I-525 | 50 | 9 |

TABLE 10

Inhibition of an established carrageenan induced rat paw edema

| Compound | Dose (mg/kg) | % inhibition |
|---|---|---|
| I-191 | 0.6 | 26 |
| | 2 | 40* |
| | 3 | 46*** |
| | 6 | 48* |
| | 10 | 50*** |
| | 30 | 57*** |
| I-343 | 3 | 32** |
| | 10 | 49** |
| | 30 | 58** |
| | 60 | 70*** |

Example 64: Rat Tryptase-Induced Mechanical Hypersensitivity Model

Peripheral sensitization was induced by intra-dermal administration of 500 ng of tryptase in a volume of 10 ul PBS under isoflurane anesthesia. Rats were then placed on a wire mesh grid in separate compartments and allowed to acclimatize before testing. Mechanical hypersensitivity was assessed 30 min after tryptase injection using calibrated von Frey filaments applied perpendicular to the plantar surface of the affected paw using the up-and-down method. Test compounds or vehicle (0.5% MC/0.1% SDS) were systemically administered at doses indicated in a volume of 5 mL/kg 3-18 h before the tryptase challenge (Table 11) or 30 minutes post tryptase challenge (Table 12).

TABLE 11

| Inhibition of tryptase-induced nociception | | |
|---|---|---|
| Compound | Dose (mg/kg) | % inhibition |
| I-191 | 1 | 26 |
| | 3 | 36 |
| | 10 | 40** |
| I-201 | 1.5 | 16* |
| | 5 | 52** |
| | 15 | 65*** |

TABLE 12

| Inhibition of an established tryptase-induced nociception | | |
|---|---|---|
| Compound | Dose (mg/kg) | % inhibition |
| I-244 | 2 | 21* |
| | 6 | 43* |
| | 20 | 48* |
| I-343 | 3 | 12 |
| | 10 | 23 |
| | 30 | 49* |

Example 65: Mouse TNBS-Induced Colitis Model

Colitis was induced by intra-colonic administration of 1.5 mg of TNBS in 75 μl of 40% v/volume ethanol solution under isoflurane anesthesia at a depth of 4 cm from the anal verge. Mice were kept with their heads down for 30 additional seconds post administration to ensure distribution of TNBS. Disease activity scores were assessed for a period of 5 days starting prior to TNBS injection (baseline reading). Disease activity was based on the combined scores of the following parameters; extend of prolapse (0, normal; 1, partial; 2, moderate; 3, full), stool consistency (0, normal; 1, soft but still formed; 2, very soft; 3, diarrhea), and sickness behavior exhibited by mice (0, normal; 1, for each of the following signs: pilo-erection, hunchback, decreased activity, eyes partially or fully closed, walking on tip-toes, blocked anus). Test compounds or vehicle (0.5% MC/0.1% SDS) were systemically administered at the indicated doses in a volume of 10 mL/kg each day for 5 days and starting 1 day before TNBS.

TABLE 13

| Inhibition of a TNBS-induced colitis in mice. Improvements in clinical scores | | |
|---|---|---|
| Compound | Dose (mg/kg) | % improvement in Disease activity scores |
| I-191 | 15 | 21** |
| | 50 | 36*** |
| I-343 | 15 | 24 |
| | 50 | 33* |
| | 150 | 62*** |

Data Analysis for Examples 62-65

Data are expressed as the mean % effect. Statistical significance was assessed using t-test for comparison between naive and inflamed rats, and one-way ANOVA followed by post-hoc comparison test for overall drug effectiveness. A difference between groups is considered significant with a p value of <0.05. *, p<0.05; , p<0.01; *, p<0.001 vs. vehicle.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997.

The invention claimed is:

1. A compound of formula II:

II

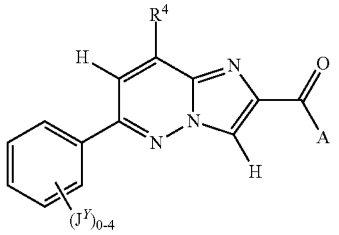

or a pharmaceutically acceptable salt thereof, wherein A is

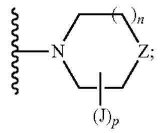

wherein n is 1 or 2;

Z is —O—, —$CH_2$—, or —NX—;

X is $R^5$, —C(O)$R^5$, or —$S(O)_2R^5$;

J is CN; oxo; a $C_{1-6}$aliphatic wherein up to three carbon units of said $C_{1-6}$aliphatic can each be optionally and independently replaced with —O—, —NR—, —S— or —C(O)—; or a 3-7 membered saturated, partially unsaturated, or aromatic monocyclic ring having 0-4 heteroatoms selected from oxygen, nitrogen, or sulfur; wherein said J is optionally and independently substituted with 1-3 occurrences of halo or $C_{1-4}$alkyl, wherein up to one methylene unit of said $C_{1-4}$alkyl is optionally and independently replaced with —O—, —NR—, or —S—;

or two J groups on the same or different atom(s), together with the atom(s) to which they are bound, form a 3-6 membered saturated monocyclic ring having 0-2 heteroatoms selected from oxygen, nitrogen, or sulfur; wherein said 3-6 membered ring is optionally substituted with one occurrence of oxo;

p is 0-4;

$R^5$ is —$(V)_b$—Y; wherein

V is $C_{1-6}$aliphatic wherein up to three carbon units of said $C_{1-6}$aliphatic can each be optionally and independently replaced with —O—, —NR—, —S— or —C(O)—; wherein V is optionally and independently substituted with 1-3 occurrences of halo or $C_{1-6}$alkyl, wherein up to three methylene units of said $C_{1-6}$alkyl are optionally and independently replaced with —O—, —NR—, —S—, or C(O);

Y is H; CN; a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein Y is optionally substituted with 1-4 occurrences of $J^Y$;

$J^Y$ is oxo, halo, CN, —OP(═O)$(OR)_2$, phenyl, or $C_{1-6}$aliphatic, wherein up to three carbon units of said $C_{1-6}$aliphatic can each be optionally and independently replaced with O, NR, S, or C(O), wherein said $C_{1-6}$aliphatic optionally and independently substituted with 1-3 occurrences of halo or OR;

b is independently 0 or 1; and $R^4$ is H; halo; CN; $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein said $R^4$ is optionally and independently substituted with 1-3 occurrences of oxo, halo, or $C_{1-6}$aliphatic wherein up to three carbon units of said $C_{1-6}$aliphatic can each be optionally and independently replaced with O, NR, S or C(O); and each R independently is H or $C_{1-4}$alkyl.

2. The compound of claim 1, wherein:

J is CN; oxo; a $C_{1-6}$aliphatic wherein up to three carbon units of said $C_{1-6}$aliphatic can each be optionally and independently replaced with —O—, —NR—, —S— or —C(O)—; or a 3-7 membered saturated, partially unsaturated, or aromatic monocyclic ring having 0-4 heteroatoms selected from oxygen, nitrogen, or sulfur; wherein said J is optionally and independently substituted with 1-2 occurrences of halo or $C_{1-4}$alkyl, wherein up to one methylene unit of said $C_{1-4}$alkyl is optionally and independently replaced with —O—, —NR—, or —S—;

or two J groups on the same or different atom(s), together with the atom(s) to which they are bound, form a 3-6 membered saturated monocyclic ring having 0-2 heteroatoms selected from oxygen, nitrogen, or sulfur; wherein said 3-6 membered ring is optionally substituted with one occurrence of oxo; and $R^5$ is —$(V)_b$—Y; wherein V is $C_{1-6}$aliphatic wherein up to three carbon units of said $C_{1-6}$aliphatic can each be optionally and independently replaced with —O—, —NR—, —S— or —C(O)—; wherein V is optionally substituted with 1-3 occurrences of halo or $C_{1-4}$alkyl, wherein up to two methylene units of said $C_{1-4}$alkyl are optionally replaced with —O—, —NR—, —S—, or C(O);

Y is H, a 3-7 membered saturated, partially unsaturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein Y is optionally substituted with 1-4 occurrences of $J^Y$; and $J^Y$ is oxo, halo, phenyl, or $C_{1-6}$aliphatic, wherein up to three carbon units of said $C_{1-6}$aliphatic can each be optionally and independently replaced with O, NR, S, or C(O); and $R^4$ is halo; CN; $C_{1-6}$aliphatic wherein up to three carbon units of said $C_{1-6}$aliphatic can each be optionally and independently replaced with —O—, —NR—, —S— or —C(O)—; a 3-7 membered saturated, partially saturated, or aromatic monocyclic ring having 0-4 heteroatoms selected from oxygen, nitrogen, or sulfur; or a 6-10 membered saturated, partially unsaturated, or aromatic bicyclic ring having 0-6 heteroatoms selected from oxygen, nitrogen, or sulfur; wherein said $R^4$ is optionally and independently substituted with 1-3 occurrences of oxo, halo, or $C_{1-6}$aliphatic wherein up to three carbon units of said $C_{1-6}$aliphatic can each be optionally and independently replaced with O, NR, S or C(O); and R is H or $C_{1-4}$alkyl.

3. The compound of claim 1, wherein J is oxo, CN, halo, —OH, —O($C_{1-6}$alkyl), —NHC(═O)O($C_{1-6}$alkyl), —C(═O)NR, —C(═O)O($C_{1-6}$alkyl), or $C_{1-4}$alkyl optionally substituted with 1-3 occurrences of halo.

4. The compound of claim 1, wherein A is

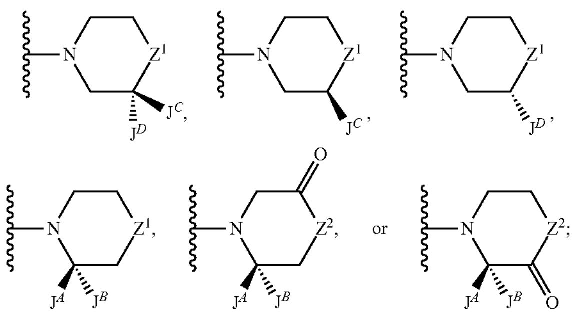

wherein $Z^1$ is —O—, —$CH_2$—, or —NX—; wherein X is $X^1$;

$Z^2$ is —$CH_2$— or —NX—; wherein X is $X^2$;

$X^1$ is $R^5$, —C(O)$R^5$, or —$S(O)_2R^5$;

$X^2$ is $R^5$;

$J^A$ is $C_{1-4}$alkyl;

$J^B$ is $C_{1-4}$alkyl;

or $J^A$ and $J^B$, together with the carbon atom to which they are bound, form a 3-6 membered saturated monocyclic ring having 0-1 heteroatom selected from oxygen, nitrogen, or sulfur; and $J^C$ is methyl; and $J^D$ is methyl.

5. The compound of claim 4, wherein:

$R^5$ is —$(V)_b$—Y;

V is $C_{1-6}$aliphatic wherein up to three carbon units of said $C_{1-6}$aliphatic can each be optionally and independently replaced with —O—, —NR—, —S— or —C(O)—; wherein V is optionally and independently substituted with halo, $C_{1-4}$alkyl, OH, $NH_2$, or —NRC(O)$C_{1-4}$alkyl;

Y is H or a 3-7 membered saturated, partially unsaturated, or aromatic monocyclic ring having 0-4 heteroatoms selected from oxygen, nitrogen, or sulfur; wherein Y is optionally substituted with 1-4 occurrences of $J^Y$; and $J^Y$ is oxo, halo, phenyl, or $C_{1-6}$aliphatic, wherein up to three carbon units of said $C_{1-6}$aliphatic can each be optionally and independently replaced with O, NR, S or C(O), and wherein said $C_{1-6}$aliphatic is optionally substituted with 1-3 occurrences of halo.

6. The compound of claim 1, wherein $R^4$ is H, $C_{1-4}$ aliphatic, or a 3-7 membered saturated, partially saturated, or aromatic monocyclic ring having 0-4 heteroatoms selected from oxygen, nitrogen, or sulfur, wherein said $C_{1-4}$ aliphatic is optionally substituted with 1-3 occurrences of halo, —OH, or —O($C_{1-4}$ alkyl), and wherein said monocyclic ring is optionally substituted with 1-3 occurrences of halo, $C_{1-4}$ alkyl, —$CF_3$, —OH, or —O($C_{1-4}$ alkyl).

7. The compound of claim 1, wherein

A is

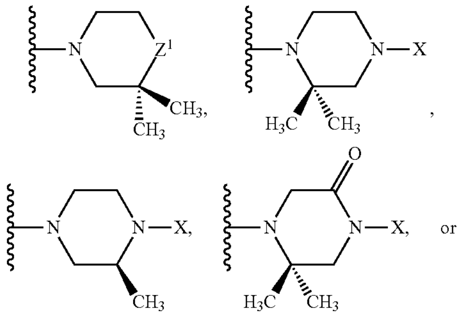

, , or

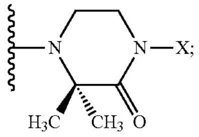

$R^4$ is iso-propyl, tert-butyl, cyclopropyl, methylcyclopropyl, or $CF_3$;

X is $R^5$ or —C(O)$R^5$;

$R^5$ is $(V)_b$—Y; wherein

V is —CH(OH)—, —CH(OH)$CH_2$—, —$CH_2$—, —$CH_2CH_2$—, or —O—; and

Y is H, $C_{1-4}$aliphatic, a 3-6 membered cycloalkyl, isoxazolyl, oxetanyl, thienyl, phenyl, azetidinyl, tetrahydrofuranyl, tetrahydropyranyl, piperidinyl, imidazolyl, pyrazolyl, pyridinyl, triazolyl, oxadiazolyl, tetrazolyl, pyrimidinyl, pyridazinyl, isothiazolyl, or bicycle[1.1.1]pentanyl, wherein Y is optionally substituted with 1-4 occurrences of $J^Y$;

$J^Y$ is halo or $C_{1-4}$alkyl optionally substituted with 1-3 occurrences of halo; and b is 0 or 1.

8. The compound of claim 1, wherein

A is

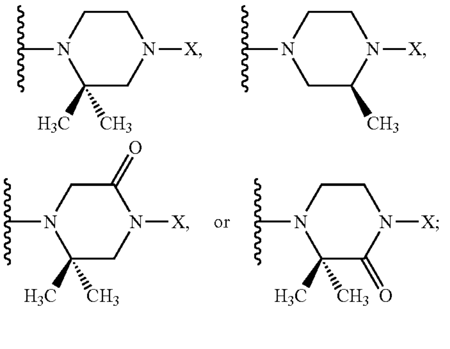

$R^4$ is iso-propyl, tert-butyl, cyclopropyl, methylcyclopropyl, or $CF_3$;

X is $R^5$ or —C(O)$R^5$;

$R^5$ is V-Y; wherein

V is —CH(OH)—, —CH(OH)$CH_2$—, —$CH_2$—, —$CH_2CH_2$—, or —O—; and

Y is H, $C_{1-4}$aliphatic, a 3-6 membered cycloalkyl, isoxazolyl, thienyl, or phenyl, wherein Y is optionally substituted with 1-4 occurrences of $J^Y$; and $J^Y$ is halo or $C_{1-4}$alkyl.

9. The compound of claim 1, as represented by any one of the following structures or a pharmaceutically acceptable salt thereof:

I-1

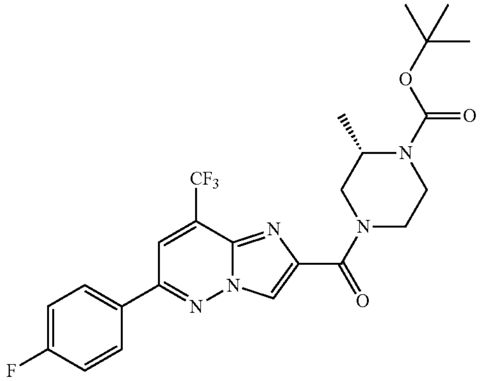

I-2

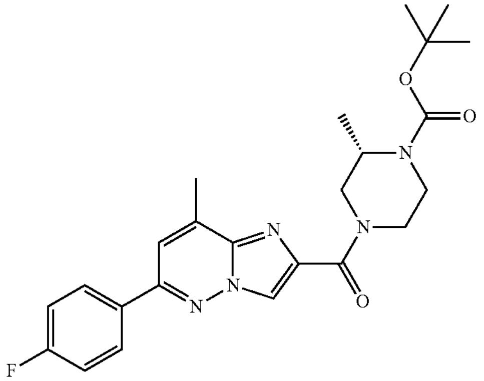

I-3

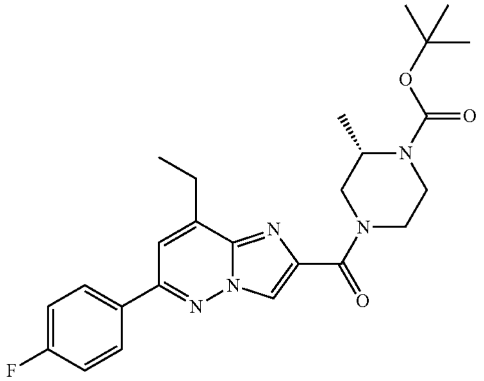

-continued
I-4
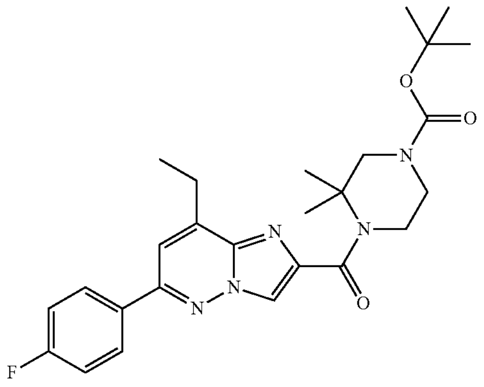
I-5
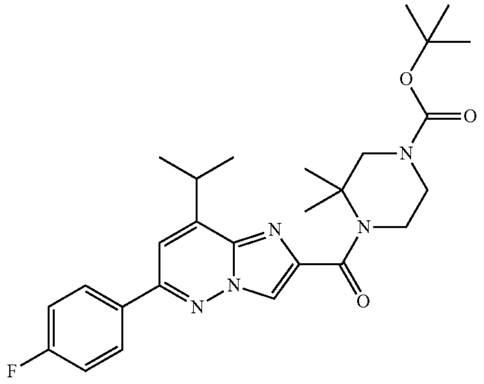
I-6
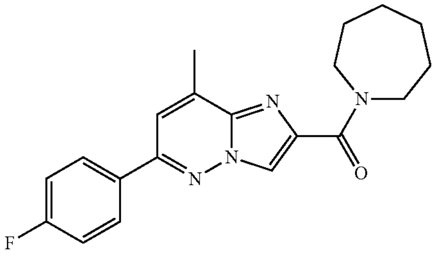
I-7
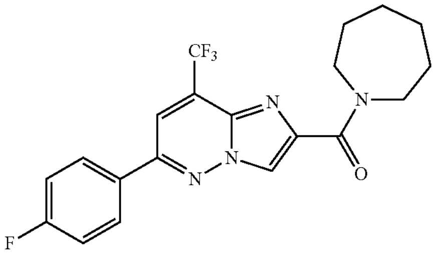
-continued
I-8
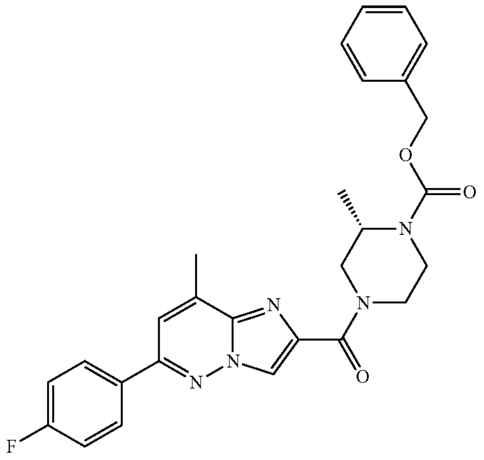
I-9
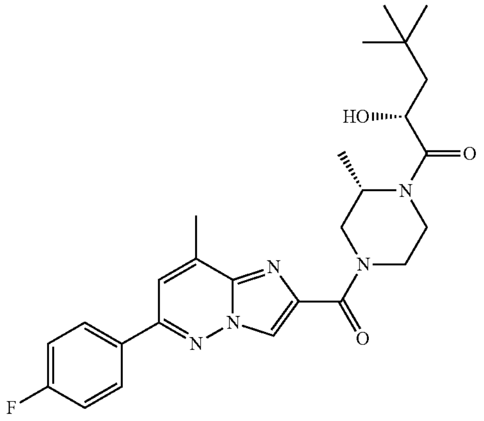
I-10
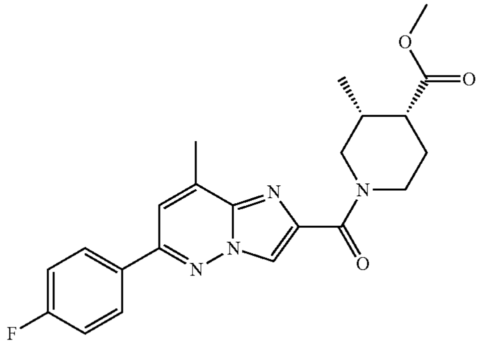

-continued
I-11
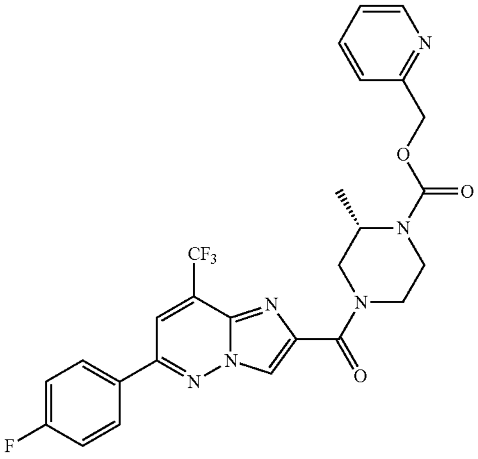
I-12
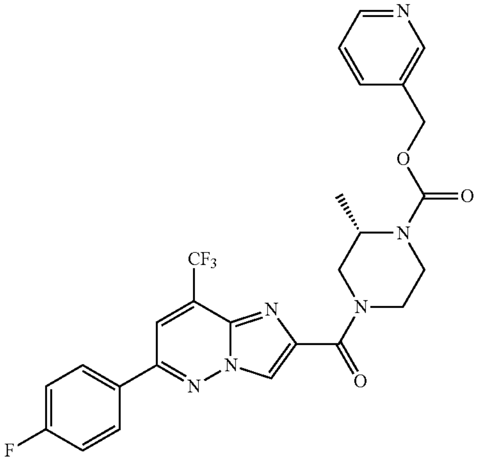
I-13
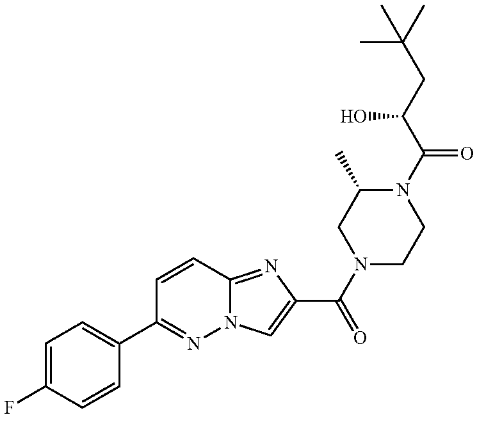
-continued
I-14
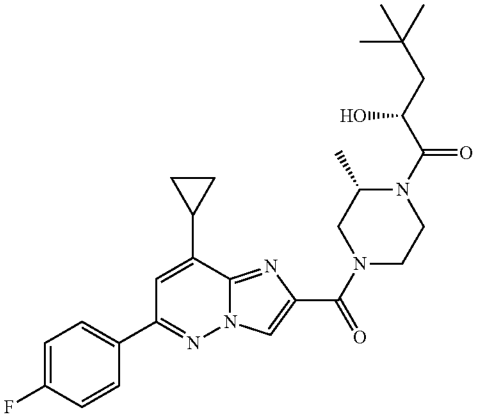
I-15
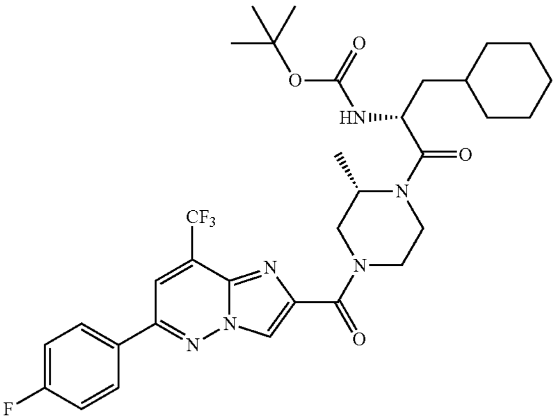
I-16
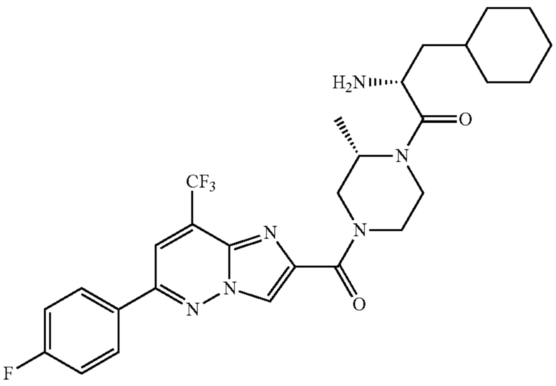
I-17
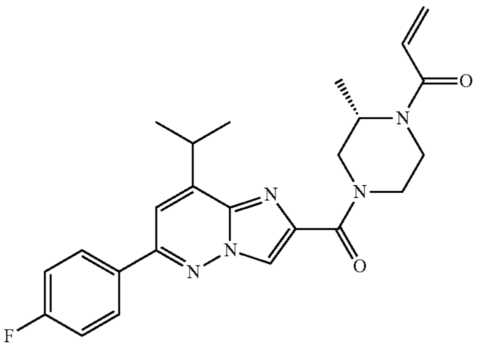

-continued
I-18
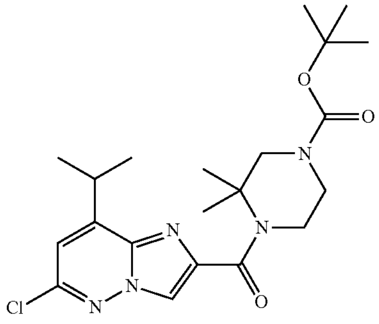
I-19
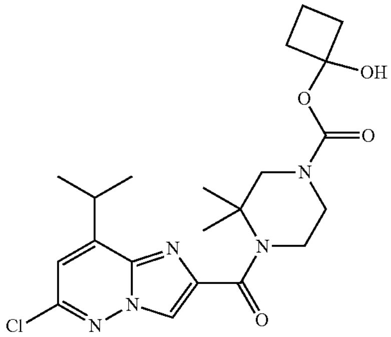
I-20
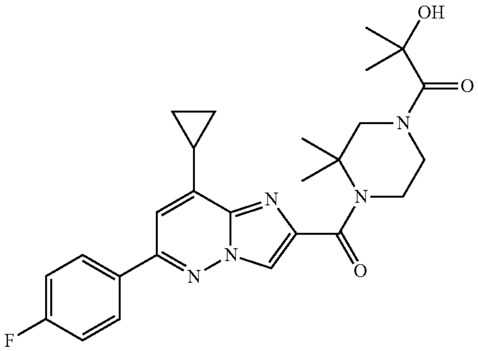
I-21
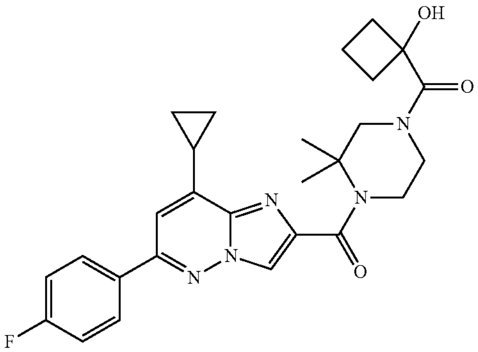
-continued
I-22
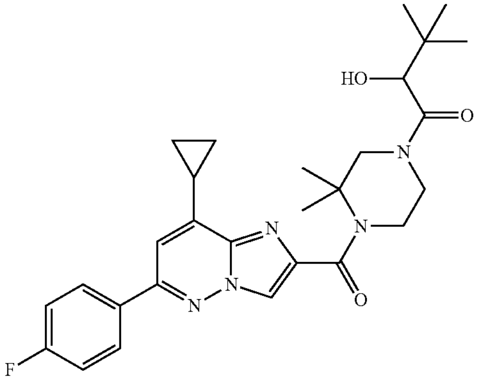
I-23
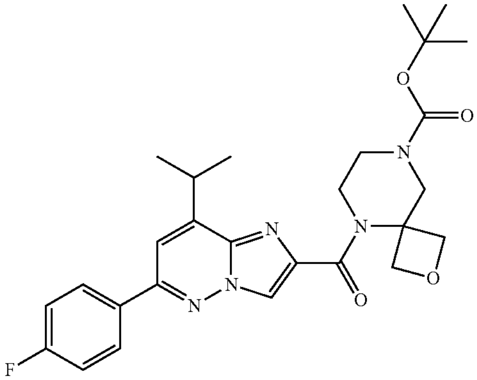
I-24
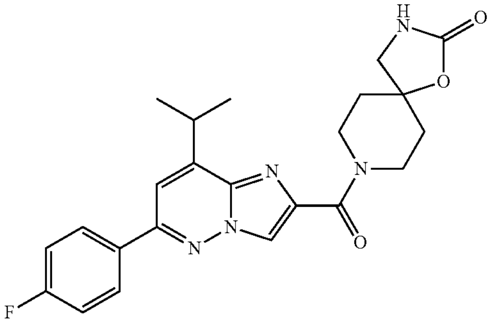
I-25
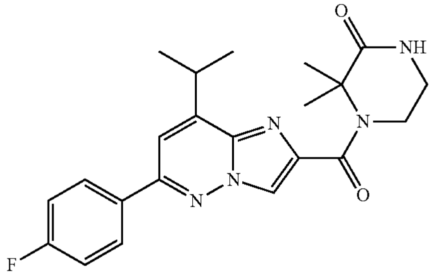

I-26
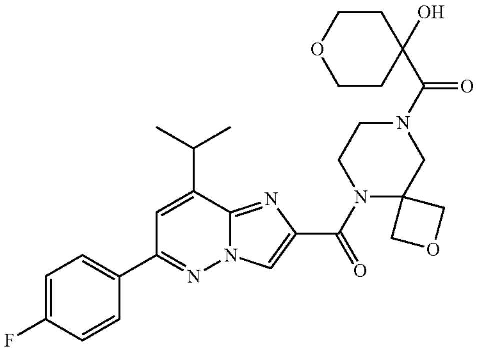
I-27
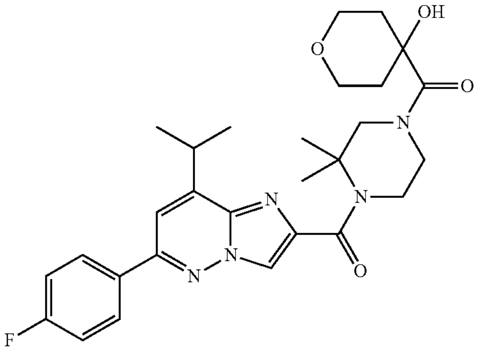
I-28
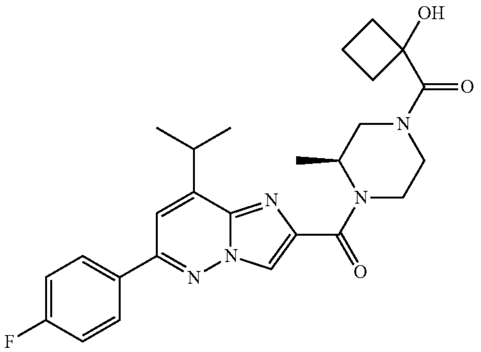
I-29
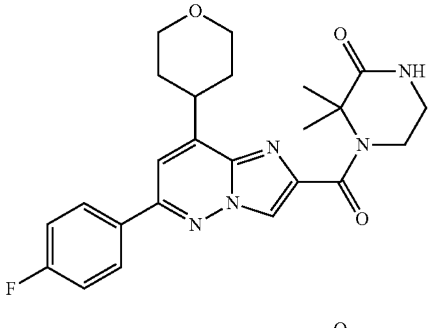
I-30
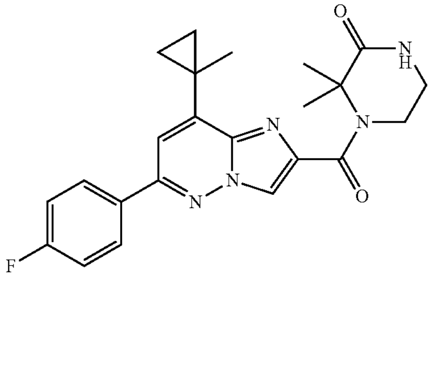
I-31
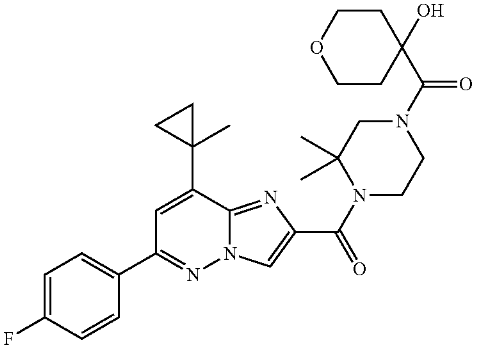
I-32
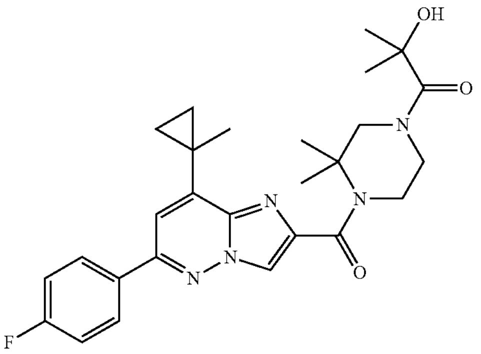
I-33
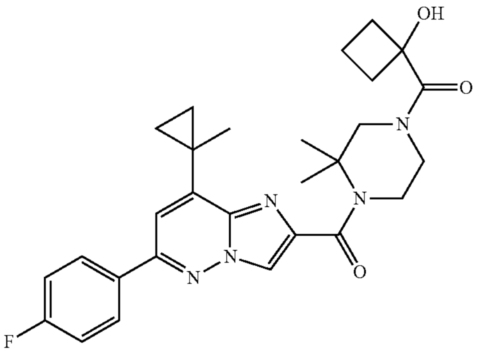
I-34
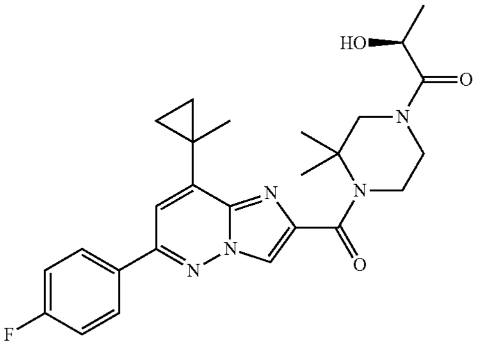

-continued
I-35
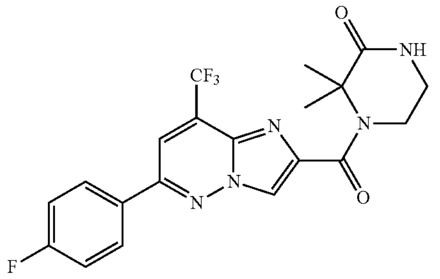
I-36
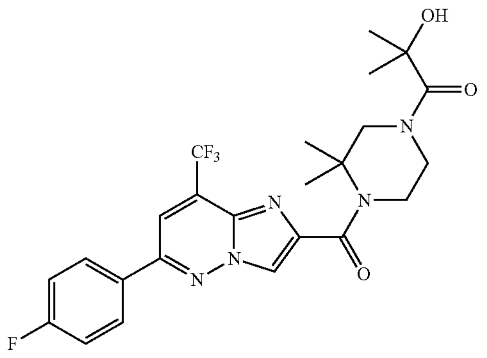
I-37
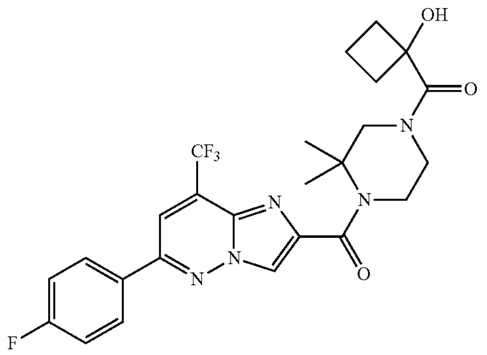
I-38
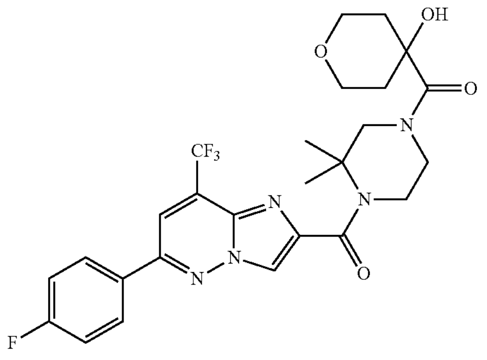
-continued
I-39
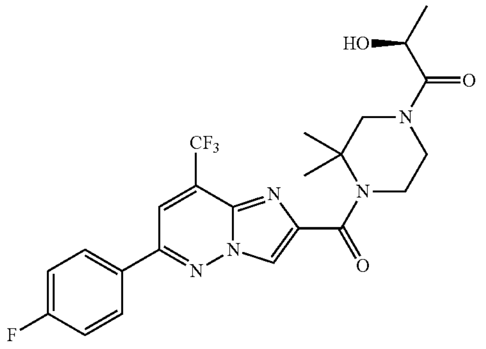
I-46
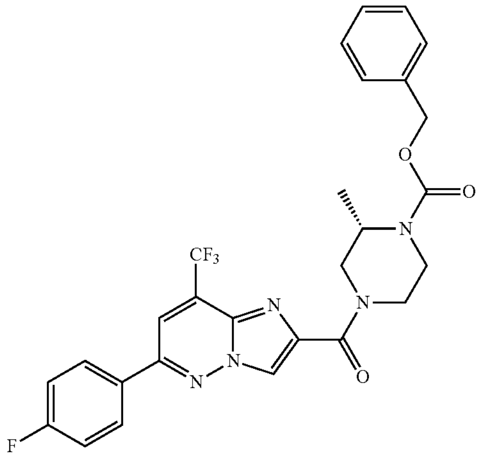
I-47
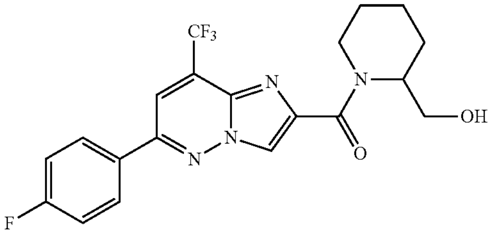
I-48
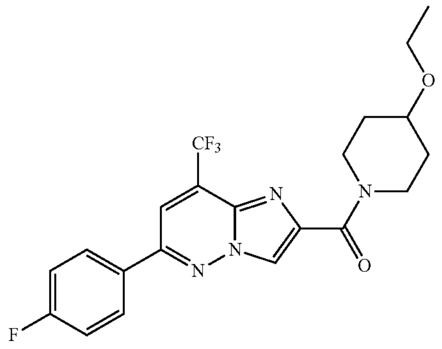

I-49
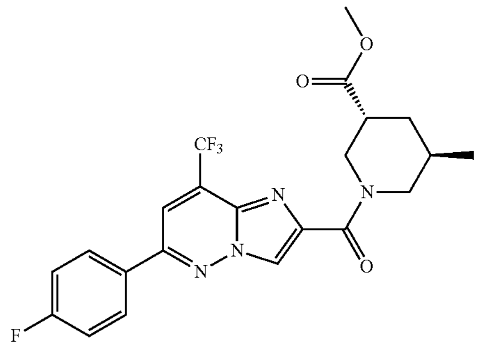
I-50
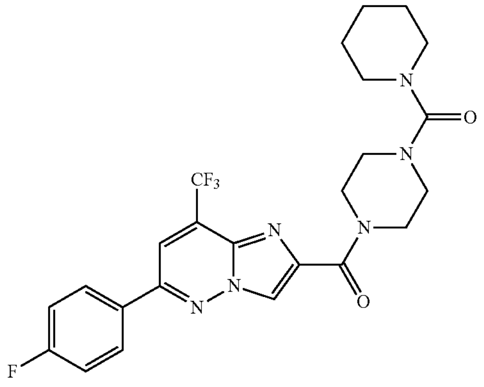
I-51
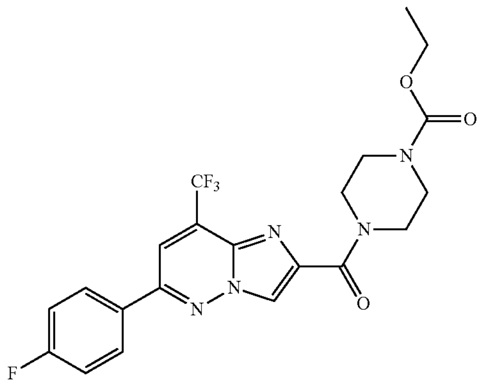
I-52
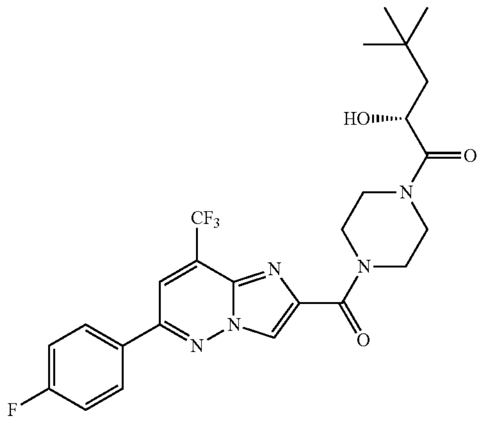
I-53
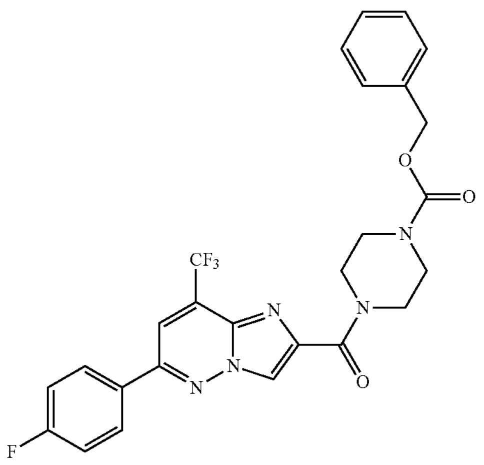
I-54
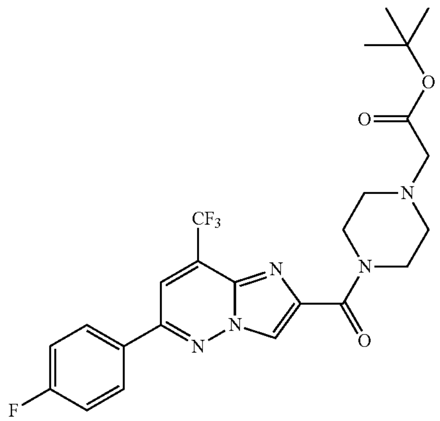
I-55
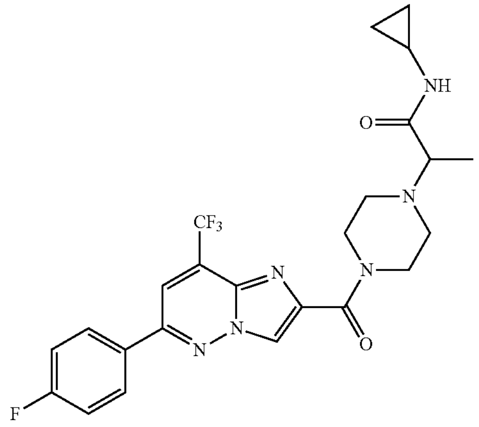

-continued
I-56
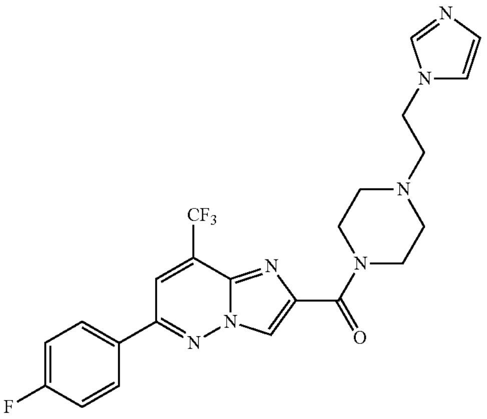
I-57
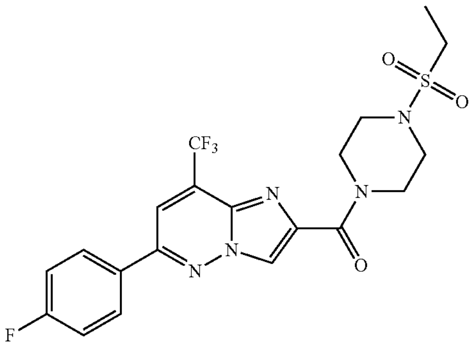
I-58
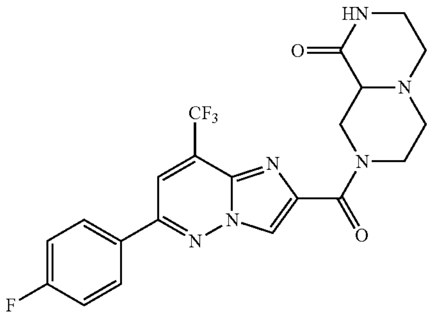
I-59
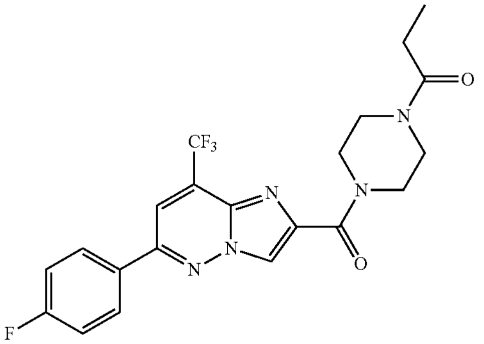
-continued
I-60
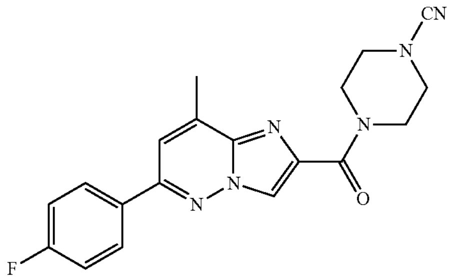
I-61
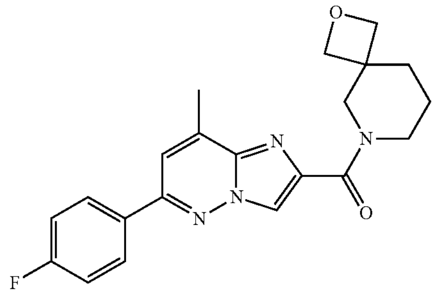
I-62
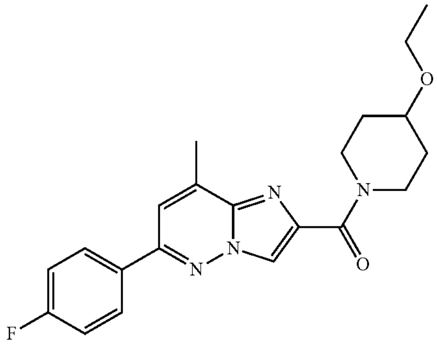
I-63
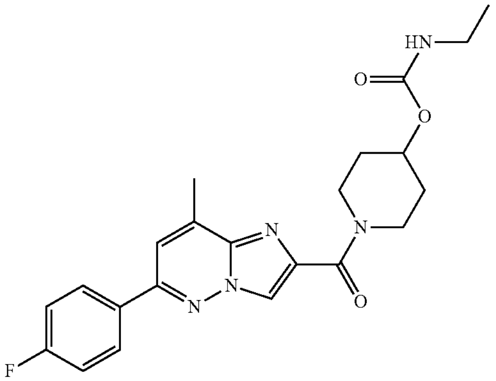

-continued
I-64
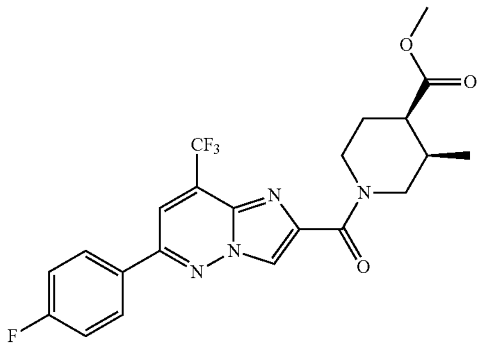
I-65
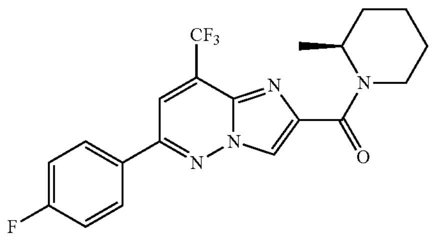
I-66
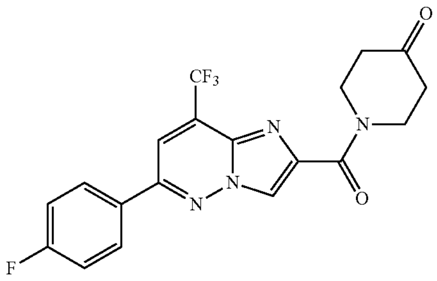
I-67
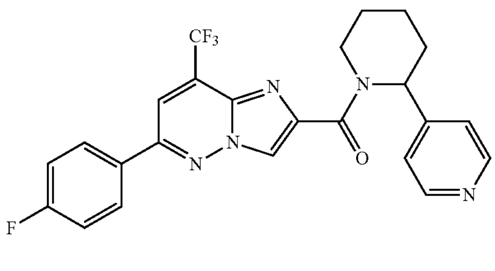
I-68
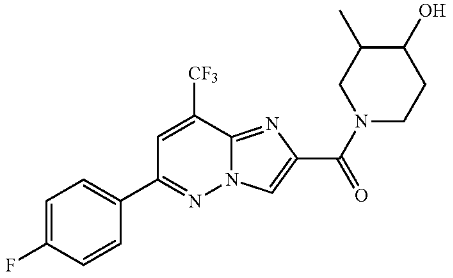
-continued
I-69
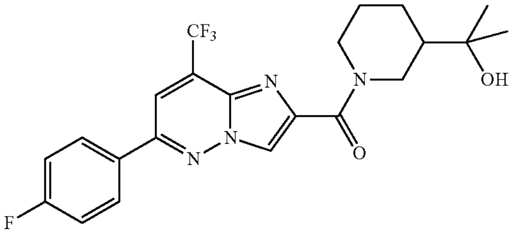
I-70
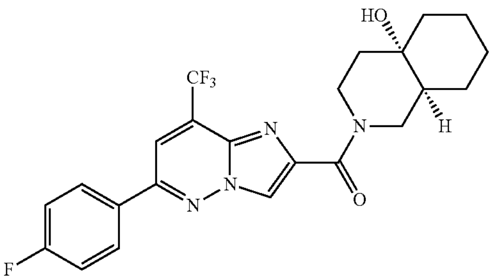
I-71
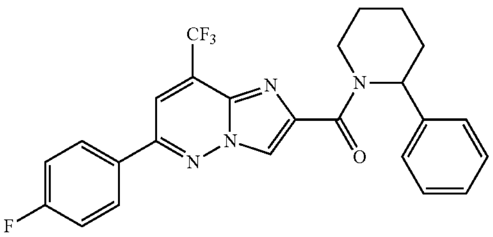
I-72
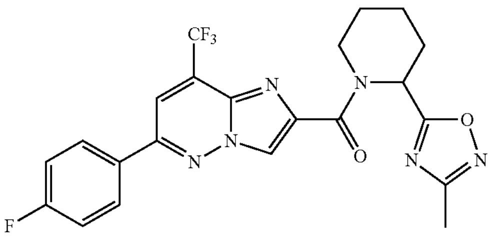
I-73
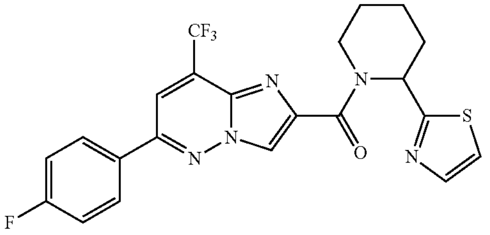

-continued
I-74
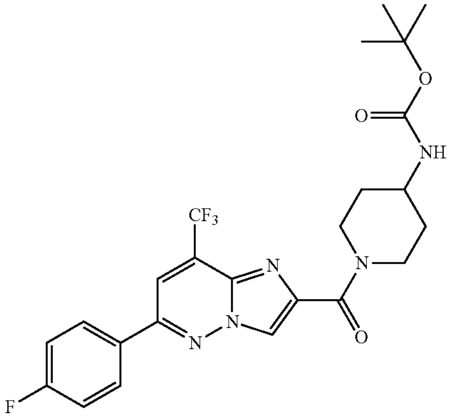
I-75
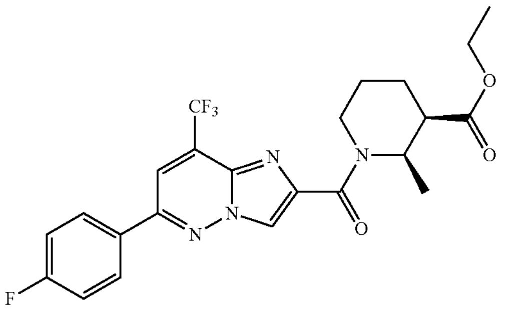
I-76
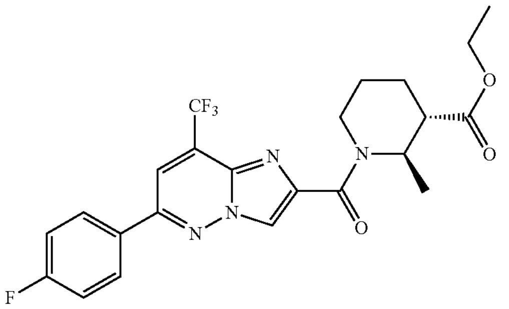
I-77
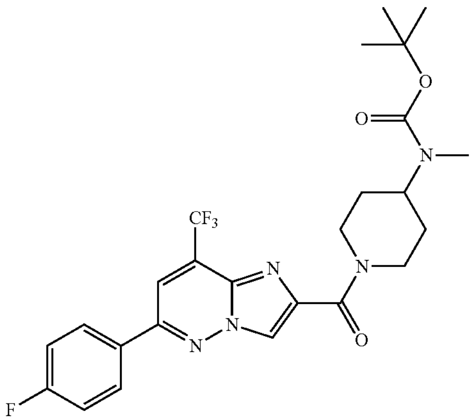
-continued
I-78
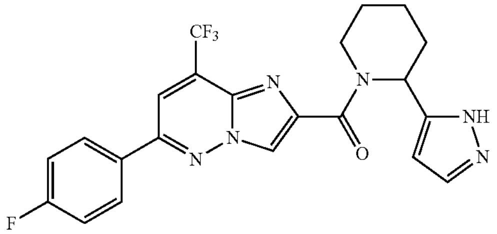
I-79
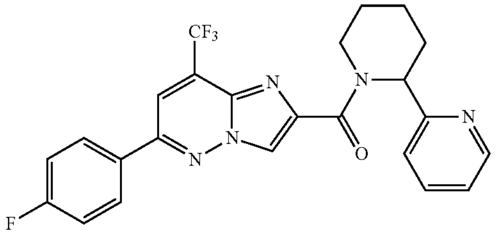
I-80
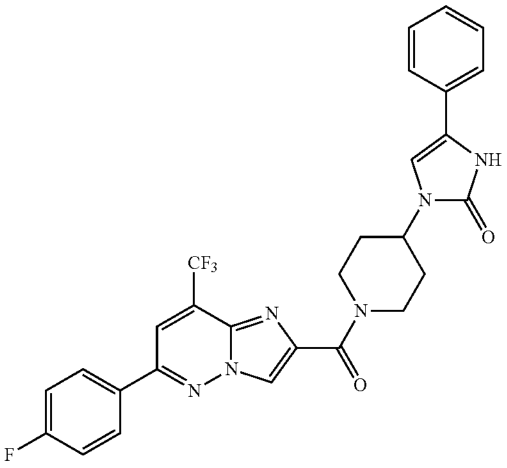
I-81
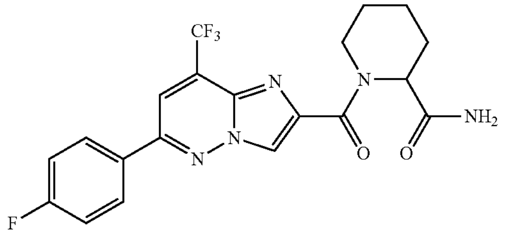
I-82
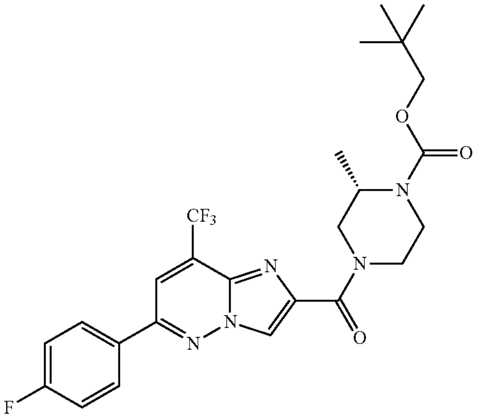

-continued
I-83
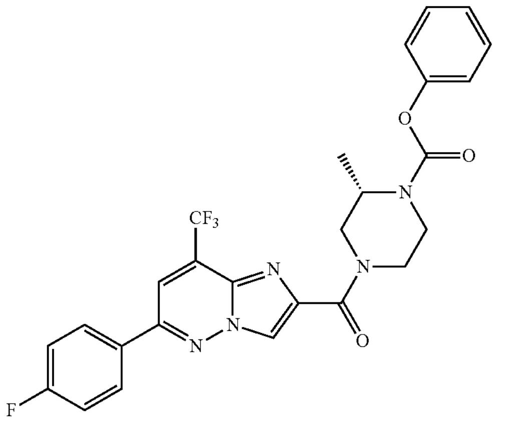
I-84
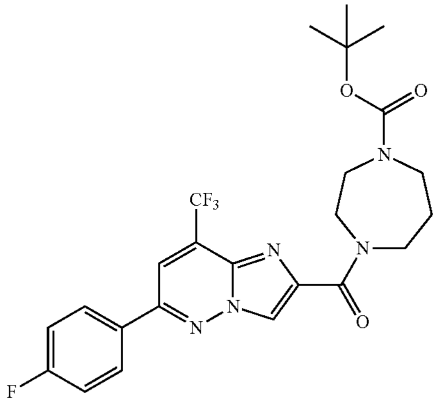
I-85
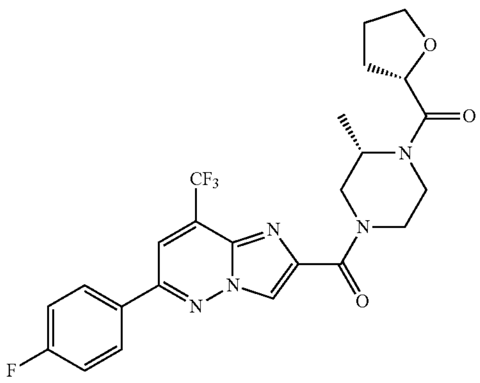
I-86
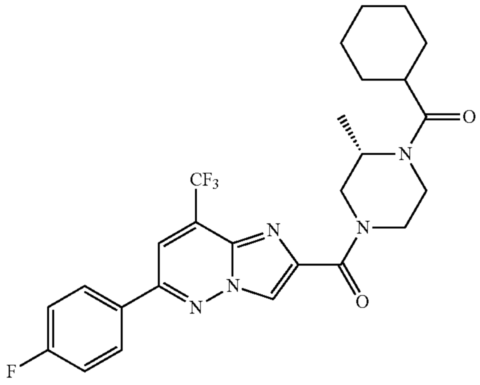
-continued
I-87
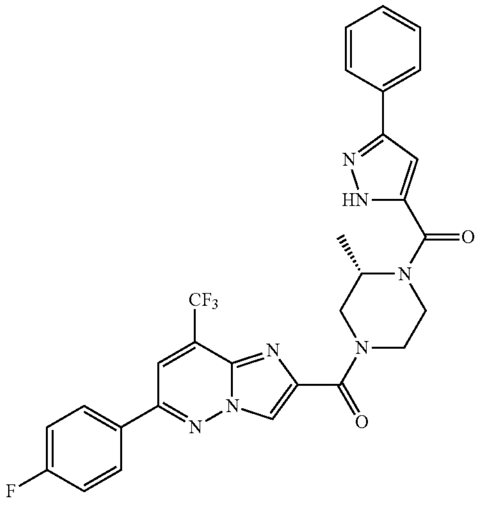
I-88
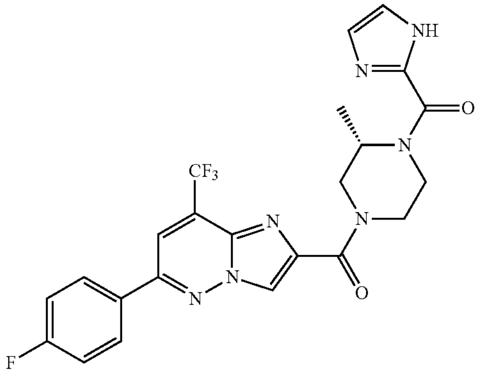
I-89
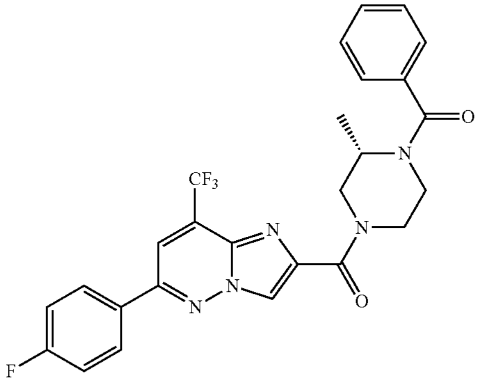

-continued
I-90
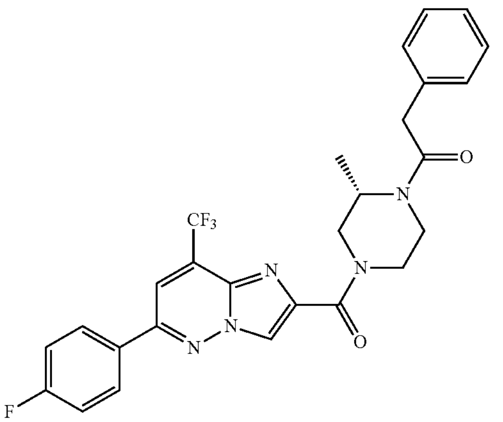
I-91
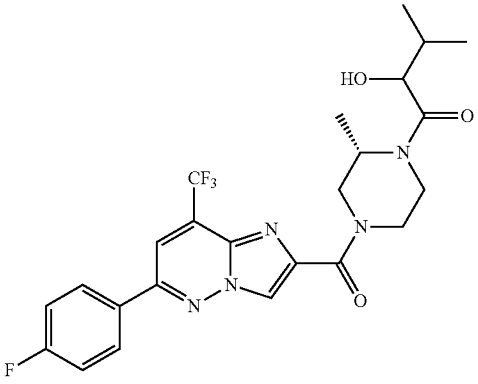
I-92
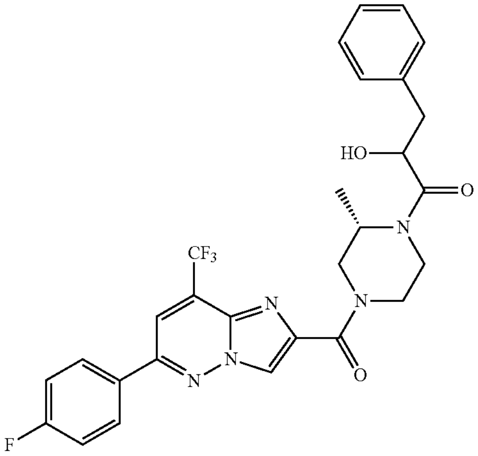
-continued
I-93
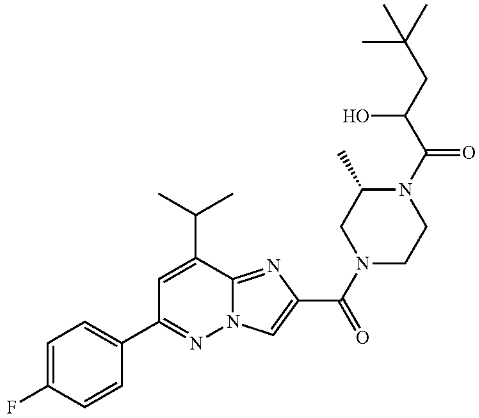
I-94
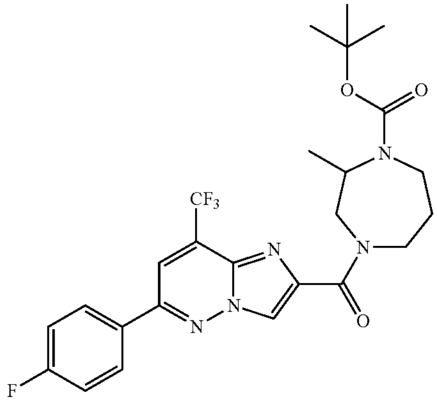
I-95
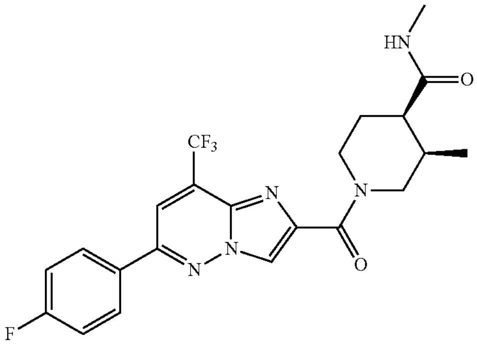
I-96
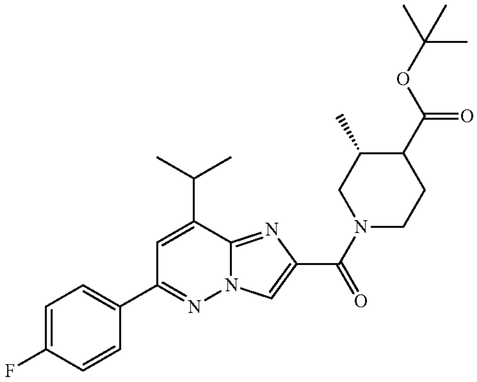

-continued
I-97
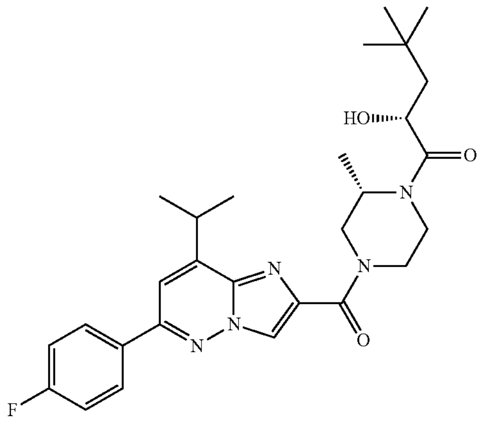
I-98
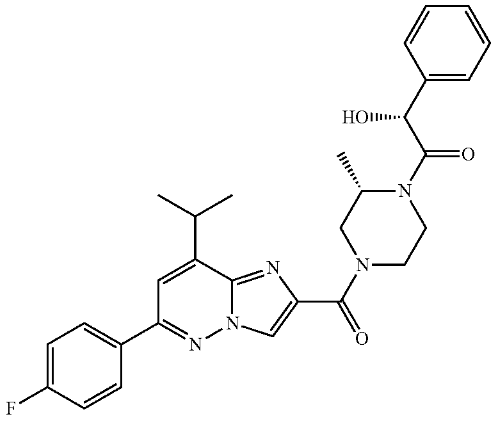
I-99
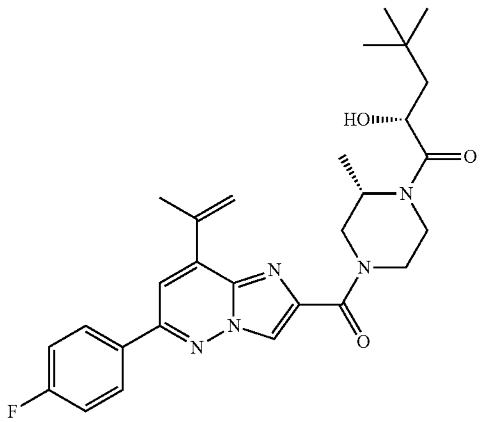
-continued
I-100
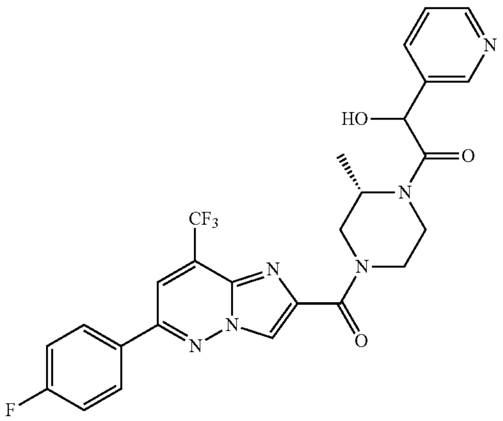
I-101
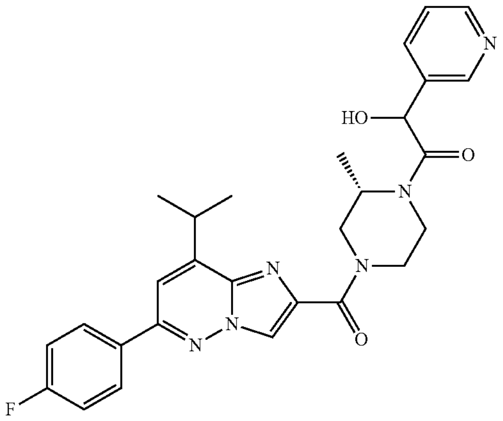
I-102
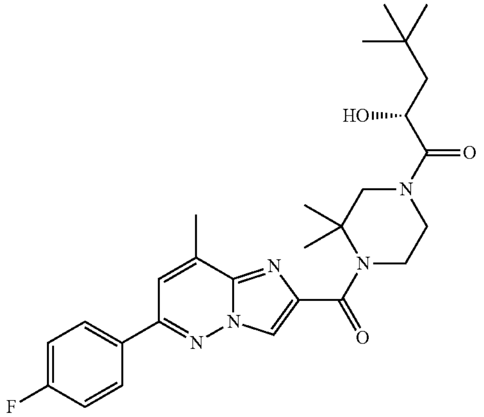

-continued
I-103
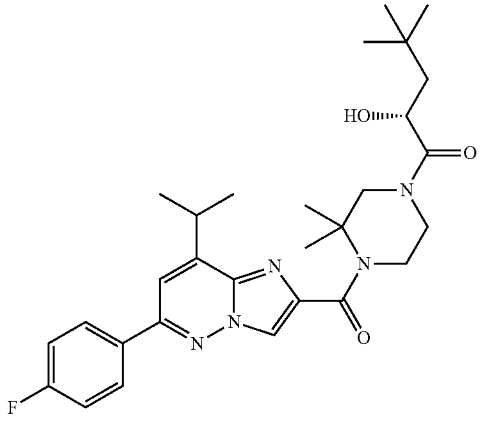
I-104
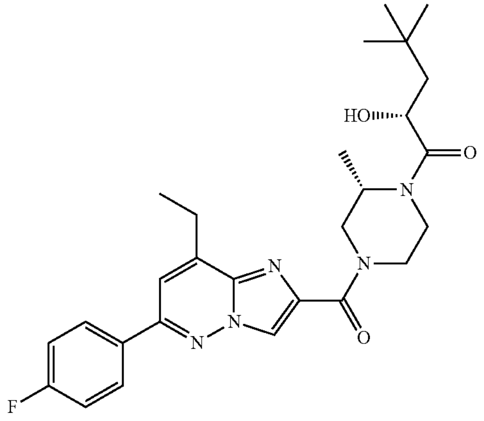
I-105
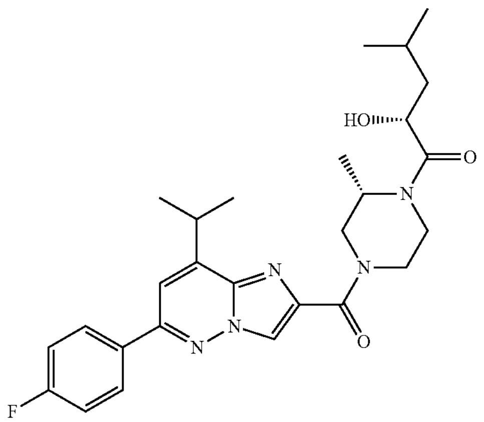
-continued
I-106
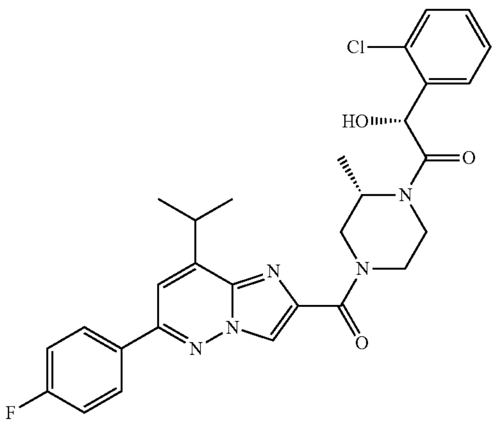
I-107
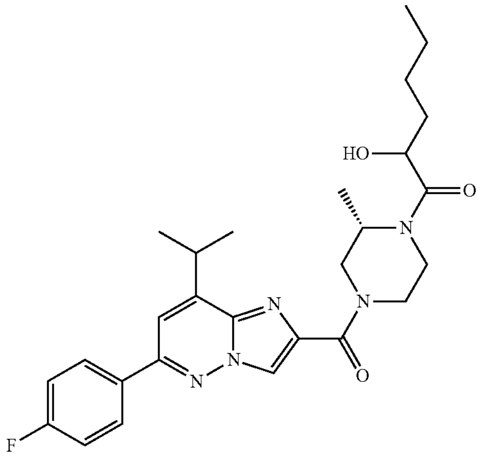
I-108
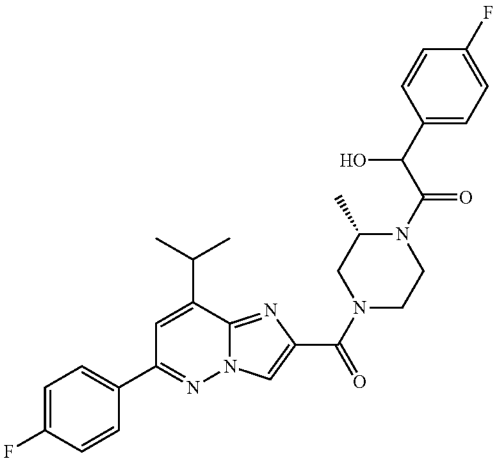

-continued
I-109
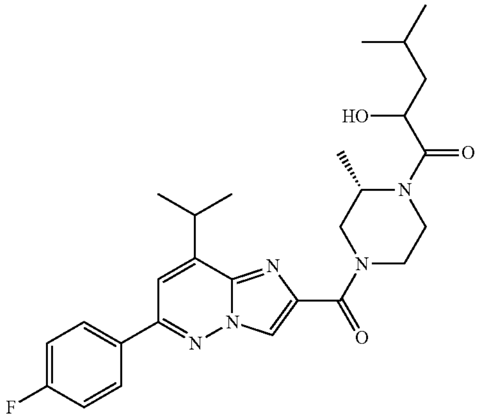
I-110
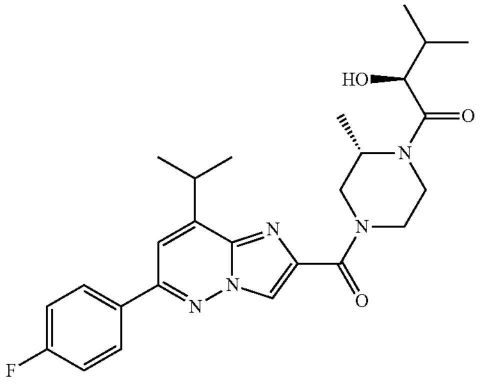
I-111
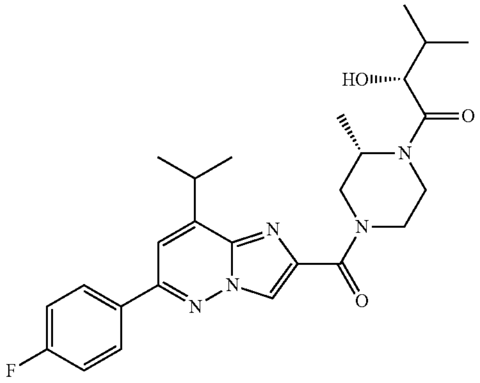
I-112
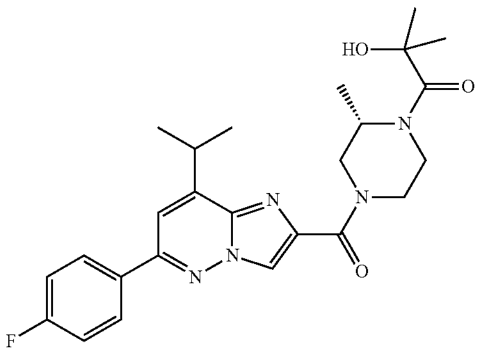
-continued
I-113
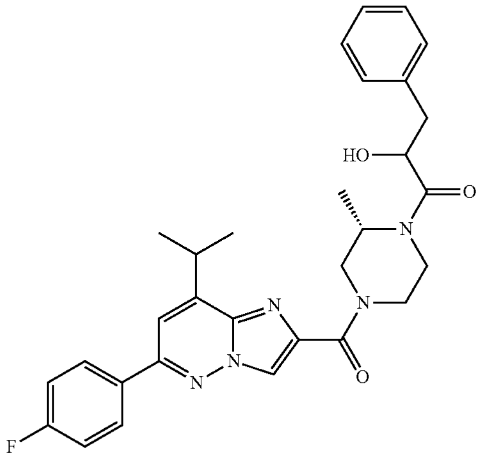
I-114
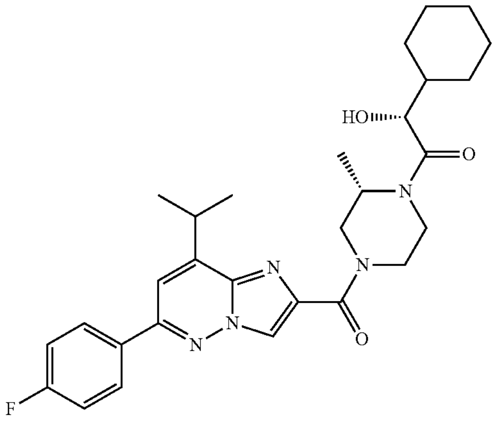
I-115
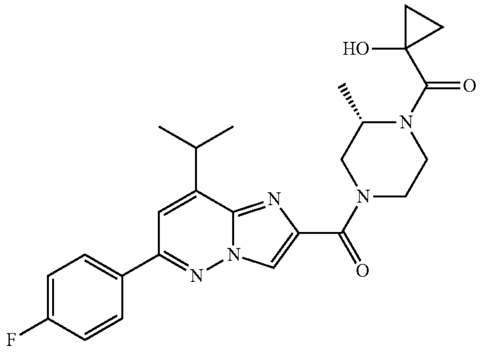
I-116
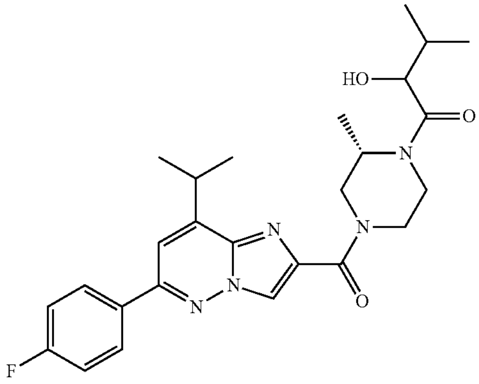

-continued
I-117
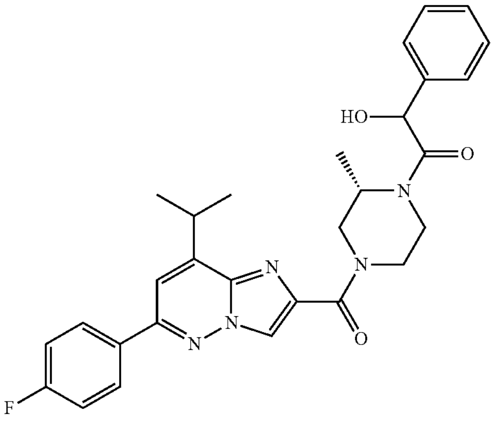
I-118
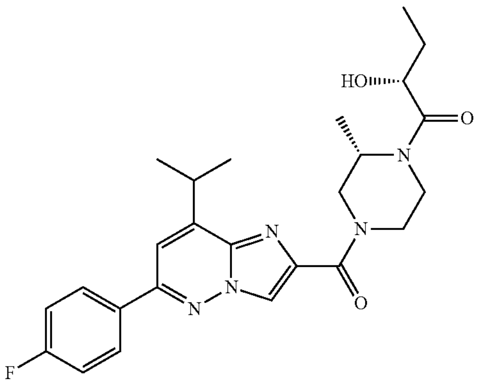
I-119
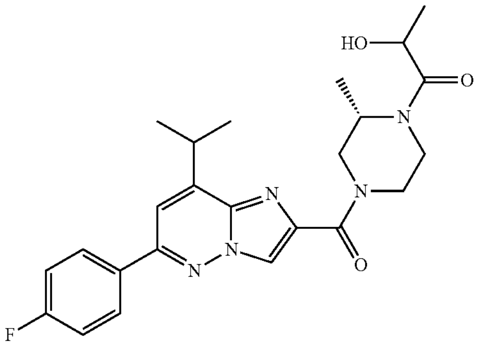
I-120
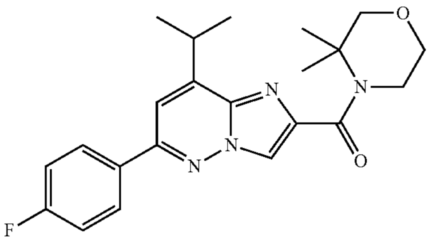
-continued
I-121
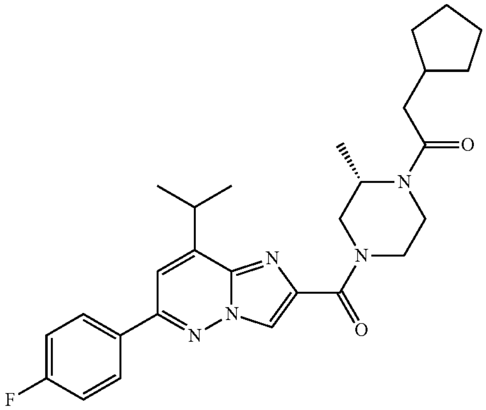
I-122
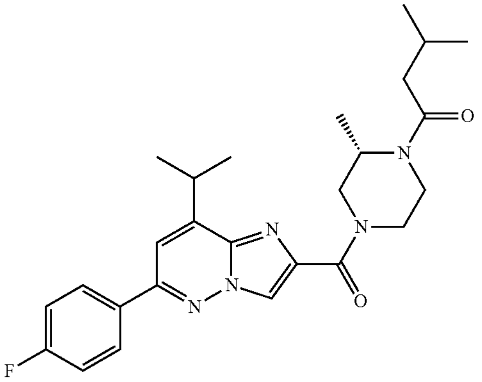
I-123
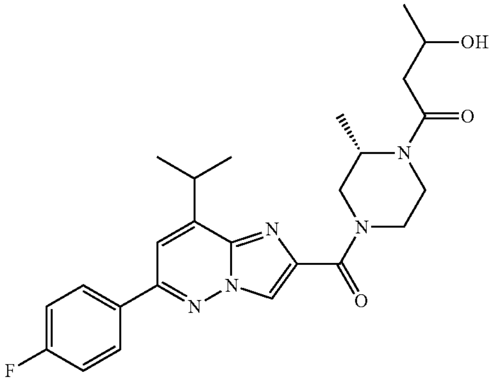
I-124
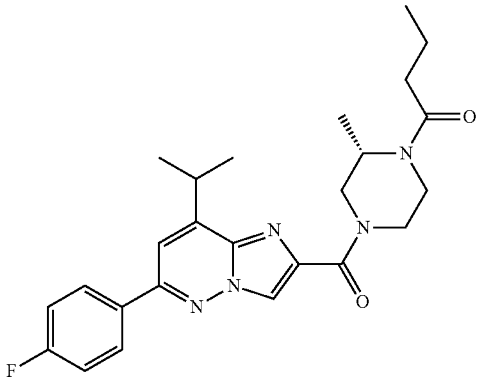

-continued
I-125
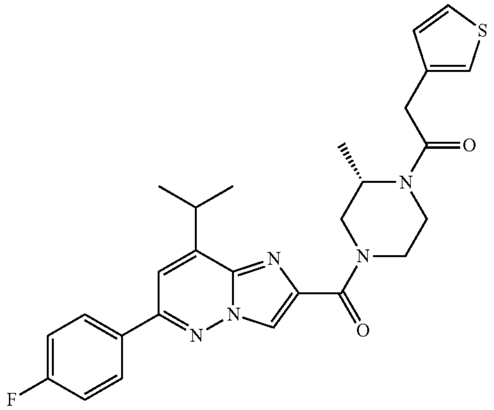
I-126
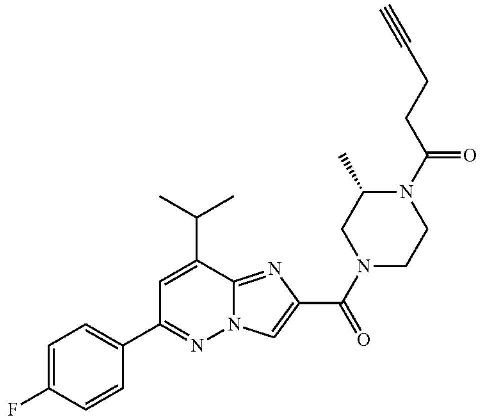
I-127
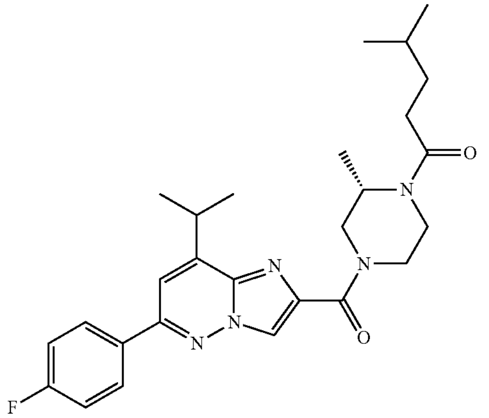
-continued
I-128
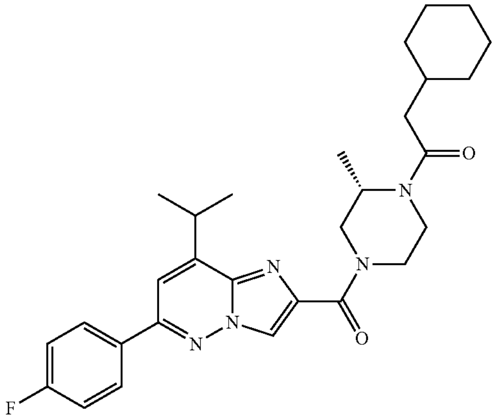
I-129
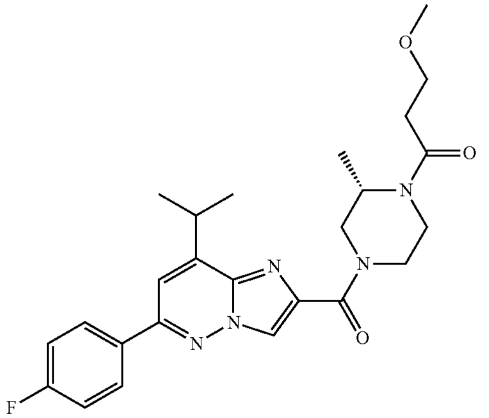
I-130
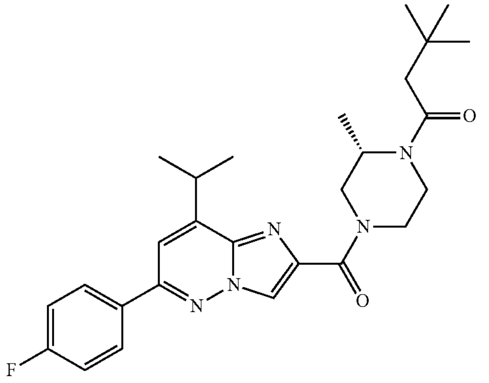

-continued
I-131
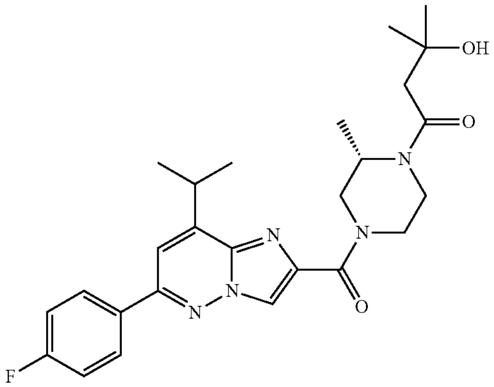
I-132
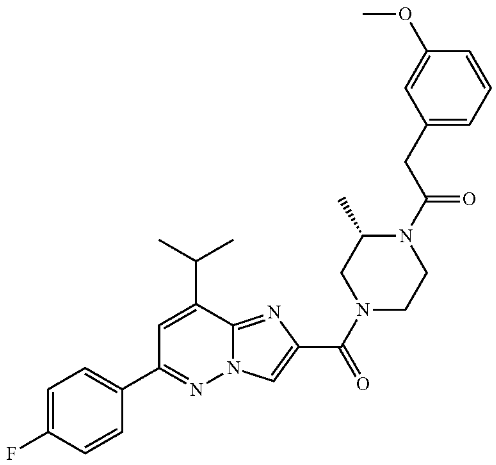
I-133
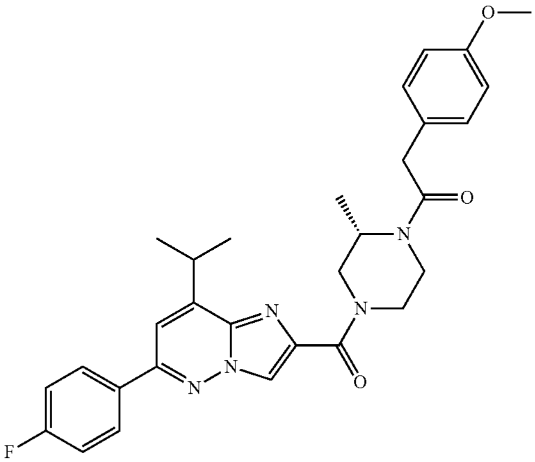
-continued
I-134
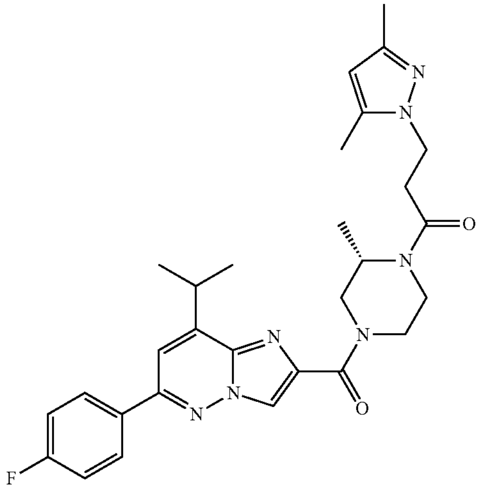
I-135
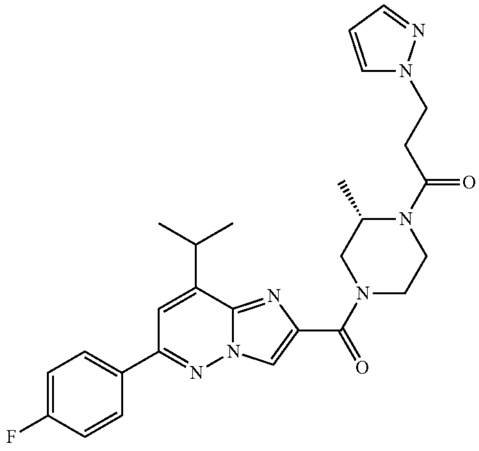
I-136
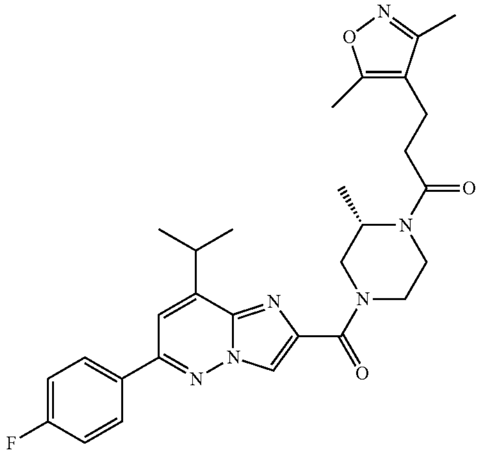

-continued
I-137
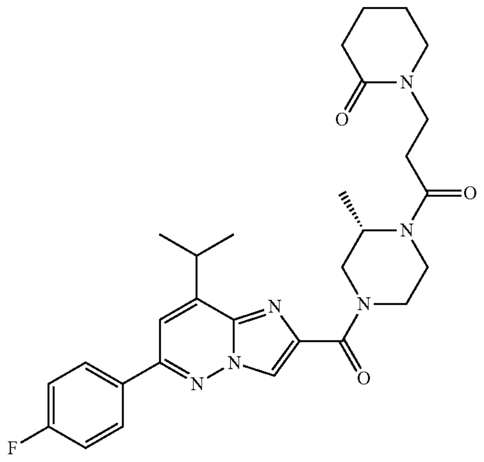
I-138
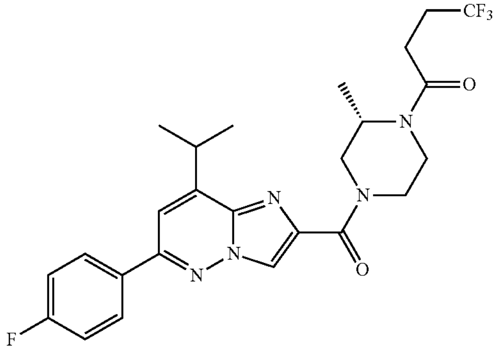
I-139
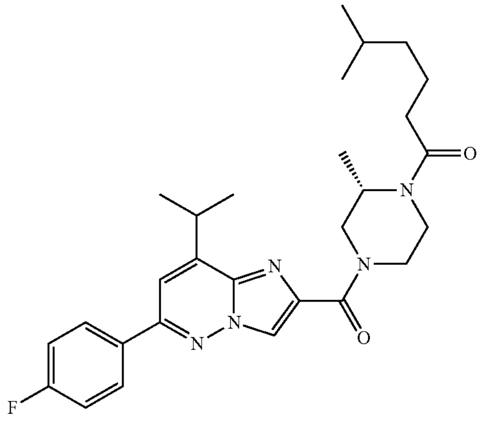
I-140
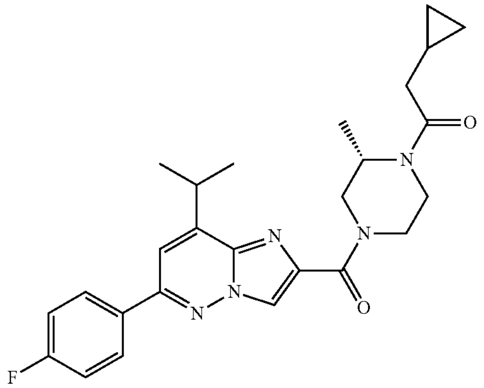
-continued
I-141
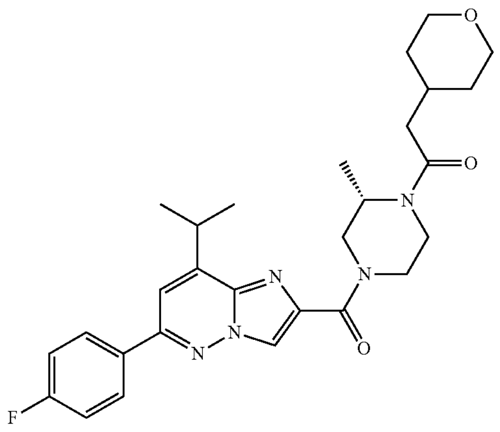
I-142
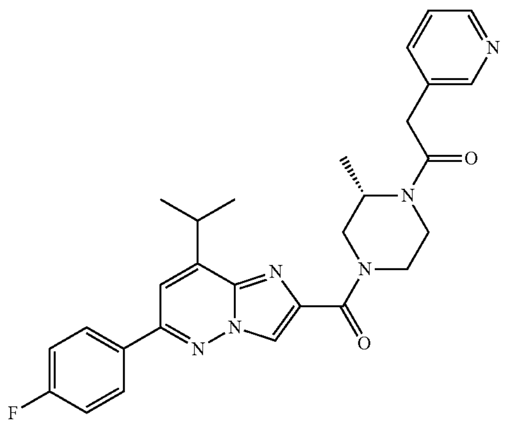
I-143
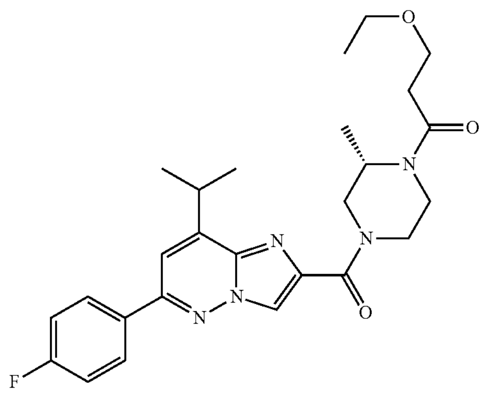

-continued
I-144
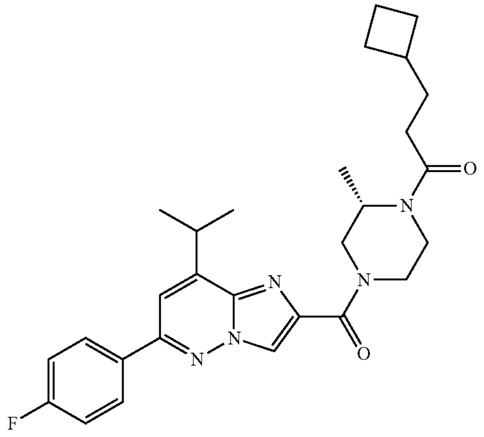
I-145
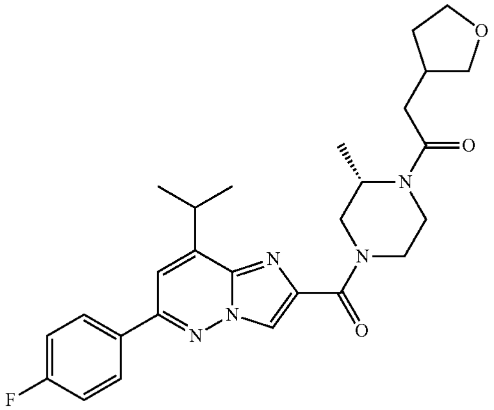
I-146
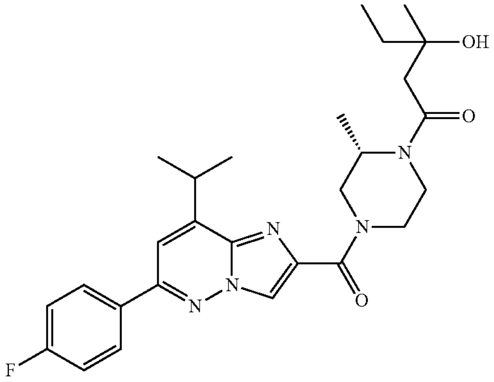
-continued
I-147
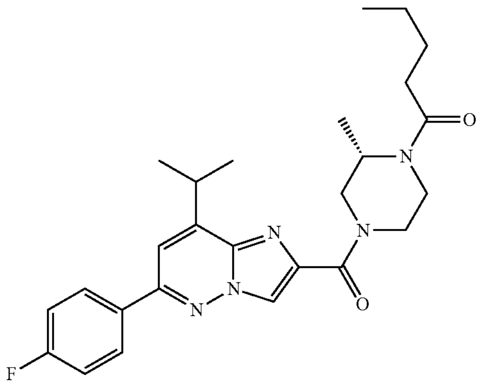
I-148
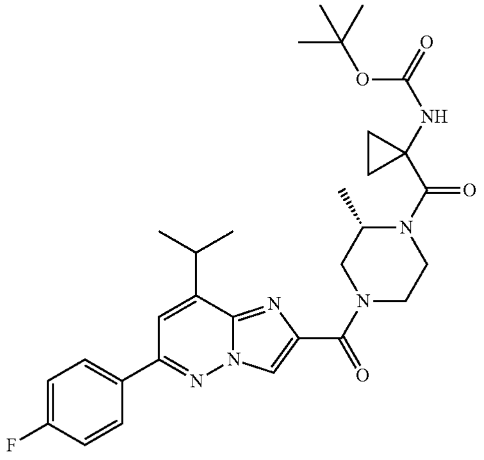
I-149
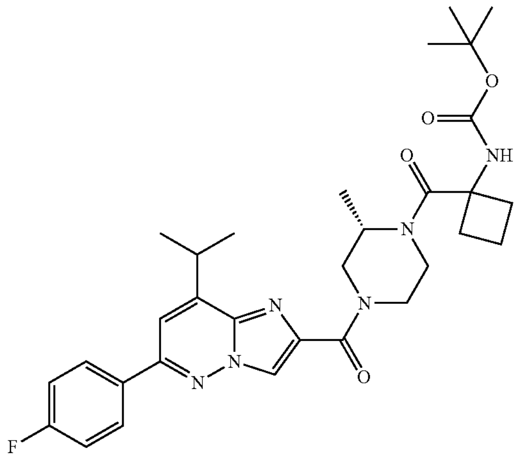

-continued
I-150
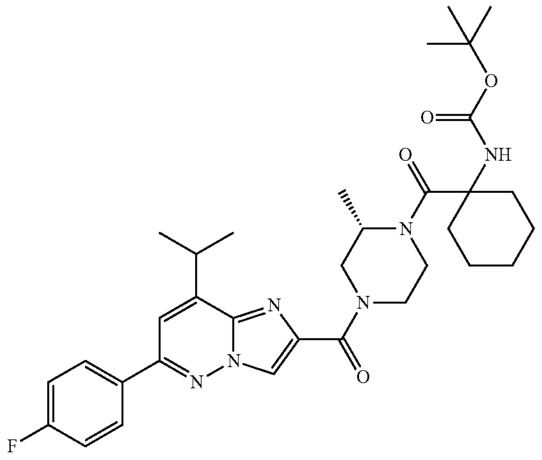
I-151
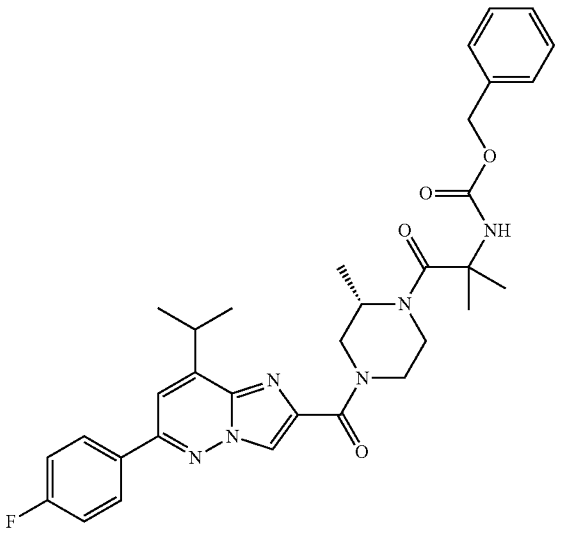
I-152
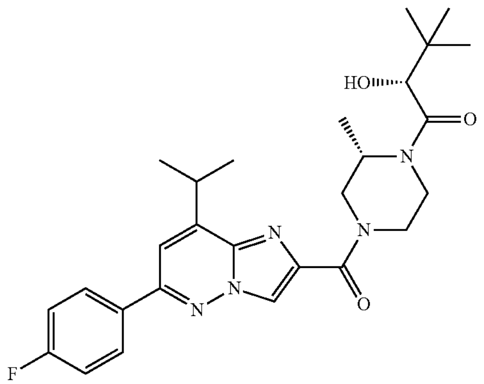
-continued
I-153
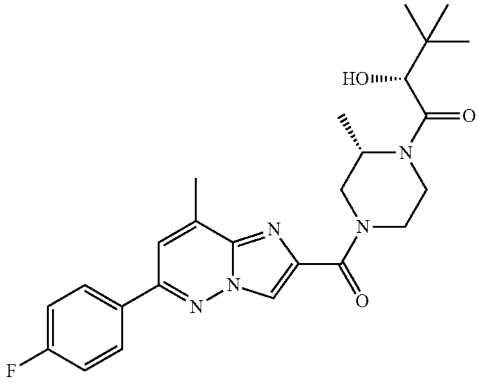
I-154
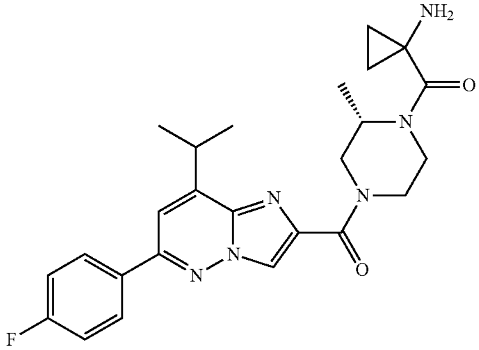
I-155
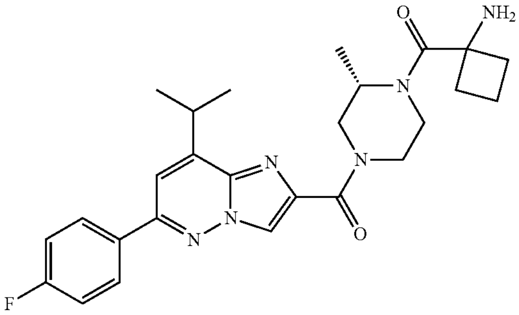
I-156
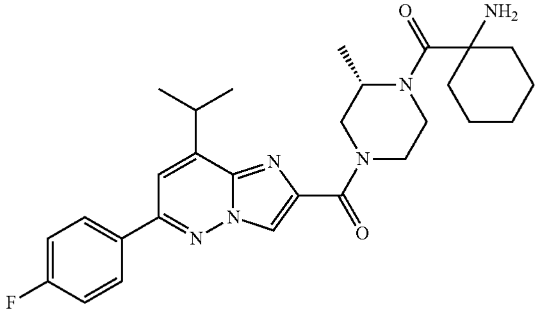

-continued
I-157
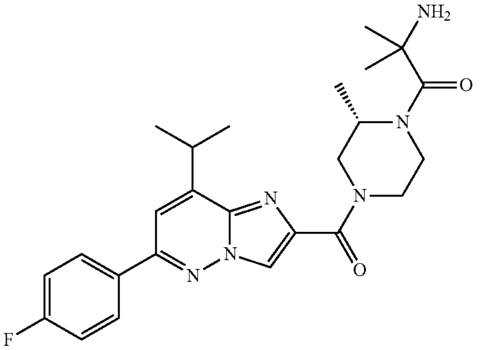
I-158
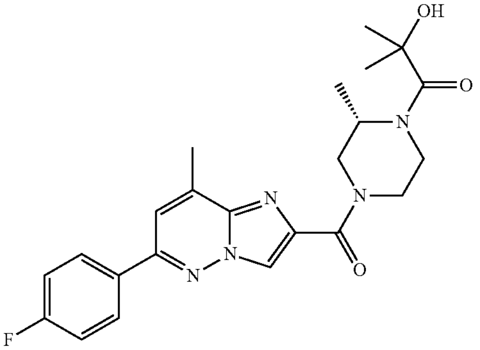
I-159
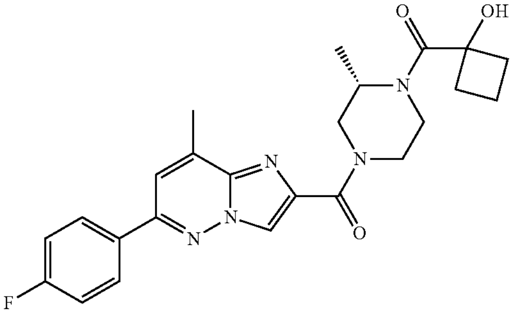
I-160
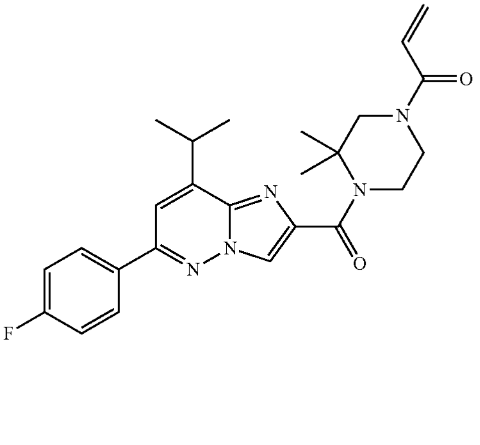
-continued
I-161
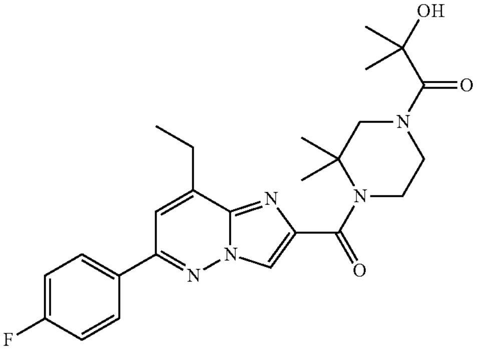
I-162
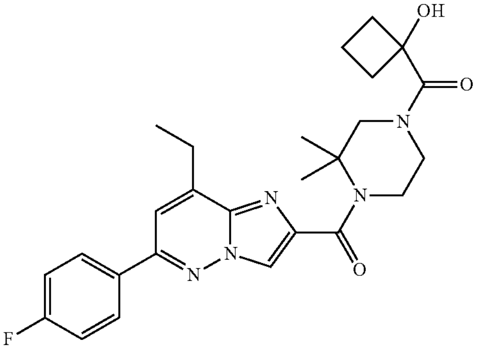
I-163
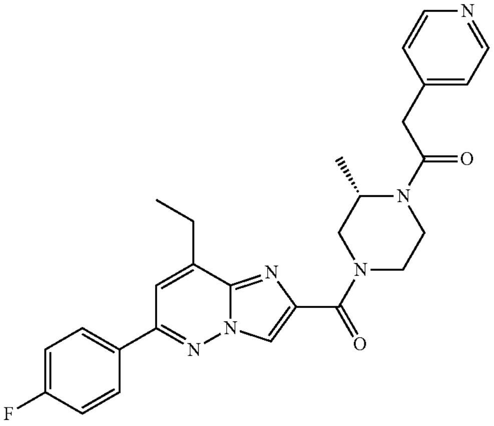
I-164
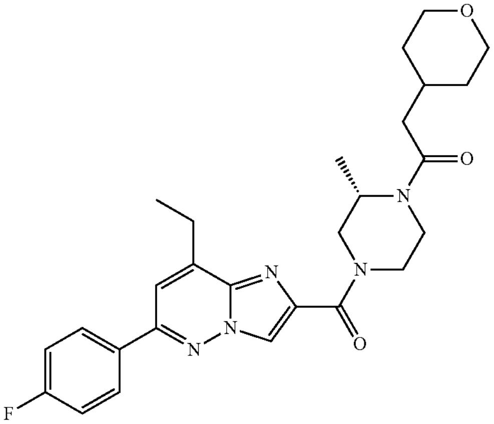

-continued
I-165
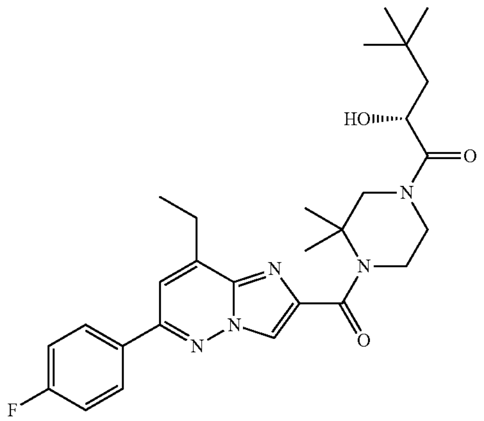
I-166
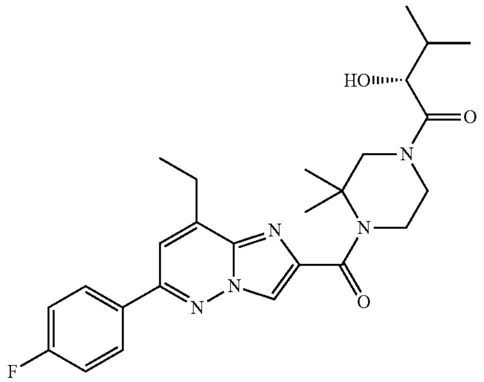
I-167
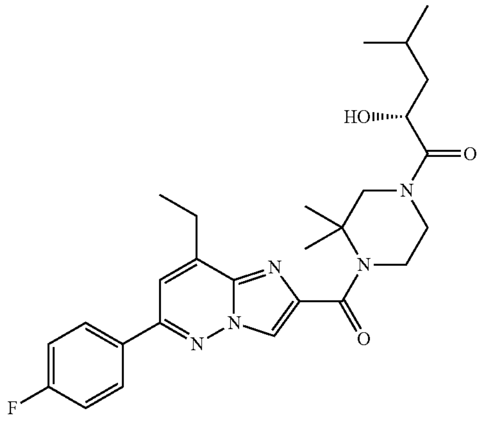
I-168
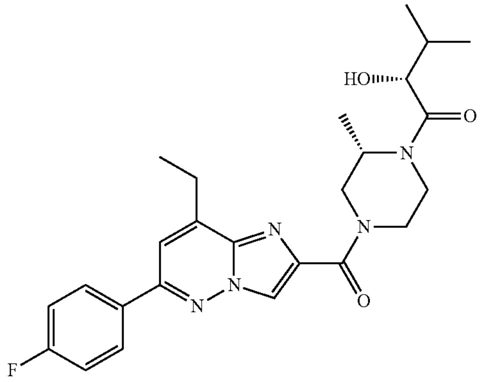
-continued
I-169
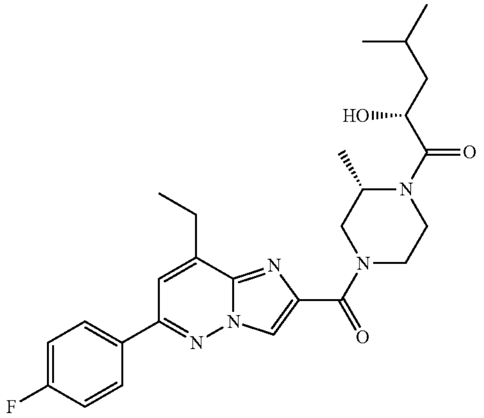
I-170
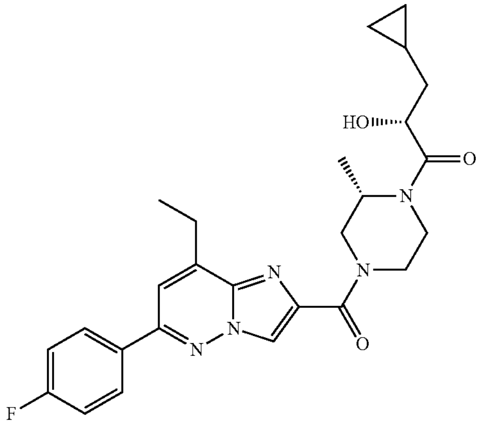
I-171
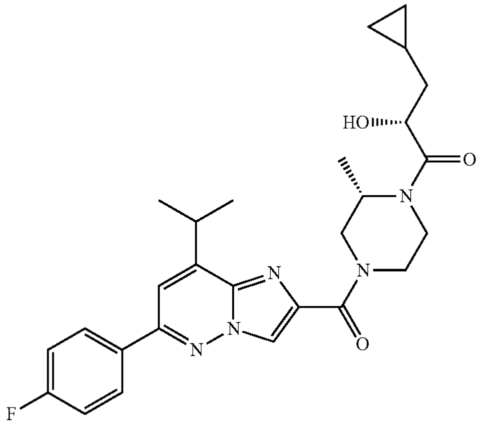

I-172
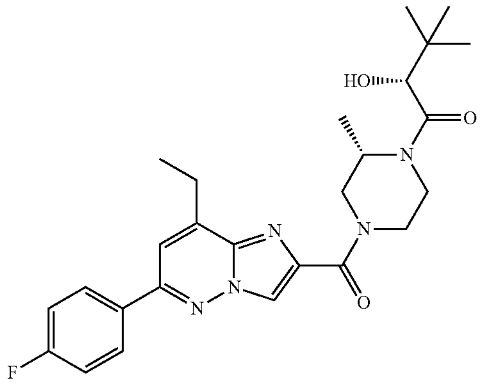
I-173
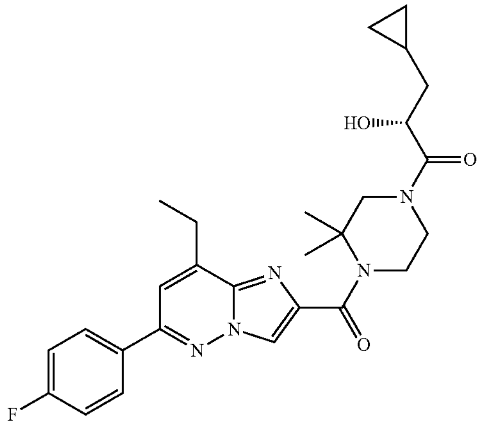
I-174
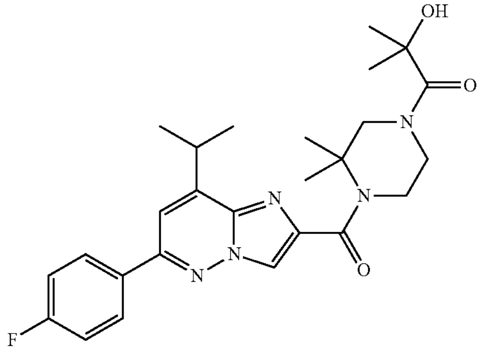
I-175
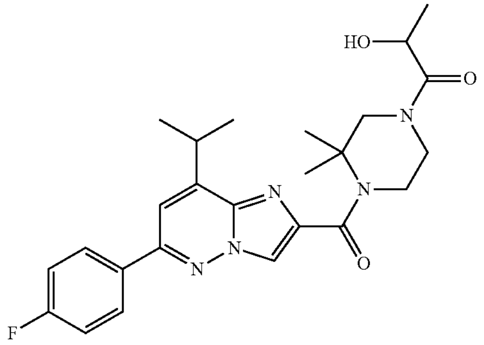
I-176
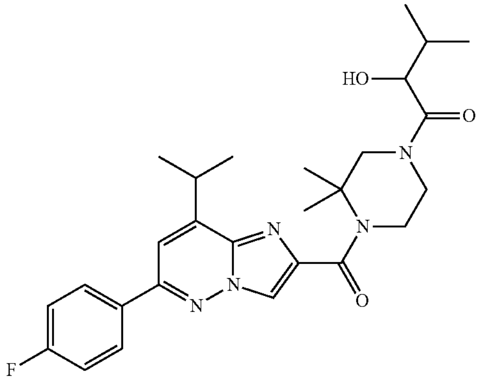
I-177
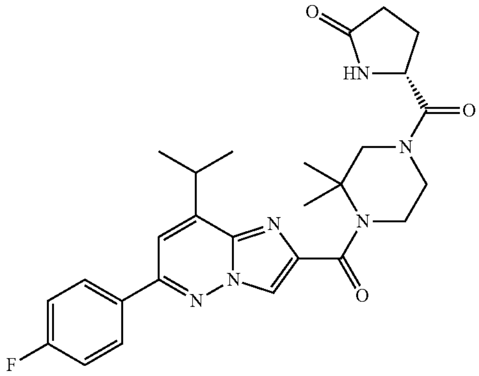
I-178
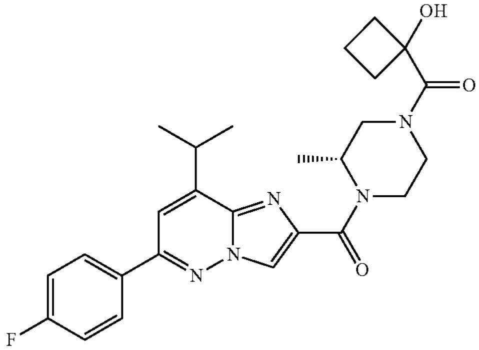
I-179
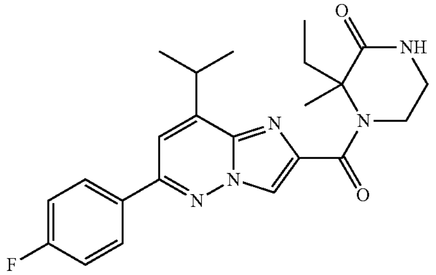

-continued
I-180
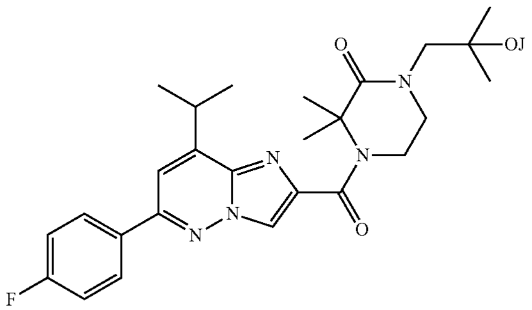
I-181
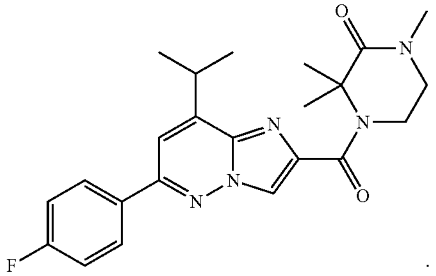
10. The compound of claim 1, as represented by any one of the following structures or a pharmaceutically acceptable salt thereof:
I-182
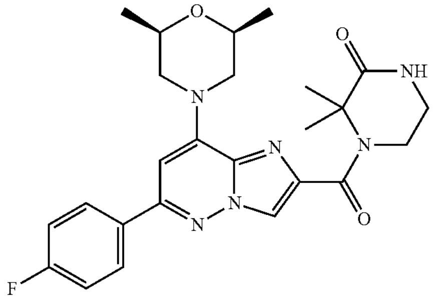
I-183
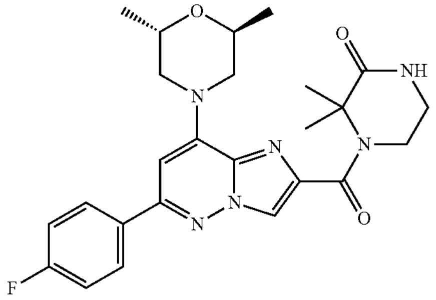
-continued
I-184
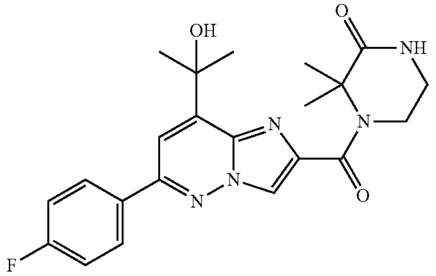
I-185
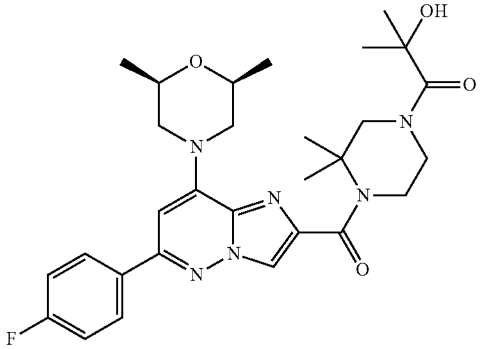
I-186
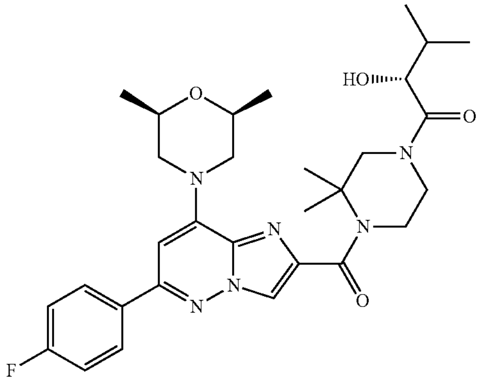
I-187
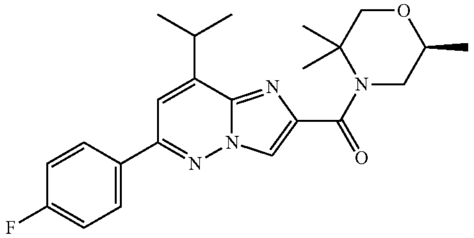
I-188
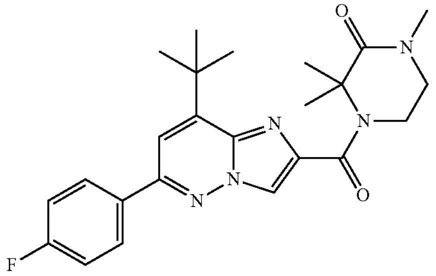

-continued
I-189
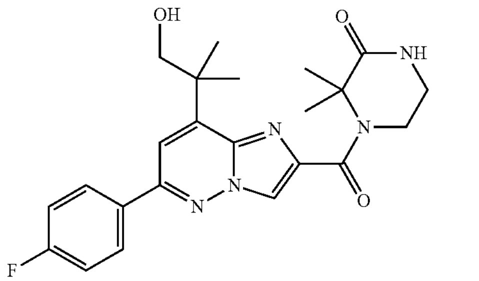
I-190
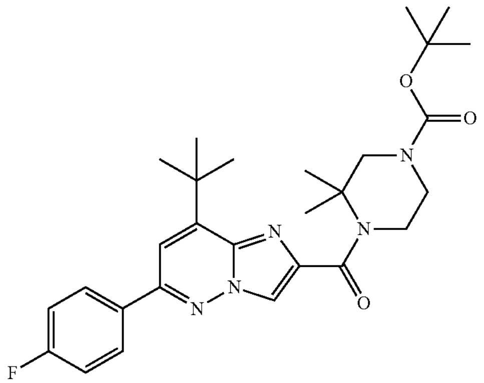
I-191
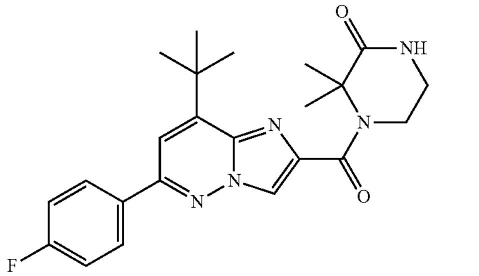
I-192
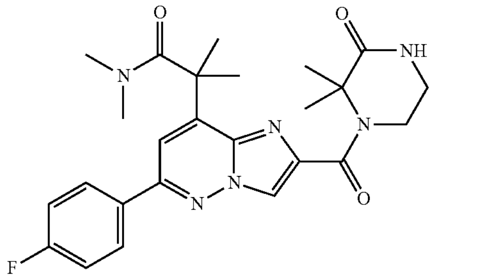
I-193
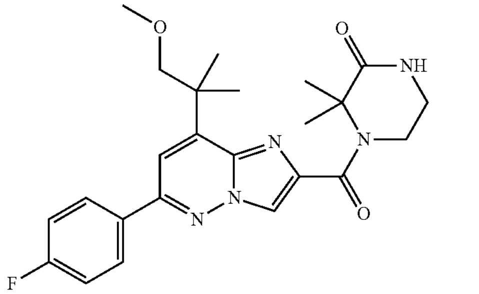
-continued
I-194
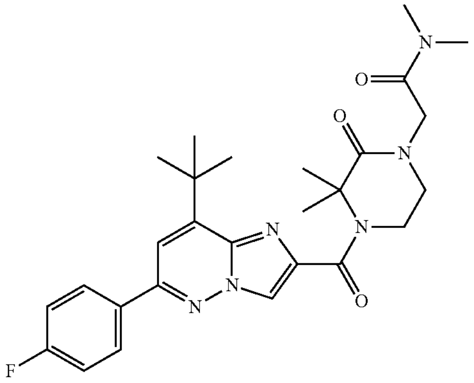
I-195
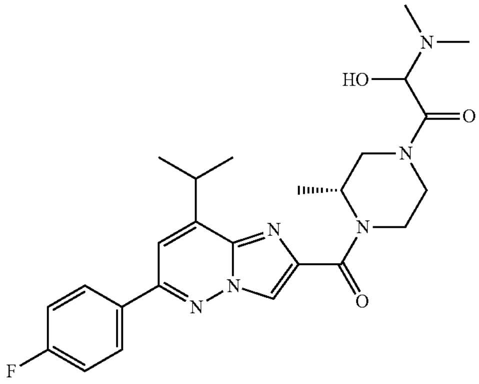
I-196
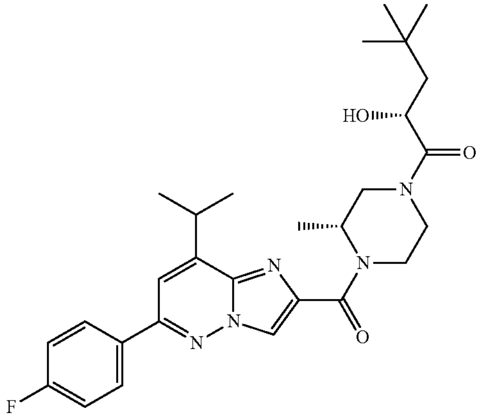
I-197
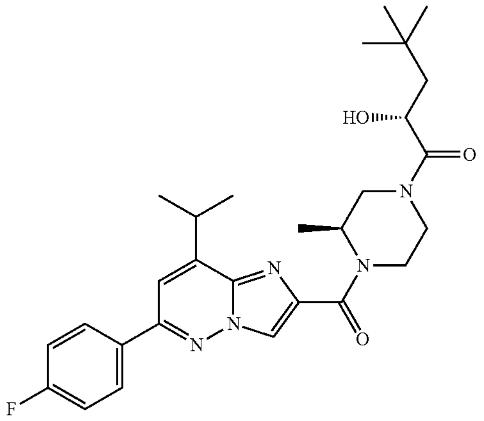

I-198
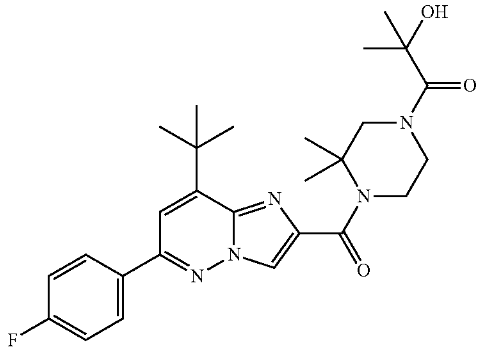
I-199
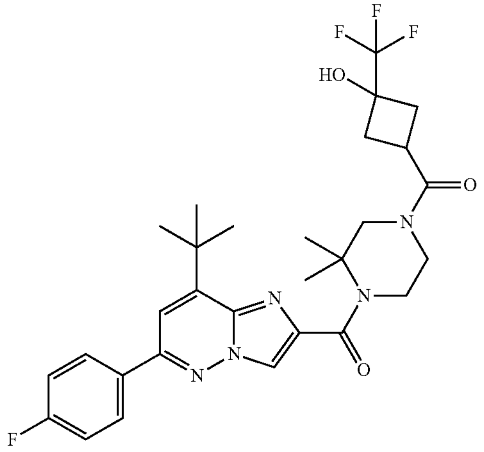
I-200
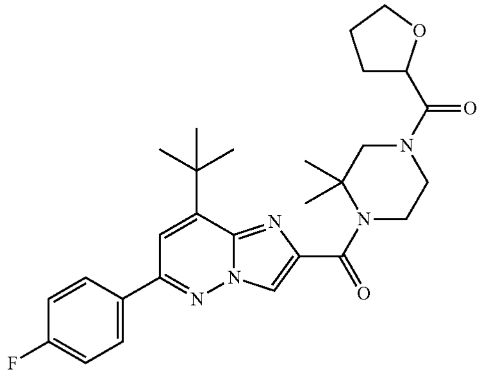
I-201
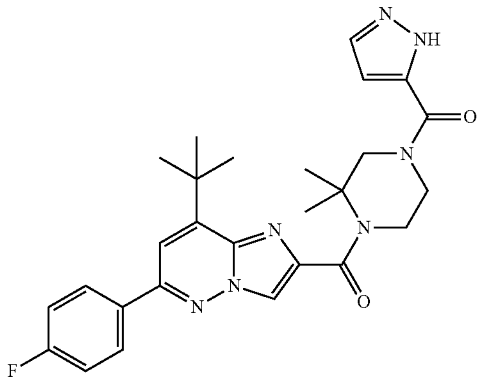
I-202
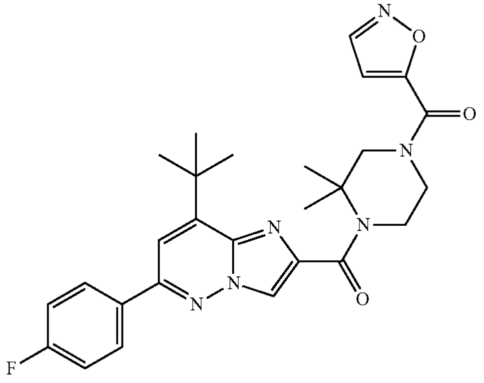
I-203
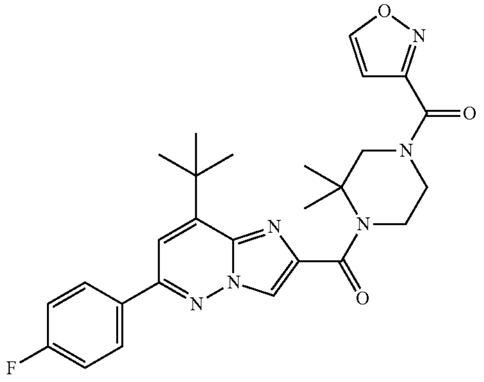
I-204
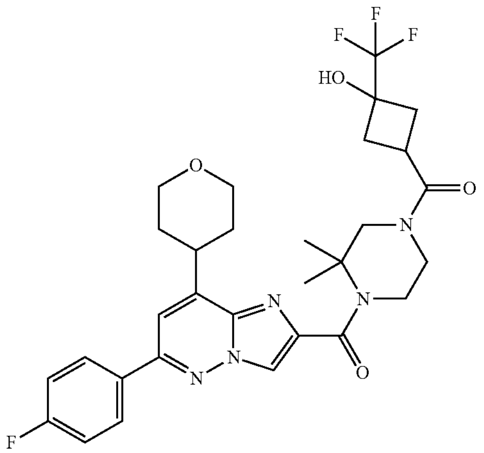
I-205
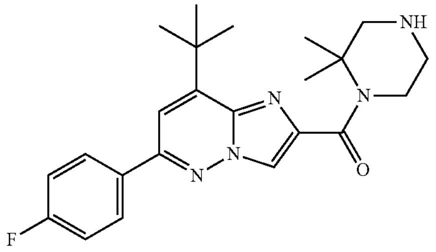

-continued
I-206
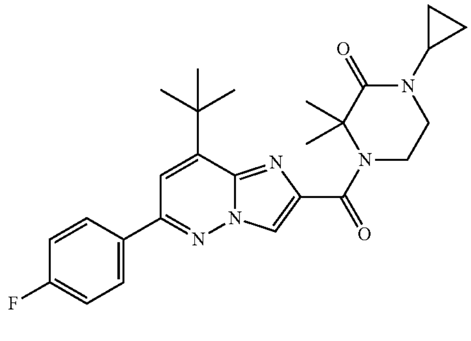
I-207
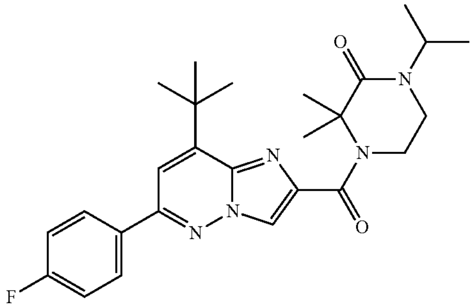
I-208
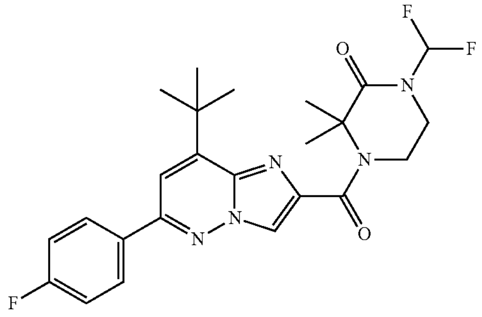
I-209
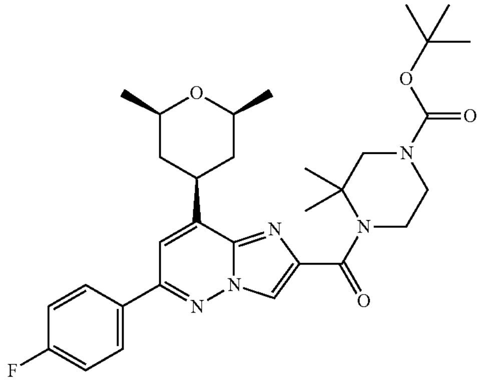
-continued
I-210
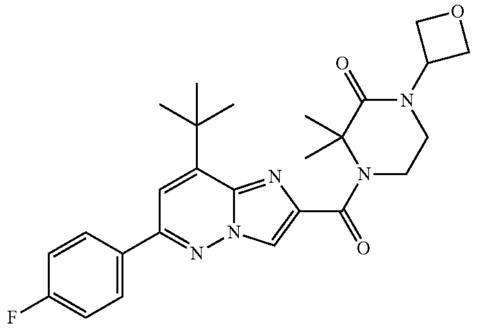
I-211
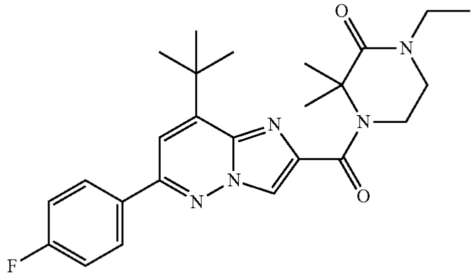
I-212
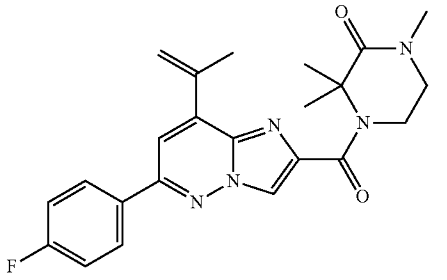
I-213
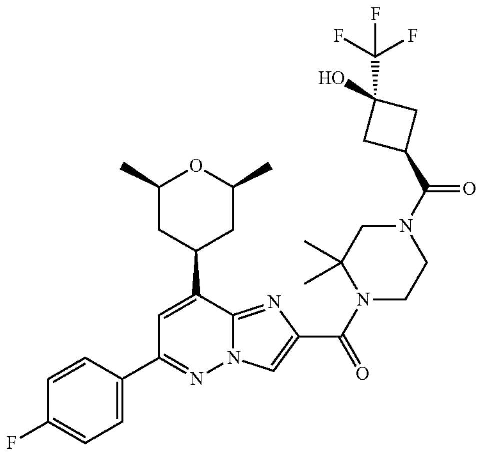

-continued
I-214
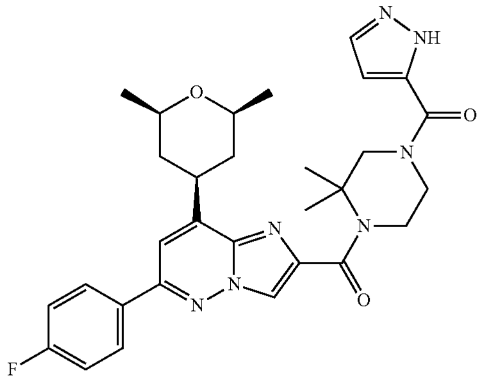
I-215
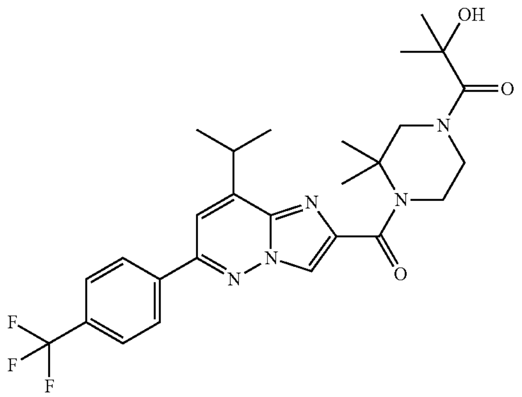
I-216
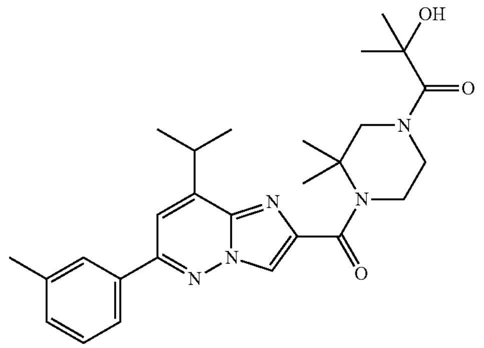
I-217
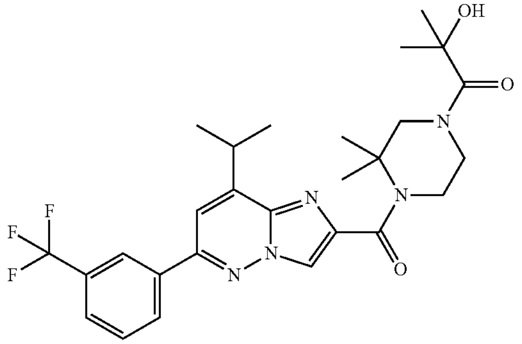
-continued
I-218
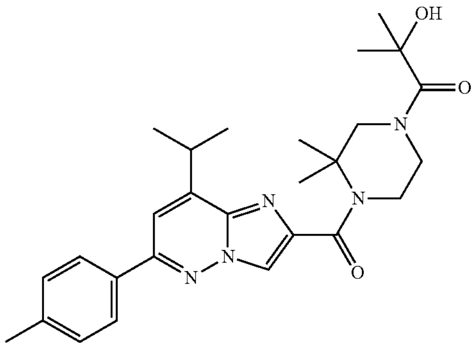
I-219
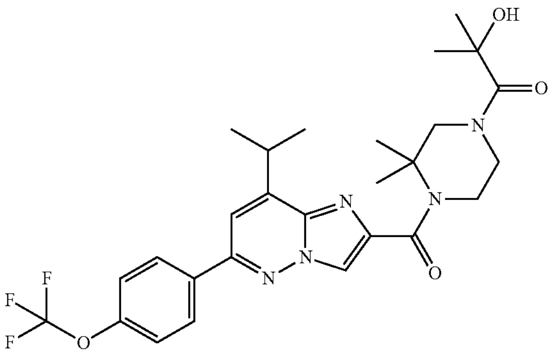
I-220
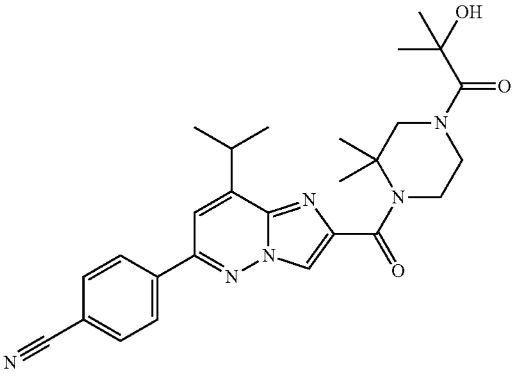
I-221
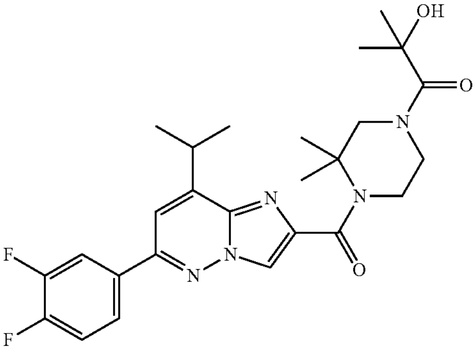

-continued
I-222
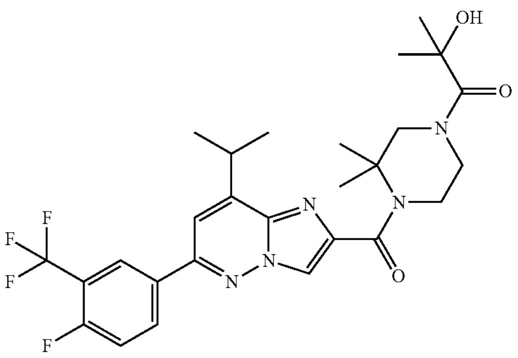
I-223
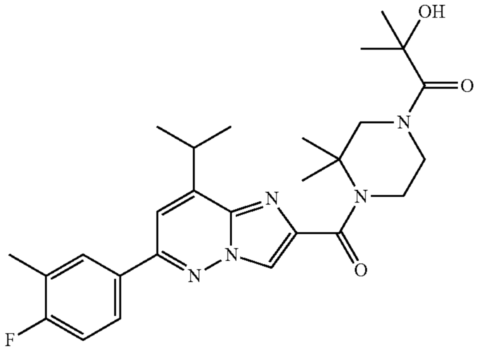
I-224
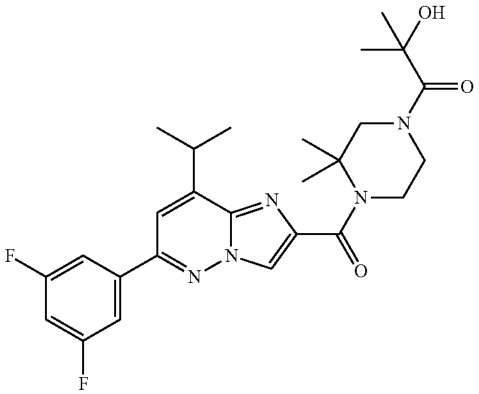
I-225
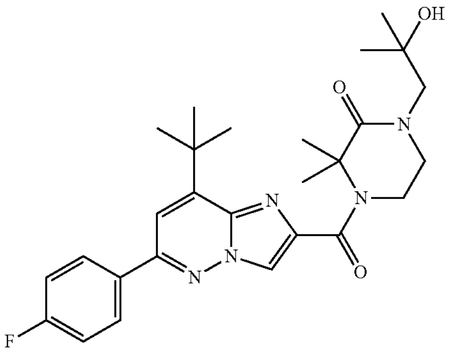
-continued
I-226
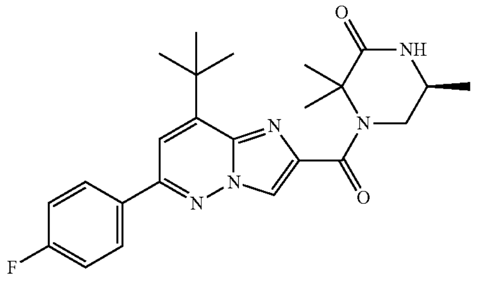
I-227
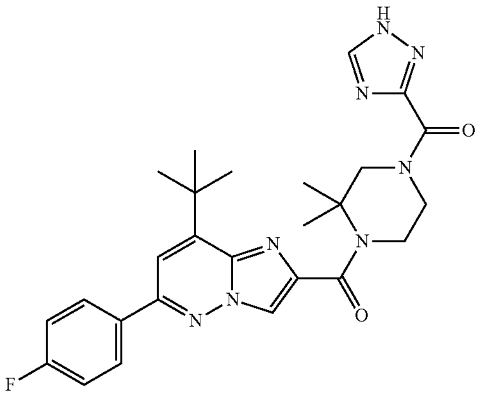
I-228
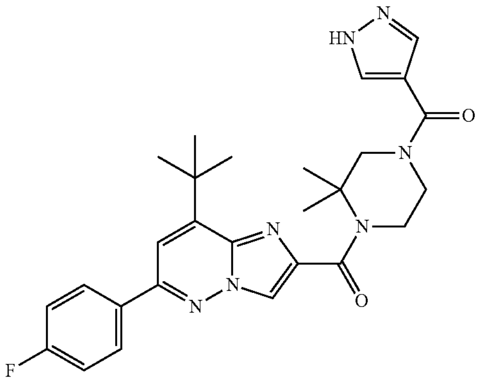
I-229
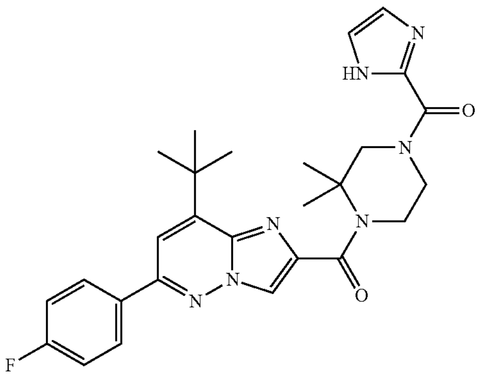

-continued
I-230
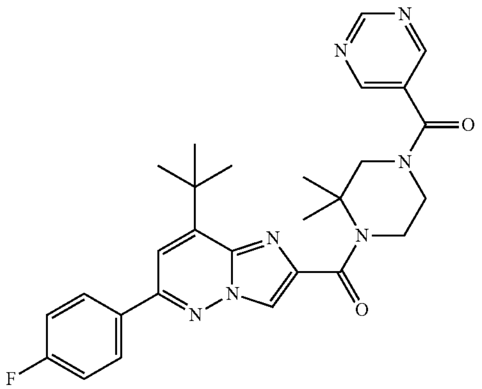
I-231
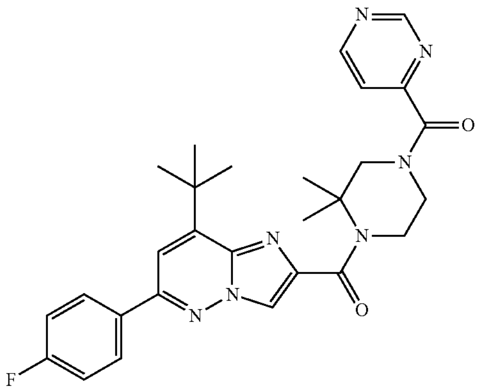
I-232
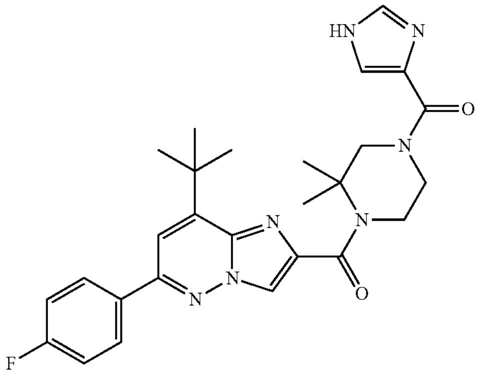
I-233
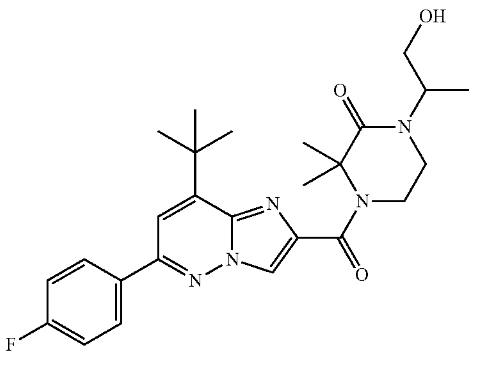
-continued
I-234
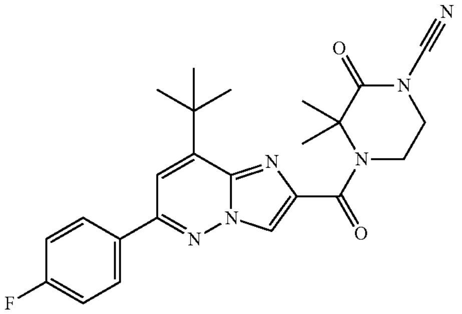
I-235
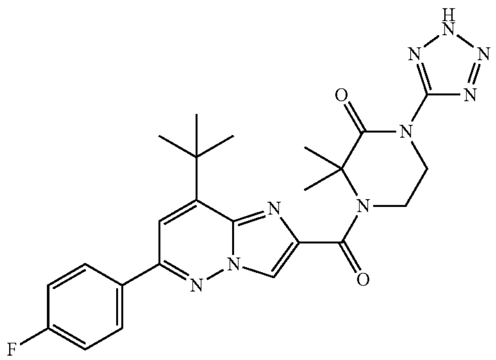
I-236
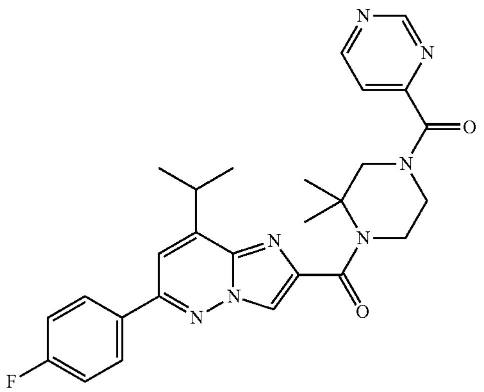
I-237
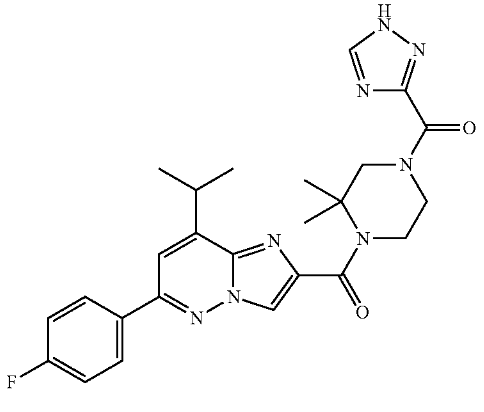

-continued
I-238
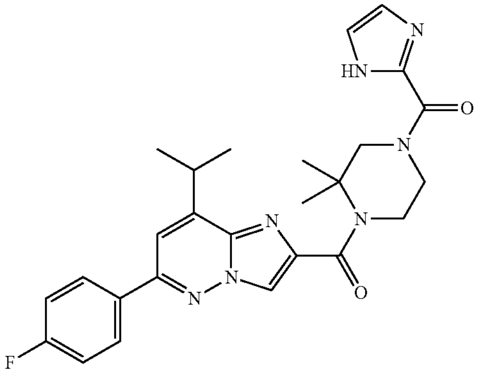
I-239
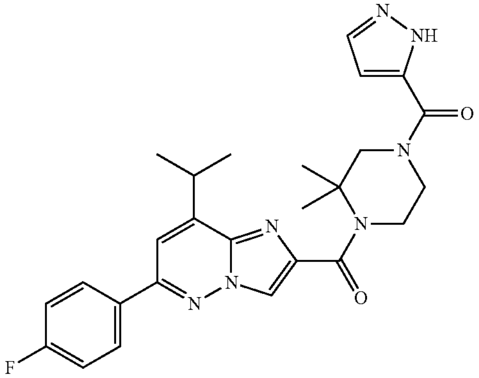
I-240
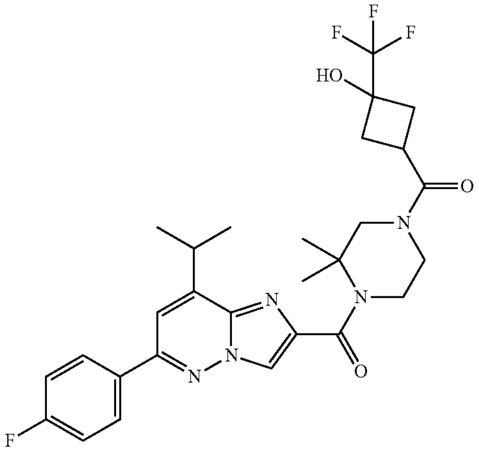
I-241
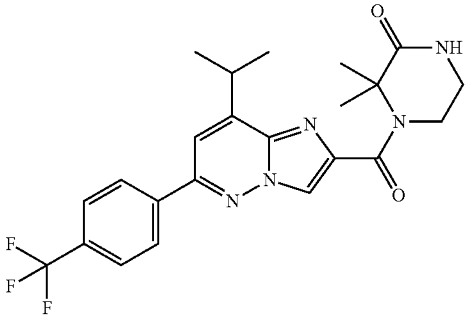
-continued
I-242
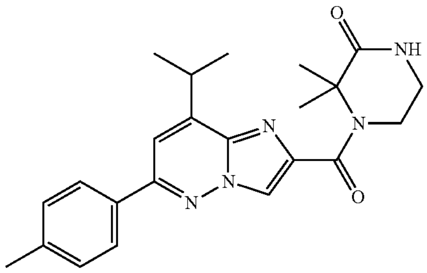
I-243
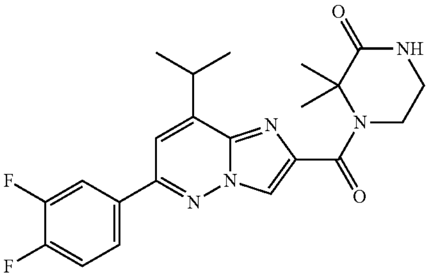
I-244
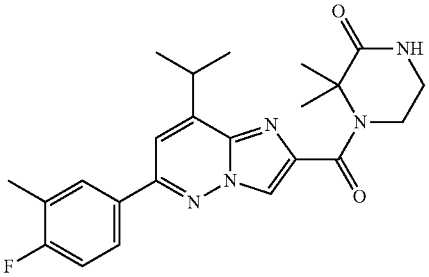
I-245
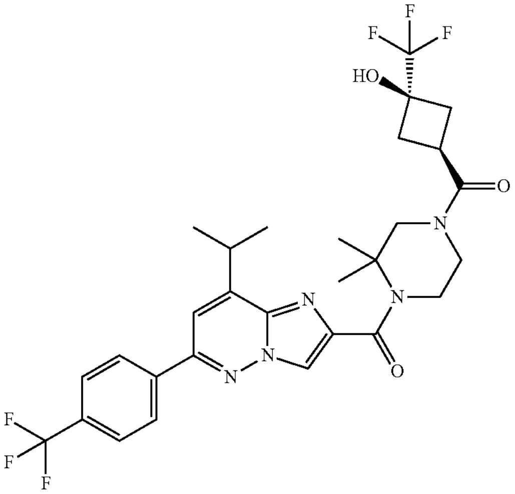

-continued
I-246
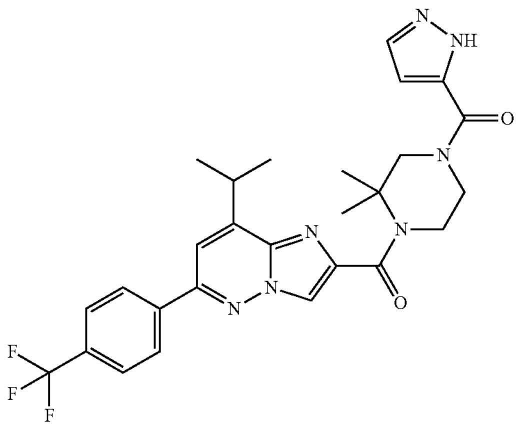
I-247
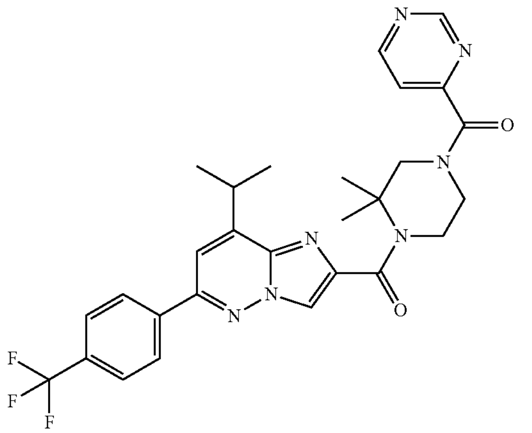
I-248
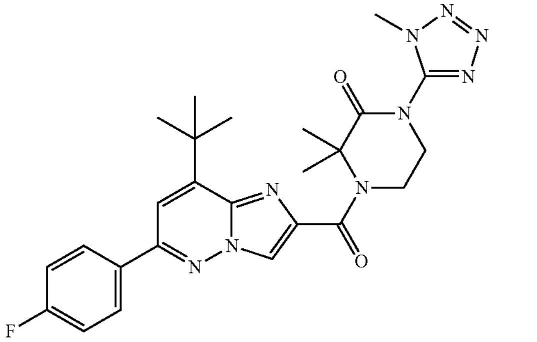
I-249
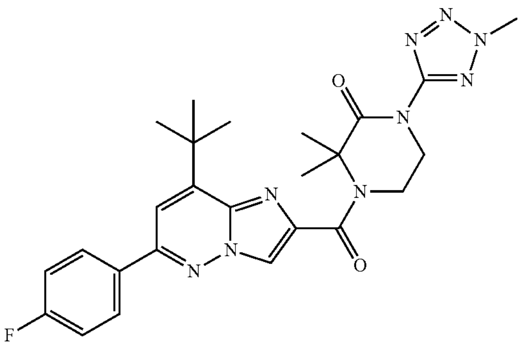
-continued
I-250
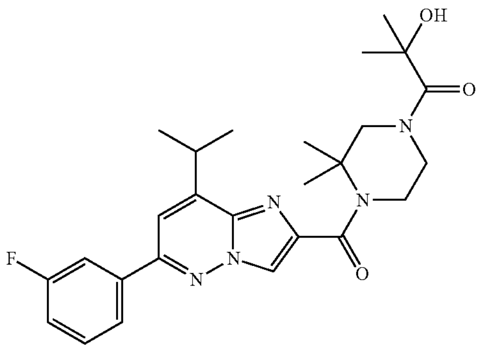
I-251
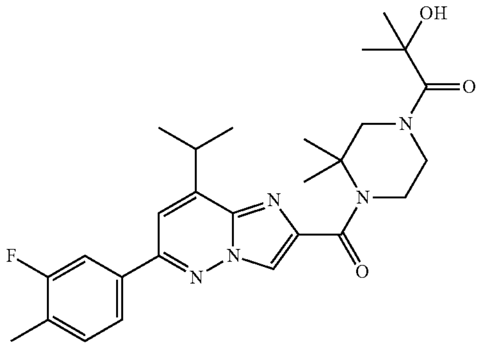
I-252
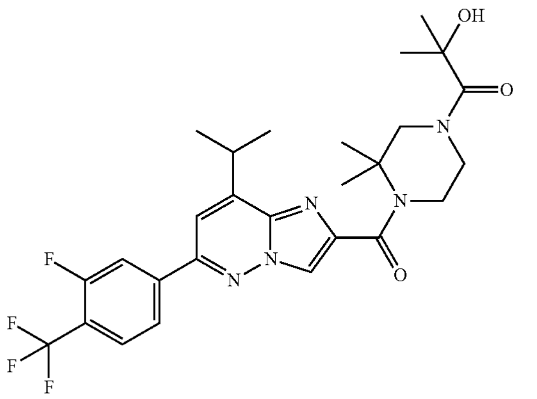
I-253
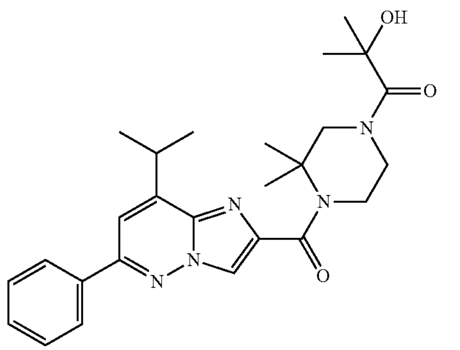

-continued
I-254
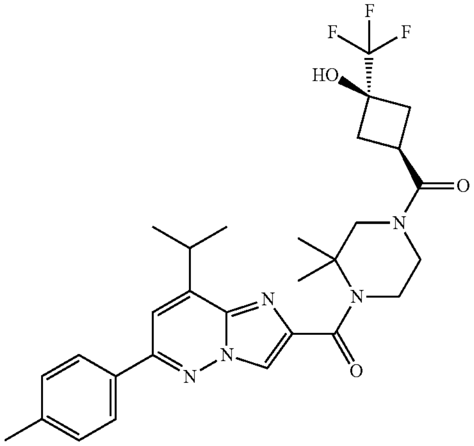
I-255
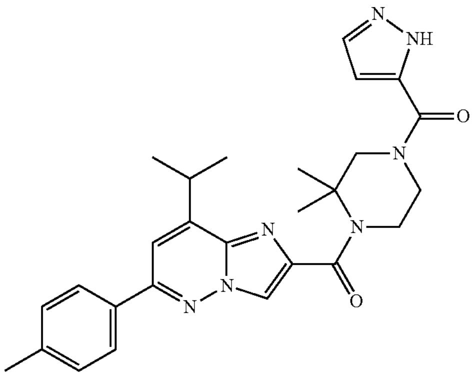
I-256
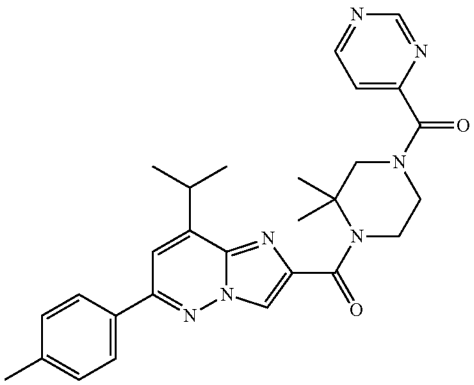
-continued
I-257
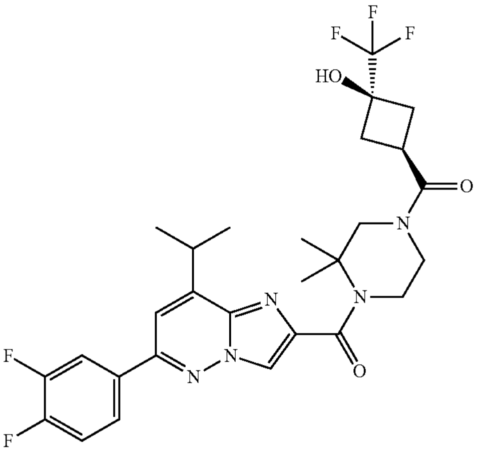
I-258
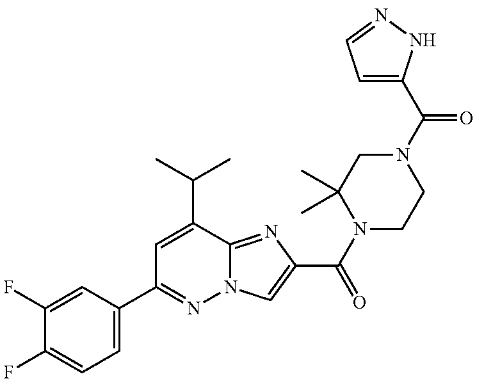
I-259
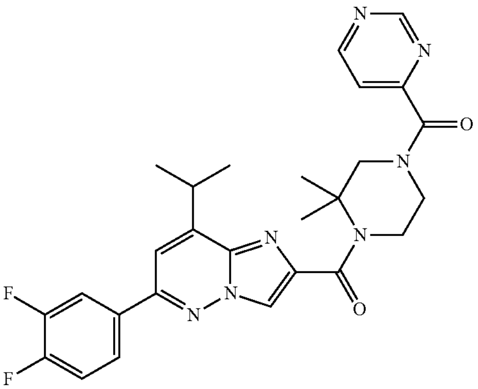

-continued
I-260
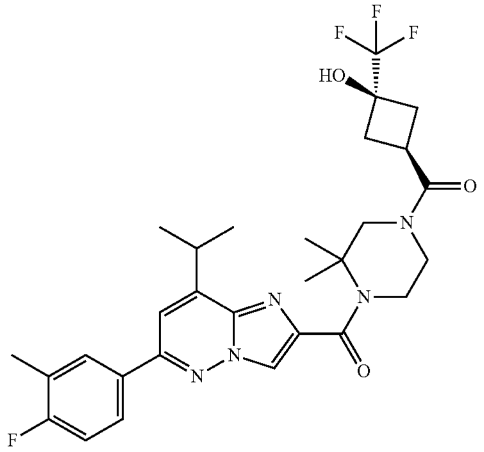
I-261
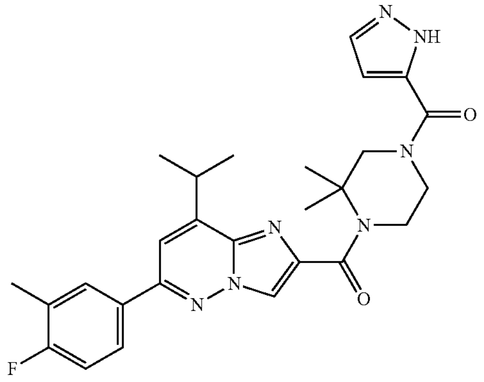
I-262
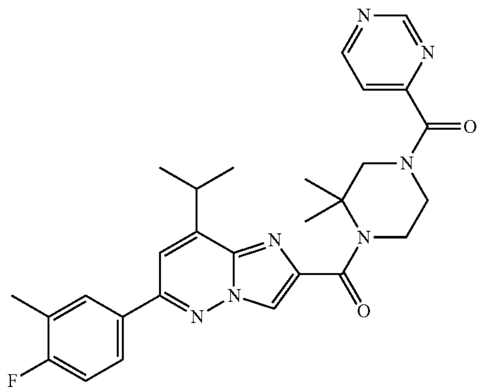
-continued
I-263
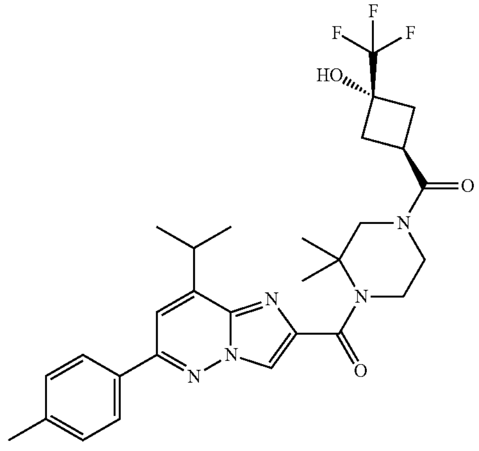
I-264
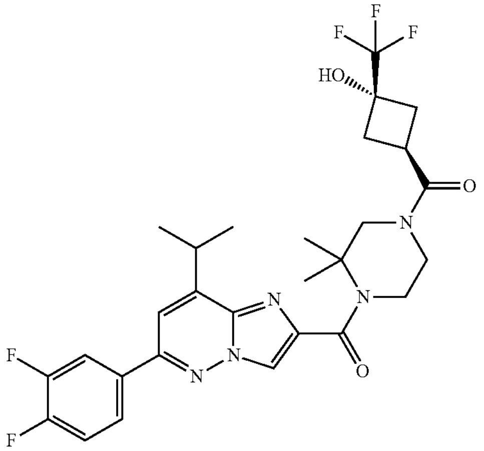
I-265
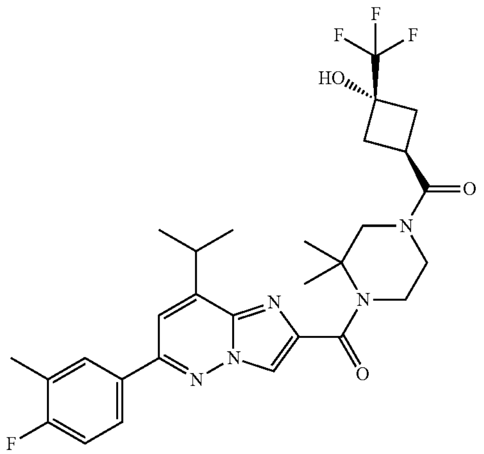

-continued
I-266
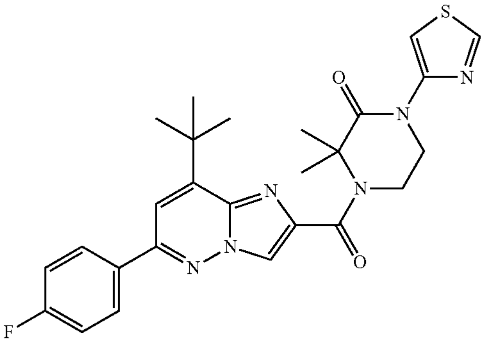
I-267
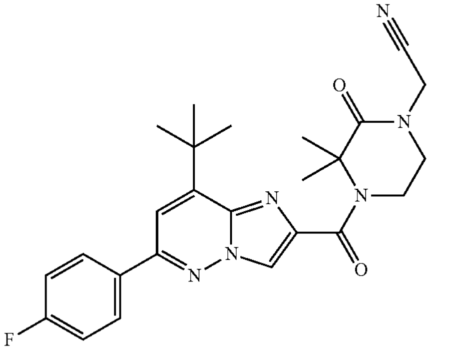
I-268
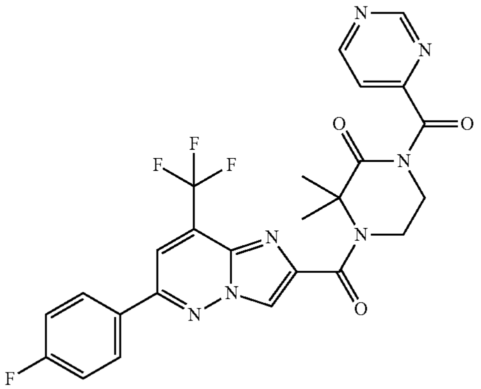
I-269
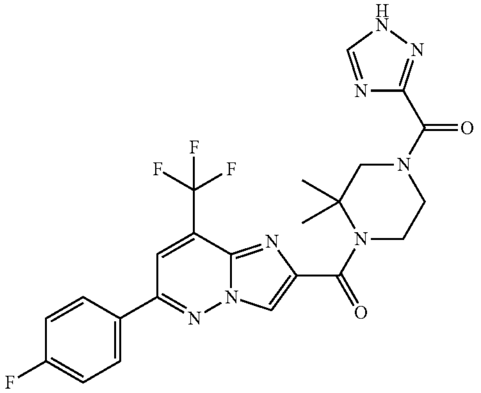
-continued
I-270
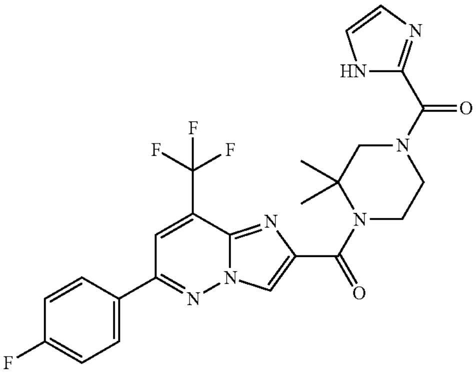
I-271
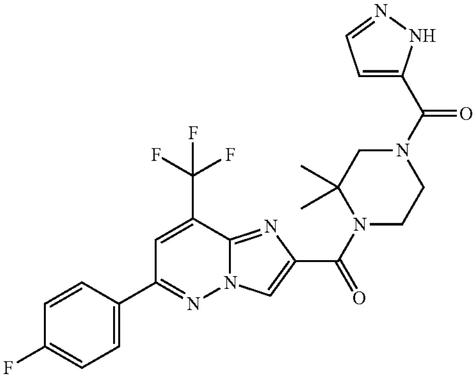
I-272
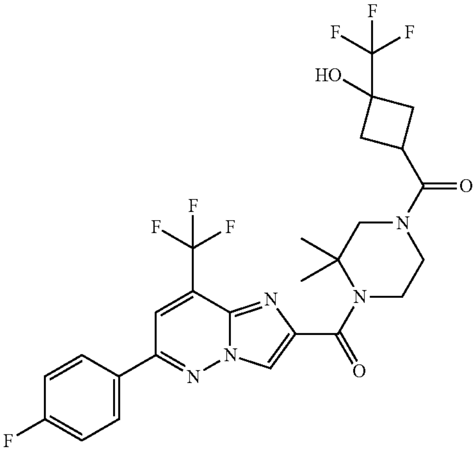
I-273
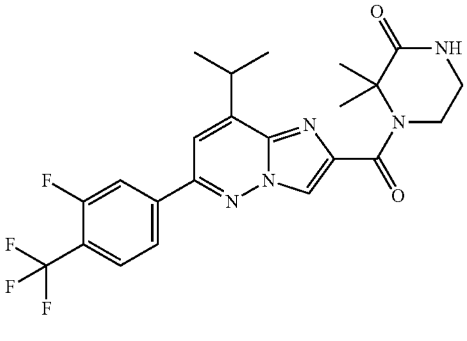

-continued
I-274
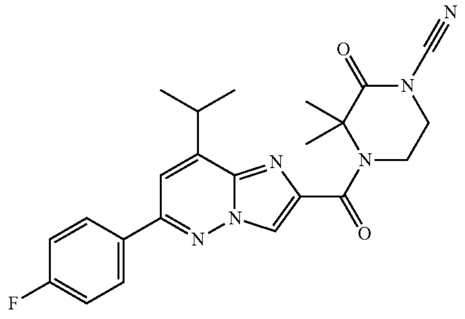
I-275
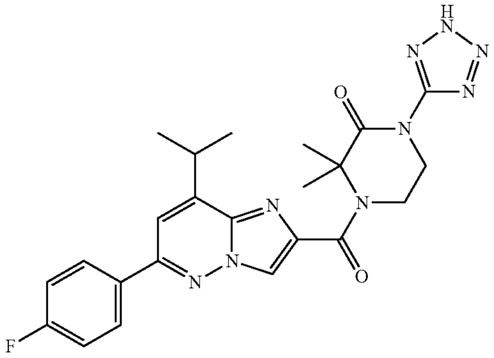
I-276
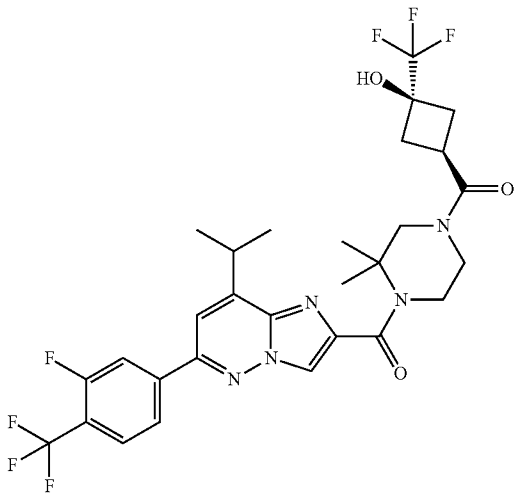
I-277
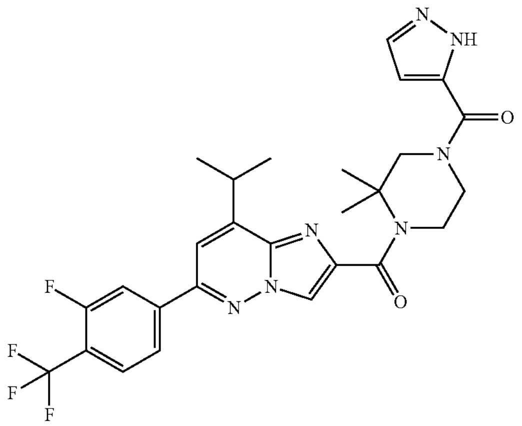
-continued
I-278
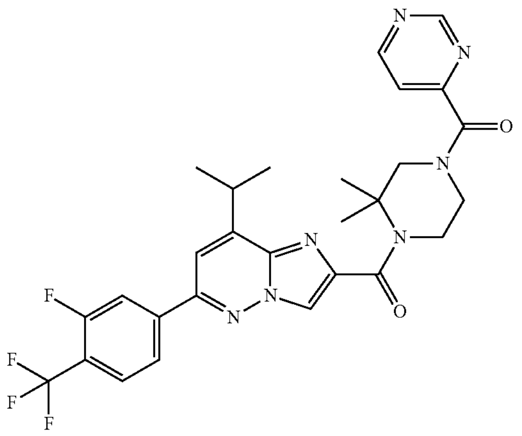
I-279
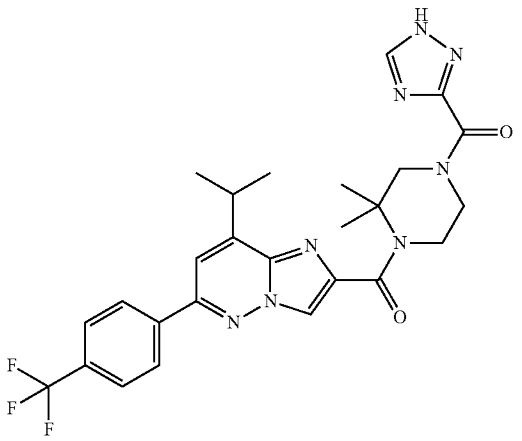
I-280
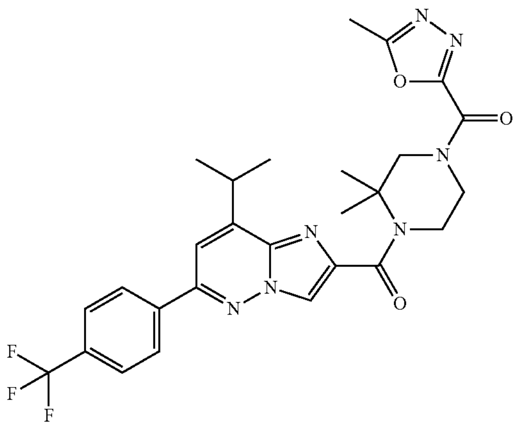

-continued
I-281
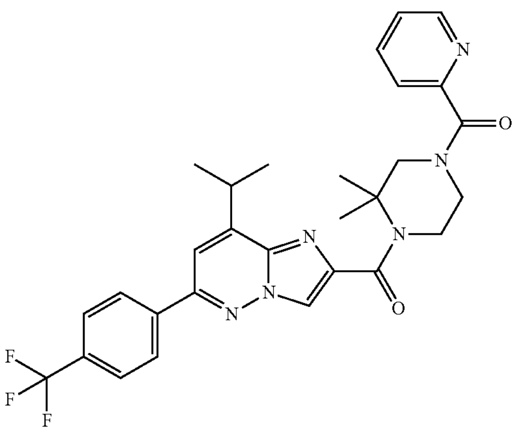
I-282
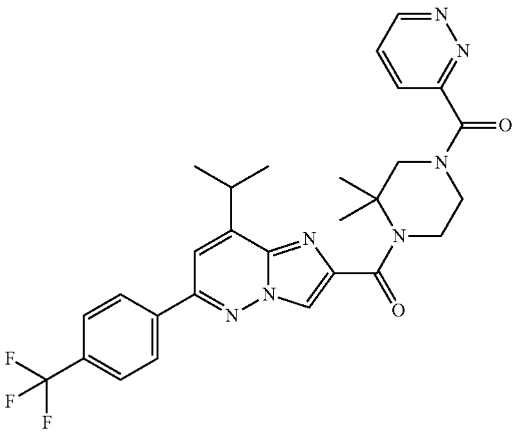
I-283
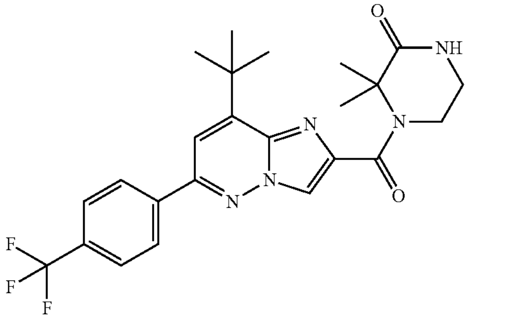
I-284
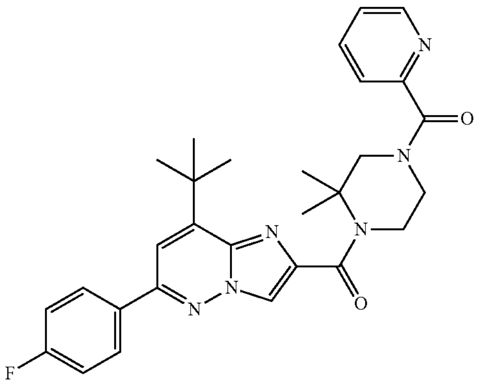
-continued
I-285
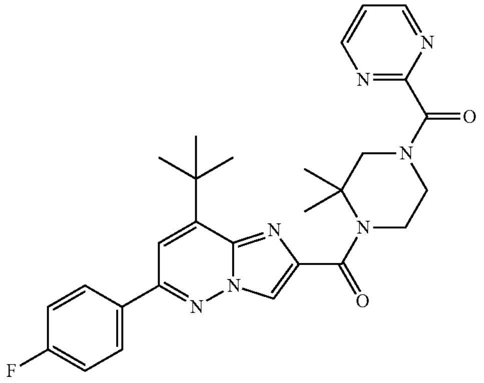
I-286
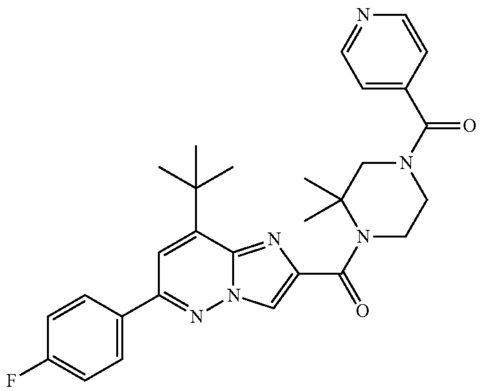
I-287
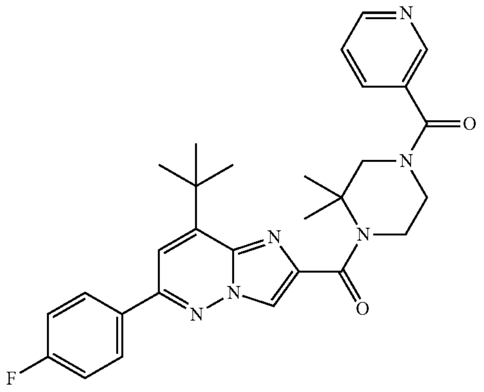
I-288
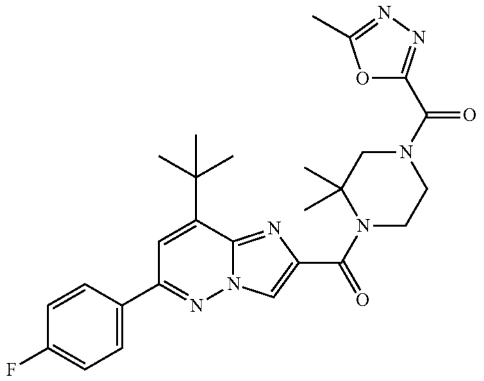

-continued
I-289
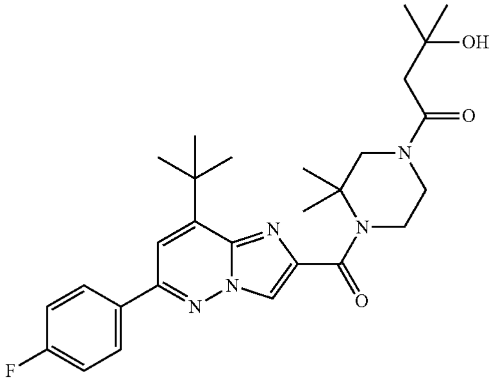
I-290
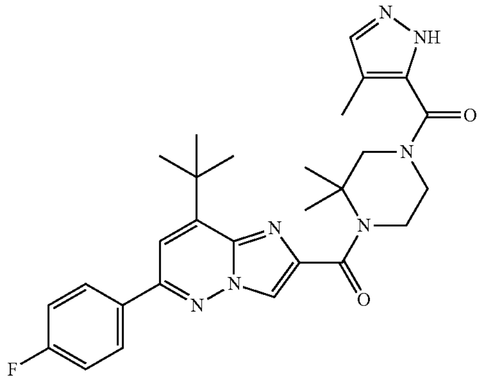
I-291
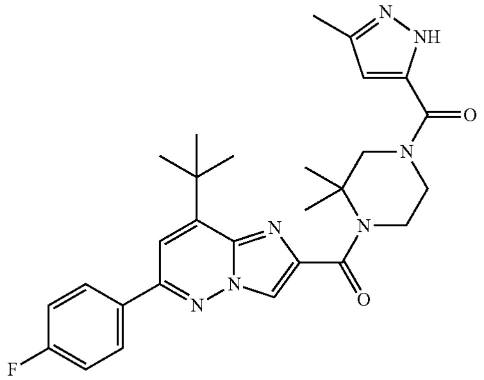
I-292
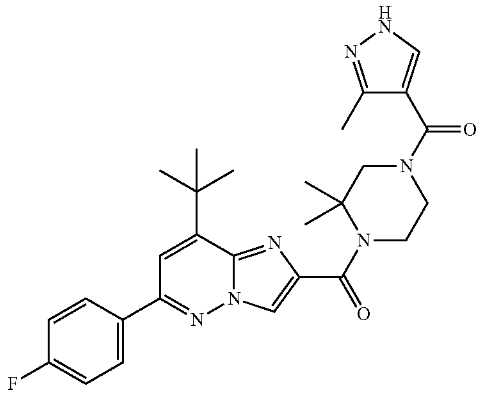
-continued
I-293
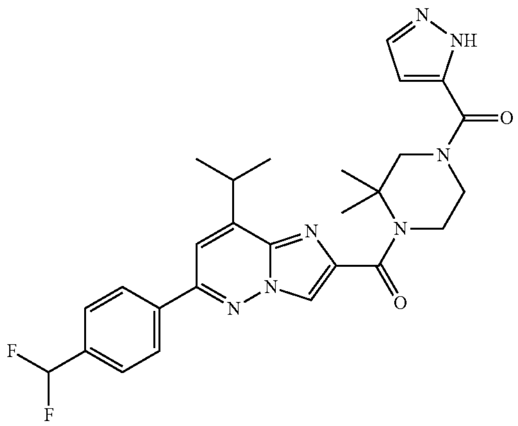
I-294
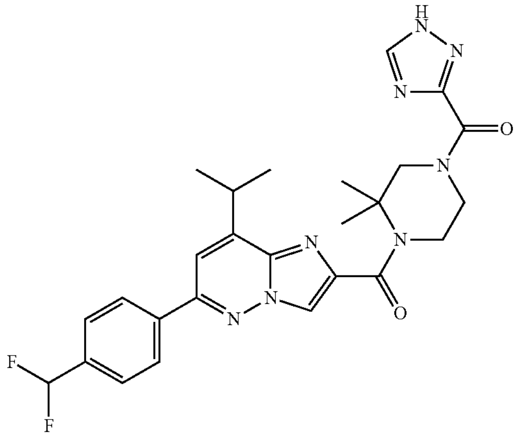
I-295
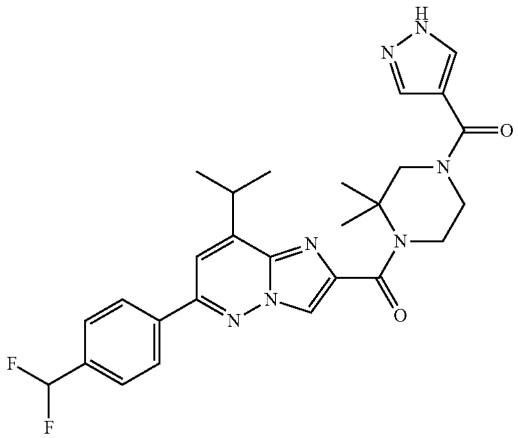

I-296
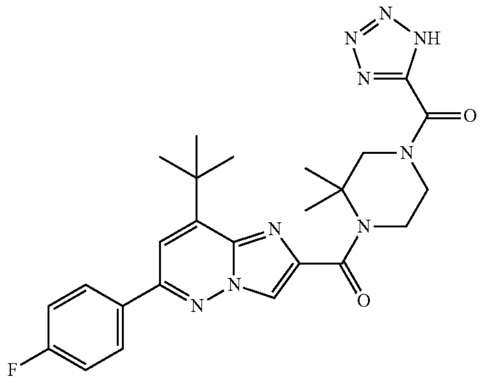
I-297
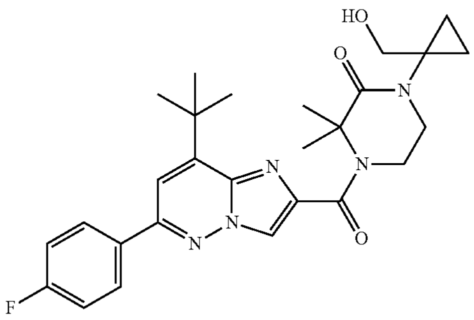
I-298
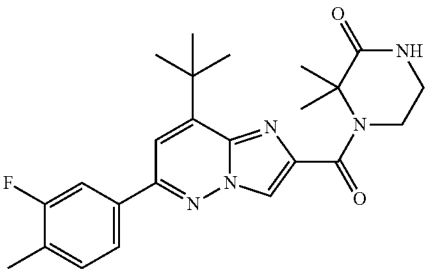
I-299
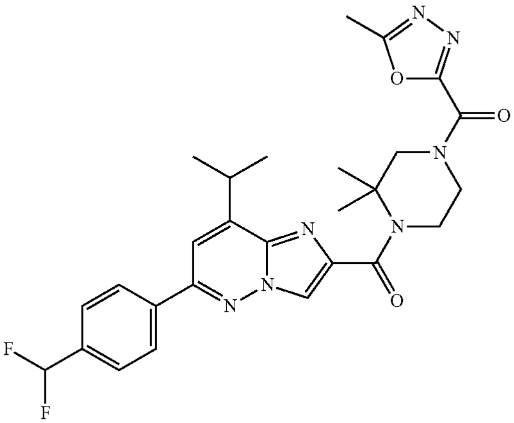
I-300
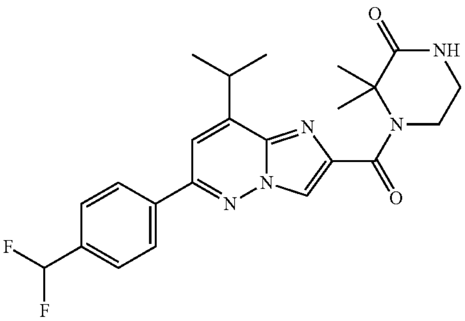
I-301
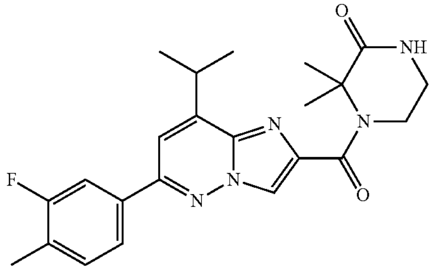
I-302
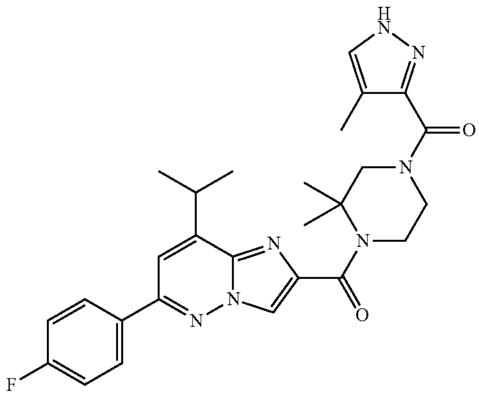
I-303
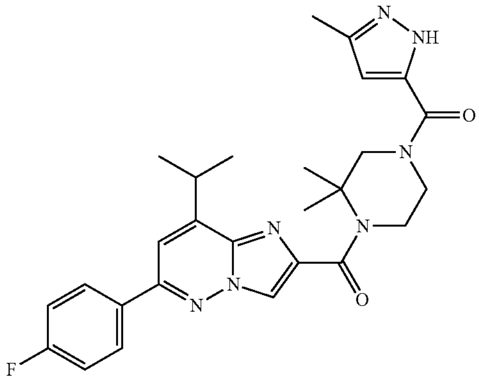

-continued
I-304
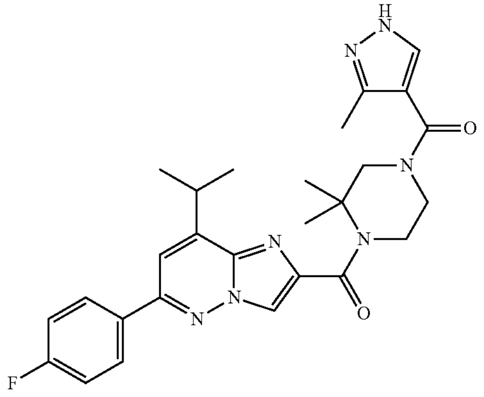
I-305
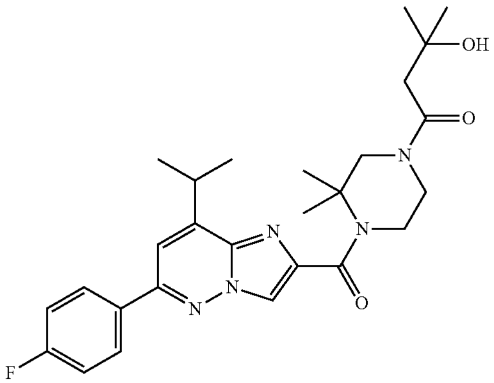
I-306
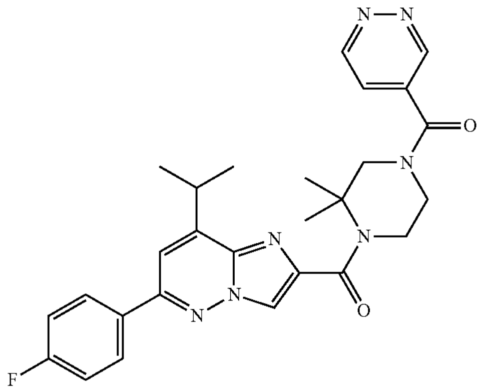
I-307
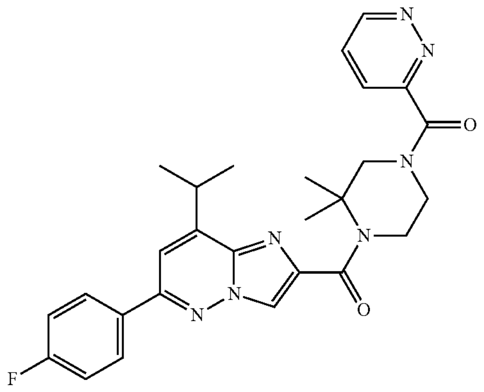
-continued
I-308
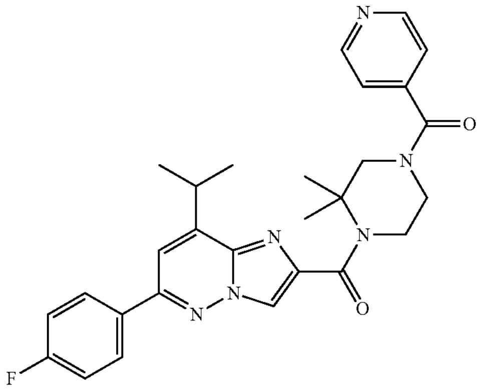
I-309
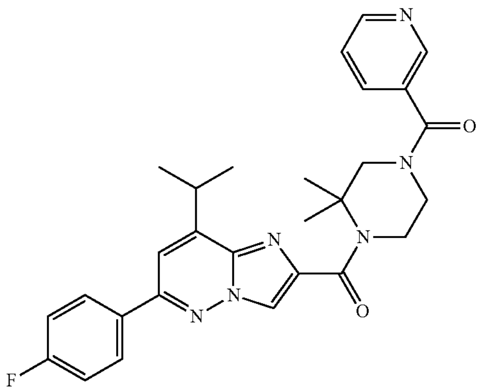
I-310
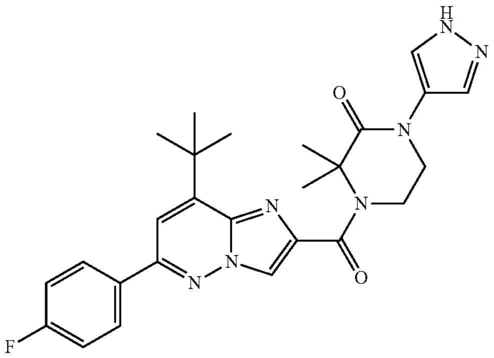
I-311
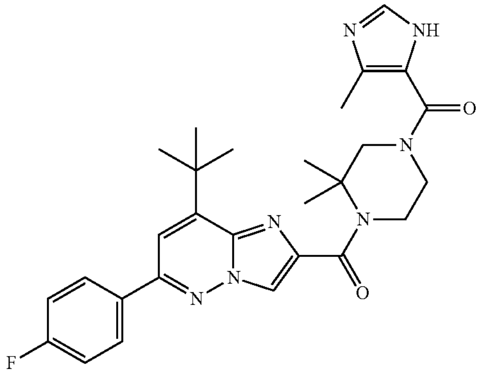

-continued
I-312
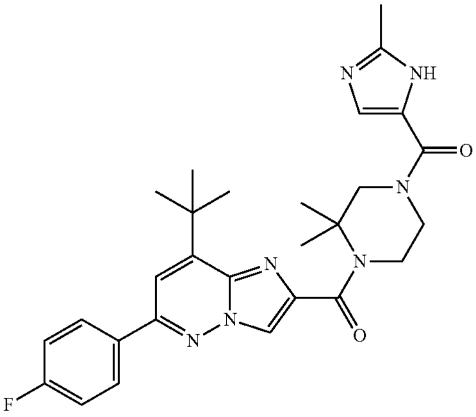
I-313
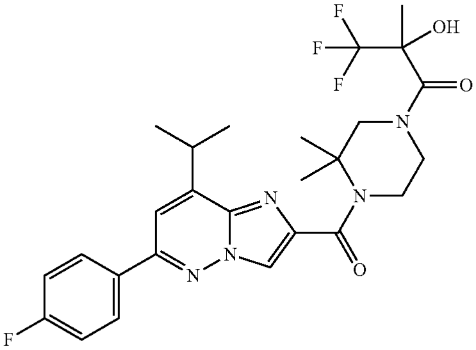
I-314
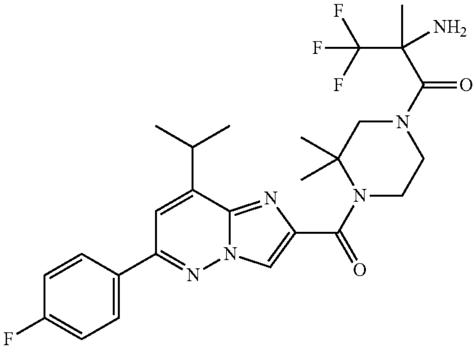
I-315
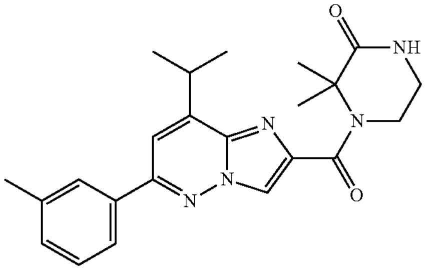
-continued
I-316
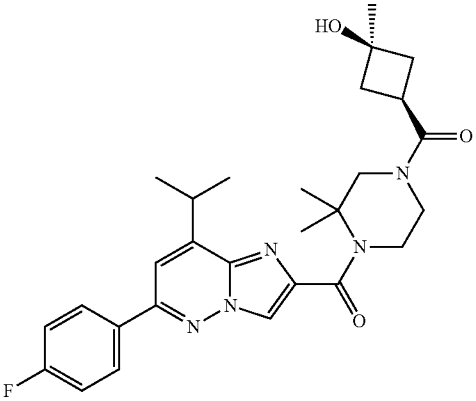
I-317
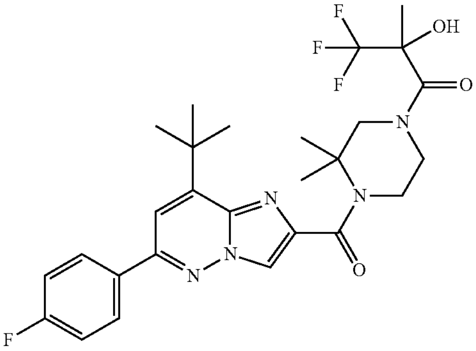
I-318
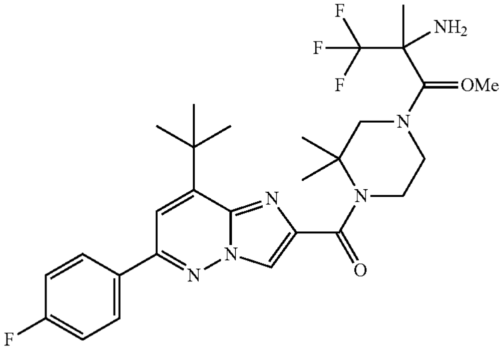
I-319
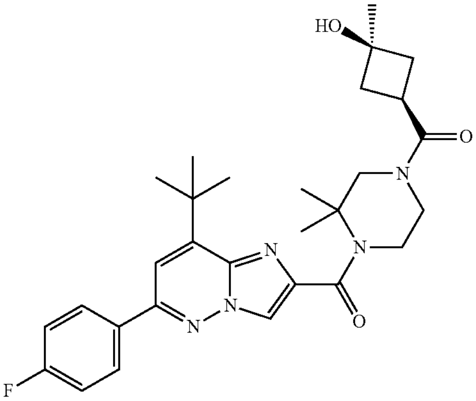

-continued
I-320
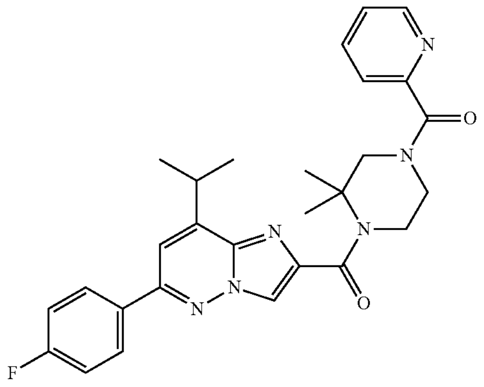
I-321
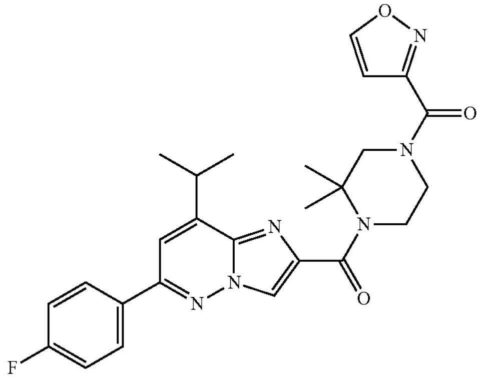
I-322
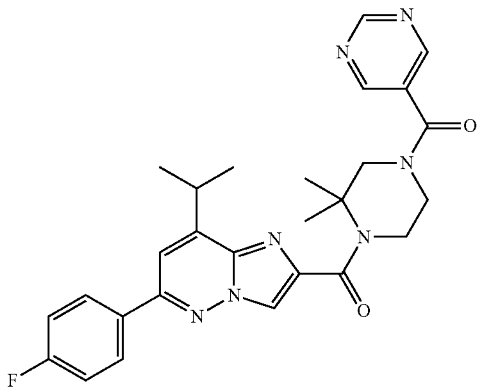
I-323
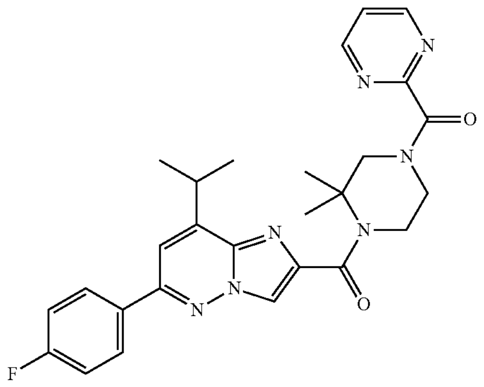
-continued
I-324
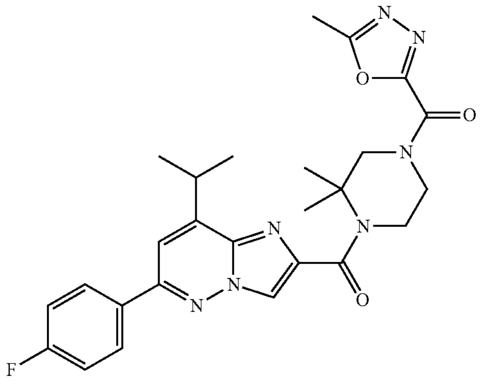
I-325
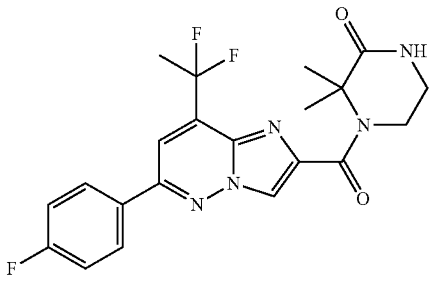
I-326
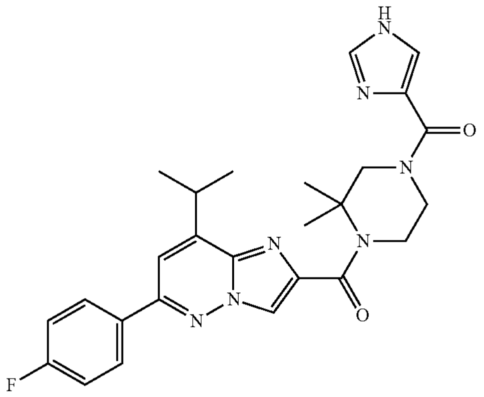
I-327
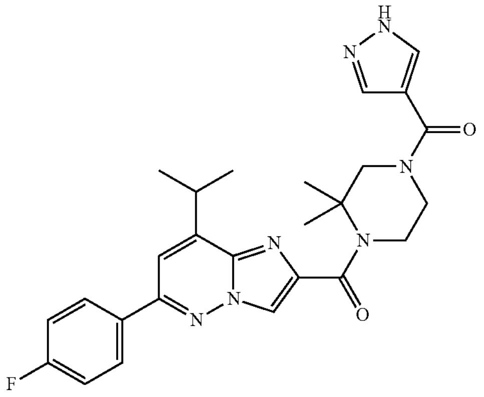

I-328
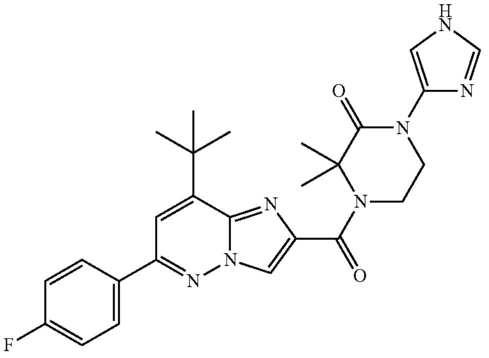
I-329
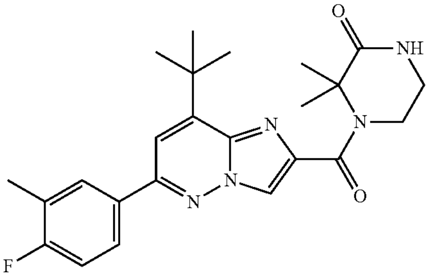
I-330
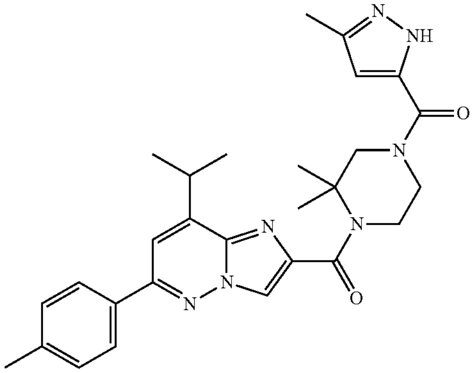
I-331
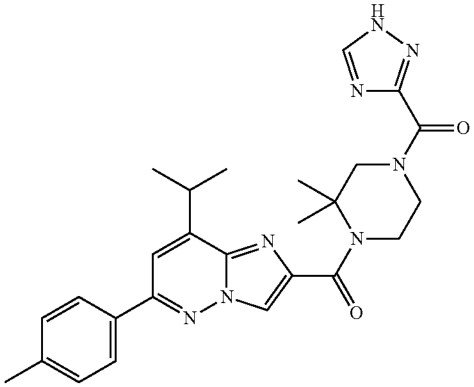
I-332
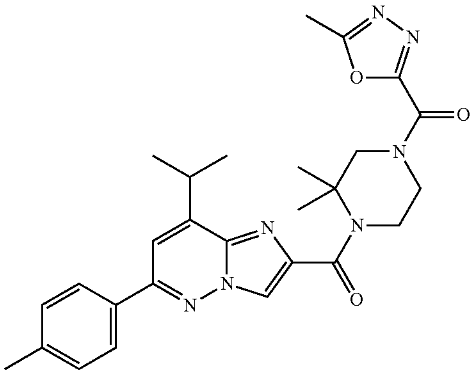
I-333
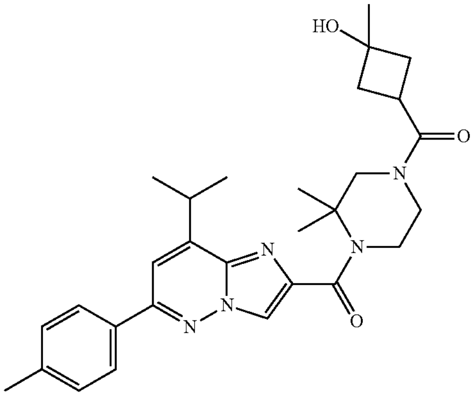
I-334
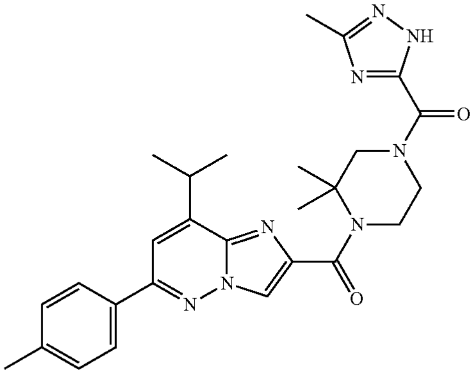
I-335
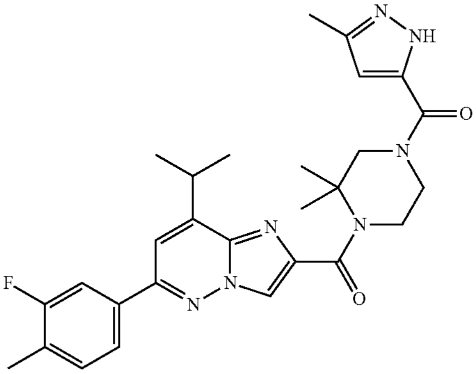

-continued
I-336
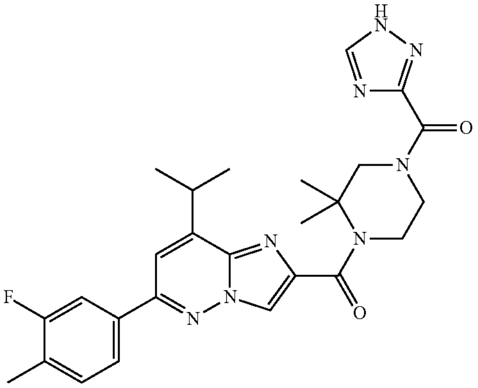
I-337
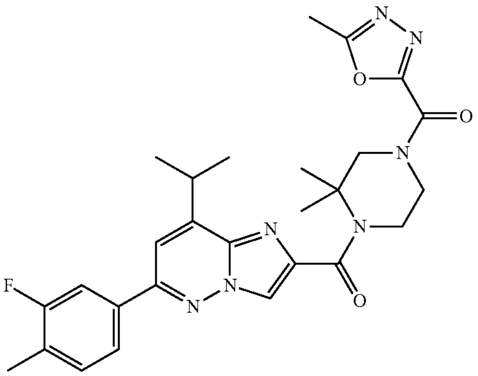
I-338
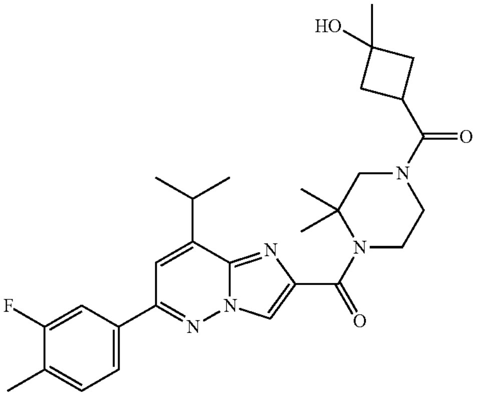
I-339
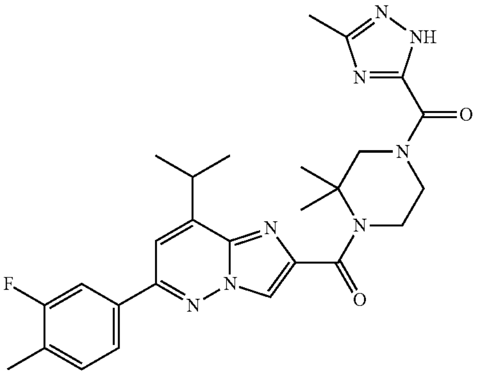
-continued
I-340
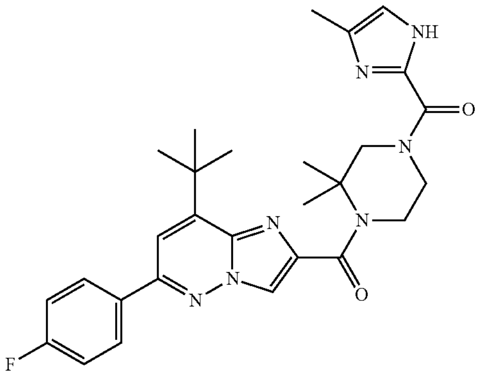
I-341
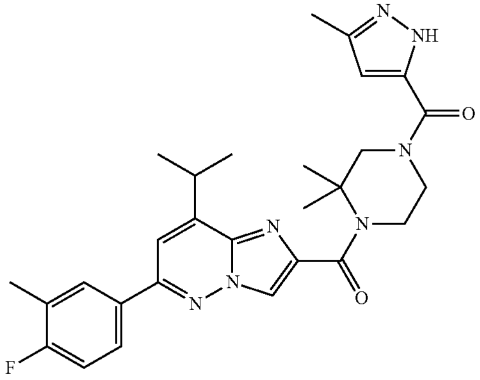
I-342
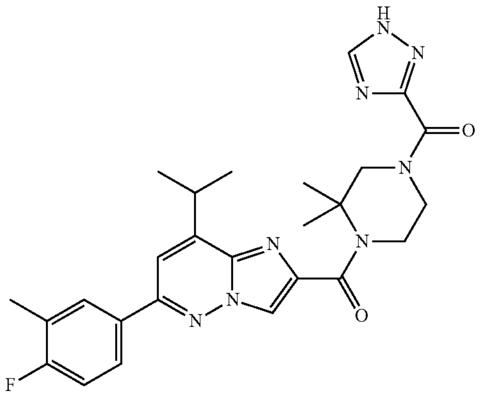
I-343
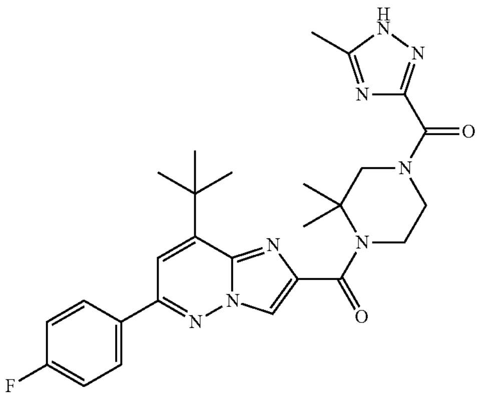

-continued
I-344
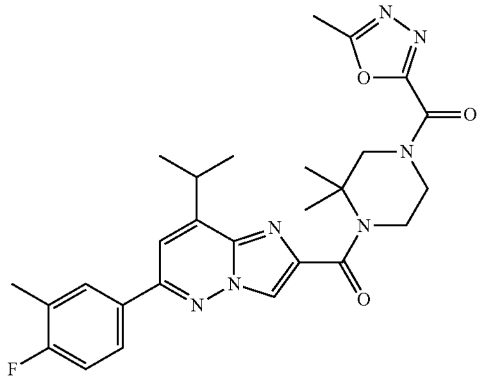
I-345
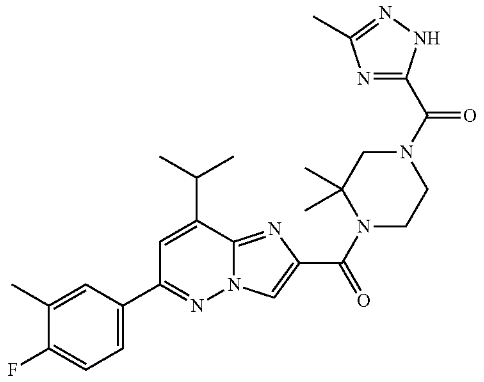
I-346
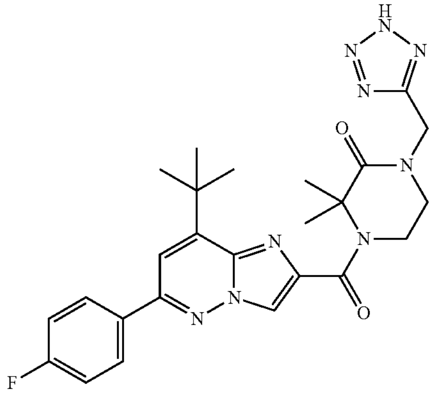
I-347
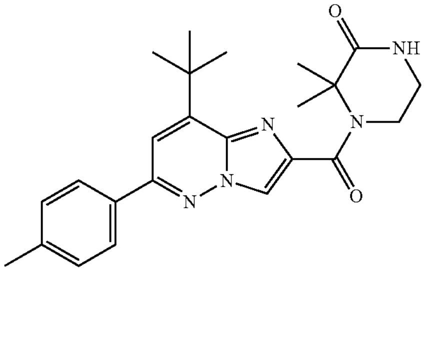
-continued
I-348
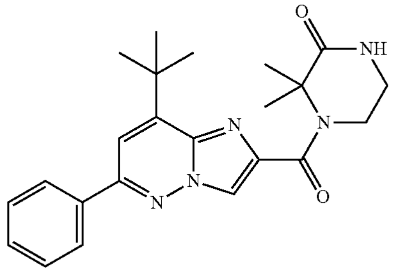
I-349
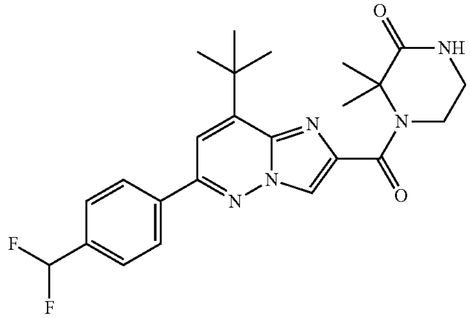
I-350
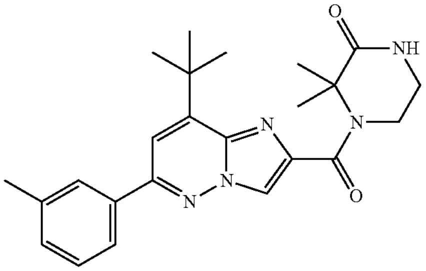
I-351
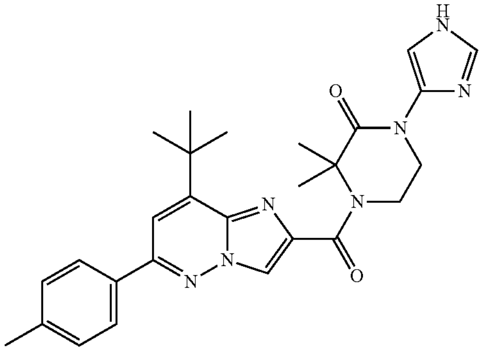
I-352
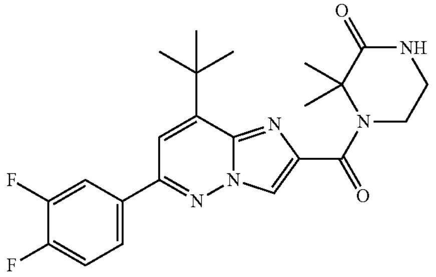

-continued
I-353
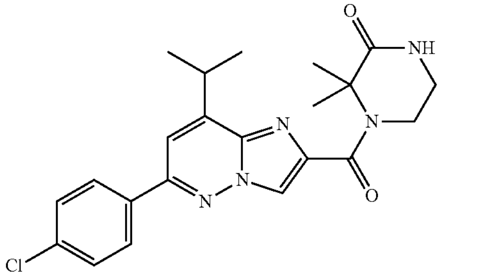
I-354
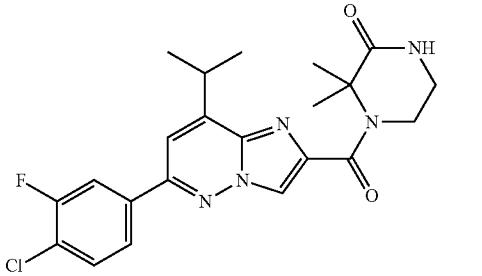
I-355
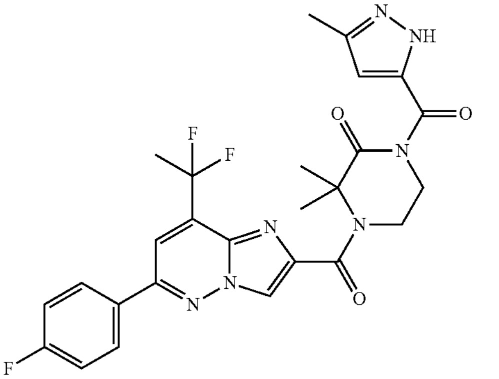
I-356
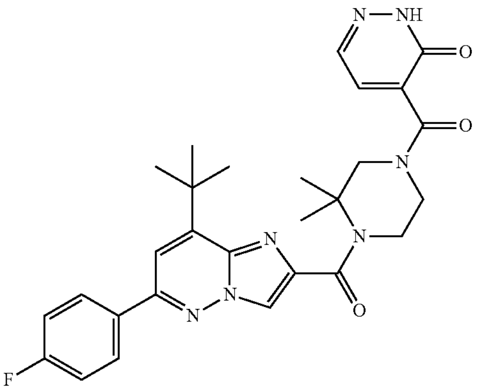
-continued
I-357
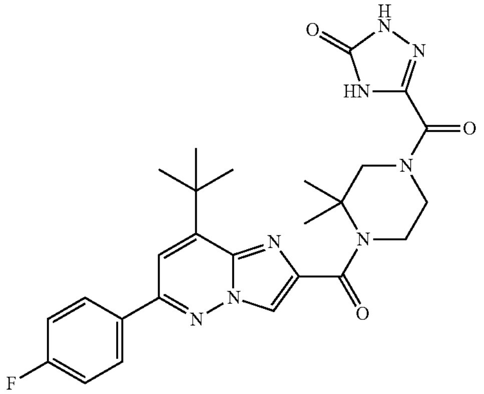
I-358
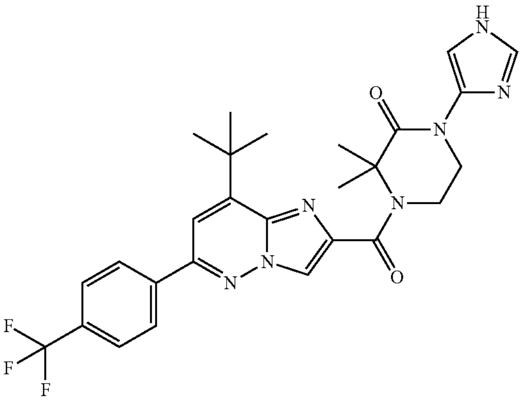
I-359
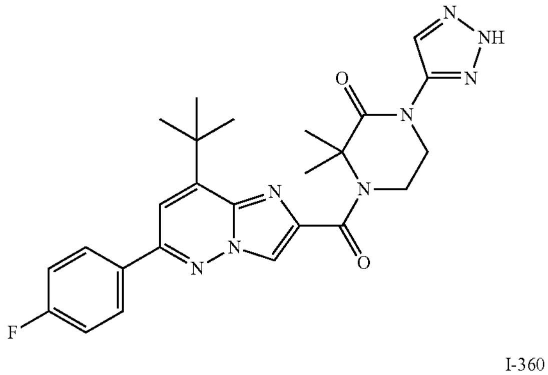
I-360
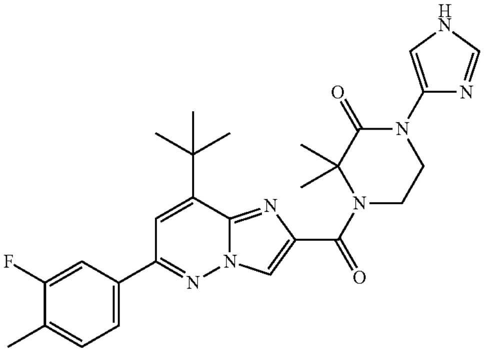

I-361
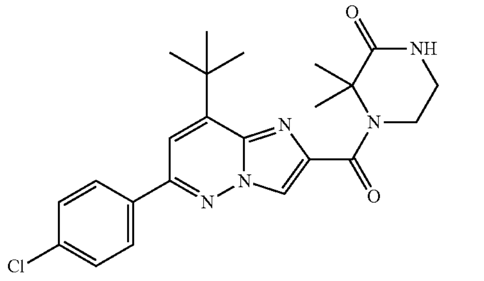
I-362
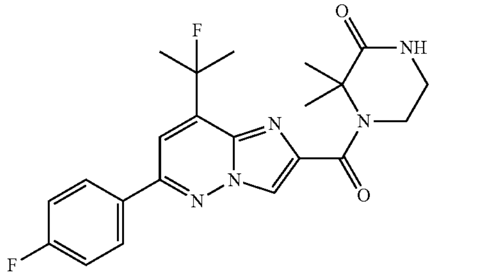
I-363
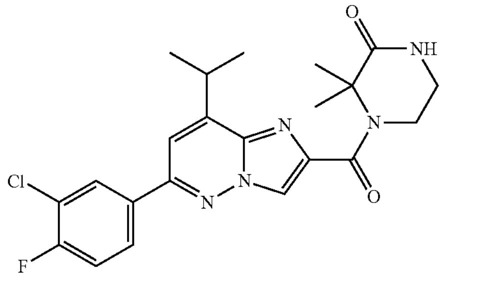
I-364
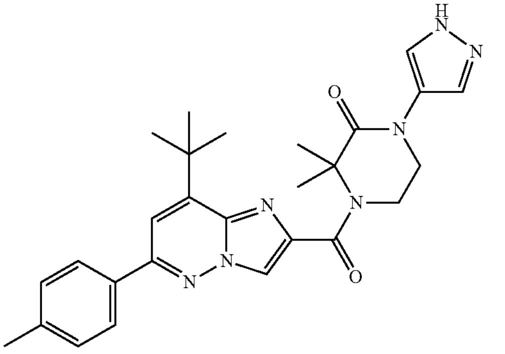
I-365
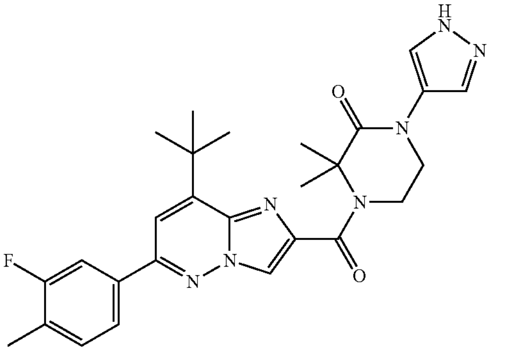
I-366
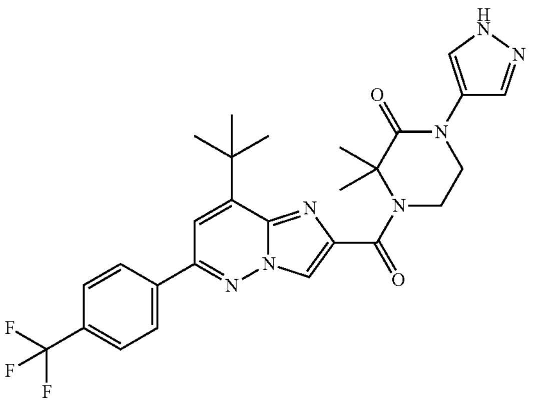
I-367
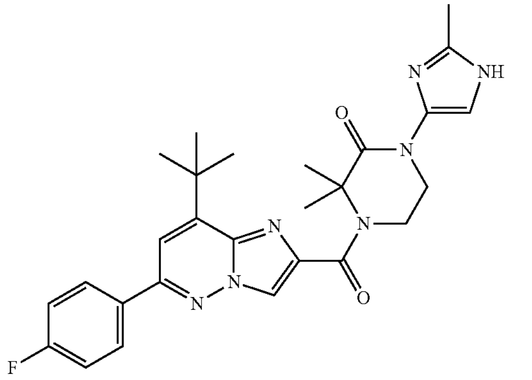
I-368
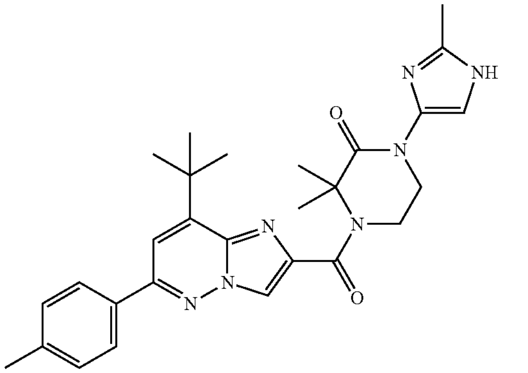
I-369
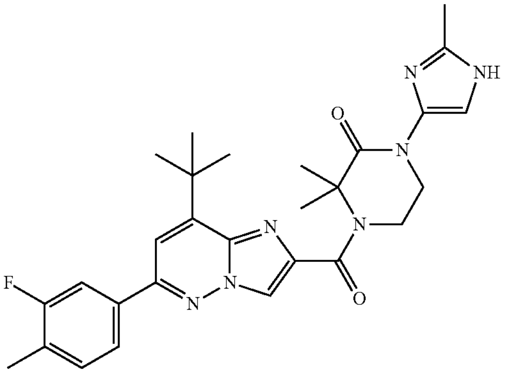

-continued
I-370
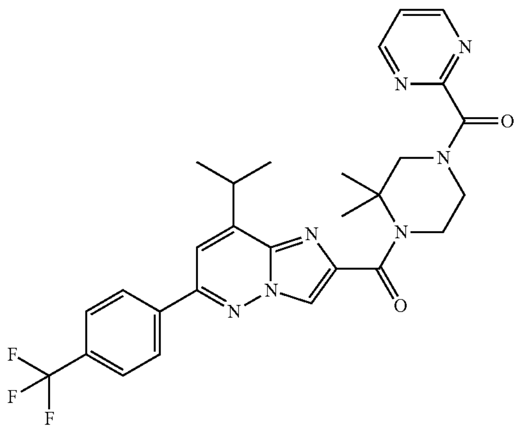
I-371
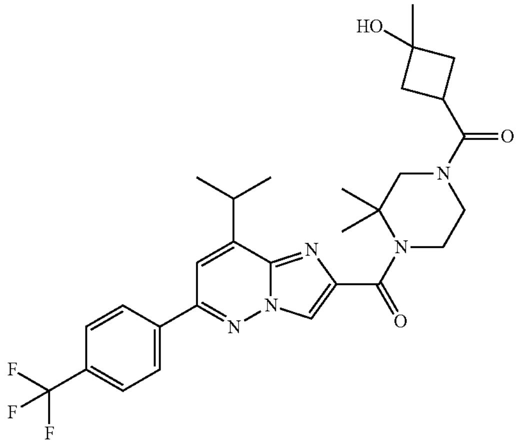
I-372
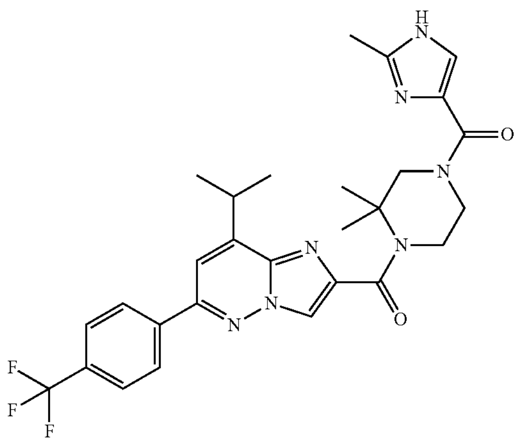
-continued
I-373
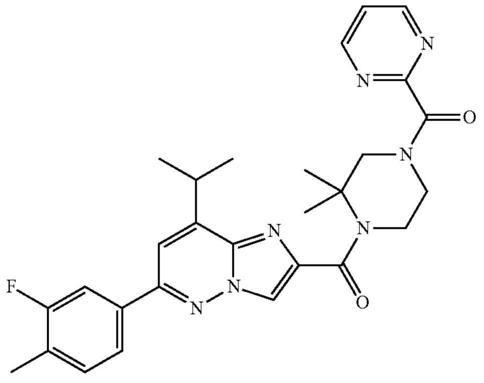
I-374
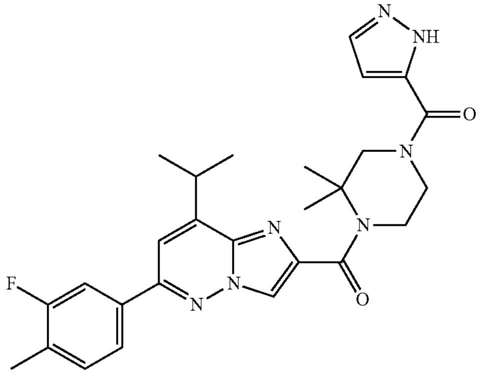
I-375
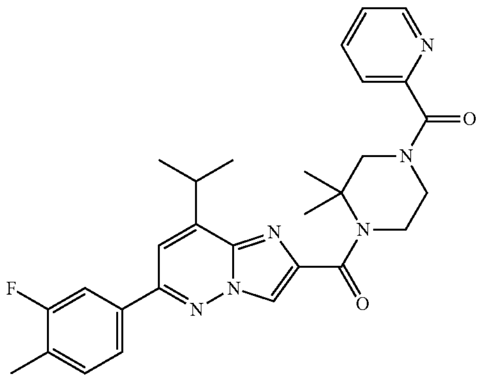
I-376
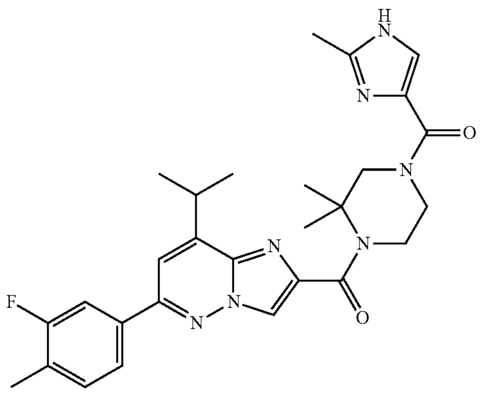

I-377
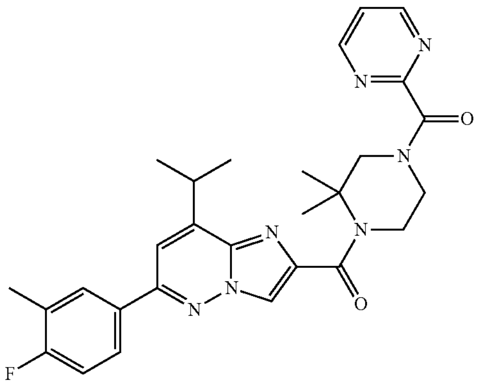
I-378
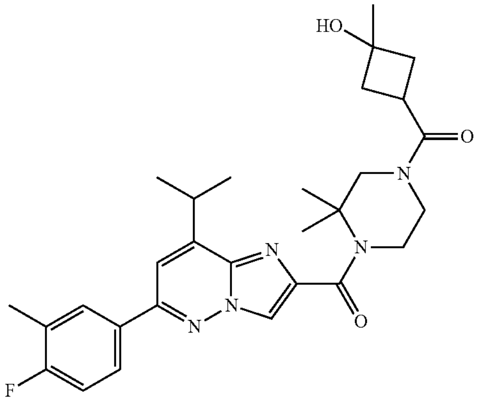
I-379
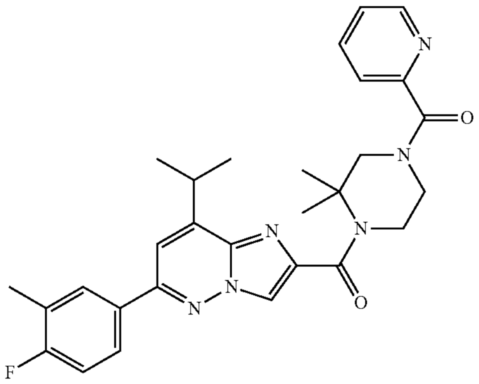
I-380
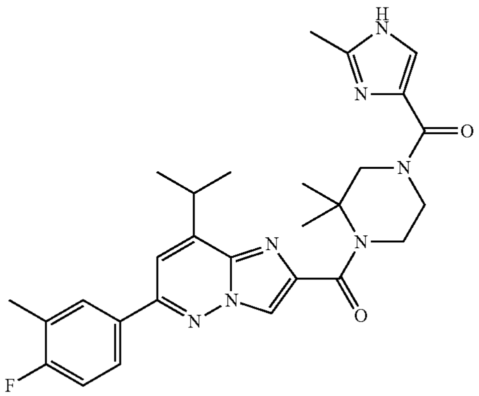
-continued
I-381
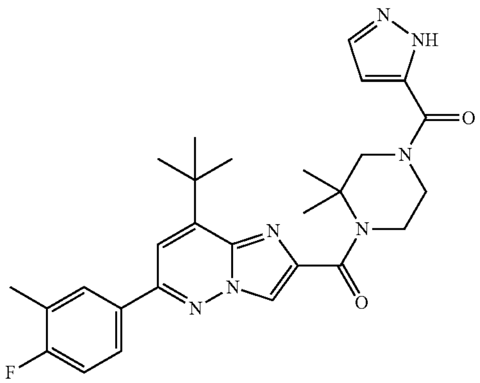
I-382
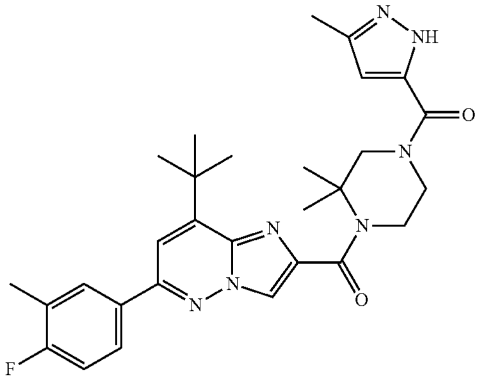
I-383
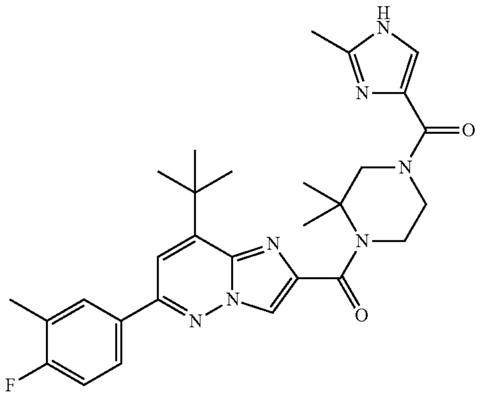
I-384
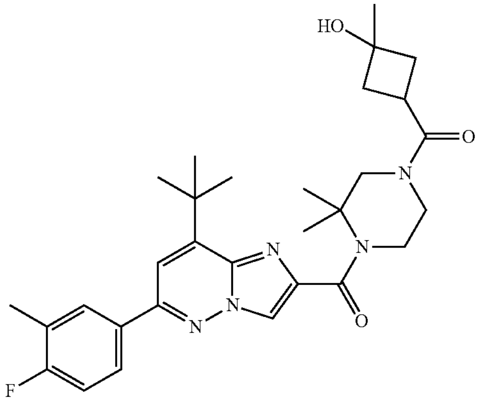

-continued
I-385
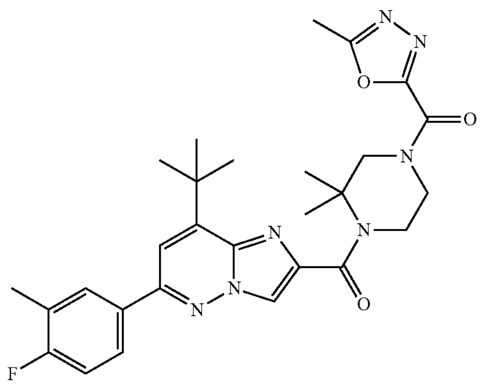
I-386
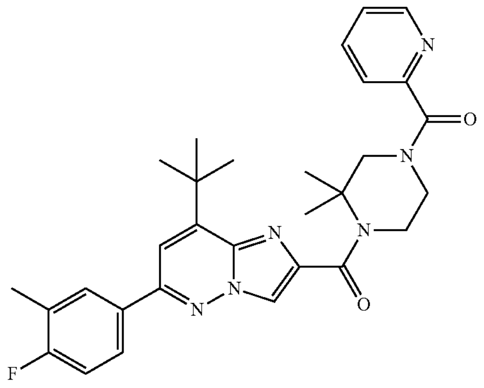
I-387
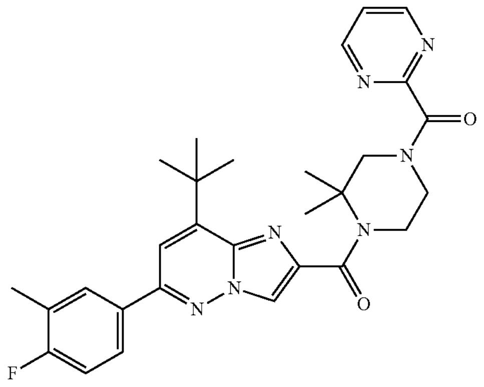
I-388
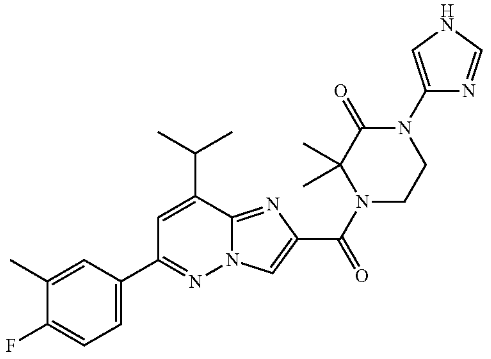
-continued
I-389
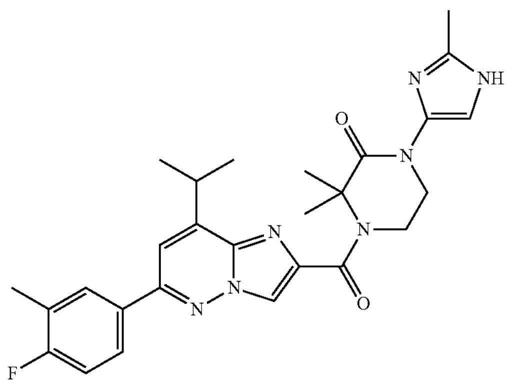
I-390
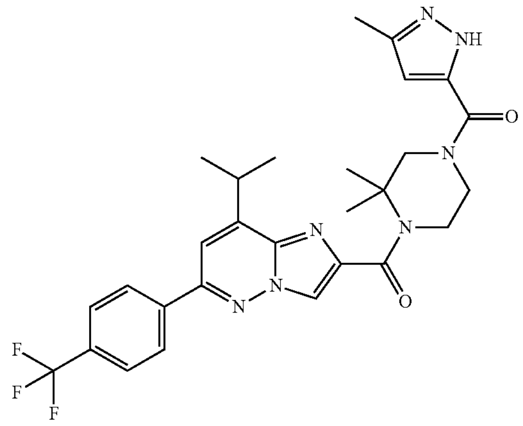
I-391
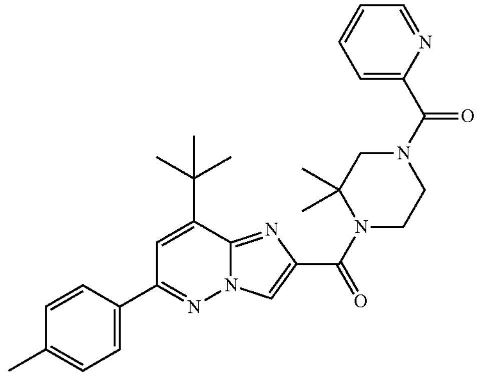
I-392
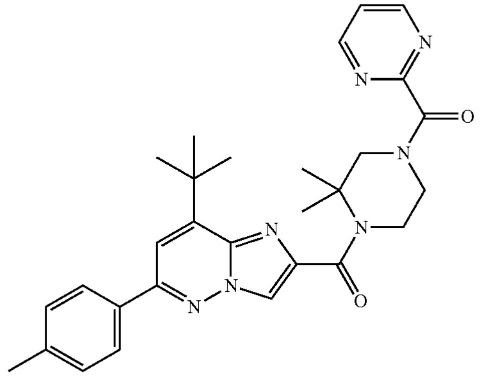

-continued
I-393
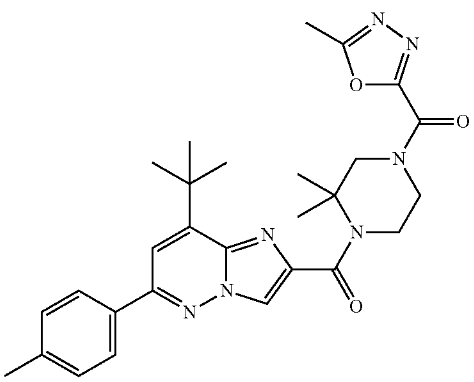
I-394
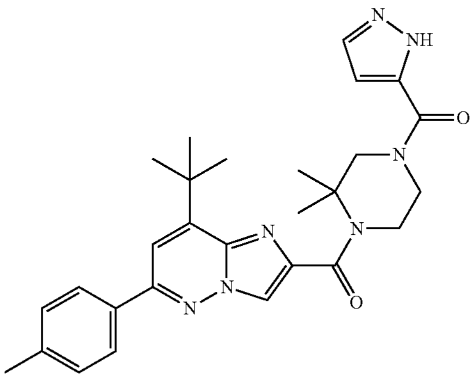
I-395
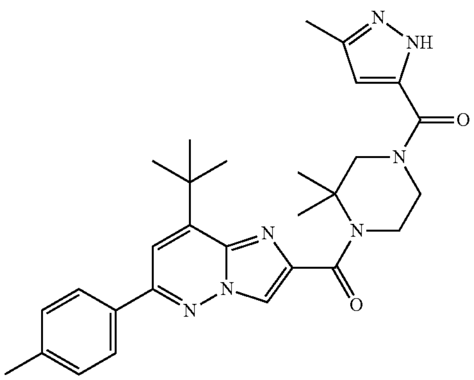
I-396
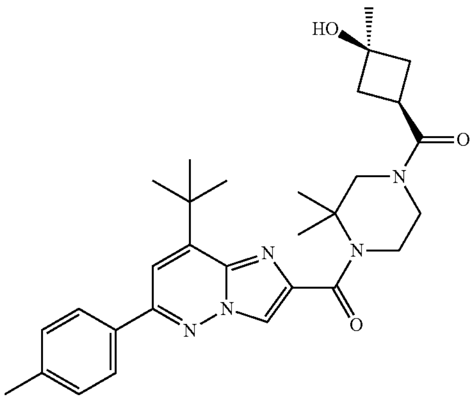
-continued
I-397
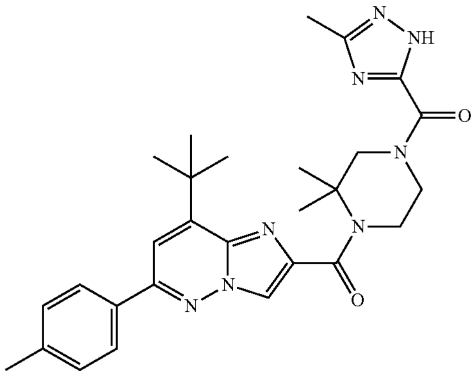
I-398
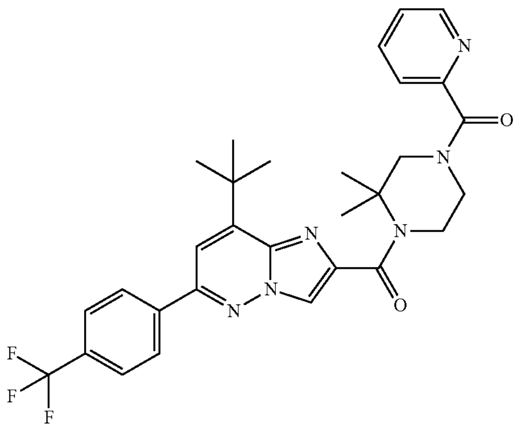
I-399
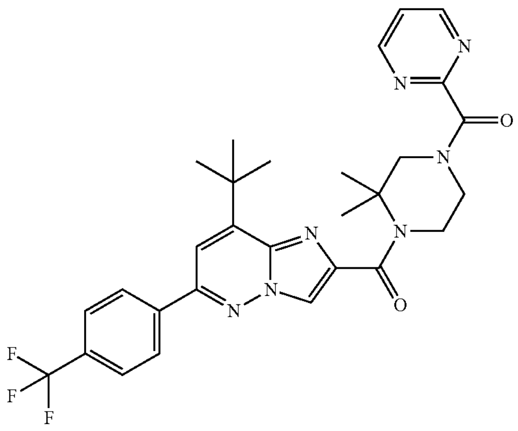

-continued
I-400
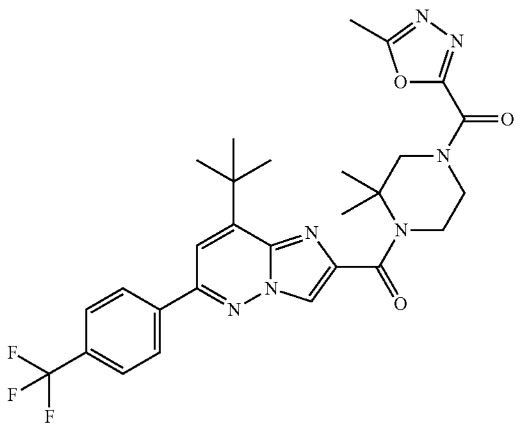
I-401
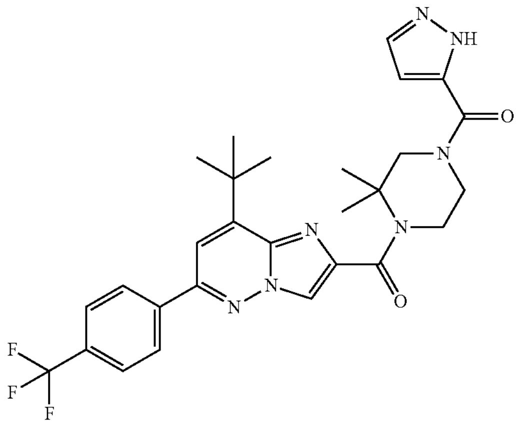
I-402
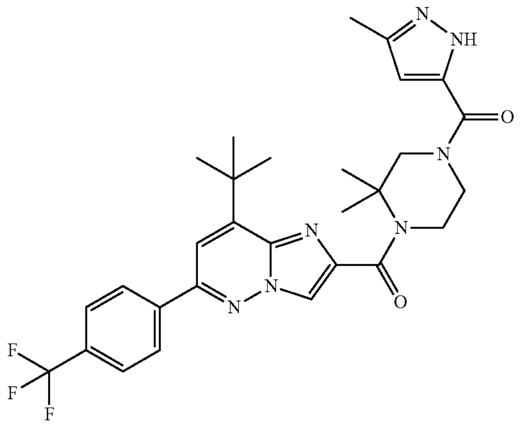
-continued
I-403
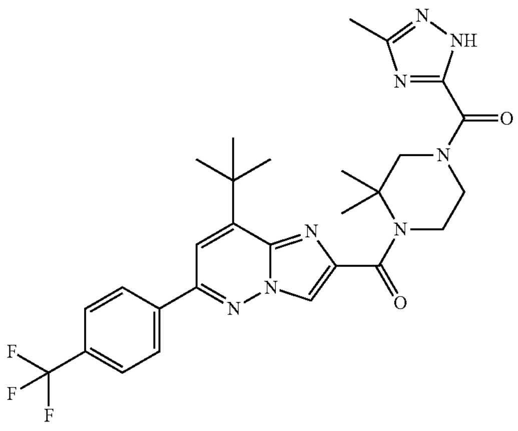
I-404
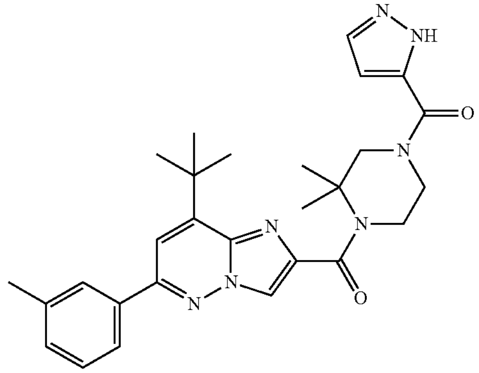
I-405
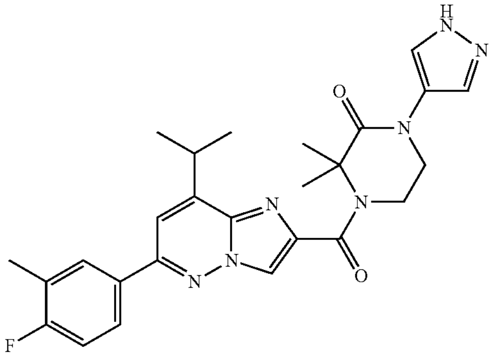
I-406
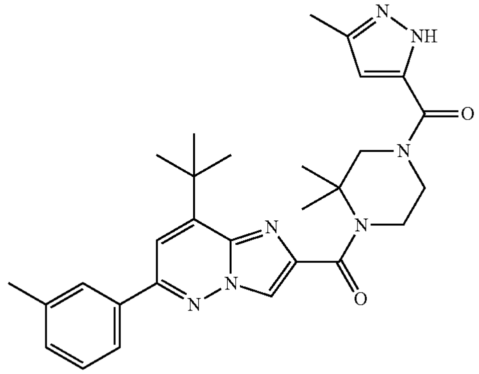

-continued
I-407
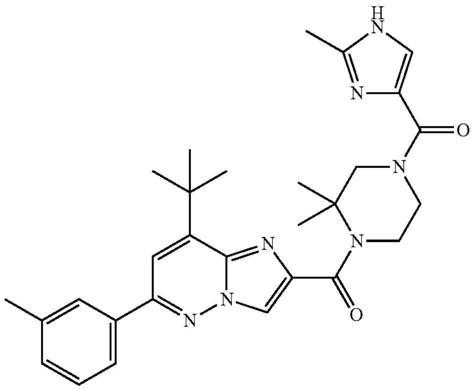
I-408
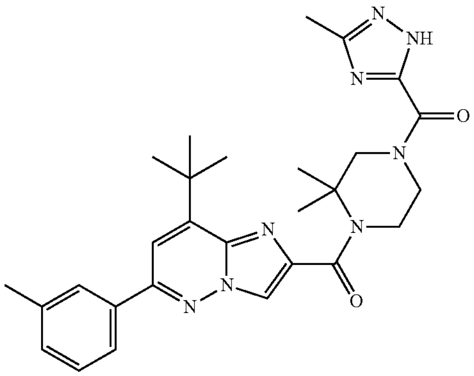
I-409
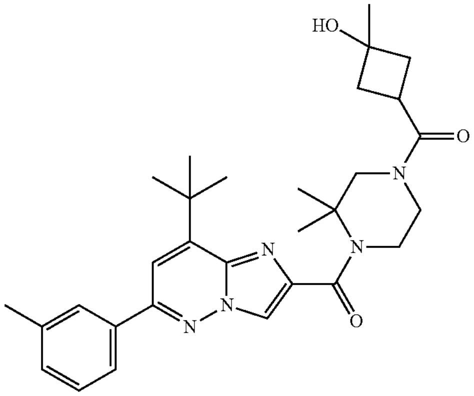
I-410
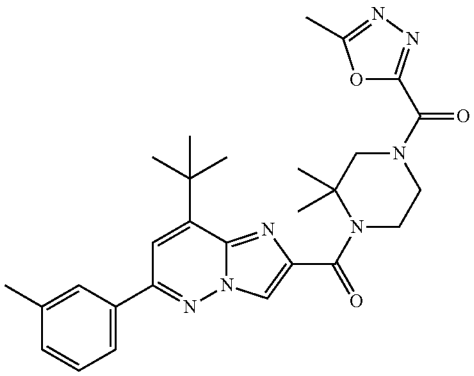
-continued
I-411
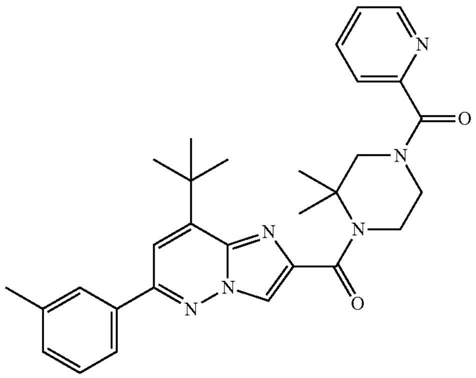
I-412
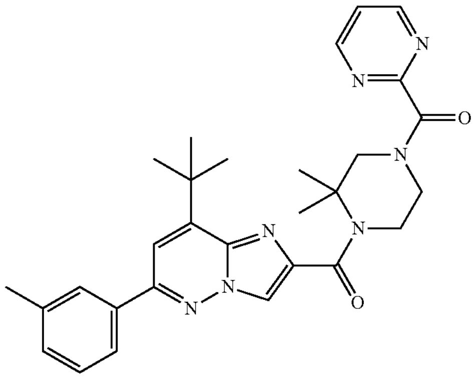
I-413
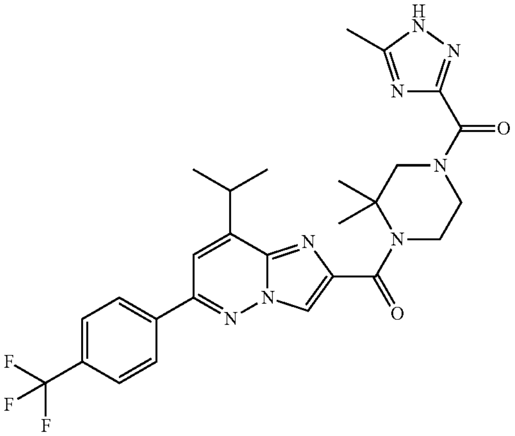
I-414
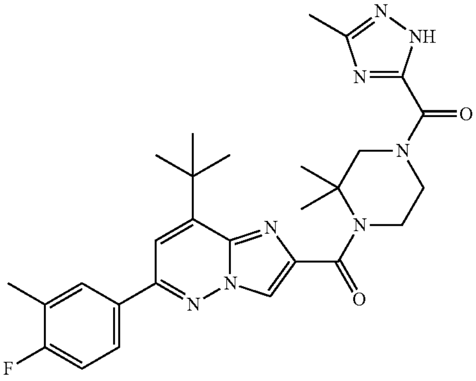

-continued
I-415
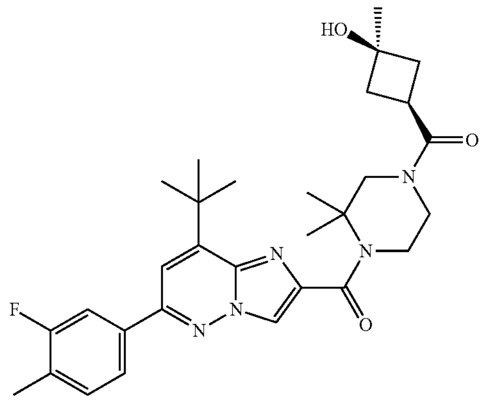
I-416
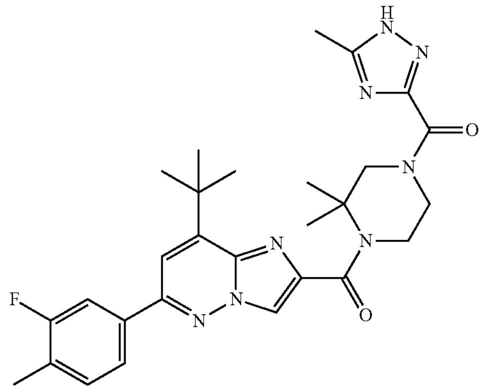
I-417
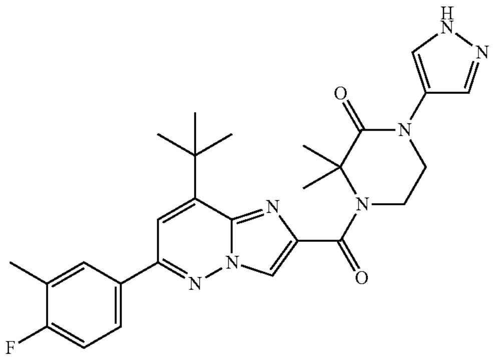
I-418
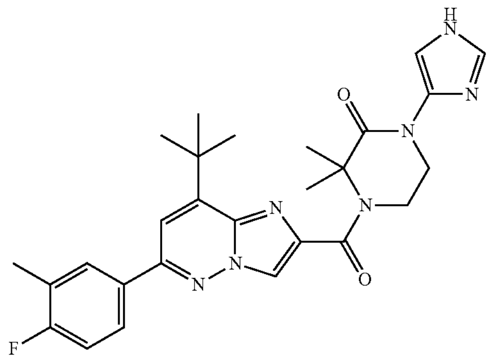
-continued
I-419
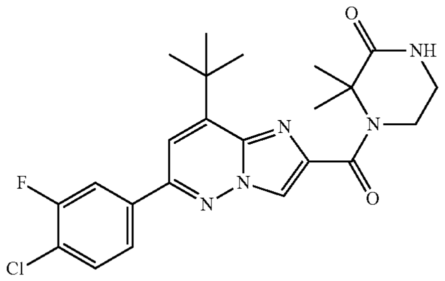
I-420
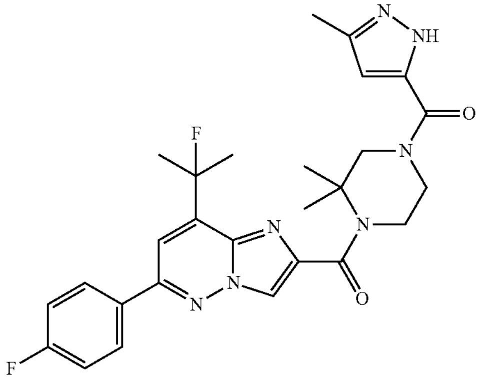
I-421
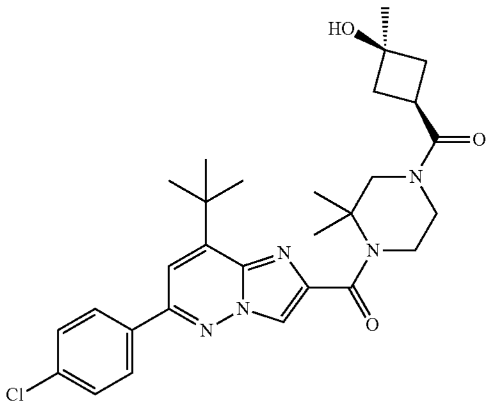
I-422
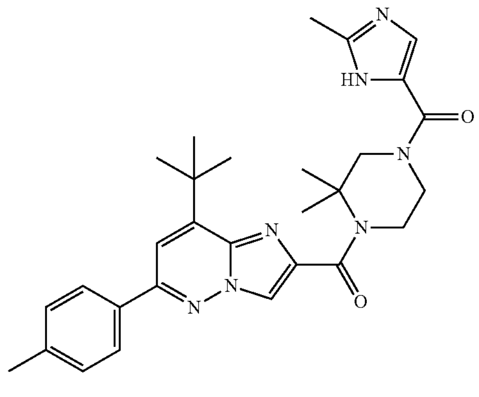

-continued
I-423
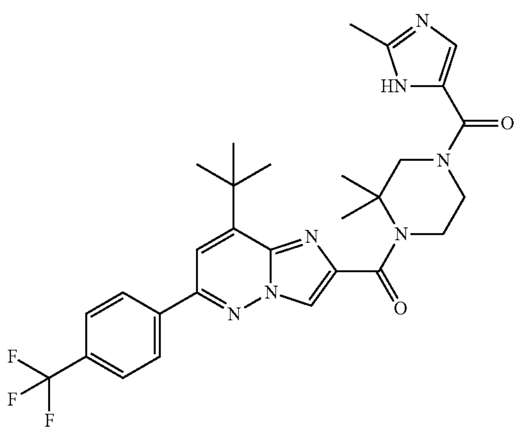
I-424
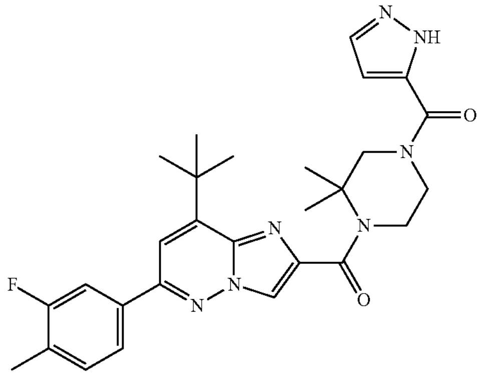
I-425
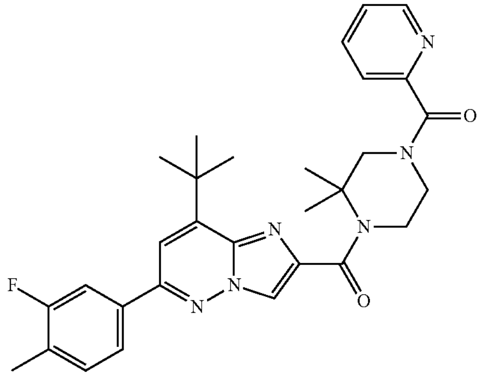
I-426
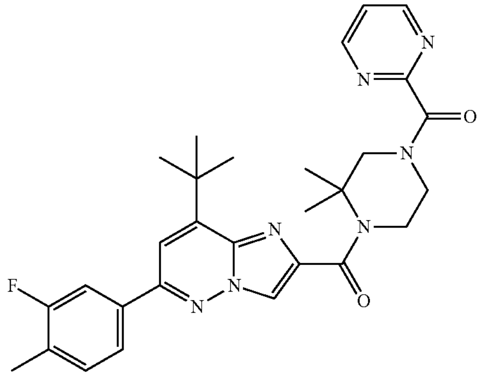
-continued
I-427
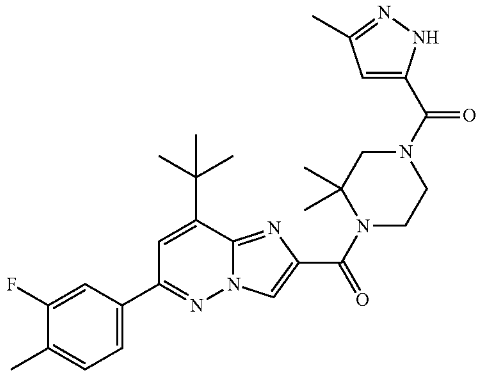
I-431
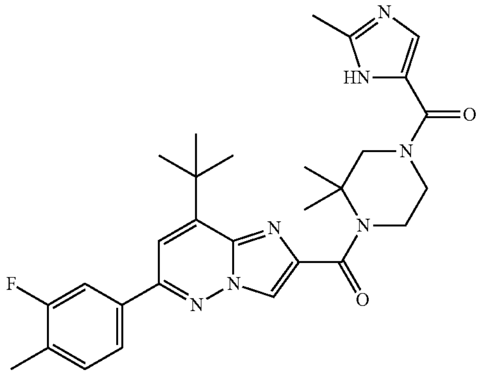
I-432
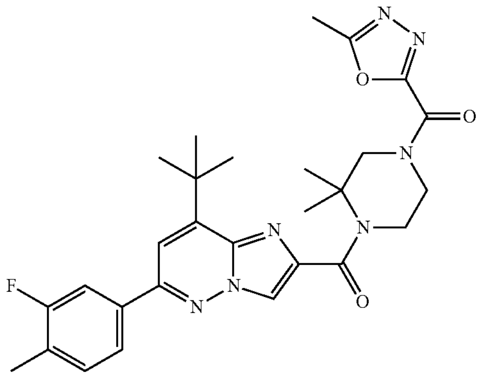
I-433
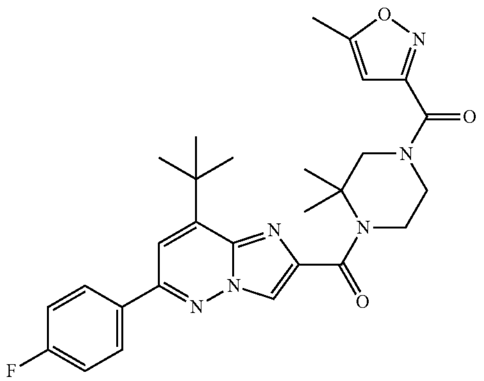

-continued
I-434
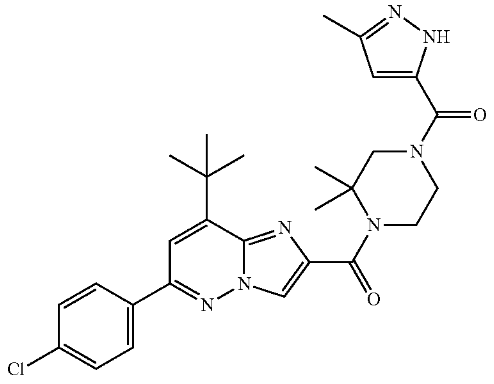
I-435
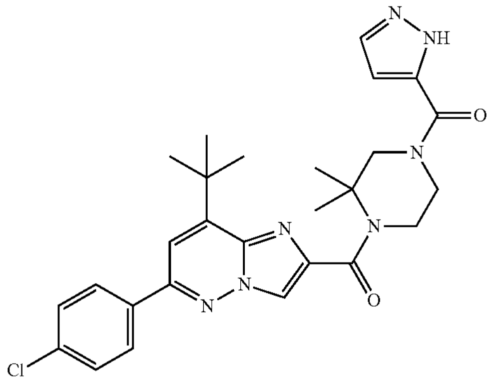
I-436
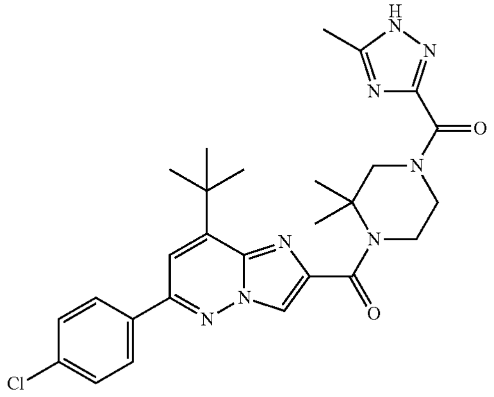
I-438
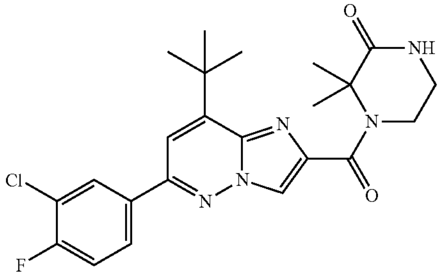
-continued
I-439
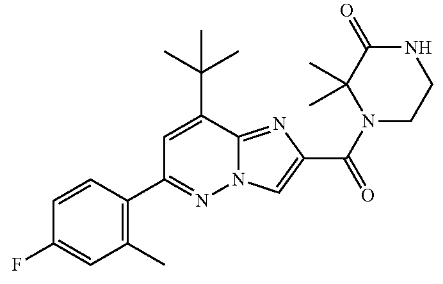
I-440
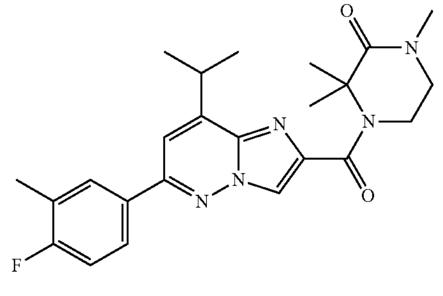
I-441
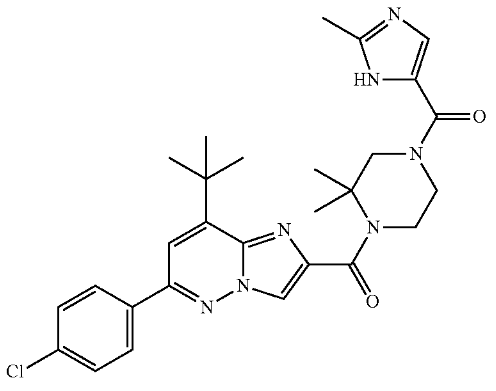
I-442
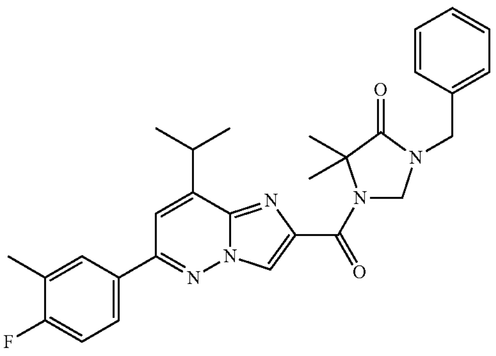

-continued
I-443
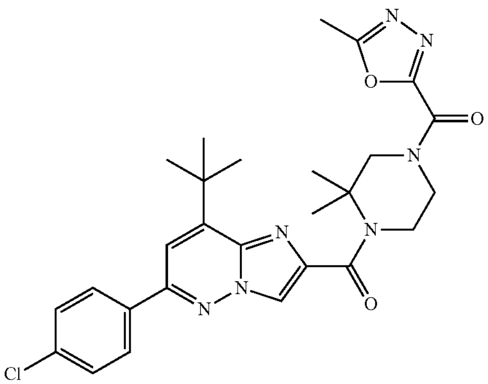
I-444
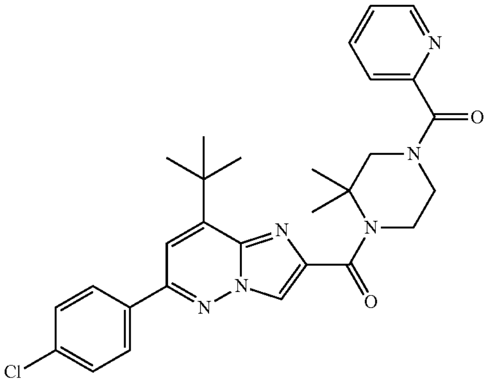
I-445
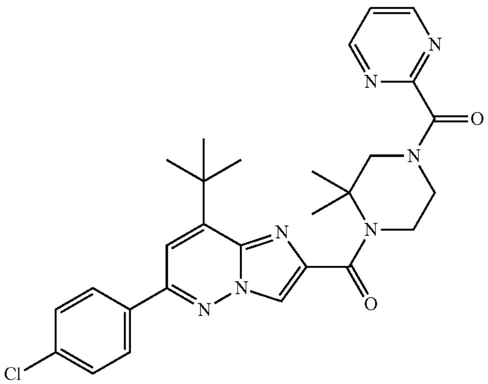
I-446
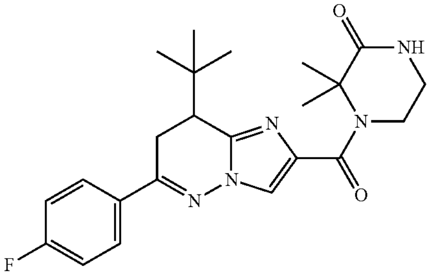
-continued
I-447
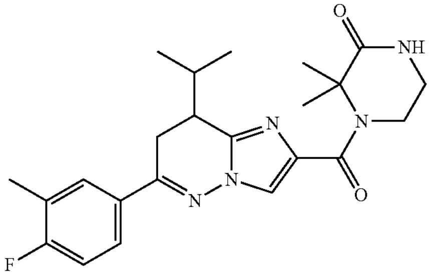
I-449
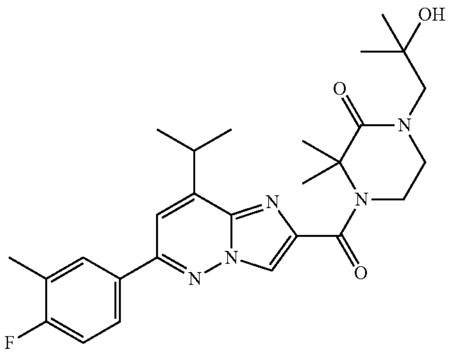
I-450
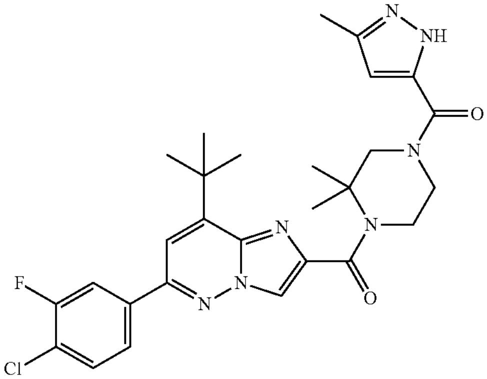
I-451
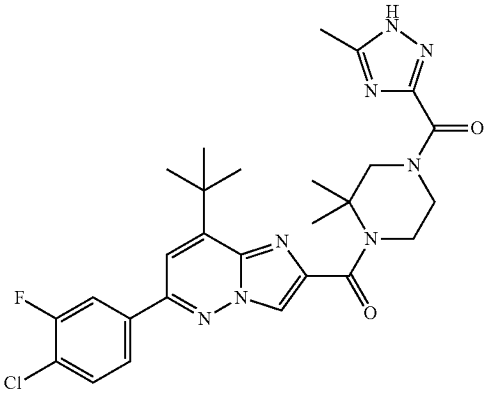

-continued
I-453
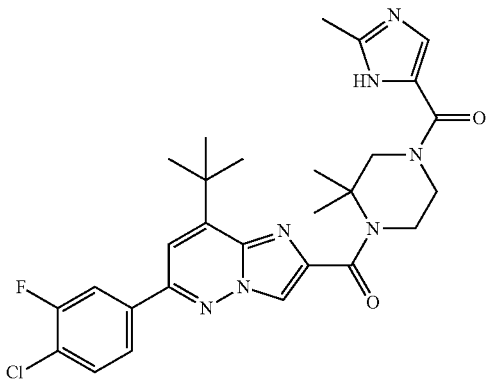
I-454
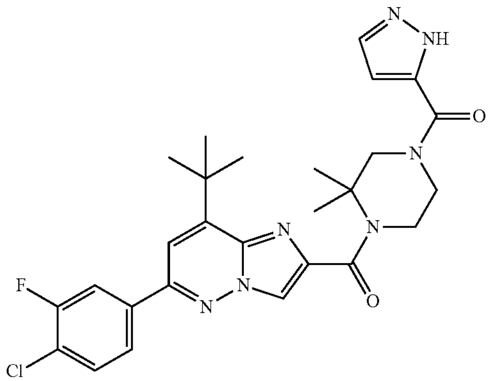
I-455
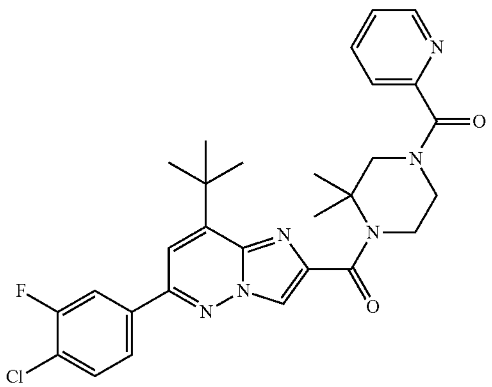
I-456
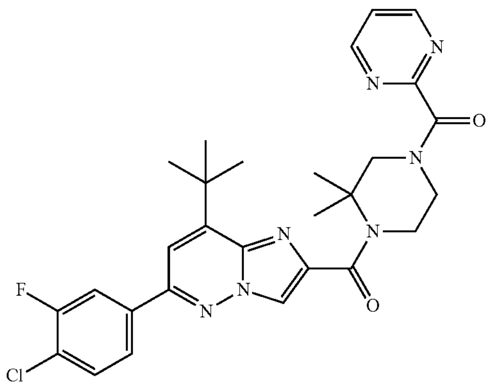
-continued
I-457
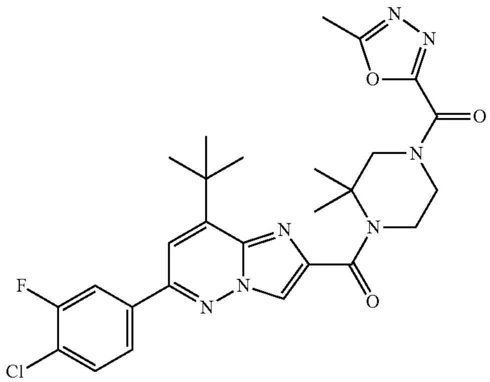
I-458
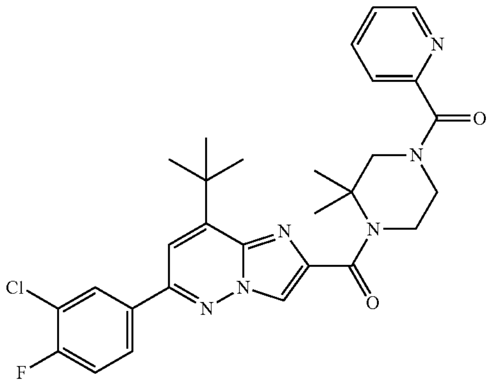
I-459
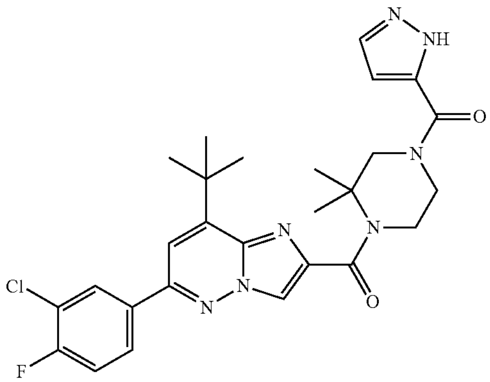
I-460
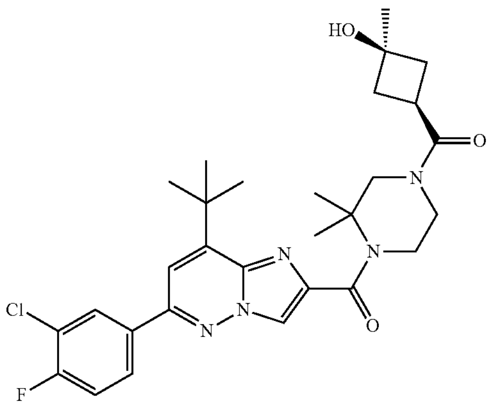

-continued
I-462
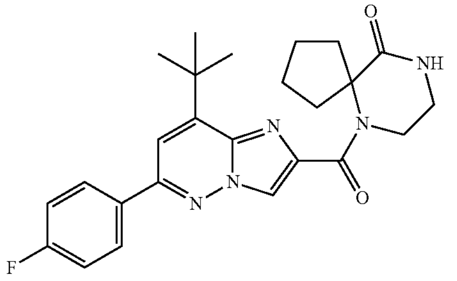
I-463
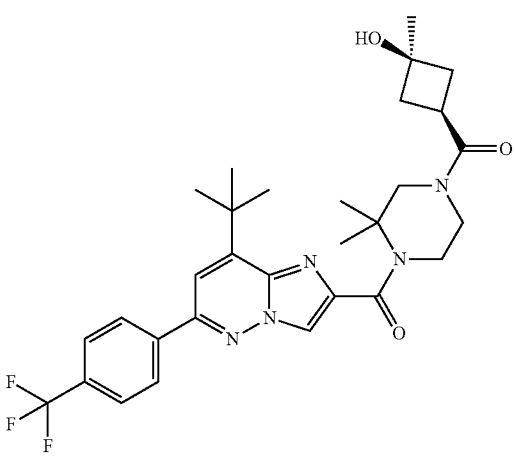
I-464
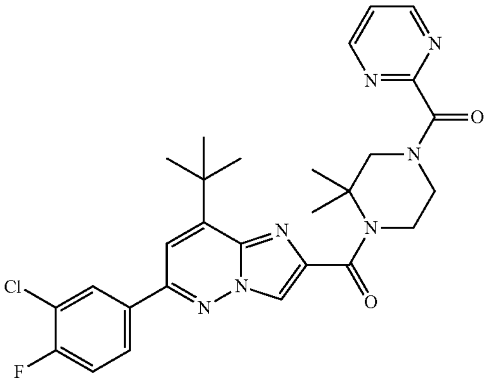
I-465
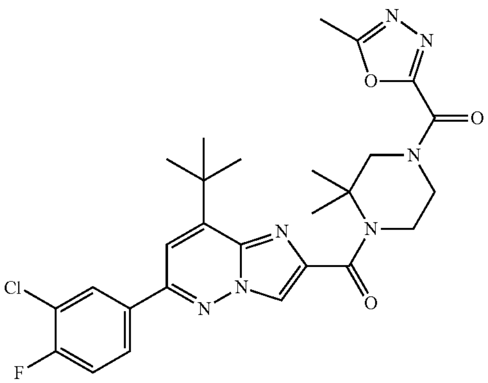
-continued
I-466
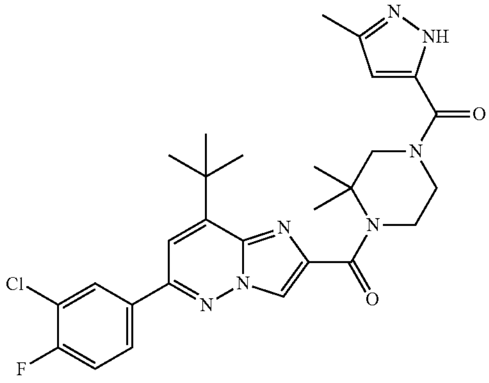
I-467
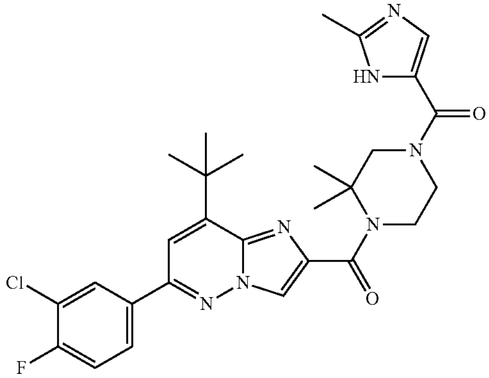
I-468
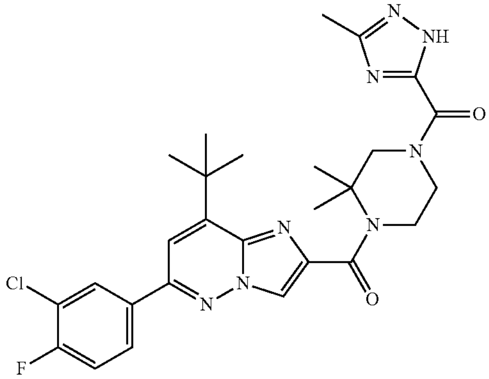
I-469
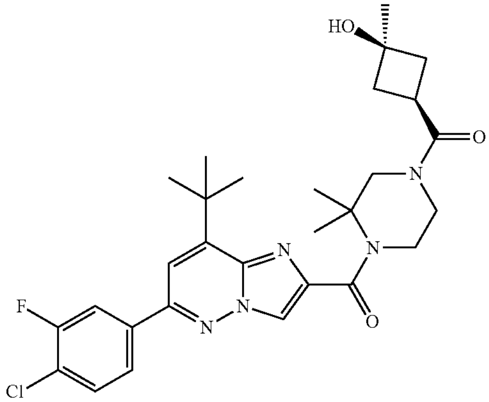

-continued
I-470
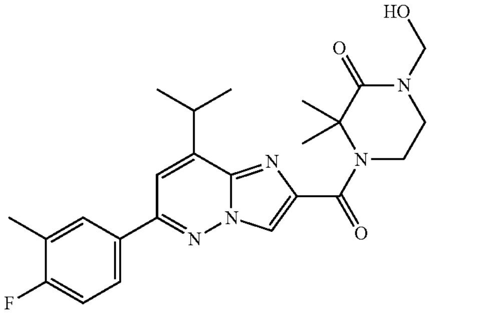
I-471
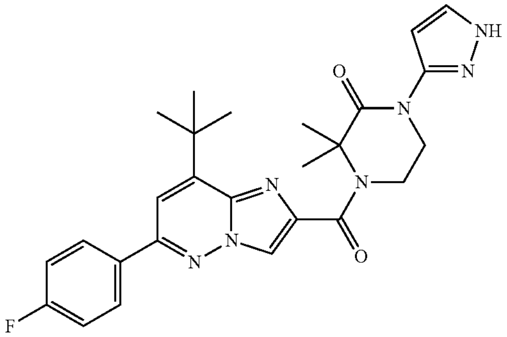
I-472
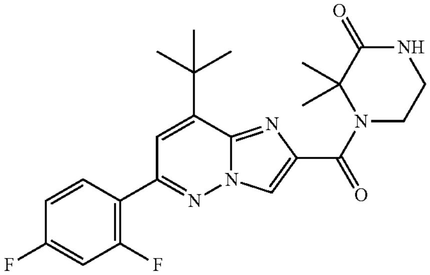
I-473
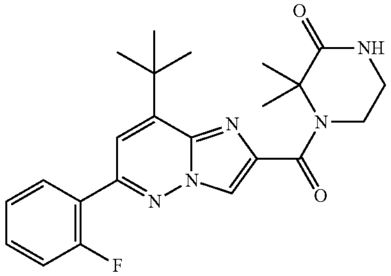
I-475
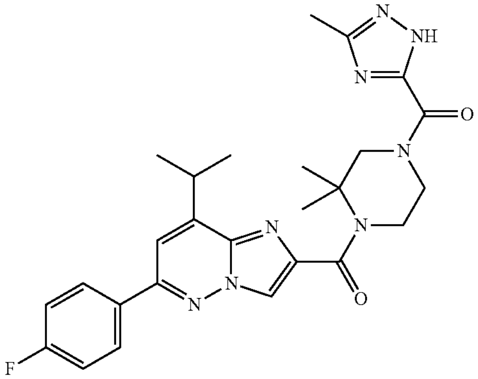
-continued
I-476
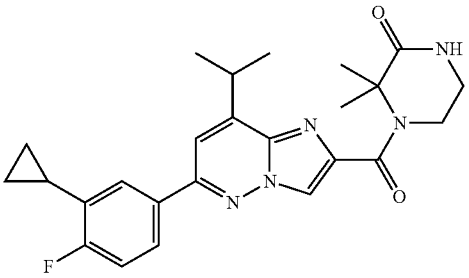
I-477
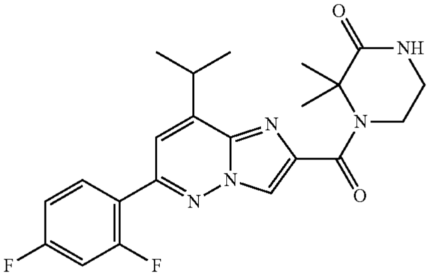
I-478
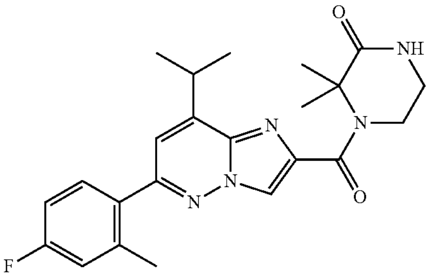
I-479
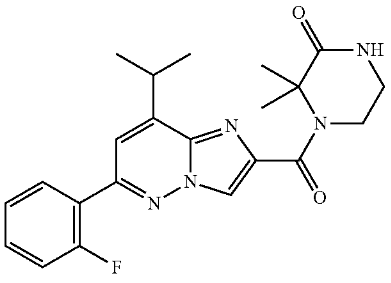
I-480
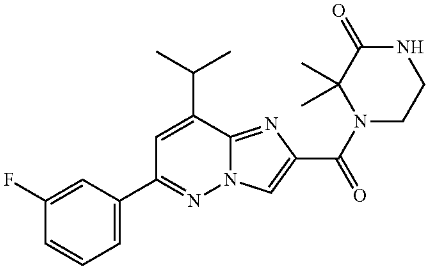

-continued
I-481
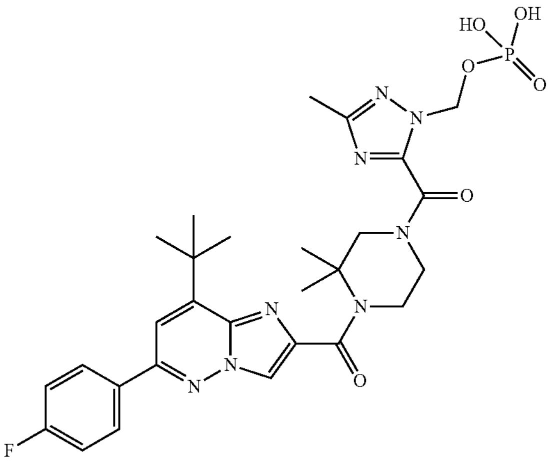
I-482
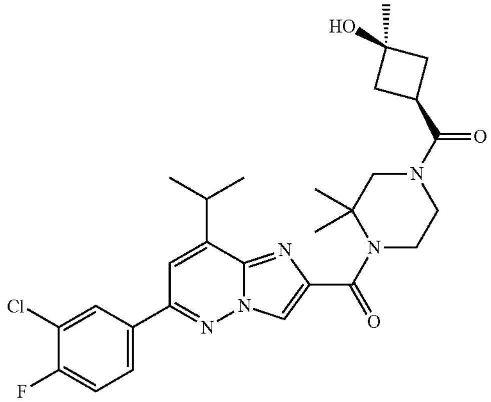
I-483
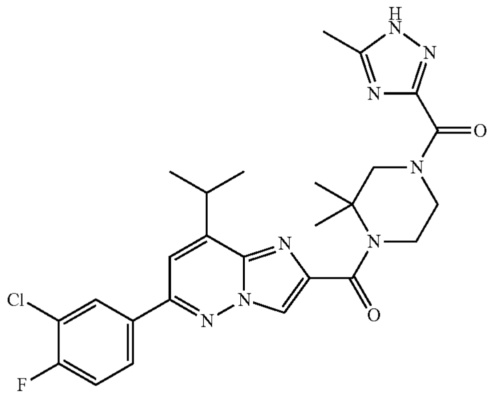
I-484
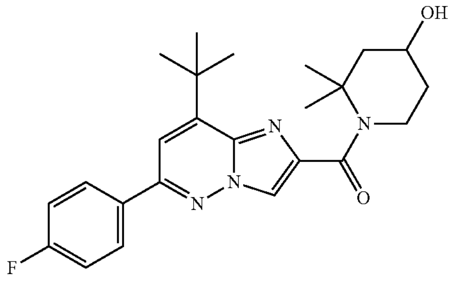
-continued
I-485
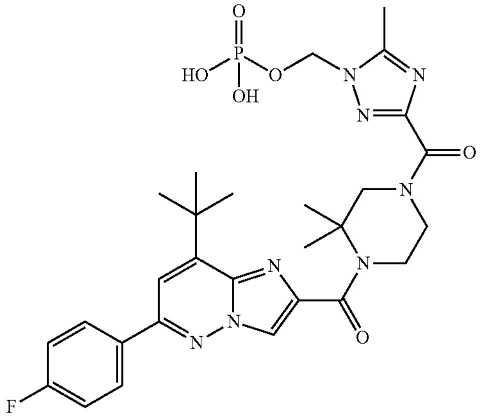
I-486
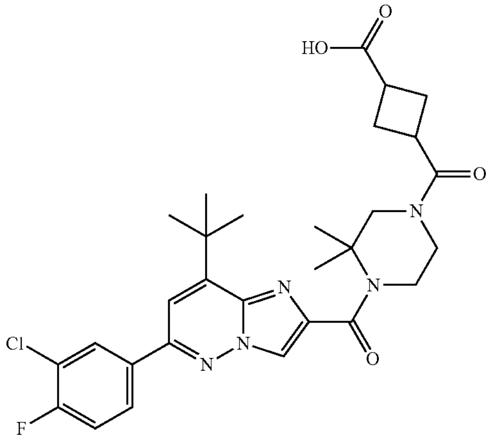
I-487
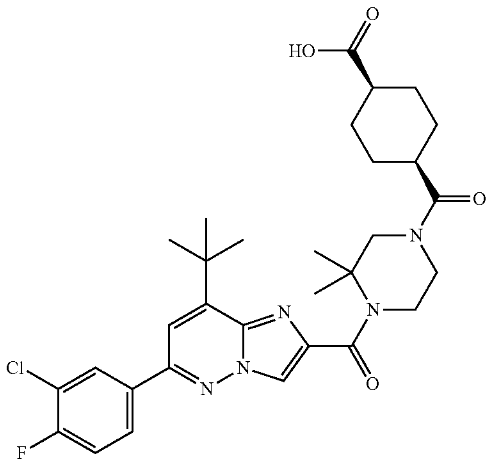

-continued
I-488
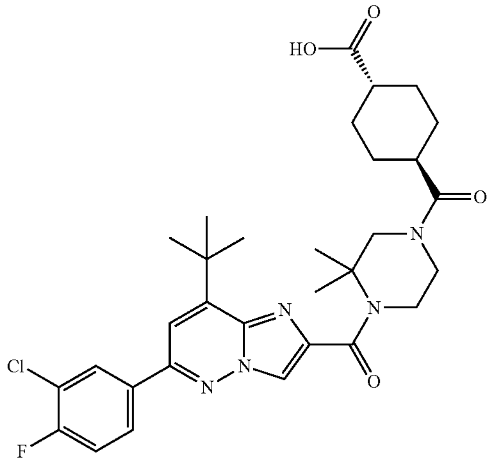
I-489
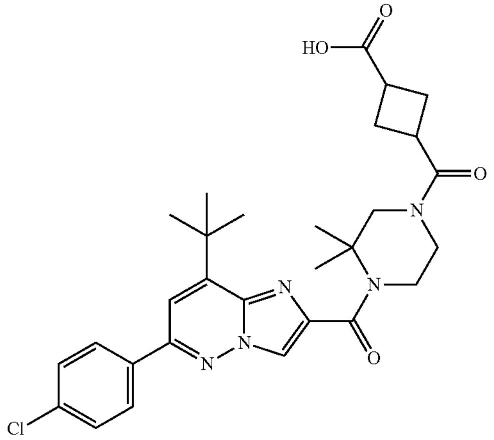
I-490
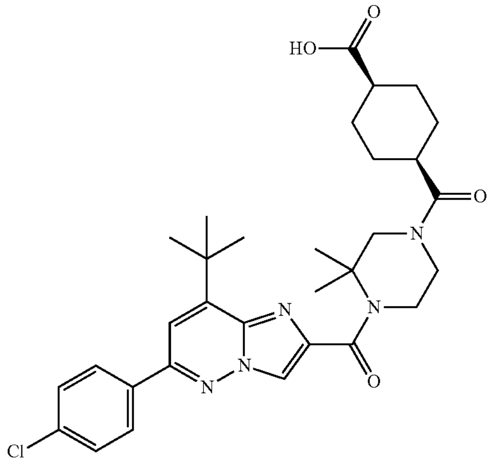
-continued
I-491
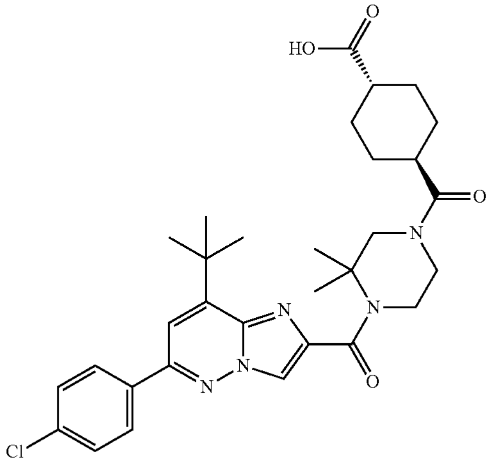
I-492
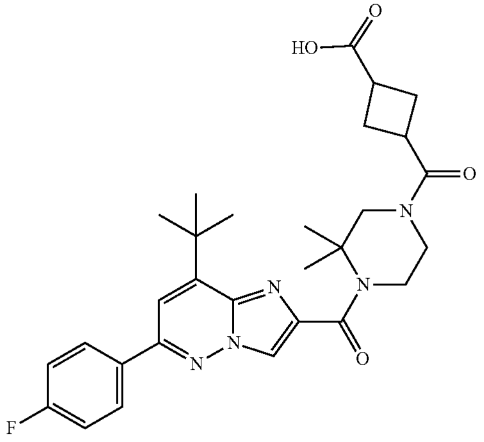
I-493
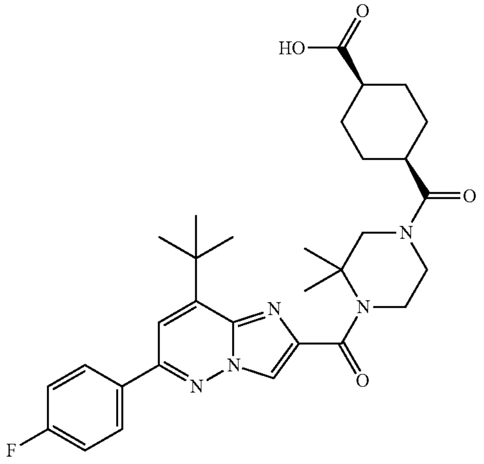

-continued
I-494
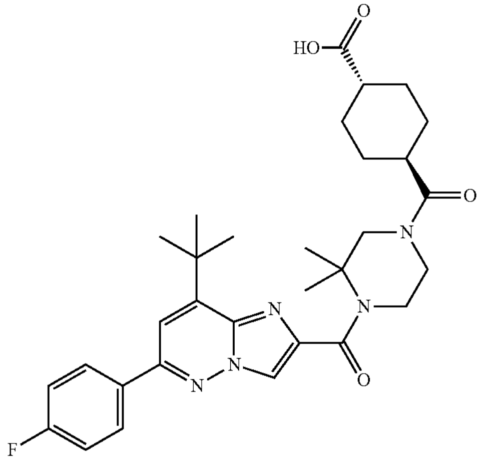
I-495
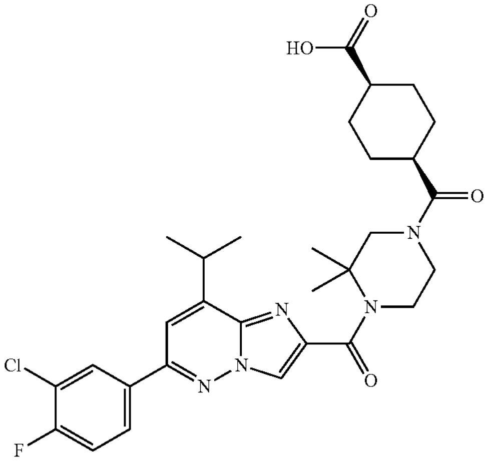
I-496
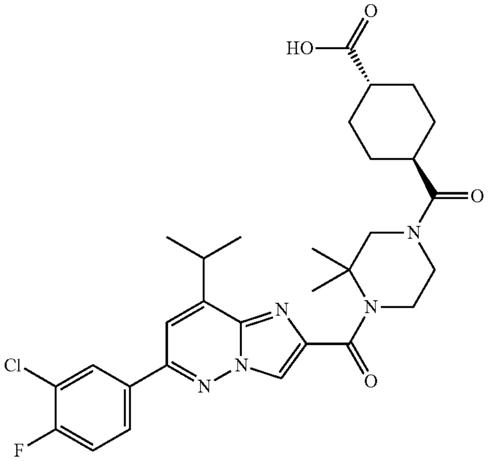
I-497
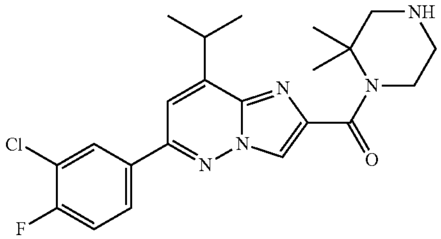
-continued
I-498
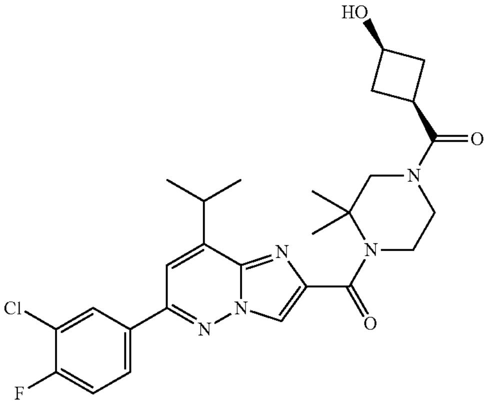
I-499
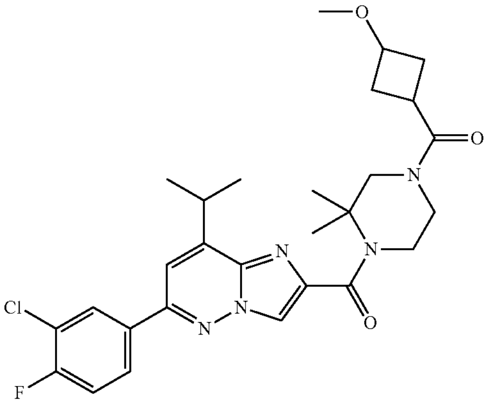
I-500
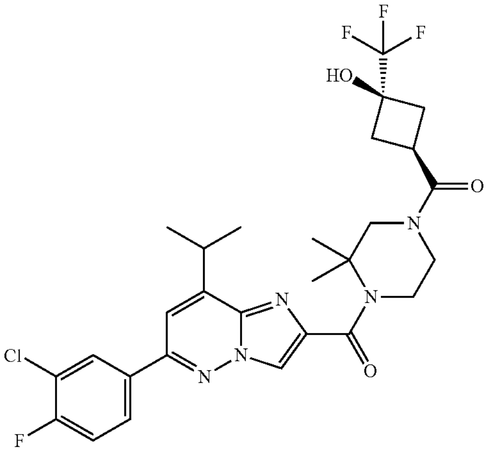

-continued
I-501
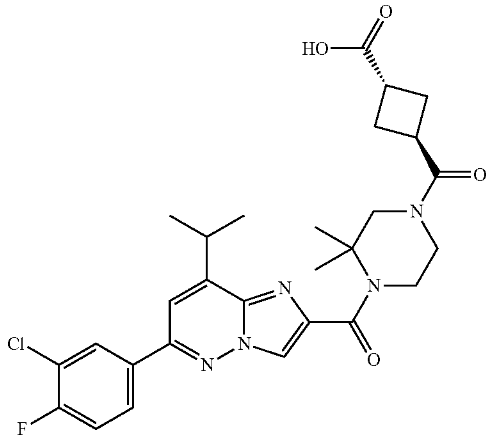
I-502
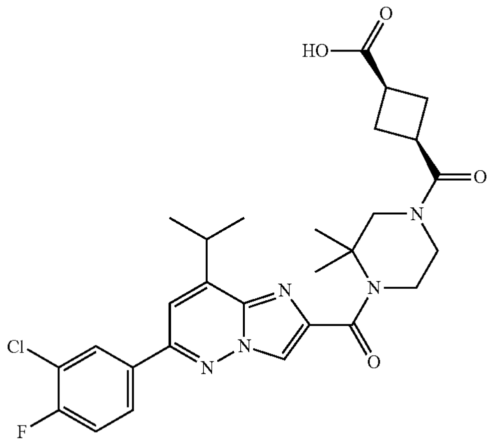
I-503
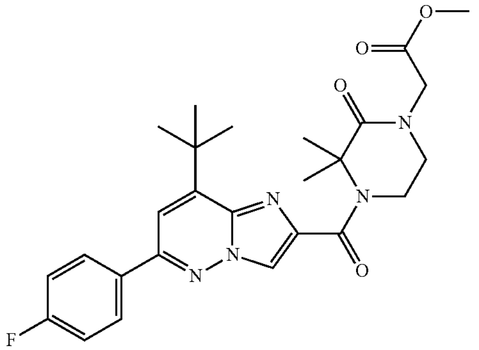
I-504
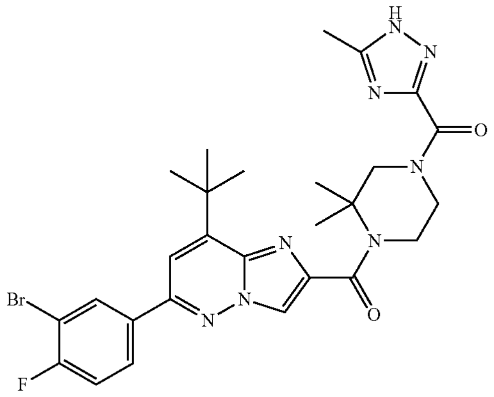
-continued
I-505
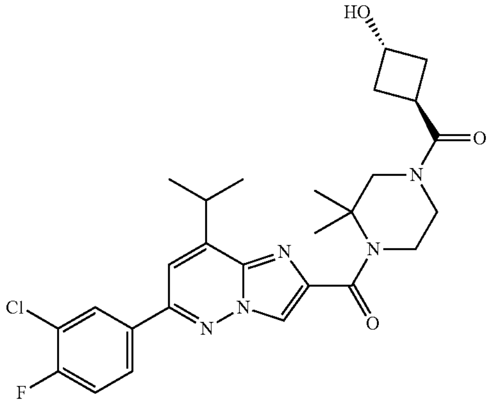
I-507
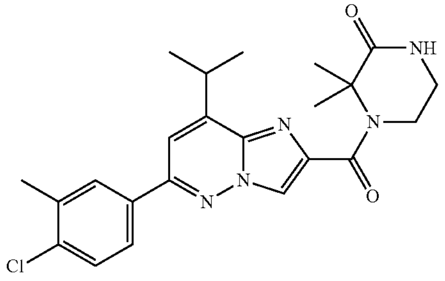
I-508
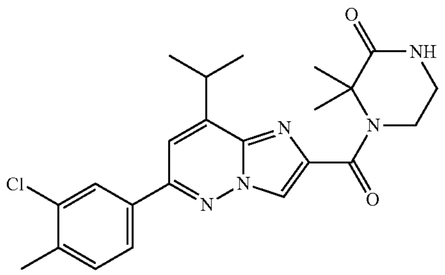
I-509
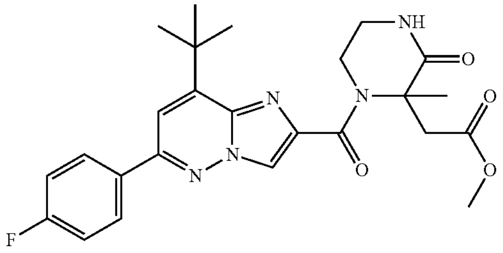
I-510
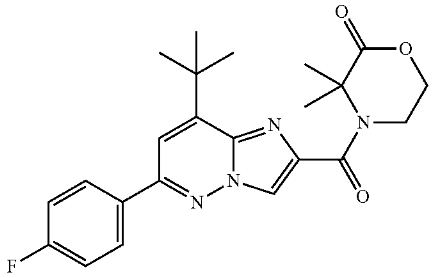

-continued
I-511
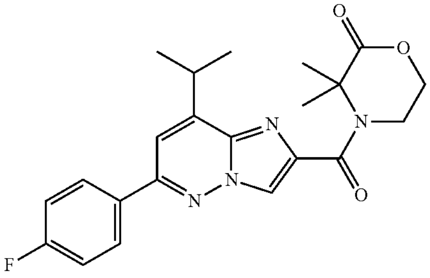
I-512
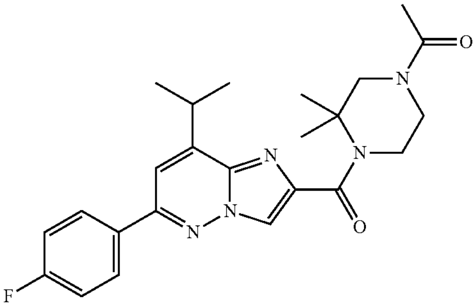
I-513
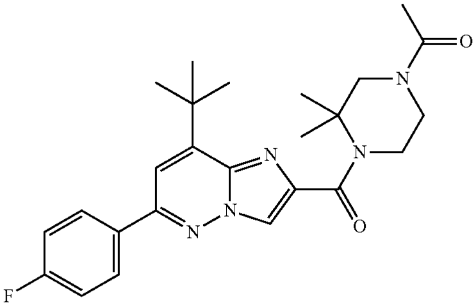
I-514
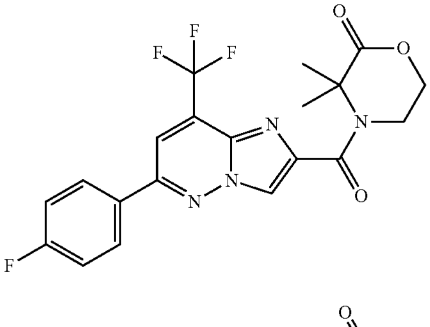
I-517
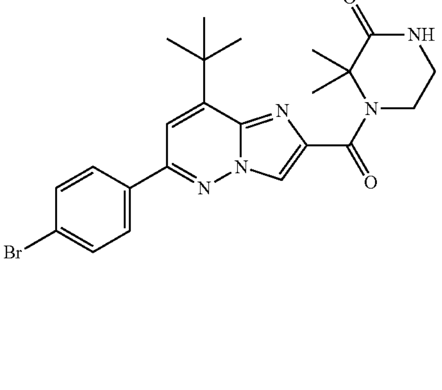
-continued
I-518
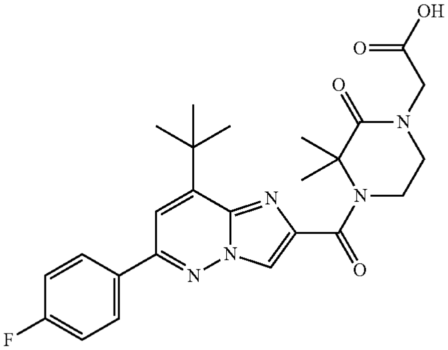
I-519
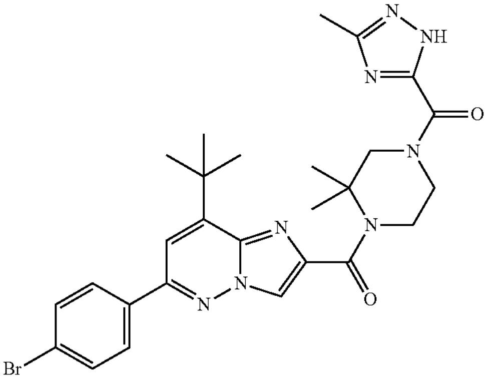
I-520
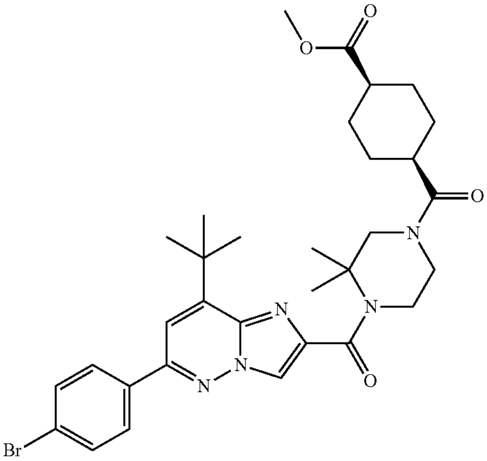
I-521
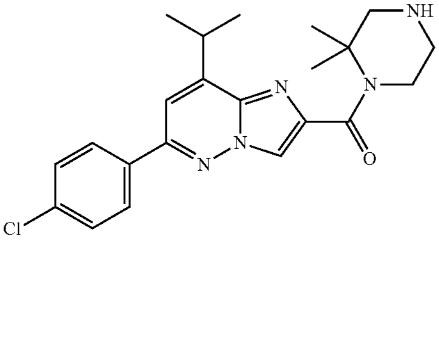

-continued
I-522
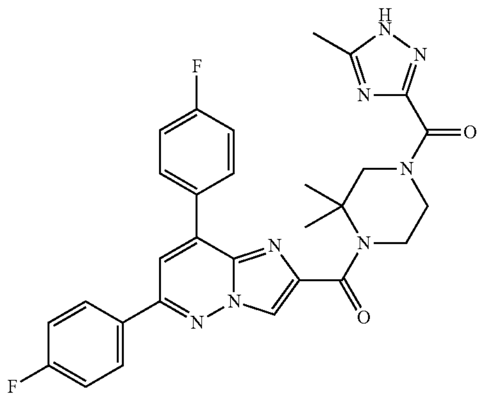
I-523
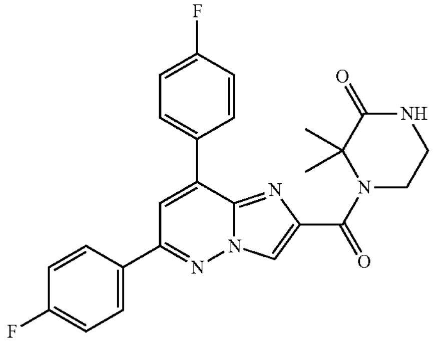
I-524
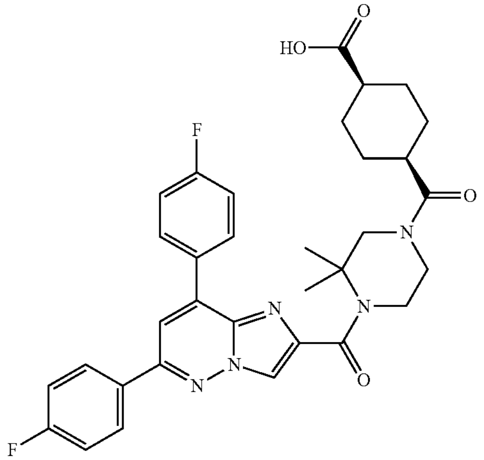
I-525
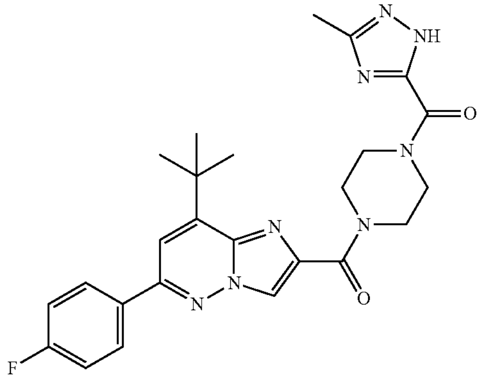
-continued
I-526
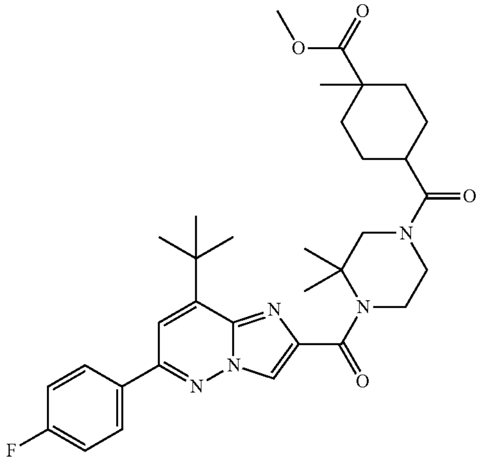
I-527
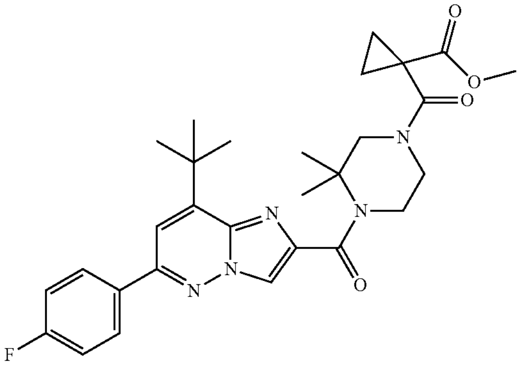
I-528
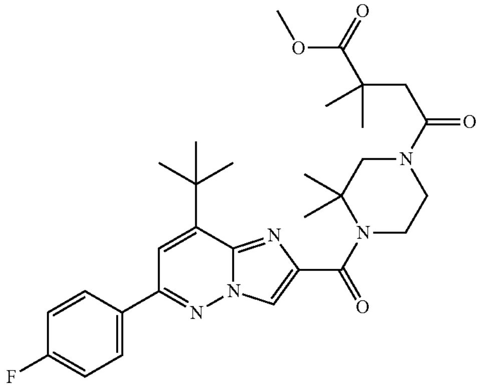
I-529
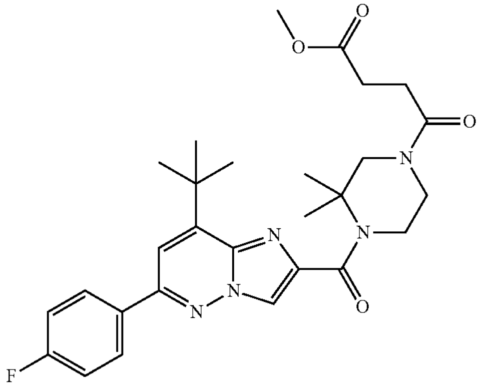

-continued
I-530
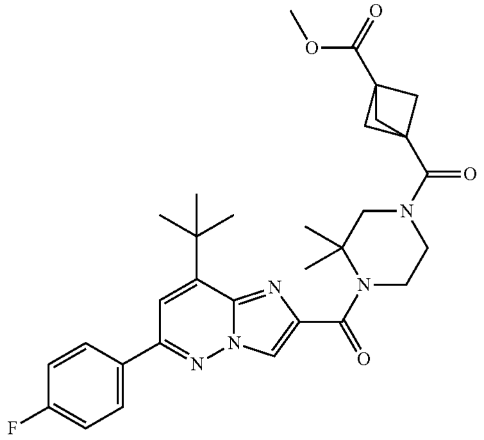
I-531
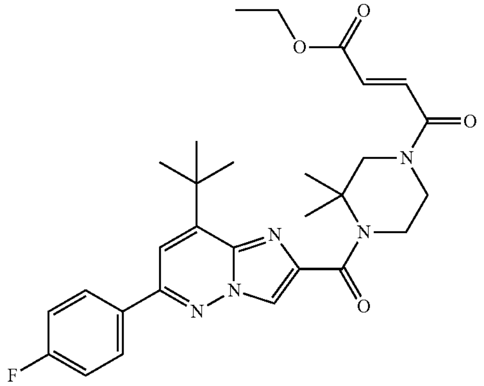
I-532
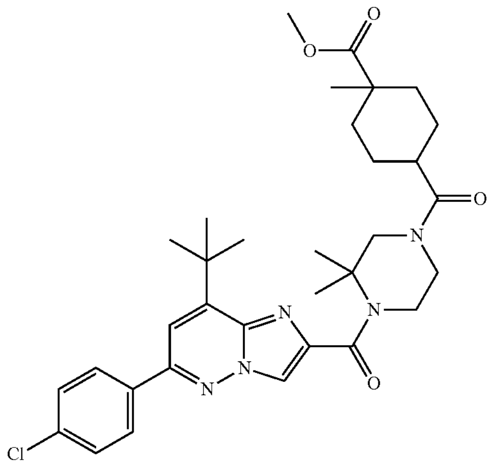
-continued
I-534
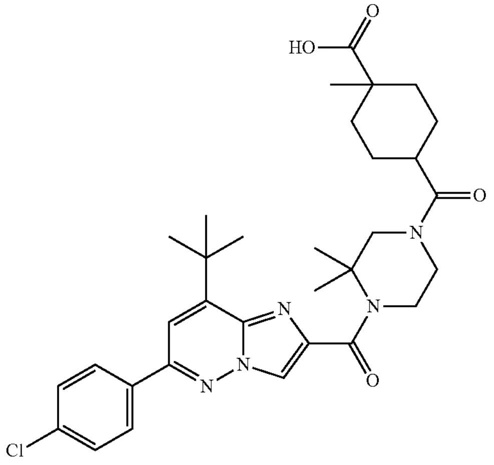
I-535
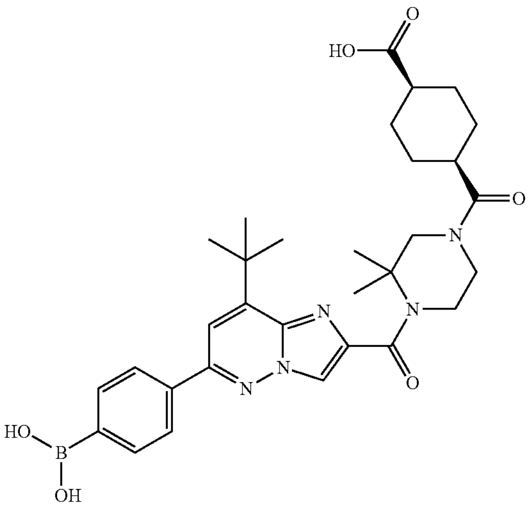
I-536
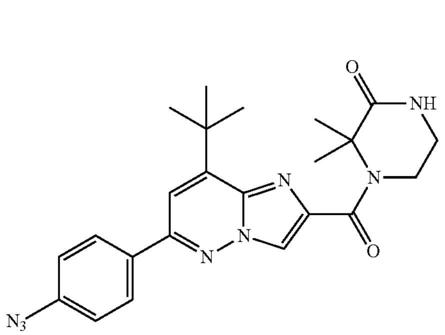

-continued
I-537
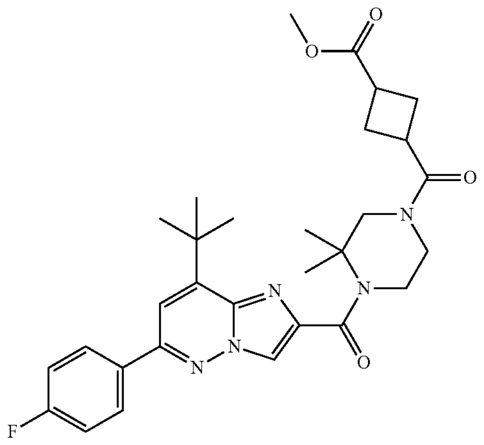
I-538
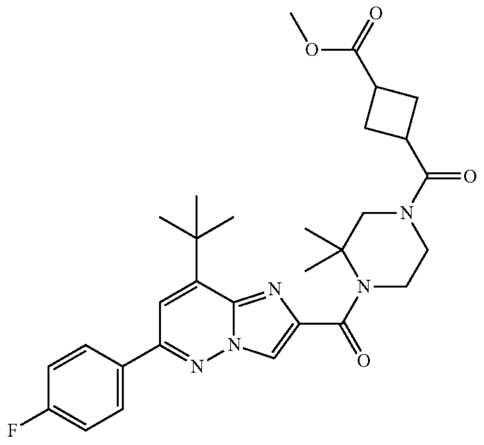
I-539
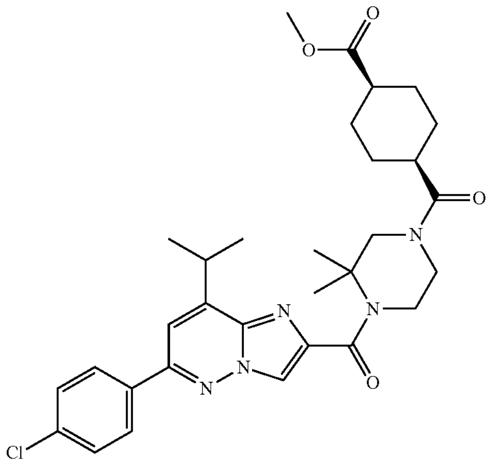
-continued
I-540
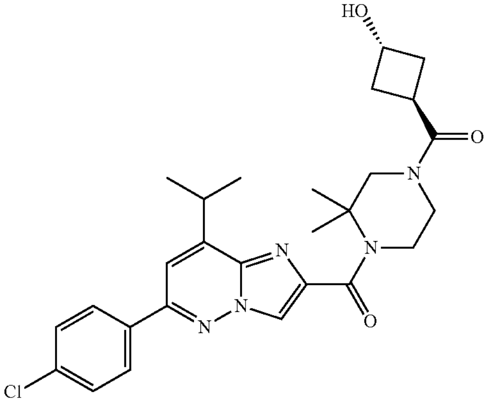
I-541
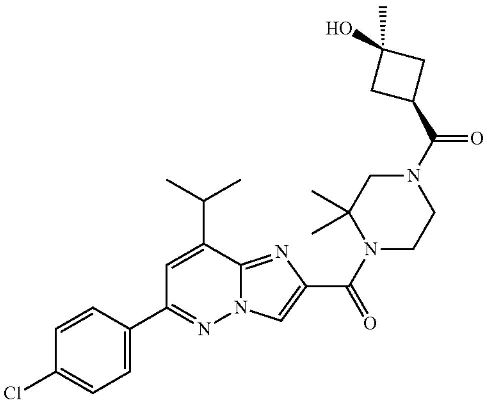
I-542
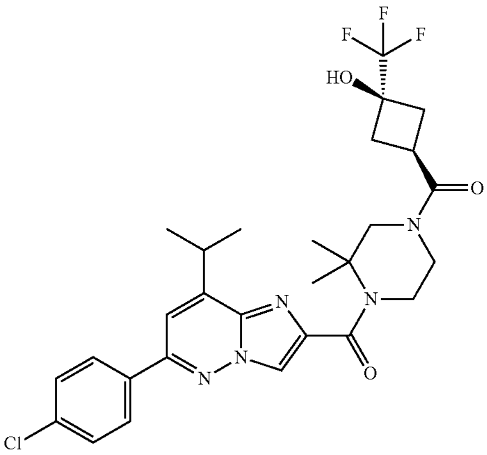

-continued
I-543
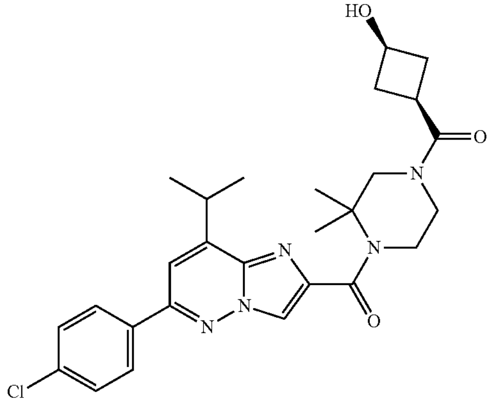
I-544
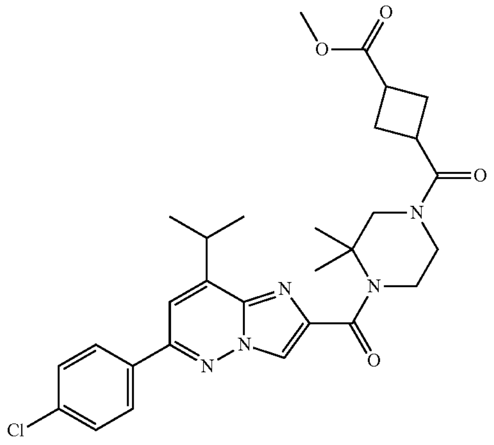
I-545
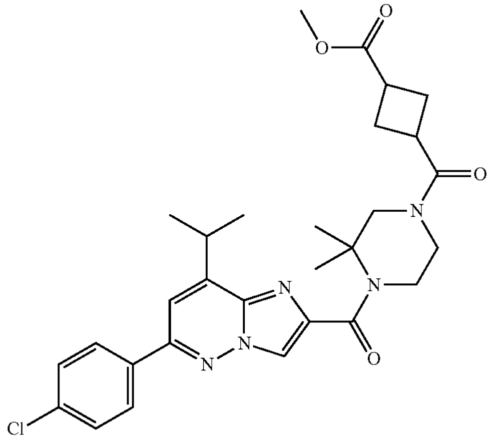
-continued
I-546
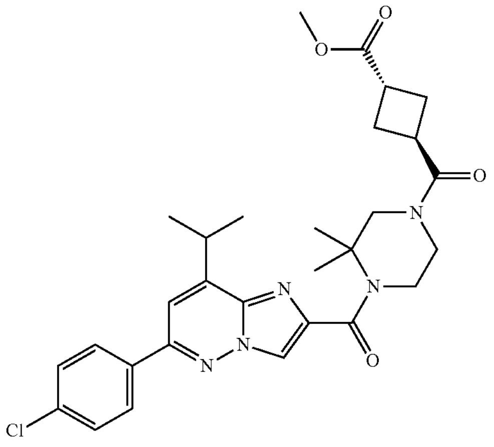
I-547
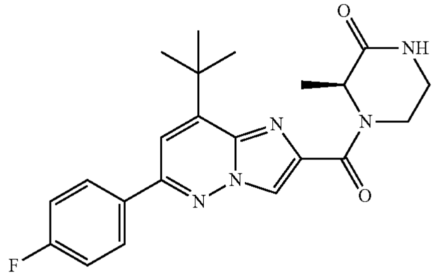
I-548
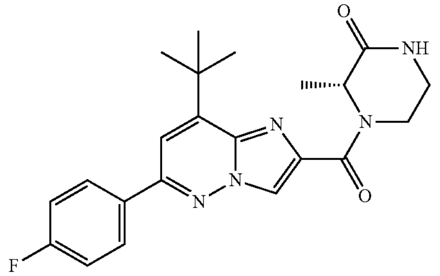
I-549
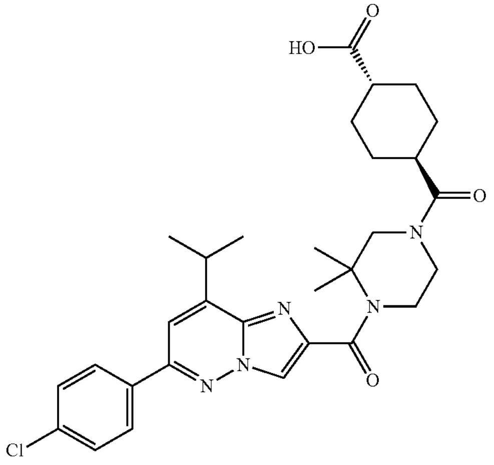

-continued
I-552
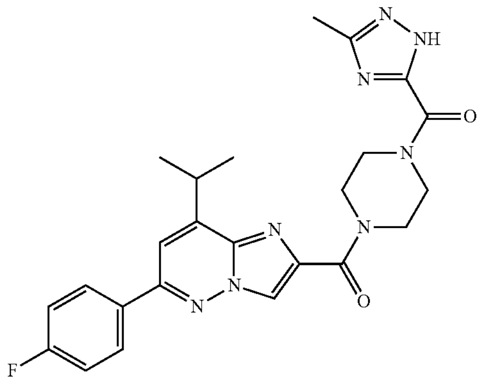
I-553
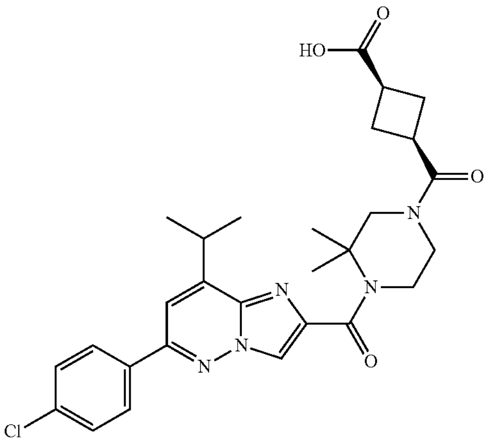
I-554
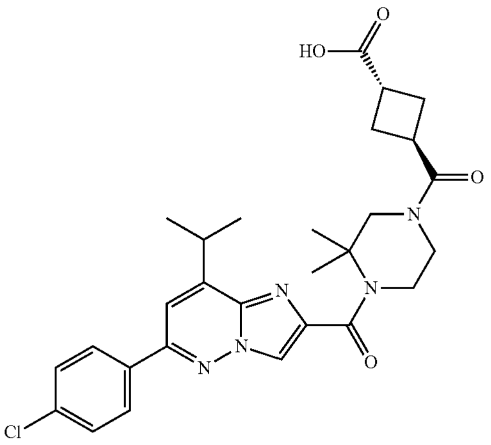
-continued
I-555
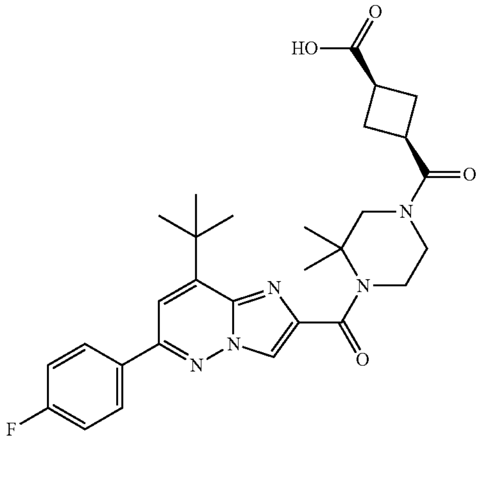
I-556
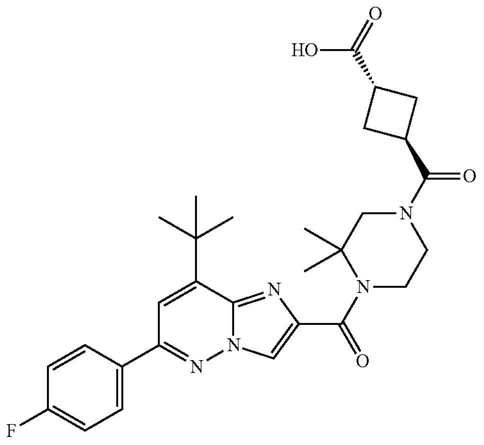
I-557
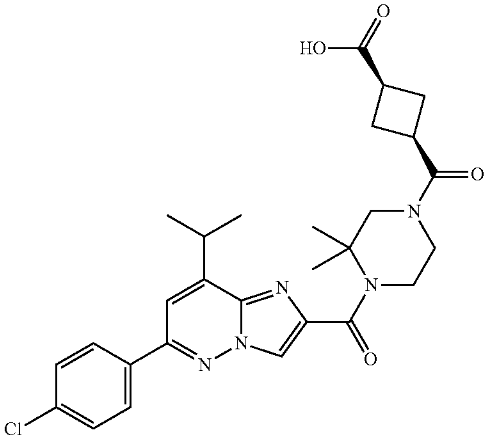

-continued
I-558
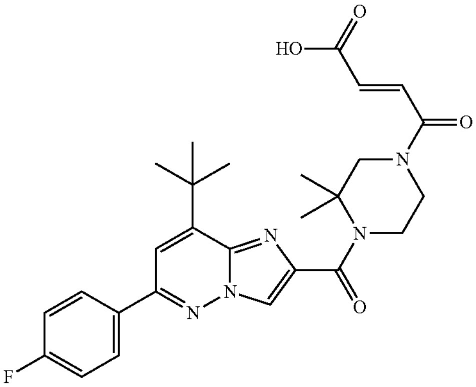
I-559
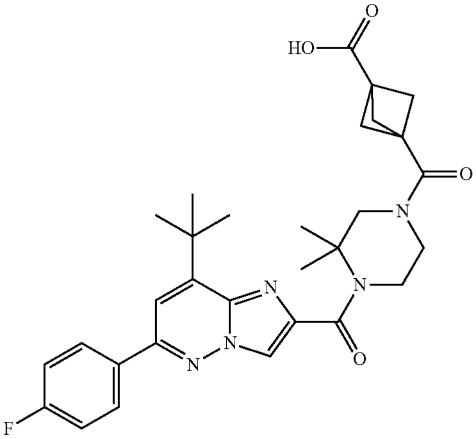
I-560
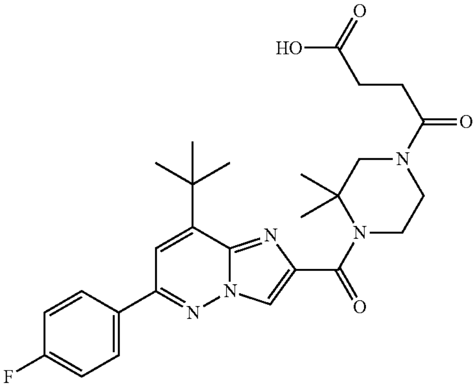
I-561
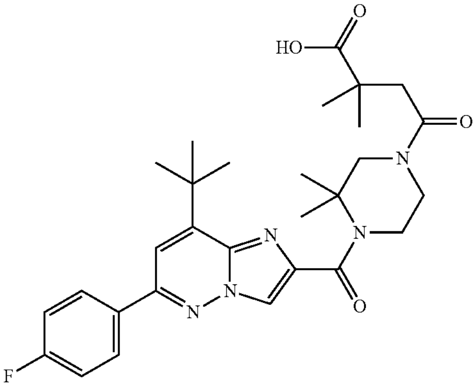
-continued
I-562
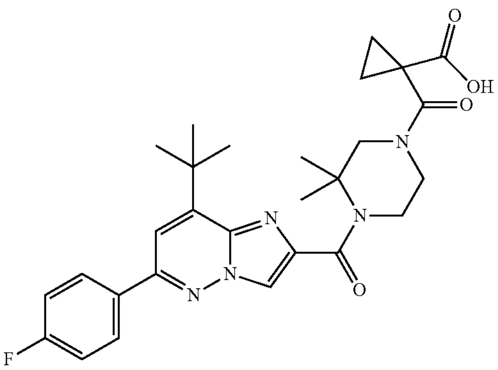
I-563
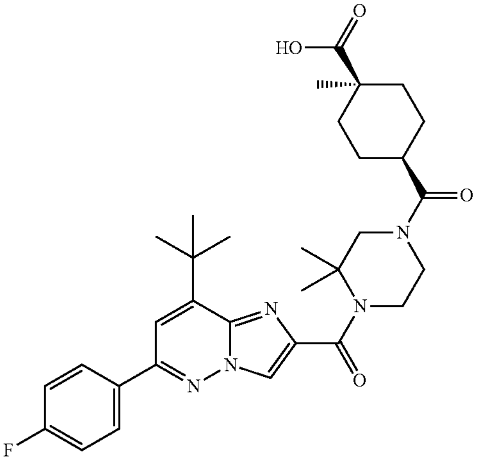
I-564
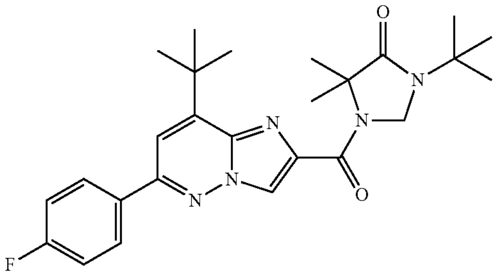
I-565
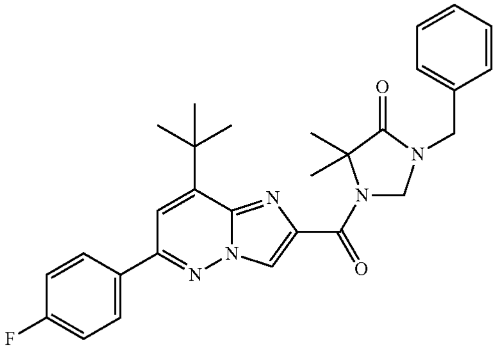

-continued
I-566
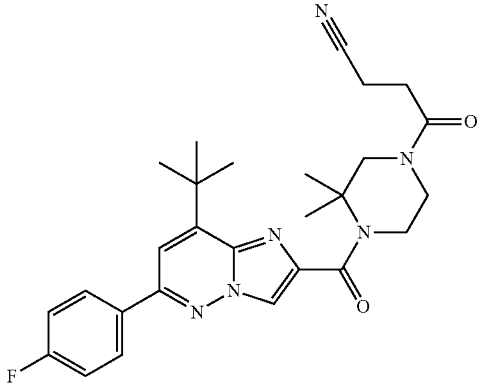
I-567
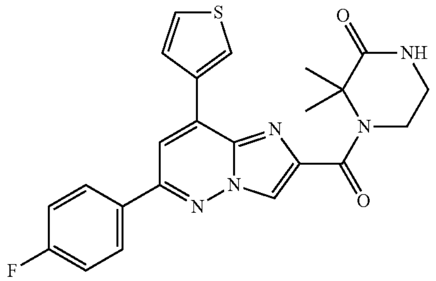
I-568
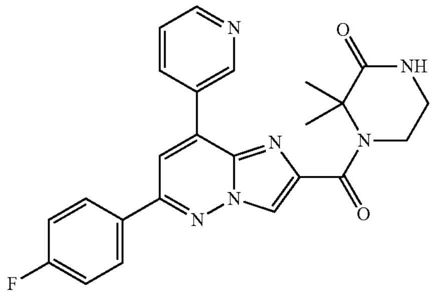
I-569
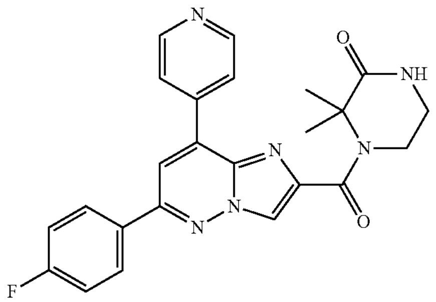
-continued
I-570
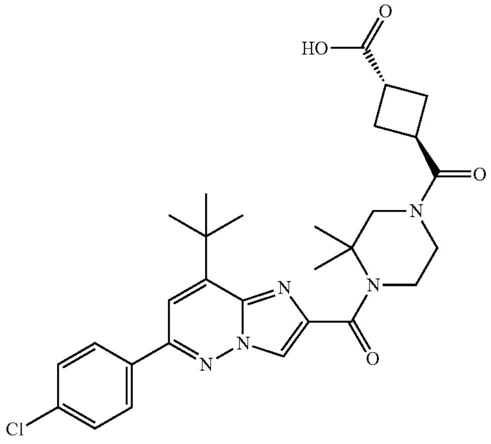
I-571
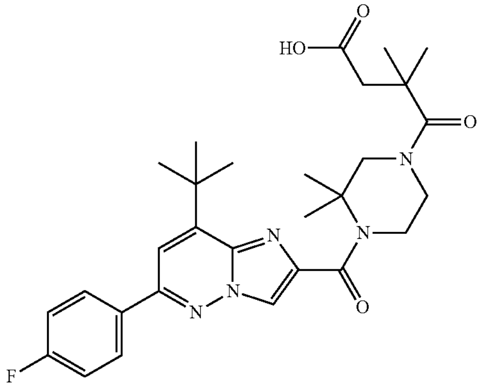
I-572
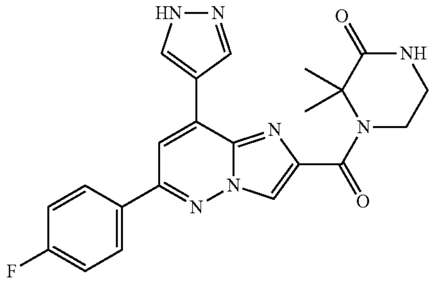
I-573
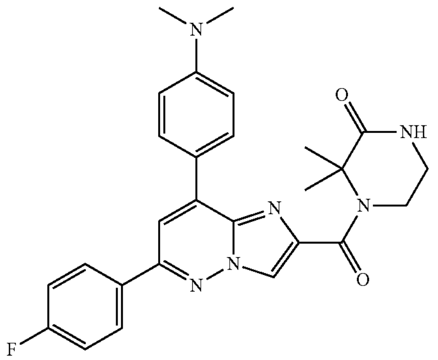

-continued

I-574

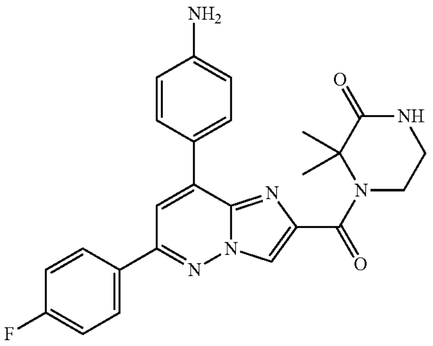

I-575

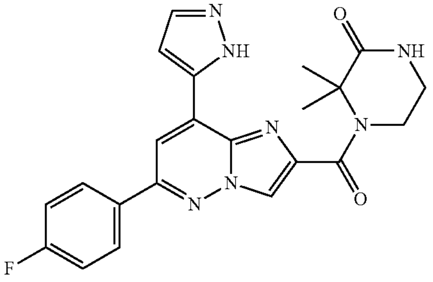

I-576

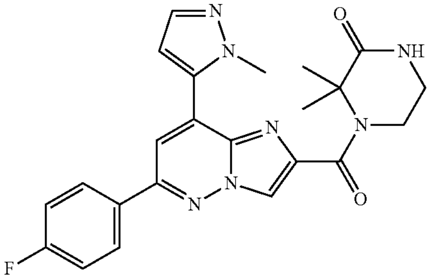

I-577

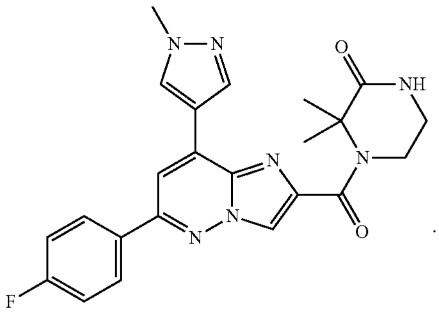

.

11. A pharmaceutical composition comprising a compound of claim 1 and a pharmaceutically acceptable carrier.

12. A method for treating or reducing inflammation in a patient comprising administering to the patient a compound of claim 1 or a pharmaceutically acceptable salt thereof.

13. The method of claim 12, wherein the inflammation is caused by inflammatory bowel disease, irritable bowel syndrome, asthma, rheumatoid arthritis, osteoarthritis, fibrosis, gingivitis, periodontitis, atopic dermatitis, psoriasis, scleroderma, polymyositis, dermatomyositis, uveitis, vasculitis, or adipose inflammation.

14. A method of preparing a compound of formula (II) or pharmaceutically acceptable salt thereof:

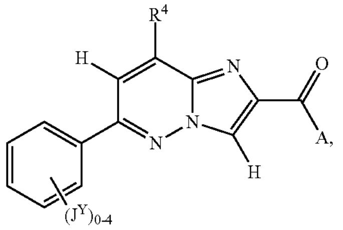

wherein the variables of formula (II) are each and independently as described above in claim 1, comprising:

reacting Compound (X-1) with Compound (Y-1) to form a compound of formula (II) or a pharmaceutically acceptable salt thereof:

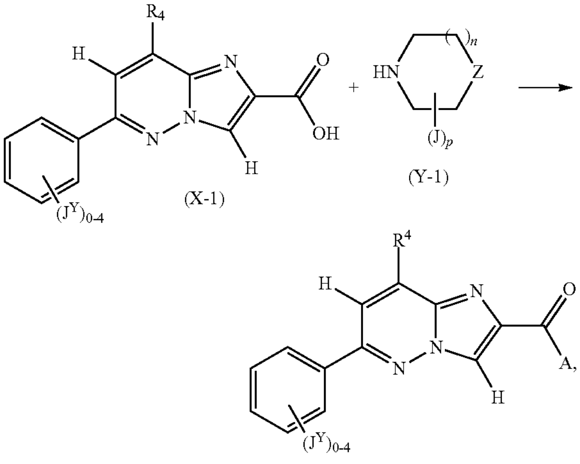

(X-1) (Y-1)

(II)

wherein the variables of Compound (X-1) with Compound (Y-1) are each and independently as described for formula (II) in claim 1.

15. A method of preparing a compound of formula (II) or pharmaceutically acceptable salt thereof:

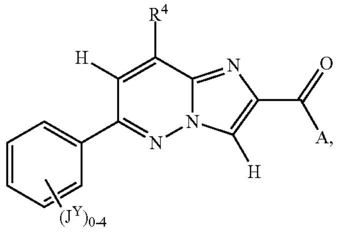

wherein A is

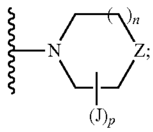

Z is —NX—; and the remaining variables of formula (II) are each and independently as described above in claim 1, comprising:

reacting Compound (X-2) with X-$L^1$ to form a compound of formula (II) or a pharmaceutically acceptable salt thereof:

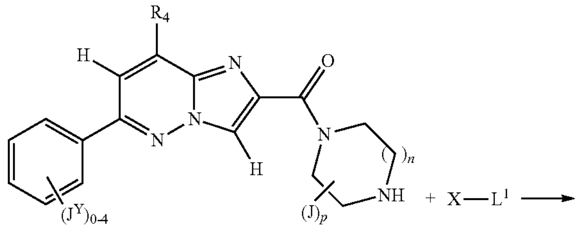

(X-2)

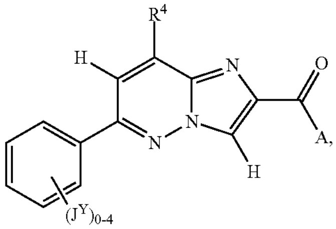

II wherein X of X-$L^1$ is as described for formula (II) in claim 1 and $L^1$ of X-$L^1$ is halo or —OH, and wherein the variables of Compound (X-2) are each and independently as described for formula (II) in claim 1.

16. A method of preparing a compound of formula (II) or pharmaceutically acceptable salt thereof:

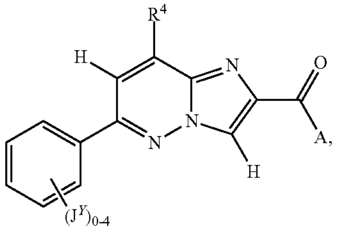

wherein the variables of formula (II) are each and independently as described above in claim 1, comprising:

reacting Compound (X-3) with $R^2$-$L^3$ to form a compound of formula (II) or a pharmaceutically acceptable salt thereof:

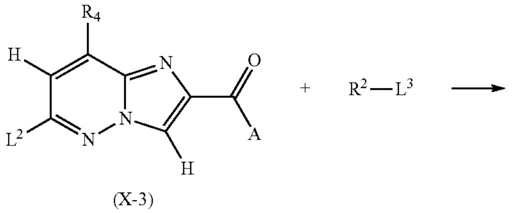

(X-3)

-continued

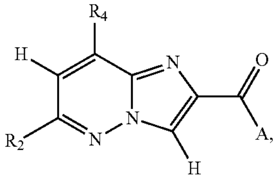

(I)

wherein the compound of formula (I) is a compound of formula (II), $L^2$ of Compound (X-3) is halo, and the remaining variables of Compound (X-3) are each and independently as described for formula (II) in claim 1, and wherein $L^3$ of $R^2$-$L^3$ is —$B(OR^a)_2$, wherein $R^a$ is —H or two $R^a$ together with the atom to which they are attached form a dioxaborolane optionally substituted with $C_{1-2}$alkyl, and $R^2$ of $R^2$-$L^3$ is as described for formula (II) in claim 1.

17. The compound of claim 1, wherein the compound is:

(I-525)

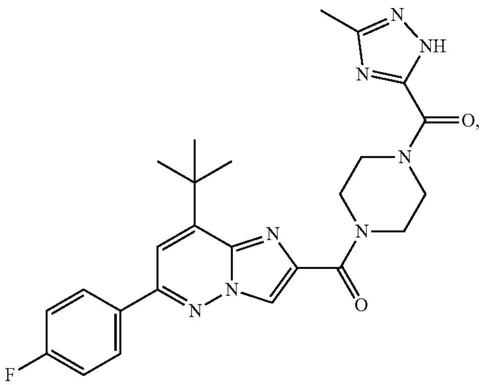

or a pharmaceutically acceptable salt thereof.

18. The compound of claim 1, wherein the compound is:

(I-191)

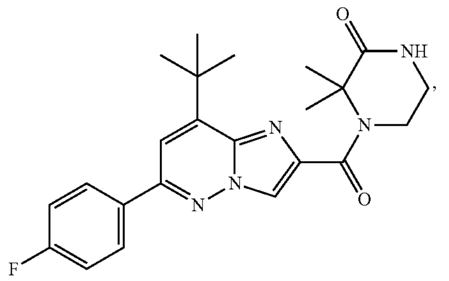

or a pharmaceutically acceptable salt thereof.

19. The compound of claim 1, wherein the compound is:

(I-310)

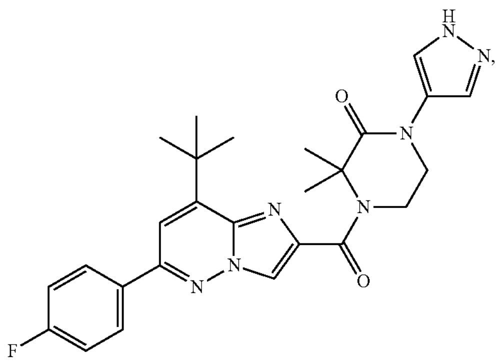

or a pharmaceutically acceptable salt thereof.

20. A method for treating or reducing nociception (pain) in a patient comprising administering to the patient a compound of claim 1 or a pharmaceutically acceptable salt thereof.

21. The method of claim 20, wherein the pain is inflammatory pain, post-operative incision pain, neuropathic pain, fracture pain, osteoporotic fracture pain, or gout joint pain.

22. A method for treating or reducing pruritus in a patient comprising administering to the patient a compound of claim 1 or a pharmaceutically acceptable salt thereof.

23. The method of claim 13, wherein the inflammation is caused by atopic dermatitis.

* * * * *